US012227754B2

(12) United States Patent
Exline et al.

(10) Patent No.: US 12,227,754 B2
(45) Date of Patent: Feb. 18, 2025

(54) ADENOVIRAL EXPRESSION VECTOR AND METHODS AND CELL LINES FOR PRODUCTION

(71) Applicant: Lung Biotechnology PBC, Silver Spring, MD (US)

(72) Inventors: Colin Exline, San Diego, CA (US); Huizhu Liu, San Deigo, CA (US); Sean Stevens, Del Mar, CA (US)

(73) Assignee: Lung Biotechnology PBC, Silver Spring, MD (US)

( * ) Notice: Subject to any disclaimer, the term of this patent is extended or adjusted under 35 U.S.C. 154(b) by 794 days.

(21) Appl. No.: 17/223,785

(22) Filed: Apr. 6, 2021

(65) Prior Publication Data

US 2021/0310025 A1 Oct. 7, 2021

Related U.S. Application Data

(60) Provisional application No. 63/006,266, filed on Apr. 7, 2020.

(51) Int. Cl.
*C12N 15/86* (2006.01)
*C07K 14/54* (2006.01)
*C12N 15/10* (2006.01)

(52) U.S. Cl.
CPC .......... *C12N 15/86* (2013.01); *C07K 14/5428* (2013.01); *C12N 15/102* (2013.01); *C12N 2710/10043* (2013.01); *C12N 2710/10051* (2013.01); *C12N 2830/001* (2013.01); *C12N 2830/50* (2013.01)

(58) Field of Classification Search
CPC .................. C12N 15/86; C12N 15/102; C12N 2710/10043; C12N 2710/10051; C12N 2830/001; C12N 2830/50; C07K 14/5428
See application file for complete search history.

(56) References Cited

U.S. PATENT DOCUMENTS 10,738,282 B2 * 8/2020 Nimmerjahn .......... A61P 37/06
2004/0142893 A1 7/2004 Ikeda et al.
2006/0270041 A1 11/2006 Howe et al.
2014/0248305 A1 9/2014 Ertl et al.

FOREIGN PATENT DOCUMENTS

WO WO-2005/010146 A2 2/2005
WO WO-2019/199859 A1 10/2019

OTHER PUBLICATIONS

Shen, Jikui, et al. "Ex vivo adenovirus mediated gene transfection of human conjunctival epithelium." British journal of ophthalmology 85.7: 861-867. (Year: 2001).*

BigEasy® v2.0: Linear Cloning Kits, Lucigen Corporation, Jan. 1, 2018, 20 pages.

Fischer et al., "In vivo transtracheal adenovirus-mediated transfer of human interleukin-10 gene to donor lungs ameliorates ischemia-reperfusion injury and improves early posttransplant graft function in the rat," Hum Gene Ther., Aug. 10, 2001, 12(12):1513-1526.

GenBank accession No. AY339865, Aug. 13, 2007, 18 pages.

Martins et al., "Transbronchial administration of adenoviral-mediated interleukin-10 gene to the donor improves function in a pig lung transplant model," Gene Therapy, Oct. 7, 2004, 11:1786-1796.

Yeung et al., "Ex vivo adenoviral vector gene delivery results in decreased vector-associated inflammation pre- and post-lung transplantation in the pig," Molecular Therapy, Mar. 27, 2012, 20(6):1204-1211.

Rea et al., "Recombinant Adenovirus-Transduced Human Dendritic Cells Engineered to Secrete Interleukin-10 (IL-10) Suppress Th1-Type Responses While Selectively Activating IL-10-Producing CD4 T Cells," Human Immunology, 2004, 65:1344-1355.

Wold et al., "Adenovirus Vectors for Gene Therapy, Vaccination and Cancer Gene Therapy," Current Gene Therapy, 2013, 13(6):421-433.

* cited by examiner

*Primary Examiner* — Maria G Leavitt
*Assistant Examiner* — Michael Angelo Riga
(74) *Attorney, Agent, or Firm* — Foley & Lardner LLP

(57) ABSTRACT

An adenovirus expression vector is provided. The adenovirus expression vector may include: a) one or more mutations that render the adenovirus replication incompetent and b) at least one nucleotide sequence encoding a protein or an RNA is provided. A method of synthesizing an adenovirus vector is also provided. The synthesis may include: a) producing a plurality of overlapping adenovirus sub-fragments, each sub-fragment comprising a portion of the full genome of the adenovirus; b) circularizing the sub-fragments to form plasmid structures; and c) assembling the circularized sub-fragments into a linear structure, wherein the vector comprises a combination of two or more sub-fragments. A mammalian cell line configured to replicate adenoviral vectors, wherein the cell line comprises nucleotide sequences expressing E1A and E1B gene products but is devoid of other adenovirus sequences is also provided.

7 Claims, 10 Drawing Sheets

Specification includes a Sequence Listing.

FIG. 1
Start
End
BspDI - ClaI
BstZ17I
PmeI
AsiSI
SrfI
CAG full promoter
CMV Enhancer
Adenovirus E2B pTP 75K
Adenovirus E2B IVa2
Adenovirus L1
Adenovirus L1 pIIIa
Adenovirus L2 pVII
Adenovirus L2 p5 precursor
Adenovirus E2A DNA binding protein
Adenovirus L4
Adenovirus L5 pVI
Adenovirus E4 orf 3/4
Adenovirus E4 orf 4
beta-Globin intron (CAG)

Sub-fragment 1 of overlapping fragments

Sub-fragment 2: overlapping fragments

FIG. 8
truncEnv
Adenovirus E1B
PGK
Adenovirus E1A
WPRE
Psi
truncGag
RRE
cPPT
pA SV40 (full)
MiniCMV
EFa1 minimal promoter
hEF1-HTLV hybrid promoter
HIV1 LTR (delta U3)
Puromycin R

ADENOVIRAL EXPRESSION VECTOR AND METHODS AND CELL LINES FOR PRODUCTION

CROSS-REFERENCE TO RELATED APPLICATIONS

This application claims priority to U.S. Provisional Application No. 63/006,266, filed Apr. 7, 2020, the entire contents of which are incorporated herein.

SEQUENCE LISTING

The instant application contains a Sequence Listing which has been submitted electronically in ASCII format and is hereby incorporated by reference in its entirety. Said ASCII copy, created on Jun. 8, 2021, is named 080618-2006_SL.txt and is 1,311,016 bytes in size.

FIELD OF USE

This application relates generally to adenoviral vectors and gene therapy, and, more specifically, to non-replicating adenovirus expression vectors, methods of synthesis, and modes of replication.

BACKGROUND

Adenoviral vector nucleotide sequences are often many kilobases long, which makes in vitro manipulation less convenient and harder to achieve. Manipulation of adenoviral vectors, if done improperly, can also leaded to unchecked replication of the vector. Moreover, common mammalian cell lines used to produce adenovirus often possess endogenous copies of adenoviral genes, which can recombine with mutant adenoviral vectors and create infectious replicating viruses. Thus, there exists a need for safe, non-infectious, recombinant, non-replicating adenoviral vectors with effective expression cassettes for therapeutic use. It would also be desirable to provide a protocol for more efficient production of these recombinant vectors in bacteria, overcoming the difficulties in manipulating large adenoviral sequences. Finally, it would further be desirable to provide a mammalian cell line for replication of the engineered adenoviral vector to eliminate possible contamination of a replication competent adenovirus.

SUMMARY

The present disclosure provides an adenovirus vector possessing a) one or more mutations that render it replication incompetent, and b) carrying a nucleotide expression cassette that allows expression of therapeutics when transduced into host cells. Sequences of the engineered adenovirus vectors are disclosed herein. Protocols and methods for more efficient production in bacteria of the synthesized adenovirus vectors are also provided herein. Finally, creation of an engineered mammalian cell line for replication of the engineered adenoviral vector to eliminate possible contamination of replication competent adenovirus is produced herewith.

The non-replicating adenovirus expression vector may include a) one or more mutations that render the adenovirus replication incompetent and b) at least one nucleotide sequence encoding a protein or an RNA. In some embodiments, the vector comprises a nucleotide sequence having at least 80% sequence identity to any of SEQ ID NOs: 1-2.

SEQ ID NO: 1 encodes a full vector with plasmid backbone. SEQ ID NO: 2 encodes a full adenoviral vector of the present disclosure without a plasmid backbone. In certain preferred embodiments, the vector is an adenovirus serotype 5 vector. The mutations may comprise deletion of either an E1 gene or an E3 gene or both. At least one nucleotide sequence in the non-replicating adenovirus expression vector may be a transgene. In certain embodiments, the transgene expresses human IL10. In some embodiments, the transgene further comprises at least one of an enhancer/promoter region including CAG, human IL10 cDNA, or a polyadenylation signal, or any combination thereof. The polyadenylation signal further may be an SV40 region and/or a full polyA signal. The polyadenylation signal may be inserted, in some embodiments, between nucleotides 440 and 3515 in SEQ ID NO: 3. SEQ ID NO: 3 may be derived from accession number AY3339865 in the GenBank database.

Insertion of the transgene in the adenoviral vector may replace the E1 gene but leaves the pIX gene intact. In some aspects of the disclosure, the recombinant vector can include a nucleic acid sequence having at least about 80%, about 85%, about 90%, about 95%, about 96%, about 97%, about 98%, about 99%, or greater than 99% sequence identity to SEQ ID NOs: 1-2.

A method of synthesizing an adenovirus vector is also disclosed herein. The method may include: a) producing a plurality of overlapping adenovirus sub-fragments, each sub-fragment including a portion of the full genome of the adenovirus; b) circularizing the sub-fragments to form plasmid structures; c) assembling the circularized sub-fragments into a linear structure, wherein the vector includes a combination of two or more sub-fragments. In some aspects of the method, the adenovirus vector may be adenovirus serotype 5. In certain embodiments, the vector may replicate at high efficiency.

A first sub-fragment may include at least one sequence as set forth in SEQ ID NOs: 4-5. In some embodiments, a second sub-fragment may include at least one sequence as set forth in SEQ ID NOs: 6-7.

In some embodiments, each sub-fragment may include about 50% of the full adenovirus genome. At least one fragment may include a transgene that expresses human IL-10. The transgene further may include at least one of an enhancer/promoter region, human IL10 cDNA, or a polyadenylation signal, or any combination thereof. The enhancer or promoter region may be a CAG promoter. The transgene further may include at least a polyadenylation signal comprising an SV40 promoter or a full poly(A) signal. The vector sequence also may have a linear cloning vector and or a backbone linear cloning vector. In certain embodiment, the linear cloning vector may be pJazz-OK. The human IL10 cDNA sequence may be optimized and encoded from SEQ ID NO: 8.

A mammalian cell configured to replicate adenoviral vectors, wherein the cell line comprises nucleotide sequences expressing E1A and E1B gene products but is devoid of other adenovirus sequences is also provided herein. The cell line further may comprise a lentiviral vector engineered to express the E1A and E1B gene products, wherein the lentiviral vector inhibits reconstitution of functional adenovirus when a mutant adenoviral viral vector is introduced into the cell line. In some embodiments, the cell line may comprise HeLa cells. In some embodiments, the cell line is produced by transfecting HEK293 cells with a lentiviral genome plasmid comprising at least an E1A encoding sequence and an E1B-encoding sequence.

The plasmid further may comprise at least an E1A encoding sequence and an E1B-encoding sequence contains E1A and E1B sequences arranged in a bidirectional expression unit with a bidirectional promoter to prevent recombination with a mutant adenoviral vector. In some aspects of the cell line, the bidirectional promoter may be a combination of truncated CMV and PGK promoters.

The cell line further can include a puromycin drug resistance gene in the lentiviral genome sequence to differentiate cells which have integrated the lentiviral sequence when the puromycin drug resistance gene is expressed. In some embodiments, a final vector of SEQ ID NO: 9 is used to produce lentivirus and HeLa cells, transduced and selected for puromycin resistance.

A method of producing and/or expanding the synthetic non-replicating adenoviral vector disclosed above is also provided herein. The method may include transforming a mammalian cell with an adenovirus vector comprising: a) one or more mutations that render the adenovirus replication incompetent and b) at least one nucleotide sequence encoding human IL-10, wherein the mammalian cell comprises nucleotide sequences expressing E1A and E1B gene products but is otherwise devoid of other adenovirus sequences, culturing the transformed mammalian cell in a cell line containing an inserted lentiviral E1A and E1B vector, and isolating the adenovirus vector.

In a further aspect of the disclosure, a method of treating a subject in need of a gene product is also provided herein. In some embodiments, the method may comprise, consist essentially of, or further, consist of administering to the subject a vector comprising (a) one or more mutations that render the adenovirus replication incompetent and (b) at least one nucleotide sequence encoding the gene product. In some embodiments of the method, the vector comprises a nucleotide sequence having at least 80% sequence identity over the entire sequence of SEQ ID NO: 1 or SEQ ID NO: 2, or a complementary sequence thereto. In certain embodiments, the vector may be an adenovirus serotype 5 vector. Additionally or alternatively, the one or more mutations may be a deletion of either an E1 gene or an E3 gene or both. The at least one nucleotide sequence further may include a transgene. In some embodiments, the transgene expresses human IL10.

In some embodiments of the method, the subject may be a human. In certain embodiments, the gene product is a peptide, including human peptides. In some embodiments, the gene product can be RNA.

DETAILED DESCRIPTION

Definitions

Figure 1:
FIG. 1 is a schematic diagram of the genomic organization of a full non-replicating, adenoviral vector of the present disclosure, without a plasmid backbone.

As used in this specification and the appended claims, the singular forms “a,” “an,” and “the” include plural referents unless the content clearly dictates otherwise. For example, reference to “a cell” includes a combination of two or more cells, and the like.

As used herein, the term “about” encompasses the range of experimental error that may occur in a measurement and will be clear to the skilled artisan.

As used herein, “adenovirus” means a medium-sized (90-100 nm), nonenveloped polyhedral virus that may include a capsid and a double-stranded linear DNA genome. The adenovirus can be a naturally occurring, but isolated, adenovirus or a recombinant adenovirus, or a chimeric variant thereof.

As used herein, “administering” means a method of giving a dosage of a pharmaceutical composition (e.g., a recombinant adenovirus of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraocularly, orally, topically, locally, by inhalation, by injection, by infusion, by continuous infusion, by localized perfusion bathing target cells directly, by catheter, by lavage, by gavage, in crèmes, or in lipid compositions. The preferred method of administration can vary depending on various factors (e.g., the components of the composition being administered and the severity of the condition being treated).

Throughout this specification and claims, the word “comprise,” or variations such as “comprises” or “comprising,” will be understood to imply the inclusion of a stated integer or group of integers but not the exclusion of any other integer or group of integers.

As used herein, “protein” includes peptides, polypeptides, or proteins of any length and any secondary or tertiary structure.

As used herein, “gene product” is meant to include mRNAs, other nucleic acids (e.g., microRNAs) transcribed from a gene as well as proteins, including polypeptides, translated from those mRNAs. A gene product can be a soluble protein, chemokine, cytokine, soluble receptor, an antibody, antibody fragments, an antibody-like molecule, or enzyme. For example, the gene product can be an antigen-binding fragment of an antibody, or the gene product can be some or all of the variable portion of IgG or IgM. In some embodiments, the gene product can be an antibody fragment lacking the Fc domain. The gene product can comprise or consist of a complementarity-determining region (CDR). In some embodiments, the gene product can be an anti-IL6 antibody or antibody fragment. In some embodiments, the gene product is from a virus. In some embodiments, the gene product is a therapeutic gene product, including, but not limited to, the interleukins (e.g., human IL-10), interferon proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, insulin-like growth factors, superoxide dismutase, immune responder modifiers, parathyroid hormone and interferon, nerve growth factors, tissue plasminogen activators, and colony stimulating factors.

By "portion" or "fragment" is meant a part of a whole. A portion may comprise at least 10%, 20%, 30%, 40%, 50%, 60%, 70%, 80%, 90%, or 95% of the entire length of an polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000 or more contiguous nucleotides of a reference polynucleotide molecule. For polypeptides, for example, a portion may include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, or 350 or more contiguous amino acids of a reference polypeptide molecule.

As used herein, "sequence identity" or "sequence similarity" means that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting. Such software may match similar sequences by assigning degrees of homology to various substitutions, deletions, and other modifications.

A "subject" is a vertebrate, such as a mammal (e.g., primates and humans). Mammals also include, but are not limited to, farm animals (such as cows), sport animals (e.g., horses), pets (such as cats and dogs), mice, and rats. A subject to be treated according to the methods described herein (e.g., a subject having a disease such as cancer and/or a disease caused by an infective agent, e.g., a bacterium, virus, fungus, or parasite) may be one who has been diagnosed by a medical practitioner as having such a condition. Diagnosis may be performed by any suitable means. A subject in whom the development of an infection or disease (or disease symptoms) is being prevented may or may not have received such a diagnosis. One skilled in the art will understand that a subject to be treated according to the present invention may have been subjected to standard tests or may have been identified, without examination, as one at high risk due to the presence of one or more risk factors (e.g., exposure to a biological agent, such as a virus).

As used herein, "vector" refers to a composition that includes one or more genes (non-structural or structural), or fragments thereof, from a viral species, such as an adenoviral species (e.g., sAd5, sAd1, etc.), that may be used to transmit one or more heterologous genes from a viral or non-viral source to a host or subject. The nucleic acid material of the viral vector may be encapsulated, e.g., in a lipid membrane or by structural proteins (e.g., capsid proteins), that may include one or more viral polypeptides (e.g., a glycoprotein). The viral vector can be used to infect cells of a subject, which, in turn, promotes the translation of the heterologous gene(s) of the viral vector into a protein product.

The term "virus," as used herein, is defined as an infectious agent that is unable to grow or reproduce outside a host cell and that infects mammals (e.g., humans) or birds.

Other features and advantages of the invention will be apparent from the following Detailed Description, the drawings, and the claims.

Adenoviral Polynucleotides of the Disclosure

The complete genome sequences of novel adenoviral vectors are disclosed below. The adenovirus 5 genome is over thirty-five kilobases in size, making in vitro manipulation less convenient. Thus, synthetic DNA methods were used to generate two or more small fragments to allow for higher efficiency molecular cloning using bacterial hosts. The final, non-replicating adenovirus expression vector may include a) one or more mutations that render the adenovirus replication incompetent and b) at least one nucleotide sequence encoding a protein or an RNA.

Figure 2:
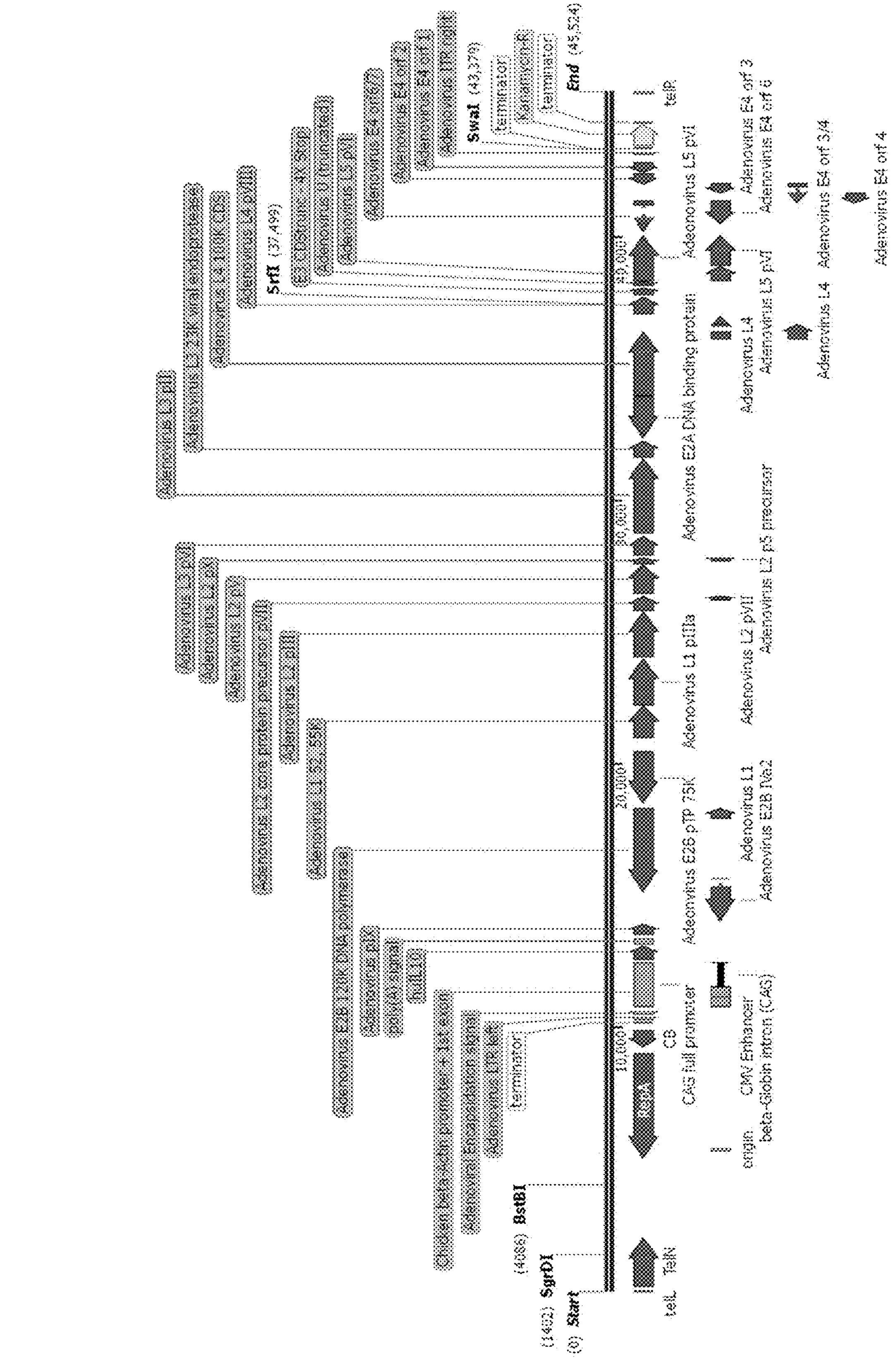
FIG. 2 is a schematic diagram of the genome organization of a non-replicating, adenoviral vector of the present disclosure, with a plasmid backbone.

FIG. 1 is a schematic diagram of the genome organization of a non-replicating, adenoviral vector of the present disclosure, without a plasmid backbone. FIG. 2 is a schematic diagram of the genome organization of a non-replicating, adenoviral vector of the present disclosure, with a plasmid backbone. In some aspects of the disclosure, the vector comprises a nucleotide sequence having at least 80% sequence identity to SEQ ID NOs: 1-2. In some aspects of the disclosure, the recombinant vector can include a nucleic acid sequence having at least about 80%, about 85%, about 90%, about 95%, about 96%, about 97%, about 98%, about 99%, greater than 99%, or any value therebetween sequence identity to SEQ ID NOs: 1-2.

In certain preferred embodiments, the vector is an adenovirus serotype 5 vector. The mutations may comprise deletion of either an E1 gene or an E3 gene or both, to prevent adenoviral replication in vivo. At least one nucleotide sequence in the non-replicating adenovirus expression vector may be a transgene. In certain embodiments, the transgene expresses human IL10. In some embodiments, the transgene further comprises at least one of an enhancer/promoter region including CAG, human IL10 cDNA, or a polyadenylation signal, or any combination thereof. The polyadenylation signal further may be an SV40 region and/or a full polyA signal. The polyadenylation signal may be inserted, in some embodiments, between nucleotides 440 and 3515 in SEQ ID NO: 3. SEQ ID NO: 3 may be derived from accession number AY3339865 in the GenBank database. In certain preferred embodiments, a transgene for expression of human IL10 is included in the adenoviral sequence, which further includes an enhancer/promoter region (CAG), human IL10 cDNA, and a polyadenylation signal (SV40, full polyA signal), which is inserted between nucleotide 440 and 3515 relative to Adenovirus sequence (GenBank accession number AY339865), replacing the E1 genes but leaving the pIX gene intact.

Sequences encoding an inserted transgene in the adenoviral vector may include a variety of gene products, and RNA or DNA transcribed therapeutics, including, but not limited to, interferon (IFN) proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and/or colony stimulating factors, or fragments thereof.

The engineered adenoviral vector may include any nucleotide (DNA or RNA) sequence configured for inclusion with the expression cassette. Exemplary transgenes that may be inserted into the adenoviral construct include, but are not limited to, Angiotensin-converting enzyme 2 precursor (ACE2) antibodies (SEQ ID NO: 14 [no plasmid backbone], SEQ ID NO: 15 [with plasmid backbone]), chimeric monoclonal antibodies such as Unitixin scFv (SEQ ID NO: 16 [no plasmid backbone], SEQ ID NO: 17 [with plasmid backbone]), transforming growth factor (TGF) beta res IL-10 (SEQ ID NO: 18 [with plasmid backbone], SEQ ID NO: 19 [no plasmid backbone]), interleukin 13 (SEQ ID NO: 20 [no plasmid backbone], SEQ ID NO: 21 [with plasmid backbone]), interleukin 8 with short hairpin RNA (shRNA) (SEQ ID NO: 22 [with plasmid backbone], SEQ ID NO: 23 [no plasmid backbone]), IL-1 receptor agonist 2 and IL-10 (SEQ ID NO: 24 [with plasmid backbone], SEQ ID NO: 25 [no plasmid backbone]), IL-1 receptor agonist (SEQ ID NO: 26 [with plasmid backbone], SEQ ID NO: 27 [no plasmid backbone]), endothelial nitric oxide synthase (eNOS) (SEQ ID NO: 28 [with plasmid backbone], SEQ ID NO: 29 [no plasmid backbone]), cystic fibrosis transmembrane conductance regulator (CFTR) (SEQ ID NO: 30 [with plasmid backbone], SEQ ID NO: 31 [no plasmid backbone]), Beta-1,4-galactosyltransferase 1 (B4GALT1) enzymes (SEQ ID NO: 32 [with plasmid backbone], SEQ ID NO: 33 [no plasmid backbone]).

Protocol for More Efficient Adenoviral Production in Bacteria

A method of synthesizing an adenovirus vector is also disclosed herein. The method may include: a) producing a plurality of overlapping adenovirus sub-fragments, each sub-fragment including a portion of the full genome of the adenovirus; b) circularizing the sub-fragments to form plasmid structures; c) assembling the circularized sub-fragments into a linear structure, wherein the vector includes a combination of two or more sub-fragments. In some aspects of the method, the adenovirus vector may be adenovirus serotype 5. In certain embodiments, the vector may replicate at high efficiency.

Figure 3:
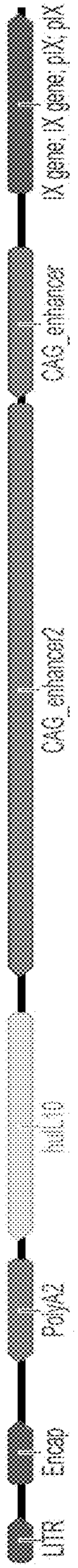
FIG. 3 is a schematic diagram of the genomic organization of an exemplary first sub-fragment in linear form.
Figure 4:
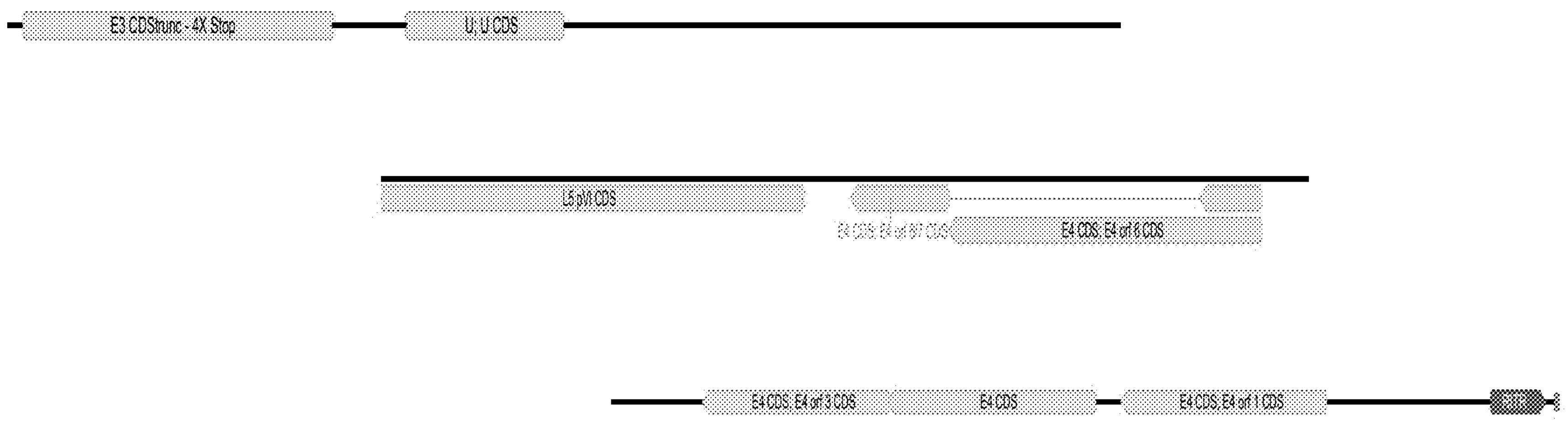
FIG. 4 depicts a schematic diagram of the genomic organization of an exemplary second sub-fragment in linear form.
Figure 5:
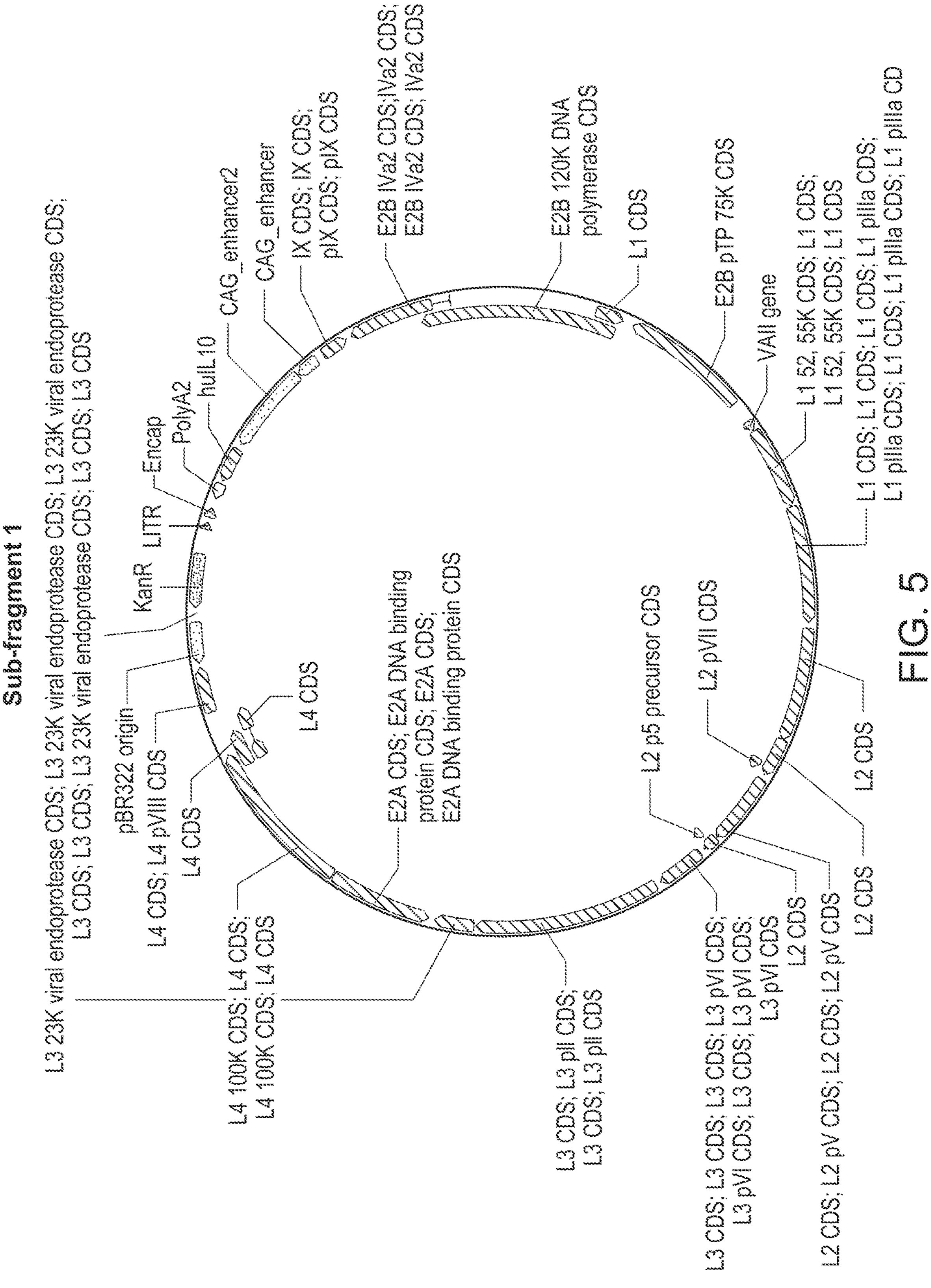
FIG. 5 shows a schematic diagram of the genomic organization of an exemplary first sub-fragment in circularized form.
Figure 6:
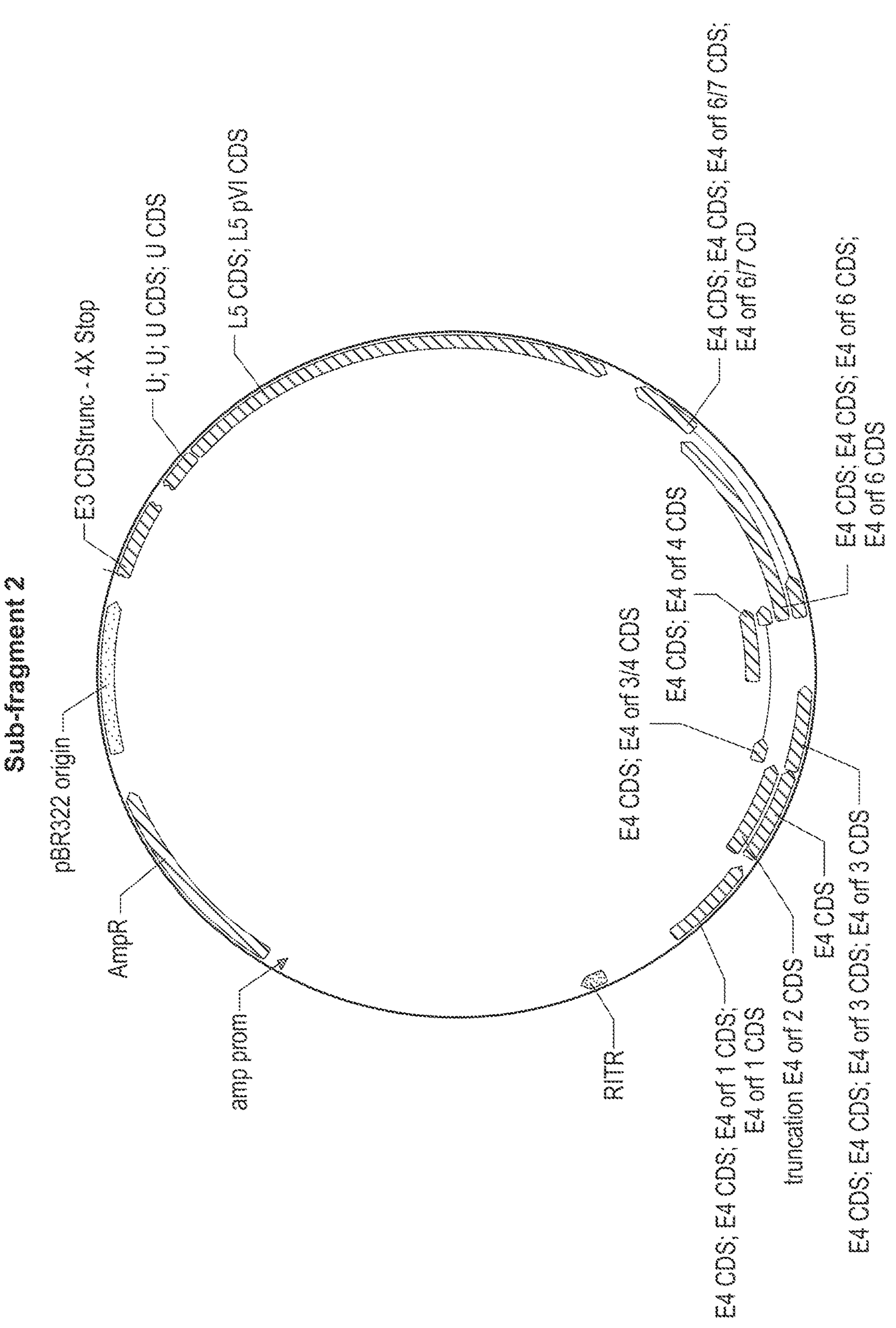
FIG. 6 shows a schematic diagram of the genomic organization of an exemplary first second-fragment in circularized form.

A first sub-fragment may include at least one sequence as set forth in SEQ ID NOs: 4-5. In some embodiments, a second sub-fragment may include at least one sequence as set forth in SEQ ID NOs: 6-7. FIG. 3 depicts a schematic diagram of the genomic organization of an exemplary first sub-fragment in linear form. FIG. 4 depicts a schematic diagram of the genomic organization of an exemplary second sub-fragment in linear form. FIG. 5 shows a schematic diagram of the genomic organization of an exemplary first sub-fragment in circularized form and FIG. 6 shows a schematic diagram of the genomic organization of an exemplary first second-fragment in circularized form.

Figure 7:
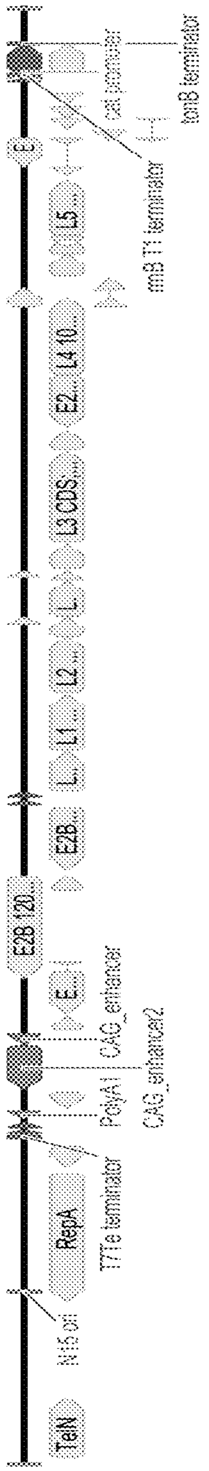
FIG. 7 shows a schematic diagram of genomic organization of the final vector combining a first sub-fragment and a second sub-fragment.

FIG. 7 shows a schematic diagram of genomic organization of the final vector combining a first sub-fragment and a second sub-fragment. Here it is shown that the final adenovirus serotype 5 genome may be assembled from the plurality of circularized fragments, which creates a linear structure for high level DNA replication in bacteria used in viral production. The high level of DNA replication and design allow for greater amounts of DNA to use for transfection and first round viral production. This is particularly useful when manipulating larger adenoviral vectors, such as the serotype 5 adenoviral vector, which is over 35 kilobases in size.

In some embodiments, each sub-fragment may include about 50% of the full adenovirus genome. At least one fragment may include a transgene that expresses human IL-10. The transgene further may include at least one of an enhancer/promoter region, human IL10 cDNA, or a polyadenylation signal, or any combination thereof. The enhancer or promoter region may be a CAG promoter. The transgene further may include at least a polyadenylation signal comprising an SV40 promoter or a full poly(A) signal. The vector sequence also may have a linear cloning vector and or a backbone linear cloning vector. In certain embodiments, the linear cloning vector may be pJazz-OK (see, e.g., *BigEasy® v*2.0: *Linear Cloning Kits*, Lucigen Corporation, Jan. 1, 2018), hereby incorporated by reference). The teachings of the human IL10 cDNA sequence may be optimized and encoded from SEQ ID NO: 8.

Engineered Mammalian Cell Line for Replication of the Engineered Adenoviral Vector A mammalian cell configured to replicate adenoviral vectors, wherein the cell line comprises nucleotide sequences expressing E1A and E1B gene products but is devoid of other adenovirus sequences is also provided herein.

The adenoviral vectors disclosed above may have been mutated to remove the viral E1 and E3 genes in order to prevent the viruses from replicating and thus being infectious. Mammalian cell lines supplied with the two E1 gene products, E1A and E1B, can support replication of the mutant virus. However, a common mammalian cell line used to produce adenovirus, HEK293, possesses an endogenous copy of the adenoviral E1 gene, which can recombine with mutant adenoviral vector and recreate infectious replicating virus. Therefore, a novel cell line, devoid of adenoviral sequences, is provided herein to express the E1A and E1B gene products using a vector which does not allow reconstitution of functional adenovirus when the mutant viral vector is introduced.

The cell line may comprise a lentiviral vector engineered to express the E1A and E1B gene products, wherein the lentiviral vector inhibits reconstitution of functional adenovirus when a mutant adenoviral viral vector is introduced into the cell line. In some embodiments, the cell line may comprise HeLa cells. In some embodiments, the cell line is produced by transfecting HEK293 cells with a lentiviral genome plasmid comprising at least an E1A encoding sequence and an E1B-encoding sequence.

The plasmid further may comprise at least an E1A encoding sequence and an E1B-encoding sequence contains E1A and E1B sequences arranged in a bidirectional expression unit with a bidirectional promoter to prevent recombination with a mutant adenoviral vector. In some aspects of the cell line, the bidirectional promoter may be a combination of truncated CMV and PGK promoters.

Figure 8:
FIG. 8 is a schematic diagram of genomic organization of a vector used to produce lentivirus and HeLa cell lines transduced and selected for puromycin resistance.

The cell line further can include a puromycin drug resistance gene in the lentiviral genome sequence to differentiate cells which have integrated the lentiviral sequence when the puromycin drug resistance gene is expressed. In some embodiments, a final E1 cell creation vector of SEQ ID NO: 9 is used to produce lentivirus and HeLa cells, transduced and selected for puromycin resistance. FIG. 8 is a schematic diagram of genomic organization of a vector used to produce lentivirus and HeLa cell lines transduced and selected for puromycin resistance.

The polynucleotide sequence of SEQ ID NO: 9 does not include a plasmid backbone. SEQ ID NO: 10, however, encodes a full E1 cell creation vector with a plasmid backbone, as depicted in the schematic diagram of the plasmid genome in FIG. 10.

A method of producing and/or expanding the synthetic non-replicating adenoviral vector disclosed above is also provided herein. The method may include transforming a mammalian cell with an adenovirus vector comprising: a) one or more mutations that render the adenovirus replication incompetent and b) at least one nucleotide sequence encoding human IL-10, wherein the mammalian cell comprises nucleotide sequences expressing E1A and E1B gene products but is otherwise devoid of other adenovirus sequences, culturing the transformed mammalian cell in a cell line containing an inserted lentiviral E1A and E1B vector, and isolating the adenovirus vector.

Figure 9:
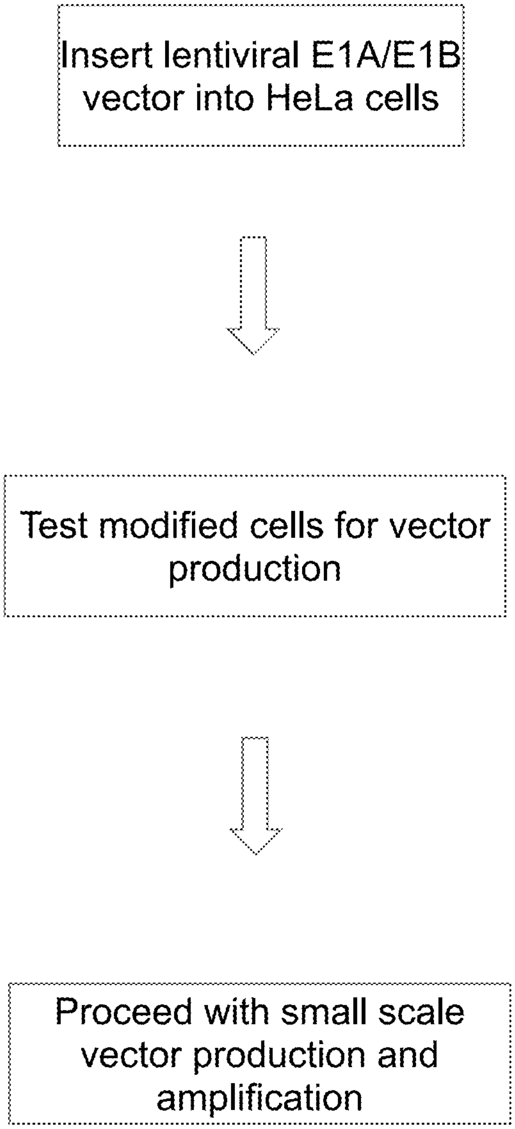
FIG. 9 is a flowchart of a disclosed production process of safe, replication incompetent adenoviral serotype 5 vectors.

In some embodiments, the engineered adenoviral serotype 5 vector of the disclosure is introduced into engineered cells in order to generate mutant adenovirus which expresses human IL-10. FIG. 9 is a flowchart, wherein it can be seen that in this mode of production a lentiviral E1A/E1B vector is first introduced into HeLa cells. The modified HeLa cell lines may then be tested for vector production to be sure there is no contamination of the cell line. Assuming there is no infection contamination or unexpected replication, one can then proceed with small scale vector production and amplification.

Together, the mutant adenoviral vector of the present disclosure and the associated production cell line allow for the expansion of non-infectious therapeutic agents expressing adenovirus without the risk of recombination and restoration of replication competence.

Potential applications may include, but are not limited to, adenoviral expression of human IL-10, which in turn can inhibit immune activity in autoimmune disorders as well as reduce rejection risk in allo-transplant or xenotransplant.

In a further aspect of the disclosure, a method of treating a subject in need of a gene product is also provided herein. In some embodiments, the method may comprise, consist essentially of, or further, consist of administering to the subject a vector comprising (a) one or more mutations that render the adenovirus replication incompetent and (b) at least one nucleotide sequence encoding the gene product. In some embodiments of the method, the vector comprises a nucleotide sequence having at least 80% sequence identity over the entire sequence of SEQ ID NO: 1 or SEQ ID NO: 2, or a complementary sequence thereto. In certain embodiments, the vector may be an adenovirus serotype 5 vector. Additionally or alternatively, the one or more mutations may be a deletion of either an E1 gene or an E3 gene or both. The at least one nucleotide sequence further may include a transgene. In some embodiments, the transgene expresses human IL10.

In some embodiments of the method, the subject may be a human. In certain embodiments, the gene product is a peptide, including human peptides. In some embodiments, the gene product can be RNA.

EXAMPLES

The following examples are to illustrate the invention. They are not meant to limit the invention in any way.

The practice of this invention may employ, unless otherwise indicated, conventional techniques of molecular biology, cell biology, and recombinant DNA, which are within the skill of the person skilled in the art (see, e.g., Green and Sambrook. *Molecular Cloning: A Laboratory Manuel,* 4th edition, 2012; Ausubel, et al. *Current Protocols in Molecular Biology,* 1987.

Example 1: Sequence of Engineered Adenovirus Serotype 5 Vector

Synthesis and description of an engineered adenovirus serotype 5 vector is described in Example 1. The adenovirus sequence used for synthesis was derived from public domain sources, notably sequence AY339865, available in GenBank. Two smaller fragments were generated using synthetic DNA methods to allow for higher efficiency cloning using bacterial hosts. The synthetic fragments were designed to include deletions of the E1 and E3 genes to prevent adenoviral replication in vivo. A transgene for expression of human IL-10 was included in the adenoviral sequence, which includes an enhancer/promoter region (CAG), human IL10 cDNA, and a polyadenylation signal (SV40, full poly A signal), which was inserted between nucleotides 440 and 3515 relative to Adenovirus sequence AY339865, which replaces the E1 gene, but leaves the pIX gene intact.

Example 2: Protocol for More Efficient Production of AdVector in Bacteria

Here, the construction of a plasmid-based system to generate recombinant sAd5 vectors and protocol for more production in bacteria is described. In a first step of an aspect of the disclosure, adenovirus 5 genome was synthesized as several overlapping DNA fragments. The overlapping DNA fragments were assembled into two linear sub-fragments, each bearing approximately one half of the full genome.

A first sub-fragment may include at least one sequence as set forth in SEQ ID NOs: 4-5. In some embodiments, a second sub-fragment may include at least one sequence as set forth in SEQ ID NOs: 6-7. FIG. 3 depicts a schematic diagram of the genomic organization of an exemplary first sub-fragment in linear form. FIG. 4 depicts a schematic diagram of the genomic organization of an exemplary second sub-fragment in linear form.

In a second step of the protocol, adenovirus serotype 5 genomic sub-fragments were circularized to form traditional plasmid structures to enable efficient replication in bacterial hosts.

FIG. 5 shows a schematic diagram of the genomic organization of an exemplary first sub-fragment in circularized form and FIG. 6 shows a schematic diagram of the genomic organization of an exemplary first second-fragment in circularized form.

In a third step of the protocol, the final adenovirus serotype 5 genome was assembled from the two circularized fragments, creating a linear structure for high level DNA replication in bacteria use in viral production. The high level of DNA replication and design allow for greater amounts of DNA to use for transfection and first round viral production. The final vector may comprise additive combination of the first sub-fragment and the second sub-fragment.

Creation of the DNA sequences encoding the Adenovirus 5 vector for replication at high efficiency in bacteria allows for better initial vector creation. Vector sequences to allow for high efficiency bacterial replication can include pJazz-OK from Lucigen Catalog No. 43036. pJazz-OK allows for less DNA loss due to replication stress and much more convenient cloning. See, e.g., *Lucigen BigEasy® v2.0 Linear Cloning Kits* training manual. The sequence also may include human IL10 complementary DNA sequences, as a non-limiting example. The human IL-10 cDNA sequence may be sequence codon optimized from NM_00572.3 using the codon optimization tool in Geneious version 9.0, as disclosed in SEQ ID NO: 8.

Other adenoviral genome sequence listings may be derived from public sources.

Example 3: Creation of Engineered Mammalian Cell Line for Replication of the Engineered Adenoviral Vector Here, the creation of an engineered mammalian cell line for replication of the engineered adenoviral vector to eliminate possible contamination of the replication competent adenovirus is described. Described above, the adenoviral vector was mutated to remove the viral E1 and E3 genes in order to prevent the virus from replicating and thus being infectious. Mammalian cells supplied with the two E1 gene products, E1A and E1B, can support replication of the mutant virus. A common mammalian cell line used to produce adenovirus, HEK293, possesses an endogenous copy of the adenoviral E1 gene, which can recombine with mutant adenoviral vectors and recreate infectious replicating virus. Thus, a novel cell line devoid of adenoviral sequences is engineered here to express the E1A and E1B gene products using a lentiviral vector which does not allow reconstitution of functional adenovirus when the mutant adenoviral vector is introduced.

The adenoviral E1 gene products, E1A and E1B, were inserted into a plasmid backbone comprising the backbone viral elements and Puromycin resistance from Systems Biosciences Catalog Number CD510B-1 and the bidirectional promoter from ABM Catalog Number LV039. The bidirectional promoter was situated such that the E1A and E1B were in different orientations and driven by separate parts of the promoter element.

The lentiviral genome plasmid and accessory plasmids from CellBioLabs Catalog Number VPK-206 were transfected into HEK293T (ATCC Catalog Number CRL-3216) cells to create a lentiviral vector. The E1A and E1B sequences were arranged in a bidirectional expression unit, to prevent recombination with the mutant adenoviral vector created in Examples 1 and 2, discussed above. The bidirectional promoter is a combination of truncated CMV and PGK promoters. A puromycin drug resistance gene is included in the lentiviral sequence to allow selection of cells which have integrated the lentiviral sequence. The final vector is diagrammed and mapped in FIG. 8, and was used to produce lentivirus, and HeLa cells (ATCC Catalog Number CCL2) transduced and selected for puromycin resistance.

Figure 10:
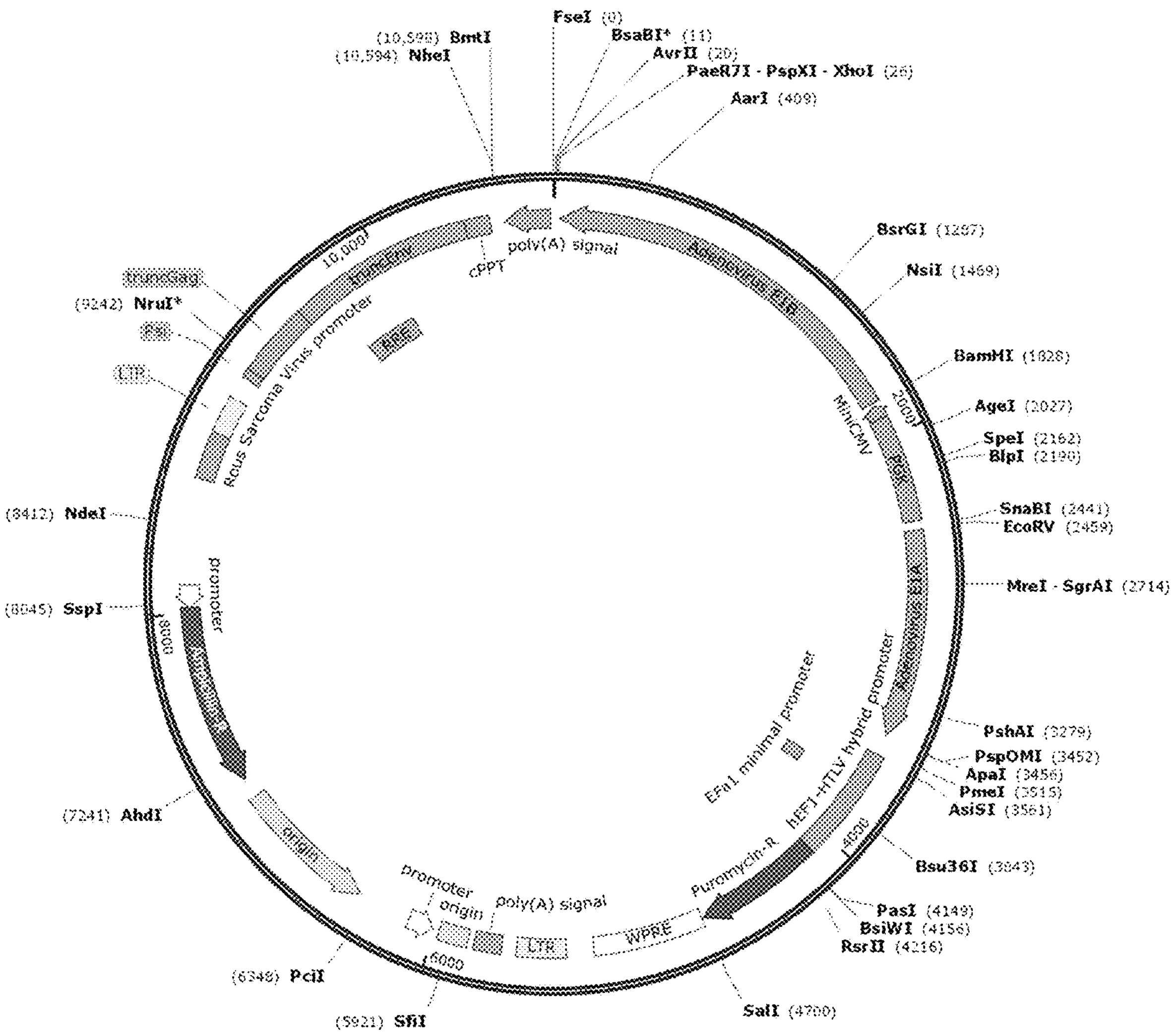
FIG. 10 shows a schematic diagram of the full E1 cell creation vector with a plasmid backbone.

The vector described in Examples 1 and 2 was introduced into the cells created in this Example 3 in order to generate mutant adenovirus capable of expressing human IL-10. FIG. 9 is a brief flowchart of the process of this Example. As illustrated, the lentiviral E1A/E1B vector is inserted into the HeLa cells. The modified cells are then tested for vector production. Finally, a user may proceed with vector production and amplification of the cell line. SEQ ID NO: 9 SEQ encodes the full E1 cell creation vector without the plasmid backbone. SEQ ID NO: 10 encodes the full E1 cell creation vector and includes the plasmid backbone. FIG. 10 shows a schematic diagram of the full E1 cell creation vector with the plasmid backbone.

In summary, a method of producing a vector as in Examples 1 and 2 is disclosed herein. The method may include transforming a mammalian cell with an adenovirus vector comprising: a) one or more mutations that render the adenovirus replication incompetent and b) at least one nucleotide sequence encoding a transgene, wherein the mammalian cell comprises nucleotide sequences expressing E1A and E1B gene products but is otherwise devoid of other adenovirus sequences, culturing the transformed mammalian cell in a cell line containing an inserted lentiviral E1A and E1B vector, and isolating the adenovirus vector.

One advantage of the methods, vectors, and cell lines described above is that the mutant adenoviral vector and associated production cells allow the production of non-infectious human IL-10 expressing adenovirus without the risk of recombination and restoration of replication competence. A potential application of the disclosed vectors, methods, and cells include adenoviral expression of human IL-10 to inhibit immune activity in autoimmune disorders. The aspects of the disclosure may also be used to reduce rejection risk in allotransplant and xerotransplant procedures.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

TABLE 1

| SEQUENCE LISTINGS |
|---|
| Adenovector no plasmid backbone |
| (SEQ ID NO: 1) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccactagttattaatagtaatcaattacggggtcattagttcatagcccatatatggagttccgc |
| gttacataacttacggtaaatggcccgcctggctgaccgcccaacgacccccgcccattgacgtcaataatgacgtatgttcccatagta |
| acgccaatagggactttccattgacgtcaatgggtggagtatttacggtaaactgcccacttggcagtacatcaagtgtatcatatgccaa |
| gtacgccccctattgacgtcaatgacggtaaatggcccgcctggcattatgcccagtacatgaccttatgggactttcctacttggcagtac |
| atctacgtattagtcatcgctattaccatggtcgaggtgagccccacgttctgcttcactctccccatctcccccccctccccacccccaatt |
| ttgtatttatttattttttaattattttgtgcagcgatgggggcgggggggggggggggggggggccaggcggggcggggggggcgag |
| gggcgggggggggcgaggcggagaggtgcggcggcagccaatcagagcggcgcgctccgaaagtttccttttatggcgaggcgg |
| cggcggcggcggccctataaaaagcgaagcgcgcggggggggagtcgctgcgttgccttcgccccgtgccccgctccgcgccg |
| cctcgcgccgcccgccccggctctgactgaccgcgttactcccacaggtgagcgggggggacggcccttctcctccgggctgtaatta |
| gcgcttggtttaatgacggctcgtttcttttctgtggctgcgtgaaagccttaaagggctccgggagggccctttgtgcgggggggagcg |
| gctcggggggtgcgtgcgtgtgtgtgtgcgtggggagcgccgcgtgcggctccgcgctgcccggcggctgtgagcgctgcgggcg |
| cggcgcggggctttgtgcgctccgcagtgtgcgcgaggggagcgcggccgggggcggtgccccgcggtgcgggggggggctgcg |
| aggggaacaaaggctgcgtgcggggtgtgtgcgtgggggggtgagcagggggtgtgggcgcgtcggtcgggctgcaacccccccct |
| gcacccccctccccgagttgctgagcacggcccggcttcgggtgcggggctccgtacggggcgtggcgcggggctcgccgtgccg |
| ggcggggggtggcggcaggtgggggtgccgggcggggcggggccgcctcgggccggggagggctcgggggaggggcgcgg |
| cggcccccggagcgccggcggctgtcgaggcgcggcgagccgcagccattgccttttatggtaatcgtgcgagagggcgcaggga |
| cttcctttgtcccaaatctgtgcggagccgaaatctgggaggcgccgccgcaccccctctagcgggcgcggggcgaagcggtgcggc |
| gccggcaggaaggaaatgggcggggagggccttcgtgcgtcgccgcgccgccgtccccttctccctctccagcctcggggctgtcc |
| gcggggggacggctgccttcgggggggacggggcagggcggggttcggcttctggcgtgtgaccggcggctctagagcctctgcta |
| accatgttcatgccttcttctttttcctacagctcctgggcaacgtgctggttattgtgctgtctcatcattttggcaaagaattccgctgcgact |
| cggcggagtcccggcggcgcgtccttgttctaacccggcgcgccagcttggcaatccggtactgttggtaaagccaccatgcatagttc |
| tgccctgttgtgttgcttggtgctgttgacgggggttagagcgagtccaggtcaaggcacgcagtctgaaaactcctgtacacacttcccc |
| ggcaacctccctaatatgctcagagaccttcgagacgccttctcccgagtaaaaactttctttcagatgaaggaccagctcgacaacttgc |
| tgttgaaggaatcactcctcgaagattttaaggggtacctcggttgtcaagctctgtctgaaatgatacaattctatctcgaggaagtcatgc |
| ctcaagcggaaaaccaggacccagatattaaggcccatgtgaatagcctcggcgaaaatcttaaaactcttcgccttagactccgaagat |

TABLE 1 -continued

| SEQUENCE LISTINGS |
|---|
| gccataggtttttgccgtgcgaaaataaatccaaagctgtggaacaggtaaaaaatgcgtttaacaagttgcaagagaagggcatctaca |
| aagcgatgtcagagttcgatatattcataaattatattgaagcatacatgactatgaagatcaggaattaataattctagagtcggggcggc |
| cggccgcttcgagcagacatgataagatacattgatgagtttggacaaaccacaactagaatgcagtgaaaaaaatgctttatttgtgaaa |
| tttgtgatgctattgctttatttgtaaccattataagctgcaataaacaagttaacaacaacaattgcattcattttatgtttcaggttcagggga |
| ggtgtgggaggttttttaaagcaagtaaaacctctacaaatgtggtaaaatcgataaggatccgaattcgatatcactagtggtaccagtac |
| tgaaatgtgtgggcgtggcttaagggtgggaaagaatatataaggtgggggtcttatgtagttttgtatctgttttgcagcagccgccgccg |
| ccatgagcaccaactcgtttgatggaagcattgtgagctcatatttgacaacgcgcatgcccccatgggccggggtgcgtcagaatgtg |
| atgggctccagcattgatggtcgccccgtcctgcccgcaaactctactaccttgacctacgagaccgtgtctggaacgccgttggagact |
| gcagcctccgccgccgcttcagccgctgcagccaccgcccgcgggattgtgactgactttgctttcctgagcccgcttgcaagcagtgc |
| agcttcccgttcatccgcccgcgatgacaagttgacggctcttttggcacaattggattctttgacccgggaacttaatgtcgtttctcagca |
| gctgttggatctgcgccagcaggtttctgccctgaaggcttcctcccctcccaatgcggtttaacggtccgggccagagtggccaacata |
| aataaaaaaccagactctgtttggatttggatcaagcaagtgtcttgctgtctttatttaggggttttgcgcgcgcggtaggcccgggacca |
| gcggtctcggtcgttgagggtcctgtgtattttttccaggacgtggtaaaggtgactctggatgttcagatacatgggcataagcccgtctc |
| tggggtggaggtagcaccactgcagagcttcatgctgcggggtggtgttgtagatgatccagtcgtagcaggagcgctgggcgtggtg |
| cctaaaaatgtctttcagtagcaagctgattgccaggggcaggcccttggtgtaagtgtttacaaagcggttaagctgggatgggtgcata |
| cgtggggatatgagatgcatcttggactgtatttttaggttggctatgttcccagccatatccctccggggattcatgttgtgcagaaccacc |
| agcacagtgtatccggtgcacttgggaaatttgtcatgtagcttagaaggaaatgcgtggaagaacttggagacgcccttgtgacctcca |
| agattttccatgcattcgtccataatgatggcaatgggcccacgggcggcggcctgggcgaagatatttctgggatcactaacgtcatagt |
| tgtgttccaggatgagatcgtcataggccatttttacaaagcgcgggcggagggtgccagactgcggtataatggttccatccggccca |
| ggggcgtagttaccctcacagatttgcatttcccacgctttgagttcagatgggggatcatgtctacctgcggggcgatgaagaaaacg |
| gtttccggggtaggggagatcagctgggaagaaagcaggttcctgagcagctgcgacttaccgcagccggtgggcccgtaaatcaca |
| cctattaccggctgcaactggtagttaagagagctgcagctgccgtcatccctgagcaggggggccacttcgttaagcatgtccctgact |
| cgcatgttttccctgaccaaatccgccagaaggcgctcgccgcccagcgatagcagttcttgcaaggaagcaaagtttttcaacggtttg |
| agaccgtccgccgtaggcatgcttttgagcgtttgaccaagcagttccaggcggtcccacagctcggtcacctgctctacggcatctcga |
| tccagcatatctcctcgtttcgcgggttggggcggctttcgctgtacggcagtagtcggtgctcgtccagacgggccagggtcatgtcttt |
| ccacgggcgcagggtcctcgtcagcgtagtctgggtcacggtgaaggggtgcgctccgggctgcgcgctggccagggtgcgcttga |
| ggctggtcctgctggtgctgaagcgctgccggtcttcgccctgcgcgtcggccaggtagcatttgaccatggtgtcatagtccagcccct |
| ccgcggcgtggcccttggcgcgcagcttgcccttggaggaggcgccgcacgaggggcagtgcagacttttgagggcgtagagcttg |
| ggcgcgagaaataccgattccggggagtaggcatccgcgccgcaggccccgcagacggtctcgcattccacgagccaggtgagctc |
| tggccgttcggggtcaaaaaccaggtttcccccatgcttttttgatgcgtttcttacctctggtttccatgagccggtgtccacgctcggtgac |
| gaaaaggctgtccgtgtccccgtatacagacttgagaggcctgtcctcgagcggtgttccgcggtcctcctcgtatagaaactcggacca |
| ctctgagacaaaggctcgcgtccaggccagcacgaaggaggctaagtgggaggggtagcggtcgttgtccactagggggtccactc |
| gctccagggtgtgaagacacatgtcgccctcttcggcatcaaggaaggtgattggtttgtaggtgtaggccacgtgaccgggtgttcctg |
| aaggggggctataaaaggggggtgggggcgcgttcgtcctcactctcttccgcatcgctgtctgcgagggccagctgttggggtgagta |
| ctccctctgaaaagcgggcatgacttctgcgctaagattgtcagtttccaaaaacgaggaggatttgatattcacctggcccgcggtgatg |
| cctttgagggtggccgcatccatctggtcagaaaagacaatctttttgttgtcaagcttggtggcaaacgacccgtagagggcgttggac |
| agcaacttggcgatggagcgcagggtttggtttttgtcgcgatcggcgcgctccttggccgcgatgtttagctgcacgtattcgcgcgca |
| acgcaccgccattcgggaaagacggtggtgcgctcgtcgggcaccaggtgcacgcgccaaccgcggttgtgcagggtgacaaggtc |
| aacgctggtggctacctctccgcgtaggcgctcgttggtccagcagaggcggccgcccttgcgcgagcagaatggcggtagggggtc |

TABLE 1 -continued

| SEQUENCE LISTINGS |
|---|
| tagctgcgtctcgtccggggggtctgcgtccacggtaaagaccccgggcagcaggcgcgcgtcgaagtagtctatcttgcatccttgca |
| agtctagcgcctgctgccatgcgcgggcggcaagcgcgcgctcgtatgggttgagtgggggaccccatggcatggggtgggtgagc |
| gcggaggcgtacatgccgcaaatgtcgtaaacgtagaggggctctctgagtattccaagatatgtagggtagcatcttccaccgcggat |
| gctggcgcgcacgtaatcgtatagttcgtgcgagggagcgaggaggtcgggaccgaggttgctacgggcgggctgctctgctcggaa |
| gactatctgcctgaagatggcatgtgagttggatgatatggttggacgctggaagacgttgaagctggcgtctgtgagacctaccgcgtc |
| acgcacgaaggaggcgtaggagtcgcgcagcttgttgaccagctcggcggtgacctgcacgtctagggcgcagtagtccagggtttc |
| cttgatgatgtcatacttatcctgtcccttttttttccacagctcgcggttgaggacaaactcttcgcggtctttccagtactcttggatcggaaa |
| cccgtcggcctccgaacggtaagagcctagcatgtagaactggttgacggcctggtaggcgcagcatcccttttctacgggtagcgcgt |
| atgcctgcgcggccttccggagcgaggtgtgggtgagcgcaaaggtgtccctgaccatgactttgaggtactggtatttgaagtcagtgt |
| cgtcgcatccgccctgctcccagagcaaaaagtccgtgcgctttttggaacgcggatttggcagggcgaaggtgacatcgttgaagagt |
| atctttcccgcgcgaggcataaagttgcgtgtgatgcggaagggtcccggcacctcggaacggttgttaattacctgggcggcgagcac |
| gatctcgtcaaagccgttgatgttgtggcccacaatgtaaagttccaagaagcgcgggatgcccttgatggaaggcaatttttaagttcct |
| cgtaggtgagctcttcaggggagctgagcccgtgctctgaaagggcccagtctgcaagatgagggttggaagcgacgaatgagctcc |
| acaggtcacgggccattagcatttgcaggtggtcgcgaaaggtcctaaactggcgacctatggccattttttctggggtgatgcagtaga |
| aggtaagcgggtcttgttcccagcggtcccatccaaggttcgcggctaggtctcgcgcggcagtcactagaggctcatctccgccgaac |
| ttcatgaccagcatgaagggcacgagctgcttcccaaaggcccccatccaagtataggtctctacatcgtaggtgacaaagagacgctc |
| ggtgcgaggatgcgagccgatcgggaagaactggatctcccgccaccaattggaggagtggctattgatgtggtgaaagtagaagtcc |
| ctgcgacgggccgaacactcgtgctggcttttgtaaaaacgtgcgcagtactggcagcggtgcacgggctgtacatcctgcacgaggtt |
| gacctgacgaccgcgcacaaggaagcagagtgggaatttgagcccctcgcctggcgggtttggctggtggtcttctacttcggctgctt |
| gtccttgaccgtctggctgctcgaggggagttacggtggatcggaccaccacgccgcgcgagcccaaagtccagatgtccgcgcgcg |
| gcggtcggagcttgatgacaacatcgcgcagatgggagctgtccatggtctggagctcccgcggcgtcaggtcaggcgggagctcct |
| gcaggtttacctcgcatagacgggtcagggcgcgggctagatccaggtgatacctaatttccaggggctggttggtggcggcgtcgat |
| ggcttgcaagaggccgcatccccgcggcgcgactacggtaccgcgcggcgggcggtgggccgcgggggtgtccttggatgatgca |
| tctaaaagcggtgacgcgggcgagcccccggaggtagggggggctccggacccgccgggagagggggcaggggcacgtcggc |
| gccgcgcgcgggcaggagctggtgctgcgcgcgtaggttgctggcgaacgcgacgacgcggcggttgatctcctgaatctggcgcc |
| tctgcgtgaagacgacgggcccggtgagcttgaacctgaaagagagttcgacagaatcaatttcggtgtcgttgacggcggcctggcg |
| caaaatctcctgcacgtctcctgagttgtcttgataggcgatctcggccatgaactgctcgatctcttcctcctggagatctccgcgtccgg |
| ctcgctccacggtggcggcgaggtcgttggaaatgcgggccatgagctgcgagaaggcgttgaggcctccctcgttccagacgcggc |
| tgtagaccacgccccttcggcatcgcgggcgcgcatgaccacctgcgcgagattgagctccacgtgccgggcgaagacggcgtag |
| tttcgcaggcgctgaaagaggtagttgagggtggtggcggtgtgttctgccacgaagaagtacataacccagcgtcgcaacgtggattc |
| gttgatatcccccaaggcctcaaggcgctccatggcctcgtagaagtccacggcgaagttgaaaaactgggagttgcgcgccgacacg |
| gttaactcctcctccagaagacggatgagctcggcgacagtgtcgcgcacctcgcgctcaaaggctacaggggcctcttcttcttcttca |
| atctcctcttccataagggcctccccttcttcttcttctggcggcggtgggggagggggggacacggcggcgacgacggcgcaccggga |
| ggcggtcgacaaagcgctcgatcatctccccgcggcgacggcgcatggtctcggtgacggcgcggccgttctcgcgggggcgcagt |
| tggaagacgccgcccgtcatgtcccggttatgggttggcgggggggctgccatgcggcagggatacggcgctaacgatgcatctcaac |
| aattgttgtgtaggtactccgccgccgagggacctgagcgagtccgcatcgaccggatcggaaaacctctcgagaaaggcgtctaacc |
| agtcacagtcgcaaggtaggctgagcaccgtggcgggcggcagcgggcggcggtcggggttgtttctggcggaggtgctgctgatg |
| atgtaattaaagtaggcggtcttgagacggcggatggtcgacagaagcaccatgtccttgggtccggcctgctgaatgcgcaggcggt |
| cggccatgccccaggcttcgttttgacatcggcgcaggtctttgtagtagtcttgcatgagcctttctaccggcacttcttcttctccttcctct |

TABLE 1 -continued

| SEQUENCE LISTINGS |
|---|
| tgtcctgcatctcttgcatctatcgctgcggcggcggcggagtttggccgtaggtggcgccctcttcctcccatgcgtgtgaccccgaag |
| cccctcatcggctgaagcagggctaggtcggcgacaacgcgctcggctaatatggcctgctgcacctgcgtgagggtagactggaag |
| tcatccatgtccacaaagcggtggtatgcgcccgtgttgatggtgtaagtgcagttggccataacggaccagttaacggtctggtgaccc |
| ggctgcgagagctcggtgtacctgagacgcgagtaagccctcgagtcaaatacgtagtcgttgcaagtccgcaccaggtactggtatcc |
| caccaaaaagtgcggcggcggctggcggtagaggggccagcgtagggtggccggggctccgggggcgagatcttccaacataag |
| gcgatgatatccgtagatgtacctggacatccaggtgatgccggcggcggtggtggaggcgcgcggaaagtcgcggacgcggttcc |
| agatgttgcgcagcggcaaaaagtgctccatggtcgggacgctctggccggtcaggcgcgcgcaatcgttgacgctctagaccgtgc |
| aaaaggagagcctgtaagcgggcactcttccgtggtctggtggataaattcgcaagggtatcatggcggacgaccggggttcgagccc |
| cgtatccggccgtccgccgtgatccatgcggttaccgcccgcgtgtcgaacccaggtgtgcgacgtcagacaacgggggagtgctcct |
| tttggcttccttccaggcgcggcggctgctgcgctagctttttggccactggccgcgcgcagcgtaagcggttaggctggaaagcgaa |
| agcattaagtggctcgctccctgtagccggagggttattttccaagggttgagtcgcgggacccccggttcgagtctcggaccggccgg |
| actgcggcgaacgggggtttgcctccccgtcatgcaagaccccgcttgcaaattcctccggaaacagggacgagcccctttttttgcttttc |
| ccagatgcatccggtgctgcggcagatgcgcccccctcctcagcagcggcaagagcaagagcagcggcagacatgcagggcaccc |
| tcccctcctcctaccgcgtcaggaggggcgacatccgcggttgacgcggcagcagatggtgattacgaacccccgcggcgccgggc |
| ccggcactacctggacttggaggagggcgagggcctggcgcggctaggagcgccctctcctgagcggcacccaagggtgcagctg |
| aagcgtgatacgcgtgaggcgtacgtgccgcggcagaacctgtttcgcgaccgcgagggagaggagcccgaggagatgcgggatc |
| gaaagttccacgcagggcgcgagctgcggcatggcctgaatcgcgagcggttgctgcgcgaggaggactttgagcccgacgcgcg |
| aaccgggattagtcccgcgcgcgcacacgtggcggccgccgacctggtaaccgcatacgagcagacggtgaaccaggagattaact |
| ttcaaaaaagctttaacaaccacgtgcgtacgcttgtggcgcgcgaggaggtggctataggactgatgcatctgtgggactttgtaagcg |
| cgctggagcaaaacccaaatagcaagccgctcatggcgcagctgttccttatagtgcagcacagcagggacaacgaggcattcaggg |
| atgcgctgctaaacatagtagagcccgagggccgctggctgctcgatttgataaacatcctgcagagcatagtggtgcaggagcgcag |
| cttgagcctggctgacaaggtggccgccatcaactattccatgcttagcctgggcaagttttacgcccgcaagatataccataccccttac |
| gttcccatagacaaggaggtaaagatcgaggggttctacatgcgcatggcgctgaaggtgcttaccttgagcgacgacctgggcgttta |
| tcgcaacgagcgcatccacaaggccgtgagcgtgagccggggcgcgagctcagcgaccgcgagctgatgcacagcctgcaaag |
| ggccctggctggcacgggcagcggcgatagagaggccgagtcctactttgacgcgggcgctgacctgcgctgggccccaagccga |
| cgcgccctggaggcagctggggccggacctgggctggcggtggcacccgcgcgcgctggcaacgtcggcggcgtggaggaatat |
| gacgaggacgatgagtacgagccagaggacggcgagtactaagcggtgatgtttctgatcagatgatgcaagacgcaacggacccg |
| gcggtgcgggcggcgctgcagagccagccgtccggccttaactccacggacgactggcgccaggtcatggaccgcatcatgtcgct |
| gactgcgcgcaatcctgacgcgttccggcagcagccgcaggccaaccggctctccgcaattctggaagcggtggtcccggcgcgcg |
| caaaccccacgcacgagaaggtgctggcgatcgtaaacgcgctggccgaaaacagggccatccggcccgacgaggccggcctggt |
| ctacgacgcgctgcttcagcgcgtggctcgttacaacagcggcaacgtgcagaccaacctggaccggctggtgggggatgtgcgcga |
| ggccgtggcgcagcgtgagcgcgcgcagcagcagggcaacctgggctccatggttgcactaaacgccttcctgagtacacagcccg |
| ccaacgtgccgcggggacaggaggactacaccaactttgtgagcgcactgcggctaatggtgactgagacaccgcaaagtgaggtgt |
| accagtctgggccagactatttttttccagaccagtagacaaggcctgcagaccgtaaacctgagccaggctttcaaaaacttgcagggg |
| ctgtgggggtgcgggctcccacaggcgaccgcgcgaccgtgtctagcttgctgacgcccaactcgcgcctgttgctgctgctaatag |
| cgcccttcacggacagtggcagcgtgtcccgggacacatacctaggtcacttgctgacactgtaccgcgaggccataggtcaggcgca |
| tgtggacgagcatactttccaggagattacaagtgtcagccgcgcgctggggcaggaggacacgggcagcctggaggcaaccctaa |
| actacctgctgaccaaccggcggcagaagatcccctcgttgcacagtttaaacagcgaggaggagcgcattttgcgctacgtgcagca |
| gagcgtgagccttaacctgatgcgcgacggggtaacgcccagcgtggcgctggacatgaccgcgcgcaacatggaaccgggcatgt |

TABLE 1 -continued

| SEQUENCE LISTINGS |
|---|
| atgcctcaaaccggccgtttatcaaccgcctaatggactacttgcatcgcgcggccgccgtgaaccccgagtatttcaccaatgccatctt |
| gaacccgcactggctaccgccccctggtttctacaccggggggattcgaggtgcccgagggtaacgatggattcctctgggacgacata |
| gacgacagcgtgttttccccgcaaccgcagaccctgctagagttgcaacagcgcgagcaggcagaggcggcgctgcgaaaggaaa |
| gcttccgcaggccaagcagcttgtccgatctaggcgctgcggccccgcggtcagatgctagtagcccatttccaagcttgatagggtct |
| cttaccagcactcgcaccacccgcccgcgcctgctgggcgaggaggagtacctaaacaactcgctgctgcagccgcagcgcgaaaa |
| aaacctgcctccggcatttcccaacaacgggatagagagcctagtggacaagatgagtagatggaagacgtacgcgcaggagcaca |
| gggacgtgccaggcccgcgcccgcccacccgtcgtcaaaggcacgaccgtcagcggggtctggtgtgggaggacgatgactcggc |
| agacgacagcagcgtcctggatttgggagggagtggcaacccgtttgcgcaccttcgccccaggctggggagaatgttttaaaaaaaa |
| aaaaaagcatgatgcaaaataaaaaactcaccaaggccatggcaccgagcgttggttttcttgtattccccttagtatgcggcgcgcggc |
| gatgtatgaggaaggtcctcctccctcctacgagagtgtggtgagcgcggcgccagtggcggcggcgctgggttctcccttcgatgctc |
| ccctggacccgccgtttgtgcctccgcggtacctgcggcctaccggggggagaaacagcatccgttactctgagttggcacccctattc |
| gacaccacccgtgtgtacctggtggacaacaagtcaacggatgtggcatccctgaactaccagaacgaccacagcaactttctgacca |
| cggtcattcaaaacaatgactacagcccgggggaggcaagcacacagaccatcaatcttgacgaccggtcgcactggggcggcgac |
| ctgaaaaccatcctgcataccaacatgccaaatgtgaacgagttcatgtttaccaataagtttaaggcgcgggtgatggtgtcgcgcttgc |
| ctactaaggacaatcaggtggagctgaaatacgagtgggtggagttcacgctgcccgagggcaactactccgagaccatgaccataga |
| ccttatgaacaacgcgatcgtggagcactacttgaaagtgggcagacagaacggggttctggaaagcgacatcggggtaaagtttgac |
| acccgcaacttcagactggggtttgaccccgtcactggtcttgtcatgcctggggtatatacaaacgaagccttccatccagacatcatttt |
| gctgccaggatgcggggggacttcacccacagccgcctgagcaacttgttgggcatccgcaagcggcaacccttccaggagggcttt |
| aggatcacctacgatgatctggagggtggtaacattcccgcactgttggatgtggacgcctaccaggcgagcttgaaagatgacaccga |
| acagggcgggggtggcgcaggcggcagcaacagcagtggcagcggcgcggaagagaactccaacgcggcagccgcggcaatg |
| cagccggtggaggacatgaacgatcatgccattcgcggcgacacctttgccacacgggctgaggagaagcgcgctgaggccgaagc |
| agcggccgaagctgccgcccccgctgcgcaacccgaggtcgagaagcctcagaagaaaccggtgatcaaacccctgacagaggac |
| agcaagaaacgcagttacaacctaataagcaatgacagcaccttcacccagtaccgcagctggtaccttgcatacaactacggcgacc |
| ctcagaccggaatccgctcatggaccctgctttgcactcctgacgtaacctgcggctcggagcaggtctactggtcgttgccagacatga |
| tgcaagaccccgtgaccttccgctccacgcgccagatcagcaactttccggtggtgggcgccgagctgttgcccgtgcactccaagag |
| cttctacaacgaccaggccgtctactcccaactcatccgccagtttacctctctgacccacgtgttcaatcgctttcccgagaaccagatttt |
| ggcgcgcccgccagcccccaccatcaccaccgtcagtgaaaacgttcctgctctcacagatcacgggacgctaccgctgcgcaacag |
| catcggaggagtccagcgagtgaccattactgacgccagacgccgcacctgcccctacgtttacaaggccctgggcatagtctcgccg |
| cgcgtcctatcgagccgcactttttgagcaagcatgtccatccttatatcgcccagcaataacacaggctggggcctgcgcttcccaagc |
| aagatgtttggcggggccaagaagcgctccgaccaacacccagtgcgcgtgcgcgggcactaccgcgcgccctggggcgcgcaca |
| aacgcggccgcactgggcgcaccaccgtcgatgacgccatcgacgcggtggtggaggaggcgcgcaactacacgcccacgccgc |
| caccagtgtccacagtggacgcggccattcagaccgtggtgcgcggagcccggcgctatgctaaaatgaagagacggcggaggcg |
| cgtagcacgtcgccaccgccgccgacccggcactgccgcccaacgcgcggcggcggccctgcttaaccgcgcacgtcgcaccggc |
| cgacgggcggccatgcgagcagctcgaaggctggccgcgggtattgtcactgtgccccccaggtccaggcgacgagcggccgccg |
| cagcagccgcggccattagtgctatgactcagggtcgcaggggcaacgtgtattgggtgcgcgactcggttagcggcctgcgcgtgc |
| ccgtgcgcacccgcccccccgcgcaactagattgcaagaaaaaactacttagactcgtactgttgtatgtatccagcggcggcggcgcg |
| caacgaagctatgtccaagcgcaaaatcaaagaagagatgctccaggtcatcgcgccggagatctatggcccccccgaagaaggaag |
| agcaggattacaagccccgaaagctaaagcgggtcaaaaagaaaaagaaagatgatgatgatgaacttgacgacgaggtggaactgc |
| tgcacgctaccgcgcccaggcgacgggtacagtggaaaggtcgacgcgtaaaacgtgttttgcgacccggcaccaccgtagtctttac |

TABLE 1 -continued

| SEQUENCE LISTINGS |
|---|
| gcccggtgagcgctccacccgcacctacaagcgcgtgtatgatgaggtgtacggcgacgaggacctgcttgagcaggccaacgagc |
| gcctcggggagtttgcctacggaaagcggcataaggacatgctggcgttgccgctggacgagggcaacccaacacctagcctaaagc |
| ccgtaacactgcagcaggtgctgcccgcgcttgcaccgtccgaagaaaagcgcggcctaaagcgcgagtctggtgacttggcaccca |
| ccgtgcagctgatggtacccaagcgccagcgactggaagatgtcttggaaaaaatgaccgtggaacctgggctggagcccgaggtcc |
| gcgtgcggccaatcaagcaggtggcgccgggactgggcgtgcagaccgtggacgttcagatacccactaccagtagcaccagtattg |
| ccaccgccacagagggcatggagacacaaacgtccccggttgcctcagcggtggcggatgccgcggtgcaggcggtcgctgcggc |
| cgcgtccaagacctctacggaggtgcaaacggacccgtggatgtttcgcgtttcagccccccggcgcccgcgccgttcgaggaagta |
| cggcgccgccagcgcgctactgcccgaatatgccctacatccttccattgcgcctacccccggctatcgtggctacacctaccgcccca |
| gaagacgagcaactacccgacgccgaaccaccactggaacccgccgccgccgtcgccgtcgccagcccgtgctggccccgatttcc |
| gtgcgcagggtggctcgcgaaggaggcaggaccctggtgctgccaacagcgcgctaccaccccagcatcgtttaaaagccggtcttt |
| gtggttcttgcagatatggccctcacctgccgcctccgtttcccggtgccgggattccgaggaagaatgcaccgtaggaggggcatggc |
| cggccacggcctgacgggcggcatgcgtcgtgcgcaccaccggcggcggcgcgcgtcgcaccgtcgcatgcgcggcggtatcctg |
| cccctccttattccactgatcgccgcggcgattggcgccgtgcccggaattgcatccgtggccttgcaggcgcagagacactgattaaa |
| aacaagttgcatgtggaaaaatcaaaataaaaagtctggactctcacgctcgcttggtcctgtaactattttgtagaatggaagacatcaac |
| tttgcgtctctggccccgcgacacggctcgcgcccgttcatgggaaactggcaagatatcggcaccagcaatatgagcggtggcgcctt |
| cagctggggctcgctgtggagcggcattaaaaatttcggttccaccgttaagaactatggcagcaaggcctggaacagcagcacaggc |
| cagatgctgagggataagttgaaagagcaaaatttccaacaaaaggtggtagatggcctggcctctggcattagcggggtggtggacct |
| ggccaaccaggcagtgcaaaataagattaacagtaagcttgatccccgccctcccgtagaggagcctccaccggccgtggagacagt |
| gtctccagaggggcgtggcgaaaagcgtccgcgccccgacagggaagaaactctggtgacgcaaatagacgagcctccctcgtacg |
| aggaggcactaaagcaaggcctgcccaccacccgtcccatcgcgcccatggctaccggagtgctgggccagcacacacccgtaacg |
| ctggacctgcctcccccgccgacacccagcagaaacctgtgctgccaggcccgaccgccgttgttgtaacccgtcctagccgcgcgt |
| ccctgcgccgcgccgccagcggtccgcgatcgttgcggcccgtagccagtggcaactggcaaagcacactgaacagcatcgtgggt |
| ctgggggtgcaatccctgaagcgccgacgatgcttctgatagctaacgtgtcgtatgtgtgtcatgtatgcgtccatgtcgccgccagag |
| gagctgctgagccgccgcgcgcccgctttccaagatggctaccccttcgatgatgccgcagtggtcttacatgcacatctcgggccagg |
| acgcctcggagtacctgagccccgggctggtgcagtttgcccgcgccaccgagacgtacttcagcctgaataacaagtttagaaaccc |
| cacggtggcgcctacgcacgacgtgaccacagaccggtcccagcgtttgacgctgcggttcatccctgtggaccgtgaggatactgcg |
| tactcgtacaaggcgcggttcaccctagctgtgggtgataaccgtgtgctggacatggcttccacgtactttgacatccgcggcgtgctg |
| gacaggggccctacttttaagccctactctggcactgcctacaacgccctggctcccaagggtgccccaaatccttgcgaatgggatga |
| agctgctactgctcttgaaataaacctagaagaagaggacgatgacaacgaagacgaagtagacgagcaagctgagcagcaaaaaac |
| tcacgtatttgggcaggcgccttattctggtataaatattacaaaggagggtattcaaataggtgtcgaaggtcaaacacctaaatatgccg |
| ataaaacatttcaacctgaacctcaaataggagaatctcagtggtacgaaacagaaattaatcatgcagctgggagagtcctaaaaaaga |
| ctaccccaatgaaaccatgttacggttcatatgcaaaacccacaaatgaaaatggagggcaaggcattcttgtaaagcaacaaaatgga |
| aagctagaaagtcaagtggaaatgcaatttttctcaactactgaggcagccgcaggcaatggtgataacttgactcctaaagtggtattgt |
| acagtgaagatgtagatatagaaaccccagacactcatatttcttacatgcccactattaaggaaggtaactcacgagaactaatgggcca |
| acaatctatgcccaacaggcctaattacattgcttttagggacaattttattggtctaatgtattacaacagcacgggtaatatgggtgttctg |
| gcgggccaagcatcgcagttgaatgctgttgtagatttgcaagacagaaacacagagctttcataccagcttttgcttgattccattggtga |
| tagaaccaggtacttttctatgtggaatcaggctgttgacagctatgatccagatgttagaattattgaaaatcatggaactgaagatgaact |
| tccaaattactgctttccactgggaggtgtgattaatacagagactcttaccaaggtaaaacctaaaacaggtcaggaaaatggatggga |
| aaaagatgctacagaattttcagataaaaatgaaataagagttggaaataattttgccatggaaatcaatctaaatgccaacctgtggagaa |

TABLE 1 -continued

| SEQUENCE LISTINGS |
|---|
| atttcctgtactccaacatagcgctgtatttgcccgacaagctaaagtacagtccttccaacgtaaaaatttctgataacccaaacacctacg |
| actacatgaacaagcgagtggtggctcccgggctagtggactgctacattaaccttggagcacgctggtcccttgactatatggacaacg |
| tcaacccatttaaccaccaccgcaatgctggcctgcgctaccgctcaatgttgctgggcaatggtcgctatgtgcccttccacatccaggt |
| gcctcagaagttctttgccattaaaaacctccttctcctgccgggctcatacacctacgagtggaacttcaggaaggatgttaacatggttct |
| gcagagctccctaggaaatgacctaagggttgacggagccagcattaagtttgatagcatttgcctttacgccaccttcttccccatggcc |
| cacaacaccgcctccacgcttgaggccatgcttagaaacgacaccaacgaccagtcctttaacgactatctctccgccgccaacatgct |
| ctaccctatacccgccaacgctaccaacgtgcccatatccatcccctcccgcaactgggggctttccgcggctgggccttcacgcgcc |
| ttaagactaaggaaaccccatcactgggctcgggctacgacccttattacacctactctggctctataccctacctagatggaacctttac |
| ctcaaccacacctttaagaaggtggccattacctttgactcttctgtcagctggcctggcaatgaccgcctgcttacccccaacgagtttga |
| aattaagcgctcagttgacggggagggttacaacgttgcccagtgtaacatgaccaaagactggttcctggtacaaatgctagctaactat |
| aacattggctaccagggcttctatatcccagagagctacaaggaccgcatgtactccttctttagaaacttccagcccatgagccgtcagg |
| tggtggatgatactaaatacaaggactaccaacaggtgggcatcctacaccaacacaacaactctggatttgttggctaccttgcccccca |
| ccatgcgcgaaggacaggcctaccctgctaacttcccctatccgcttataggcaagaccgcagttgacagcattacccagaaaaagtttc |
| tttgcgatcgcaccctttggcgcatcccattctccagtaactttatgtccatgggcgcactcacagacctgggccaaaaccttctctacgcc |
| aactccgcccacgcgctagacatgacttttgaggtggatcccatggacgagcccacccttctttatgttttgtttgaagtctttgacgtggtc |
| cgtgtgcaccagccgcaccgcggcgtcatcgaaaccgtgtacctgcgcacgcccttctcggccggcaacgccacaacataaagaagc |
| aagcaacatcaacaacagctgccgccatgggctccagtgagcaggaactgaaagccattgtcaaagatcttggttgtgggccatattttt |
| gggcacctatgacaagcgctttccaggctttgtttctccacacaagctcgcctgcgccatagtcaatacggccggtcgcgagactgggg |
| gcgtacactggatggcctttgcctggaacccgcactcaaaaacatgctacctctttgagccctttggcttttctgaccagcgactcaagca |
| ggtttaccagtttgagtacgagtcactcctgcgccgtagcgccattgcttcttcccccgaccgctgtataacgctggaaaagtccacccaa |
| agcgtacaggggcccaactcggccgcctgtggactattctgctgcatgtttctccacgcctttgccaactggccccaaactcccatggat |
| cacaaccccaccatgaaccttattaccggggtacccaactccatgctcaacagtccccaggtacagcccaccctgcgtcgcaaccagg |
| aacagctctacagcttcctggagcgccactcgccctacttccgcagccacagtgcgcagattaggagcgccacttctttttgtcacttgaa |
| aaacatgtaaaaataatgtactagagacactttcaataaaggcaaatgcttttatttgtacactctcgggtgattatttacccccacccttgcc |
| gtctgcgccgtttaaaaatcaaaggggttctgccgcgcatcgctatgcgccactggcagggacacgttgcgatactggtgtttagtgctc |
| cacttaaactcaggcacaaccatccgcggcagctcggtgaagttttcactccacaggctgcgcaccatcaccaacgcgtttagcaggtc |
| gggcgccgatatcttgaagtcgcagttggggcctccgccctgcgcgcgcgagttgcgatacacagggttgcagcactggaacactatc |
| agcgccgggtggtgcacgctggccagcacgctcttgtcggagatcagatccgcgtccaggtcctccgcgttgctcagggcgaacgga |
| gtcaactttggtagctgccttcccaaaaagggcgcgtgcccaggctttgagttgcactcgcaccgtagtggcatcaaaaggtgaccgtg |
| cccggtctgggcgttaggatacagcgcctgcataaaagccttgatctgcttaaaagccacctgagcctttgcgccttcagagaagaacat |
| gccgcaagacttgccggaaaactgattggccggacacgcggcgtcgtgcacgcagcaccttgcgtcggtgttggagatctgcaccac |
| atttcggccccaccggttcttcacgatcttggccttgctagactgctccttcagcgcgcgctgcccgttttcgctcgtcacatccatttcaatc |
| acgtgctccttatttatcataatgcttccgtgtagacacttaagctcgccttcgatctcagcgcagcggtgcagccacaacgcgcagcccg |
| tgggctcgtgatgcttgtaggtcacctctgcaaacgactgcaggtacgcctgcaggaatcgccccatcatcgtcacaaaggtcttgttgct |
| ggtgaaggtcagctgcaacccgcggtgctcctcgttcagccaggtcttgcatacggccgccagagcttccacttggtcaggcagtagttt |
| gaagttcgcctttagatcgttatccacgtggtacttgtccatcagcgcgcgcgcagcctccatgcccttctcccacgcagacacgatcgg |
| cacactcagcgggttcatcaccgtaatttcactttccgcttcgctgggctcttcctcttcctcttgcgtccgcataccacgcgccactgggtc |
| gtcttcattcagccgccgcactgtgcgcttacctcctttgccatgcttgattagcaccggtgggttgctgaaacccaccatttgtagcgcca |
| catcttctctttcttcctcgctgtccacgattacctctggtgatggcgggcgctcgggcttgggagaagggcgcttctttttcttcttgggcgc |

TABLE 1 -continued

| SEQUENCE LISTINGS |
| --- |
| aatggccaaatccgccgccgaggtcgatggccgcgggctgggtgtgcgcggcaccagcgcgtcttgtgatgagtcttcctcgtcctcg |
| gactcgatacgccgcctcatccgctttttggggggcgcccggggaggcggcggcgacggggacggggacgacacgtcctccatggtt |
| ggggacgtcgcgccgcaccgcgtccgcgctcgggggtggtttcgcgctgctcctcttcccgactggccatttccttctcctataggca |
| gaaaaagatcatggagtcagtcgagaagaaggacagcctaaccgcccctctgagttcgccaccaccgcctccaccgatgccgccaa |
| cgcgcctaccaccttccccgtcgaggcacccccgcttgaggaggaggaagtgattatcgagcaggacccaggttttgtaagcgaagac |
| gacgaggaccgctcagtaccaacagaggataaaaagcaagaccaggacaacgcagaggcaaacgaggaacaagtcgggcgggg |
| ggacgaaaggcatggcgactacctagatgtgggagacgacgtgctgttgaagcatctgcagcgccagtgcgccattatctgcgacgc |
| gttgcaagagcgcagcgatgtgcccctcgccatagcggatgtcagccttgcctacgaacgccacctattctcaccgcgcgtaccccca |
| aacgccaagaaaacggcacatgcgagcccaacccgcgcctcaacttctaccccgtatttgccgtgccagaggtgcttgccacctatcac |
| atctttttccaaaactgcaagatacccctatcctgccgtgccaaccgcagccgagcggacaagcagctggccttgcggcagggcgctgt |
| catacctgatatcgcctcgctcaacgaagtgccaaaaatctttgagggtcttggacgcgacgagaagcgcgcggcaaacgctctgcaa |
| caggaaaacagcgaaaatgaaagtcactctggagtgttggtggaactcgagggtgacaacgcgcgcctagccgtactaaaacgcagc |
| atcgaggtcacccactttgcctacccggcacttaacctacccccaaggtcatgagcacagtcatgagtgagctgatcgtgcgccgtgc |
| gcagcccctggagagggatgcaaatttgcaagaacaaacagaggagggcctacccgcagttggcgacgagcagctagcgcgctgg |
| cttcaaacgcgcgagcctgccgacttggaggagcgacgcaaactaatgatggccgcagtgctcgttaccgtggagcttgagtgcatgc |
| agcggttctttgctgacccggagatgcagcgcaagctagaggaaacattgcactacacctttcgacagggctacgtacgccaggcctg |
| caagatctccaacgtggagctctgcaacctggtctcctaccttggaattttgcacgaaaaccgccttgggcaaaacgtgcttcattccacg |
| ctcaagggcgaggcgcgccgcgactacgtccgcgactgcgtttacttatttctatgctacacctggcagacggccatgggcgtttggca |
| gcagtgcttggaggagtgcaacctcaaggagctgcagaaactgctaaagcaaaacttgaaggacctatggacggccttcaacgagcg |
| ctccgtggccgcgcacctggcggacatcattttccccgaacgcctgcttaaaaccctgcaacagggtctgccagacttcaccagtcaaa |
| gcatgttgcagaactttaggaactttatcctagagcgctcaggaatcttgcccgccacctgctgtgcacttcctagcgactttgtgcccatta |
| agtaccgcgaatgccctccgccgctttggggccactgctaccttctgcagctagccaactaccttgcctaccactctgacataatggaag |
| acgtgagcggtgacggtctactggagtgtcactgtcgctgcaacctatgcaccccgcaccgctccctggtttgcaattcgcagctgctta |
| acgaaagtcaaattatcggtacctttgagctgcagggtccctcgcctgacgaaaagtccgcggctccggggttgaaactcactccgggg |
| ctgtggacgtcggcttaccttcgcaaatttgtacctgaggactaccacgcccacgagattaggttctacgaagaccaatcccgcccgcct |
| aatgcggagcttaccgcctgcgtcattacccagggccacattcttggccaattgcaagccatcaacaaagcccgccaagagtttctgcta |
| cgaaagggacggggggtttacttggacccccagtccggcgaggagctcaacccaatcccccgccgccgcagccctatcagcagca |
| gccgcgggcccttgcttcccaggatggcacccaaaaagaagctgcagctgccgccgccacccacggacgaggaggaatactggga |
| cagtcaggcagaggaggttttggacgaggaggaggaggacatgatggaagactgggagagcctagacgaggaagcttccgaggtc |
| gaagaggtgtcagacgaaacaccgtcaccctcggtcgcattcccctcgccggcgccccagaaatcggcaaccggttccagcatggct |
| acaacctccgctcctcaggcgccgccggcactgcccgttcgccgacccaaccgtagatgggacaccactggaaccagggccggtaa |
| gtccaagcagccgccgccgttagcccaagagcaacaacagcgccaaggctaccgctcatggcgcgggcacaagaacgccatagttg |
| cttgcttgcaagactgtgggggcaacatctccttcgcccgccgctttcttctctaccatcacggcgtggccttcccccgtaacatcctgcatt |
| actaccgtcatctctacagcccatactgcaccggcggcagcggcagcaacagcagcggccacacagaagcaaaggcgaccggata |
| gcaagactctgacaaagcccaagaaatccacagcggcggcagcagcaggaggaggagcgctgcgtctggcgcccaacgaacccg |
| tatcgacccgcgagcttagaaacaggatttttcccactctgtatgctatatttcaacagagcaggggccaagaacaagagctgaaaataa |
| aaaacaggtctctgcgatccctcacccgcagctgcctgtatcacaaaagcgaagatcagcttcggcgcacgctggaagacgcggagg |
| ctctcttcagtaaatactgcgcgctgactcttaaggactagtttcgcgccctttctcaaatttaagcgcgaaaactacgtcatctccagcggc |
| cacacccggcgccagcacctgttgtcagcgccattatgagcaaggaaattcccacgccctacatgtggagttaccagccacaaatggg |

TABLE 1 -continued

| SEQUENCE LISTINGS |
|---|
| acttgcggctggagctgcccaagactactcaacccgaataaactacatgagcgcgggaccccacatgatatcccgggtcaacggaata |
| cgcgcccaccgaaaccgaattctcctggaacaggcggctattaccaccacacctcgtaataaccttaatccccgtagttggcccgctgc |
| cctggtgtaccaggaaagtcccgctcccaccactgtggtacttcccagagacgcccaggccgaagttcagatgactaactcaggggcg |
| cagcttgcgggcggctttcgtcacagggtgcggtcgcccgggcagggtataactcacctgacaatcagagggcgaggtattcagctca |
| acgacgagtcggtgagctcctcgcttggtctccgtccggacgggacatttcagatcggcggcgccggccgctcttcattcacgcctcgt |
| caggcaatcctaactctgcagacctcgtcctctgagccgcgctctggaggcattggaactctgcaatttattgaggagtttgtgccatcggt |
| ctactttaaccccttctcgggacctcccggccactatccggatcaatttattcctaactttgacgcggtaaaggactcggcggacggctac |
| gactgaatgttaagtggccaatgaggcctgacgctaataatagctggtccactgtcgccgccacaagtgctttgcccgcgactccggtga |
| gttttgctactttgaattgcccgaggatcatatcgagggcccggcgcacggcgtccggcttaccgcccagggagagcttgcccgtagcc |
| tgattcgggagtttacccagcgccccctgctagttgagcgggacaggggaccctgtgttctcactgtgatttgcaactgtcctaaccttgg |
| attacatcaagatccagatcttctagacccgggagcggccgctgtcgacctgcaggatccgaattcgatatcactagtggtaccgatctta |
| ttccctttaactaataaaaaaaaataataaagcatcacttacttaaaatcagttagcaaatttctgtccagtttattcagcagcacctccttgcc |
| ctcctcccagctctggtattgcagcttcctcctggctgcaaactttctccacaatctaaagggaatgtcagtttcctcctgttcctgtccatcc |
| gcacccactatcttcatgttgttgcagatgaagcgcgcaagaccgtctgaagataccttcaaccccgtgtatccatatgacacggaaacc |
| ggtcctccaactgtgccttttcttactcctccctttgtatcccccaatgggtttcaagagagtcccccctggggtactctctttgcgcctatccga |
| acctctagttacctccaatggcatgcttgcgctcaaaatgggcaacggcctctctctggacgaggccggcaaccttacctcccaaaatgt |
| aaccactgtgagcccacctctcaaaaaaaccaagtcaaacataaacctggaaatatctgcacccctcacagttacctcagaagccctaac |
| tgtggctgccgccgcacctctaatggtcgcgggcaacacactcaccatgcaatcacaggccccgctaaccgtgcacgactccaaactt |
| agcattgccacccaaggacccctcacagtgtcagaaggaaagctagccctgcaaacatcaggcccccctcaccaccaccgatagcagt |
| acccttactatcactgcctcacccccctctaactactgccactggtagcttgggcattgacttgaaagagcccatttatacacaaaatggaaa |
| actaggactaaagtacggggctcctttgcatgtaacagacgacctaaacactttgaccgtagcaactggtccaggtgtgactattaataat |
| acttccttgcaaactaaagttactggagccttgggttttgattcacaaggcaatatgcaacttaatgtagcaggaggactaaggattgattct |
| caaaacagacgccttatacttgatgttagttatccgtttgatgctcaaaaccaactaaatctaagactaggacagggccctctttttataaact |
| cagcccacaacttggatattaactacaacaaaggcctttacttgtttacagcttcaaacaattccaaaaagcttgaggttaacctaagcactg |
| ccaaggggttgatgtttgacgctacagccatagccattaatgcaggagatgggcttgaatttggttcacctaatgcaccaaacacaaatcc |
| cctcaaaacaaaaattggccatggcctagaatttgattcaaacaaggctatggttcctaaactaggaactggccttagttttgacagcacag |
| gtgccattacagtaggaaacaaaaataatgataagctaactttgtggaccacaccagctccatctcctaactgtagactaaatgcagagaa |
| agatgctaaactcactttggtcttaacaaaatgtggcagtcaaatacttgctacagtttcagttttggctgttaaaggcagtttggctccaatat |
| ctggaacagttcaaagtgctcatcttattataagatttgacgaaaatggagtgctactaaacaattccttcctggacccagaatattggaactt |
| tagaaatggagatcttactgaaggcacagcctatacaaacgctgttggatttatgcctaacctatcagcttatccaaaatctcacggtaaaa |
| ctgccaaaagtaacattgtcagtcaagtttacttaaacggagacaaaactaaacctgtaacactaaccattacactaaacggtacacagga |
| aacaggagacacaactccaagtgcatactctatgtcattttcatgggactggtctggccacaactacattaatgaaatatttgccacatcctc |
| ttacactttttcatacattgcccaagaataaagaatcgtttgtgttatgtttcaacgtgtttatttttcaattgcagaaaatttcaagtcatttttcatt |
| cagtagtatagccccaccaccacatagcttatacagatcaccgtaccttaatcaaactcacagaaccctagtattcaacctgccacctccct |
| cccaacacacagagtacacagtcctttctccccggctggccttaaaaagcatcatatcatgggtaacagacatattcttaggtgttatattcc |
| acacggtttcctgtcgagccaaacgctcatcagtgatattaataaactccccgggcagctcacttaagttcatgtcgctgtccagctgctga |
| gccacaggctgctgtccaacttgcggttgcttaacgggcggcgaaggagaagtccacgcctacatgggggtagagtcataatcgtgca |
| tcaggatagggcggtggtgctgcagcagcgcgcgaataaactgctgccgccgccgctccgtcctgcaggaatacaacatggcagtgg |
| tctcctcagcgatgattcgcaccgcccgcagcataaggcgccttgtcctccgggcacagcagcgcaccctgatctcacttaaatcagca |

TABLE 1 -continued

| SEQUENCE LISTINGS |
|---|
| cagtaactgcagcacagcaccacaatattgttcaaaatcccacagtgcaaggcgctgtatccaaagctcatggggggaccacagaac |
| ccacgtggccatcataccacaagcgcaggtagattaagtggcgacccctcataaacacgctggacataaacattacctcttttggcatgtt |
| gtaattcaccacctcccggtaccatataaacctctgattaaacatggcgccatccaccaccatcctaaaccagctggccaaaacctgccc |
| gccggctatacactgcagggaaccgggactggaacaatgacagtggagagcccaggactcgtaaccatggatcatcatgctcgtcatg |
| atatcaatgttggcacaacacaggcacacgtgcatacacttcctcaggattacaagctcctcccgcgttagaaccatatcccagggaaca |
| acccattcctgaatcagcgtaaatcccacactgcagggaagacctcgcacgtaactcacgttgtgcattgtcaaagtgttacattcgggca |
| gcagcggatgatcctccagtatggtagcgcgggtttctgtctcaaaaggaggtagacgatccctactgtacggagtgcgccgagacaa |
| ccgagatcgtgttggtcgtagtgtcatgccaaatggaacgccggacgtagtcatatttcctgaagcaaaaccaggtgcgggcgtgacaa |
| acagatctgcgtctccggtctcgccgcttagatcgctctgtgtagtagttgtagtatatccactctctcaaagcatccaggcgccccctggc |
| ttcgggttctatgtaaactccttcatgcgccgctgccctgataacatccaccaccgcagaataagccacacccagccaacctacacattcg |
| ttctgcgagtcacacacgggaggagcgggaagagctggaagaaccatgtttttttttttttattccaaaagattatccaaaacctcaaaatga |
| agatctattaagtgaacgcgctcccctccggtggcgtggtcaaactctacagccaaagaacagataatggcatttgtaagatgttgcaca |
| atggcttccaaaaggcaaacggccctcacgtccaagtggacgtaaaggctaaacccttcagggtgaatctcctctataaacattccagca |
| ccttcaaccatgcccaaataattctcatctcgccaccttctcaatatatctctaagcaaatcccgaatattaagtccggccattgtaaaaatct |
| gctccagagcgccctccaccttcagcctcaagcagcgaatcatgattgcaaaaattcaggttcctcacagacctgtataagattcaaaag |
| cggaacattaacaaaaataccgcgatcccgtaggtcccttcgcagggccagctgaacataatcgtgcaggtctgcacggaccagcgcg |
| gccacttccccgccaggaaccatgacaaaagaacccacactgattatgacacgcatactcggagctatgctaaccagcgtagccccga |
| tgtaagcttgttgcatgggcggcgatataaaatgcaaggtgctgctcaaaaaatcaggcaaagcctcgcgcaaaaaagaaagcacatc |
| gtagtcatgctcatgcagataaaggcaggtaagctccggaaccaccacagaaaaagacaccatttttctctcaaacatgtctgcgggtttc |
| tgcataaacacaaaataaaataacaaaaaaacatttaaacattagaagcctgtcttacaacaggaaaaacaacccttataagcataagac |
| ggactacggccatgccggcgtgaccgtaaaaaaactggtcaccgtgattaaaaagcaccaccgacagctcctcggtcatgtccggagt |
| cataatgtaagactcggtaaacacatcaggttgattcacatcggtcagtgctaaaaagcgaccgaaatagcccgggggaatacataccc |
| gcaggcgtagagacaacattacagcccccataggaggtataacaaaattaataggagagaaaaacacataaacacctgaaaaaccctc |
| ctgcctaggcaaaatagcaccctcccgctccagaacaacatacagcgcttccacagcggcagccataacagtcagccttaccagtaaa |
| aaagaaaacctattaaaaaaacaccactcgacacggcaccagctcaatcagtcacagtgtaaaaaagggccaagtgcagagcgagtat |
| atataggactaaaaaatgacgtaacggttaaagtccacaaaaaacacccagaaaaccgcacgcgaacctacgcccagaaacgaaagc |
| caaaaaacccacaacttcctcaaatcgtcacttccgttttcccacgttacgtaacttcccattttaagaaaactacaattcccaacacatacaa |
| gttactccgccctaaaacctacgtcacccgccccgttcccacgccccgcgccacgtcacaaactccaccccctcattatcatattggcttc |
| aatccaaaataaggtatattattgatgatg |

TABLE 2

| Full Vector with Plasmid Backbone |
|---|
| (SEQ ID NO: 2) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |

TABLE 2-continued gactaataaaaaaatatccagattggagttttgctcttagtgatttaaacagtgatgattggaaggagcgccgtgactatctttataagttattc
caacaaggctctgcgttgttagaagaactacaccagctcaaggtcaaccatgaggttctgtaccatctgcagctaagccctgcggagcgt
acatctatacagcaacgatgggccgatgttctgcgcgagaagaagcgtaatgttgtggttattgactacccaacatacatgcagtctatcta
tgatattttgaataatcctgcgactttatttagtttaaacactcgttctggaatggcacctttggcctttgctctggctgcggtatcagggcgaa
gaatgattgagataatgtttcagggtgaatttgccgtttcaggaaagtatacggttaatttctcagggcaagctaaaaaacgctctgaagat
aaaagcgtaaccagaacgatttatactttatgcgaagcaaaattattcgttgaattattaacagaattgcgttcttgctctgctgcatctgatttc
gatgaggttgttaaaggatatggaaaggatgatacaaggtctgagaacggcaggataaatgctattttagcaaaagcatttaacccttggg
ttaaatcatttttcggcgatgaccgtcgtgtttataaagatagccgcgctatttacgctcgcatcgcttatgagatgttcttccgcgtcgatcca
cggtggaaaaacgtcgacgaggatgtgttcttcatggagattctcggacacgacgatgagaacacccagctgcactataagcagttcaa
gctggccaacttctccagaacctggcgacctgaagttggggatgaaaacaccaggctggtggctctgcagaaactggacgatgaaatg
ccaggctttgccagaggtgacgctggcgtccgtctccatgaaaccgttaagcagctggtggagcaggacccatcagcaaaaataacca
acagcactctccgggcctttaaatttagcccgacgatgattagccggtacctggagtttgccgctgatgcattggggcagttcgttggcga
gaacgggcagtggcagctgaagatagagacacctgcaatcgtcctgcctgatgaagaatccgttgagaccatcgacgaaccggatgat
gagtcccaagacgacgagctggatgaagatgaaattgagctcgacgagggtggcggcgatgaaccaaccgaagaggaagggccag
aagaacatcagccaactgctctaaaacccgtcttcaagcctgcaaaaaataacggggacggaacgtacaagatagagtttgaatacgat
ggaaagcattatgcctggtccggccccgccgatagccctatggccgcaatgcgatccgcatgggaaacgtactacagctaaaagaaaa
gccaccggtgttaatcggtggctttttttattgaggcctgtccctacccatcccctgcaagggacggaaggattaggcggaaactgcagct
gcaactacggacatcgccgtcccgactgcagggacttccccgcgtaaagcggggcttaaattcgggctggccaaccctatttttctgca
atcgctggcgatgttagtttcgtggatagcgtttccagcttttcaatggccagctcaaaatgtgctggcagcaccttctccagttccgtatca
atatcggtgatcggcagctctccacaagacatactccggcgaccgccacgaactacatcgcgcagcagctcccgttcgtagacacgca
tgttgcccagagccgtttctgcagccgttaatatccggcgcagctcggcgatgattgccgggagatcatccacggttattgggttcggtga
tgggttcctgcaggcgcggcggagagccatccagacgccgctaacccatgcgttacggtactgaaaactttgtgctatgtcgtttatcag
gccccgaagttcttctttctgccgccagtccagtggttcaccggcgttcttaggctcaggctcgacaaaagcatactcgccgtttttccgga
tagctggcagaacctcgttcgtcacccacttgcggaaccgccaggctgtcgtcccctgtttcaccgcgtcgcggcagcggaggattatg
gtgtagagaccagattccgataccacatttacttccctggccatccgatcaagtttttgtgcctcggttaaaccgagggtcaatttttcatcat
gatccagcttacgcaatgcatcagaagggttggctatattcaatgcagcacagatatccagcgccacaaaccacgggtcaccaccgac
aagaaccacccgtatagggtggctttcctgaaatgaaaagacggagagagccttcattgcgcctccccggatttcagctgctcagaaag
ggacagggagcagccgcgagcttcctgcgtgagttcgcgcgcgacctgcagaagttccgcagcttcctgcaaatacagcgtggcctc
ataactggagatagtgcggtgagcagagcccacaagcgcttcaacctgcagcaggcgttcctcaatcgtctccagcaggccctgggcg
tttaactgaatctggttcatgcgatcacctcgctgaccgggatacgggctgacagaacgaggacaaaacggctggcgaactggcgacg
agcttctcgctcggatgatgcagtggtggaaaggcggtggatatgggatttttttgtccgtgcggacgacagctgcaaatttgaatttgaac
atggtatgcattcctatcttgtatagggtgctaccaccagagttgagaatctctatagggggtagcccagacagggttctcaacaccgg
tacaagaagaaaccggcccaaccgaagttggccccatctgagccaccataattcaggtatgcgcagatttaacacacaaaaaaacacg
ctggcgcgtgttgtgcgcttcttgtcattcggggttgagaggcccggctgcagattttgctgcagcggggtaactctaccgccaaagcag
aacgcacgtcaataatttaggtggatattttaccccgtgaccagtcacgtgcacaggtgtttttatagtttgctttactgactgatcagaacct
gatcagttattggagtccggtaatcttattgatgaccgcagccaccttagatgttgtctcaaaccccatacggccacgaatgagccactgg
aacggaatagtcagcaggtacagcggaacgaaccacaaacggttcagacgctgccagaacgtcgcatcacgacgttccatccattcg
gtattgtcgacgacctggtaagcgtattgtcctggcgtttttgctgcttccgagtagcaatcctcttcaccacaaagaaagttacttatctgctt
ccagttttcgaacccttcttctttgagccgcttttccagctcattcctccacaaaacaggcacccatcctctgcgataaatcatgattatttgtc
ctttaaataaggctgtagaactgcaaaatcgctctcgttcacatgctgtacgtagatgcgtagcaaattgccgttccatccctgtaatccacc TABLE 2-continued ttctttggaaagatcgtccttgacctcacgaagaactttatccaatagccctgcggcacaagaaattgcctgctctggatcagcaaattcat attgattaataggtgattgccacacaccaaaaacaggaatcatcttttcggctaaacgcctctcctgttctttcttaatctcaagttgtaagcg gaccagctcaccatccatcatttttttgtagatcatgcgccactattcacccccactggccatcagcaaataaagcttcatactcggacaccg gcaggcggcttccacggattgaaaggtcaagccaaccacgtccagatgggtcagccttatccgattcttcccaccgttctgcagctgtag caaccaggcattctaccgccttcatgtagtcttctgtacggaaccagccgtagttaatgccaccatcagtaactgcccaggccatctttttct cttcggcctcaatagcccggatgcggttatcgcacagctcgcgacagtacttcagctgttcgtaatccagttgcttcaggaactctggtgtc gacgtcatagtggcttcaccttataggcttttagaagcgccctggcttcgtctgtgtggtcttccatgctcttatcgctggcaatgcagcaata aactccctcactatctgagaacccgttcatccgaatgatcgtgaatggaagttcccggccagttttataatcgctatagcttgtcgcgtcgtg gctgaccttgaccacataagggtcgtagccctccacgatgacaaggcattcccgttgttttcccattacccctccggttatatcgccacgg cttgccgctggcttagaaacgctttcagcagccttatttcgcgtactgatagcaggtccataaattcggtcatgtacagcgaggcgaacgtt ctcgcgatgctggccactggccacaggcgtaccgcctccatttcggttgctggcaacgcgttctccgcccacgcctccggtaccgccac cgggatagcctccagtgcctggataattactgattgtggggcgtccggaacgtgctctgttttggatcgagggttaccatgtatatctatatt tagatccaaatcgcgatccacttcgatggtggtttttttccaccttacgtgcgtgaattgataaaccggcctcgcggcgcttctccacgatatt catgaggaactcgaccgagtccgggtcaatggaacgcatcgtggggcgtgcatcgccgtctctggcgcgtctggtcttactggatagcc ccatagactccaggatgcctatgcagaggtctgcaggcgctttcttcttgcctttctctgtgttgaagccgccgatgcgtaaaacgttgttta gcagatcgcgccgttccggcgtgagcaggttatctctggcgcgtttgagggcgtccatgtctgcttcaccttccagggtttttggatcgata ccgcagtcgcggaagtactgctgcagcgtcgccgatttgagggtgtagaaaccacgcatgcctatctcaacagcaggggtcgatttcac tcggtaatcggttatggccgggaatttagcctggaactctgcgtcggcctgttcccgcgtcatggccgtagtgacgaactgctgccatctt ccggcaacgcgataagcgtaggtaaagtgaatcaacgcttcttcacggtcaaggcgacgggcggttatctcatccagctgcatggtttca aacaggcgcactttttttcaggccgccgtcgaaatagaattttaacgccacctcgtcgacatccagctgcagctccttttcgatgtcccagc ggaccagctgggcctgctcatccagggacagggtgcgtttttttatcaactcatcgtgttcggcctggtcaggagtatcgacactcaggtg gcgctccataagctgctcaaagaccagttcacgggcttctttacgtaaatccttaccgatgctgtttgcaagcgcgtcggtggccataggc gcgacctgatagccatcatcatgcatgatgcaaatcatgttgctggcataatcatttctggccgatgcctcgagcgcggcggctttaatttt gagctgcatgaatgaagagttagccacgccgagtgaaattcggtcaccgtcaaagacaacgtctgtcagcagcccggagtggccagc cgtttcgagcaaggcctgcgcgtaggcgcgtttgatttttttccggatcggtttcacgtttaccgcgaagcttgtcgaaaccgataatgtattc ctgagctgtacggtcgcggcgcagcatctggatggcgtcgctggggaccacttcgccgcagaacatgccgaaatggcggtggaagtg tttctcctcaatcgatacacctgaagatatcgacgggctgtagatgaggccgtcatatttttttcaccatcactttaggctggttggtgaaatcg tcgacttccttctcctgtttgtttttctggttaacgcagagaaactttttgtcagggaactgtagtctcagctgcatggtaacgtcttcggcgaa cgtcgaactgtcggtggccagcatgattcgttcgccgcgttgcactgcagcgataacctcggtcatgatccgatttttctcggtataaaata cgcggataggcttgttggtttcgcggttgcgaacgtcgaccgggagttcaatcacgtgaatttgcagccaggcaggtaggcccagctcc tcgcgtcgcttcatcgccagttcagccaggtcaacaagcagatcgttggcatcggcatccaccataatggcatgctcttcagtacgcgcc agcgcgtcgataagcgtgttgaatacgcctaccgggttttccatcgcacgcccggccagaatggcacgcaggccctgtgttgcttcatc gaagccgaagaagtcatgctggcgcatcagcggttgccagcagcctttaagtatggagttgatgcaaatagtcagcttgttggcatatgg cgccatttcctgatagccgggatcctgataatgcagaatgtcggctttcgcgcctttcccttcggtcatcatttcatgcaggccgcctatcag ggatacgcggtgcgcgacggaaacgccacgcgtggactgcagcatcagtggacgcaggaggcctgtcgatttacccgaccccatcc cggcgcggacaataacgatgccctgcagctgtgcggcgtatgtcatcacctcatcggtcatcctggaggtttcaaaccgtttgtaagtgat gtgtgacgggcgaaggttcgggttggtgatgcgttcactgaacgaacgtgatgtttgcgcggcacggcatttgcgattcaaccggcgcg taatgtgatctttaacggtaccgttataaatttctgcgatacccatatcccgcagcgtgctgctgaaaaggcgcataagttctttcggctgtt tggtaccgggcatgtcagcatgccaatatcaacggcgcgaagcagttctttggcaaaagtgcgtctgttcagacgcgggagagtacgc agcttattcagcgtgatcgacaacagatcggttgcacggctcagatgatttctcgttaactggcgagcgacttccttcagccctctcaggct TABLE 2-continued gtgcaggtcgttaaaatcgctgcattccagctcagggtcatcctcaaaagttgggtaaacacatttgacgccggaaaacttctccatgatgt cgaatccggtgcggaggcctgtgttgccttttccttcagctgaggatttgcggtcgttatcgagagcgcaagtgatttgcgcagccgggta catgttcaccagctgctcgacaacgtgaatcatgttgttagcggaaaccgcaatgactaccgcgtcaaagcgtttttttcgggtcgtttctgg tcgccagccagatggatgccccggtggcgaaaccctctgcagtcgcaatttttttgcgccccctgcaggtcgccaataacaaagcatgca ccgacgaaatcaccgttagtgatggcgctggtctggaacttgccaccattcagatcgatacgttgccagccaacaatccgcccgtcttttc ttccgtccaggtgggacagaggtatcgccatgtaagttgttggtccacggctccatttcgcactgtcgtgactggtcacgcgacgtatatc acaagcgccaaatacgtcacgaattccctttttttaccgcataaggccaggagccatcttcagctggcgaatgttcccaggcgcgatggaa agccaaccatccaagcaggcgttcctgctccatctgattgtttttttaaatcattaacgcgttgttgttcagctcggaggcggcgtgcttcagc ctggcgctccatgcgtgcacgttcttcttccggctgagcgaccacggtcgcaccattccgttgctgttcacggcgatactccgaaaacag gaatgaaaagccactccaggagccagcgtcatgcgctttttcaacgaagttaacgaaaggataactgatgccatccttgctctgctcaag gcgtgaatagatttccacacggcctttaaggctcttctgcagagcttccggggaggaattattgtaggtggtatagcgctctacaccaccg cgcggattgagctgaatcttatcagcacacgcaggccagttgataccggccatcttcgccagctcagtcagctcatcacgtgccgcgtca agcagtgaaaacggatcgctgccaaagcgctccgcgtagaattcttgtaaggtcatttttttagcctttccatgcgaattagcatttttttcgggt tgaaaaaatccgcaggagcagccacaataaacgcactatctttctgaaggacgtatctgcgttatcgtggctacttcctgaaaaaggccc gagtttgccgactcggtttttttttcgtctttttttcggctgctacggtctggttcaaccccgacaaagtatagatcggattaaaccagaattata gtcagcaataaaccctgttattgtatcatctaccctcaaccatgaacgatttgatcgtaccgactacttggtgcacaaattgaagatcactttt atcatggataacccgttgagagttagcactatcaaggtagtaatgctgctcgtcataacgggctaatcgttgaattgtgatctcgccgttatt atcacaaaccagtacatcctcacccggtacaagcgtaagtgaagaatcgaccaggataacgtctcccggctggtagtttcgctgaatctg gttcccgaccgtcagtgcgtaaacggtgttccgttgactcacgaacggcaggaatcgctctgtgttggcaggttctccaggctgccagtc tctatccggtccggtctctgtcgtaccaataacaggaacgcggtctggatcagattcagtgccatacagtatccattgcacgggcttacgc aggcattttgccagcgatagcccgatctccagcgacggcatcacgtcgccacgttctaagttttggacgcccggaagagagattcctac agcttctgccacttgcttcagcgtcagtttcagctctaaacggcgtgctttcagtcgttcgcctcgtgttttcatacccttaatcataaatgatct ctttatagctggctataatttttataaattatacctagctttaattttcacttattgattataataatccccatgaaacccgaagaacttgtgcgcca tttcggcgatgtggaaaaagcagcggttggcgtgggcgtgacacccggcgcagtctatcaatggctgcaagctggggagattccacct ctacgacaaagcgatatagaggtccgtaccgcgtacaaattaaagagtgatttcacctctcagcgcatgggtaaggaagggcataacaa ggggatcctctagacgcagaaaggcccacccgaaggtgagccagtgtgattacatttgcggcctaactgtggccagtccagttacgctg gagtcactagtgcggccgcgacaacttgtctagggcccaatggcccaaattaattaacatcatcaataatataccttattttggattgaagc caatatgataatgagggggtggagtttgtgacgtggcgcggggcgtgggaacggggcgggtgacgtagtagtgtggcggaagtgtga tgttgcaagtgtggcggaacacatgtaagcgacggatgtggcaaaagtgacgtttttggtgtgcgccggtgtacacaggaagtgacaatt ttcgcgcggttttaggcggatgttgtagtaaatttgggcgtaaccgagtaagatttggccattttcgcgggaaaactgaataagaggaagt gaaatctgaataatttgtgttactcatagcgcgtaatatttgtctagggccgcggggactttgaccgtttacgtggagactcgcccaggtgt ttttctcaggtgttttccgcgttccgggtcaaagttggcgttttagatcttctagacccgggagcggccgctgtcgacctgcaggatccact agttattaatagtaatcaattacggggtcattagttcatagcccatatatggagttccgcgttacataacttacggtaaatggcccgcctggct gaccgcccaacgacccccgcccattgacgtcaataatgacgtatgttcccatagtaacgccaatagggactttccattgacgtcaatggg tggagtatttacggtaaactgcccacttggcagtacatcaagtgtatcatatgccaagtacgccccctattgacgtcaatgacggtaaatgg cccgcctggcattatgcccagtacatgaccttatgggactttcctacttggcagtacatctacgtattagtcatcgctattaccatggtcgag gtgagccccacgttctgcttcactctccccatctcccccccctccccacccccaattttgtatttatttattttttaattattttgtgcagcgatgg gggcggggggggggggggggggggccaggcggggcggggcggggcgaggggcggggcggggcgaggcggagaggtgcg gcggcagccaatcagagcggcgcgctccgaaagtttccttttatggcgaggcggcggcggcggcggccctataaaaagcgaagcgc gcggcagccaatcagagcggcgcgctccgaaagtttccttttatggcgaggcggcggcggcggcggccctataaaaagcgaagcgc TABLE 2-continued gcgggggggagtcgctgcgttgccttcgccccgtgccccgctccgcgccgcctcgcgccgcccgccccggctctgactgaccg cgttactcccacaggtgagcgggcgggacggcccttctcctccgggctgtaattagcgcttggtttaatgacggctcgtttcttttctgtgg ctgcgtgaaagccttaaagggctccgggagggccctttgtgcgggggggagcggctcgggggtgcgtgcgtgtgtgtgtgcgtgg ggagcgccgcgtgcggctccgcgctgcccggcggctgtgagcgctgcgggcgcggcgcggggctttgtgcgctccgcagtgtgcg cgaggggagcgcggccgggggcggtgccccgcggtgcgggggggggctgcgaggggaacaaaggctgcgtgcggggtgtgtgc gtgggggggtgagcagggggtgtgggcgcgtcggtcgggctgcaaccccccctgcacccccctccccgagttgctgagcacggcc cggcttcgggtgcggggctccgtacggggcgtggcgcggggctcgccgtgccgggcggggggtggcggcaggtgggggtgccg ggcggggcggggccgcctcgggccggggagggctcgggggaggggcgcggcggcccccggagcgccggcggctgtcgaggc gcggcgagccgcagccattgccttttatggtaatcgtgcgagagggcgcagggacttcctttgtcccaaatctgtgcggagccgaaatct gggaggcgccgccgcaccccctctagcgggcgcggggcgaagcggtgcggcgccggcaggaaggaaatgggcggggagggcc ttcgtgcgtcgccgcgccgccgtccccttctccctctccagcctcggggctgtccgcgggggggacggctgccttcgggggggacggg gcagggcggggttcggcttctggcgtgtgaccggcggctctagagcctctgctaaccatgttcatgccttcttctttttcctacagctcctg ggcaacgtgctggttattgtgctgtctcatcattttggcaaagaattccgctgcgactcggcggagtcccggggcgcgtccttgttctaac ccggcgcgccagcttggcaatccggtactgttggtaaagccaccatgcatagttctgccctgttgtgttgcttggtgctgttgacgggggtt agagcgagtccaggtcaaggcacgcagtctgaaaactcctgtacacacttccccggcaacctccctaatatgctcagagaccttcgaga cgccttctcccgagtaaaaactttctttcagatgaaggaccagctcgacaacttgctgttgaaggaatcactcctcgaagattttaaggggt acctcggttgtcaagctctgtctgaaatgatacaattctatctcgaggaagtcatgcctcaagcggaaaaccaggacccagatattaaggc ccatgtgaatagcctcggcgaaaatcttaaaactcttcgccttagactccgaagatgccataggtttttgccgtgcgaaaataaatccaaag ctgtggaacaggtaaaaaatgcgtttaacaagttgcaagagaagggcatctacaaagcgatgtcagagttcgatatattcataaattatatt gaagcatacatgactatgaagatcaggaattaataattctagagtcggggcggccggccgcttcgagcagacatgataagatacattgat gagtttggacaaaccacaactagaatgcagtgaaaaaaatgctttatttgtgaaatttgtgatgctattgctttatttgtaaccattataagctg caataaacaagttaacaacaacaattgcattcattttatgtttcaggttcagggggaggtgtgggaggttttttaaagcaagtaaaacctcta caaatgtggtaaaatcgataaggatccgaattcgatatcactagtggtaccagtactgaaatgtgtgggcgtggcttaagggtgggaaag aatatataaggtgggggtcttatgtagttttgtatctgttttgcagcagccgccgccgccatgagcaccaactcgtttgatggaagcattgtg agctcatatttgacaacgcgcatgcccccatgggccggggtgcgtcagaatgtgatgggctccagcattgatggtcgccccgtcctgcc cgcaaactctactaccttgacctacgagaccgtgtctggaacgccgttggagactgcagcctccgccgccgcttcagccgctgcagcc accgcccgcgggattgtgactgactttgctttcctgagcccgcttgcaagcagtgcagcttcccgttcatccgcccgcgatgacaagttg acggctcttttggcacaattggattctttgacccgggaacttaatgtcgtttctcagcagctgttggatctgcgccagcaggtttctgccctg aaggcttcctcccctcccaatgcggtttaacggtccgggccagagtggccaacataaataaaaaaccagactctgtttggatttggatcaa gcaagtgtcttgctgtctttatttaggggttttgcgcgcgcggtaggcccgggaccagcggtctcggtcgttgagggtcctgtgtatttttc caggacgtggtaaaggtgactctggatgttcagatacatgggcataagcccgtctctgggggaggtagcaccactgcagagcttcat gctgcggggtggtgttgtagatgatccagtcgtagcaggagcgctgggcgtggtgcctaaaaatgtctttcagtagcaagctgattgcca ggggcaggcccttggtgtaagtgtttacaaagcggttaagctgggatgggtgcatacgtggggatatgagatgcatcttggactgtatttt aggttggctatgttcccagccatatccctccggggattcatgttgtgcagaaccaccagcacagtgtatccggtgcacttgggaaatttgtc atgtagcttagaaggaaatgcgtggaagaacttggagacgcccttgtgacctccaagattttccatgcattcgtccataatgatggcaatg ggcccacgggcggcggcctgggcgaagatatttctgggatcactaacgtcatagttgtgttccaggatgagatcgtcataggccatttta caaagcgcgggcggagggtgccagactgcggtataatggttccatccggcccaggggcgtagttaccctcacagatttgcatttcccac gctttgagttcagatggggggatcatgtctacctgcggggcgatgaagaaaacggtttccggggtaggggagatcagctgggaagaaa gcaggttcctgagcagctgcgacttaccgcagccggtgggcccgtaaatcacacctattaccggctgcaactggtagttaagagagctg cagctgccgtcatccctgagcagggggccacttcgttaagcatgtccctgactcgcatgttttccctgaccaaatccgccagaaggcg TABLE 2-continued ctcgccgcccagcgatagcagttcttgcaaggaagcaaagtttttcaacggtttgagaccgtccgccgtaggcatgcttttgagcgtttga ccaagcagttccaggcggtcccacagctcggtcacctgctctacggcatctcgatccagcatatctcctcgtttcgcgggttggggcggc tttcgctgtacggcagtagtcggtgctcgtccagacgggccagggtcatgtctttccacgggcgcagggtcctcgtcagcgtagtctgg gtcacggtgaaggggtgcgctccgggctgcgcgctggccagggtgcgcttgaggctggtcctgctggtgctgaagcgctgccggtctt cgccctgcgcgtcggccaggtagcatttgaccatggtgtcatagtccagcccctccgcggcgtggcccttggcgcgcagcttgcccttg gaggaggcgccgcacgaggggcagtgcagacttttgagggcgtagagcttgggcgcgagaaataccgattccggggagtaggcatc cgcgccgcaggccccgcagacggtctcgcattccacgagccaggtgagctctggccgttcggggtcaaaaaccaggtttcccccatg ctttttgatgcgtttcttacctctggtttccatgagccggtgtccacgctcggtgacgaaaaggctgtccgtgtccccgtatacagacttgag aggcctgtcctcgagcggtgttccgcggtcctcctcgtatagaaactcggaccactctgagacaaaggctcgcgtccaggccagcacg aaggaggctaagtgggaggggtagcggtcgttgtccactaggggtccactcgctccagggtgtgaagacacatgtcgccctcttcgg catcaaggaaggtgattggtttgtaggtgtaggccacgtgaccgggtgttcctgaaggggggctataaaagggggtgggggcgcgttc gtcctcactctcttccgcatcgctgtctgcgagggccagctgttggggtgagtactccctctgaaaagcgggcatgacttctgcgctaaga ttgtcagtttccaaaaacgaggaggatttgatattcacctggcccgcggtgatgcctttgagggtggccgcatccatctggtcagaaaaga caatctttttgttgtcaagcttggtggcaaacgacccgtagagggcgttggacagcaacttggcgatggagcgcagggtttggtttttgtc gcgatcggcgcgctccttggccgcgatgtttagctgcacgtattcgcgcgcaacgcaccgccattcgggaaagacggtggtgcgctcg tcgggcaccaggtgcacgcgccaaccgcggttgtgcagggtgacaaggtcaacgctggtggctacctctccgcgtaggcgctcgttg gtccagcagaggcggccgcccttgcgcgagcagaatggcggtagggggtctagctgcgtctcgtccggggggtctgcgtccacggt aaagaccccgggcagcaggcgcgcgtcgaagtagtctatcttgcatccttgcaagtctagcgcctgctgccatgcgcgggggcaag cgcgcgctcgtatgggttgagtgggggaccccatggcatggggtgggtgagcgcggaggcgtacatgccgcaaatgtcgtaaacgta gaggggctctctgagtattccaagatatgtagggtagcatcttccaccgcggatgctggcgcgcacgtaatcgtatagttcgtgcgaggg agcgaggaggtcgggaccgaggttgctacgggcgggctgctctgctcggaagactatctgcctgaagatggcatgtgagttggatgat atggttggacgctggaagacgttgaagctggcgtctgtgagacctaccgcgtcacgcacgaaggaggcgtaggagtcgcgcagcttg ttgaccagctcggcggtgacctgcacgtctagggcgcagtagtccagggtttccttgatgatgtcatacttatcctgtccctttttttccaca gctcgcggttgaggacaaactcttcgcggtctttccagtactcttggatcggaaacccgtcggcctccgaacggtaagagcctagcatgt agaactggttgacggcctggtaggcgcagcatcccttttctacgggtagcgcgtatgcctgcgcggccttccggagcgaggtgtgggt gagcgcaaaggtgtccctgaccatgactttgaggtactggtatttgaagtcagtgtcgtcgcatccgccctgctcccagagcaaaaagtc cgtgcgctttttggaacgcggatttggcagggcgaaggtgacatcgttgaagagtatctttcccgcgcgaggcataaagttgcgtgtgat gcggaagggtcccggcacctcggaacggttgttaattacctgggcggcgagcacgatctcgtcaaagccgttgatgttgtggcccaca atgtaaagttccaagaagcgcgggatgcccttgatggaaggcaatttttttaagttcctcgtaggtgagctcttcaggggagctgagcccgt gctctgaaagggcccagtctgcaagatgagggttggaagcgacgaatgagctccacaggtcacgggccattagcatttgcaggtggtc gcgaaaggtcctaaactggcgacctatggccatttttttctggggtgatgcagtagaaggtaagcgggtcttgttcccagcggtcccatcc aaggttcgcggctaggtctcgcgcggcagtcactagaggctcatctccgccgaacttcatgaccagcatgaagggcacgagctgcttc ccaaaggcccccatccaagtataggtctctacatcgtaggtgacaaagagacgctcggtgcgaggatgcgagccgatcgggaagaac tggatctcccgccaccaattggaggagtggctattgatgtggtgaaagtagaagtccctgcgacgggccgaacactcgtgctggcttttg taaaaacgtgcgcagtactggcagcggtgcacgggctgtacatcctgcacgaggttgacctgacgaccgcgcacaaggaagcagagt gggaatttgagcccctcgcctggcgggtttggctggtggtcttctacttcggctgcttgtccttgaccgtctggctgctcgaggggagttac ggtggatcggaccaccacgccgcgcgagcccaaagtccagatgtccgcgcgcggcggtcggagcttgatgacaacatcgcgcagat gggagctgtccatggtctggagctcccgcggcgtcaggtcaggcgggagctcctgcaggtttacctcgcatagacgggtcagggcgc gggctagatccaggtgatacctaatttccaggggctggttggtggcggcgtcgatggcttgcaagaggccgcatccccgcggcgcga ctacggtaccgcgcggcgggcggtgggccgcgggggtgtccttggatgatgcatctaaaagcggtgacgcgggcgagcccccgga TABLE 2-continued ggtagggggggctccggacccgccgggagagggggcaggggcacgtcggcgccgcgcgcgggcaggagctggtgctgcgcgc gtaggttgctggcgaacgcgacgacgcggcggttgatctcctgaatctggcgcctctgcgtgaagacgacgggcccggtgagcttga acctgaaagagagttcgacagaatcaatttcggtgtcgttgacggcggcctggcgcaaaatctcctgcacgtctcctgagttgtcttgata ggcgatctcggccatgaactgctcgatctcttcctcctggagatctccgcgtccggctcgctccacggtggcggcgaggtcgttggaaat gcgggccatgagctgcgagaaggcgttgaggcctccctcgttccagacgcggctgtagaccacgccccccttcggcatcgcgggcgc gcatgaccacctgcgcgagattgagctccacgtgccgggcgaagacggcgtagtttcgcaggcgctgaaagaggtagttgagggtgg tggcggtgtgttctgccacgaagaagtacataacccagcgtcgcaacgtggattcgttgatatcccccaaggcctcaaggcgctccatg gcctcgtagaagtccacggcgaagttgaaaaactgggagttgcgcgccgacacggttaactcctcctccagaagacggatgagctcg gcgacagtgtcgcgcacctcgcgctcaaaggctacaggggcctcttcttcttcttcaatctcctcttccataagggcctccccttcttcttctt ctggcggcggtgggggagggggggacacggcggcgacgacggcgcaccgggaggcggtcgacaaagcgctcgatcatctccccg cggcgacggcgcatggtctcggtgacggcgcggccgttctcgcgggggcgcagttggaagacgccgcccgtcatgtcccggttatg ggttggcgggggggctgccatgcggcagggatacggcgctaacgatgcatctcaacaattgttgtgtaggtactccgccgccgaggga cctgagcgagtccgcatcgaccggatcggaaaacctctcgagaaaggcgtctaaccagtcacagtcgcaaggtaggctgagcaccgt ggcgggcggcagcgggcggcggtcggggttgtttctggcggaggtgctgctgatgatgtaattaaagtaggcggtcttgagacggcg gatggtcgacagaagcaccatgtccttgggtccggcctgctgaatgcgcaggcggtcggccatgccccaggcttcgttttgacatcggc gcaggtctttgtagtagtcttgcatgagcctttctaccggcacttcttcttctccttcctcttgtcctgcatctcttgcatctatcgctgcggcgg cggcggagtttggccgtaggtggcgccctcttcctcccatgcgtgtgaccccgaagcccctcatcggctgaagcagggctaggtcggc gacaacgcgctcggctaatatggcctgctgcacctgcgtgagggtagactggaagtcatccatgtccacaaagcggtggtatgcgccc gtgttgatggtgtaagtgcagttggccataacggaccagttaacggtctggtgacccggctgcgagagctcggtgtacctgagacgcga gtaagccctcgagtcaaatacgtagtcgttgcaagtccgcaccaggtactggtatcccaccaaaaagtgcggcggcggctggcggtag aggggccagcgtagggtggccggggctccgggggcgagatcttccaacataaggcgatgatatccgtagatgtacctggacatccag gtgatgccggcggcggtggtggaggcgcgcggaaagtcgcggacgcggttccagatgttgcgcagcggcaaaaagtgctccatggt cgggacgctctggccggtcaggcgcgcgcaatcgttgacgctctagaccgtgcaaaaggagagcctgtaagcgggcactcttccgtg gtctggtggataaattcgcaagggtatcatggcggacgaccggggttcgagccccgtatccggccgtccgccgtgatccatgcggttac cgcccgcgtgtcgaacccaggtgtgcgacgtcagacaacgggggagtgctccttttggcttccttccaggcgcggcggctgctgcgct agctttttggccactggccgcgcgcagcgtaagcggttaggctggaaagcgaaagcattaagtggctcgctccctgtagccggaggg ttattttccaagggttgagtcgcgggacccccggttcgagtctcggaccggccggactgcggcgaacgggggtttgcctccccgtcatg caagaccccgcttgcaaattcctccggaaacagggacgagcccctttttgcttttcccagatgcatccggtgctgcggcagatgcgccc ccctcctcagcagcggcaagagcaagagcagcggcagacatgcagggcaccctcccctcctcctaccgcgtcaggaggggcgaca tccgcggttgacgcggcagcagatggtgattacgaaccccgcggcgccgggcccggcactacctggacttggaggagggcgagg gcctggcgcggctaggagcgccctctcctgagcggcacccaagggtgcagctgaagcgtgatacgcgtgaggcgtacgtgccgcg gcagaacctgtttcgcgaccgcgagggagaggagcccgaggagatgcgggatcgaaagttccacgcagggcgcgagctgcggcat ggcctgaatcgcgagcggttgctgcgcgaggaggactttgagcccgacgcgcgaaccgggattagtcccgcgcgcgcacacgtggc ggccgccgacctggtaaccgcatacgagcagacggtgaaccaggagattaactttcaaaaaagctttaacaaccacgtgcgtacgctt gtggcgcgcgaggaggtggctataggactgatgcatctgtgggactttgtaagcgcgctggagcaaaacccaaatagcaagccgctc atggcgcagctgttccttatagtgcagcacagcagggacaacgaggcattcagggatgcgctgctaaacatagtagagcccgagggc cgctggctgctcgatttgataaacatcctgcagagcatagtggtgcaggagcgcagcttgagcctggctgacaaggtggccgccatca actattccatgcttagcctgggcaagttttacgcccgcaagatataccataccccttacgttcccatagacaaggaggtaaagatcgaggg gttctacatgcgcatggcgctgaaggtgcttaccttgagcgacgacctgggcgtttatcgcaacgagcgcatccacaaggccgtgagc gtgagccggcggcgcgagctcagcgaccgcgagctgatgcacagcctgcaaagggccctggctggcacgggcagcggcgataga TABLE 2-continued gaggccgagtcctactttgacgcgggcgctgacctgcgctgggccccaagccgacgcgccctggaggcagctggggccggacctg
ggctggcggtggcacccgcgcgcgctggcaacgtcggcggcgtggaggaatatgacgaggacgatgagtacgagccagaggacg
gcgagtactaagcggtgatgtttctgatcagatgatgcaagacgcaacggacccggcggtgcgggcggcgctgcagagccagccgt
ccggccttaactccacggacgactggcgccaggtcatggaccgcatcatgtcgctgactgcgcgcaatcctgacgcgttccggcagca
gccgcaggccaaccggctctccgcaattctggaagcggtggtcccggcgcgcgcaaaccccacgcacgagaaggtgctggcgatc
gtaaacgcgctggccgaaaacagggccatccggcccgacgaggccggcctggtctacgacgcgctgcttcagcgcgtggctcgtta
caacagcggcaacgtgcagaccaacctggaccggctggtgggggatgtgcgcgaggccgtggcgcagcgtgagcgcgcgcagca
gcagggcaacctgggctccatggttgcactaaacgccttcctgagtacacagcccgccaacgtgccgcggggacaggaggactaca
ccaactttgtgagcgcactgcggctaatggtgactgagacaccgcaaagtgaggtgtaccagtctgggccagactattttttccagacca
gtagacaaggcctgcagaccgtaaacctgagccaggctttcaaaaacttgcaggggctgtggggggtgcgggctcccacaggcgac
cgcgcgaccgtgtctagcttgctgacgcccaactcgcgcctgttgctgctgctaatagcgcccttcacggacagtggcagcgtgtcccg
ggacacatacctaggtcacttgctgacactgtaccgcgaggccataggtcaggcgcatgtggacgagcatactttccaggagattacaa
gtgtcagccgcgcgctggggcaggaggacacgggcagcctggaggcaaccctaaactacctgctgaccaaccggcggcagaagat
cccctcgttgcacagtttaaacagcgaggaggagcgcattttgcgctacgtgcagcagagcgtgagccttaacctgatgcgcgacggg
gtaacgcccagcgtggcgctggacatgaccgcgcgcaacatggaaccgggcatgtatgcctcaaaccggccgtttatcaaccgccta
atggactacttgcatcgcgcggccgccgtgaaccccgagtatttcaccaatgccatcttgaacccgcactggctaccgcccccctggtttct
acaccgggggattcgaggtgcccgagggtaacgatggattcctctgggacgacatagacgacagcgtgttttccccgcaaccgcaga
ccctgctagagttgcaacagcgcgagcaggcagaggcggcgctgcgaaaggaaagcttccgcaggccaagcagcttgtccgatcta
ggcgctgcggccccgcggtcagatgctagtagcccatttccaagcttgatagggtctcttaccagcactcgcaccacccgcccgcgcct
gctgggcgaggaggagtacctaaacaactcgctgctgcagccgcagcgcgaaaaaaacctgcctccggcatttcccaacaacgggat
agagagcctagtggacaagatgagtagatggaagacgtacgcgcaggagcacagggacgtgccaggcccgcgcccgcccacccg
tcgtcaaaggcacgaccgtcagcggggtctggtgtgggaggacgatgactcggcagacgacagcagcgtcctggatttgggaggga
gtggcaacccgtttgcgcaccttcgccccaggctggggagaatgttttaaaaaaaaaaaaaagcatgatgcaaaataaaaaactcacca
aggccatggcaccgagcgttggttttcttgtattccccttagtatgcggcgcgcggcgatgtatgaggaaggtcctcctccctcctacgag
agtgtggtgagcgcggcgccagtggcggcggcgctgggttctcccttcgatgctcccctggacccgccgtttgtgcctccgcggtacct
gcggcctaccggggggagaaacagcatccgttactctgagttggcacccctattcgacaccacccgtgtgtacctggtggacaacaag
tcaacggatgtggcatccctgaactaccagaacgaccacagcaactttctgaccacggtcattcaaaacaatgactacagcccggggg
aggcaagcacacagaccatcaatcttgacgaccggtcgcactggggggcgacctgaaaaccatcctgcataccaacatgccaaatgt
gaacgagttcatgtttaccaataagtttaaggcgcgggtgatggtgtcgcgcttgcctactaaggacaatcaggtggagctgaaatacga
gtgggtggagttcacgctgcccgagggcaactactccgagaccatgaccatagaccttatgaacaacgcgatcgtggagcactacttg
aaagtgggcagacagaacggggttctggaaagcgacatcggggtaaagtttgacacccgcaacttcagactggggtttgaccccgtca
ctggtcttgtcatgcctggggtatatacaaacgaagccttccatccagacatcattttgctgccaggatgcggggtggacttcacccacag
ccgcctgagcaacttgttgggcatccgcaagcggcaacccttccaggagggctttaggatcacctacgatgatctggagggtggtaaca
ttcccgcactgttggatgtggacgcctaccaggcgagcttgaaagatgacaccgaacaggggggggtggcgcaggggcagcaac
agcagtggcagcggcgcggaagagaactccaacgcggcagccgcggcaatgcagccggtggaggacatgaacgatcatgccattc
gcggcgacacctttgccacacgggctgaggagaagcgcgctgaggccgaagcagcggccgaagctgccgcccccgctgcgcaac
ccgaggtcgagaagcctcagaagaaaccggtgatcaaacccctgacagaggacagcaagaaacgcagttacaacctaataagcaat
gacagcaccttcacccagtaccgcagctggtaccttgcatacaactacggcgaccctcagaccggaatccgctcatggaccctgcttg
cactcctgacgtaacctgcggctcggagcaggtctactggtcgttgccagacatgatgcaagaccccgtgaccttccgctccacgcgcc
agatcagcaactttccggtggtgggcgccgagctgttgcccgtgcactccaagagcttctacaacgaccaggccgtctactcccaactc TABLE 2-continued atccgccagtttacctctctgacccacgtgttcaatcgctttcccgagaaccagattttggcgcgcccgccagcccccaccatcaccacc gtcagtgaaaacgttcctgctctcacagatcacgggacgctaccgctgcgcaacagcatcggaggagtccagcgagtgaccattactg acgccagacgccgcacctgcccctacgtttacaaggccctgggcatagtctcgccggcgtcctatcgagccgcactttttgagcaagc atgtccatccttatatcgcccagcaataacacaggctggggcctgcgcttcccaagcaagatgtttgggggccaagaagcgctccga ccaacacccagtgcgcgtgcgcgggcactaccgcgcgccctggggcgcgcacaaacgcggccgcactgggcgcaccaccgtcga tgacgccatcgacgcggtggtggaggaggcgcgcaactacacgcccacgccgccaccagtgtccacagtggacgcggccattcag accgtggtgcgcggagcccggcgctatgctaaaatgaagagacggcggaggcgcgtagcacgtcgccaccgccgccgacccggc actgccgcccaacgcgcggcggcggccctgcttaaccgcgcacgtcgcaccggccgacgggcggccatgcgagcagctcgaagg ctggccgcgggtattgtcactgtgcccccaggtccaggcgacgagcggccgccgcagcagccgcggccattagtgctatgactcag ggtcgcaggggcaacgtgtattgggtgcgcgactcggttagcggcctgcgcgtgcccgtgcgcacccgcccccgcgcaactagatt gcaagaaaaaactacttagactcgtactgttgtatgtatccagcggcggcggcgcgcaacgaagctatgtccaagcgcaaaatcaaag aagagatgctccaggtcatcgcgccggagatctatggcccccgaagaaggaagagcaggattacaagccccgaaagctaaagcgg gtcaaaaagaaaaagaaagatgatgatgatgaacttgacgacgaggtggaactgctgcacgctaccgcgcccaggcgacgggtaca gtggaaaggtcgacgcgtaaaacgtgttttgcgacccggcaccaccgtagtctttacgcccggtgagcgctccacccgcacctacaag cgcgtgtatgatgaggtgtacggcgacgaggacctgcttgagcaggccaacgagcgcctcggggagtttgcctacggaaagcggcat aaggacatgctggcgttgccgctggacgagggcaacccaacacctagcctaaagcccgtaacactgcagcaggtgctgcccgcgctt gcaccgtccgaagaaaagcgcggcctaaagcgcgagtctggtgacttggcacccaccgtgcagctgatggtacccaagcgccagcg actggaagatgtcttggaaaaaatgaccgtggaacctgggctggagcccgaggtccgcgtgcggccaatcaagcaggtggcgccgg gactgggcgtgcagaccgtggacgttcagatacccactaccagtagcaccagtattgccaccgccacagagggcatggagacacaaa cgtccccggttgcctcagcggtggcggatgccgcggtgcaggcggtcgctgcggccgcgtccaagacctctacggaggtgcaaacg gacccgtggatgtttcgcgtttcagcccccggcgcccgcgccgttcgaggaagtacggcgccgccagcgcgctactgcccgaatat gccctacatccttccattgcgcctacccccggctatcgtggctacacctaccgccccagaagacgagcaactacccgacgccgaacca ccactggaacccgccgccgccgtcgccgtcgccagcccgtgctggccccgatttccgtgcgcagggtggctcgcgaaggaggcag gaccctggtgctgccaacagcgcgctaccaccccagcatcgtttaaaagccggtctttgtggttcttgcagatatggccctcacctgccg cctccgtttcccggtgccgggattccgaggaagaatgcaccgtaggaggggcatggccggccacggcctgacgggcggcatgcgtc gtgcgcaccaccggcggcggcgcgcgtcgcaccgtcgcatgcgcggcggtatcctgcccctccttattccactgatcgccgcggcga ttggcgccgtgcccggaattgcatccgtggccttgcaggcgcagagacactgattaaaaacaagttgcatgtggaaaaatcaaaataaa aagtctggactctcacgctcgcttggtcctgtaactattttgtagaatggaagacatcaactttgcgtctctggccccgcgacacggctcgc gcccgttcatgggaaactggcaagatatcggcaccagcaatatgagcggtggcgccttcagctggggctcgctgtggagcggcattaa aaatttcggttccaccgttaagaactatggcagcaaggcctggaacagcagcacaggccagatgctgagggataagttgaaagagcaa aatttccaacaaaaggtggtagatggcctggcctctggcattagcggggtggtggacctggccaaccaggcagtgcaaaataagattaa cagtaagcttgatccccgccctcccgtagaggagcctccaccggccgtggagacagtgtctccagaggggcgtggcgaaaagcgtcc gcgccccgacagggaagaaactctggtgacgcaaatagacgagcctccctcgtacgaggaggcactaaagcaaggcctgcccacca cccgtcccatcgcgcccatggctaccggagtgctgggccagcacacacccgtaacgctggacctgcctcccccgccgacacccag cagaaacctgtgctgccaggcccgaccgccgttgttgtaacccgtcctagccgcgcgtccctgcgccgcgccgccagcggtccgcga tcgttgcggcccgtagccagtggcaactggcaaagcacactgaacagcatcgtgggtctgggggtgcaatccctgaagcgccgacga tgcttctgatagctaacgtgtcgtatgtgtgtcatgtatgcgtccatgtcgccgccagaggagctgctgagccgccgcgcgcccgctttcc aagatggctaccccttcgatgatgccgcagtggtcttacatgcacatctcgggccaggacgcctcggagtacctgagccccgggctggt gcagtttgcccgcgccaccgagacgtacttcagcctgaataacaagtttagaaccccacggtggcgcctacgcacgacgtgaccaca gaccggtcccagcgtttgacgctgcggttcatccctgtggaccgtgaggatactgcgtactcgtacaaggcgcggttcaccctagctgtg TABLE 2-continued ggtgataaccgtgtgctggacatggcttccacgtactttgacatccgcggcgtgctggacaggggccctacttttaagccctactctggca ctgcctacaacgccctggctcccaagggtgccccaaatccttgcgaatgggatgaagctgctactgctcttgaaataaacctagaagaa gaggacgatgacaacgaagacgaagtagacgagcaagctgagcagcaaaaaactcacgtatttgggcaggcgccttattctggtataa atattacaaaggagggtattcaaataggtgtcgaaggtcaaacacctaaatatgccgataaaacatttcaacctgaacctcaaataggaga atctcagtggtacgaaacagaaattaatcatgcagctgggagagtcctaaaaaagactaccccaatgaaaccatgttacggttcatatgc aaaacccacaaatgaaaatggagggcaaggcattcttgtaaagcaacaaaatggaaagctagaaagtcaagtggaaatgcaatttttctc aactactgaggcagccgcaggcaatggtgataacttgactcctaaagtggtattgtacagtgaagatgtagatatagaaaccccagacac tcatatttcttacatgcccactattaaggaaggtaactcacgagaactaatgggccaacaatctatgcccaacaggcctaattacattgctttt agggacaattttattggtctaatgtattacaacagcacgggtaatatgggtgttctggcgggccaagcatcgcagttgaatgctgttgtaga tttgcaagacagaaacacagagctttcataccagcttttgcttgattccattggtgatagaaccaggtacttttctatgtggaatcaggctgtt gacagctatgatccagatgttagaattattgaaaatcatggaactgaagatgaacttccaaattactgctttccactgggaggtgtgattaat acagagactcttaccaaggtaaaacctaaaacaggtcaggaaaatggatgggaaaaagatgctacagaattttcagataaaaatgaaat aagagttggaaataattttgccatggaaatcaatctaaatgccaacctgtggagaaatttcctgtactccaacatagcgctgtatttgcccga caagctaaagtacagtccttccaacgtaaaaatttctgataacccaaacacctacgactacatgaacaagcgagtggtggctcccgggct agtggactgctacattaaccttggagcacgctggtcccttgactatatggacaacgtcaacccatttaaccaccaccgcaatgctggcctg cgctaccgctcaatgttgctgggcaatggtcgctatgtgcccttccacatccaggtgcctcagaagttctttgccattaaaaacctccttctc ctgccgggctcatacacctacgagtggaacttcaggaaggatgttaacatggttctgcagagctccctaggaaatgacctaagggttgac ggagccagcattaagtttgatagcatttgcctttacgccaccttcttccccatggcccacaacaccgcctccacgcttgaggccatgcttag aaacgacaccaacgaccagtcctttaacgactatctctccgccgccaacatgctctaccctatacccgccaacgctaccaacgtgcccat atccatcccctcccgcaactgggcggctttccgcggctgggccttcacgcgccttaagactaaggaaaccccatcactgggctcgggct acgaccctta ttacacctactctggctctataccctacctagatggaaccttttacctcaaccacacctttaagaaggtggccattacctttga ctcttctgtcagctggcctggcaatgaccgcctgcttacccccaacgagtttgaaattaagcgctcagttgacggggagggttacaacgtt gcccagtgtaacatgaccaaagactggttcctggtacaaatgctagctaactataacattggctaccagggcttctatatcccagagagct acaaggaccgcatgtactccttctttagaaacttccagcccatgagccgtcaggtggtggatgatactaaatacaaggactaccaacagg tgggcatcctacaccaacacaacaactctggatttgttggctaccttgcccccaccatgcgcgaaggacaggcctaccctgctaacttcc cctatccgcttataggcaagaccgcagttgacagcattacccagaaaaagtttctttgcgatcgcaccctttggcgcatcccattctccagt aactttatgtccatgggcgcactcacagacctgggccaaaaccttctctacgccaactccgcccacgcgctagacatgacttttgaggtg gatcccatggacgagcccacccttctttatgttttgtttgaagtctttgacgtggtccgtgtgcaccagccgcaccgcggcgtcatcgaaac cgtgtacctgcgcacgcccttctcggccggcaacgccacaacataaagaagcaagcaacatcaacaacagctgccgccatgggctcc agtgagcaggaactgaaagccattgtcaaagatcttggttgtgggccatatttttttgggcacctatgacaagcgctttccaggctttgtttct ccacacaagctcgcctgcgccatagtcaatacggccggtcgcgagactgggggcgtacactggatggcctttgcctggaacccgcact caaaaacatgctacctctttgagccctttggcttttctgaccagcgactcaagcaggtttaccagtttgagtacgagtcactcctgcgccgta gcgccattgcttcttcccccgaccgctgtataacgctggaaaagtccacccaaagcgtacaggggcccaactcggccgcctgtggact attctgctgcatgtttctccacgcctttgccaactggccccaaactcccatggatcacaaccccaccatgaaccttattaccggggtaccca actccatgctcaacagtccccaggtacagcccaccctgcgtcgcaaccaggaacagctctacagcttcctggagcgccactcgcccta cttccgcagccacagtgcgcagattaggagcgccacttctttttgtcacttgaaaaacatgtaaaaataatgtactagagacactttcaataa aggcaaatgcttttatttgtacactctcgggtgattatttacccccacccttgccgtctgcgccgtttaaaaatcaaaggggttctgccgcgc atcgctatgcgccactggcagggacacgttgcgatactggtgtttagtgctccacttaaactcaggcacaaccatccgcggcagctcggt gaagttttcactccacaggctgcgcaccatcaccaacgcgtttagcaggtcggggccgatatcttgaagtcgcagttggggcctccgc cctgcgcgcgcgagttgcgatacacagggttgcagcactggaacactatcagcgccgggtggtgcacgctggccagcacgctcttgtc TABLE 2-continued ggagatcagatccgcgtccaggtcctccgcgttgctcagggcgaacggagtcaactttggtagctgccttcccaaaaagggcgcgtgc
ccaggctttgagttgcactcgcaccgtagtggcatcaaaaggtgaccgtgcccggtctgggcgttaggatacagcgcctgcataaaagc
cttgatctgcttaaaagccacctgagcctttgcgccttcagagaagaacatgccgcaagacttgccggaaaactgattggccggacacg
cggcgtcgtgcacgcagcaccttgcgtcggtgttggagatctgcaccacatttcggccccaccggttcttcacgatcttggccttgctaga
ctgctccttcagcgcgcgctgcccgttttcgctcgtcacatccatttcaatcacgtgctccttatttatcataatgcttccgtgtagacacttaa
gctcgccttcgatctcagcgcagcggtgcagccacaacgcgcagcccgtgggctcgtgatgcttgtaggtcacctctgcaaacgactg
caggtacgcctgcaggaatcgccccatcatcgtcacaaaggtcttgttgctggtgaaggtcagctgcaacccgcggtgctcctcgttcag
ccaggtcttgcatacggccgccagagcttccacttggtcaggcagtagtttgaagttcgcctttagatcgttatccacgtggtacttgtccat
cagcgcgcgcgcagcctccatgcccttctcccacgcagacacgatcggcacactcagcgggttcatcaccgtaatttcactttccgcttc
gctgggctcttcctcttcctcttgcgtccgcataccacgcgccactgggtcgtcttcattcagccgccgcactgtgcgcttacctcctttgcc
atgcttgattagcaccggtgggttgctgaaacccaccatttgtagcgccacatcttctctttcttcctcgctgtccacgattacctctggtgat
ggcgggcgctcgggcttgggagaagggcgcttctttttcttcttgggcgcaatggccaaatccgccgccgaggtcgatggccgcgggc
tgggtgtgcgcggcaccagcgcgtcttgtgatgagtcttcctcgtcctcggactcgatacgccgcctcatccgcttttttgggggcgcccg
gggaggcggcggcgacggggacggggacgacacgtcctccatggttggggggacgtcgcgccgcaccgcgtccgcgctcgggggt
ggtttcgcgctgctcctcttcccgactggccatttccttctcctataggcagaaaaagatcatggagtcagtcgagaagaaggacagccta
accgcccccctctgagttcgccaccaccgcctccaccgatgccgccaacgcgcctaccaccttccccgtcgaggcaccccccgcttgag
gaggaggaagtgattatcgagcaggacccaggttttgtaagcgaagacgacgaggaccgctcagtaccaacagaggataaaaagca
agaccaggacaacgcagaggcaaacgaggaacaagtcgggggggggggacgaaaggcatggcgactacctagatgtgggagacg
acgtgctgttgaagcatctgcagcgccagtgcgccattatctgcgacgcgttgcaagagcgcagcgatgtgcccctcgccatagcggat
gtcagccttgcctacgaacgccacctattctcaccgcgcgtaccccccaaacgccaagaaaacggcacatgcgagcccaacccgcgc
ctcaacttctaccccgtatttgccgtgccagaggtgcttgccacctatcacatctttttccaaaactgcaagatacccctatcctgccgtgcc
aaccgcagccgagcggacaagcagctggccttgcggcagggcgctgtcatacctgatatcgcctcgctcaacgaagtgccaaaaatc
tttgagggtcttggacgcgacgagaagcgcgcggcaaacgctctgcaacaggaaaacagcgaaaatgaaagtcactctggagtgttg
gtggaactcgagggtgacaacgcgcgcctagccgtactaaaacgcagcatcgaggtcacccactttgcctacccggcacttaacctac
cccccaaggtcatgagcacagtcatgagtgagctgatcgtgcgccgtgcgcagcccctggagagggatgcaaatttgcaagaacaaa
cagaggagggcctacccgcagttggcgacgagcagctagcgcgctggcttcaaacgcgcgagcctgccgacttggaggagcgacg
caaactaatgatggccgcagtgctcgttaccgtggagcttgagtgcatgcagcggttctttgctgacccggagatgcagcgcaagctag
aggaaacattgcactacacctttcgacagggctacgtacgccaggcctgcaagatctccaacgtggagctctgcaacctggtctcctac
cttggaattttgcacgaaaaccgccttgggcaaaacgtgcttcattccacgctcaagggcgaggcgcgccgcgactacgtccgcgact
gcgtttacttatttctatgctacacctggcagacggccatgggcgtttggcagcagtgcttggaggagtgcaacctcaaggagctgcaga
aactgctaaagcaaaacttgaaggacctatggacggccttcaacgagcgctccgtggccgcgcacctggcggacatcattttccccga
acgcctgcttaaaaccctgcaacagggtctgccagacttcaccagtcaaagcatgttgcagaactttaggaactttatcctagagcgctca
ggaatcttgcccgccacctgctgtgcacttcctagcgactttgtgcccattaagtaccgcgaatgccctccgccgctttggggccactgct
accttctgcagctagccaactaccttgcctaccactctgacataatggaagacgtgagcggtgacggtctactggagtgtcactgtcgctg
caacctatgcaccccgcaccgctccctggtttgcaattcgcagctgcttaacgaaagtcaaattatcggtacctttgagctgcagggtccc
tcgcctgacgaaaagtccgcggctccggggttgaaactcactccggggctgtggacgtcggcttaccttcgcaaatttgtacctgagga
ctaccacgcccacgagattaggttctacgaagaccaatcccgcccgcctaatgcggagcttaccgcctgcgtcattacccagggccac
attcttggccaattgcaagccatcaacaaagcccgccaagagtttctgctacgaaagggacggggggtttacttggacccccagtccgg
cgaggagctcaacccaatccccccgccgccgcagccctatcagcagcagccgcgggcccttgcttcccaggatggcacccaaaaag
aagctgcagctgccgccgccacccacggacgaggaggaatactgggacagtcaggcagaggaggttttggacgaggaggaggag TABLE 2-continued gacatgatggaagactgggagagcctagacgaggaagcttccgaggtcgaagaggtgtcagacgaaacaccgtcaccctcggtcgc
attcccctcgccggcgccccagaaatcggcaaccggttccagcatggctacaacctccgctcctcaggcgccgccggcactgcccgtt
cgccgacccaaccgtagatgggacaccactggaaccagggccggtaagtccaagcagccgccgccgttagcccaagagcaacaac
agcgccaaggctaccgctcatggcgcgggcacaagaacgccatagttgcttgcttgcaagactgtgggggcaacatctccttcgcccg
ccgctttcttctctaccatcacggcgtggccttcccccgtaacatcctgcattactaccgtcatctctacagcccatactgcaccggcggca
gcggcagcaacagcagcggccacacagaagcaaaggcgaccggatagcaagactctgacaaagcccaagaaatccacagcggcg
gcagcagcaggaggaggagcgctgcgtctggcgcccaacgaacccgtatcgacccgcgagcttagaaacaggatttttcccactctgt
atgctatatttcaacagagcaggggccaagaacaagagctgaaaataaaaaacaggtctctgcgatccctcacccgcagctgcctgtat
cacaaaagcgaagatcagcttcggcgcacgctggaagacgcggaggctctcttcagtaaatactgcgcgctgactcttaaggactagtt
tcgcgccctttctcaaatttaagcgcgaaaactacgtcatctccagcggccacacccggcgccagcacctgttgtcagcgccattatgag
caaggaaattcccacgccctacatgtggagttaccagccacaaatgggacttgcggctggagctgcccaagactactcaacccgaata
aactacatgagcgcgggaccccacatgatatcccgggtcaacggaatacgcgcccaccgaaaccgaattctcctggaacaggcggct
attaccaccacacctcgtaataaccttaatccccgtagttggcccgctgccctggtgtaccaggaaagtcccgctcccaccactgtggtac
ttcccagagacgcccaggccgaagttcagatgactaactcaggggcgcagcttgcgggcggctttcgtcacagggtgcggtcgcccg
ggcagggtataactcacctgacaatcagagggcgaggtattcagctcaacgacgagtcggtgagctcctcgcttggtctccgtccggac
gggacatttcagatcggcggcgccggccgctcttcattcacgcctcgtcaggcaatcctaactctgcagacctcgtcctctgagccgcg
ctctggaggcattggaactctgcaatttattgaggagtttgtgccatcggtctactttaaccccttctcgggacctcccggccactatccgga
tcaatttattcctaactttgacgcggtaaaggactcggcggacggctacgactgaatgttaagtggccaatgaggcctgacgctaataata
gctggtccactgtcgccgccacaagtgctttgcccgcgactccggtgagttttgctactttgaattgcccgaggatcatatcgagggcccg
gcgcacggcgtccggcttaccgcccagggagagcttgcccgtagcctgattcgggagtttacccagcgcccccctgctagttgagcgg
gacaggggaccctgtgttctcactgtgatttgcaactgtcctaaccttggattacatcaagatccagatcttctagacccgggagcggccg
ctgtcgacctgcaggatccgaattcgatatcactagtggtaccgatcttattccctttaactaataaaaaaaaataataaagcatcacttactt
aaaatcagttagcaaatttctgtccagtttattcagcagcacctccttgccctcctcccagctctggtattgcagcttcctcctggctgcaaac
tttctccacaatctaaagggaatgtcagtttcctcctgttcctgtccatccgcacccactatcttcatgttgttgcagatgaagcgcgcaagac
cgtctgaagataccttcaaccccgtgtatccatatgacacggaaaccggtcctccaactgtgccttttcttactcctccctttgtatcccccaa
tgggtttcaagagagtccccctggggtactctctttgcgcctatccgaacctctagttacctccaatggcatgcttgcgctcaaaatgggca
acggcctctctctggacgaggccggcaaccttacctcccaaaatgtaaccactgtgagcccacctctcaaaaaaaccaagtcaaacata
aacctggaaatatctgcacccctcacagttacctcagaagccctaactgtggctgccgccgcacctctaatggtcgcgggcaacacact
caccatgcaatcacaggccccgctaaccgtgcacgactccaaacttagcattgccacccaaggacccctcacagtgtcagaaggaaag
ctagccctgcaaacatcaggcccccctcaccaccaccgatagcagtacccttactatcactgcctcacccccctctaactactgccactggta
gcttgggcattgacttgaaagagcccatttatacacaaaatggaaaactaggactaaagtacggggctcctttgcatgtaacagacgacc
taaacactttgaccgtagcaactggtccaggtgtgactattaataatacttccttgcaaactaaagttactggagccttgggttttgattcaca
aggcaatatgcaacttaatgtagcaggaggactaaggattgattctcaaaacagacgccttatacttgatgttagttatccgtttgatgctca
aaaccaactaaatctaagactaggacagggccctctttttataaactcagcccacaacttggatattaactacaacaaaggcctttacttgtt
tacagcttcaaacaattccaaaaagcttgaggttaacctaagcactgccaaggggttgatgtttgacgctacagccatagccattaatgca
ggagatgggcttgaatttggttcacctaatgcaccaaacacaaatcccctcaaaacaaaaattggccatggcctagaatttgattcaaaca
aggctatggttcctaaactaggaactggccttagttttgacagcacaggtgccattacagtaggaaacaaaaataatgataagctaactttg
tggaccacaccagctccatctcctaactgtagactaaatgcagagaaagatgctaaactcactttggtcttaacaaaatgtggcagtcaaa
tacttgctacagtttcagttttggctgttaaaggcagtttggctccaatatctggaacagttcaaagtgctcatcttattataagatttgacgaaa
atggagtgctactaaacaattccttcctggacccagaatattggaactttagaaatggagatcttactgaaggcacagcctatacaaacgct TABLE 2-continued gttggatttatgcctaacctatcagcttatccaaaatctcacggtaaaactgccaaaagtaacattgtcagtcaagtttacttaaacggagac aaaactaaacctgtaacactaaccattacactaaacggtacacaggaaacaggagacacaactccaagtgcatactctatgtcattttcat gggactggtctggccacaactacattaatgaaatatttgccacatcctcttacacttttttcatacattgcccaagaataaagaatcgtttgtgtt atgtttcaacgtgtttatttttcaattgcagaaaatttcaagtcatttttcattcagtagtatagccccaccaccacatagcttatacagatcacc gtaccttaatcaaactcacagaaccctagtattcaacctgccacctccctcccaacacacagagtacacagtcctttctccccggctggcc ttaaaaagcatcatatcatgggtaacagacatattcttaggtgttatattccacacggtttcctgtcgagccaaacgctcatcagtgatattaa taaactccccgggcagctcacttaagttcatgtcgctgtccagctgctgagccacaggctgctgtccaacttgcggttgcttaacgggcg gcgaaggagaagtccacgcctacatgggggtagagtcataatcgtgcatcaggatagggcggtggtgctgcagcagcgcgcgaata aactgctgccgccgccgctccgtcctgcaggaatacaacatggcagtggtctcctcagcgatgattcgcaccgcccgcagcataaggc gccttgtcctccgggcacagcagcgcaccctgatctcacttaaatcagcacagtaactgcagcacagcaccacaatattgttcaaaatcc cacagtgcaaggcgctgtatccaaagctcatggcggggaccacagaacccacgtggccatcataccacaagcgcaggtagattaagt ggcgacccctcataaacacgctggacataaacattacctcttttggcatgttgtaattcaccacctcccggtaccatataaacctctgattaa acatggcgccatccaccaccatcctaaaccagctggccaaaacctgcccgccggctatacactgcagggaaccgggactggaacaat gacagtggagagcccaggactcgtaaccatggatcatcatgctcgtcatgatatcaatgttggcacaacacaggcacacgtgcatacac ttcctcaggattacaagctcctcccgcgttagaaccatatcccagggaacaacccattcctgaatcagcgtaaatcccacactgcaggga agacctcgcacgtaactcacgttgtgcattgtcaaagtgttacattcgggcagcagcggatgatcctccagtatggtagcgcgggtttctg tctcaaaaggaggtagacgatccctactgtacggagtgcgccgagacaaccgagatcgtgttggtcgtagtgtcatgccaaatggaacg ccggacgtagtcatatttcctgaagcaaaaccaggtgcgggcgtgacaaacagatctgcgtctccggtctcgccgcttagatcgctctgt gtagtagttgtagtatatccactctctcaaagcatccaggcgcccctggcttcgggttctatgtaaactccttcatgcgccgctgccctgat aacatccaccaccgcagaataagccacacccagccaacctacacattcgttctgcgagtcacacacgggaggagcgggaagagctg gaagaaccatgtttttttttttattccaaaagattatccaaaacctcaaaatgaagatctattaagtgaacgcgctcccctccggtggcgtgg tcaaactctacagccaaagaacagataatggcatttgtaagatgttgcacaatggcttccaaaaggcaaacggccctcacgtccaagtgg acgtaaaggctaaacccttcagggtgaatctcctctataaacattccagcaccttcaaccatgcccaaataattctcatctcgccaccttctc aatatatctctaagcaaatcccgaatattaagtccggccattgtaaaaatctgctccagagcgccctccaccttcagcctcaagcagcgaa tcatgattgcaaaaattcaggttcctcacagacctgtataagattcaaaagcggaacattaacaaaaataccgcgatcccgtaggtcccttc gcagggccagctgaacataatcgtgcaggtctgcacggaccagcgcggccacttccccgccaggaaccatgacaaaagaacccaca ctgattatgacacgcatactcggagctatgctaaccagcgtagccccgatgtaagcttgttgcatgggcggcgatataaaatgcaaggtg ctgctcaaaaaatcaggcaaagcctcgcgcaaaaaagaaagcacatcgtagtcatgctcatgcagataaaggcaggtaagctccggaa ccaccacagaaaaagacaccatttttctctcaaacatgtctgcgggtttctgcataaacacaaaataaaataacaaaaaaacatttaaacat tagaagcctgtcttacaacaggaaaaacaacccttataagcataagacggactacggccatgccggcgtgaccgtaaaaaaactggtc accgtgattaaaaagcaccaccgacagctcctcggtcatgtccggagtcataatgtaagactcggtaaacacatcaggttgattcacatc ggtcagtgctaaaaagcgaccgaaatagcccgggggaatacatacccgcaggcgtagagacaacattacagccccccataggaggtat aacaaaattaataggagagaaaaacacataaacacctgaaaaaccctcctgcctaggcaaaatagcaccctcccgctccagaacaaca tacagcgcttccacagcggcagccataacagtcagccttaccagtaaaaaagaaaacctattaaaaaaacaccactcgacacggcacc agctcaatcagtcacagtgtaaaaaagggccaagtgcagagcgagtatatataggactaaaaaatgacgtaacggttaaagtccacaaa aaacacccagaaaaccgcacgcgaacctacgcccagaaacgaaagccaaaaaacccacaacttcctcaaatcgtcacttccgttttcc cacgttacgtaacttcccattttaagaaaactacaattcccaacacatacaagttactccgccctaaaacctacgtcacccgccccgttccc acgccccgcgccacgtcacaaactccacccccctcattatcatattggcttcaatccaaaataaggtatattattgatgatgttaatttgggcc attagacttgaagtcaagcggccgcttacaactggaccttgctggtacatagaactgattaactgaccatttaaatcataccaacatggtca aataaaacgaaaggctcagtcgaaagactgggcctttcgttttaatctgatcggcacgtaagaggttccaactttcaccataatgaaataa TABLE 2-continued

| |
|---|
| gatcactaccgggcgtatttttttgagttatcgagattttcaggagctaaggaagctaaaatgagccatattcaacgggaaacgtcttgctcg |
| aggccgcgattaaattccaacatggatgctgatttatatgggtataaatgggctcgcgataatgtcgggcaatcaggtgcgacaatctatc |
| gattgtatgggaagcccgatgcgccagagttgtttctgaaacatggcaaaggtagcgttgccaatgatgttacagatgagatggtcaggc |
| taaactggctgacggaatttatgcctcttccgaccatcaagcattttatccgtactcctgatgatgcatggttactcaccactgcgatcccag |
| ggaaaacagcattccaggtattagaagaatatcctgattcaggtgaaaatattgttgatgcgctggcagtgttcctgcgccggttgcattcg |
| attcctgtttgtaattgtccttttaacggcgatcgcgtatttcgtctcgctcaggcgcaatcacgaatgaataacggtttggttggtgcgagtg |
| attttgatgacgagcgtaatggctggcctgttgaacaagtctggaaagaaatgcataaacttttgccattctcaccggattcagtcgtcactc |
| atggtgatttctcacttgataaccttatttttgacgaggggaaattaataggttgtattgatgttggacgagtcggaatcgcagaccgatacc |
| aggatcttgccatcctatggaactgcctcggtgagttttctccttcattacagaaacggctttttcaaaaatatggtattgataatcctgatatg |
| aataaattgcagtttcacttgatgctcgatgagtttttctaacctaggtgacagaagtcaaaagcctccggtcggaggcttttgactttctgct |
| agatctgtttcaatgcggtgaagggccaggcagctggggattatgtcgagacccggccagcatgttggttttatcgcatattcagcgttgt |
| cgcgtttacccaggtaaaatggaagcagtgtatcgtctgcgtgaatgtgcaaatcaggaacgtaaccgtggtacatagatgcagtccctt |
| gcgggtcgttcccttcaacgagtaggacgcggtgcccttgcaaggctaaccattgcgcctggtgtactgcagatgaggttttataaaccc |
| ctcccttgtgtgacataacggaaagtacaaccgggtttttatcgtcaggtctttggtttgggttaccaaacacactccgcatatggctaatttg |
| gtcaattgtgtagccagcgcgacgttctactcggcccctcatctcaaaatcaggagccggtagacgaccagctttttccgcgtctctgata |
| gcctgcggtgttacgccgatcaggtctgcaacttctgttataccccagcggcgagtaatacgacgcgcttccgggctgtcatcgccgaac |
| tgtgcgatggcaatagcgcgcgtcatttcctgaccgcgattgatacagtctttcagcaaattaattaacgacatcctgtttcctctcaaacat |
| gcccttatctttgtgtttttcatcatactttacgtttttaaagcaaagcaacataaaaaaagcaaagtgacttagaaaacgcaaagttaaggttc |
| aaatcaatttttttgatgcgctacagaagctatttagcttcatctaagcgcaacggtattacttacgttggtatatttaaaacctaacttaatgattt |
| taaatgataataaatcataccaattgctatcaaaagttaagcgaacatgctgattttcacgctgtttatacactttgaggcatctctatctcttcc |
| gtctctatattgaaacacaatcaaagaacatcaatccatgtgacatcccccactatctaagaacaccataacagaacacaacataggaatg |
| caacattaatgtatcaataattcggaacatatgcactatatcatatctcaattacggaacatatcagcacacaattgcccattatacgc |

TABLE 3

| Ad5 Vector Full |
|---|
| (SEQ ID NO: 3) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttattattatagtcagctga |
| cgtgtagtgtatttatacccggtgagttcctcaagaggccactcttgagtgccagcgagtagagttttctcctccgagccgctccgacacc |
| gggactgaaaatgagacatattatctgccacggaggtgttattaccgaagaaatggccgccagtcttttggaccagctgatcgaagaggt |
| actggctgataatcttccacctcctagccattttgaaccacctacccttcacgaactgtatgatttagacgtgacggcccccgaagatccca |
| acgaggaggcggtttcgcagatttttcccgactctgtaatgttggcggtgcaggaagggattgacttactcacttttccgccggcgcccgg |
| ttctccggagccgcctcacctttcccggcagcccgagcagccggagcagagagccttgggtccggtttctatgccaaaccttgtaccgg |
| aggtgatcgatcttacctgccacgaggctggctttccacccagtgacgacgaggatgaagagggtgaggagtttgtgttagattatgtgg |
| agcaccccgggcacggttgcaggtcttgtcattatcaccggaggaatacgggggacccagatattatgtgttcgctttgctatatgagga |
| cctgtggcatgtttgtctacagtaagtgaaaattatgggcagtgggtgatagagtggtgggtttggtgtggtaatttttttttttaatttttacagtt |
| ttgtggtttaaagaattttgtattgtgatttttttaaaaggtcctgtgtctgaacctgagcctgagcccgagccagaaccggagcctgcaaga |

TABLE 3-continued

| Ad5 Vector Full |
|---|
| cctacccgccgtcctaaaatggcgcctgctatcctgagacgcccgacatcacctgtgtctagagaatgcaatagtagtacggatagctgt |
| gactccggtccttctaacacacctcctgagatacacccggtggtcccgctgtgccccattaaaccagttgccgtgagagttggtgggcgt |
| cgccaggctgtggaatgtatcgaggacttgcttaacgagcctgggcaacctttggacttgagctgtaaacgccccaggccataaggtgt |
| aaacctgtgattgcgtgtgtggttaacgcctttgtttgctgaatgagttgatgtaagtttaataaagggtgagataatgtttaacttgcatggcg |
| tgttaaatggggggggcttaaagggtatataatgcgccgtgggctaatcttggttacatctgacctcatggaggcttgggagtgtttgga |
| agatttttctgctgtgcgtaacttgctggaacagagctctaacagtacctcttggttttggaggtttctgtggggctcatcccaggcaaagtta |
| gtctgcagaattaaggaggattacaagtgggaatttgaagagcttttgaaatcctgtggtgagctgtttgattctttgaatctgggtcaccag |
| gcgcttttccaagagaaggtcatcaagactttggatttttccacaccggggcgcgctgcggctgctgttgcttttttgagttttataaaggata |
| aatggagcgaagaaacccatctgagcggggggtacctgctggattttctggccatgcatctgtggagagcggttgtgagacacaagaat |
| cgcctgctactgttgtcttccgtccgcccggcgataataccgacggaggagcagcagcagcagcaggaggaagccaggcggcggc |
| ggcaggagcagagcccatggaacccgagagccggcctggaccctcgggaatgaatgttgtacaggtggctgaactgtatccagaact |
| gagacgcattttgacaattacagaggatgggcaggggctaaagggggtaaagagggagcgggggggcttgtgaggctacagaggag |
| gctaggaatctagcttttagcttaatgaccagacaccgtcctgagtgtattacttttcaacagatcaaggataattgcgctaatgagcttgatc |
| tgctggcgcagaagtattccatagagcagctgaccacttactggctgcagccaggggatgattttgaggaggctattagggtatatgcaa |
| aggtggcacttaggccagattgcaagtacaagatcagcaaacttgtaaatatcaggaattgttgctacatttctgggaacggggccgagg |
| tggagatagatacggaggatagggtggcctttagatgtagcatgataaatatgtggccgggggtgcttggcatggacgggggtgtatta |
| tgaatgtaaggtttactggccccaattttagcggtacggttttcctggccaataccaaccttatcctacacggtgtaagcttctatgggtttaa |
| caatacctgtgtggaagcctggaccgatgtaagggttcggggctgtgccttttactgctgctggaagggggtggtgtgtcgccccaaaa |
| gcagggcttcaattaagaaatgcctctttgaaaggtgtaccttgggtatcctgtctgagggtaactccagggtgcgccacaatgtggcctc |
| cgactgtggttgcttcatgctagtgaaaagcgtggctgtgattaagcataacatggtatgtggcaactgcgaggacagggcctctcagat |
| gctgacctgctcggacggcaactgtcacctgctgaagaccattcacgtagccagccactctcgcaaggcctggccagtgtttgagcata |
| acatactgacccgctgttccttgcatttgggtaacaggaggggggtgttcctaccttaccaatgcaatttgagtcacactaagatattgcttg |
| agcccgagagcatgtccaaggtgaacctgaacggggtgtttgacatgaccatgaagatctggaaggtgctgaggtacgatgagaccc |
| gcaccaggtgcagaccctgcgagtgtggcggtaaacatattaggaaccagcctgtgatgctggatgtgaccgaggagctgaggcccg |
| atcacttggtgctggcctgcacccgcgctgagtttggctctagcgatgaagatacagattgaggtactgaaatgtgtgggcgtggcttaa |
| gggtgggaaagaatatataaggtgggggtcttatgtagttttgtatctgttttgcagcagccgccgccgccatgagcaccaactcgtttgat |
| ggaagcattgtgagctcatatttgacaacgcgcatgcccccatgggccggggtgcgtcagaatgtgatgggctccagcattgatggtcg |
| ccccgtcctgcccgcaaactctactaccttgacctacgagaccgtgtctggaacgccgttggagactgcagcctccgccgccgcttcag |
| ccgctgcagccaccgcccgcgggattgtgactgactttgctttcctgagcccgcttgcaagcagtgcagcttcccgttcatccgcccgcg |
| atgacaagttgacggctcttttggcacaattggattctttgacccgggaacttaatgtcgtttctcagcagctgttggatctgcgccagcagg |
| tttctgccctgaaggcttcctcccctcccaatgcggtttaaaacataaataaaaaaccagactctgtttggatttggatcaagcaagtgtcttg |
| ctgtctttatttaggggttttgcgcgcgcggtaggcccgggaccagcggtctcggtcgttgagggtcctgtgtattttttccaggacgtggt |
| aaaggtgactctggatgttcagatacatgggcataagcccgtctctggggtggaggtagcaccactgcagagcttcatgctgcggggtg |
| gtgttgtagatgatccagtcgtagcaggagcgctgggcgtggtgcctaaaaatgtctttcagtagcaagctgattgccaggggcaggcc |
| cttggtgtaagtgtttacaaagcggttaagctgggatgggtgcatacgtggggatatgagatgcatcttggactgtatttttaggttggctat |
| gttcccagccatatccctccggggattcatgttgtgcagaaccaccagcacagtgtatccggtgcacttgggaaatttgtcatgtagcttag |
| aaggaaatgcgtggaagaacttggagacgcccttgtgacctccaagattttccatgcattcgtccataatgatggcaatgggcccacggg |
| cggcggcctgggcgaagatatttctgggatcactaacgtcatagttgtgttccaggatgagatcgtcataggccatttttacaaagcgcgg |
| gcggagggtgccagactgcggtataatggttccatccggcccaggggcgtagttaccctcacagatttgcatttcccacgctttgagttca |

TABLE 3-continued

| Ad5 Vector Full |
|---|
| gatgggggatcatgtctacctgcggggcgatgaagaaaacggtttccggggtaggggagatcagctgggaagaaagcaggttcctg |
| agcagctgcgacttaccgcagccggtgggcccgtaaatcacacctattaccggctgcaactggtagttaagagagctgcagctgccgt |
| catccctgagcaggggggccacttcgttaagcatgtccctgactcgcatgttttccctgaccaaatccgccagaaggcgctcgccgccc |
| agcgatagcagttcttgcaaggaagcaaagtttttcaacggtttgagaccgtccgccgtaggcatgcttttgagcgtttgaccaagcagtt |
| ccaggcggtcccacagctcggtcacctgctctacggcatctcgatccagcatatctcctcgtttcgcgggttggggcggctttcgctgtac |
| ggcagtagtcggtgctcgtccagacgggccagggtcatgtctttccacgggcgcagggtcctcgtcagcgtagtctgggtcacggtga |
| aggggtgcgctccgggctgcgcgctggccagggtgcgcttgaggctggtcctgctggtgctgaagcgctgccggtcttcgccctgcg |
| cgtcggccaggtagcatttgaccatggtgtcatagtccagcccctccgcggcgtggcccttggcgcgcagcttgcccttggaggaggc |
| gccgcacgaggggcagtgcagacttttgagggcgtagagcttgggcgcgagaaataccgattccggggagtaggcatccgcgccgc |
| aggccccgcagacggtctcgcattccacgagccaggtgagctctggccgttcggggtcaaaaaccaggtttcccccatgctttttgatgc |
| gtttcttacctctggtttccatgagccggtgtccacgctcggtgacgaaaaggctgtccgtgtccccgtatacagacttgagaggcctgtc |
| ctcgagcggtgttccgcggtcctcctcgtatagaaactcggaccactctgagacaaaggctcgcgtccaggccagcacgaaggaggct |
| aagtgggaggggtagcggtcgttgtccactagggggtccactcgctccagggtgtgaagacacatgtcgccctcttcggcatcaagga |
| aggtgattggtttgtaggtgtaggccacgtgaccgggtgttcctgaaggggggctataaaagggggtgggggcgcgttcgtcctcactc |
| tcttccgcatcgctgtctgcgagggccagctgttggggtgagtactccctctgaaaagcgggcatgacttctgcgctaagattgtcagtttc |
| caaaaacgaggaggatttgatattcacctggcccgcggtgatgcctttgagggtggccgcatccatctggtcagaaaagacaatctttttg |
| ttgtcaagcttggtggcaaacgacccgtagagggcgttggacagcaacttggcgatggagcgcagggtttggtttttgtcgcgatcggc |
| gcgctccttggccgcgatgtttagctgcacgtattcgcgcgcaacgcaccgccattcgggaaagacggtggtgcgctcgtcgggcacc |
| aggtgcacgcgccaaccgcggttgtgcagggtgacaaggtcaacgctggtggctacctctccgcgtaggcgctcgttggtccagcag |
| aggcggccgcccttgcgcgagcagaatggcggtagggggtctagctgcgtctcgtccggggggtctgcgtccacggtaaagacccc |
| gggcagcaggcgcgcgtcgaagtagtctatcttgcatccttgcaagtctagcgcctgctgccatgcgcgggggcaagcgcgcgctc |
| gtatgggttgagtgggggaccccatggcatggggtgggtgagcgcggaggcgtacatgccgcaaatgtcgtaaacgtagaggggct |
| ctctgagtattccaagatatgtagggtagcatcttccaccgcggatgctggcgcgcacgtaatcgtatagttcgtgcgagggagcgagg |
| aggtcgggaccgaggttgctacgggcgggctgctctgctcggaagactatctgcctgaagatggcatgtgagttggatgatatggttgg |
| acgctggaagacgttgaagctggcgtctgtgagacctaccgcgtcacgcacgaaggaggcgtaggagtcgcgcagcttgttgaccag |
| ctcggcggtgacctgcacgtctagggcgcagtagtccagggtttccttgatgatgtcatacttatcctgtcccttttttttccacagctcgcg |
| gttgaggacaaactcttcgcggtctttccagtactcttggatcggaaacccgtcggcctccgaacggtaagagcctagcatgtagaactg |
| gttgacggcctggtaggcgcagcatcccttttctacgggtagcgcgtatgcctgcgcggccttccggagcgaggtgtgggtgagcgca |
| aaggtgtccctgaccatgactttgaggtactggtatttgaagtcagtgtcgtcgcatccgccctgctcccagagcaaaaagtccgtgcgct |
| ttttggaacgcggatttggcagggcgaaggtgacatcgttgaagagtatctttcccgcgcgaggcataaagttgcgtgtgatgcggaag |
| ggtcccggcacctcggaacggttgttaattacctgggcggcgagcacgatctcgtcaaagccgttgatgttgtggcccacaatgtaaagt |
| tccaagaagcgcgggatgcccttgatggaaggcaattttttaagttcctcgtaggtgagctcttcaggggagctgagcccgtgctctgaa |
| agggcccagtctgcaagatgagggttggaagcgacgaatgagctccacaggtcacgggccattagcatttgcaggtggtcgcgaaag |
| gtcctaaactggcgacctatggccatttttctggggtgatgcagtagaaggtaagcgggtcttgttcccagcggtcccatccaaggttcg |
| cggctaggtctcgcgcggcagtcactagaggctcatctccgccgaacttcatgaccagcatgaagggcacgagctgcttcccaaaggc |
| ccccatccaagtataggtctctacatcgtaggtgacaaagagacgctcggtgcgaggatgcgagccgatcgggaagaactggatctcc |
| cgccaccaattggaggagtggctattgatgtggtgaaagtagaagtccctgcgacgggccgaacactcgtgctggcttttgtaaaaacgt |
| gcgcagtactggcagcggtgcacgggctgtacatcctgcacgaggttgacctgacgaccgcgcacaaggaagcagagtgggaatttg |
| agcccctcgcctggcgggtttggctggtggtcttctacttcggctgcttgtccttgaccgtctggctgctcgaggggagttacggtggatc |

TABLE 3-continued

| Ad5 Vector Full |
|---|
| ggaccaccacgccgcgcgagcccaaagtccagatgtccgcgcgcggcggtcggagcttgatgacaacatcgcgcagatgggagct |
| gtccatggtctggagctcccgcggcgtcaggtcaggcgggagctcctgcaggtttacctcgcatagacgggtcagggcgcgggctag |
| atccaggtgatacctaatttccaggggctggttggtggcggcgtcgatggcttgcaagaggccgcatccccgcggcgcgactacggta |
| ccgcgcggcgggggggccgcgggggtgtccttggatgatgcatctaaaagcggtgacgcgggcgagcccccggaggtaggg |
| ggggctccggacccgccgggagagggggcaggggcacgtcggcgccgcgcgcgggcaggagctggtgctgcgcgcgtaggttg |
| ctggcgaacgcgacgacgcggcggttgatctcctgaatctggcgcctctgcgtgaagacgacgggcccggtgagcttgaacctgaaa |
| gagagttcgacagaatcaatttcggtgtcgttgacggcggcctggcgcaaaatctcctgcacgtctcctgagttgtcttgataggcgatct |
| cggccatgaactgctcgatctcttcctcctggagatctccgcgtccggctcgctccacggtggcggcgaggtcgttggaaatgcgggcc |
| atgagctgcgagaaggcgttgaggcctccctcgttccagacgcggctgtagaccacgcccccttcggcatcgcgggcgcgcatgacc |
| acctgcgcgagattgagctccacgtgccgggcgaagacggcgtagtttcgcaggcgctgaaagaggtagttgagggtggtggcggtg |
| tgttctgccacgaagaagtacataacccagcgtcgcaacgtggattcgttgatatcccccaaggcctcaaggcgctccatggcctcgtag |
| aagtccacggcgaagttgaaaaactgggagttgcgcgccgacacggttaactcctcctccagaagacggatgagctcggcgacagtg |
| tcgcgcacctcgcgctcaaaggctacaggggcctcttcttcttcttcaatctcctcttccataagggcctccccttcttcttcttctggcggcg |
| gtgggggagggggggacacggcggcgacgacggcgcaccgggaggcggtcgacaaagcgctcgatcatctccccgcggcgacgg |
| cgcatggtctcggtgacggcgcggccgttctcgcgggggcgcagttggaagacgccgcccgtcatgtcccggttatgggttggcggg |
| gggctgccatgcggcagggatacggcgctaacgatgcatctcaacaattgttgtgtaggtactccgccgccgagggacctgagcgagt |
| ccgcatcgaccggatcggaaaacctctcgagaaaggcgtctaaccagtcacagtcgcaaggtaggctgagcaccgtggcgggcggc |
| agcgggcggcggtcggggttgtttctggcggaggtgctgctgatgatgtaattaaagtaggcggtcttgagacggcggatggtcgaca |
| gaagcaccatgtccttgggtccggcctgctgaatgcgcaggcggtcggccatgccccaggcttcgttttgacatcggcgcaggtctttgt |
| agtagtcttgcatgagcctttctaccggcacttcttcttctccttcctcttgtcctgcatctcttgcatctatcgctgcggcggcggcggagttt |
| ggccgtaggtggcgccctcttcctcccatgcgtgtgaccccgaagcccctcatcggctgaagcagggctaggtcggcgacaacgcgc |
| tcggctaatatggcctgctgcacctgcgtgagggtagactggaagtcatccatgtccacaaagcggtggtatgcgcccgtgttgatggtg |
| taagtgcagttggccataacggaccagttaacggtctggtgacccggctgcgagagctcggtgtacctgagacgcgagtaagccctcg |
| agtcaaatacgtagtcgttgcaagtccgcaccaggtactggtatcccaccaaaaagtgcggcggcggctggcggtagaggggccagc |
| gtagggtggccggggctccgggggcgagatcttccaacataaggcgatgatatccgtagatgtacctggacatccaggtgatgccggc |
| ggcggtggtggaggcgcgcggaaagtcgcggacgcggttccagatgttgcgcagcggcaaaaagtgctccatggtcgggacgctct |
| ggccggtcaggcgcgcgcaatcgttgacgctctagaccgtgcaaaaggagagcctgtaagcgggcactcttccgtggtctggtggata |
| aattcgcaagggtatcatggcggacgaccggggttcgagccccgtatccggccgtccgccgtgatccatgcggttaccgcccgcgtgt |
| cgaacccaggtgtgcgacgtcagacaacgggggagtgctccttttggcttccttccaggcgcggcggctgctgcgctagcttttttggcc |
| actggccgcgcgcagcgtaagcggttaggctggaaagcgaaagcattaagtggctcgctccctgtagccggagggttattttccaagg |
| gttgagtcgcgggacccccggttcgagtctcggaccggccggactgcggcgaacgggggtttgcctccccgtcatgcaagaccccgc |
| ttgcaaattcctccggaaacagggacgagcccctttttttgcttttcccagatgcatccggtgctgcggcagatgcgcccccctcctcagca |
| gcggcaagagcaagagcagcggcagacatgcagggcaccctcccctcctcctaccgcgtcaggaggggcgacatccgcggttgac |
| gcggcagcagatggtgattacgaacccccgcggcgccgggcccggcactacctggacttggaggagggcgagggcctggcgcgg |
| ctaggagcgccctctcctgagcggcacccaagggtgcagctgaagcgtgatacgcgtgaggcgtacgtgccgcggcagaacctgttt |
| cgcgaccgcgagggagaggagcccgaggagatgcgggatcgaaagttccacgcagggcgcgagctgcggcatggcctgaatcgc |
| gagcggttgctgcgcgaggaggactttgagcccgacgcgcgaaccgggattagtcccgcgcgcgcacacgtggcggccgccgacc |
| tggtaaccgcatacgagcagacggtgaaccaggagattaactttcaaaaaagctttaacaaccacgtgcgtacgcttgtggcgcgcgag |
| gaggtggctataggactgatgcatctgtgggactttgtaagcgcgctggagcaaaacccaaatagcaagccgctcatggcgcagctgtt |

TABLE 3-continued

| Ad5 Vector Full |
|---|
| ccttatagtgcagcacagcagggacaacgaggcattcagggatgcgctgctaaacatagtagagcccgagggccgctggctgctcga |
| tttgataaacatcctgcagagcatagtggtgcaggagcgcagcttgagcctggctgacaaggtggccgccatcaactattccatgcttag |
| cctgggcaagttttacgcccgcaagatataccataccccttacgttcccatagacaaggaggtaaagatcgaggggttctacatgcgcat |
| ggcgctgaaggtgcttaccttgagcgacgacctgggcgtttatcgcaacgagcgcatccacaaggccgtgagcgtgagccggcggc |
| gcgagctcagcgaccgcgagctgatgcacagcctgcaaagggccctggctggcacgggcagcggcgatagagaggccgagtccta |
| ctttgacgcgggcgctgacctgcgctgggccccaagccgacgcgccctggaggcagctggggccggacctgggctggcggtggca |
| cccgcgcgcgctggcaacgtcggcggcgtggaggaatatgacgaggacgatgagtacgagccagaggacggcgagtactaagcg |
| gtgatgtttctgatcagatgatgcaagacgcaacggacccggcggtgcgggcggcgctgcagagccagccgtccggccttaactcca |
| cggacgactggcgccaggtcatggaccgcatcatgtcgctgactgcgcgcaatcctgacgcgttccggcagcagccgcaggccaac |
| cggctctccgcaattctggaagcggtggtcccggcgcgcgcaaaccccacgcacgagaaggtgctggcgatcgtaaacgcgctggc |
| cgaaaacagggccatccggcccgacgaggccggcctggtctacgacgcgctgcttcagcgcgtggctcgttacaacagcggcaacg |
| tgcagaccaacctggaccggctggtgggggatgtgcgcgaggccgtggcgcagcgtgagcgcgcgcagcagcagggcaacctgg |
| gctccatggttgcactaaacgccttcctgagtacacagcccgccaacgtgccgcggggacaggaggactacaccaactttgtgagcgc |
| actgcggctaatggtgactgagacaccgcaaagtgaggtgtaccagtctgggccagactatttttttccagaccagtagacaaggcctgc |
| agaccgtaaacctgagccaggctttcaaaaacttgcaggggctgtggggggtgcgggctcccacaggcgaccgcgcgaccgtgtcta |
| gcttgctgacgcccaactcgcgcctgttgctgctgctaatagcgcccttcacggacagtggcagcgtgtcccgggacacatacctaggt |
| cacttgctgacactgtaccgcgaggccataggtcaggcgcatgtggacgagcatactttccaggagattacaagtgtcagccgcgcgct |
| ggggcaggaggacacgggcagcctggaggcaaccctaaactacctgctgaccaaccggcggcagaagatcccctcgttgcacagtt |
| taaacagcgaggaggagcgcattttgcgctacgtgcagcagagcgtgagccttaacctgatgcgcgacggggtaacgcccagcgtgg |
| cgctggacatgaccgcgcgcaacatggaaccgggcatgtatgcctcaaaccggccgtttatcaaccgcctaatggactacttgcatcgc |
| gcggccgccgtgaaccccgagtatttcaccaatgccatcttgaacccgcactggctaccgccccctggtttctacaccgggggattcga |
| ggtgcccgagggtaacgatggattcctctgggacgacatagacgacagcgtgttttccccgcaaccgcagaccctgctagagttgcaa |
| cagcgcgagcaggcagaggcggcgctgcgaaaggaaagcttccgcaggccaagcagcttgtccgatctaggcgctgcggccccgc |
| ggtcagatgctagtagcccatttccaagcttgatagggtctcttaccagcactcgcaccacccgcccgcgcctgctgggcgaggagga |
| gtacctaaacaactcgctgctgcagccgcagcgcgaaaaaaacctgcctccggcatttcccaacaacgggatagagagcctagtgga |
| caagatgagtagatggaagacgtacgcgcaggagcacagggacgtgccaggcccgcgcccgcccacccgtcgtcaaaggcacga |
| ccgtcagcggggtctggtgtgggaggacgatgactcggcagacgacagcagcgtcctggatttgggagggagtggcaacccgtttgc |
| gcaccttcgccccaggctggggagaatgttttaaaaaaaaaaaaagcatgatgcaaaataaaaaactcaccaaggccatggcaccgag |
| cgttggttttcttgtattccccttagtatgcggcgcgcggcgatgtatgaggaaggtcctcctccctcctacgagagtgtggtgagcgcgg |
| cgccagtggcggcggcgctgggttctcccttcgatgctcccctggacccgccgtttgtgcctccgcggtacctgcggcctaccgggggg |
| gagaaacagcatccgttactctgagttggcacccctattcgacaccacccgtgtgtacctggtggacaacaagtcaacggatgtggcatc |
| cctgaactaccagaacgaccacagcaactttctgaccacggtcattcaaaacaatgactacagcccgggggaggcaagcacacagac |
| catcaatcttgacgaccggtcgcactggggcggcgacctgaaaaccatcctgcataccaacatgccaaatgtgaacgagttcatgtttac |
| caataagtttaaggcgcgggtgatggtgtcgcgcttgcctactaaggacaatcaggtggagctgaaatacgagtgggtggagttcacgc |
| tgcccgagggcaactactccgagaccatgaccatagaccttatgaacaacgcgatcgtggagcactacttgaaagtgggcagacagaa |
| cggggttctggaaagcgacatcggggtaaagtttgacacccgcaacttcagactggggtttgaccccgtcactggtcttgtcatgcctgg |
| ggtatatacaaacgaagccttccatccagacatcattttgctgccaggatgcggggtggacttcacccacagccgcctgagcaacttgtt |
| gggcatccgcaagcggcaacccttccaggagggctttaggatcacctacgatgatctggagggtggtaacattcccgcactgttggatg |
| tggacgcctaccaggcgagcttgaaagatgacaccgaacagggggggtggcgcaggcggcagcaacagcagtggcagcggc |

TABLE 3-continued

| Ad5 Vector Full |
|---|
| gcggaagagaactccaacgcggcagccgcggcaatgcagccggtggaggacatgaacgatcatgccattcgcggcgacacctttgc |
| cacacgggctgaggagaagcgcgctgaggccgaagcagcggccgaagctgccgcccccgctgcgcaacccgaggtcgagaagc |
| ctcagaagaaaccggtgatcaaacccctgacagaggacagcaagaaacgcagttacaacctaataagcaatgacagcaccttcaccc |
| agtaccgcagctggtaccttgcatacaactacggcgaccctcagaccggaatccgctcatggaccctgctttgcactcctgacgtaacct |
| gcggctcggagcaggtctactggtcgttgccagacatgatgcaagaccccgtgaccttccgctccacgcgccagatcagcaactttccg |
| gtggtgggcgccgagctgttgcccgtgcactccaagagcttctacaacgaccaggccgtctactcccaactcatccgccagtttacctct |
| ctgacccacgtgttcaatcgctttcccgagaaccagattttggcgcgcccgccagcccccaccatcaccaccgtcagtgaaaacgttcct |
| gctctcacagatcacgggacgctaccgctgcgcaacagcatcggaggagtccagcgagtgaccattactgacgccagacgccgcac |
| ctgcccctacgtttacaaggccctgggcatagtctcgccgcgcgtcctatcgagccgcactttttgagcaagcatgtccatccttatatcgc |
| ccagcaataacacaggctggggcctgcgcttcccaagcaagatgtttggcggggccaagaagcgctccgaccaacacccagtgcgc |
| gtgcgcgggcactaccgcgcgccctggggcgcgcacaaacgcggccgcactgggcgcaccaccgtcgatgacgccatcgacgcg |
| gtggtggaggaggcgcgcaactacacgcccacgccgccaccagtgtccacagtggacgcggccattcagaccgtggtgcgcggag |
| cccggcgctatgctaaaatgaagagacggcggaggcgcgtagcacgtcgccaccgccgccgacccggcactgccgcccaacgcg |
| cggcggcggccctgcttaaccgcgcacgtcgcaccggccgacgggcggccatgcgggccgctcgaaggctggccgcgggtattgt |
| cactgtgccccccaggtccaggcgacgagcggccgccgcagcagccgcggccattagtgctatgactcagggtcgcaggggcaac |
| gtgtattgggtgcgcgactcggttagcggcctgcgcgtgcccgtgcgcacccgccccccgcgcaactagattgcaagaaaaaactact |
| tagactcgtactgttgtatgtatccagcggcggcggcgcgcaacgaagctatgtccaagcgcaaaatcaaagaagagatgctccaggt |
| catcgcgccggagatctatggccccccgaagaaggaagagcaggattacaagccccgaaagctaaagcgggtcaaaaagaaaaag |
| aaagatgatgatgatgaacttgacgacgaggtggaactgctgcacgctaccgcgcccaggcgacgggtacagtggaaaggtcgacg |
| cgtaaaacgtgttttgcgacccggcaccaccgtagtctttacgcccggtgagcgctccacccgcacctacaagcgcgtgtatgatgagg |
| tgtacggcgacgaggacctgcttgagcaggccaacgagcgcctcggggagtttgcctacggaaagcggcataaggacatgctggcg |
| ttgccgctggacgagggcaacccaacacctagcctaaagcccgtaacactgcagcaggtgctgcccgcgcttgcaccgtccgaagaa |
| aagcgcggcctaaagcgcgagtctggtgacttggcacccaccgtgcagctgatggtacccaagcgccagcgactggaagatgtcttg |
| gaaaaaatgaccgtggaacctgggctggagcccgaggtccgcgtgcggccaatcaagcaggtggcgccgggactgggcgtgcaga |
| ccgtggacgttcagatacccactaccagtagcaccagtattgccaccgccacagagggcatggagacacaaacgtccccggttgcctc |
| agcggtggcggatgccgcggtgcaggcggtcgctgcggccgcgtccaagacctctacggaggtgcaaacggacccgtggatgtttc |
| gcgtttcagccccccggcgcccgcgccgttcgaggaagtacggcgccgccagcgcgctactgcccgaatatgccctacatccttccat |
| tgcgcctacccccggctatcgtggctacacctaccgccccagaagacgagcaactacccgacgccgaaccaccactggaacccgcc |
| gccgccgtcgccgtcgccagcccgtgctggccccgatttccgtgcgcagggtggctcgcgaaggaggcaggaccctggtgctgcca |
| acagcgcgctaccaccccagcatcgtttaaaagccggtctttgtggttcttgcagatatggccctcacctgccgcctccgtttcccggtgc |
| cgggattccgaggaagaatgcaccgtaggaggggcatggccggccacggcctgacgggcggcatgcgtcgtgcgcaccaccggc |
| ggcggcgcgcgtcgcaccgtcgcatgcgcggcggtatcctgcccctccttattccactgatcgccgcggcgattggcgccgtgcccg |
| gaattgcatccgtggccttgcaggcgcagagacactgattaaaaacaagttgcatgtggaaaaatcaaaataaaaagtctggactctcac |
| gctcgcttggtcctgtaactattttgtagaatggaagacatcaactttgcgtctctggccccgcgacacggctcgcgcccgttcatgggaa |
| actggcaagatatcggcaccagcaatatgagcggtggcgccttcagctggggctcgctgtggagcggcattaaaaatttcggttccacc |
| gttaagaactatggcagcaaggcctggaacagcagcacaggccagatgctgagggataagttgaaagagcaaaatttccaacaaaag |
| gtggtagatggcctggcctctggcattagcggggtggtggacctggccaaccaggcagtgcaaaataagattaacagtaagcttgatcc |
| ccgccctcccgtagaggagcctccaccggccgtggagacagtgtctccagaggggcgtggcgaaaagcgtccgcgccccgacagg |
| gaagaaactctggtgacgcaaatagacgagcctccctcgtacgaggaggcactaaagcaaggcctgcccaccacccgtcccatcgcg |

TABLE 3-continued

| Ad5 Vector Full |
|---|
| cccatggctaccggagtgctgggccagcacacacccgtaacgctggacctgcctcccccgccgacacccagcagaaacctgtgctg |
| ccaggcccgaccgccgttgttgtaacccgtcctagccgcgcgtccctgcgccgcgccgccagcggtccgcgatcgttgcggcccgta |
| gccagtggcaactggcaaagcacactgaacagcatcgtgggtctgggggtgcaatccctgaagcgccgacgatgcttctgatagctaa |
| cgtgtcgtatgtgtgtcatgtatgcgtccatgtcgccgccagaggagctgctgagccgccgcgcgcccgctttccaagatggctacccct |
| tcgatgatgccgcagtggtcttacatgcacatctcgggccaggacgcctcggagtacctgagccccgggctggtgcagtttgcccgcg |
| ccaccgagacgtacttcagcctgaataacaagtttagaaccccacggtggcgcctacgcacgacgtgaccacagaccggtcccagc |
| gtttgacgctgcggttcatccctgtggaccgtgaggatactgcgtactcgtacaaggcgcggttcaccctagctgtgggtgataaccgtgt |
| gctggacatggcttccacgtactttgacatccgcggcgtgctggacaggggccctacttttaagccctactctggcactgcctacaacgc |
| cctggctcccaagggtgccccaaatccttgcgaatgggatgaagctgctactgctcttgaaataaacctagaagaagaggacgatgaca |
| acgaagacgaagtagacgagcaagctgagcagcaaaaaactcacgtatttgggcaggcgccttattctggtataaatattacaaaggag |
| ggtattcaaataggtgtcgaaggtcaaacacctaaatatgccgataaaacatttcaacctgaacctcaaataggagaatctcagtggtacg |
| aaacagaaattaatcatgcagctgggagagtcctaaaaaagactaccccaatgaaaccatgttacggttcatatgcaaaacccacaaatg |
| aaaatggagggcaaggcattcttgtaaagcaacaaaatggaaagctagaaagtcaagtggaaatgcaatttttctcaactactgaggcag |
| ccgcaggcaatggtgataacttgactcctaaagtggtattgtacagtgaagatgtagatatagaaaccccagacactcatatttcttacatg |
| cccactattaaggaaggtaactcacgagaactaatgggccaacaatctatgcccaacaggcctaattacattgcttttagggacaattttatt |
| ggtctaatgtattacaacagcacgggtaatatgggtgttctggcgggccaagcatcgcagttgaatgctgttgtagatttgcaagacagaa |
| acacagagctttcataccagcttttgcttgattccattggtgatagaaccaggtacttttctatgtggaatcaggctgttgacagctatgatcc |
| agatgttagaattattgaaaatcatggaactgaagatgaacttccaaattactgctttccactgggaggtgtgattaatacagagactcttac |
| caaggtaaaacctaaaacaggtcaggaaaatggatgggaaaaagatgctacagaattttcagataaaaatgaaataagagttggaaata |
| attttgccatggaaatcaatctaaatgccaacctgtggagaaatttcctgtactccaacatagcgctgtatttgcccgacaagctaaagtaca |
| gtccttccaacgtaaaaatttctgataacccaaacacctacgactacatgaacaagcgagtggtggctcccgggctagtggactgctaca |
| ttaaccttggagcacgctggtcccttgactatatggacaacgtcaacccatttaaccaccaccgcaatgctggcctgcgctaccgctcaat |
| gttgctgggcaatggtcgctatgtgcccttccacatccaggtgcctcagaagttctttgccattaaaaacctccttctcctgccgggctcata |
| cacctacgagtggaacttcaggaaggatgttaacatggttctgcagagctccctaggaaatgacctaagggttgacggagccagcatta |
| agtttgatagcatttgcctttacgccaccttcttccccatggcccacaacaccgcctccacgcttgaggccatgcttagaaacgacaccaa |
| cgaccagtcctttaacgactatctctccgccgccaacatgctctaccctatacccgccaacgctaccaacgtgcccatatccatcccctcc |
| cgcaactgggcggctttccgcggctgggccttcacgcgccttaagactaaggaaaccccatcactgggctcgggctacgacccttatta |
| cacctactctggctctataccctacctagatggaaccttttacctcaaccacacctttaagaaggtggccattacctttgactcttctgtcagc |
| tggcctggcaatgaccgcctgcttaccccaacgagtttgaaattaagcgctcagttgacggggagggttacaacgttgcccagtgtaac |
| atgaccaaagactggttcctggtacaaatgctagctaactataacattggctaccagggcttctatatcccagagagctacaaggaccgc |
| atgtactccttctttagaaacttccagcccatgagccgtcaggtggtggatgatactaaatacaaggactaccaacaggtgggcatcctac |
| accaacacaacaactctggatttgttggctaccttgcccccaccatgcgcgaaggacaggcctaccctgctaacttcccctatccgcttat |
| aggcaagaccgcagttgacagcattacccagaaaaagtttctttgcgatcgcaccctttggcgcatcccattctccagtaactttatgtcca |
| tgggcgcactcacagacctgggccaaaaccttctctacgccaactccgcccacgcgctagacatgacttttgaggtggatcccatggac |
| gagcccacccttctttatgttttgtttgaagtctttgacgtggtccgtgtgcaccagccgcaccgcggcgtcatcgaaaccgtgtacctgcg |
| cacgcccttctggccggcaacgccacaacataaagaagcaagcaacatcaacaacagctgccgccatgggctccagtgagcagga |
| actgaaagccattgtcaaagatcttggttgtgggccatatttttgggcacctatgacaagcgctttccaggctttgtttctccacacaagctc |
| gcctgcgccatagtcaatacggccggtcgcgagactgggggcgtacactggatggcctttgcctggaacccgcactcaaaaacatgct |
| acctctttgagccctttggcttttctgaccagcgactcaagcaggtttaccagtttgagtacgagtcactcctgcgccgtagcgccattgctt |

TABLE 3-continued

| Ad5 Vector Full |
| --- |
| cttcccccgaccgctgtataacgctggaaaagtccacccaaagcgtacaggggcccaactcggccgcctgtggactattctgctgcatg |
| tttctccacgcctttgccaactggccccaaactcccatggatcacaaccccaccatgaaccttattaccggggtacccaactccatgctca |
| acagtccccaggtacagcccaccctgcgtcgcaaccaggaacagctctacagcttcctggagcgccactcgccctacttccgcagcca |
| cagtgcgcagattaggagcgccacttctttttgtcacttgaaaaacatgtaaaaataatgtactagagacactttcaataaaggcaaatgctt |
| ttatttgtacactctcgggtgattatttacccccacccttgccgtctgcgccgtttaaaaatcaaaggggttctgccgcgcatcgctatgcgc |
| cactggcagggacacgttgcgatactggtgtttagtgctccacttaaactcaggcacaaccatccgcggcagctcggtgaagttttcactc |
| cacaggctgcgcaccatcaccaacgcgtttagcaggtcgggcgccgatatcttgaagtcgcagttggggcctccgccctgcgcgcgc |
| gagttgcgatacacagggttgcagcactggaacactatcagcgccgggtggtgcacgctggccagcacgctcttgtcggagatcagat |
| ccgcgtccaggtcctccgcgttgctcagggcgaacggagtcaactttggtagctgccttcccaaaaagggcgcgtgcccaggctttga |
| gttgcactcgcaccgtagtggcatcaaaaggtgaccgtgcccggtctgggcgttaggatacagcgcctgcataaaagccttgatctgctt |
| aaaagccacctgagcctttgcgccttcagagaagaacatgccgcaagacttgccggaaaactgattggccggacaggccgcgtcgtg |
| cacgcagcaccttgcgtcggtgttggagatctgcaccacatttcggccccaccggttcttcacgatcttggccttgctagactgctccttca |
| gcgcgcgctgcccgttttcgctcgtcacatccatttcaatcacgtgctccttatttatcataatgcttccgtgtagacacttaagctcgccttcg |
| atctcagcgcagcggtgcagccacaacgcgcagcccgtgggctcgtgatgcttgtaggtcacctctgcaaacgactgcaggtacgcct |
| gcaggaatcgccccatcatcgtcacaaaggtcttgttgctggtgaaggtcagctgcaacccgcggtgctcctcgttcagccaggtcttgc |
| atacggccgccagagcttccacttggtcaggcagtagtttgaagttcgcctttagatcgttatccacgtggtacttgtccatcagcgcgcgc |
| gcagcctccatgcccttctcccacgcagacacgatcggcacactcagcgggttcatcaccgtaatttcactttccgcttcgctgggctcttc |
| ctcttcctcttgcgtccgcataccacgcgccactgggtcgtcttcattcagccgccgcactgtgcgcttacctcctttgccatgcttgattag |
| caccggtgggttgctgaaacccaccatttgtagcgccacatcttctctttcttcctcgctgtccacgattacctctggtgatggcgggcgctc |
| gggcttgggagaagggcgcttctttttcttcttgggcgcaatggccaaatccgccgccgaggtcgatggccgcgggctgggtgtgcgc |
| ggcaccagcgcgtcttgtgatgagtcttcctcgtcctcggactcgatacgccgcctcatccgctttttttgggggcgcccggggaggcgg |
| cggcgacggggacggggacgacacgtcctccatggttgggggacgtcgcgccgcaccgcgtccgcgctcgggggtggtttcgcgc |
| tgctcctcttcccgactggccatttccttctcctataggcagaaaaagatcatggagtcagtcgagaagaaggacagcctaaccgccccc |
| tctgagttcgccaccaccgcctccaccgatgccgccaacgcgcctaccaccttccccgtcgaggcacccccgcttgaggaggaggaa |
| gtgattatcgagcaggacccaggttttgtaagcgaagacgacgaggaccgctcagtaccaacagaggataaaaagcaagaccaggac |
| aacgcagaggcaaacgaggaacaagtcgggcgggggacgaaaggcatggcgactacctagatgtgggagacgacgtgctgttga |
| agcatctgcagcgccagtgcgccattatctgcgacgcgttgcaagagcgcagcgatgtgcccctcgccatagcggatgtcagccttgc |
| ctacgaacgccacctattctcaccgcgcgtacccccaaacgccaagaaaacggcacatgcgagcccaacccgcgcctcaacttctac |
| cccgtatttgccgtgccagaggtgcttgccacctatcacatctttttccaaaactgcaagatacccctatcctgccgtgccaaccgcagcc |
| gagcggacaagcagctggccttgcggcagggcgctgtcatacctgatatcgcctcgctcaacgaagtgccaaaaatctttgagggtctt |
| ggacgcgacgagaagcgcgcggcaaacgctctgcaacaggaaaacagcgaaaatgaaagtcactctggagtgttggtggaactcga |
| gggtgacaacgcgcgcctagccgtactaaaacgcagcatcgaggtcacccactttgcctacccggcacttaacctacccccccaaggtc |
| atgagcacagtcatgagtgagctgatcgtgcgccgtgcgcagcccctggagagggatgcaaatttgcaagaacaaacagaggaggg |
| cctacccgcagttggcgacgagcagctagcgcgctggcttcaaacgcgcgagcctgccgacttggaggagcgacgcaaactaatgat |
| ggccgcagtgctcgttaccgtggagcttgagtgcatgcagcggttctttgctgacccggagatgcagcgcaagctagaggaaacattgc |
| actacacctttcgacagggctacgtacgccaggcctgcaagatctccaacgtggagctctgcaacctggtctcctaccttggaattttgca |
| cgaaaaccgccttgggcaaaacgtgcttcattccacgctcaagggcgaggcgcgccgcgactacgtccgcgactgcgtttacttatttct |
| atgctacacctggcagacggccatgggcgtttggcagcagtgcttggaggagtgcaacctcaaggagctgcagaaactgctaaagca |
| aaacttgaaggacctatggacggccttcaacgagcgctccgtggccgcgcacctggcggacatcattttccccgaacgcctgcttaaaa |

TABLE 3-continued

| Ad5 Vector Full |
|---|
| ccctgcaacagggtctgccagacttcaccagtcaaagcatgttgcagaactttaggaactttatcctagagcgctcaggaatcttgcccgc |
| cacctgctgtgcacttcctagcgactttgtgcccattaagtaccgcgaatgccctccgccgctttggggccactgctaccttctgcagctag |
| ccaactaccttgcctaccactctgacataatggaagacgtgagcggtgacggtctactggagtgtcactgtcgctgcaacctatgcaccc |
| cgcaccgctccctggtttgcaattcgcagctgcttaacgaaagtcaaattatcggtacctttgagctgcagggtccctcgcctgacgaaaa |
| gtccgcggctccggggttgaaactcactccggggctgtggacgtcggcttaccttcgcaaatttgtacctgaggactaccacgcccacg |
| agattaggttctacgaagaccaatcccgcccgcctaatgcggagcttaccgcctgcgtcattacccagggccacattcttggccaattgc |
| aagccatcaacaaagcccgccaagagtttctgctacgaaagggacggggggtttacttggacccccagtccggcgaggagctcaacc |
| caatcccccgccgccgcagccctatcagcagcagccgcgggcccttgcttcccaggatggcacccaaaaagaagctgcagctgcc |
| gccgccacccacggacgaggaggaatactgggacagtcaggcagaggaggttttggacgaggaggaggaggacatgatggaaga |
| ctgggagagcctagacgaggaagcttccgaggtcgaagaggtgtcagacgaaacaccgtcaccctcggtcgcattcccctcgccggc |
| gccccagaaatcggcaaccggttccagcatggctacaacctccgctcctcaggcgccgccggcactgcccgttcgccgacccaaccg |
| tagatgggacaccactggaaccagggccggtaagtccaagcagccgccgccgttagcccaagagcaacaacagcgccaaggctac |
| cgctcatggcgcgggcacaagaacgccatagttgcttgcttgcaagactgtgggggcaacatctccttcgcccgccgctttcttctctacc |
| atcacggcgtggccttcccccgtaacatcctgcattactaccgtcatctctacagcccatactgcaccggcggcagcggcagcaacagc |
| agcggccacacagaagcaaaggcgaccggatagcaagactctgacaaagcccaagaaatccacagcggcggcagcagcaggag |
| gaggagcgctgcgtctggcgcccaacgaacccgtatcgacccgcgagcttagaaacaggatttttcccactctgtatgctatatttcaac |
| agagcaggggccaagaacaagagctgaaaataaaaaacaggtctctgcgatccctcacccgcagctgcctgtatcacaaaagcgaag |
| atcagcttcggcgcacgctggaagacgcggaggctctcttcagtaaatactgcgcgctgactcttaaggactagtttcgcgccctttctca |
| aatttaagcgcgaaaactacgtcatctccagcggccacacccggcgccagcacctgttgtcagcgccattatgagcaaggaaattccca |
| cgccctacatgtggagttaccagccacaaatgggacttgcggctggagctgcccaagactactcaacccgaataaactacatgagcgc |
| gggaccccacatgatatcccgggtcaacggaatacgcgcccaccgaaaccgaattctcctggaacaggcggctattaccaccacacct |
| cgtaataaccttaatccccgtagttggcccgctgccctggtgtaccaggaaagtcccgctcccaccactgtggtacttcccagagacgcc |
| caggccgaagttcagatgactaactcaggggcgcagcttgcgggcggctttcgtcacagggtgcggtcgcccgggcagggtataact |
| cacctgacaatcagagggcgaggtattcagctcaacgacgagtcggtgagctcctcgcttggtctccgtccggacgggacatttcagat |
| cggcggcgccggccgctcttcattcacgcctcgtcaggcaatcctaactctgcagacctcgtcctctgagccgcgctctggaggcattg |
| gaactctgcaatttattgaggagtttgtgccatcggtctactttaaccccttctcgggacctcccggccactatccggatcaatttattcctaa |
| ctttgacgcggtaaaggactcggcggacggctacgactgaatgttaagtggagaggcagagcaactgcgcctgaaacacctggtcca |
| ctgtcgccgccacaagtgctttgcccgcgactccggtgagttttgctactttgaattgcccgaggatcatatcgagggcccggcgcacgg |
| cgtccggcttaccgcccagggagagcttgcccgtagcctgattcgggagtttacccagcgccccctgctagttgaggggacagggg |
| accctgtgttctcactgtgatttgcaactgtcctaaccctggattacatcaagatctttgttgccatctctgtgctgagtataataaatacagaa |
| attaaaatatactggggctcctatcgccatcctgtaaacgccaccgtcttcacccgcccaagcaaaccaaggcgaaccttacctggtactt |
| ttaacatctctccctctgtgatttacaacagtttcaacccagacggagtgagtctacgagagaacctctccgagctcagctactccatcaga |
| aaaaacaccaccctccttacctgccgggaacgtacgagtgcgtcaccggccgctgcaccacacctaccgcctgaccgtaaaccagact |
| ttttccggacagacctcaataactctgtttaccagaacaggaggtgagcttagaaaacccttagggtattaggccaaaggcgcagctact |
| gtggggtttatgaacaattcaagcaactctacgggctattctaattcaggtttctctagaatcggggttggggttattctctgtcttgtgattctc |
| tttattcttatactaacgcttctctgcctaaggctcgccgcctgctgtgtgcacatttgcatttattgtcagctttttaaacgctggggtcgccac |
| ccaagatgattaggtacataatcctaggtttactcaccccttgcgtcagcccacggtaccacccaaaaggtggattttaaggagccagcctg |
| taatgttacattcgcagctgaagctaatgagtgcaccactcttataaaatgcaccacagaacatgaaaagctgcttattcgccacaaaaac |
| aaaattggcaagtatgctgtttatgctatttggcagccaggtgacactacagagtataatgttacagttttccagggtaaaagtcataaaactt |

TABLE 3-continued

| Ad5 Vector Full |
|---|
| ttatgtatacttttccattttatgaaatgtgcgacattaccatgtacatgagcaaacagtataagttgtggcccccacaaaattgtgtggaaaa |
| cactggcactttctgctgcactgctatgctaattacagtgctcgctttggtctgtaccctactctatattaaatacaaaagcagacgcagcttt |
| attgaggaaaagaaaatgccttaatttactaagttacaaagctaatgtcaccactaactgctttactcgctgcttgcaaaacaaattcaaaaa |
| gttagcattataattagaataggatttaaaccccccggtcatttcctgctcaataccattcccctgaacaattgactctatgtgggatatgctcc |
| agcgctacaaccttgaagtcaggcttcctggatgtcagcatctgactttggccagcacctgtcccgcggatttgttccagtccaactacag |
| cgacccaccctaacagagatgaccaacacaaccaacgcggccgccgctaccggacttacatctaccacaaatacaccccaagtttctg |
| cctttgtcaataactgggataacttgggcatgtggtggttctccatagcgcttatgtttgtatgccttattattatgtggctcatctgctgcctaa |
| agcgcaaacgcgcccgaccacccatctatagtcccatcattgtgctacacccaaacaatgatggaatccatagattggacggactgaaa |
| cacatgttcttttctcttacagtatgattaaatgagacatgattcctcgagtttttatattactgacccttgttgcgctttttttgtgcgtgctccaca |
| ttggctgcggtttctcacatcgaagtagactgcattccagccttcacagtctatttgctttacggatttgtcaccctcacgctcatctgcagcct |
| catcactgtggtcatcgcctttatccagtgcattgactgggtctgtgtgcgctttgcatatctcagacaccatccccagtacagggacagga |
| ctatagctgagcttcttagaattctttaattatgaaatttactgtgacttttctgctgattatttgcaccctatctgcgttttgttccccgacctccaa |
| gcctcaaagacatatatcatgcagattcactcgtatatggaatattccaagttgctacaatgaaaaaagcgatctttccgaagcctggttata |
| tgcaatcatctctgttatggtgttctgcagtaccatcttagccctagctatatatccctaccttgacattggctggaacgcaatagatgccatg |
| aaccacccaactttccccgcgcccgctatgcttccactgcaacaagttgttgccggcggctttgtcccagccaatcagcctcgcccacctt |
| ctcccaccccccactgaaatcagctactttaatctaacaggaggagatgactgacaccctagatctagaaatggacggaattattacagag |
| cagcgcctgctagaaagacgcagggcagcggccgagcaacagcgcatgaatcaagagctccaagacatggttaacttgcaccagtg |
| caaaaggggtatcttttgtctggtaaagcaggccaaagtcacctacgacagtaataccaccggacaccgccttagctacaagttgccaac |
| caagcgtcagaaattggtggtcatggtgggagaaaagcccattaccataactcagcactcggtagaaaccgaaggctgcattcactcac |
| cttgtcaaggacctgaggatctctgcacccttattaagaccctgtgcggtctcaaagatcttattccctttaactaataaaaaaaaataataaa |
| gcatcacttacttaaaatcagttagcaaatttctgtccagtttattcagcagcacctccttgccctcctcccagctctggtattgcagcttcctc |
| ctggctgcaaactttctccacaatctaaatggaatgtcagtttcctcctgttcctgtccatccgcacccactatcttcatgttgttgcagatgaa |
| gcgcgcaagaccgtctgaagataccttcaaccccgtgtatccatatgacacggaaaccggtcctccaactgtgccttttcttactcctccct |
| ttgtatcccccaatgggtttcaagagagtccccctggggtactctctttgcgcctatccgaacctctagttacctccaatggcatgcttgcgc |
| tcaaaatgggcaacggcctctctctggacgaggccggcaaccttacctcccaaaatgtaaccactgtgagcccacctctcaaaaaaacc |
| aagtcaaacataaacctggaaatatctgcacccctcacagttacctcagaagccctaactgtggctgccgccgcacctctaatggtcgcg |
| ggcaacacactcaccatgcaatcacaggccccgctaaccgtgcacgactccaaacttagcattgccacccaaggacccctcacagtgt |
| cagaaggaaagctagccctgcaaacatcaggcccccctcaccaccaccgatagcagtacccttactatcactgcctcaccccctctaact |
| actgccactggtagcttgggcattgacttgaaagagcccatttatacacaaaatggaaaactaggactaaagtacggggctcctttgcatg |
| taacagacgacctaaacactttgaccgtagcaactggtccaggtgtgactattaataatacttccttgcaaactaaagttactggagccttg |
| ggttttgattcacaaggcaatatgcaacttaatgtagcaggaggactaaggattgattctcaaaacagacgccttatacttgatgttagttatc |
| cgtttgatgctcaaaaccaactaaatctaagactaggacagggccctctttttataaactcagcccacaacttggatattaactacaacaaa |
| ggcctttacttgtttacagcttcaaacaattccaaaaagcttgaggttaacctaagcactgccaaggggttgatgtttgacgctacagccata |
| gccattaatgcaggagatgggcttgaatttggttcacctaatgcaccaaacacaaatcccctcaaaacaaaaattggccatggcctagaat |
| ttgattcaaacaaggctatggttcctaaactaggaactggccttagttttgacagcacaggtgccattacagtaggaaacaaaaataatgat |
| aagctaactttgtggaccacaccagctccatctcctaactgtagactaaatgcagagaaagatgctaaactcactttggtcttaacaaaatg |
| tggcagtcaaatacttgctacagtttcagttttggctgttaaaggcagtttggctccaatatctggaacagttcaaagtgctcatcttattataa |
| gatttgacgaaaatggagtgctactaaacaattccttcctggacccagaatattggaactttagaaatggagatcttactgaaggcacagc |
| ctatacaaacgctgttggatttatgcctaacctatcagcttatccaaaatctcacggtaaaactgccaaaagtaacattgtcagtcaagtttac |

TABLE 3-continued

| Ad5 Vector Full |
|---|
| ttaaacggagacaaaactaaacctgtaacactaaccattacactaaacggtacacaggaaacaggagacacaactccaagtgcatactc |
| tatgtcattttcatgggactggtctggccacaactacattaatgaaatatttgccacatcctcttacactttttcatacattgcccaagaataaag |
| aatcgtttgtgttatgtttcaacgtgtttatttttcaattgcagaaaatttcaagtcatttttcattcagtagtatagccccaccaccacatagcttat |
| acagatcaccgtaccttaatcaaactcacagaaccctagtattcaacctgccacctccctcccaacacacagagtacacagtcctttctcc |
| ccggctggccttaaaaagcatcatatcatgggtaacagacatattcttaggtgttatattccacacggtttcctgtcgagccaaacgctcatc |
| agtgatattaataaactccccgggcagctcacttaagttcatgtcgctgtccagctgctgagccacaggctgctgtccaacttgcggttgct |
| taacgggcggcgaaggagaagtccacgcctacatgggggtagagtcataatcgtgcatcaggatagggcggtggtgctgcagcagc |
| gcgcgaataaactgctgccgccgccgctccgtcctgcaggaatacaacatggcagtggtctcctcagcgatgattcgcaccgcccgca |
| gcataaggcgccttgtcctccgggcacagcagcgcaccctgatctcacttaaatcagcacagtaactgcagcacagcaccacaatattg |
| ttcaaaatcccacagtgcaaggcgctgtatccaaagctcatggcgggaccacagaacccacgtggccatcataccacaagcgcagg |
| tagattaagtggcgacccctcataaacacgctggacataaacattacctcttttggcatgttgtaattcaccacctcccggtaccatataaac |
| ctctgattaaacatggcgccatccaccaccatcctaaaccagctggccaaaacctgcccgccggctatacactgcagggaaccgggac |
| tggaacaatgacagtggagagcccaggactcgtaaccatggatcatcatgctcgtcatgatatcaatgttggcacaacacaggcacacg |
| tgcatacacttcctcaggattacaagctcctcccgcgttagaaccatatcccagggaacaacccattcctgaatcagcgtaaatcccacac |
| tgcagggaagacctcgcacgtaactcacgttgtgcattgtcaaagtgttacattcgggcagcagcggatgatcctccagtatggtagcgc |
| gggtttctgtctcaaaaggaggtagacgatccctactgtacggagtgcgccgagacaaccgagatcgtgttggtcgtagtgtcatgccaa |
| atggaacgccggacgtagtcatatttcctgaagcaaaaccaggtgcgggcgtgacaaacagatctgcgtctccggtctcgccgcttaga |
| tcgctctgtgtagtagttgtagtatatccactctctcaaagcatccaggcgccccctggcttcgggttctatgtaaactccttcatgcgccgct |
| gccctgataacatccaccaccgcagaataagccacacccagccaacctacacattcgttctgcgagtcacacacgggaggagcggga |
| agagctggaagaaccatgtttttttttttattccaaaagattatccaaaacctcaaaatgaagatctattaagtgaacgcgctcccctccggt |
| ggcgtggtcaaactctacagccaaagaacagataatggcatttgtaagatgttgcacaatggcttccaaaaggcaaacggccctcacgt |
| ccaagtggacgtaaaggctaaacccttcagggtgaatctcctctataaacattccagcaccttcaaccatgcccaaataattctcatctcgc |
| caccttctcaatatatctctaagcaaatcccgaatattaagtccggccattgtaaaaatctgctccagagcgccctccaccttcagcctcaa |
| gcagcgaatcatgattgcaaaaattcaggttcctcacagacctgtataagattcaaaagcggaacattaacaaaaataccgcgatcccgt |
| aggtcccttcgcagggccagctgaacataatcgtgcaggtctgcacggaccagcgcggccacttccccgccaggaaccatgacaaaa |
| gaacccacactgattatgacacgcatactcggagctatgctaaccagcgtagccccgatgtaagcttgttgcatgggcggcgatataaaa |
| tgcaaggtgctgctcaaaaaatcaggcaaagcctcgcgcaaaaaagaaagcacatcgtagtcatgctcatgcagataaaggcaggtaa |
| gctccggaaccaccacagaaaaagacaccatttttctctcaaacatgtctgcgggtttctgcataaacacaaaataaaataacaaaaaaac |
| atttaaacattagaagcctgtcttacaacaggaaaaacaacccttataagcataagacggactacggccatgccggcgtgaccgtaaaa |
| aaactggtcaccgtgattaaaaagcaccaccgacagctcctcggtcatgtccggagtcataatgtaagactcggtaaacacatcaggttg |
| attcacatcggtcagtgctaaaaagcgaccgaaatagcccgggggaatacatacccgcaggcgtagagacaacattacagcccccata |
| ggaggtataacaaaattaataggagagaaaaacacataaacacctgaaaaaccctcctgcctaggcaaaatagcaccctcccgctcca |
| gaacaacatacagcgcttccacagcggcagccataacagtcagccttaccagtaaaaaagaaaacctattaaaaaaacaccactcgac |
| acggcaccagctcaatcagtcacagtgtaaaaaagggccaagtgcagagcgagtatatataggactaaaaaatgacgtaacggttaaa |
| gtccacaaaaaacacccagaaaaccgcacgcgaacctacgcccagaaacgaaagccaaaaaacccacaacttcctcaaatcgtcact |
| tccgttttcccacgttacgtcacttcccattttaagaaaactacaattcccaacacatacaagttactccgccctaaaacctacgtcacccgc |
| cccgttcccacgccccgcgccacgtcacaaactccaccccctcattatcatattggcttcaatccaaaataaggtatattattgatgatg |

TABLE 4

| 3' End Fragment 1 |
|---|
| (SEQ ID NO: 4) |
| ctcgagatttaaattaattaaaattttggccaatgaggcctgacgctaataatagctggtccactgtcgccgccacaagtgctttgcccgcg |
| actccggtgagttttgctactttgaattgcccgaggatcatatcgagggcccggcgcacggcgtccggcttaccgcccagggagagctt |
| gcccgtagcctgattcgggagtttacccagcgccccctgctagttgagcgggacaggggaccctgtgttctcactgtgatttgcaactgt |
| cctaaccttggattacatcaagatccagatcttctagacccgggagcggccgctgtcgacctgcaggatccgaattcgatatcactagtg |
| gtaccgatcttattccctttaactaataaaaaaaaataataaagcatcacttacttaaaatcagttagcaaatttctgtccagtttattcagcagc |
| acctccttgccctcctcccagctctggtattgcagcttcctcctggctgcaaactttctccacaatctaaagggaatgtcagtttcctcctgttc |
| ctgtccatccgcacccactatcttcatgttgttgcagatgaagcgcgcaagaccgtctgaagataccttcaaccccgtgtatccatatgaca |
| cggaaaccggtcctccaactgtgccttttcttactcctccctttgtatcccccaatgggtttcaagagagtccccctggggtactctctttgcg |
| cctatccgaacctctagttacctccaatggcatgcttgcgctcaaaatgggcaacggcctctctctggacgaggccggcaaccttacctc |
| ccaaaatgtaaccactgtgagcccacctctcaaaaaaaccaagtcaaacataaacctggaaatatctgcacccctcacagttacctcaga |
| agccctaactgtggctgccgccgcacctctaatggtcgcgggcaacacactcaccatgcaatcacaggccccgctaaccgtgcacgac |
| tccaaacttagcattgccacccaaggacccctcacagtgtcagaaggaaagctagccctgcaaacatcaggcccccctcaccaccaccg |
| atagcagtacccttactatcactgcctcacccccctctaactactgccactggtagcttgggcattg |

TABLE 5

| 5′ End Fragment 1 |
|---|
| (SEQ ID NO: 5) |
| aaattaattaacatcatcaataatataccttattttggattgaagccaatatgataatgaggggggtggagtttgtgacgtggcgcggggcgt |
| gggaacggggcgggtgacgtagtagtgtggcggaagtgtgatgttgcaagtgtggcggaacacatgtaagcgacggatgtggcaaa |
| agtgacgtttttggtgtgcgccggtgtacacaggaagtgacaattttcgcgcggttttaggcggatgttgtagtaaatttgggcgtaaccga |
| gtaagatttggccattttcgcgggaaaactgaataagaggaagtgaaatctgaataattttgtgttactcatagcgcgtaatatttgtctagg |
| gccgcggggactttgaccgtttacgtggagactcgcccaggtgtttttctcaggtgttttccgcgttccgggtcaaagttggcgttttagatc |
| ttctagacccgggagcggccgctgtcgacctgcaggatccactagttattaatagtaatcaattacggggtcattagttcatagcccatata |
| tggagttccgcgttacataacttacggtaaatggcccgcctggctgaccgcccaacgacccccgcccattgacgtcaataatgacgtatg |
| ttcccatagtaacgccaatagggactttccattgacgtcaatgggtggagtatttacggtaaactgcccacttggcagtacatcaagtgtat |
| catatgccaagtacgccccctattgacgtcaatgacggtaaatggcccgcctggcattatgcccagtacatgaccttatgggactttccta |
| cttggcagtacatctacgtattagtcatcgctattaccatggtcgaggtgagccccacgttctgcttcactctccccatctcccccccctccc |
| cacccccaattttgtatttatttattttttaattattttgtgcagcgatgggggcggggggggggggggggggccaggcggggggg |
| cggggcgaggggggggcggggcgaggcggagaggtgcggcggcagccaatcagagcggcgcgctccgaaagtttccttttatg |
| gcgaggcggcggcggcggcggccctataaaaagcgaagcgcgcggggggggagtcgctgcgttgccttcgccccgtgccccg |
| ctccgcgccgcctcgcgccgcccgccccggctctgactgaccgcgttactcccacaggtgagcgggggggacggcccttctcctccg |
| ggctgtaattagcgcttggtttaatgacggctcgtttcttttctgtggctgcgtgaaagccttaaagggctccgggagggccctttgtgcgg |
| gggggagcggctcgggggggtgcgtgcgtgtgtgtgtgcgtggggagcgccgcgtgcggctccgcgctgcccggcggctgtgagcg |
| ctgcgggcgcggcgcggggctttgtgcgctccgcagtgtgcgcgaggggagcgcggccgggggcggtgccccgcggtgcgggg |
| ggggctgcgaggggaacaaaggctgcgtgcggggtgtgtgcgtgggggggtgagcagggggtgtgggcgcgtcggtcgggctgc |
| aaccccccctgcacccccctccccgagttgctgagcacggcccggcttcgggtgcggggctccgtacggggcgtggcgcggggctc |
| gccgtgccgggggggggtggcggcaggtgggggtgccgggcggggggggccgcctcgggccggggagggctcgggggag |
| gggcgcggcggcccccggagcgccggcggctgtcgaggcgcggcgagccgcagccattgccttttatggtaatcgtgcgagaggg |
| cgcagggacttcctttgtcccaaatctgtgcggagccgaaatctgggaggcgccgccgcacccccctctagcgggcgcggggcgaag |

TABLE 5-continued

| 5′ End Fragment 1 |
|---|
| cggtgcggcgccggcaggaaggaaatgggggggagggccttcgtgcgtcgccgcgccgccgtccccttctccctctccagcctcg |
| gggctgtccgcgggggggacggctgccttcggggggggacggggcagggcggggttcggcttctggcgtgtgaccggcggctctaga |
| gcctctgctaaccatgttcatgccttcttctttttcctacagctcctgggcaacgtgctggttattgtgctgtctcatcattttggcaaagaattc |
| cgctgcgactcggcggagtcccggcggcgcgtccttgttctaacccggcgcgccagcttggcaatccggtactgttggtaaagccacc |
| atgcatagttctgccctgttgtgttgcttggtgctgttgacgggggttagagcgagtccaggtcaaggcacgcagtctgaaaactcctgta |
| cacacttccccggcaacctccctaatatgctcagagaccttcgagacgccttctcccgagtaaaaactttctttcagatgaaggaccagct |
| cgacaacttgctgttgaaggaatcactcctcgaagattttaaggggtacctcggttgtcaagctctgtctgaaatgatacaattctatctcga |
| ggaagtcatgcctcaagcggaaaaccaggacccagatattaaggcccatgtgaatagcctcggcgaaaatcttaaaactcttcgcctta |
| gactccgaagatgccataggtttttgccgtgcgaaaataaatccaaagctgtggaacaggtaaaaaatgcgtttaacaagttgcaagaga |
| agggcatctacaaagcgatgtcagagttcgatatattcataaattatattgaagcatacatgactatgaagatcaggaattaataattctaga |
| gtcggggcggccggccgcttcgagcagacatgataagatacattgatgagtttggacaaaccacaactagaatgcagtgaaaaaaatg |
| ctttatttgtgaaatttgtgatgctattgctttatttgtaaccattataagctgcaataaacaagttaacaacaacaattgcattcattttatgtttca |
| ggttcagggggaggtgtgggaggttttttaaagcaagtaaaacctctacaaatgtggtaaaatcgataaggatccgaattcgatatcacta |
| gtggtaccagtactgaaatgtgtgggcgtggcttaagggtgggaaagaatatataaggtgggggtcttatgtagttttgtatctgttttgcag |
| cagccgccgccgccatgagcaccaactcgtttgatggaagcattgtgagctcatatttgacaacgcgcatgccccccatgggccggggt |
| gcgtcagaatgtgatgggctccagcattgatggtcgccccgtcctgcccgcaaactctactaccttgacctacgagaccgtgtctggaac |
| gccgttggagactgcagcctccgccgccgcttcagccgctgcagccaccgcccgcgggattgtgactgactttgctttcctgagcccgc |
| ttgcaagcagtgcagcttcccgttcatccgcccgcgatgacaagttgacggctcttttggcacaattggattctttgacccgggaacttaat |
| gtcgtttctcagcagctgttggatctgcgccagcaggtttctgccctgaaggcttcctcccctcccaatgcggtttaacggtccgggccag |
| ag |

TABLE 6

| 3′ End Fragment 2 |
|---|
| (SEQ ID NO: 6) |
| ctactgccactggtagcttgggcattgacttgaaagagcccatttatacacaaaatggaaaactaggactaaagtacggggctcctttgca |
| tgtaacagacgacctaaacactttgaccgtagcaactggtccaggtgtgactattaataatacttccttgcaaactaaagttactggagcctt |
| gggttttgattcacaaggcaatatgcaacttaatgtagcaggaggactaaggattgattctcaaaacagacgccttatacttgatgttagtta |
| tccgtttgatgctcaaaaccaactaaatctaagactaggacagggccctctttttataaactcagcccacaacttggatattaactacaacaa |
| aggcctttacttgtttacagcttcaaacaattccaaaaagcttgaggttaacctaagcactgccaaggggttgatgtttgacgctacagccat |
| agccattaatgcaggagatgggcttgaatttggttcacctaatgcaccaaacacaaatcccctcaaaacaaaaattggccatggcctaga |
| atttgattcaaacaaggctatggttcctaaactaggaactggccttagttttgacagcacaggtgccattacagtaggaaacaaaaataatg |
| ataagctaactttgtggaccacaccagctccatctcctaactgtagactaaatgcagagaaagatgctaaactcactttggtcttaacaaaa |
| tgtggcagtcaaatacttgctacagtttcagttttggctgttaaaggcagtttggctccaatatctggaacagttcaaagtgctcatcttattat |
| aagatttgacgaaaatggagtgctactaaacaattccttcctggacccagaatattggaactttagaaatggagatcttactgaaggcaca |
| gcctatacaaacgctgttggatttatgcctaacctatcagcttatccaaaatctcacggtaaaactgccaaaagtaacattgtcagtcaagttt |
| acttaaacggagacaaaactaaacctgtaacactaaccattacactaaacggtacacaggaaacaggagacacaactccaagtgcata |
| ctctatgtcattttcatgggactggtctggccacaactacattaatgaaatatttgccacatcctcttacactttttcatacattgcccaagaata |
| aagaatcgtttgtgttatgtttcaacgtgtttatttttcaattgcagaaaatttcaagtcatttttcattcagtagtatagccccaccaccacatag |
| cttatacagatcaccgtaccttaatcaaactcacagaaccctagtattcaacctgccacctccctcccaacacacagagtacacagtccttt |

TABLE 6-continued

| 3′ End Fragment 2 |
|---|
| ctccccggctggccttaaaaagcatcatatcatgggtaacagacatattcttaggtgttatattccacacggtttcctgtcgagccaaacgct |
| catcagtgatattaataaactccccgggcagctcacttaagttcatgtcgctgtccagctgctgagccacaggctgctgtccaacttgcggt |
| tgcttaacgggggcgaaggagaagtccacgcctacatggggtagagtcataatcgtgcatcaggatagggcggtggtgctgcagc |
| agcgcgcgaataaactgctgccgccgccgctccgtcctgcaggaatacaacatggcagtggtctcctcagcgatgattcgcaccgccc |
| gcagcataaggcgccttgtcctccgggcacagcagcgcaccctgatctcacttaaatcagcacagtaactgcagcacagcaccacaat |
| attgttcaaaatcccacagtgcaaggcgctgtatccaaagctcatggggggaccacagaacccacgtggccatcataccacaagcgc |
| aggtagattaagtggcgacccctcataaacacgctggacataaacattacctcttttggcatgttgtaattcaccacctcccggtaccatata |
| aacctctgattaaacatggcgccatccaccaccatcctaaaccagctggccaaaacctgcccgccggctatacactgcagggaaccgg |
| gactggaacaatgacagtggagagcccaggactcgtaaccatggatcatcatgctcgtcatgatatcaatgttggcacaacacaggcac |
| acgtgcatacacttcctcaggattacaagctcctcccgcgttagaaccatatcccagggaacaacccattcctgaatcagcgtaaatccca |
| cactgcagggaagacctcgcacgtaactcacgttgtgcattgtcaaagtgttacattcgggcagcagcggatgatcctccagtatggtag |
| cgcgggtttctgtctcaaaaggaggtagacgatccctactgtacggagtgcgccgagacaaccgagatcgtgttggtcgtagtgtcatg |
| ccaaatggaacgccggacgtagtcatatttcctgaagcaaaaccaggtgcgggcgtgacaaacagatctgcgtctccggtctcgccgct |
| tagatcgctctgtgtagtagttgtagtatatccactctctcaaagcatccaggcgcccccctggcttcgg |

TABLE 7

| 5′ End Fragment 2 |
|---|
| (SEQ ID NO: 7) |
| tggccaacataaataaaaaaaccagactctgtttggatttggatcaagcaagtgtcttgctgtctttatttaggggttttgcgcgcgcggtagg |
| cccgggaccagcggtctcggtcgttgagggtcctgtgtatttttttccaggacgtggtaaaggtgactctggatgttcagatacatgggcat |
| aagcccgtctctgggggaggtagcaccactgcagagcttcatgctgcggggtggtgttgtagatgatccagtcgtagcaggagcgct |
| gggcgtggtgcctaaaaatgtctttcagtagcaagctgattgccaggggcaggcccttggtgtaagtgtttacaaagcggttaagctggg |
| atgggtgcatacgtggggatatgagatgcatcttggactgtatttttaggttggctatgttcccagccatatccctccggggattcatgttgtg |
| cagaaccaccagcacagtgtatccggtgcacttgggaaatttgtcatgtagcttagaaggaaatgcgtggaagaacttggagacgccctt |
| gtgacctccaagattttccatgcattcgtccataatgatggcaatgggcccacgggcggcggcctgggcgaagatatttctgggatcact |
| aacgtcatagttgtgttccaggatgagatcgtcataggccatttttacaaagcgcgggcggagggtgccagactgcggtataatggttcc |
| atccggcccaggggcgtagttaccctcacagatttgcatttcccacgctttgagttcagatggggggatcatgtctacctgcggggcgat |
| gaagaaaacggtttccggggtaggggagatcagctgggaagaaagcaggttcctgagcagctgcgacttaccgcagccggtgggcc |
| cgtaaatcacacctattaccgggtgcaactggtagttaagagagctgcagctgccgtcatccctgagcaggggggccacttcgttaagc |
| atgtccctgactcgcatgttttccctgaccaaatccgccagaaggcgctcgccgcccagcgatagcagttcttgcaaggaagcaaagttt |
| ttcaacggtttgagaccgtccgccgtaggcatgcttttgagcgtttgaccaagcagttccaggcggtcccacagctcggtcacctgctcta |
| cggcatctcgatccagcatatctcctcgtttcgcgggttggggcggctttcgctgtacggcagtagtcggtgctcgtccagacgggccag |
| ggtcatgtctttccacgggcgcagggtcctcgtcagcgtagtctgggtcacggtgaaggggtgcgctccgggctgcgcgctggccag |
| ggtgcgcttgaggctggtcctgctggtgctgaagcgctgccggtcttcgccctgcgcgtcggccaggtagcatttgaccatggtgtcata |
| gtccagcccctccgcggcgtggcccttggcgcgcagcttgcccttggaggaggcgccgcacgaggggcagtgcagacttttgaggg |
| cgtagagcttgggcgcgagaaataccgattccggggagtaggcatccgcgccgcaggccccgcagacggtctcgcattccacgagc |
| caggtgagctctggccgttcggggtcaaaaaccaggtttcccccatgctttttgatgcgtttcttacctctggtttccatgagccggtgtcca |
| cgctcggtgacgaaaaggctgtccgtgtccccgtatacagacttgagaggcctgtcctcgagcggtgttccgcggtcctcctcgtataga |
| aactcggaccactctgagacaaaggctcgcgtccaggccagcacgaaggaggctaagtgggaggggtagcggtcgttgtccactag |

TABLE 7-continued

| 5′ End Fragment 2 |
|---|
| ggggtccactcgctccagggtgtgaagacacatgtcgccctcttcggcatcaaggaaggtgattggtttgtaggtgtaggccacgtgac |
| cgggtgttcctgaagggggctataaagggggtgggggcgcgttcgtcctcactctcttccgcatcgctgtctgcgagggccagctgt |
| tggggtgagtactccctctgaaaagcgggcatgacttctgcgctaagattgtcagtttccaaaaacgaggaggatttgatattcacctggc |
| ccgcggtgatgcctttgagggtggccgcatccatctggtcagaaaagacaatctttttgttgtcaagcttggtggcaaacgacccgtaga |
| gggcgttggacagcaacttggcgatggagcgcagggtttggtttttgtcgcgatcggcgcgctccttggccgcgatgtttagctgcacgt |
| attcgcgcgcaacgcaccgccattcgggaaagacggtggtgcgctcgtcgggcaccaggtgcacgcgccaaccgcggttgtgcagg |
| gtgacaaggtcaacgctggtggctacctctccgcgtaggcgctcgttggtccagcagaggcggccgcccttgcgcgagcagaatggc |
| ggtagggggtctagctgcgtctcgtccggggggtctgcgtccacggtaaagaccccgggcagcaggcgcgcgtcgaagtagtctatc |
| ttgcatccttgcaagtctagcgcctgctgccatgcgcgggcggcaagcgcgcgctcgtatgggttgagtgggggaccccatggcatgg |
| ggtgggtgagcgcggaggcgtacatgccgcaaatgtcgtaaacgtagaggggctctctgagtattccaagatatgtagggtagcatctt |
| ccaccgcggatgctggcgcgcacgtaatcgtatagttcgtgcgagggagcgaggaggtcgggaccgaggttgctacgggcgggctg |
| ctctgctcggaagactatctgcctgaagatggcatgtgagttggatgatatggttggacgctggaagacgttgaagctggcgtctgtgag |
| acctaccgcgtcacgcacgaaggaggcgtaggagtcgcgcagcttgttgaccagctcggcggtgacctgcacgtctagggcgcagta |
| gtccagggtttccttgatgatgtcatacttatcctgtccctttttttttccacagctcgcggttgaggacaaactcttcgcggtctttccagtactc |
| ttggatcggaaacccgtcggcctccgaacggtaagagcctagcatgtagaactggttgacggcctggtaggcgcagcatccctttttcta |
| cgggtagcgcgtatgcctgcgcggccttccggagcgaggtgtgggtgagcgcaaaggtgtccctgaccatgactttgaggtactggta |
| tttgaagtcagtgtcgtcgcatccgccctgctcccagagcaaaaagtccgtgcgctttttggaacgcggatttggcagggcgaaggtgac |
| atcgttgaagagtatctttcccgcgcgaggcataaagttgcgtgtgatgcggaagggtcccggcacctcggaacggttgttaattacctg |
| ggcggcgagcacgatctcgtcaaagccgttgatgttgtggcccacaatgtaaagttccaagaagcgcgggatgcccttgatggaaggc |
| aatttttttaagttcctcgtaggtgagctcttcaggggagctgagcccgtgctctgaaagggcccagtctgcaagatgagggttggaagcg |
| acgaatgagctccacaggtcacgggccattagcatttgcaggtggtcgcgaaaggtcctaaactggcgacctatggccatttttttctggg |
| gtgatgcagtagaaggtaagcgggtcttgttcccagcggtcccatccaaggttcgcggctaggtctcgcgcggcagtcactagaggctc |
| atctccgccgaacttcatgaccagcatgaagggcacgagctgcttcccaaaggcccccatccaagtataggtctctacatcgtaggtga |
| caaagagacgctcggtgcgaggatgcgagccgatcgggaagaactggatctcccgccaccaattggaggagtggctattgatgtggt |
| gaaagtagaagtccctgcgacgggccgaacactcgtgctggcttttgtaaaaacgtgcgcagtactggcagcggtgcacgggctgtac |
| atcctgcacgaggttgacctgacgaccgcgcacaaggaagcagagtgggaatttgagcccctcgcctggcgggtttggctggtggtct |
| tctacttcggctgcttgtccttgaccgtctggctgctcgaggggagttacggtggatcggaccaccacgccgcgcgagcccaaagtcca |
| gatgtccgcgcgcggcggtcggagcttgatgacaacatcgcgcagatgggagctgtccatggtctggagctcccgcggcgtcaggtc |
| aggcgggagctcctgcaggtttacctcgcatagacgggtcagggcgcgggctagatccaggtgatacctaatttccaggggctggttg |
| gtggcggcgtcgatggcttgcaagaggccgcatccccgcggcgcgactacggtaccgcgcggcgggcggtgggccgcgggggtg |
| tccttggatgatgcatctaaaagcggtgacgcgggcgagcccccggaggtagggggggctccggacccgccgggagagggggca |
| ggggcacgtcggcgccgcgcgcgggcaggagctggtgctgcgcgcgtaggttgctggcgaacgcgacgacgcggcggttgatctc |
| ctgaatctggcgcctctgcgtgaagacgacgggcccggtgagcttgagcctgaaagagagttcgacagaatcaatttcggtgtcgttga |
| cggcggcctggcgcaaaatctcctgcacgtctcctgagttgtcttgataggcgatctcggccatgaactgctcgatctcttcctcctggag |
| atctccgcgtccggctcgctccacggtggcggcgaggtcgttggaaatgcgggccatgagctgcgagaaggcgttgaggcctccctc |
| gttccagacgcggctgtagaccacgccccttcggcatcgcgggcgcgcatgaccacctgcgcgagattgagctccacgtgccgggc |
| gaagacggcgtagtttcgcaggcgctgaaagaggtagttgagggtggtggcggtgtgttctgccacgaagaagtacataacccagcgt |
| cgcaacgtggattcgttgatatcccccaaggcctcaaggcgctccatggcctcgtagaagtccacggcgaagttgaaaaactgggagtt |
| gcgcgccgacacggttaactcctcctccagaagacggatgagctcggcgacagtgtcgcgcacctcgcgctcaaaggctacagggg |

TABLE 7-continued

| 5′ End Fragment 2 |
|---|
| cctcttcttcttcttcaatctcctcttccataagggcctccccttcttcttcttctggcggcggtgggggagggggggacacggcggcgacga<br>cggcgcaccgggaggcggtcgacaaagcgctcgatcatctccccgcggcgacggcgcatggtctcggtgacggcgcggccgttctc<br>gcgggggcgcagttggaagacgccgcccgtcatgtcccggttatgggttggcggggggctgccatgcggcagggatacggcgctaa<br>cgatgcatctcaacaattgttgtgtaggtactccgccgccgagggacctgagcgagtccgcatcgaccggatcggaaaacctctcgag<br>aaaggcgtctaaccagtcacagtcgcaaggtaggctgagcaccgtggcgggcggcagcgggcggcggtcggggttgtttctggcgg<br>aggtgctgctgatgatgtaattaaagtaggcggtcttgagacggcggatggtcgacagaagcaccatgtccttgggtccggcctgctga<br>atgcgcaggcggtcggccatgccccaggcttcgttttgacatcggcgcaggtctttgtagtagtcttgcatgagcctttctaccggcacttc<br>ttcttctccttcctcttgtcctgcatctcttgcatctatcgctgcggcggcggcggagtttggccgtaggtggcgccctcttcctcccatgcgt<br>gtgaccccgaagcccctcatcggctgaagcagggctaggtcggcgacaacgcgctcggctaatatggcctgctgcacctgcgtgagg<br>gtagactggaagtcatccatgtccacaaagcggtggtatgcgcccgtgttgatggtgtaagtgcagttggccataacggaccagttaacg<br>gtctggtgacccggctgcgagagctcggtgtacctgagacgcgagtaagccctcgagtcaaatacgtagtcgttgcaagtccgcacca<br>ggtactggtatcccaccaaaaagtgcggcggcggctggcggtagaggggccagcgtagggtggccggggctccgggggcgagat<br>cttccaacataaggcgatgatatccgtagatgtacctggacatccaggtgatgccggcggcggtggtggaggcgcgcggaaagtcgc<br>ggacgcggttccagatgttgcgcagcggcaaaaagtgctccatggtcgggacgctctggccggtcaggcgcgcgcaatcgttgacgc<br>tctagaccgtgcaaaaggagagcctgtaagcgggcactcttccgtggtctggtggataaattcgcaagggtatcatggcggacgaccg<br>gggttcgagccccgtatccggccgtccgccgtgatccatgcggttaccgcccgcgtgtcgaacccaggtgtgcgacgtcagacaacg<br>ggggagtgctccttttggcttccttccaggcgcggcggctgctgcgctagctttttggccactggccgcgcgcagcgtaagcggttagg<br>ctggaaagcgaaagcattaagtggctcgctccctgtagccggagggttattttccaagggttgagtcgcgggacccccggttcgagtct<br>cggaccggccggactgcggcgaacgggggtttgcctccccgtcatgcaagaccccgcttgcaaattcctccggaaacagggacgag<br>ccccttttttgcttttcccagatgcatccggtgctgcggcagatggccccccctcctcagcagcggcaagagcaagagcagcggcagac<br>atgcagggcaccctcccctcctcctaccgcgtcaggaggggcgacatccgcggttgacgcggcagcagatggtgattacgaaccccc<br>gcggcgccgggcccggcactacctggacttggaggagggcgagggcctggcgcggctaggagcgccctctcctgagcggtaccca<br>agggtgcagctgaagcgtgatacgcgtgaggcgtacgtgccgcggcagaacctgtttcgcgaccgcgagggagaggagcccgagg<br>agatgcgggatcgaaagttccacgcagggcgcgagctgcggcatggcctgaatcgcgagcggttgctgcgcgaggaggactttgag<br>cccgacgcgcgaaccgggattagtcccgcgcgcgcacacgtggcggccgccgacctggtaaccgcatacgagcagacggtgaacc<br>aggagattaactttcaaaaaagctttaacaaccacgtgcgtacgcttgtggcgcgcgaggaggtggctataggactgatgcatctgtggg<br>actttgtaagcgcgctggagcaaaacccaaatagcaagccgctcatggcgcagctgttccttatagtgcagcacagcagggacaacga<br>ggcattcagggatgcgctgctaaacatagtagagcccgagggccgctggctgctcgatttgataaacatcctgcagagcatagtggtgc<br>aggagcgcagcttgagcctggctgacaaggtggccgccatcaactattccatgcttagcctgggcaagttttacgcccgcaagatatac<br>catacccccttacgttcccatagacaaggaggtaaagatcgaggggttctacatgcgcatggcgctgaaggtgcttaccttgagcgacga<br>cctgggcgtttatcgcaacgagcgcatccacaaggccgtgagcgtgagccggcggcgcgagctcagcgaccgcgagctgatgcaca<br>gcctgcaaagggccctggctggcacgggcagcggcgatagagaggccgagtcctactttgacgcgggcgctgacctgcgctgggc<br>cccaagccgacgcgccctggaggcagctggggccggacctgggctggcggtggcacccgcgcgcgctggcaacgtcggcggcgt<br>ggaggaatatgacgaggacgatgagtacgagccagaggacggcgagtactaagcggtgatgtttctgatcagatgatgcaagacgca<br>acggacccggcggtgcgggcggcgctgcagagccagccgtccggccttaactccacggacgactggcgccaggtcatggaccgca<br>tcatgtcgctgactgcgcgcaatcctgacgcgttccggcagcagccgcaggccaaccggctctccgcaattctggaagcggtggtccc<br>ggcgcgcgcaaaccccacgcacgagaaggtgctggcgatcgtaaacgcgctggccgaaaacagggccatccggcccgacgaggc<br>cggcctggtctacgacgcgctgcttcagcgcgtggctcgttacaacagcggcaacgtgcagaccaacctggaccggctggtgggga<br>tgtgcgcgaggccgtggcgcagcgtgagcgcgcgcagcagcagggcaacctgggctccatggttgcactaaacgccttcctgagtac |

TABLE 7-continued

| 5′ End Fragment 2 |
|---|
| acagcccgccaacgtgccgcggggacaggaggactacaccaactttgtgagcgcactgcggctaatggtgactgagacaccgcaaa |
| gtgaggtgtaccagtctgggccagactatttttccagaccagtagacaaggcctgcagaccgtaaacctgagccaggctttcaaaaact |
| tgcaggggctgtgggggtgcgggctcccacaggcgaccgcgcgaccgtgtctagcttgctgacgcccaactcgcgcctgttgctgc |
| tgctaatagcgcccttcacggacagtggcagcgtgtcccgggacacatacctaggtcacttgctgacactgtaccgcgaggccataggt |
| caggcgcatgtggacgagcatactttccaggagattacaagtgtcagccgcgcgctggggcaggaggacacgggcagcctggaggc |
| aaccctaaactacctgctgaccaaccggcggcagaagatcccctcgttgcacagtttaaacagcgaggaggagcgcattttgcgctac |
| gtgcagcagagcgtgagccttaacctgatgcgcgacggggtaacgcccagcgtggcgctggacatgaccgcgcgcaacatggaacc |
| gggcatgtatgcctcaaaccggccgtttatcaaccgcctaatggactacttgcatcgcgcggccgccgtgaaccccgagtatttcaccaa |
| tgccatcttgaacccgcactggctaccgcccccctggtttctacaccgggggattcgaggtgcccgagggtaacgatggattcctctggg |
| acgacatagacgacagcgtgttttccccgcaaccgcagaccctgctagagttgcaacagcgcgagcaggcagaggcggcgctgcga |
| aaggaaagcttccgcaggccaagcagcttgtccgatctaggcgctgcggccccgcggtcagatgctagtagcccatttccaagcttgat |
| agggtctcttaccagcactcgcaccacccgcccgcgcctgctgggcgaggaggagtacctaaacaactcgctgctgcagccgcagcg |
| cgaaaaaaacctgcctccggcatttcccaacaacgggatagagagcctagtggacaagatgagtagatggaagacgtacgcgcagga |
| gcacagggacgtgccaggcccgcgcccgcccacccgtcgtcaaaggcacgaccgtcagcggggtctggtgtgggaggacgatgac |
| tcggcagacgacagcagcgtcctggatttgggagggagtggcaacccgtttgcgcaccttcgccccaggctggggagaatgttttaaa |
| aaaaaaaaagcatgatgcaaaataaaaaactcaccaaggccatggcaccgagcgttggttttcttgtattccccttagtatgcggcgcgc |
| ggcgatgtatgaggaaggtcctcctccctcctacgagagtgtggtgagcgcggcgccagtggcggcggcgctgggttctcccttcgat |
| gctcccctggacccgccgtttgtgcctccgcggtacctgcggcctaccggggggagaaacagcatccgttactctgagttggcacccct |
| attcgacaccacccgtgtgtacctggtggacaacaagtcaacggatgtggcatccctgaactaccagaacgaccacagcaactttctga |
| ccacggtcattcaaaacaatgactacagcccgggggaggcaagcacacagaccatcaatcttgacgaccggtcgcactggggcggc |
| gacctgaaaaccatcctgcataccaacatgccaaatgtgaacgagttcatgtttaccaataagtttaaggcgcgggtgatggtgtcgcgct |
| tgcctactaaggacaatcaggtggagctgaaatacgagtgggtggagttcacgctgcccgagggcaactactccgagaccatgaccat |
| agaccttatgaacaacgcgatcgtggagcactacttgaaagtgggcagacagaacggggttctggaaagcgacatcggggtaaagttt |
| gacacccgcaacttcagactggggtttgaccccgtcactggtcttgtcatgcctggggtatatacaaacgaagccttccatccagacatca |
| ttttgctgccaggatgcggggtggacttcacccacagccgcctgagcaacttgttgggcatccgcaagcggcaacccttccaggaggg |
| ctttaggatcacctacgatgatctggagggtggtaacattcccgcactgttggatgtggacgcctaccaggcgagcttgaaagatgacac |
| cgaacaggggggggtggcgcaggcggcagcaacagcagtggcagcggcgcggaagagaactccaacgcggcagccgcggca |
| atgcagccggtggaggacatgaacgatcatgccattcgcggcgacacctttgccacacgggctgaggagaagcgcgctgaggccga |
| agcagcggccgaagctgccgcccccgctgcgcaacccgaggtcgagaagcctcagaagaaaccggtgatcaaacccctgacagag |
| gacagcaagaaacgcagttacaacctaataagcaatgacagcaccttcacccagtaccgcagctggtaccttgcatacaactacggcg |
| accctcagaccggaatccgctcatggaccctgctttgcactcctgacgtaacctgcggctcggagcaggtctactggtcgttgccagac |
| atgatgcaagaccccgtgaccttccgctccacgcgccagatcagcaactttccggtggtgggcgccgagctgttgcccgtgcactccaa |
| gagcttctacaacgaccaggccgtctactcccaactcatccgccagtttacctctctgacccacgtgttcaatcgctttcccgagaaccag |
| attttggcgcgcccgccagcccccaccatcaccaccgtcagtgaaaacgttcctgctctcacagatcacgggacgctaccgctgcgca |
| acagcatcggaggagtccagcgagtgaccattactgacgccagacgccgcacctgcccctacgtttacaaggccctgggcatagtctc |
| gccgcgcgtcctatcgagccgcacttttttgagcaagcatgtccatccttatatcgcccagcaataacacaggctggggcctgcgcttccc |
| aagcaagatgtttggcggggccaagaagcgctccgaccaacacccagtgcgcgtgcgcgggcactaccgcgcgccctggggcgcg |
| cacaaacgcggccgcactgggcgcaccaccgtcgatgacgccatcgacgcggtggtggaggaggcgcgcaactacacgcccacg |
| ccgccaccagtgtccacagtggacgcggccattcagaccgtggtgcgcggagcccggcgctatgctaaaatgaagagacggcggag |

TABLE 7-continued

| 5′ End Fragment 2 |
|---|
| gcgcgtagcacgtcgccaccgccgccgacccggcactgccgcccaacgcgcggcggcggccctgcttaaccgcgcacgtcgcacc |
| ggccgacgggcggccatgcgagcagctcgaaggctggccgcgggtattgtcactgtgccccccaggtccaggcgacgagcggccg |
| ccgcagcagccgcggccattagtgctatgactcagggtcgcaggggcaacgtgtattgggtgcgcgactcggttagcggcctgcgcg |
| tgcccgtgcgcacccgcccccccgcgcaactagattgcaagaaaaaactacttagactcgtactgttgtatgtatccagcggcggcggcg |
| cgcaacgaagctatgtccaagcgcaaaatcaaagaagagatgctccaggtcatcgcgccggagatctatggcccccccgaagaagga |
| agagcaggattacaagccccgaaagctaaagcgggtcaaaaagaaaaagaaagatgatgatgatgaacttgacgacgaggtggaact |
| gctgcacgctaccgcgcccaggcgacgggtacagtggaaaggtcgacgcgtaaaacgtgttttgcgacccggcaccaccgtagtcttt |
| acgcccggtgagcgctccacccgcacctacaagcgcgtgtatgatgaggtgtacggcgacgaggacctgcttgagcaggccaacga |
| gcgcctcggggagtttgcctacggaaagcggcataaggacatgctggcgttgccgctggacgagggcaacccaacacctagcctaaa |
| gcccgtaacactgcagcaggtgctgcccgcgcttgcaccgtccgaagaaaagcgcggcctaaagcgcgagtctggtgacttggcacc |
| caccgtgcagctgatggtacccaagcgccagcgactggaagatgtcttggaaaaaatgaccgtggaacctgggctggagcccgaggt |
| ccgcgtgcggccaatcaagcaggtggcgccgggactgggcgtgcagaccgtggacgttcagatacccactaccagtagcaccagtat |
| tgccaccgccacagagggcatggagacacaaacgtccccggttgcctcagcggtggcggatgccgcggtgcaggcggtcgctgcg |
| gccgcgtccaagacctctacggaggtgcaaacggacccgtggatgtttcgcgtttcagccccccggcgcccgcgcggttcgaggaag |
| tacggcgccgccagcgcgctactgcccgaatatgccctacatccttccattgcgcctacccccggctatcgtggctacacctaccgccc |
| cagaagacgagcaactacccgacgccgaaccaccactggaacccgccgccgccgtcgccgtcgccagcccgtgctggccccgattt |
| ccgtgcgcagggtggctcgcgaaggaggcaggaccctggtgctgccaacagcgcgctaccaccccagcatcgtttaaaagccggtct |
| ttgtggttcttgcagatatggccctcacctgccgcctccgtttcccggtgccgggattccgaggaagaatgcaccgtaggaggggcatg |
| gccggccacggcctgacgggggcatgcgtcgtgcgcaccaccggcggcggcgcgcgtcgcaccgtcgcatgcgcggcggtatc |
| ctgcccctccttattccactgatcgccgcggcgattggcgccgtgcccggaattgcatccgtggccttgcaggcgcagagacactgatta |
| aaaacaagttgcatgtggaaaaatcaaaataaaaagtctggactctcacgctcgcttggtcctgtaactattttgtagaatggaagacatca |
| actttgcgtctctggccccgcgacacggctcgcgcccgttcatgggaaactggcaagatatcggcaccagcaatatgagcggtggcgc |
| cttcagctggggctcgctgtggagcggcattaaaaatttcggttccaccgttaagaactatggcagcaaggcctggaacagcagcacag |
| gccagatgctgagggataagttgaaagagcaaaatttccaacaaaaggtggtagatggcctggcctctggcattagcggggtggtgga |
| cctggccaaccaggcagtgcaaaataagattaacagtaagcttgatccccgccctcccgtagaggagcctccaccggccgtggagac |
| agtgtctccagaggggcgtggcgaaaagcgtccgcgccccgacagggaagaaactctggtgacgcaaatagacgagcctccctcgt |
| acgaggaggcactaaagcaaggcctgcccaccacccgtcccatcgcgcccatggctaccggagtgctgggccagcacacacccgta |
| acgctggacctgcctcccccgccgacacccagcagaaacctgtgctgccaggcccgaccgccgttgttgtaacccgtcctagccgc |
| gcgtccctgcgccgcgccgccagcggtccgcgatcgttgcggcccgtagccagtggcaactggcaaagcacactgaacagcatcgt |
| gggtctgggggtgcaatccctgaagcgccgacgatgcttctgaatagctaacgtgtcgtatgtgtgtcatgtatgcgtccatgtcgccgcc |
| agaggagctgctgagccgccgcgcgcccgctttccaagatggctaccccttcgatgatgccgcagtggtcttacatgcacatctcgggc |
| caggacgcctcggagtacctgagccccgggctggtgcagtttgcccgcgccaccgagacgtacttcagcctgaataacaagtttagaa |
| accccacggtggcgcctacgcacgacgtgaccacagaccggtcccagcgtttgacgctgcggttcatccctgtggaccgtgaggatac |
| tgcgtactcgtacaaggcgcggttcaccctagctgtgggtgataaccgtgtgctggacatggcttccacgtactttgacatccgcggcgt |
| gctggacaggggccctacttttaagccctactctggcactgcctacaacgccctggctcccaagggtgccccaaatccttgcgaatggg |
| atgaagctgctactgctcttgaaataaacctagaagaagaggacgatgacaacgaagacgaagtagacgagcaagctgagcagcaaa |
| aaactcacgtatttgggcaggcgccttattctggtataaatattacaaaggagggtattcaaataggtgtcgaaggtcaaacacctaaatat |
| gccgataaaacatttcaacctgaacctcaaataggagaatctcagtggtacgaaactgaaattaatcatgcagctgggagagtccttaaa |
| aagactaccccaatgaaaccatgttacggttcatatgcaaaacccacaaatgaaaatggagggcaaggcattcttgtaaagcaacaaaat |

TABLE 7-continued

| 5′ End Fragment 2 |
|---|
| ggaaagctagaaagtcaagtggaaatgcaatttttctcaactactgaggcgaccgcaggcaatggtgataacttgactcctaaagtggtat |
| tgtacagtgaagatgtagatatagaaaccccagacactcatatttcttacatgcccactattaaggaaggtaactcacgagaactaatggg |
| ccaacaatctatgcccaacaggcctaattacattgcttttagggacaattttattggtctaatgtattacaacagcacgggtaatatgggtgtt |
| ctggcgggccaagcatcgcagttgaatgctgttgtagatttgcaagacagaaacacagagctttcataccagcttttgcttgattccattgg |
| tgatagaaccaggtacttttctatgtggaatcaggctgttgacagctatgatccagatgttagaattattgaaaatcatggaactgaagatga |
| acttccaaattactgctttccactgggaggtgtgattaatacagagactcttaccaaggtaaaacctaaaacaggtcaggaaaatggatgg |
| gaaaaagatgctacagaattttcagataaaaatgaaataagagttggaaataattttgccatggaaatcaatctaaatgccaacctgtggag |
| aaatttcctgtactccaacatagcgctgtatttgcccgacaagctaaagtacagtccttccaacgtaaaaatttctgataacccaaacaccta |
| cgactacatgaacaagcgagtggtggctcccgggttagtggactgctacattaaccttggagcacgctggtcccttgactatatggacaa |
| cgtcaacccatttaaccaccaccgcaatgctggcctgcgctaccgctcaatgttgctgggcaatggtcgctatgtgcccttccacatccag |
| gtgcctcagaagttctttgccattaaaaacctccttctcctgccgggctcatacacctacgagtggaacttcaggaaggatgttaacatggt |
| tctgcagagctccctaggaaatgacctaagggttgacggagccagcattaagtttgatagcatttgcctttacgccaccttcttccccatgg |
| cccacaacaccgcctccacgcttgaggccatgcttagaaacgacaccaacgaccagtcctttaacgactatctctccgccgccaacatg |
| ctctaccctatacccgccaacgctaccaacgtgcccatatccatcccctcccgcaactgggggctttccgcggctgggccttcacgcg |
| ccttaagactaaggaaaccccatcactgggctcgggctacgacccttattacacctactctggctctataccctacctagatggaaccttt t |
| acctcaaccacacctttaagaaggtggccattacctttgactcttctgtcagctggcctggcaatgaccgcctgcttacccccaacgagttt |
| gaaattaagcgctcagttgacggggagggttacaacgttgcccagtgtaacatgaccaaagactggttcctggtacaaatgctagctaac |
| tacaacattggctaccagggcttctatatcccagagagctacaaggaccgcatgtactccttctttagaaacttccagcccatgagccgtc |
| aggtggtggatgatactaaatacaaggactaccaacaggtgggcatcctacaccaacacaacaactctggatttgttggctaccttgccc |
| ccaccatgcgcgaaggacaggcctaccctgctaacttcccctatccgcttataggcaagaccgcagttgacagcattacccagaaaaag |
| tttctttgcgatcgcaccctttggcgcatcccattctccagtaactttatgtccatgggcgcactcacagacctgggccaaaaccttctctac |
| gccaactccgcccacgcgctagacatgacttttgaggtggatcccatggacgagcccacccttctttatgttttgtttgaagtctttgacgtg |
| gtccgtgtgcaccggccgcaccgcggcgtcatcgaaaccgtgtacctgcgcacgcccttctcggccggcaacgccacaacataaaga |
| agcaagcaacatcaacaacagctgccgccatgggctccagtgagcaggaactgaaagccattgtcaaagatcttggttgtgggccatat |
| tttttgggcacctatgacaagcgctttccaggctttgtttctccacacaagctcgcctgcgccatagtcaatacggccggtcgcgagactg |
| gggcgtacactggatggcctttgcctggaacccgcactcaaaaacatgctacctctttgagccctttggcttttctgaccagcgactcaa |
| gcaggtttaccagtttgagtacgagtcactcctgcgccgtagcgccattgcttcttcccccgaccgctgtataacgctggaaaagtccacc |
| caaagcgtacaggggcccaactcggccgcctgtggactattctgctgcatgtttctccacgcctttgccaactggccccaaactcccatg |
| gatcacaaccccaccatgaaccttattaccggggtacccaactccatgctcaacagtccccaggtacagcccaccctgcgtcgcaacca |
| ggaacagctctacagcttcctggagcgccactcgccctacttccgcagccacagtgcgcagattaggagcgccacttctttttgtcacttg |
| aaaaacatgtaaaaataatgtactagagacactttcaataaaggcaaatgcttttatttgtacactctcgggtgattatttaccccacccttg |
| ccgtctgcgccgtttaaaaatcaaaggggttctgccgcgcatcgctatgcgccactggcagggacacgttgcgatactggtgtttagtgc |
| tccacttaaactcaggcacaaccatccgcggcagctcggtgaagttttcactccacaggctgcgcaccatcaccaacgcgtttagcaggt |
| cgggcgccgatatcttgaagtcgcagttggggcctccgccctgcgcgcgcgagttgcgatacacagggttgcagcactggaacactat |
| cagcgccgggtggtgcacgctggccagcacgctcttgtcggagatcagatccgcgtccaggtcctccgcgttgctcagggcgaacgg |
| agtcaactttggtagctgccttcccaaaaagggcgcgtgcccaggctttgagttgcactcgcaccgtagtggcatcaaaaggtgaccgt |
| gcccggtctgggcgttaggatacagcgcctgcataaaagccttgatctgcttaaaagccacctgagcctttgcgccttcagagaagaac |
| atgccgcaagacttgccggaaaactgattggccggacacgcggcgtcgtgcacgcagcaccttgcgtcggtgttggagatctgcacca |
| catttcggccccaccggttcttcacgatcttggccttgctagactgctccttcagcgcgcgctgcccgttttcgctcgtcacatccatttcaat |

TABLE 7-continued

| 5′ End Fragment 2 |
|---|
| cacgtgctccttatttatcataatgcttccgtgtagacacttaagctcgccttcgatctcagcgcagcggtgcagccacaacgcgcagccc |
| gtgggctcgtgatgcttgtaggtcacctctgcaaacgactgcaggtacgcctgcaggaatcgccccatcatcgtcacaaaggtcttgttg |
| ctggtgaaggtcagctgcaacccgcggtgctcctcgttcagccaggtcttgcatacggccgccagagcttccacttggtcaggcagtag |
| tttgaagttcgcctttagatcgttatccacgtggtacttgtccatcagcgcgcgcgcagcctccatgcccttctcccacgcagacacgatcg |
| gcacactcagcgggttcatcaccgtaatttcactttccgcttcgctgggctcttcctcttcctcttgcgtccgcataccacgcgccactgggt |
| cgtcttcattcagccgccgcactgtgcgcttacctcctttgccatgcttgattagcaccggtgggttgctgaaacccaccatttgtagcgcc |
| acatcttctctttcttcctcgctgtccacgattacctctggtgatggcgggcgctcgggcttgggagaagggcgcttctttttcttcttgggcg |
| caatggccaaatccgccgccgaggtcgatggccgcgggctgggtgtgcgcggcaccagcgcgtcttgtgatgagtcttcctcgtcctc |
| ggactcgatacgccgcctcatccgctttttttgggggcgcccggggaggcggcggcgacggggacggggacgacacgtcctccatgg |
| ttgggggacgtcgcgccgcaccgcgtccgcgctcgggggtggtttcgcgctgctcctcttcccgactggccatttccttctcctataggc |
| agaaaaagatcatggagtcagtcgagaagaaggacagcctaaccgcccccctctgagttcgccaccaccgcctccaccgatgccgcca |
| acgcgcctaccaccttccccgtcgaggcacccccgcttgaggaggaggaagtgattatcgagcaggacccaggttttgtaagcgaaga |
| cgacgaggaccgctcagtaccaacagaggataaaaagcaagaccaggacaacgcagaggcaaacgaggaacaagtcgggggg |
| gggacgaaaggcatggcgactacctagatgtgggagacgacgtgctgttgaagcatctgcagcgccagtgcgccattatctgcgacg |
| cgttgcaagagcgcagcgatgtgcccctcgccatagcggatgtcagccttgcctacgaacgccacctattctcaccgcgcgtaccccc |
| aaacgccaagaaaacggcacatgcgagcccaacccgcgcctcaacttctaccccgtatttgccgtgccagaggtgcttgccacctatca |
| catctttttccaaaactgcaagatacccctatcctgccgtgccaaccgcagccgagcggacaagcagctggccttgcggcagggcgct |
| gtcatacctgatatcgcctcgctcaacgaagtgccaaaaatctttgagggtcttggacgcgacgagaagcgcgcggcaaacgctctgca |
| acaggaaaacagcgaaaatgaaagtcactctggagtgttggtggaactcgagggtgacaacgcgcgcctagccgtactaaaacgcag |
| catcgaggtcacccactttgcctacccggcacttaacctacccccaaggtcatgagcacagtcatgagtgagctgatcgtgcgccgtg |
| cgcagcccctggagagggatgcaaatttgcaagaacaaacagaggagggcctacccgcagttggcgacgagcagctagcgcgctg |
| gcttcaaacgcgcgagcctgccgacttggaggagcgacgcaaactaatgatggccgcagtgctcgttaccgtggagcttgagtgcatg |
| cagcggttctttgctgacccggagatgcagcgcaagctagaggaaacattgcactacacctttcgacagggctacgtacgccaggcct |
| gcaagatctccaacgtggagctctgcaacctggtctcctaccttggaattttgcacgaaaaccgccttgggcaaaacgtgcttcattccac |
| gctcaagggcgaggcgcgccgcgactacgtccgcgactgcgtttacttatttctatgctacacctggcagacggccatgggcgtttggc |
| agcagtgcttggaggagtgcaacctcaaggagctgcagaaactgctaaagcaaaacttgaaggacctatggacggccttcaacgagc |
| gctccgtggccgcgcacctggcggacatcattttccccgaacgcctgcttaaaaccctgcaacagggtctgccagacttcaccagtcaa |
| agcatgttgcagaactttaggaactttatcctagagcgctcaggaatcttgcccgccacctgctgtgcacttcctagcgactttgtgcccatt |
| aagtaccgcgaatgccctccgccgctttggggccactgctaccttctgcagctagccaactaccttgcctaccactctgacataatggaa |
| gacgtgagcggtgacggtctactggagtgtcactgtcgctgcaacctatgcaccccgcaccgctccctggtttgcaattcgcagctgctt |
| aacgaaagtcaaattatcggtacctttgagctgcagggtccctcgcctgacgaaaagtccgcggctccggggttgaaactcactccggg |
| gctgtggacgtcggcttaccttcgcaaatttgtacctgaggactaccacgcccacgagattaggttctacgaagaccaatcccgcccgcc |
| aaatgcggagcttaccgcctgcgtcattacccagggccacattcttggccaattgcaagccatcaacaaagcccgccaagagtttctgct |
| acgaaagggacgggggggtttacttggacccccagtccggcgaggagctcaacccaatccccccgccgccgcagccctatcagcagc |
| agccgcgggcccttgcttcccaggatggcacccaaaaagaagctgcagctgccgccgccacccacggacgaggaggaatactggg |
| acagtcaggcagaggaggttttggacgaggaggaggaggacatgatggaagactgggagagcctagacgaggaagcttccgaggt |
| cgaagaggtgtcagacgaaacaccgtcaccctcggtcgcattcccctcgccggcgccccagaaatcggcaaccggttccagcatggc |
| tacaacctccgctcctcaggcgccgccggcactgcccgttcgccgacccaaccgtagatgggacaccactggaaccagggccggta |
| agtccaagcagccgccgccgttagcccaagagcaacaacagcgccaaggctaccgctcatggcgcgggcacaagaacgccatagtt |

TABLE 7-continued

| 5′ End Fragment 2 |
| --- |
| gcttgcttgcaagactgtgggggcaacatctccttcgcccgccgctttcttctctaccatcacggcgtggccttcccccgtaacatcctgca |
| ttactaccgtcatctctacagcccatactgcaccggcggcagcggcagcggcagcaacagcagcggccacacagaagcaaaggcga |
| ccggatagcaagactctgacaaagcccaagaaatccacagcggcggcagcagcaggaggaggagcgctgcgtctggcgcccaac |
| gaacccgtatcgacccgcgagcttagaaacaggatttttcccactctgtatgctatatttcaacagagcaggggccaagaacaagagctg |
| aaaataaaaaacaggtctctgcgatccctcacccgcagctgcctgtatcacaaaagcgaagatcagcttcggcgcacgctggaagacg |
| cggaggctctcttcagtaaatactgcgcgctgactcttaaggactagtttcgcgccctttctcaaatttaagcgcgaaaactacgtcatctcc |
| agcggccacacccggcgccagcacctgtcgtcagcgccattatgagcaaggaaattcccacgccctacatgtggagttaccagccac |
| aaatgggacttgcggctggagctgcccaagactactcaacccgaataaactacatgagcgcgggaccccacatgatatcccgggtcaa |
| cggaatccgcgcccaccgaaaccgaattctcctggaacaggcggctattaccaccacacctcgtaataaccttaatccccgtagttggc |
| ccgctgccctggtgtaccaggaaagtcccgctcccaccactgtggtacttcccagagacgcccaggccgaagttcagatgactaactca |
| ggggcgcagcttgcgggggctttcgtcacagggtgcggtcgcccgggcagggtataactcacctgacaatcagagggcgaggtatt |
| cagctcaacgacgagtcggtgagctcctcgcttggtctccgtccggacgggacatttcagatcggcggcgccggccgtccttcattcac |
| gcctcgtcaggcaatcctaactctgcagacctcgtcctctgagccgcgctctggaggcattggaactctgcaatttattgaggagtttgtgc |
| catcggtctactttaaccccttctcgggacctcccggccactatccggatcaatttattcctaactttgacgcggtaaaggactcggcggac |
| ggctacgactgaatgttaagtggccaatg |

TABLE 8

| Codon Optimized Human IL10 cDNA |
| --- |
| (SEQ ID NO: 8) |
| atgcatagttctgccctgttgtgttgcttggtgctgttgacgggggttagagcgagtccaggtcaaggcacgcagtctgaaaactcctgta |
| cacacttccccggcaacctccctaatatgctcagagaccttcgagacgccttctcccgagtaaaaactttctttcagatgaaggaccagct |
| cgacaacttgctgttgaaggaatcactcctcgaagattttaaggggtacctcggttgtcaagctctgtctgaaatgatacaattctatctcga |
| ggaagtcatgcctcaagcggaaaaccaggacccagatattaaggcccatgtgaatagcctcggcgaaaatcttaaaactcttcgcctta |
| gactccgaagatgccataggtttttgccgtgcgaaaataaatccaaagctgtggaacaggtaaaaaatgcgtttaacaagttgcaagaga |
| agggcatctacaaagcgatgtcagagttcgatatattcataaattatattgaagcatacatgactatgaagatcaggaattga |

TABLE 9

| E1 Cell Creation Vector |
| --- |
| (SEQ ID NO: 9) |
| ggtctctctggttagaccagatctgagcctgggagctctctggctaactagggaacccactgcttaagcctcaataaagcttgccttgagt |
| gcttcaagtagtgtgtgcccgtctgttgtgtgactctggtaactagagatccctcagacccttttagtcagtgtggaaaatctctagcagtgg |
| cgcccgaacagggacctgaaagcgaaagggaaaccagagctctctcgacgcaggactcggcttgctgaagcgcgcacggcaagag |
| gcgaggggcggcgactggtgagtacgccaaaaattttgactagcggaggctagaaggagagagatgggtgcgagagcgtcagtatt |
| aagcgggggagaattagatcgcgatgggaaaaaattcggttaaggccagggggaaagaaaaaatataaattaaaacatatagtatggg |
| caagcagggagctagaacgattcgcagttaatcctggcctgttagaaacatcagaaggctgtagacaaatactgggacagctacaacc |
| atcccttcagacaggatcagaagaacttagatcattatataatacagtagcaaccctctattgtgtgcatcaaaggatagagataaaagac |
| accaaggaagctttagacaagatagaggaagagcaaaacaaaagtaagaccaccgcacagcaagcggccactgatcttcagacctg |
| gaggaggagatatgagggacaattggagaagtgaattatataaatataaagtagtaaaaattgaaccattaggagtagcacccaccaag |

TABLE 9-continued

| E1 Cell Creation Vector |
| --- |
| gcaaagagaagagtggtgcagagagaaaaaagagcagtgggaataggagctttgttccttgggttcttgggagcagcaggaagcact |
| atgggcgcagcgtcaatgacgctgacggtacaggccagacaattattgtctggtatagtgcagcagcagaacaatttgctgagggctatt |
| gaggcgcaacagcatctgttgcaactcacagtctggggcatcaagcagctccaggcaagaatcctggctgtggaaagatacctaaagg |
| atcaacagctcctggggatttggggttgctctggaaaactcatttgcaccactgctgtgccttggaatgctagttggagtaataaatctctgg |
| aacagatttggaatcacacgacctggatggagtgggacagagaaattaacaattacacaagcttaatacactccttaattgaagaatcgc |
| aaaaccagcaagaaaagaatgaacaagaattattggaattagataaatgggcaagtttgtggaattggtttaacataacaaattggctgtg |
| gtatataaaattattcataatgatagtaggaggcttggtaggtttaagaatagtttttgctgtactttctatagtgaatagagttaggcagggat |
| attcaccattatcgtttcagacccacctcccaaccccgaggggacccgacaggcccgaaggaatagaagaagaaggtggagagaga |
| gacagagacagatccattcgattagtgaacggatctcgacggtatcggttaacttttaaaagaaaaggggggattggggggtacagtgc |
| aggggaaagaatagtagacataatagcaacagacatacaaactaaagaattacaaaaacaaattacaaaattcaaaattttatcgatcatg |
| gtcctgctggagttcgtgctcctatctagagctagcgaattcccttatcgattttaccacatttgtagaggttttacttgctttaaaaaacctccc |
| acacctccccctgaacctgaaacataaaatgaatgcaattgttgttgttaacttgtttattgcagcttataatggttacaaataaagcaatagc |
| atcacaaatttcacaaataaagcatttttttcactgcattctagttgtggtttgtccaaactcatcaatgtatcttatcatgtctgctcgaagcggc |
| cggccggctgattatgatctcacctaggctcgagtcaatctgtatcttcatcgctagagccaaactcagcgcgggtgcaggccagcacc |
| aagtgatcgggcctcagctcctcggtcacatccagcatcacaggctggttcctaatatgtttaccgccacactcgcagggtctgcacctg |
| gtgcgggtctcatcgtacctcagcaccttccagatcttcatggtcatgtcaaacaccccgttcaggttcaccttggacatgctctcgggctc |
| aagcaatatcttagtgtgactcaaattgcattggtaaggtaggaacacccccctcctgttacccaaatgcaaggaacagcgggtcagtat |
| gttatgctcaaacactggccaggccttgcgagagtggctggctacgtgaatggtcttcagcaggtgacagttgccgtccgagcaggtca |
| gcatctgagaggccctgtcctcgcagttgccacataccatgttatgcttaatcacagccacgcttttcactagcatgaagcaaccacagtc |
| ggaggccacattgtggcgcaccctggagttaccctcagacaggatacccaaggtacacctttcaaagaggcatttcttaattgaagccct |
| gcttttggggcgacacaccacccccttccagcagcagtaaaaggcacagccccgaacccttacatcggtccaggcttccacacaggta |
| ttgttaaacccatagaagcttacaccgtgtaggataaggttggtattggccaggaaaaccgtaccgctaaaattggggccagtaaacctta |
| cattcataataaccaccccgtccatgccaagcacccccggccacatatttatcatgctacatctaaaggccaccctatcctccgtatctatct |
| ccacctcggccccgttcccagaaatgtagcaacaattcctgatatttacaagtttgctgatcttgtacttgcaatctggcctaagtgccacctt |
| tgcatataccctaatagcctcctcaaaatcatcccctggctgcagccagtaagtggtcagctgctctatggaatacttctgcgccagcagat |
| caagctcattagcgcaattatccttgatctgttgaaaagtaatacactcaggacggtgtctggtcattaagctaaaagctagattcctagcct |
| cctctgtagcctcacaagcccccgctccctctttacccctttagcccctgcccatcctctgtaattgtcaaaatgcgtctcagttctggata |
| cagttcagccacctgtacaacattcattcccgagggtccaggccggctctcgggttccatgggctctgctcctgccgccgccgcctggct |
| tcctcctgctgctgctgctgctcctccgtcggtattatcgccgggcggacggaagacaacagtagcaggcgattcttgtgtctcacaacc |
| gctctccacagatgcatggccagaaaatccagcaggtacccccgctcagatgggtttcttcgctccatttatcctttataaaactcaaaaa |
| agcaacagcagccgcagcgcgccccggtgtggaaaaatccaaagtcttgatgaccttctcttggaaaagcgcctggtgacccagattc |
| aaagaatcaaacagctcaccacaggatttcaaaagctcttcaaattcccacttgtaatcctccttaattctgcagactaactttgcctgggat |
| gagccccacagaaacctccaaaaccaagaggtactgttagagctctgttccagcaagttacgcacagcagaaaaatcttccaaacactc |
| ccaagcctccatggatcccccgggcgatctgacggttcactaaacgagctctgcttatataggcctcccaccgtacacgccacctcgac |
| ataaattctaccgggtaggggaggcgcttttcccaaggcagtctggagcatgcgctttagcagccccgctgggcacttggcgctacaca |
| agtggcctctggcctcgcacacattccacatccaccggtaggcgccaaccggctccgttctttggtggccccttcgcgccaccttctactc |
| ctcccctagtcaggaagttcccccccgccccgcagctcgcgtcgtgcaggacgtgacaaatggaagtagcacgtctcactagtctcgtg |
| cagatggacagcaccgctgagcaatggaagcgggtaggcctttggggcagcggccaatagcagctttgctccttcgctttctgggctca |
| gaggctgggaaggggtgggtccgggggggctcagggcgggctcagggggggcgggcgcccgaaggtcctccggaggc |

TABLE 9-continued

| E1 Cell Creation Vector |
|---|
| ccggcattctgcacgcttcaaaagcgcacgtctgccgcgctgttctcctcttcctcatctccgggcctttcgacctatcgatcaattgagtac |
| ttacgtaggtaccgaattcgatatcatgagacatattatctgccacggaggtgttattaccgaagaaatggccgccagtcttttggaccagc |
| tgatcgaagaggtactggctgataatcttccacctcctagccattttgaaccacctacccttcacgaactgtatgatttagacgtgacggcc |
| cccgaagatcccaacgaggaggcggtttcgcagatttttcccgactctgtaatgttggcggtgcaggaagggattgacttactcacttttc |
| cgccggcgcccggttctccggagccgcctcacctttcccggcagcccgagcagccggagcagagagccttgggtccggtttctatgc |
| caaaccttgtaccggaggtgatcgatcttacctgccacgaggctggctttccacccagtgacgacgaggatgaagagggtgaggagttt |
| gtgttagattatgtggagcaccccgggcacggttgcaggtcttgtcattatcaccggaggaatacgggggacccagatattatgtgttcgc |
| tttgctatatgaggacctgtggcatgtttgtctacagtaagtgaaaattatgggcagtgggtgatagagtggtgggtttggtgtggtaattttttt |
| ttttaatttttacagttttgtggtttaaagaatttttgtattgtgatttttttaaaaggtcctgtgtctgaacctgagcctgagcccgagccagaacc |
| ggagcctgcaagacctacccgccgtcctaaaatggcgcctgctatcctgagacgcccgacatcacctgtgtctagagaatgcaatagta |
| gtacggatagctgtgactccggtccttctaacacacctcctgagatacacccggtggtcccgctgtgccccattaaaccagttgccgtga |
| gagttggtgggcgtcgccaggctgtggaatgtatcgaggacttgcttaacgagcctgggcaacctttggacttgagctgtaaacgcccc |
| aggccataaatcgggcccgcggccgcgtctagatgagtcgagtacccatacgacgtcccagactacgcttgagtttaaacacgcgtgg |
| tgtggaaagtccgcggccgcgaaggatctgcgatcgctccggtgcccgtcagtgggcagagcgcacatcgcccacagtccccgaga |
| agttggggggaggggtcggcaattgaacgggtgcctagagaaggtggcgcggggtaaactgggaaagtgatgtcgtgtactggctcc |
| gcctttttcccgagggggggagaaccgtatataagtgcagtagtcgccgtgaacgttctttttcgcaacgggtttgccgccagaacac |
| agctgaagcttcgaggggctcgcatctctccttcacgcgcccgccgccctacctgaggccgccatccacgccggttgagtcgcgttctg |
| ccgcctcccgcctgtggtgcctcctgaactgcgtccgccgtctaggtaagtttaaagctcaggtcgagaccgggcctttgtccggcgctc |
| ccttggagcctacctagactcagccggctctccacgctttgcctgaccctgcttgctcaactctacgtctttgtttcgttttctgttctgcgccg |
| ttacagatccaagctgtgaccggcgcctacgctagatgaccgagtacaagcccacggtgcgcctcgccacccgcgacgacgtcccca |
| gggccgtacgcaccctcgccgccgcgttcgccgactaccccgccacgcgccacaccgtcgatccggaccgccacatcgagcgggtc |
| accgagctgcaagaactcttcctcacgcgcgtcgggctcgacatcggcaaggtgtgggtcgcggacgacggcgccgcggtggcggt |
| ctggaccacgccggagagcgtcgaagcgggggcggtgttcgccgagatcggcccgcgcatggccgagttgagcggttcccggctg |
| gccgcgcagcaacagatggaaggcctcctggcgccgcaccggcccaaggagcccgcgtggttcctggccaccgtcggcgtctcgc |
| ccgaccaccagggcaagggtctgggcagcgccgtcgtgctccccggagtggaggcggccgagcgcgccggggtgcccgccttcct |
| ggagacctccgcgccccgcaacctccccttctacgagcggctcggcttcaccgtcaccgccgacgtcgaggtgcccgaaggaccgc |
| gcacctggtgcatgacccgcaagcccggtgcctgagtcgacaatcaacctctggattacaaaatttgtgaaagattgactggtattcttaa |
| ctatgttgctccttttacgctatgtggatacgctgctttaatgcctttgtatcatgctattgcttcccgtatggctttcattttctcctccttgtataaa |
| tcctggttgctgtctctttatgaggagttgtggcccgttgtcaggcaacgtggcgtggtgtgcactgtgtttgctgacgcaacccccactgg |
| ttggggcattgccaccacctgtcagctcctttccgggactttcgctttccccctccctattgccacggcggaactcatcgccgcctgccttg |
| cccgctgctggacaggggctcggctgttgggcactgacaattccgtggtgttgtcggggaaatcatcgtcctttccttggctgctcgcctg |
| tgttgccacctggattctgcgcgggacgtccttctgctacgtcccttcggccctcaatccagcggaccttccttcccgcggcctgctgccg |
| gctctgcggcctcttccgcgtcttcgccttcgccctcagacgagtcggatctccctttgggccgcctccccgcctggtacctttaagacca |
| atgacttacaaggcagctgtagatcttagccactttttaaaagaaaaggggggactggaagggctaattcactcccaacgaagataagat |
| ctgctttttgcttgtactgggtctctctggttagaccagatctgagcctgggagctctctggctaactagggaacccactgcttaagcctcaa |
| taaagcttgccttgagtgcttcaagtagtgtgtgcccgtctgttgtgtgactctggtaactagagatccctcagacccttttagtcagtgtgga |
| aaatctctagca |

TABLE 10

| Full E1 Cell Creation Vector with Plasmid Backbone |
|---|
| (SEQ ID NO: 10)<br>ccggctgattatgatctcacctaggctcgagtcaatctgtatcttcatcgctagagccaaactcagcgcgggtgcaggccagcaccaagt<br>gatcgggcctcagctcctcggtcacatccagcatcacaggctggttcctaatatgtttaccgccacactcgcagggtctgcacctggtgc<br>gggtctcatcgtacctcagcaccttccagatcttcatggtcatgtcaaacaccccgttcaggttcaccttggacatgctctcgggctcaagc<br>aatatcttagtgtgactcaaattgcattggtaaggtaggaacaccccctcctgttacccaaatgcaaggaacagcgggtcagtatgttatg<br>ctcaaacactggccaggccttgcgagagtggctggctacgtgaatggtcttcagcaggtgacagttgccgtccgagcaggtcagcatct<br>gagaggccctgtcctcgcagttgccacataccatgttatgcttaatcacagccacgcttttcactagcatgaagcaaccacagtcggagg<br>ccacattgtggcgcaccctggagttaccctcagacaggatacccaaggtacacctttcaaagaggcatttcttaattgaagccctgcttttg<br>gggcgacacaccaccccccttccagcagcagtaaaaggcacagccccgaacccttacatcggtccaggcttccacacaggtattgttaa<br>acccatagaagcttacaccgtgtaggataaggttggtattggccaggaaaaccgtaccgctaaaattggggccagtaaaccttacattca<br>taataaccaccccgtccatgccaagcaccccccggccacatatttatcatgctacatctaaaggccaccctatcctccgtatctatctccacc<br>tcggccccgttcccagaaatgtagcaacaattcctgatatttacaagtttgctgatcttgtacttgcaatctggcctaagtgccacctttgcat<br>ataccctaatagcctcctcaaaatcatcccctggctgcagccagtaagtggtcagctgctctatggaatacttctgcgccagcagatcaag<br>ctcattagcgcaattatccttgatctgttgaaaagtaatacactcaggacggtgtctggtcattaagctaaaagctagattcctagcctcctct<br>gtagcctcacaagcccccgctccctctttaccccctttagcccctgcccatcctctgtaattgtcaaaatgcgtctcagttctggatacagtt<br>cagccacctgtacaacattcattcccgagggtccaggccggctctcgggttccatgggctctgctcctgccgccgccgcctggcttcctc<br>ctgctgctgctgctgctcctccgtcggtattatcgccgggcggacggaagacaacagtagcaggcgattcttgtgtctcacaaccgctct<br>ccacagatgcatggccagaaaatccagcaggtacccccccgctcagatgggtttcttcgctccatttatcctttataaaactcaaaaaagca<br>acagcagccgcagcgcgccccggtgtggaaaaatccaaagtcttgatgaccttctcttggaaaagcgcctggtgacccagattcaaag<br>aatcaaacagctcaccacaggatttcaaaagctcttcaaattcccacttgtaatcctccttaattctgcagactaactttgcctgggatgagc<br>cccacagaaacctccaaaaccaagaggtactgttagagctctgttccagcaagttacgcacagcagaaaaatcttccaaacactcccaa<br>gcctccatggatcccccgggcgatctgacggttcactaaacgagctctgcttatataggcctcccaccgtacacgccacctcgacataaa<br>ttctaccgggtaggggaggcgcttttcccaaggcagtctggagcatgcgctttagcagccccgctgggcacttggcgctacacaagtgg<br>cctctggcctcgcacacattccacatccaccggtaggcgccaaccggctccgttctttggtggccccttcgcgccaccttctactcctccc<br>ctagtcaggaagttcccccccgccccgcagctcgcgtcgtgcaggacgtgacaaatggaagtagcacgtctcactagtctcgtgcagat<br>ggacagcaccgctgagcaatggaagcgggtaggcctttggggcagcggccaatagcagctttgctccttcgctttctgggctcagagg<br>ctgggaaggggtgggtccgggggggctcaggggcgggctcaggggggggggggcccgaaggtcctccggaggcccgg<br>cattctgcacgcttcaaaagcgcacgtctgccgcgctgttctcctcttcctcatctccgggcctttcgacctatcgatcaattgagtacttacg<br>taggtaccgaattcgatatcatgagacatattatctgccacggaggtgttattaccgaagaaatggccgccagtcttttggaccagctgatc<br>gaagaggtactggctgataatcttccacctcctagccattttgaaccacctacccttcacgaactgtatgatttagacgtgacggcccccga<br>agatcccaacgaggaggcggtttcgcagatttttcccgactctgtaatgttggcggtgcaggaagggattgacttactcacttttccgccg<br>gcgcccggttctccggagccgcctcacctttcccggcagcccgagcagccggagcagagagccttgggtccggtttctatgccaaacc<br>ttgtaccggaggtgatcgatcttacctgccacgaggctggctttccacccagtgacgacgaggatgaagagggtgaggagtttgtgttag<br>attatgtggagcaccccgggcacggttgcaggtcttgtcattatcaccggaggaatacgggggacccagatattatgtgttcgctttgctat<br>atgaggacctgtggcatgtttgtctacagtaagtgaaaattatgggcagtgggtgatagagtggtgggtttggtgtggtaatttttttttaattt<br>ttacagttttgtggtttaaagaattttgtattgtgatttttttaaaaggtcctgtgtctgaacctgagcctgagcccgagccagaaccggagcct<br>gcaagacctacccgccgtcctaaaatggcgcctgctatcctgagacgcccgacatcacctgtgtctagagaatgcaatagtagtacgga<br>tagctgtgactccggtccttctaacacacctcctgagatacacccggtggtcccgctgtgccccattaaaccagttgccgtgagagttggt<br>gggcgtcgccaggctgtggaatgtatcgaggacttgcttaacgagcctgggcaacctttggacttgagctgtaaacgccccaggccata<br>aatcgggcccgcggccgcgtctagatgagtcgagtacccatacgacgtcccagactacgcttgagtttaaacacgcgtggtgtggaaa |

TABLE 10-continued

| Full E1 Cell Creation Vector with Plasmid Backbone |
|---|
| gtccgcggccgcgaaggatctgcgatcgctccggtgcccgtcagtgggcagagcgcacatcgcccacagtccccgagaagttgggg |
| ggaggggtcggcaattgaacgggtgcctagagaaggtggcgcggggtaaactgggaaagtgatgtcgtgtactggctccgcctttttc |
| ccgagggggggagaaccgtatataagtgcagtagtcgccgtgaacgttctttttcgcaacgggtttgccgccagaacacagctgaag |
| cttcgaggggctcgcatctctccttcacgcgcccgccgccctacctgaggccgccatccacgccggttgagtcgcgttctgccgcctcc |
| cgcctgtggtgcctcctgaactgcgtccgccgtctaggtaagtttaaagctcaggtcgagaccgggcctttgtccggcgctcccttggag |
| cctacctagactcagccggctctccacgctttgcctgaccctgcttgctcaactctacgtctttgtttcgttttctgttctgcgccgttacagat |
| ccaagctgtgaccggcgcctacgctagatgaccgagtacaagcccacggtgcgcctcgccacccgcgacgacgtccccagggccgt |
| acgcaccctcgccgccgcgttcgccgactaccccgccacgcgccacaccgtcgatccggaccgccacatcgagcgggtcaccgag |
| ctgcaagaactcttcctcacgcgcgtcgggctcgacatcggcaaggtgtgggtcgcggacgacggcgccgcggtggcggtctggac |
| cacgccggagagcgtcgaagcgggggcggtgttcgccgagatcggcccgcgcatggccgagttgagcggttcccggctggccgcg |
| cagcaacagatggaaggcctcctggcgccgcaccggcccaaggagcccgcgtggttcctggccaccgtcggcgtctcgcccgacca |
| ccagggcaagggtctgggcagcgccgtcgtgctccccggagtggaggcggccgagcgcgccggggtgcccgccttcctggagac |
| ctccgcgccccgcaacctccccttctacgagcggctcggcttcaccgtcaccgccgacgtcgaggtgcccgaaggaccgcgcacctg |
| gtgcatgacccgcaagcccggtgcctgagtcgacaatcaacctctggattacaaaatttgtgaaagattgactggtattcttaactatgttg |
| ctccttttacgctatgtggatacgctgctttaatgcctttgtatcatgctattgcttcccgtatggctttcattttctcctccttgtataaatcctggtt |
| gctgtctctttatgaggagttgtggcccgttgtcaggcaacgtggcgtggtgtgcactgtgtttgctgacgcaacccccactggttggggc |
| attgccaccacctgtcagctcctttccgggactttcgctttccccctccctattgccacggcggaactcatcgccgcctgccttgcccgctg |
| ctggacaggggctcggctgttgggcactgacaattccgtggtgttgtcggggaaatcatcgtcctttccttggctgctcgcctgtgttgcca |
| cctggattctgcgcgggacgtccttctgctacgtcccttcggccctcaatccagcggaccttccttcccgcggcctgctgccggctctgc |
| ggcctcttccgcgtcttcgccttcgccctcagacgagtcggatctccctttgggccgcctccccgcctggtacctttaagaccaatgactta |
| caaggcagctgtagatcttagccactttttaaaagaaaaggggggactggaagggctaattcactcccaacgaagataagatctgcttttt |
| gcttgtactgggtctctctggttagaccagatctgagcctgggagctctctggctaactagggaacccactgcttaagcctcaataaagctt |
| gccttgagtgcttcaagtagtgtgtgcccgtctgttgtgtgactctggtaactagagatccctcagacccttttagtcagtgtggaaaatctct |
| agcagtagtagttcatgtcatcttattattcagtatttataacttgcaaagaaatgaatatcagagagtgagaggaacttgtttattgcagcttat |
| aatggttacaaataaagcaatagcatcacaaatttcacaaataaagcatttttttcactgcattctagttgtggtttgtccaaactcatcaatgta |
| tcttatcatgtctggctctagctatcccgcccctaactccgcccatcccgcccctaactccgcccagttccgcccattctccgccccatggc |
| tgactaattttttttatttatgcagaggccgaggccgcctcggcctctgagctattccagaagtagtgaggaggcttttttggaggcctagac |
| ttttgcagagacggcccaaattcgtaatcatggtcatagctgtttcctgtgtgaaattgttatccgctcacaattccacacaacatacgagcc |
| ggaagcataaagtgtaaagcctggggtgcctaatgagtgagctaactcacattaattgcgttgcgctcactgcccgctttccagtcggga |
| aacctgtcgtgccagctgcattaatgaatcggccaacgcgcggggagaggcggtttgcgtattgggcgctcttccgcttcctcgctcact |
| gactcgctgcgctcggtcgttcggctgcggcgagcggtatcagctcactcaaaggcggtaatacggttatccacagaatcaggggata |
| acgcaggaaagaacatgtgagcaaaaggccagcaaaaggccaggaaccgtaaaaaggccgcgttgctggcgtttttccataggctcc |
| gcccccctgacgagcatcacaaaaatcgacgctcaagtcagaggtggcgaaacccgacaggactataaagataccaggcgtttcccc |
| ctggaagctccctcgtgcgctctcctgttccgaccctgccgcttaccggatacctgtccgcctttctcccttcgggaagcgtggcgctttct |
| catagctcacgctgtaggtatctcagttcggtgtaggtcgttcgctccaagctgggctgtgtgcacgaaccccccgttcagcccgaccgc |
| tgcgccttatccggtaactatcgtcttgagtccaacccggtaagacacgacttatcgccactggcagcagccactggtaacaggattagc |
| agagcgaggtatgtaggcggtgctacagagttcttgaagtggtggcctaactacggctacactagaaggacagtatttggtatctgcgct |
| ctgctgaagccagttaccttcggaaaaagagttggtagctcttgatccggcaaacaaaccaccgctggtagcggtggtttttttgtttgcaa |
| gcagcagattacgcgcagaaaaaaaggatctcaagaagatcctttgatcttttctacggggtctgacgctcagtggaacgaaaactcacg |

TABLE 10-continued

| Full E1 Cell Creation Vector with Plasmid Backbone |
| --- |
| ttaagggatttggtcatgagattatcaaaaaggatcttcacctagatccttttaaattaaaaatgaagttttaaatcaatctaaagtatatatga |
| gtaaacttggtctgacagttaccaatgcttaatcagtgaggcacctatctcagcgatctgtctatttcgttcatccatagttgcctgactcccc |
| gtcgtgtagataactacgatacgggagggcttaccatctggccccagtgctgcaatgataccgcgagacccacgctcaccggctccag |
| atttatcagcaataaaccagccagccggaagggccgagcgcagaagtggtcctgcaactttatccgcctccatccagtctattaattgttg |
| ccgggaagctagagtaagtagttcgccagttaatagtttgcgcaacgttgttgccattgctacaggcatcgtggtgtcacgctcgtcgtttg |
| gtatggcttcattcagctccggttcccaacgatcaaggcgagttacatgatcccccatgttgtgcaaaaaagcggttagctccttcggtcct |
| ccgatcgttgtcagaagtaagttggccgcagtgttatcactcatggttatggcagcactgcataattctcttactgtcatgccatccgtaaga |
| tgcttttctgtgactggtgagtactcaaccaagtcattctgagaatagtgtatgcggcgaccgagttgctcttgcccggcgtcaatacggga |
| taataccgcgccacatagcagaactttaaaagtgctcatcattggaaaacgttcttcggggcgaaaactctcaaggatcttaccgctgttg |
| agatccagttcgatgtaacccactcgtgcacccaactgatcttcagcatcttttactttcaccagcgtttctgggtgagcaaaaacaggaag |
| gcaaaatgccgcaaaaaagggaataagggcgacacggaaatgttgaatactcatactcttcctttttcaatattattgaagcatttatcagg |
| gttattgtctcatgagcggatacatatttgaatgtatttagaaaaataaacaaataggggttccgcgcacatttccccgaaaagtgccacctg |
| acgtctaagaaaccattattatcatgacattaacctataaaaataggcgtatcacgaggccctttcgtctcgcgcgtttcggtgatgacggt |
| gaaaacctctgacacatgcagctcccggagacggtcacagcttgtctgtaagcggatgccgggagcagacaagcccgtcagggcgc |
| gtcagcgggtgttggcgggtgtcggggctggcttaactatgcggcatcagagcagattgtactgagagtgcaccatatgcggtgtgaaa |
| taccgcacagatgcgtaaggagaaaataccgcatcaggcgccattcgccattcaggctgcgcaactgttgggaagggcgatcggtgc |
| gggcctcttcgctattacgccagctggcgaaagggggatgtgctgcaaggcgattaagttgggtaacgccagggttttcccagtcacga |
| cgttgtaaaacgacggccagtgccaagctgacgcgtgtagtcttatgcaatactcttgtagtcttgcaacatggtaacgatgagttagcaa |
| catgccttacaaggagagaaaaagcaccgtgcatgccgattggtggaagtaaggtggtacgatcgtgccttattaggaaggcaacaga |
| cgggtctgacatggattggacgaaccactgaattgccgcattgcagagatattgtatttaagtgcctagctcgatacaataaacgggtctct |
| ctggttagaccagatctgagcctgggagctctctggctaactagggaacccactgcttaagcctcaataaagcttgccttgagtgcttcaa |
| gtagtgtgtgcccgtctgttgtgtgactctggtaactagagatccctcagacccttttagtcagtgtggaaaatctctagcagtggcgcccg |
| aacagggacctgaaagcgaaagggaaaccagagctctctcgacgcaggactcggcttgctgaagcgcgcacggcaagaggcgag |
| gggcggcgactggtgagtacgccaaaaattttgactagcggaggctagaaggagagagatgggtgcgagagcgtcagtattaagcg |
| ggggagaattagatcgcgatgggaaaaaattcggttaaggccagggggaaagaaaaaatataaattaaaacatatagtatgggcaagc |
| agggagctagaacgattcgcagttaatcctggcctgttagaaacatcagaaggctgtagacaaatactgggacagctacaaccatccctt |
| cagacaggatcagaagaacttagatcattatataatacagtagcaaccctctattgtgtgcatcaaaggatagagataaaagacaccaag |
| gaagctttagacaagatagaggaagagcaaaacaaaagtaagaccaccgcacagcaagcggccactgatcttcagacctggaggag |
| gagatatgagggacaattggagaagtgaattatataaatataaagtagtaaaaattgaaccattaggagtagcacccaccaaggcaaag |
| agaagagtggtgcagagagaaaaaagagcagtgggaataggagctttgttccttgggttcttgggagcagcaggaagcactatgggc |
| gcagcgtcaatgacgctgacggtacaggccagacaattattgtctggtatagtgcagcagcagaacaatttgctgagggctattgaggc |
| gcaacagcatctgttgcaactcacagtctggggcatcaagcagctccaggcaagaatcctggctgtggaaagatacctaaaggatcaa |
| cagctcctggggatttggggttgctctggaaaactcatttgcaccactgctgtgccttggaatgctagttggagtaataaatctctggaaca |
| gatttggaatcacacgacctggatggagtgggacagagaaattaacaattacacaagcttaatacactccttaattgaagaatcgcaaaa |
| ccagcaagaaaagaatgaacaagaattattggaattagataaatgggcaagtttgtggaattggtttaacataacaaattggctgtggtata |
| taaaattattcataatgatagtaggaggcttggtaggtttaagaatagtttttgctgtactttctatagtgaatagagttaggcagggatattca |
| ccattatcgtttcagacccacctcccaaccccgaggggacccgacaggcccgaaggaatagaagaagaaggtggagagagagaca |
| gagacagatccattcgattagtgaacggatctcgacggtatcggttaacttttaaaagaaaaggggggattggggggtacagtgcaggg |
| gaaagaatagtagacataatagcaacagacatacaaactaaagaattacaaaaacaaattacaaaattcaaaattttatcgatcatggtcct |

TABLE 10-continued

| Full E1 Cell Creation Vector with Plasmid Backbone |
|---|
| gctggagttcgtgctcctatctagagctagcgaattcccttatcgattttaccacatttgtagaggttttacttgctttaaaaaacctcccacac |
| ctccccctgaacctgaaacataaaatgaatgcaattgttgttgttaacttgtttattgcagcttataatggttacaaataaagcaatagcatcac |
| aaatttcacaaataaagcatttttttcactgcattctagttgtggtttgtccaaactcatcaatgtatcttatcatgtctgctcgaagcggccgg |

TABLE 11

| Adenovirus 3' End (Right Side Second Product) |
|---|
| SEQ ID NO: 11 |
| aggcctgacgctaataatagctggtccactgtcgccgccacaagtgctttgcccgcgactccggtgagttttgctactttgaattgcccga |
| ggatcatatcgagggcccggcgcacggcgtccggcttaccgcccagggagagcttgcccgtagcctgattcgggagtttacccagcg |
| ccccctgctagttgagcgggacaggggaccctgtgttctcactgtgatttgcaactgtcctaaccttggattacatcaagatccagatcttct |
| agacccgggagcggccgctgtcgacctgcaggatccgaattcgatatcactagtggtaccgatcttattccctttaactaataaaaaaaaa |
| taataaagcatcacttacttaaaatcagttagcaaatttctgtccagtttattcagcagcacctccttgccctcctcccagctctggtattgcag |
| cttcctcctggctgcaaactttctccacaatctaaagggaatgtcagtttcctcctgttcctgtccatccgcacccactatcttcatgttgttgc |
| agatgaagcgcgcaagaccgtctgaagataccttcaaccccgtgtatccatatgacacggaaaccggtcctccaactgtgccttttcttac |
| tcctccctttgtatcccccaatgggtttcaagagagtcccccctggggtactctctttgcgcctatccgaacctctagttacctccaatggcat |
| gcttgcgctcaaaatgggcaacggcctctctctggacgaggccggcaaccttacctcccaaaatgtaaccactgtgagcccacctctca |
| aaaaaaccaagtcaaacataaacctggaaatatctgcacccctcacagttacctcagaagccctaactgtggctgccgccgcacctctaa |
| tggtcgcgggcaacacactcaccatgcaatcacaggccccgctaaccgtgcacgactccaaacttagcattgccacccaaggacccct |
| cacagtgtcagaaggaaagctagccctgcaaacatcaggcccccctcaccaccaccgatagcagtacccttactatcactgcctcacccc |
| ctctaactactgccactggtagcttgggcattgacttgaaagagcccatttatacacaaaatggaaaactaggactaaagtacggggctcc |
| tttgcatgtaacagacgacctaaacactttgaccgtagcaactggtccaggtgtgactattaataatacttccttgcaaactaaagttactgg |
| agccttgggttttgattcacaaggcaatatgcaacttaatgtagcaggaggactaaggattgattctcaaaacagacgccttatacttgatgt |
| tagttatccgtttgatgctcaaaaccaactaaatctaagactaggacagggccctctttttataaactcagcccacaacttggatattaactac |
| aacaaaggcctttacttgtttacagcttcaaacaattccaaaaagcttgaggttaacctaagcactgccaaggggttgatgtttgacgctac |
| agccatagccattaatgcaggagatgggcttgaatttggttcacctaatgcaccaaacacaaatcccctcaaaacaaaaattggccatgg |
| cctagaatttgattcaaacaaggctatggttcctaaactaggaactggccttagttttgacagcacaggtgccattacagtaggaaacaaa |
| aataatgataagctaactttgtggaccacaccagctccatctcctaactgtagactaaatgcagagaaagatgctaaactcactttggtctta |
| acaaaatgtggcagtcaaatacttgctacagtttcagttttggctgttaaaggcagtttggctccaatatctggaacagttcaaagtgctcatc |
| ttattataagatttgacgaaaatggagtgctactaaacaattccttcctggacccagaatattggaactttagaaatggagatcttactgaag |
| gcacagcctatacaaacgctgttggatttatgcctaacctatcagcttatccaaaatctcacggtaaaactgccaaaagtaacattgtcagt |
| caagtttacttaaacggagacaaaactaaacctgtaacactaaccattacactaaacggtacacaggaaacaggagacacaactccaag |
| tgcatactctatgtcattttcatgggactggtctggccacaactacattaatgaaatatttgccacatcctcttacacttttcatacattgccca |
| agaataaagaatcgtttgtgttatgtttcaacgtgtttatttttcaattgcagaaaatttcaagtcatttttcattcagtagtatagccccaccacc |
| acatagcttatacagatcaccgtaccttaatcaaactcacagaaccctagtattcaacctgccacctccctcccaacacacagagtacaca |
| gtcctttctccccggctggccttaaaaagcatcatatcatgggtaacagacatattcttaggtgttatattccacacggtttcctgtcgagcca |
| aacgctcatcagtgatattaataaactccccgggcagctcacttaagttcatgtcgctgtccagctgctgagccacaggctgctgtccaac |
| ttgcggttgcttaacgggcggcgaaggagaagtccacgcctacatgggggtagagtcataatcgtgcatcaggatagggcggtggtgc |
| tgcagcagcgcgcgaataaactgctgccgccgccgctccgtcctgcaggaatacaacatggcagtggtctcctcagcgatgattcgca |
| ccgcccgcagcataaggcgccttgtcctccgggcacagcagcgcaccctgatctcacttaaatcagcacagtaactgcagcacagcac |

TABLE 11-continued

| Adenovirus 3' End (Right Side Second Product) |
|---|
| cacaatattgttcaaaatcccacagtgcaaggcgctgtatccaaagctcatggggggaccacagaacccacgtggccatcataccaca |
| agcgcaggtagattaagtggcgacccctcataaacacgctggacataaacattacctcttttggcatgttgtaattcaccacctcccggtac |
| catataaacctctgattaaacatggcgccatccaccaccatcctaaaccagctggccaaaacctgcccgccggctatacactgcaggga |
| accgggactggaacaatgacagtggagagcccaggactcgtaaccatggatcatcatgctcgtcatgatatcaatgttggcacaacaca |
| ggcacacgtgcatacacttcctcaggattacaagctcctcccgcgttagaaccatatcccagggaacaacccattcctgaatcagcgtaa |
| atcccacactgcagggaagacctcgcacgtaactcacgttgtgcattgtcaaagtgttacattcgggcagcagcggatgatcctccagta |
| tggtagcgcgggtttctgtctcaaaaggaggtagacgatccctactgtacggagtgcgccgagacaaccgagatcgtgttggtcgtagt |
| gtcatgccaaatggaacgccggacgtagtcatatttcctgaagcaaaaccaggtgcgggcgtgacaaacagatctgcgtctccggtctc |
| gccgcttagatcgctctgtgtagtagttgtagtatatccactctctcaaagcatccaggcgccccctggcttcgggttctatgtaaactccttc |
| atgcgccgctgccctgataacatccaccaccgcagaataagccacacccagccaacctacacattcgttctgcgagtcacacacggga |
| ggagcgggaagagctggaagaaccatgtttttttttttttattccaaaagattatccaaaacctcaaaatgaagatctattaagtgaacgcgct |
| cccctccggtggcgtggtcaaactctacagccaaagaacagataatggcatttgtaagatgttgcacaatggcttccaaaaggcaaacg |
| gccctcacgtccaagtggacgtaaaggctaaacccttcagggtgaatctcctctataaacattccagcaccttcaaccatgcccaaataat |
| tctcatctcgccaccttctcaatatatctctaagcaaatcccgaatattaagtccggccattgtaaaaatctgctccagagcgccctccacctt |
| cagcctcaagcagcgaatcatgattgcaaaaattcaggttcctcacagacctgtataagattcaaaagcggaacattaacaaaaataccg |
| cgatcccgtaggtcccttcgcagggccagctgaacataatcgtgcaggtctgcacggaccagcgcggccacttccccgccaggaacc |
| atgacaaaagaacccacactgattatgacacgcatactcggagctatgctaaccagcgtagccccgatgtaagcttgttgcatgggcgg |
| cgatataaaatgcaaggtgctgctcaaaaaatcaggcaaagcctcgcgcaaaaaagaaagcacatcgtagtcatgctcatgcagataaa |
| ggcaggtaagctccggaaccaccacagaaaaagacaccatttttctctcaaacatgtctgcgggtttctgcataaacacaaaataaaata |
| acaaaaaaacatttaaacattagaagcctgtcttacaacaggaaaaacaacccttataagcataagacggactacggccatgccggcgt |
| gaccgtaaaaaaactggtcaccgtgattaaaaagcaccaccgacagctcctcggtcatgtccggagtcataatgtaagactcggtaaac |
| acatcaggttgattcacatcggtcagtgctaaaaagcgaccgaaatagcccggggggaatacatacccgcaggcgtagagacaacatta |
| cagccccatagg aggtataacaaaattaataggagagaaaaacacataaacacctgaaaaaccctcctgcctaggcaaaatagcacc |
| ctcccgctccagaacaacatacagcgcttccacagcggcagccataacagtcagccttaccagtaaaaaagaaaacctattaaaaaaac |
| accactcgacacggcaccagctcaatcagtcacagtgtaaaaaagggccaagtgcagagcgagtatatataggactaaaaaatgacgt |
| aacggttaaagtccacaaaaaacacccagaaaaccgcacgcgaacctacgcccagaaacgaaagccaaaaaacccacaacttcctc |
| aaatcgtcacttccgttttcccacgttacgtaacttcccattttaagaaaactacaattcccaacacatacaagttactccgccctaaaaccta |
| cgtcacccgccccgttcccacgccccgcgccacgtcacaaactccacccctcattatcatattggcttcaatccaaaataaggtatattat |
| tgatgatgttaattt |

TABLE 12

| Adenovirus 5' End (Left Side Second Product) |
|---|
| (SEQ ID NO: 12) |
| aaattaattaacatcatcaataatataccttattttggattgaagccaatatgataatgaggggtggagtttgtgacgtggcgcggggcgt |
| gggaacggggcgggtgacgtagtagtgtggcggaagtgtgatgttgcaagtgtggcggaacacatgtaagcgacggatgtggcaaa |
| agtgacgtttttggtgtgcgccggtgtacacaggaagtgacaattttcgcgcggttttaggcggatgttgtagtaaatttgggcgtaaccga |
| gtaagatttggccattttcgcgggaaaactgaataagaggaagtgaaatctgaataattttgtgttactcatagcgcgtaatatttgtctagg |
| gccgcggggactttgaccgtttacgtggagactcgcccaggtgtttttctcaggtgttttccgcgttccgggtcaaagttggcgttttagatc |
| ttctagacccgggagcggccgctgtcgacctgcaggatccactagttattaatagtaatcaattacggggtcattagttcatagcccatata |

TABLE 12-continued

| Adenovirus 5' End (Left Side Second Product) |
|---|
| tggagttccgcgttacataacttacggtaaatggcccgcctggctgaccgcccaacgacccccgcccattgacgtcaataatgacgtatg |
| ttcccatagtaacgccaatagggactttccattgacgtcaatgggtggagtatttacggtaaactgcccacttggcagtacatcaagtgtat |
| catatgccaagtacgccccctattgacgtcaatgacggtaaatggcccgcctggcattatgcccagtacatgaccttatgggactttccta |
| cttggcagtacatctacgtattagtcatcgctattaccatggtcgaggtgagccccacgttctgcttcactctccccatctcccccccctccc |
| cacccccaattttgtatttatttattttttaattattttgtgcagcgatgggggcgggggggggggggggggggcgcgccaggcggggcgggg |
| cggggcgaggggggggcggggcgaggcggagaggtgcggcggcagccaatcagagcggcgcgctccgaaagtttccttttatg |
| gcgaggcggcggcggcggcggccctataaaaagcgaagcgcgcggcgggcgggagtcgctgcgttgccttcgccccgtgccccg |
| ctccgcgccgcctcgcgccgcccgccccggctctgactgaccgcgttactcccacaggtgagcgggcgggacggcccttctcctccg |
| ggctgtaattagcgcttggtttaatgacggctcgtttcttttctgtggctgcgtgaaagccttaaagggctccgggagggccctttgtgcgg |
| gggggagcggctcggggggtgcgtgcgtgtgtgtgtgcgtggggagcgccgcgtgcggctccgcgctgcccggcggctgtgagcg |
| ctgcgggcgcggcgcggggctttgtgcgctccgcagtgtgcgcgaggggagcgcggccgggggcggtgccccgcggtgcgggg |
| ggggctgcgaggggaacaaaggctgcgtgcggggtgtgtgcgtgggggggtgagcagggggtgtgggcgcgtcggtcgggctgc |
| aaccccccctgcacccccctccccgagttgctgagcacggcccggcttcgggtgcggggctccgtacggggcgtggcgcggggctc |
| gccgtgccgggcggggggtggcggcaggtgggggtgccgggcggggcggggccgcctcgggccggggagggctcgggggag |
| gggcgcggcggcccccggagcgccggcggctgtcgaggcgcggcgagccgcagccattgccttttatggtaatcgtgcgagaggg |
| cgcagggacttcctttgtcccaaatctgtgcggagccgaaatctgggaggcgccgccgcaccccctctagcgggcgcggggcgaag |
| cggtgcggcgccggcaggaaggaaatgggcggggagggccttcgtgcgtcgccgcgccgccgtccccttctccctctccagcctcg |
| gggctgtccgcggggggacggctgccttcgggggggacggggcagggcggggttcggcttctggcgtgtgaccggcggctctaga |
| gcctctgctaaccatgttcatgccttcttctttttcctacagctcctgggcaacgtgctggttattgtgctgtctcatcattttggcaaagaattc |
| cgctgcgactcggcggagtcccggcggcgcgtccttgttctaacccggcgcgccagcttggcaatccggtactgttggtaaagccacc |
| atgcatagttctgccctgttgtgttgcttggtgctgttgacgggggttagagcgagtccaggtcaaggcacgcagtctgaaaactcctgta |
| cacacttccccggcaacctccctaatatgctcagagaccttcgagacgccttctcccgagtaaaaactttctttcagatgaaggaccagct |
| cgacaacttgctgttgaaggaatcactcctcgaagattttaaggggtacctcggttgtcaagctctgtctgaaatgatacaattctatctcga |
| ggaagtcatgcctcaagcggaaaaccaggacccagatattaaggcccatgtgaatagcctcggcgaaaatcttaaaactcttcgcctta |
| gactccgaagatgccataggttttgccgtgcgaaaataaatccaaagctgtggaacaggtaaaaaatgcgtttaacaagttgcaagaga |
| agggcatctacaaagcgatgtcagagttcgatatattcataaattatattgaagcatacatgactatgaagatcaggaattaataattctaga |
| gtcggggcggccggccgcttcgagcagacatgataagatacattgatgagtttggacaaaccacaactagaatgcagtgaaaaaaatg |
| ctttatttgtgaaatttgtgatgctattgctttatttgtaaccattataagctgcaataaacaagttaacaacaacaattgcattcattttatgtttca |
| ggttcaggggggaggtgtgggaggttttttaaagcaagtaaaacctctacaaatgtggtaaaatcgataaggatccgaattcgatatcacta |
| gtggtaccagtactgaaatgtgtgggcgtggcttaagggtgggaaagaatatataaggtgggggtcttatgtagttttgtatctgttttgcag |
| cagccgccgccgccatgagcaccaactcgtttgatggaagcattgtgagctcatatttgacaacgcgcatgcccccatgggccggggt |
| gcgtcagaatgtgatgggctccagcattgatggtcgccccgtcctgcccgcaaactctactaccttgacctacgagaccgtgtctggaac |
| gccgttggagactgcagcctccgccgccgcttcagccgctgcagccaccgcccgcgggattgtgactgactttgctttcctgagcccgc |
| ttgcaagcagtgcagcttcccgttcatccgcccgcgatgacaagttgacggctcttttggcacaattggattctttgacccgggaacttaat |
| gtcgtttctcagcagctgttggatctgcgccagcaggtttctgccctgaaggcttcctcccctcccaatgcggtttaacggtccgggccag |
| agtggccaacataaataaaaaaccagactctgtttggatttggatcaagcaagtgtcttgctgtctttatttaggggttttgcgcgcgcggta |
| ggcccgggaccagcggtctcggtcgttgagggtcctgtgtatttttttccaggacgtggtaaaggtgactctggatgttcagatacatgggc |
| ataagcccgtctctggggtggaggtagcaccactgcagagcttcatgctgcggggtggtgttgtagatgatccagtcgtagcaggagcg |
| ctgggcgtggtgcctaaaaatgtctttcagtagcaagctgattgccaggggcaggcccttggtgtaagtgtttacaaagcggttaagctg |

TABLE 12-continued

| Adenovirus 5' End (Left Side Second Product) |
|---|
| ggatgggtgcatacgtggggatatgagatgcatcttggactgtatttttaggttggctatgttcccagccatatccctccggggattcatgtt |
| gtgcagaaccaccagcacagtgtatccggtgcacttgggaaatttgtcatgtagcttagaaggaaatgcgtggaagaacttggagacgc |
| ccttgtgacctccaagattttccatgcattcgtccataatgatggcaatgggcccacgggcggcggcctgggcgaagatatttctgggatc |
| actaacgtcatagttgtgttccaggatgagatcgtcataggccatttttacaaagcgcgggcggagggtgccagactgcggtataatggtt |
| ccatccggcccaggggcgtagttaccctcacagatttgcatttcccacgctttgagttcagatggggggatcatgtctacctgcggggcg |
| atgaagaaaacggtttccggggtaggggagatcagctgggaagaaagcaggttcctgagcagctgcgacttaccgcagccggtggg |
| cccgtaaatcacacctattaccgggtgcaactggtagttaagagagctgcagctgccgtcatccctgagcaggggggccacttcgttaa |
| gcatgtccctgactcgcatgttttccctgaccaaatccgccagaaggcgctcgccgcccagcgatagcagttcttgcaaggaagcaaag |
| tttttcaacggtttgagaccgtccgccgtaggcatgcttttgagcgtttgaccaagcagttccaggcggtcccacagctcggtcacctgctc |
| tacggcatctcgatccagcatatctcctcgtttcgcgggttggggcggctttcgctgtacggcagtagtcggtgctcgtccagacgggcc |
| agggtcatgtctttccacgggcgcagggtcctcgtcagcgtagtctgggtcacggtgaaggggtgcgctccgggctgcgcgctggcca |
| gggtgcgcttgaggctggtcctgctggtgctgaagcgctgccggtcttcgccctgcgcgtcggccaggtagcatttgaccatggtgtcat |
| agtccagcccctccgcggcgtggcccttggcgcgcagcttgcccttggaggaggcgccgcacgaggggcagtgcagacttttgagg |
| gcgtagagcttgggcgcgagaaataccgattccggggagtaggcatccgcgccgcaggccccgcagacggtctcgcattccacgag |
| ccaggtgagctctggccgttcggggtcaaaaaccaggtttcccccatgctttttgatgcgtttcttacctctggtttccatgagccggtgtcc |
| acgctcggtgacgaaaaggctgtccgtgtccccgtatacagacttgagaggcctgtcctcgagcggtgttccgcggtcctcctcgtatag |
| aaactcggaccactctgagacaaaggctcgcgtccaggccagcacgaaggaggctaagtgggaggggtagcggtcgttgtccacta |
| gggggtccactcgctccagggtgtgaagacacatgtcgccctcttcggcatcaaggaaggtgattggtttgtaggtgtaggccacgtga |
| ccgggtgttcctgaaggggggctataaaagggggtgggggcgcgttcgtcctcactctcttccgcatcgctgtctgcgagggccagct |
| gttggggtgagtactccctctgaaaagcgggcatgacttctgcgctaagattgtcagtttccaaaaacgaggaggatttgatattcacctg |
| gcccgcggtgatgcctttgagggtggccgcatccatctggtcagaaaagacaatctttttgttgtcaagcttggtggcaaacgacccgta |
| gagggcgttggacagcaacttggcgatggagcgcagggtttggtttttgtcgcgatcggcgcgctccttggccgcgatgtttagctgcac |
| gtattcgcgcgcaacgcaccgccattcgggaaagacggtggtgcgctcgtcgggcaccaggtgcacgcgccaaccgcggttgtgca |
| gggtgacaaggtcaacgctggtggctacctctccgcgtaggcgctcgttggtccagcagaggcggccgcccttgcgcgagcagaatg |
| gcggtagggggtctagctgcgtctcgtccggggggtctgcgtccacggtaaagaccccgggcagcaggcgcgcgtcgaagtagtct |
| atcttgcatccttgcaagtctagcgcctgctgccatgcgcgggcggcaagcgcgcgctcgtatgggttgagtgggggaccccatggca |
| tggggtgggtgagcgcggaggcgtacatgccgcaaatgtcgtaaacgtagaggggctctctgagtattccaagatatgtagggtagcat |
| cttccaccgcggatgctggcgcgcacgtaatcgtatagttcgtgcgagggagcgaggaggtcgggaccgaggttgctacgggcggg |
| ctgctctgctcggaagactatctgcctgaagatggcatgtgagttggatgatatggttggacgctggaagacgttgaagctggcgtctgtg |
| agacctaccgcgtcacgcacgaaggaggcgtaggagtcgcgcagcttgttgaccagctcggcggtgacctgcacgtctagggcgca |
| gtagtccagggtttccttgatgatgtcatacttatcctgtcccttttttttccacagctcgcggttgaggacaaactcttcgcggtctttccagta |
| ctcttggatcggaaacccgtcggcctccgaacggtaagagcctagcatgtagaactggttgacggcctggtaggcgcagcatcccttttt |
| ctacgggtagcgcgtatgcctgcgcggccttccggagcgaggtgtgggtgagcgcaaaggtgtccctgaccatgactttgaggtactg |
| gtatttgaagtcagtgtcgtcgcatccgccctgctcccagagcaaaaagtccgtgcgctttttggaacgcggatttggcagggcgaaggt |
| gacatcgttgaagagtatctttcccgcgcgaggcataaagttgcgtgtgatgcggaagggtcccggcacctcggaacggttgttaattac |
| ctgggcggcgagcacgatctcgtcaaagccgttgatgttgtggcccacaatgtaaagttccaagaagcgcgggatgcccttgatggaa |
| ggcaatttttttaagttcctcgtaggtgagctcttcaggggagctgagcccgtgctctgaaagggcccagtctgcaagatgagggttggaa |
| gcgacgaatgagctccacaggtcacgggccattagcatttgcaggtggtcgcgaaaggtcctaaactggcgacctatggccatttttttct |
| ggggtgatgcagtagaaggtaagcgggtcttgttcccagcggtcccatccaaggttcgcggctaggtctcgcgcggcagtcactagag |

TABLE 12-continued

| Adenovirus 5' End (Left Side Second Product) |
|---|
| gctcatctccgccgaacttcatgaccagcatgaagggcacgagctgcttcccaaaggcccccatccaagtataggtctctacatcgtag |
| gtgacaaagagacgctcggtgcgaggatgcgagccgatcgggaagaactggatctcccgccaccaattggaggagtggctattgatg |
| tggtgaaagtagaagtccctgcgacgggccgaacactcgtgctggcttttgtaaaaacgtgcgcagtactggcagcggtgcacgggct |
| gtacatcctgcacgaggttgacctgacgaccgcgcacaaggaagcagagtgggaatttgagcccctcgcctggcgggtttggctggtg |
| gtcttctacttcggctgcttgtccttgaccgtctggctgctcgaggggagttacggtggatcggaccaccacgccgcgcgagcccaaagt |
| ccagatgtccgcgcgcggcggtcggagcttgatgacaacatcgcgcagatgggagctgtccatggtctggagctcccgcggcgtcag |
| gtcaggcgggagctcctgcaggtttacctcgcatagacgggtcagggcgcgggctagatccaggtgatacctaatttccaggggctgg |
| ttggtggcggcgtcgatggcttgcaagaggccgcatccccgcggcgcgactacggtaccgcgcggcgggcggtgggccgcgggg |
| gtgtccttggatgatgcatctaaaagcggtgacgcgggcgagcccccggaggtagggggggctccggacccgccgggagagggg |
| gcaggggcacgtcggcgccgcgcgcgggcaggagctggtgctgcgcgcgtaggttgctggcgaacgcgacgacgcggcggttga |
| tctcctgaatctggcgcctctgcgtgaagacgacgggcccggtgagcttgagcctgaaagagagttcgacagaatcaatttcggtgtcgt |
| tgacggcggcctggcgcaaaatctcctgcacgtctcctgagttgtcttgataggcgatctcggccatgaactgctcgatctcttcctcctgg |
| agatctccgcgtccggctcgctccacggtggcggcgaggtcgttggaaatgcgggccatgagctgcgagaaggcgttgaggcctccc |
| tcgttccagacgcggctgtagaccacgcccccttcggcatcgcgggcgcgcatgaccacctgcgcgagattgagctccacgtgccgg |
| gcgaagacggcgtagtttcgcaggcgctgaaagaggtagttgagggtggtggcggtgtgttctgccacgaagaagtacataacccag |
| cgtcgcaacgtggattcgttgatatcccccaaggcctcaaggcgctccatggcctcgtagaagtccacggcgaagttgaaaaactggg |
| agttgcgcgccgacacggttaactcctcctccagaagacggatgagctcggcgacagtgtcgcgcacctcgcgctcaaaggctacag |
| gggcctcttcttcttcttcaatctcctcttccataagggcctccccttcttcttcttctggcggcggtgggggaggggggacacggcggcg |
| acgacggcgcaccgggaggcggtcgacaaagcgctcgatcatctccccgcggcgacggcgcatggtctcggtgacggcgcggcc |
| gttctcgcgggggcgcagttggaagacgccgcccgtcatgtcccggttatgggttggcgggggctgccatgcggcagggatacgg |
| cgctaacgatgcatctcaacaattgttgtgtaggtactccgccgccgagggacctgagcgagtccgcatcgaccggatcggaaaacctc |
| tcgagaaaggcgtctaaccagtcacagtcgcaaggtaggctgagcaccgtgggggcggcagcgggcggcggtcggggttgtttct |
| ggcggaggtgctgctgatgatgtaattaaagtaggcggtcttgagacggcggatggtcgacagaagcaccatgtccttgggtccggcct |
| gctgaatgcgcaggcggtcggccatgccccaggcttcgttttgacatcggcgcaggtctttgtagtagtcttgcatgagcctttctaccgg |
| cacttcttcttctccttcctcttgtcctgcatctcttgcatctatcgctgcggcggcggcggagtttggccgtaggtggcgccctcttcctccc |
| atgcgtgtgaccccgaagcccctcatcggctgaagcagggctaggtcggcgacaacgcgctcggctaatatggcctgctgcacctgc |
| gtgagggtagactggaagtcatccatgtccacaaagcggtggtatgcgcccgtgttgatggtgtaagtgcagttggccataacggacca |
| gttaacggtctggtgacccggctgcgagagctcggtgtacctgagacgcgagtaagccctcgagtcaaatacgtagtcgttgcaagtcc |
| gcaccaggtactggtatcccaccaaaaagtgcggcggcggctggcggtagaggggccagcgtagggtggccggggctccggggg |
| cgagatcttccaacataaggcgatgatatccgtagatgtacctggacatccaggtgatgccggcggcggtggtggaggcgcgcggaa |
| agtcgcggacgcggttccagatgttgcgcagcggcaaaaagtgctccatggtcgggacgctctggccggtcaggcgcgcgcaatcgt |
| tgacgctctagaccgtgcaaaaggagagcctgtaagcgggcactcttccgtggtctggtggataaattcgcaagggtatcatggcggac |
| gaccggggttcgagccccgtatccggccgtccgccgtgatccatgcggttaccgcccgcgtgtcgaacccaggtgtgcgacgtcaga |
| caacgggggagtgctccttttggcttccttccaggcgcggcggctgctgcgctagctttttggccactggccgcgcgcagcgtaagcg |
| gttaggctggaaagcgaaagcattaagtggctcgctccctgtagccggagggttattttccaagggttgagtcgcgggacccccggttc |
| gagtctcggaccggccggactgcggcgaacgggggtttgcctccccgtcatgcaagaccccgcttgcaaattcctccggaaacaggg |
| acgagccccttttttgcttttcccagatgcatccggtgctgcggcagatgcgcccccctcctcagcagcggcaagagcaagagcagcg |
| gcagacatgcagggcaccctcccctcctcctaccgcgtcaggaggggcgacatccgcggttgacgcggcagcagatggtgattacga |
| acccccgcggcgccgggcccggcactacctggacttggaggagggcgagggcctggcgcggctaggagcgccctctcctgagcg |

TABLE 12-continued

| Adenovirus 5' End (Left Side Second Product) |
|---|
| gtacccaagggtgcagctgaagcgtgatacgcgtgaggcgtacgtgccgcggcagaacctgtttcgcgaccgcgagggagaggag |
| cccgaggagatgcgggatcgaaagttccacgcagggcgcgagctgcggcatggcctgaatcgcgagcggttgctgcgcgaggagg |
| actttgagcccgacgcgcgaaccgggattagtcccgcgcgcgcacacgtggcggccgccgacctggtaaccgcatacgagcagac |
| ggtgaaccaggagattaactttcaaaaaagctttaacaaccacgtgcgtacgcttgtggcgcgcgaggaggtggctataggactgatgc |
| atctgtgggactttgtaagcgcgctggagcaaaacccaaatagcaagccgctcatggcgcagctgttccttatagtgcagcacagcagg |
| gacaacgaggcattcagggatgcgctgctaaacatagtagagcccgagggccgctggctgctcgatttgataaacatcctgcagagca |
| tagtggtgcaggagcgcagcttgagcctggctgacaaggtggccgccatcaactattccatgcttagcctgggcaagttttacgcccgc |
| aagatataccataccccttacgttcccatagacaaggaggtaaagatcgaggggttctacatgcgcatggcgctgaaggtgcttaccttg |
| agcgacgacctgggcgtttatcgcaacgagcgcatccacaaggccgtgagcgtgagccggcggcgcgagctcagcgaccgcgagc |
| tgatgcacagcctgcaaagggccctggctggcacgggcagcggcgatagagaggccgagtcctactttgacgcgggcgctgacctg |
| cgctgggccccaagccgacgcgccctggaggcagctggggccggacctgggctgggggcacccgcgcgcgctggcaacgtc |
| ggcggcgtggaggaatatgacgaggacgatgagtacgagccagaggacggcgagtactaagcggtgatgtttctgatcagatgatgc |
| aagacgcaacggacccggcggtgcgggcggcgctgcagagccagccgtccggccttaactccacggacgactggcgccaggtcat |
| ggaccgcatcatgtcgctgactgcgcgcaatcctgacgcgttccggcagcagccgcaggccaaccggctctccgcaattctggaagc |
| ggtggtcccggcgcgcgcaaaccccacgcacgagaaggtgctggcgatcgtaaacgcgctggccgaaaacagggccatccggccc |
| gacgaggccggcctggtctacgacgcgctgcttcagcgcgtggctcgttacaacagcggcaacgtgcagaccaacctggaccggct |
| ggtgggggatgtgcgcgaggccgtggcgcagcgtgagcgcgcgcagcagcagggcaacctgggctccatggttgcactaaacgcc |
| ttcctgagtacacagcccgccaacgtgccgcggggacaggaggactacaccaactttgtgagcgcactgcggctaatggtgactgag |
| acaccgcaaagtgaggtgtaccagtctgggccagactatttttccagaccagtagacaaggcctgcagaccgtaaacctgagccagg |
| ctttcaaaaacttgcaggggctgtgggggtgcgggctcccacaggcgaccgcgcgaccgtgtctagcttgctgacgcccaactcgc |
| gcctgttgctgctgctaatagcgcccttcacggacagtggcagcgtgtcccgggacacatacctaggtcacttgctgacactgtaccgcg |
| aggccataggtcaggcgcatgtggacgagcatactttccaggagattacaagtgtcagccgcgcgctggggcaggaggacacgggc |
| agcctggaggcaaccctaaactacctgctgaccaaccggcggcagaagatcccctcgttgcacagtttaaacagcgaggaggagcgc |
| attttgcgctacgtgcagcagagcgtgagccttaacctgatgcgcgacggggtaacgcccagcgtggcgctggacatgaccgcgcgc |
| aacatggaaccgggcatgtatgcctcaaaccggccgtttatcaaccgcctaatggactacttgcatcgcgcggccgccgtgaaccccg |
| agtatttcaccaatgccatcttgaacccgcactggctaccgccccctggtttctacaccgggggattcgaggtgcccgagggtaacgatg |
| gattcctctgggacgacatagacgacagcgtgttttccccgcaaccgcagaccctgctagagttgcaacagcgcgagcaggcagagg |
| cggcgctgcgaaaggaaagcttccgcaggccaagcagcttgtccgatctaggcgctgcggccccgcggtcagatgctagtagcccat |
| ttccaagcttgatagggtctcttaccagcactcgcaccacccgcccgcgcctgctgggcgaggaggagtacctaaacaactcgctgctg |
| cagccgcagcgcgaaaaaaacctgcctccggcatttcccaacaacgggatagagagcctagtggacaagatgagtagatggaagac |
| gtacgcgcaggagcacagggacgtgccaggcccgcgcccgcccacccgtcgtcaaaggcacgaccgtcagcggggtctggtgtgg |
| gaggacgatgactcggcagacgacagcagcgtcctggatttgggagggagtggcaacccgtttgcgcaccttcgccccaggctggg |
| gagaatgttttaaaaaaaaaaaagcatgatgcaaaataaaaaactcaccaaggccatggcaccgagcgttggttttcttgtattccccttag |
| tatgcggcgcgcggcgatgtatgaggaaggtcctcctccctcctacgagagtgtggtgagcgcggcgccagtggcggcggcgctgg |
| gttctcccttcgatgctcccctggacccgccgtttgtgcctccgcggtacctgcggcctaccggggggagaaacagcatccgttactctg |
| agttggcacccctattcgacaccacccgtgtgtacctggtggacaacaagtcaacggatgtggcatccctgaactaccagaacgaccac |
| agcaactttctgaccacggtcattcaaaacaatgactacagcccgggggaggcaagcacacagaccatcaatcttgacgaccggtcgc |
| actggggcggcgacctgaaaaccatcctgcataccaacatgccaaatgtgaacgagttcatgtttaccaataagtttaaggcgcgggtg |
| atggtgtcgcgcttgcctactaaggacaatcaggtggagctgaaatacgagtgggtggagttcacgctgcccgagggcaactactccg |

TABLE 12-continued

| Adenovirus 5' End (Left Side Second Product) |
|---|
| agaccatgaccatagaccttatgaacaacgcgatcgtggagcactacttgaaagtgggcagacagaacggggttctggaaagcgacat |
| cggggtaaagtttgacacccgcaacttcagactggggtttgaccccgtcactggtcttgtcatgcctggggtatatacaaacgaagccttc |
| catccagacatcattttgctgccaggatgcggggtggacttcacccacagccgcctgagcaacttgttgggcatccgcaagcggcaacc |
| cttccaggagggctttaggatcacctacgatgatctggagggtggtaacattcccgcactgttggatgtggacgcctaccaggcgagctt |
| gaaagatgacaccgaacagggggggtggcgcaggcggcagcaacagcagtggcagcggcgcggaagagaactccaacgcg |
| gcagccgcggcaatgcagccggtggaggacatgaacgatcatgccattcgcggcgacacctttgccacacgggctgaggagaagcg |
| cgctgaggccgaagcagcggccgaagctgccgcccccgctgcgcaacccgaggtcgagaagcctcagaagaaaccggtgatcaa |
| acccctgacagaggacagcaagaaacgcagttacaacctaataagcaatgacagcaccttcacccagtaccgcagctggtaccttgca |
| tacaactacggcgaccctcagaccggaatccgctcatggaccctgctttgcactcctgacgtaacctgcggctcggagcaggtctactg |
| gtcgttgccagacatgatgcaagaccccgtgaccttccgctccacgcgccagatcagcaactttccggtgggggcgccgagctgttgc |
| ccgtgcactccaagagcttctacaacgaccaggccgtctactcccaactcatccgccagtttacctctctgacccacgtgttcaatcgcttt |
| cccgagaaccagattttggcgcgcccgccagccccaccatcaccaccgtcagtgaaaacgttcctgctctcacagatcacgggacgc |
| taccgctgcgcaacagcatcggaggagtccagcgagtgaccattactgacgccagacgccgcacctgcccctacgtttacaaggccct |
| gggcatagtctcgccgcgcgtcctatcgagccgcactttttgagcaagcatgtccatccttatatcgcccagcaataacacaggctgggg |
| cctgcgcttcccaagcaagatgtttgggggccaagaagcgctccgaccaacacccagtgcgcgtgcgcgggcactaccgcgcgc |
| cctggggcgcgcacaaacgcggccgcactgggcgcaccaccgtcgatgacgccatcgacgcggtggtggaggaggcgcgcaact |
| acacgcccacgccgccaccagtgtccacagtggacgcggccattcagaccgtggtgcgcggagcccggcgctatgctaaaatgaag |
| agacggcggaggcgcgtagcacgtcgccaccgccgccgacccggcactgccgcccaacgcgcggcggcggccctgcttaaccgc |
| gcacgtcgcaccggccgacgggggccatgcgagcagctcgaaggctggccgcgggtattgtcactgtgcccccaggtccaggc |
| gacgagcggccgccgcagcagccgcggccattagtgctatgactcagggtcgcaggggcaacgtgtattgggtgcgcgactcggtta |
| gcggcctgcgcgtgcccgtgcgcacccgcccccgcgcaactagattgcaagaaaaaactacttagactcgtactgttgtatgtatcca |
| gcggcggcggcgcgcaacgaagctatgtccaagcgcaaaatcaaagaagagatgctccaggtcatcgcgccggagatctatggccc |
| cccgaagaaggaagagcaggattacaagccccgaaagctaaagcgggtcaaaaagaaaaagaaagatgatgatgatgaacttgacg |
| acgaggtggaactgctgcacgctaccgcgcccaggcgacgggtacagtggaaaggtcgacgcgtaaaacgtgttttgcgacccggc |
| accaccgtagtctttacgcccggtgagcgctccacccgcacctacaagcgcgtgtatgatgaggtgtacggcgacgaggacctgcttg |
| agcaggccaacgagcgcctcggggagtttgcctacggaaagcggcataaggacatgctggcgttgccgctggacgagggcaaccc |
| aacacctagcctaaagcccgtaacactgcagcaggtgctgcccgcgcttgcaccgtccgaagaaaagcgcggcctaaagcgcgagt |
| ctggtgacttggcacccaccgtgcagctgatggtacccaagcgccagcgactggaagatgtcttggaaaaaatgaccgtggaacctgg |
| gctggagcccgaggtccgcgtgcggccaatcaagcaggtggcgccgggactgggcgtgcagaccgtggacgttcagatacccacta |
| ccagtagcaccagtattgccaccgccacagagggcatggagacacaaacgtccccggttgcctcagcggtggcggatgccgcggtg |
| caggcggtcgctgcggccgcgtccaagacctctacggaggtgcaaacggacccgtggatgtttcgcgtttcagccccccggcgcccg |
| cgcggttcgaggaagtacggcgccgccagcgcgctactgcccgaatatgccctacatccttccattgcgcctacccccggctatcgtgg |
| ctacacctaccgccccagaagacgagcaactacccgacgccgaaccaccactggaacccgccgccgccgtcgccgtcgccagccc |
| gtgctggccccgatttccgtgcgcagggggctcgcgaaggaggcaggaccctggtgctgccaacagcgcgctaccaccccagcat |
| cgtttaaaagccggtctttgtggttcttgcagatatggccctcacctgccgcctccgtttcccggtgccgggattccgaggaagaatgcac |
| cgtaggaggggcatggccggccacggcctgacgggcggcatgcgtcgtgcgcaccaccggcggcggcgcgcgtcgcaccgtcgc |
| atgcgcggcggtatcctgcccctccttattccactgatcgccgcggcgattggcgccgtgcccggaattgcatccgtggccttgcaggc |
| gcagagacactgattaaaaacaagttgcatgtggaaaaatcaaaataaaaagtctggactctcacgctcgcttggtcctgtaactattttgt |
| agaatggaagacatcaactttgcgtctctggccccgcgacacggctcgcgcccgttcatgggaaactggcaagatatcggcaccagca |

TABLE 12-continued

| Adenovirus 5' End (Left Side Second Product) |
|---|
| atatgagcggtggcgccttcagctggggctcgctgtggagcggcattaaaaatttcggttccaccgttaagaactatggcagcaaggcct |
| ggaacagcagcacaggccagatgctgagggataagttgaaagagcaaaatttccaacaaaaggtggtagatggcctggcctctggca |
| ttagcggggtggtggacctggccaaccaggcagtgcaaaataagattaacagtaagcttgatccccgccctcccgtagaggagcctcc |
| accggccgtggagacagtgtctccagaggggcgtggcgaaaagcgtccgcgccccgacagggaagaaactctggtgacgcaaata |
| gacgagcctccctcgtacgaggaggcactaaagcaaggcctgcccaccacccgtcccatcgcgcccatggctaccggagtgctggg |
| ccagcacacacccgtaacgctggacctgcctcccccgccgacacccagcagaaacctgtgctgccaggcccgaccgccgttgttgt |
| aacccgtcctagccgcgcgtccctgcgccgcgccgccagcggtccgcgatcgttgcggcccgtagccagtggcaactggcaaagca |
| cactgaacagcatcgtgggtctgggggtgcaatccctgaagcgccgacgatgcttctgaatagctaacgtgtcgtatgtgtgtcatgtatg |
| cgtccatgtcgccgccagaggagctgctgagccgccgcgcgcccgctttccaagatggctaccccttcgatgatgccgcagtggtctta |
| catgcacatctcgggccaggacgcctcggagtacctgagccccgggctggtgcagtttgcccgcgccaccgagacgtacttcagcct |
| gaataacaagtttagaaccccacggtggcgcctacgcacgacgtgaccacagaccggtcccagcgtttgacgctgcggttcatccct |
| gtggaccgtgaggatactgcgtactcgtacaaggcgcggttcaccctagctgtgggtgataaccgtgtgctggacatggcttccacgta |
| ctttgacatccgcggcgtgctggacaggggccctacttttaagccctactctggcactgcctacaacgccctggctcccaagggtgccc |
| caaatccttgcgaatgggatgaagctgctactgctcttgaaataaacctagaagaagaggacgatgacaacgaagacgaagtagacga |
| gcaagctgagcagcaaaaaactcacgtatttgggcaggcgccttattctggtataaatattacaaaggagggtattcaaataggtgtcgaa |
| ggtcaaacacctaaatatgccgataaaacatttcaacctgaacctcaaataggagaatctcagtggtacgaaactgaaattaatcatgcag |
| ctgggagagtccttaaaaagactaccccaatgaaaccatgttacggttcatatgcaaaacccacaaatgaaaatggagggcaaggcatt |
| cttgtaaagcaacaaaatggaaagctagaaagtcaagtggaaatgcaatttttctcaactactgaggcgaccgcaggcaatggtgataac |
| ttgactcctaaagtggtattgtacagtgaagatgtagatatagaaaccccagacactcatatttcttacatgcccactattaaggaaggtaac |
| tcacgagaactaatgggccaacaatctatgcccaacaggcctaattacattgcttttagggacaattttattggtctaatgtattacaacagc |
| acgggtaatatgggtgttctggcgggccaagcatcgcagttgaatgctgttgtagatttgcaagacagaaacacagagctttcataccag |
| cttttgcttgattccattggtgatagaaccaggtacttttctatgtggaatcaggctgttgacagctatgatccagatgttagaattattgaaaat |
| catggaactgaagatgaacttccaaattactgctttccactgggaggtgtgattaatacagagactcttaccaaggtaaaacctaaaacag |
| gtcaggaaaatggatgggaaaaagatgctacagaattttcagataaaaatgaaataagagttggaaataattttgccatggaaatcaatct |
| aaatgccaacctgtggagaaatttcctgtactccaacatagcgctgtatttgcccgacaagctaaagtacagtccttccaacgtaaaaattt |
| ctgataacccaaacacctacgactacatgaacaagcgagtggtggctcccgggttagtggactgctacattaaccttggagcacgctgg |
| tcccttgactatatggacaacgtcaacccatttaaccaccaccgcaatgctggcctgcgctaccgctcaatgttgctgggcaatggtcgct |
| atgtgcccttccacatccaggtgcctcagaagttctttgccattaaaaacctccttctcctgccgggctcatacacctacgagtggaacttca |
| ggaaggatgttaacatggttctgcagagctccctaggaaatgacctaagggttgacggagccagcattaagtttgatagcatttgccttta |
| cgccaccttcttccccatggcccacaacaccgcctccacgcttgaggccatgcttagaaacgacaccaacgaccagtcctttaacgact |
| atctctccgccgccaacatgctctaccctatacccgccaacgctaccaacgtgcccatatccatcccctcccgcaactgggggctttcc |
| gcggctgggccttcacgcgccttaagactaaggaaaccccatcactgggctcgggctacgacccttattacacctactctggctctatac |
| cctacctagatggaacctttacctcaaccacacctttaagaaggtggccattacctttgactcttctgtcagctggcctggcaatgaccgc |
| ctgcttacccccaacgagtttgaaattaagcgctcagttgacggggagggttacaacgttgcccagtgtaacatgaccaaagactggttc |
| ctggtacaaatgctagctaactacaacattggctaccagggcttctatatcccagagagctacaaggaccgcatgtactcctctttagaaa |
| cttccagcccatgagccgtcaggtggtggatgatactaaatacaaggactaccaacaggtgggcatcctacaccaacacaacaactctg |
| gatttgttggctaccttgcccccaccatgcgcgaaggacaggcctaccctgctaacttcccctatccgcttataggcaagaccgcagttga |
| cagcattacccagaaaaagtttctttgcgatcgcaccctttggcgcatcccattctccagtaactttatgtccatgggcgcactcacagacct |
| gggccaaaaccttctctacgccaactccgcccacgcgctagacatgacttttgaggtggatcccatggacgagcccacccttctttatgtt |

TABLE 12-continued

| Adenovirus 5' End (Left Side Second Product) |
| --- |
| ttgtttgaagtctttgacgtggtccgtgtgcaccggccgcaccgcggcgtcatcgaaaccgtgtacctgcgcacgcccttctcggccggc |
| aacgccacaacataaagaagcaagcaacatcaacaacagctgccgccatgggctccagtgagcaggaactgaaagccattgtcaaag |
| atcttggttgtgggccatatttttgggcacctatgacaagcgctttccaggctttgtttctccacacaagctcgcctgcgccatagtcaatac |
| ggccggtcgcgagactgggggcgtacactggatggcctttgcctggaacccgcactcaaaaacatgctacctctttgagccctttggctt |
| ttctgaccagcgactcaagcaggtttaccagtttgagtacgagtcactcctgcgccgtagcgccattgcttcttcccccgaccgctgtataa |
| cgctggaaaagtccacccaaagcgtacaggggcccaactcggccgcctgtggactattctgctgcatgtttctccacgcctttgccaact |
| ggccccaaactcccatggatcacaaccccaccatgaaccttattaccggggtacccaactccatgctcaacagtccccaggtacagccc |
| accctgcgtcgcaaccaggaacagctctacagcttcctggagcgccactcgccctacttccgcagccacagtgcgcagattaggagcg |
| ccacttctttttgtcacttgaaaaacatgtaaaaataatgtactagagacactttcaataaaggcaaatgcttttatttgtacactctcgggtgat |
| tatttacccccacccttgccgtctgcgccgtttaaaaatcaaaggggttctgccgcgcatcgctatgcgccactggcagggacacgttgc |
| gatactggtgtttagtgctccacttaaactcaggcacaaccatccgcggcagctcggtgaagttttcactccacaggctgcgcaccatcac |
| caacgcgtttagcaggtcgggcgccgatatcttgaagtcgcagttggggcctccgccctgcgcgcgcgagttgcgatacacagggttg |
| cagcactggaacactatcagcgccgggtggtgcacgctggccagcacgctcttgtcggagatcagatccgcgtccaggtcctccgcgt |
| tgctcagggcgaacggagtcaactttggtagctgccttcccaaaaagggcgcgtgcccaggctttgagttgcactcgcaccgtagtggc |
| atcaaaaggtgaccgtgcccggtctgggcgttaggatacagcgcctgcataaaagccttgatctgcttaaaagccacctgagcctttgcg |
| ccttcagagaagaacatgccgcaagacttgccggaaaactgattggccggacacgcggcgtcgtgcacgcagcaccttgcgtcggtg |
| ttggagatctgcaccacatttcggccccaccggttcttcacgatcttggccttgctagactgctccttcagcgcgcgctgcccgttttcgctc |
| gtcacatccatttcaatcacgtgctccttatttatcataatgcttccgtgtagacacttaagctcgccttcgatctcagcgcagcggtgcagcc |
| acaacgcgcagcccgtgggctcgtgatgcttgtaggtcacctctgcaaacgactgcaggtacgcctgcaggaatcgccccatcatcgtc |
| acaaaggtcttgttgctggtgaaggtcagctgcaacccgcggtgctcctcgttcagccaggtcttgcatacggccgccagagcttccact |
| tggtcaggcagtagtttgaagttcgcctttagatcgttatccacgtggtacttgtccatcagcgcgcgcgcagcctccatgcccttctccca |
| cgcagacacgatcggcacactcagcgggttcatcaccgtaatttcactttccgcttcgctgggctcttcctcttcctcttgcgtccgcatacc |
| acgcgccactgggtcgtcttcattcagccgccgcactgtgcgcttacctcctttgccatgcttgattagcaccggtgggttgctgaaaccc |
| accatttgtagcgccacatcttctctttcttcctcgctgtccacgattacctctggtgatggcgggcgctcgggcttgggagaagggcgctt |
| ctttttcttcttgggcgcaatggccaaatccgccgccgaggtcgatggccgcgggctgggtgtgcgcggcaccagcgcgtcttgtgatg |
| agtcttcctcgtcctcggactcgatacgccgcctcatccgctttttgggggcgcccggggaggcggcggcgacggggacggggacg |
| acacgtcctccatggttgggggacgtcgcgccgcaccgcgtccgcgctcgggggtggtttcgcgctgctcctcttcccgactggccatt |
| tccttctcctataggcagaaaaagatcatggagtcagtcgagaagaaggacagcctaaccgccccctctgagttcgccaccaccgcctc |
| caccgatgccgccaacgcgcctaccaccttccccgtcgaggcacccccgcttgaggaggaggaagtgattatcgagcaggacccag |
| gttttgtaagcgaagacgacgaggaccgctcagtaccaacagaggataaaaagcaagaccaggacaacgcagaggcaaacgagga |
| acaagtcgggcgggggacgaaaggcatggcgactacctagatgtgggagacgacgtgctgttgaagcatctgcagcgccagtgcg |
| ccattatctgcgacgcgttgcaagagcgcagcgatgtgcccctcgccatagcggatgtcagccttgcctacgaacgccacctattctcac |
| cgcgcgtacccccaaacgccaagaaaacggcacatgcgagcccaacccgcgcctcaacttctaccccgtatttgccgtgccagagg |
| tgcttgccacctatcacatctttttccaaaactgcaagataccctatcctgccgtgccaaccgcagccgagcggacaagcagctggcctt |
| gcggcagggcgctgtcatacctgatatcgcctcgctcaacgaagtgccaaaaatctttgagggtcttggacgcgacgagaagcgcgcg |
| gcaaacgctctgcaacaggaaaacagcgaaaatgaaagtcactctggagtgttggtggaactcgagggtgacaacgcgcgcctagcc |
| gtactaaaacgcagcatcgaggtcacccactttgcctacccggcacttaacctacccccaaggtcatgagcacagtcatgagtgagct |
| gatcgtgcgccgtgcgcagcccctggagagggatgcaaatttgcaagaacaaacagaggagggcctacccgcagttggcgacgagc |
| agctagcgcgctggcttcaaacgcgcgagcctgccgacttggaggagcgacgcaaactaatgatggccgcagtgctcgttaccgtgg |

TABLE 12-continued

| Adenovirus 5' End (Left Side Second Product) |
| --- |
| agcttgagtgcatgcagcggttctttgctgacccggagatgcagcgcaagctagaggaaacattgcactacacctttcgacagggctac |
| gtacgccaggcctgcaagatctccaacgtggagctctgcaacctggtctcctaccttggaattttgcacgaaaaccgccttgggcaaaac |
| gtgcttcattccacgctcaagggcgaggcgcgccgcgactacgtccgcgactgcgtttacttatttctatgctacacctggcagacggcc |
| atgggcgtttggcagcagtgcttggaggagtgcaacctcaaggagctgcagaaactgctaaagcaaaacttgaaggacctatggacgg |
| ccttcaacgagcgctccgtggccgcgcacctggcggacatcattttccccgaacgcctgcttaaaaccctgcaacagggtctgccagac |
| ttcaccagtcaaagcatgttgcagaactttaggaactttatcctagagcgctcaggaatcttgcccgccacctgctgtgcacttcctagcga |
| ctttgtgcccattaagtaccgcgaatgccctccgccgctttggggccactgctaccttctgcagctagccaactaccttgcctaccactctg |
| acataatggaagacgtgagcggtgacggtctactggagtgtcactgtcgctgcaacctatgcaccccgcaccgctccctggtttgcaatt |
| cgcagctgcttaacgaaagtcaaattatcggtacctttgagctgcagggtccctcgcctgacgaaaagtccgcggctccggggttgaaa |
| ctcactccggggctgtggacgtcggcttaccttcgcaaatttgtacctgaggactaccacgcccacgagattaggttctacgaagaccaa |
| tcccgcccgccaaatgcggagcttaccgcctgcgtcattacccagggccacattcttggccaattgcaagccatcaacaaagcccgcca |
| agagtttctgctacgaaagggacggggggtttacttggacccccagtccggcgaggagctcaacccaatcccccgccgccgcagcc |
| ctatcagcagcagccgcgggcccttgcttcccaggatggcacccaaaaagaagctgcagctgccgccgccacccacggacgagga |
| ggaatactgggacagtcaggcagaggaggttttggacgaggaggaggaggacatgatggaagactgggagagcctagacgaggaa |
| gcttccgaggtcgaagaggtgtcagacgaaacaccgtcaccctcggtcgcattcccctcgccggcgccccagaaatcggcaaccggt |
| tccagcatggctacaacctccgctcctcaggcgccgccggcactgcccgttcgccgacccaaccgtagatgggacaccactggaacc |
| agggccggtaagtccaagcagccgccgccgttagcccaagagcaacaacagcgccaaggctaccgctcatggcgcgggcacaaga |
| acgccatagttgcttgcttgcaagactgtgggggcaacatctccttcgcccgccgctttcttctctaccatcacggcgtggccttcccccgt |
| aacatcctgcattactaccgtcatctctacagcccatactgcaccggggcagcggcagcggcagcaacagcagcggccacacagaa |
| gcaaaggcgaccggatagcaagactctgacaaagcccaagaaatccacagcggcggcagcagcaggaggaggagcgctgcgtct |
| ggcgcccaacgaacccgtatcgacccgcgagcttagaaacaggatttttcccactctgtatgctatatttcaacagagcaggggccaag |
| aacaagagctgaaaaaaaaaacaggtctctgcgatccctcacccgcagctgcctgtatcacaaaagcgaagatcagcttcggcgcac |
| gctggaagacgcggaggctctcttcagtaaatactgcgcgctgactcttaaggactagtttcgcgccctttctcaaatttaagcgcgaaaa |
| ctacgtcatctccagcggccacacccggcgccagcacctgtcgtcagcgccattatgagcaaggaaattcccacgccctacatgtgga |
| gttaccagccacaaatgggacttgcggctggagctgcccaagactactcaacccgaataaactacatgagcgcgggaccccacatgat |
| atcccgggtcaacggaatccgcgcccaccgaaaccgaattctcctggaacaggggctattaccaccacacctcgtaataaccttaatc |
| cccgtagttggcccgctgccctggtgtaccaggaaagtcccgctcccaccactgtggtacttcccagagacgcccaggccgaagttca |
| gatgactaactcaggggcgcagcttgcgggcggctttcgtcacagggtgcggtcgcccgggcagggtataactcacctgacaatcag |
| agggcgaggtattcagctcaacgacgagtcggtgagctcctcgcttggtctccgtccggacgggacatttcagatcggcggcgccggc |
| cgtccttcattcacgcctcgtcaggcaatcctaactctgcagacctcgtcctctgagccgcgctctggaggcattggaactctgcaatttatt |
| gaggagtttgtgccatcggtctactttaaccccttctcgggacctcccggccactatccggatcaatttattcctaactttgacgcggtaaag |
| gactcggcggacggctacgactgaatgttaagtggccaatg |

TABLE 13

| 3' End Fragment |
| --- |
| (SEQ ID NO: 13) |
| aagcatccaggcgcccccctggcttcgggttctatgtaaactccttcatgcgccgctgccctgataacatccaccaccgcagaataagcca |
| cacccagccaacctacacattcgttctgcgagtcacacacgggaggagcgggaagagctggaagaaccatgtttttttttttttattccaaa |

TABLE 13-continued

| 3' End Fragment |
|---|
| agattatccaaaacctcaaaatgaagatctattaagtgaacgcgctcccctccggtggcgtggtcaaactctacagccaaagaacagata |
| atggcatttgtaagatgttgcacaatggcttccaaaaggcaaacggccctcacgtccaagtggacgtaaaggctaaacccttcagggtg |
| aatctcctctataaacattccagcaccttcaaccatgcccaaataattctcatctcgccaccttctcaatatatctctaagcaaatcccgaatat |
| taagtccggccattgtaaaaatctgctccagagcgccctccaccttcagcctcaagcagcgaatcatgattgcaaaaattcaggttcctca |
| cagacctgtataagattcaaaagcggaacattaacaaaaataccgcgatcccgtaggtcccttcgcagggccagctgaacataatcgtg |
| caggtctgcacggaccagcgcggccacttccccgccaggaaccatgacaaaagaacccacactgattatgacacgcatactcggagc |
| tatgctaaccagcgtagccccgatgtaagcttgttgcatgggcggcgatataaaatgcaaggtgctgctcaaaaaatcaggcaaagcct |
| cgcgcaaaaaagaaagcacatcgtagtcatgctcatgcagataaaggcaggtaagctccggaaccaccacagaaaaagacaccatttt |
| tctctcaaacatgtctgcgggtttctgcataaacacaaaataaaataacaaaaaaacatttaaacattagaagcctgtcttacaacaggaaa |
| aacaacccttataagcataagacggactacggccatgccggcgtgaccgtaaaaaaactggtcaccgtgattaaaaagcaccaccgac |
| agctcctcggtcatgtccggagtcataatgtaagactcggtaaacacatcaggttgattcacatcggtcagtgctaaaaagcgaccgaaa |
| tagcccgggggaatacatacccgcaggcgtagagacaacattacagcccccataggaggtataacaaaattaataggagagaaaaac |
| acataaacacctgaaaaaccctcctgcctaggcaaaatagcaccctcccgctccagaacaacatacagcgcttccacagggcagcca |
| taacagtcagccttaccagtaaaaaagaaaacctattaaaaaaacaccactcgacacggcaccagctcaatcagtcacagtgtaaaaaa |
| gggccaagtgcagagcgagtatatataggactaaaaaatgacgtaacggttaaagtccacaaaaaacacccagaaaaccgcacgcga |
| acctacgcccagaaacgaaagccaaaaaacccacaacttcctcaaatcgtcacttccgttttcccacgttacgtaacttcccattttaagaa |
| aactacaattcccaacacatacaagttactccgccctaaaacctacgtcacccgccccgttcccacgccccgcgccacgtcacaaactc |
| cacccccctcattatcatattggcttcaatccaaaataaggtatattattgatgatgttaatttaaatttcgaagcgatcgc |

TABLE 14

| Ad5ACE2 No Plasmid |
|---|
| (SEQ ID NO: 14) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttaaggatctgc |
| gatcgctccggtgcccgtcagtgggcagagcgcacatcgcccacagtccccgagaagttggggggaggggtcggcaattgaacgg |
| gtgcctagagaaggtggcgcggggtaaactgggaaagtgatgtcgtgtactggctccgcctttttcccgagggggggggagaaccgta |
| tataagtgcagtagtcgccgtgaacgttctttttcgcaacgggtttgccgccagaacacagctgaagcttcgaggggctcgcatctctcctt |
| cacgcgcccgccgccctacctgaggccgccatccacgccggttgagtcgcgttctgccgcctcccgcctgtggtgcctcctgaactgc |
| gtccgccgtctaggtaagtttaaagctcaggtcgagaccgggcctttgtccggcgctcccttggagcctacctagactcagccggctctc |
| cacgctttgcctgaccctgcttgctcaactctacgtctttgtttcgttttctgttctgcgccgttacagatccaagctgtgaccggcgcctacct |
| cctgggcaacgtgctggttattgtgctgtctcatcattttggcaaagaattccgctgcgactcggcggagtcccggcggcgcgtccttgtt |
| ctaacccggcgcgccagcttggcaatccggtactgttggtaaagccaccatgtcaagctcttcctggctccttctcagccttgttgctgtaa |
| ctgctgctcagtccaccattgaggaacaggccaagacattttggacaagtttaaccacgaagccgaagacctgttctatcaaagttcactt |
| gcttcttggaattataacaccaatattactgaagagaatgtccaaaacatgaataatgctggggacaaatggtctgccttttaaaggaaca |
| gtccacacttgcccaaatgtatccactacaagaaattcagaatctcacagtcaagcttcagctgcaggctcttcagcaaaatgggtcttca |
| gtgctctcagaagacaagagcaaacggttgaacacaattctaaatacaatgagcaccatctacagtactggaaaagtttgtaacccagat |

TABLE 14-continued

| Ad5ACE2 No Plasmid |
| --- |
| aatccacaagaatgcttattacttgaaccaggtttgaatgaaataatggcaaacagtttagactacaatgagaggctctgggcttgggaaa |
| gctggagatctgaggtcggcaagcagctgaggccattatatgaagagtatgtggtcttgaaaaatgagatggcaagagcaaatcattatg |
| aggactatggggattattggagaggagactatgaagtaaatggggtagatggctatgactacagccgcggccagttgattgaagatgtg |
| gaacatacctttgaagagattaaaccattatatgaacatcttcatgcctatgtgagggcaaagttgatgaatgcctatccttcctatatcagtc |
| caattggatgcctccctgctcatttgcttggtgatatgtggggtagattttggacaaatctgtactctttgacagttccctttggacagaaacc |
| aaacatagatgttactgatgcaatggtggaccaggcctgggatgcacagagaatattcaaggaggccgagaagttctttgtatctgttggt |
| cttcctaatatgactcaaggattctgggaaaattccatgctaacggacccaggaaatgttcagaaagcagtctgccatcccacagcttggg |
| acctggggaagggcgacttcaggatccttatgtgcacaaaggtgacaatggacgacttcctgacagctcatcatgagatggggcatatc |
| cagtatgatatggcatatgctgcacaaccttttctgctaagaaatggagctaatgaaggattccatgaagctgttggggaaatcatgtcactt |
| tctgcagccacacctaagcatttaaaatccattggtcttctgtcacccgattttcaagaagacaatgaaacagaaataaacttcctgctcaaa |
| caagcactcacgattgttgggactctgccatttacttacatgttagagaagtggaggtggatggtctttaaaggggaaattcccaaagacc |
| agtggatgaaaaagtggtgggagatgaagcgagagatagttggggtggtggaacctgtgccccatgatgaaacatactgtgaccccgc |
| atctctgttccatgtttctaatgattactcattcattcgatattacacaaggaccctttaccaattccagtttcaagaagcactttgtcaagcagc |
| taaacatgaaggccctctgcacaaatgtgacatctcaaactctacagaagctggacagaaactgttcaatatgctgaggcttggaaaatc |
| agaaccctggaccctagcattggaaaatgttgtaggagcaaagaacatgaatgtaaggccactgctcaactactttgagcccttatttacc |
| tggctgaaagaccagaacaagaattcttttgtgggatggagtaccgactggagtccatatgcagaccaaagcatcaaagtgaggataag |
| cctaaaatcagctcttggagataaagcatatgaatggaacgacaatgaaatgtacctgttccgatcatctgttgcatatgctatgaggcagt |
| actttttaaaagtaaaaaatcagatgattcttttggggaggaggatgtgcgagtggctaatttgaaaccaagaatctcctttaatttctttgtc |
| actgcacctaaaaatgtgtctgatatcattcctagaactgaagttgaaaaggccatcaggatgtcccggagccgtatcaatgatgctttccg |
| tctgaatgacaacagcctagagtttctggggatacagccaacacttggacctcctaaccagcccctgtttccatatggctgattgtttttgg |
| agttgtgatgggagtgatagtggttggcattgtcatcctgatcttcactgggatcagagatcggaagaagaaaaataaagcaagaagtgg |
| agaaaatccttatgcctccatcgatattagcaaaggagaaaataatccaggattccaaaacactgatgatgttcagacctccttttagtaata |
| attctagagtcggggcggccggccgcttcgagatcagcctcgactgtgccttctagttgccagccatctgttgtttgcccctcccccgtgc |
| cttccttgaccctggaaggtgccactcccactgtcctttcctaataaaatgaggaaattgcatccagtactgaaatgtgtgggcgtggctta |
| agggtgggaaagaatatataaggtgggggtcttatgtagttttgtatctgttttgcagcagccgccgccgccatgagcaccaactcgtttg |
| atggaagcattgtgagctcatatttgacaacgcgcatgcccccatgggccggggtgcgtcagaatgtgatgggctccagcattgatggt |
| cgccccgtcctgcccgcaaactctactaccttgacctacgagaccgtgtctggaacgccgttggagactgcagcctccgccgccgcttc |
| agccgctgcagccaccgcccgcgggattgtgactgactttgctttcctgagcccgcttgcaagcagtgcagcttcccgttcatccgcccg |
| cgatgacaagttgacggctcttttggcacaattggattctttgacccgggaacttaatgtcgtttctcagcagctgttggatctgcgccagca |
| ggtttctgccctgaaggcttcctcccctcccaatgcggtttaacggtccgggccagagtggccaacataaataaaaaaccagactctgttt |
| ggatttggatcaagcaagtgtcttgctgtctttatttaggggttttgcgcgcgcggtaggcccgggaccagcggtctcggtcgttgagggt |
| cctgtgtatttttttccaggacgtggtaaaggtgactctggatgttcagatacatgggcataagcccgtctctgggggggaggtagcaccac |
| tgcagagcttcatgctgcggggtggtgttgtagatgatccagtcgtagcaggagcgctgggcgtggtgcctaaaaatgtctttcagtagc |
| aagctgattgccaggggcaggcccttggtgtaagtgtttacaaagcggttaagctgggatgggtgcatacgtggggatatgagatgcat |
| cttggactgtatttttaggttggctatgttcccagccatatccctccggggattcatgttgtgcagaaccaccagcacagtgtatccggtgca |
| cttgggaaatttgtcatgtagcttagaaggaaatgcgtggaagaacttggagacgcccttgtgacctccaagattttccatgcattcgtcca |
| taatgatggcaatgggcccacgggcggcggcctgggcgaagatatttctgggatcactaacgtcatagttgtgttccaggatgagatcgt |
| cataggccattttacaaagcgcgggcggagggtgccagactgcggtataatggttccatccggcccaggggcgtagttaccctcaca |
| gatttgcatttcccacgctttgagttcagatgggggatcatgtctacctgcggggcgatgaagaaaacggtttccggggtaggggagat |

TABLE 14-continued

| Ad5ACE2 No Plasmid |
|---|
| cagctgggaagaaagcaggttcctgagcagctgcgacttaccgcagccggtgggcccgtaaatcacacctattaccggctgcaactgg |
| tagttaagagagctgcagctgccgtcatccctgagcaggggggccacttcgttaagcatgtccctgactcgcatgttttccctgaccaaat |
| ccgccagaaggcgctcgccgcccagcgatagcagttcttgcaaggaagcaaagtttttcaacggtttgagaccgtccgccgtaggcat |
| gcttttgagcgtttgaccaagcagttccaggcggtcccacagctcggtcacctgctctacggcatctcgatccagcatatctcctcgtttcg |
| cgggttggggcggctttcgctgtacggcagtagtcggtgctcgtccagacgggccagggtcatgtctttccacgggcgcagggtcctc |
| gtcagcgtagtctgggtcacggtgaaggggtgcgctccgggctgcgcgctggccagggtgcgcttgaggctggtcctgctggtgctg |
| aagcgctgccggtcttcgccctgcgcgtcggccaggtagcatttgaccatggtgtcatagtccagcccctccgcggcgtggcccttggc |
| gcgcagcttgcccttggaggaggcgccgcacgaggggcagtgcagacttttgagggcgtagagcttgggcgcgagaaataccgattc |
| cggggagtaggcatccgcgccgcaggccccgcagacggtctcgcattccacgagccaggtgagctctggccgttcggggtcaaaaa |
| ccaggtttcccccatgctttttgatgcgtttcttacctctggtttccatgagccggtgtccacgctcggtgacgaaaaggctgtccgtgtccc |
| cgtatacagacttgagaggcctgtcctcgagcggtgttccgcggtcctcctcgtatagaaactcggaccactctgagacaaaggctcgc |
| gtccaggccagcacgaaggaggctaagtgggaggggtagcggtcgttgtccactagggggtccactcgctccagggtgtgaagaca |
| catgtcgccctcttcggcatcaaggaaggtgattggtttgtaggtgtaggccacgtgaccgggtgttcctgaaggggggctataaaagg |
| gggggggcgcgttcgtcctcactctcttccgcatcgctgtctgcgagggccagctgttggggtgagtactccctctgaaaagcgggc |
| atgacttctgcgctaagattgtcagtttccaaaaacgaggaggatttgatattcacctggcccgcggtgatgcctttgagggtggccgcat |
| ccatctggtcagaaaagacaatctttttgttgtcaagcttggtggcaaacgacccgtagagggcgttggacagcaacttggcgatggagc |
| gcagggtttggtttttgtcgcgatcggcgcgctccttggccgcgatgtttagctgcacgtattcgcgcgcaacgcaccgccattcgggaa |
| agacggtggtgcgctcgtcgggcaccaggtgcacgcgccaaccgcggttgtgcagggtgacaaggtcaacgctggtggctacctctc |
| cgcgtaggcgctcgttggtccagcagaggcggccgcccttgcgcgagcagaatggcggtagggggtctagctgcgtctcgtccggg |
| gggtctgcgtccacggtaaagaccccgggcagcaggcgcgcgtcgaagtagtctatcttgcatccttgcaagtctagcgcctgctgcca |
| tgcgcgggcggcaagcgcgcgctcgtatgggttgagtgggggaccccatggcatggggtgggtgagcgcggaggcgtacatgccg |
| caaatgtcgtaaacgtagaggggctctctgagtattccaagatatgtagggtagcatcttccaccgcggatgctggcgcgcacgtaatcg |
| tatagttcgtgcgagggagcgaggaggtcgggaccgaggttgctacgggggctgctctgctcggaagactatctgcctgaagatg |
| gcatgtgagttggatgatatggttggacgctggaagacgttgaagctggcgtctgtgagacctaccgcgtcacgcacgaaggaggcgt |
| aggagtcgcgcagcttgttgaccagctcggcggtgacctgcacgtctagggcgcagtagtccagggtttccttgatgatgtcatacttatc |
| ctgtcccttttttttccacagctcgcggttgaggacaaactcttcgcggtctttccagtactcttggatcggaaacccgtcggcctccgaacg |
| gtaagagcctagcatgtagaactggttgacggcctggtaggcgcagcatcccttttctacgggtagcgcgtatgcctgcgcggccttcc |
| ggagcgaggtgtgggtgagcgcaaaggtgtccctgaccatgactttgaggtactggtatttgaagtcagtgtcgtcgcatccgccctgct |
| cccagagcaaaaagtccgtgcgctttttggaacgcggatttggcagggcgaaggtgacatcgttgaagagtatctttcccgcgcgaggc |
| ataaagttgcgtgtgatgcggaagggtcccggcacctcggaacggttgttaattacctgggcggcgagcacgatctcgtcaaagccgtt |
| gatgttgtggcccacaatgtaaagttccaagaagcgcgggatgcccttgatggaaggcaatttttttaagttcctcgtaggtgagctcttcag |
| gggagctgagcccgtgctctgaaagggcccagtctgcaagatgagggttggaagcgacgaatgagctccacaggtcacgggccatta |
| gcatttgcaggtggtcgcgaaaggtcctaaactggcgacctatggccatttttttctggggtgatgcagtagaaggtaagcgggtcttgttc |
| ccagcggtcccatccaaggttcgcggctaggtctcgcgcggcagtcactagaggctcatctccgccgaacttcatgaccagcatgaag |
| ggcacgagctgcttcccaaaggcccccatccaagtataggtctctacatcgtaggtgacaaagagacgctcggtgcgaggatgcgagc |
| cgatcgggaagaactggatctcccgccaccaattggaggagtggctattgatgtggtgaaagtagaagtccctgcgacgggccgaaca |
| ctcgtgctggcttttgtaaaaacgtgcgcagtactggcagcggtgcacgggctgtacatcctgcacgaggttgacctgacgaccgcgca |
| caaggaagcagagtgggaatttgagcccctcgcctggcgggtttggctggtggtcttctacttcggctgcttgtccttgaccgtctggctg |
| ctcgaggggagttacggtggatcggaccaccacgccgcgcgagcccaaagtccagatgtccgcgcgcggcggtcggagcttgatga |

TABLE 14-continued

| Ad5ACE2 No Plasmid |
| --- |
| caacatcgcgcagatgggagctgtccatggtctggagctcccgcggcgtcaggtcaggcgggagctcctgcaggtttacctcgcatag |
| acgggtcagggcgcgggctagatccaggtgatacctaatttccaggggctggttggtggcggcgtcgatggcttgcaagaggccgcat |
| ccccgcggcgcgactacggtaccgcgcggcgggggggggccgcgggggtgtccttggatgatgcatctaaaagcggtgacgcgg |
| gcgagcccccggaggtagggggggctccggacccgccgggagagggggcaggggcacgtcggcgccgcgcgcgggcaggag |
| ctggtgctgcgcgcgtaggttgctggcgaacgcgacgacgcggcggttgatctcctgaatctggcgcctctgcgtgaagacgacggg |
| cccggtgagcttgaacctgaaagagagttcgacagaatcaatttcggtgtcgttgacggcggcctggcgcaaaatctcctgcacgtctcc |
| tgagttgtcttgataggcgatctcggccatgaactgctcgatctcttcctcctggagatctccgcgtccggctcgctccacggtggcggcg |
| aggtcgttggaaatgcgggccatgagctgcgagaaggcgttgaggcctccctcgttccagacgcggctgtagaccacgccccccttcg |
| gcatcgcgggcgcgcatgaccacctgcgcgagattgagctccacgtgccgggcgaagacggcgtagtttcgcaggcgctgaaagag |
| gtagttgagggtggtggcggtgtgttctgccacgaagaagtacataacccagcgtcgcaacgtggattcgttgatatcccccaaggcctc |
| aaggcgctccatggcctcgtagaagtccacggcgaagttgaaaaactgggagttgcgcgccgacacggttaactcctcctccagaaga |
| cggatgagctcggcgacagtgtcgcgcacctcgcgctcaaaggctacaggggcctcttcttcttcttcaatctcctcttccataagggcct |
| ccccttcttcttcttctggcggcggtgggggaggggggacacggcggcgacgacggcgcaccgggaggcggtcgacaaagcgctc |
| gatcatctccccgcggcgacggcgcatggtctcggtgacggcgcggccgttctcgcgggggcgcagttggaagacgccgcccgtca |
| tgtcccggttatgggttggcgggggggctgccatgcggcagggatacggcgctaacgatgcatctcaacaattgttgtgtaggtactccg |
| ccgccgagggacctgagcgagtccgcatcgaccggatcggaaaacctctcgagaaaggcgtctaaccagtcacagtcgcaaggtag |
| gctgagcaccgtggcgggcggcagcgggcggcggtcggggttgtttctggcggaggtgctgctgatgatgtaattaaagtaggcggt |
| cttgagacggcggatggtcgacagaagcaccatgtccttgggtccggcctgctgaatgcgcaggcggtcggccatgccccaggcttc |
| gttttgacatcggcgcaggtctttgtagtagtcttgcatgagcctttctaccggcacttcttcttctccttcctcttgtcctgcatctcttgcatcta |
| tcgctgcggcggcggcggagtttggccgtaggtggcgccctcttcctcccatgcgtgtgaccccgaagcccctcatcggctgaagcag |
| ggctaggtcggcgacaacgcgctcggctaatatggcctgctgcacctgcgtgagggtagactggaagtcatccatgtccacaaagcgg |
| tggtatgcgcccgtgttgatggtgtaagtgcagttggccataacggaccagttaacggtctggtgacccggctgcgagagctcggtgta |
| cctgagacgcgagtaagccctcgagtcaaatacgtagtcgttgcaagtccgcaccaggtactggtatcccaccaaaaagtgcggcggc |
| ggctggcggtagaggggccagcgtagggtggccggggctccgggggcgagatcttccaacataaggcgatgatatccgtagatgta |
| cctggacatccaggtgatgccggcggcggtggtggaggcgcgcggaaagtcgcggacgcggttccagatgttgcgcagcggcaaa |
| aagtgctccatggtcgggacgctctggccggtcaggcgcgcgcaatcgttgacgctctagaccgtgcaaaaggagagcctgtaagcg |
| ggcactcttccgtggtctggtggataaattcgcaagggtatcatggcggacgaccggggttcgagccccgtatccggccgtccgccgt |
| gatccatgcggttaccgcccgcgtgtcgaacccaggtgtgcgacgtcagacaacgggggagtgctccttttggcttccttccaggcgcg |
| gcggctgctgcgctagcttttttggccactggccgcgcgcagcgtaagcggttaggctggaaagcgaaagcattaagtggctcgctccc |
| tgtagccggagggttattttccaagggttgagtcgcgggacccccggttcgagtctcggaccggccggactgcggcgaacgggggttt |
| gcctccccgtcatgcaagaccccgcttgcaaattcctccggaaacagggacgagcccctttttttgcttttcccagatgcatccggtgctgc |
| ggcagatgcgcccccctcctcagcagcggcaagagcaagagcagcggcagacatgcagggcaccctcccctcctcctaccgcgtca |
| ggaggggcgacatccgcggttgacgcggcagcagatggtgattacgaaccccgcggcgccgggcccggcactacctggacttgg |
| aggagggcgagggcctggcgcggctaggagcgccctctcctgagcggcacccaagggtgcagctgaagcgtgatacgcgtgagg |
| cgtacgtgccgcggcagaacctgtttcgcgaccgcgagggagaggagcccgaggagatgcgggatcgaaagttccacgcagggcg |
| cgagctgcggcatggcctgaatcgcgagcggttgctgcgcgaggaggactttgagcccgacgcgcgaaccgggattagtcccgcgc |
| gcgcacacgtggcggccgccgacctggtaaccgcatacgagcagacggtgaaccaggagattaactttcaaaaaagctttaacaacc |
| acgtgcgtacgcttgtggcgcgcgaggaggtggctataggactgatgcatctgtgggactttgtaagcgcgctggagcaaaacccaaa |
| tagcaagccgctcatggcgcagctgttccttatagtgcagcacagcagggacaacgaggcattcagggatgcgctgctaaacatagta |

TABLE 14-continued

| Ad5ACE2 No Plasmid |
|---|
| gagcccgagggccgctggctgctcgatttgataaacatcctgcagagcatagtggtgcaggagcgcagcttgagcctggctgacaag |
| gtggccgccatcaactattccatgcttagcctgggcaagttttacgcccgcaagatataccataccccttacgttcccatagacaaggagg |
| taaagatcgaggggttctacatgcgcatggcgctgaaggtgcttaccttgagcgacgacctgggcgtttatcgcaacgagcgcatccac |
| aaggccgtgagcgtgagccggcggcgcgagctcagcgaccgcgagctgatgcacagcctgcaaagggccctggctggcacgggc |
| agcggcgatagagaggccgagtcctactttgacgcgggcgctgacctgcgctgggccccaagccgacgcgccctggaggcagctg |
| gggccggacctgggctggcggtggcacccgcgcgcgctggcaacgtcggcggcgtggaggaatatgacgaggacgatgagtacg |
| agccagaggacggcgagtactaagcggtgatgtttctgatcagatgatgcaagacgcaacggacccggcggtgcgggcggcgctgc |
| agagccagccgtccggccttaactccacggacgactggcgccaggtcatggaccgcatcatgtcgctgactgcgcgcaatcctgacg |
| cgttccggcagcagccgcaggccaaccggctctccgcaattctggaagcggtggtcccggcgcgcgcaaaccccacgcacgagaa |
| ggtgctggcgatcgtaaacgcgctggccgaaaacagggccatccggcccgacgaggccggcctggtctacgacgcgctgcttcagc |
| gcgtggctcgttacaacagcggcaacgtgcagaccaacctggaccggctggtgggggatgtgcgcgaggccgtggcgcagcgtga |
| gcgcgcgcagcagcagggcaacctgggctccatggttgcactaaacgccttcctgagtacacagcccgccaacgtgccgcggggac |
| aggaggactacaccaactttgtgagcgcactgcggctaatggtgactgagacaccgcaaagtgaggtgtaccagtctgggccagacta |
| tttttccagaccagtagacaaggcctgcagaccgtaaacctgagccaggctttcaaaaacttgcaggggctgtggggggtgcgggctc |
| ccacaggcgaccgcgcgaccgtgtctagcttgctgacgcccaactcgcgcctgttgctgctgctaatagcgcccttcacggacagtgg |
| cagcgtgtcccgggacacatacctaggtcacttgctgacactgtaccgcgaggccataggtcaggcgcatgtggacgagcatactttcc |
| aggagattacaagtgtcagccgcgcgctggggcaggaggacacgggcagcctggaggcaaccctaaactacctgctgaccaaccg |
| gcggcagaagatcccctcgttgcacagtttaaacagcgaggaggagcgcattttgcgctacgtgcagcagagcgtgagccttaacctg |
| atgcgcgacggggtaacgcccagcgtggcgctggacatgaccgcgcgcaacatggaaccgggcatgtatgcctcaaaccggccgtt |
| tatcaaccgcctaatggactacttgcatcgcgcggccgccgtgaaccccgagtatttcaccaatgccatcttgaacccgcactggctacc |
| gccccctggtttctacaccgggggattcgaggtgcccgagggtaacgatggattcctctgggacgacatagacgacagcgtgttttccc |
| cgcaaccgcagaccctgctagagttgcaacagcgcgagcaggcagaggcggcgctgcgaaaggaaagcttccgcaggccaagca |
| gcttgtccgatctaggcgctgcggccccgcggtcagatgctagtagcccatttccaagcttgatagggtctcttaccagcactcgcacca |
| cccgcccgcgcctgctgggcgaggaggagtacctaaacaactcgctgctgcagccgcagcgcgaaaaaaacctgcctccggcatttc |
| ccaacaacgggatagagagcctagtggacaagatgagtagatggaagacgtacgcgcaggagcacagggacgtgccaggcccgc |
| gcccgcccacccgtcgtcaaaggcacgaccgtcagcggggtctggtgtgggaggacgatgactcggcagacgacagcagcgtcct |
| ggatttgggagggagtggcaacccgtttgcgcaccttcgccccaggctggggagaatgttttaaaaaaaaaaaaagcatgatgcaaa |
| ataaaaaactcaccaaggccatggcaccgagcgttggttttcttgtattccccttagtatgcggcgcgcggcgatgtatgaggaaggtcct |
| cctccctcctacgagagtgtggtgagcgcggcgccagtggggcggcgctgggttctcccttcgatgctcccctggacccgccgtttgt |
| gcctccgcggtacctgcggcctaccggggggagaaacagcatccgttactctgagttggcacccctattcgacaccacccgtgtgtacc |
| tggtggacaacaagtcaacggatgtggcatccctgaactaccagaacgaccacagcaactttctgaccacggtcattcaaaacaatgac |
| tacagcccgggggaggcaagcacacagaccatcaatcttgacgaccggtcgcactggggcggcgacctgaaaaccatcctgcatac |
| caacatgccaaatgtgaacgagttcatgtttaccaataagtttaaggcgcgggtgatggtgtcgcgcttgcctactaaggacaatcaggtg |
| gagctgaaatacgagtgggtggagttcacgctgcccgagggcaactactccgagaccatgaccatagaccttatgaacaacgcgatcg |
| tggagcactacttgaaagtgggcagacagaacggggttctggaaagcgacatcggggtaaagtttgacacccgcaacttcagactggg |
| gtttgaccccgtcactggtcttgtcatgcctggggtatatacaaacgaagccttccatccagacatcattttgctgccaggatgcggggtg |
| gacttcacccacagccgcctgagcaacttgttgggcatccgcaagcggcaacccttccaggagggctttaggatcacctacgatgatct |
| ggagggtggtaacattcccgcactgttggatgtggacgcctaccaggcgagcttgaaagatgacaccgaacagggcgggggtggcg |
| caggcggcagcaacagcagtggcagcggcgcggaagagaactccaacgcggcagccgcggcaatgcagccggtggaggacatg |

TABLE 14-continued

| Ad5ACE2 No Plasmid |
| --- |
| aacgatcatgccattcgcggcgacacctttgccacacgggctgaggagaagcgcgctgaggccgaagcagcggccgaagctgccg |
| cccccgctgcgcaacccgaggtcgagaagcctcagaagaaaccggtgatcaaacccctgacagaggacagcaagaaacgcagtta |
| caacctaataagcaatgacagcaccttcacccagtaccgcagctggtaccttgcatacaactacggcgaccctcagaccggaatccgct |
| catggaccctgctttgcactcctgacgtaacctgcggctcggagcaggtctactggtcgttgccagacatgatgcaagaccccgtgacct |
| tccgctccacgcgccagatcagcaactttccggtggggcgccgagctgttgcccgtgcactccaagagcttctacaacgaccaggc |
| cgtctactcccaactcatccgccagtttacctctctgacccacgtgttcaatcgctttcccgagaaccagattttggcgcgcccgccagcc |
| cccaccatcaccaccgtcagtgaaaacgttcctgctctcacagatcacgggacgctaccgctgcgcaacagcatcggaggagtccagc |
| gagtgaccattactgacgccagacgccgcacctgcccctacgtttacaaggccctgggcatagtctcgccgcgcgtcctatcgagccg |
| cactttttgagcaagcatgtccatccttatatcgcccagcaataacacaggctggggcctgcgcttcccaagcaagatgtttggcggggc |
| caagaagcgctccgaccaacacccagtgcgcgtgcgcgggcactaccgcgcgccctggggcgcgcacaaacgcggccgcactgg |
| gcgcaccaccgtcgatgacgccatcgacgcggtggtggaggaggcgcgcaactacacgcccacgccgccaccagtgtccacagtg |
| gacgcggccattcagaccgtggtgcgcggagcccggcgctatgctaaaatgaagagacggcggaggcgcgtagcacgtcgccacc |
| gccgccgacccggcactgccgcccaacgcgcggcggcggccctgcttaaccgcgcacgtcgcaccggccgacgggggccatgc |
| gagcagctcgaaggctggccgcgggtattgtcactgtgccccccaggtccaggcgacgagcggccgccgcagcagccgcggccat |
| tagtgctatgactcagggtcgcaggggcaacgtgtattgggtgcgcgactcggttagcggcctgcgcgtgcccgtgcgcacccgcccc |
| ccgcgcaactagattgcaagaaaaaactacttagactcgtactgttgtatgtatccagcggcggcggcgcgcaacgaagctatgtccaa |
| gcgcaaaatcaaagaagagatgctccaggtcatcgcgccggagatctatggcccccgaagaaggaagagcaggattacaagcccc |
| gaaagctaaagcgggtcaaaaagaaaaagaaagatgatgatgatgaacttgacgacgaggtggaactgctgcacgctaccgcgccca |
| ggcgacgggtacagtggaaaggtcgacgcgtaaaacgtgttttgcgacccggcaccaccgtagtctttacgcccggtgagcgctccac |
| ccgcacctacaagcgcgtgtatgatgaggtgtacggcgacgaggacctgcttgagcaggccaacgagcgcctcggggagtttgccta |
| cggaaagcggcataaggacatgctggcgttgccgctggacgagggcaacccaacacctagcctaaagcccgtaacactgcagcagg |
| tgctgcccgcgcttgcaccgtccgaagaaaagcgcggcctaaagcgcgagtctggtgacttggcacccaccgtgcagctgatggtac |
| ccaagcgccagcgactggaagatgtcttggaaaaaatgaccgtggaacctgggctggagcccgaggtccgcgtgcggccaatcaag |
| caggtggcgccgggactgggcgtgcagaccgtggacgttcagatacccactaccagtagcaccagtattgccaccgccacagaggg |
| catggagacacaaacgtccccggttgcctcagcggtggcggatgccgcggtgcaggcggtcgctgcggccgcgtccaagacctcta |
| cggaggtgcaaacggacccgtggatgtttcgcgtttcagccccccggcgcccgcgccgttcgaggaagtacggcgccgccagcgcg |
| ctactgcccgaatatgccctacatccttccattgcgcctacccccggctatcgtggctacacctaccgccccagaagacgagcaactacc |
| cgacgccgaaccaccactggaacccgccgccgccgtcgccgtcgccagcccgtgctggccccgatttccgtgcgcagggtggctcg |
| cgaaggaggcaggaccctggtgctgccaacagcgcgctaccaccccagcatcgtttaaaagccggtctttgtggttcttgcagatatgg |
| ccctcacctgccgcctccgtttcccggtgccgggattccgaggaagaatgcaccgtaggaggggcatggccggccacggcctgacg |
| ggcggcatgcgtcgtgcgcaccaccggcggcggcgcgcgtcgcaccgtcgcatgcgcggcggtatcctgcccctccttattccactg |
| atcgccgcggcgattggcgccgtgcccggaattgcatccgtggccttgcaggcgcagagacactgattaaaaacaagttgcatgtgga |
| aaaatcaaaataaaaagtctggactctcacgctcgcttggtcctgtaactattttgtagaatggaagacatcaactttgcgtctctggccccg |
| cgacacggctcgcgcccgttcatgggaaactggcaagatatcggcaccagcaatatgagcggtggcgccttcagctggggctcgctgt |
| ggagcggcattaaaaatttcggttccaccgttaagaactatggcagcaaggcctggaacagcagcacaggccagatgctgagggataa |
| gttgaaagagcaaaatttccaacaaaaggtggtagatggcctggcctctggcattagcggggtggtggacctggccaaccaggcagtg |
| caaaataagattaacagtaagcttgatccccgccctcccgtagaggagcctccaccggccgtggagacagtgtctccagaggggcgtg |
| gcgaaaagcgtccgcgccccgacagggaagaaactctggtgacgcaaatagacgagcctccctcgtacgaggaggcactaaagca |
| aggcctgcccaccacccgtcccatcgcgcccatggctaccggagtgctgggccagcacacacccgtaacgctggacctgcctccccc |

TABLE 14-continued

| Ad5ACE2 No Plasmid |
| --- |
| cgccgacacccagcagaaacctgtgctgccaggcccgaccgccgttgttgtaacccgtcctagccgcgcgtccctgcgccgcgccgc |
| cagcggtccgcgatcgttgcggcccgtagccagtggcaactggcaaagcacactgaacagcatcgtgggtctgggggtgcaatccct |
| gaagcgccgacgatgcttctgaatagctaacgtgtcgtatgtgtgtcatgtatgcgtccatgtcgccgccagaggagctgctgagccgcc |
| gcgcgcccgctttccaagatggctaccccttcgatgatgccgcagtggtcttacatgcacatctcgggccaggacgcctcggagtacct |
| gagccccgggctggtgcagtttgcccgcgccaccgagacgtacttcagcctgaataacaagtttagaaccccacggtggcgcctacg |
| cacgacgtgaccacagaccggtcccagcgtttgacgctgcggttcatccctgtggaccgtgaggatactgcgtactcgtacaaggcgc |
| ggttcaccctagctgtgggtgataaccgtgtgctggacatggcttccacgtactttgacatccgcggcgtgctggacaggggccctacttt |
| taagccctactctggcactgcctacaacgccctggctcccaagggtgccccaaatccttgcgaatgggatgaagctgctactgctcttga |
| aataaacctagaagaagaggacgatgacaacgaagacgaagtagacgagcaagctgagcagcaaaaaactcacgtatttgggcagg |
| cgccttattctggtataaatattacaaaggagggtattcaaataggtgtcgaaggtcaaacacctaaatatgccgataaaacatttcaacct |
| gaacctcaaataggagaatctcagtggtacgaaacagaaattaatcatgcagctgggagagtcctaaaaaagactaccccaatgaaacc |
| atgttacggttcatatgcaaaacccacaaatgaaaatggagggcaaggcattcttgtaaagcaacaaaatggaaagctagaaagtcaag |
| tggaaatgcaatttttctcaactactgaggcagccgcaggcaatggtgataacttgactcctaaagtggtattgtacagtgaagatgtagat |
| atagaaaccccagacactcatatttcttacatgcccactattaaggaaggtaactcacgagaactaatgggccaacaatctatgcccaaca |
| ggcctaattacattgcttttagggacaattttattggtctaatgtattacaacagcacgggtaatatgggtgttctgggggccaagcatcgc |
| agttgaatgctgttgtagatttgcaagacagaaacacagagctttcataccagcttttgcttgattccattggtgatagaaccaggtacttttct |
| atgtggaatcaggctgttgacagctatgatccagatgttagaattattgaaaatcatggaactgaagatgaacttccaaattactgctttcca |
| ctgggaggtgtgattaatacagagactcttaccaaggtaaaacctaaaacaggtcaggaaaatggatgggaaaaagatgctacagaatt |
| ttcagataaaaatgaaataagagttggaaataattttgccatggaaatcaatctaaatgccaacctgtggagaaatttcctgtactccaacat |
| agcgctgtatttgcccgacaagctaaagtacagtccttccaacgtaaaaatttctgataacccaaacacctacgactacatgaacaagcga |
| gtggtggctcccgggctagtggactgctacattaaccttggagcacgctggtcccttgactatatggacaacgtcaacccatttaaccacc |
| accgcaatgctggcctgcgctaccgctcaatgttgctgggcaatggtcgctatgtgcccttccacatccaggtgcctcagaagttctttgc |
| cattaaaaacctccttctcctgccgggctcatacacctacgagtggaacttcaggaaggatgttaacatggttctgcagagctccctagga |
| aatgacctaagggttgacggagccagcattaagtttgatagcatttgcctttacgccaccttcttccccatggcccacaacaccgcctcca |
| cgcttgaggccatgcttagaaacgacaccaacgaccagtcctttaacgactatctctccgccgccaacatgctctaccctatacccgcca |
| acgctaccaacgtgcccatatccatcccctcccgcaactgggggctttccgcggctgggccttcacgcgccttaagactaaggaaacc |
| ccatcactgggctcgggctacgacccttattacacctactctggctctataccctacctagatggaaccttttacctcaaccacacctttaag |
| aaggtggccattacctttgactcttctgtcagctggcctggcaatgaccgcctgcttacccccaacgagtttgaaattaagcgctcagttga |
| cggggagggttacaacgttgcccagtgtaacatgaccaaagactggttcctggtacaaatgctagctaactataacattggctaccaggg |
| cttctatatcccagagagctacaaggaccgcatgtactccttctttagaaacttccagcccatgagccgtcaggtggtggatgatactaaat |
| acaaggactaccaacaggtgggcatcctacaccaacacaacaactctggatttgttggctaccttgcccccaccatgcgcgaaggaca |
| ggcctaccctgctaacttcccctatccgcttataggcaagaccgcagttgacagcattacccagaaaaagtttctttgcgatcgcaccctttt |
| ggcgcatcccattctccagtaactttatgtccatgggcgcactcacagacctgggccaaaaccttctctacgccaactccgcccacgcgc |
| tagacatgacttttgaggtggatcccatggacgagcccacccttctttatgttttgtttgaagtctttgacgtggtccgtgtgcaccagccgc |
| accgcggcgtcatcgaaaccgtgtacctgcgcacgcccttctcggccggcaacgccacaacataaagaagcaagcaacatcaacaac |
| agctgccgccatgggctccagtgagcaggaactgaaagccattgtcaaagatcttggttgtgggccatatttttttgggcacctatgacaag |
| cgctttccaggctttgtttctccacacaagctcgcctgcgccatagtcaatacggccggtcgcgagactgggggcgtacactggatggc |
| ctttgcctggaacccgcactcaaaaacatgctacctctttgagccctttggcttttctgaccagcgactcaagcaggtttaccagtttgagta |
| cgagtcactcctgcgccgtagcgccattgcttcttcccccgaccgctgtataacgctggaaaagtccacccaaagcgtacaggggccca |

TABLE 14-continued

| Ad5ACE2 No Plasmid |
| --- |
| actcggccgcctgtggactattctgctgcatgtttctccacgcctttgccaactggccccaaactcccatggatcacaaccccaccatgaa |
| ccttattaccggggtacccaactccatgctcaacagtccccaggtacagcccaccctgcgtcgcaaccaggaacagctctacagcttcct |
| ggagcgccactcgccctacttccgcagccacagtgcgcagattaggagcgccacttctttttgtcacttgaaaaacatgtaaaaataatgt |
| actagagacactttcaataaaggcaaatgcttttatttgtacactctcgggtgattatttacccccacccttgccgtctgcgccgtttaaaaatc |
| aaaggggttctgccgcgcatcgctatgcgccactggcagggacacgttgcgatactggtgtttagtgctccacttaaactcaggcacaac |
| catccgcggcagctcggtgaagttttcactccacaggctgcgcaccatcaccaacgcgtttagcaggtcgggcgccgatatcttgaagt |
| cgcagttggggcctccgccctgcgcgcgcgagttgcgatacacagggttgcagcactggaacactatcagcgccgggtggtgcacgc |
| tggccagcacgctcttgtcggagatcagatccgcgtccaggtcctccgcgttgctcagggcgaacggagtcaactttggtagctgccttc |
| ccaaaaagggcgcgtgcccaggctttgagttgcactcgcaccgtagtggcatcaaaaggtgaccgtgcccggtctgggcgttaggata |
| cagcgcctgcataaaagccttgatctgcttaaaagccacctgagcctttgcgccttcagagaagaacatgccgcaagacttgccggaaa |
| actgattggccggacacgcggcgtcgtgcacgcagcaccttgcgtcggtgttggagatctgcaccacatttcggccccaccggttcttc |
| acgatcttggccttgctagactgctccttcagcgcgcgctgcccgttttcgctcgtcacatccatttcaatcacgtgctccttatttatcataat |
| gcttccgtgtagacacttaagctcgccttcgatctcagcgcagcggtgcagccacaacgcgcagcccgtgggctcgtgatgcttgtagg |
| tcacctctgcaaacgactgcaggtacgcctgcaggaatcgccccatcatcgtcacaaaggtcttgttgctggtgaaggtcagctgcaacc |
| cgcggtgctcctcgttcagccaggtcttgcatacggccgccagagcttccacttggtcaggcagtagtttgaagttcgcctttagatcgtta |
| tccacgtggtacttgtccatcagcgcgcgcgcagcctccatgcccttctcccacgcagacacgatcggcacactcagcgggttcatcac |
| cgtaatttcactttccgcttcgctgggctcttcctcttcctcttgcgtccgcataccacgcgccactgggtcgtcttcattcagccgccgcact |
| gtgcgcttacctcctttgccatgcttgattagcaccggtgggttgctgaaacccaccatttgtagcgccacatcttctctttcttcctcgctgtc |
| cacgattacctctggtgatggcgggcgctcgggcttgggagaagggcgcttctttttcttcttgggcgcaatggccaaatccgccgccga |
| ggtcgatggccgcgggctgggtgtgcgcggcaccagcgcgtcttgtgatgagtcttcctcgtcctcggactcgatacgccgcctcatcc |
| gctttttggggggcgcccggggaggcggcggcgacggggacggggacgacacgtcctccatggttgggggacgtcgcgccgcacc |
| gcgtccgcgctcgggggtggtttcgcgctgctcctcttcccgactggccatttccttctcctataggcagaaaaagatcatggagtcagtc |
| gagaagaaggacagcctaaccgcccctctgagttcgccaccaccgcctccaccgatgccgccaacgcgcctaccaccttccccgtc |
| gaggcacccccgcttgaggaggaggaagtgattatcgagcaggacccaggttttgtaagcgaagacgacgaggaccgctcagtacc |
| aacagaggataaaaagcaagaccaggacaacgcagaggcaaacgaggaacaagtcgggggggggacgaaaggcatggcgact |
| acctagatgtgggagacgacgtgctgttgaagcatctgcagcgccagtgcgccattatctgcgacgcgttgcaagagcgcagcgatgt |
| gcccctcgccatagcggatgtcagccttgcctacgaacgccacctattctcaccgcgcgtaccccccaaacgccaagaaaacggcaca |
| tgcgagcccaacccgcgcctcaacttctaccccgtatttgccgtgccagaggtgcttgccacctatcacatctttttccaaaactgcaagat |
| acccctatcctgccgtgccaaccgcagccgagcggacaagcagctggccttgcggcaggggctgtcatacctgatatcgcctcgctc |
| aacgaagtgccaaaaatctttgagggtcttggacgcgacgagaagcgcgcggcaaacgctctgcaacaggaaaacagcgaaaatga |
| aagtcactctggagtgttggtggaactcgagggtgacaacgcgcgcctagccgtactaaaacgcagcatcgaggtcacccactttgcct |
| acccggcacttaacctacccccccaaggtcatgagcacagtcatgagtgagctgatcgtgcgccgtgcgcagcccctggagagggatg |
| caaatttgcaagaacaaacagaggagggcctacccgcagttggcgacgagcagctagcgcgctggcttcaaacgcgcgagcctgcc |
| gacttggaggagcgacgcaaactaatgatggccgcagtgctcgttaccgtggagcttgagtgcatgcagcggttctttgctgacccgga |
| gatgcagcgcaagctagaggaaacattgcactacacctttcgacagggctacgtacgccaggcctgcaagatctccaacgtggagctc |
| tgcaacctggtctcctaccttggaattttgcacgaaaaccgccttgggcaaaacgtgcttcattccacgctcaagggcgaggcgcgccg |
| cgactacgtccgcgactgcgtttacttatttctatgctacacctggcagacggccatgggcgtttggcagcagtgcttggaggagtgcaa |
| cctcaaggagctgcagaaactgctaaagcaaaacttgaaggacctatggacggccttcaacgagcgctccgtggccgcgcacctggc |
| ggacatcattttccccgaacgcctgcttaaaaccctgcaacagggtctgccagacttcaccagtcaaagcatgttgcagaactttaggaa |

TABLE 14-continued

| Ad5ACE2 No Plasmid |
|---|
| ctttatcctagagcgctcaggaatcttgcccgccacctgctgtgcacttcctagcgactttgtgcccattaagtaccgcgaatgccctccgc |
| cgctttggggccactgctaccttctgcagctagccaactaccttgcctaccactctgacataatggaagacgtgagcggtgacggtctact |
| ggagtgtcactgtcgctgcaacctatgcaccccgcaccgctccctggtttgcaattcgcagctgcttaacgaaagtcaaattatcggtacc |
| tttgagctgcagggtccctcgcctgacgaaaagtccgcggctccggggttgaaactcactccggggctgtggacgtcggcttaccttcg |
| caaatttgtacctgaggactaccacgcccacgagattaggttctacgaagaccaatcccgcccgcctaatgcggagcttaccgcctgcg |
| tcattacccagggccacattcttggccaattgcaagccatcaacaaagcccgccaagagtttctgctacgaaagggacgggggtttact |
| tggacccccagtccggcgaggagctcaacccaatcccccgccgccgcagccctatcagcagcagccgcgggcccttgcttcccag |
| gatggcacccaaaaagaagctgcagctgccgccgccacccacggacgaggaggaatactgggacagtcaggcagaggaggttttg |
| gacgaggaggaggaggacatgatggaagactgggagagcctagacgaggaagcttccgaggtcgaagaggtgtcagacgaaaca |
| ccgtcaccctcggtcgcattcccctcgccggcgccccagaaatcggcaaccggttccagcatggctacaacctccgctcctcaggcgc |
| cgccggcactgcccgttcgccgacccaaccgtagatgggacaccactggaaccagggccggtaagtccaagcagccgccgccgtta |
| gcccaagagcaacaacagcgccaaggctaccgctcatggcgcgggcacaagaacgccatagttgcttgcttgcaagactgtggggg |
| caacatctccttcgcccgccgctttcttctctaccatcacggcgtggccttcccccgtaacatcctgcattactaccgtcatctctacagccc |
| atactgcaccggcggcagcggcagcggcagcaacagcagcggccacacagaagcaaaggcgaccggatagcaagactctgacaa |
| agcccaagaaatccacagcggcggcagcagcaggaggaggagcgctgcgtctggcgcccaacgaacccgtatcgacccgcgagc |
| ttagaaacaggattttcccactctgtatgctatatttcaacagagcaggggccaagaacaagagctgaaaataaaaaacaggtctctgcg |
| atccctcacccgcagctgcctgtatcacaaaagcgaagatcagcttcggcgcacgctggaagacgcggaggctctcttcagtaaatact |
| gcgcgctgactcttaaggactagtttcgcgccctttctcaaatttaagcgcgaaaactacgtcatctccagcggccacacccggcgccag |
| cacctgttgtcagcgccattatgagcaaggaaattcccacgccctacatgtggagttaccagccacaaatgggacttgcggctggagct |
| gcccaagactactcaacccgaataaactacatgagcgcgggaccccacatgatatcccgggtcaacggaatacgcgcccaccgaaac |
| cgaattctcctggaacaggcggctattaccaccacacctcgtaataaccttaatccccgtagttggcccgctgccctggtgtaccaggaa |
| agtcccgctcccaccactgtggtacttcccagagacgcccaggccgaagttcagatgactaactcaggggcgcagcttgcgggcggct |
| ttcgtcacagggtgcggtcgcccgggcagggtataactcacctgacaatcagagggcgaggtattcagctcaacgacgagtcggtga |
| gctcctcgcttggtctccgtccggacgggacatttcagatcggcggcgccggccgctcttcattcacgcctcgtcaggcaatcctaactct |
| gcagacctcgtcctctgagccgcgctctggaggcattggaactctgcaatttattgaggagtttgtgccatcggtctactttaaccccttctc |
| gggacctcccggccactatccggatcaatttattcctaactttgacgcggtaaaggactcggcggacggctacgactgaatgttaagtgg |
| ccaatgaggcctgacgctaataatagctggtccactgtcgccgccacaagtgctttgcccgcgactccggtgagttttgctactttgaattg |
| cccgaggatcatatcgagggcccggcgcacggcgtccggcttaccgcccagggagagcttgcccgtagcctgattcgggagtttacc |
| cagcgcccccctgctagttgagcgggacaggggaccctgtgttctcactgtgatttgcaactgtcctaaccttggattacatcaagatccag |
| atcttctagacccgggagcggccgctgtcgacctgcaggatccgaattcgatatcactagtggtaccgatcttattccctttaactaataaa |
| aaaaaataataaagcatcacttacttaaaatcagttagcaaatttctgtccagtttattcagcagcacctccttgccctcctcccagctctggt |
| attgcagcttcctcctggctgcaaactttctccacaatctaaagggaatgtcagtttcctcctgttcctgtccatccgcacccactatcttcatg |
| ttgttgcagatgaagcgcgcaagaccgtctgaagataccttcaaccccgtgtatccatatgacacggaaaccggtcctccaactgtgcctt |
| ttcttactcctccctttgtatcccccaatgggtttcaagagagtccccctggggtactctctttgcgcctatccgaacctctagttacctccaat |
| ggcatgcttgcgctcaaaatgggcaacggcctctctctggacgaggccggcaaccttacctcccaaaatgtaaccactgtgagcccacc |
| tctcaaaaaaaccaagtcaaacataaacctggaaatatctgcacccctcacagttacctcagaagccctaactgtggctgccgccgcacc |
| tctaatggtcgcgggcaacacactcaccatgcaatcacaggccccgctaaccgtgcacgactccaaacttagcattgcccacccaagga |
| cccctcacagtgtcagaaggaaagctagccctgcaaacatcaggcccccctcaccaccaccgatagcagtacccttactatcactgcctc |
| accccctctaactactgccactggtagcttgggcattgacttgaaagagcccatttatacacaaaatggaaaactaggactaaagtacgg |

TABLE 14-continued

| Ad5ACE2 No Plasmid |
|---|
| ggctcctttgcatgtaacagacgacctaaacactttgaccgtagcaactggtccaggtgtgactattaataatacttccttgcaaactaaagt |
| tactggagccttgggttttgattcacaaggcaatatgcaacttaatgtagcaggaggactaaggattgattctcaaaacagacgccttatac |
| ttgatgttagttatccgtttgatgctcaaaaccaactaaatctaagactaggacagggccctctttttataaactcagcccacaacttggatatt |
| aactacaacaaaggcctttacttgtttacagcttcaaacaattccaaaaagcttgaggttaacctaagcactgccaaggggttgatgtttga |
| cgctacagccatagccattaatgcaggagatgggcttgaatttggttcacctaatgcaccaaacacaaatcccctcaaaacaaaaattgg |
| ccatggcctagaatttgattcaaacaaggctatggttcctaaactaggaactggccttagttttgacagcacaggtgccattacagtaggaa |
| acaaaaataatgataagctaactttgtggaccacaccagctccatctcctaactgtagactaaatgcagagaaagatgctaaactcactttg |
| gtcttaacaaaatgtggcagtcaaatacttgctacagtttcagttttggctgttaaaggcagtttggctccaatatctggaacagttcaaagtg |
| ctcatcttattataagatttgacgaaaatggagtgctactaaacaattccttcctggacccagaatattggaactttagaaatggagatcttac |
| tgaaggcacagcctatacaaacgctgttggatttatgcctaacctatcagcttatccaaaatctcacggtaaaactgccaaaagtaacattg |
| tcagtcaagtttacttaaacggagacaaaactaaacctgtaacactaaccattacactaaacggtacacaggaaacaggagacacaactc |
| caagtgcatactctatgtcattttcatgggactggtctggccacaactacattaatgaaatatttgccacatcctcttacactttttcatacattg |
| cccaagaataaagaatcgtttgtgttatgtttcaacgtgtttatttttcaattgcagaaaatttcaagtcatttttcattcagtagtatagccccac |
| caccacatagcttatacagatcaccgtaccttaatcaaactcacagaaccctagtattcaacctgccacctccctcccaacacacagagta |
| cacagtcctttctccccggctggccttaaaaagcatcatatcatgggtaacagacatattcttaggtgttatattccacacggtttcctgtcga |
| gccaaacgctcatcagtgatattaataaactccccgggcagctcacttaagttcatgtcgctgtccagctgctgagccacaggctgctgtc |
| caacttgcggttgcttaacgggcggcgaaggagaagtccacgcctacatgggggtagagtcataatcgtgcatcaggatagggcggtg |
| gtgctgcagcagcgcgcgaataaactgctgccgccgccgctccgtcctgcaggaatacaacatggcagtggtctcctcagcgatgatt |
| cgcaccgcccgcagcataaggcgccttgtcctccgggcacagcagcgcaccctgatctcacttaaatcagcacagtaactgcagcaca |
| gcaccacaatattgttcaaaatcccacagtgcaaggcgctgtatccaaagctcatggggggaccacagaacccacgtggccatcata |
| ccacaagcgcaggtagattaagtggcgacccctcataaacacgctggacataaacattacctcttttggcatgttgtaattcaccacctcc |
| cggtaccatataaacctctgattaaacatggcgccatccaccaccatcctaaaccagctggccaaaacctgcccgccggctatacactg |
| cagggaaccgggactggaacaatgacagtggagagcccaggactcgtaaccatggatcatcatgctcgtcatgatatcaatgttggca |
| caacacaggcacacgtgcatacacttcctcaggattacaagctcctcccgcgttagaaccatatcccagggaacaacccattcctgaatc |
| agcgtaaatcccacactgcagggaagacctcgcacgtaactcacgttgtgcattgtcaaagtgttacattcgggcagcagcggatgatc |
| ctccagtatggtagcgcgggtttctgtctcaaaaggaggtagacgatccctactgtacggagtgcgccgagacaaccgagatcgtgttg |
| gtcgtagtgtcatgccaaatggaacgccggacgtagtcatatttcctgaagcaaaaccaggtgcgggcgtgacaaacagatctgcgtct |
| ccggtctcgccgcttagatcgctctgtgtagtagttgtagtatatccactctctcaaagcatccaggcgccccctggcttcgggttctatgta |
| aactccttcatgcgccgctgccctgataacatccaccaccgcagaataagccacacccagccaacctacacattcgttctgcgagtcaca |
| cacgggaggagcgggaagagctggaagaaccatgtttttttttttattccaaaagattatccaaaacctcaaaatgaagatctattaagtg |
| aacgcgctcccctccggtggcgtggtcaaactctacagccaaagaacagataatggcatttgtaagatgttgcacaatggcttccaaaag |
| gcaaacggccctcacgtccaagtggacgtaaaggctaaacccttcagggtgaatctcctctataaacattccagcaccttcaaccatgcc |
| caaataattctcatctcgccaccttctcaatatatctctaagcaaatcccgaatattaagtccggccattgtaaaaatctgctccagagcgcc |
| ctccaccttcagcctcaagcagcgaatcatgattgcaaaaattcaggttcctcacagacctgtataagattcaaaagcggaacattaacaa |
| aaataccgcgatcccgtaggtcccttcgcagggccagctgaacataatcgtgcaggtctgcacggaccagcgcggccacttccccgcc |
| aggaaccatgacaaaagaacccacactgattatgacacgcatactcggagctatgctaaccagcgtagccccgatgtaagcttgttgcat |
| gggcggcgatataaaatgcaaggtgctgctcaaaaaatcaggcaaagcctcgcgcaaaaaagaaagcacatcgtagtcatgctcatgc |
| agataaaggcaggtaagctccggaaccaccacagaaaaagacaccatttttctctcaaacatgtctgcgggtttctgcataaacacaaaa |
| taaaataacaaaaaaacatttaaacattagaagcctgtcttacaacaggaaaaacaacccttataagcataagacggactacggccatgc |

TABLE 14-continued

| Ad5ACE2 No Plasmid |
|---|
| cggcgtgaccgtaaaaaaactggtcaccgtgattaaaaagcaccaccgacagctcctcggtcatgtccggagtcataatgtaagactcg |
| gtaaacacatcaggttgattcacatcggtcagtgctaaaaagcgaccgaaatagcccgggggaatacatacccgcaggcgtagagaca |
| acattacagcccccataggaggtataacaaaattaataggagagaaaaacacataaacacctgaaaaaccctcctgcctaggcaaaata |
| gcaccctcccgctccagaacaacatacagcgcttccacagcggcagccataacagtcagccttaccagtaaaaaagaaaacctattaa |
| aaaaacaccactcgacacggcaccagctcaatcagtcacagtgtaaaaaagggccaagtgcagagcgagtatatataggactaaaaa |
| atgacgtaacggttaaagtccacaaaaaacacccagaaaaccgcacgcgaacctacgcccagaaacgaaagccaaaaaacccacaa |
| cttcctcaaatcgtcacttccgttttcccacgttacgtaacttcccattttaagaaaactacaattcccaacacatacaagttactccgccctaa |
| aacctacgtcacccgccccgttcccacgccccgcgccacgtcacaaactccaccccctcattatcatattggcttcaatccaaaataaggt |
| atattattgatgatg |

TABLE 15

| Ad5ACE2 with Plasmid Backbone |
|---|
| (SEQ ID NO: 15) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |

TABLE 15-continued

| Ad5ACE2 with Plasmid Backbone |
|---|
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctataggggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |

TABLE 15-continued

| Ad5ACE2 with Plasmid Backbone |
|---|
| ccggcaacgcgataagcgtaggtaaagtgaatcaacgcttcttcacggtcaaggcgacgggcggttatctcatccagctgcatggtttca |
| aacaggcgcactttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattcccttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |

TABLE 15-continued

| Ad5ACE2 with Plasmid Backbone |
|---|
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataattttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttaaggatctgcgatcgctccggtgcccgtcagtgggcagagc |
| gcacatcgcccacagtccccgagaagttggggggaggggtcggcaattgaacgggtgcctagagaaggtggcgcggggtaaactg |
| ggaaagtgatgtcgtgtactggctccgcctttttcccgagggggggagaaccgtatataagtgcagtagtcgccgtgaacgttctttttc |
| gcaacgggtttgccgccagaacacagctgaagcttcgaggggctcgcatctctccttcacgcgcccgccgccctacctgaggccgcc |
| atccacgccggttgagtcgcgttctgccgcctcccgcctgtggtgcctcctgaactgcgtccgccgtctaggtaagtttaaagctcaggtc |
| gagaccgggcctttgtccggcgctcccttggagcctacctagactcagccggctctccacgctttgcctgaccctgcttgctcaactctac |
| gtctttgtttcgttttctgttctgcgccgttacagatccaagctgtgaccggcgcctacctcctgggcaacgtgctggttattgtgctgtctcat |
| cattttggcaaagaattccgctgcgactcggcggagtcccggcggcgcgtccttgttctaacccggcgcgccagcttggcaatccggta |
| ctgttggtaaagccaccatgtcaagctcttcctggctccttctcagccttgttgctgtaactgctgctcagtccaccattgaggaacaggcc |
| aagacatttttggacaagtttaaccacgaagccgaagacctgttctatcaaagttcacttgcttcttggaattataacaccaatattactgaag |
| agaatgtccaaaacatgaataatgctggggacaaatggtctgcctttttaaaggaacagtccacacttgcccaaatgtatccactacaaga |
| aattcagaatctcacagtcaagcttcagctgcaggctcttcagcaaaatgggtcttcagtgctctcagaagacaagagcaaacggttgaa |
| cacaattctaaatacaatgagcaccatctacagtactggaaaagtttgtaacccagataatccacaagaatgcttattacttgaaccaggttt |
| gaatgaaataatggcaaacagtttagactacaatgagaggctctgggcttgggaaagctggagatctgaggtcggcaagcagctgagg |
| ccattatatgaagagtatgtggtcttgaaaaatgagatggcaagagcaaatcattatgaggactatggggattattggagaggagactatg |
| aagtaaatggggtagatggctatgactacagccgcggccagttgattgaagatgtggaacatacctttgaagagattaaaccattatatga |
| acatcttcatgcctatgtgagggcaaagttgatgaatgcctatccttcctatatcagtccaattggatgcctccctgctcatttgcttggtgata |
| tgtggggtagattttggacaaatctgtactctttgacagttccctttggacagaaaccaaacatagatgttactgatgcaatggtggaccag |
| gcctgggatgcacagagaatattcaaggaggccgagaagttctttgtatctgttggtcttcctaatatgactcaaggattctgggaaaattc |
| catgctaacggacccaggaaatgttcagaaagcagtctgccatcccacagcttgggacctggggaagggcgacttcaggatccttatgt |
| gcacaaaggtgacaatggacgacttcctgacagctcatcatgagatggggcatatccagtatgatatggcatatgctgcacaaccttttct |
| gctaagaaatggagctaatgaaggattccatgaagctgttggggaaatcatgtcactttctgcagccacacctaagcatttaaaatccattg |
| gtcttctgtcacccgattttcaagaagacaatgaaacagaaataaacttcctgctcaaacaagcactcacgattgttgggactctgccattta |
| cttacatgttagagaagtggaggtggatggtctttaaaggggaaattcccaaagaccagtggatgaaaaagtggtgggagatgaagcg |
| agagatagttggggtggtggaacctgtgccccatgatgaaacatactgtgaccccgcatctctgttccatgtttctaatgattactcattcatt |

TABLE 15-continued

| Ad5ACE2 with Plasmid Backbone |
|---|
| cgatattacacaaggaccctttaccaattccagtttcaagaagcactttgtcaagcagctaaacatgaaggccctctgcacaaatgtgacat |
| ctcaaactctacagaagctggacagaaactgttcaatatgctgaggcttggaaaatcagaaccctggaccctagcattggaaaatgttgta |
| ggagcaaagaacatgaatgtaaggccactgctcaactactttgagcccttatttacctggctgaaagaccagaacaagaattcttttgtgg |
| gatggagtaccgactggagtccatatgcagaccaaagcatcaaagtgaggataagcctaaaatcagctcttggagataaagcatatgaa |
| tggaacgacaatgaaatgtacctgttccgatcatctgttgcatatgctatgaggcagtactttttaaaagtaaaaaatcagatgattctttttgg |
| ggaggaggatgtgcgagtggctaatttgaaaccaagaatctcctttaatttttttgtcactgcacctaaaaatgtgtctgatatcattcctaga |
| actgaagttgaaaaggccatcaggatgtcccggagccgtatcaatgatgctttccgtctgaatgacaacagcctagagtttctggggata |
| cagccaacacttggacctcctaaccagccccctgtttccatatggctgattgtttttggagttgtgatgggagtgatagtggttggcattgtc |
| atcctgatcttcactgggatcagagatcggaagaagaaaaataaagcaagaagtggagaaaatccttatgcctccatcgatattagcaaa |
| ggagaaaataatccaggattccaaaacactgatgatgttcagacctccttttagtaataattctagagtcggggcggccggccgcttcgag |
| atcagcctcgactgtgccttctagttgccagccatctgttgtttgcccctcccccgtgccttccttgaccctggaaggtgccactcccactgt |
| cctttcctaataaaatgaggaaattgcatccagtactgaaatgtgtgggcgtggcttaagggtgggaaagaatatataaggtgggggtctt |
| atgtagttttgtatctgttttgcagcagccgccgccgccatgagcaccaactcgtttgatggaagcattgtgagctcatatttgacaacgcg |
| catgcccccatgggccggggtgcgtcagaatgtgatgggctccagcattgatggtcgccccgtcctgcccgcaaactctactaccttga |
| cctacgagaccgtgtctggaacgccgttggagactgcagcctccgccgccgcttcagccgctgcagccaccgcccgcgggattgtga |
| ctgactttgctttcctgagcccgcttgcaagcagtgcagcttcccgttcatccgcccgcgatgacaagttgacggctcttttggcacaattg |
| gattctttgacccgggaacttaatgtcgtttctcagcagctgttggatctgcgccagcaggtttctgccctgaaggcttcctcccctcccaat |
| gcggtttaacggtccgggccagagtggccaacataaataaaaaaccagactctgtttggatttggatcaagcaagtgtcttgctgtctttat |
| ttaggggttttgcgcgcgcggtaggcccgggaccagcggtctcggtcgttgagggtcctgtgtatttttttccaggacgtggtaaaggtga |
| ctctggatgttcagatacatgggcataagcccgtctctggggtggaggtagcaccactgcagagcttcatgctgcggggtggtgttgtag |
| atgatccagtcgtagcaggagcgctgggcgtggtgcctaaaaatgtctttcagtagcaagctgattgccaggggcaggcccttggtgta |
| agtgtttacaaagcggttaagctgggatgggtgcatacgtggggatatgagatgcatcttggactgtatttttaggttggctatgttcccagc |
| catatccctccggggattcatgttgtgcagaaccaccagcacagtgtatccggtgcacttgggaaatttgtcatgtagcttagaaggaaat |
| gcgtggaagaacttggagacgcccttgtgacctccaagattttccatgcattcgtccataatgatggcaatgggcccacgggcggcggc |
| ctgggcgaagatatttctgggatcactaacgtcatagttgtgttccaggatgagatcgtcataggccatttttacaaagcgcgggcggagg |
| gtgccagactgcggtataatggttccatccggcccaggggcgtagttaccctcacagatttgcatttcccacgctttgagttcagatgggg |
| ggatcatgtctacctgcggggcgatgaagaaaacggtttccggggtaggggagatcagctgggaagaaagcaggttcctgagcagct |
| gcgacttaccgcagccggtgggcccgtaaatcacacctattaccggctgcaactggtagttaagagagctgcagctgccgtcatccctg |
| agcagggggggccacttcgttaagcatgtccctgactcgcatgttttccctgaccaaatccgccagaaggcgctcgccgcccagcgatag |
| cagttcttgcaaggaagcaaagtttttcaacggtttgagaccgtccgccgtaggcatgcttttgagcgtttgaccaagcagttccaggcgg |
| tcccacagctcggtcacctgctctacggcatctcgatccagcatatctcctcgtttcgcgggttggggcggctttcgctgtacggcagtag |
| tcggtgctcgtccagacgggccagggtcatgtctttccacgggcgcagggtcctcgtcagcgtagtctgggtcacggtgaaggggtgc |
| gctccgggctgcgcgctggccagggtgcgcttgaggctggtcctgctggtgctgaagcgctgccggtcttcgccctgcgcgtcggcca |
| ggtagcatttgaccatggtgtcatagtccagcccctccgcggcgtggcccttggcgcgcagcttgcccttggaggaggcgccgcacga |
| ggggcagtgcagacttttgagggcgtagagcttgggcgcgagaaataccgattccggggagtaggcatccgcgccgcaggccccgc |
| agacggtctcgcattccacgagccaggtgagctctggccgttcggggtcaaaaaccaggtttcccccatgctttttgatgcgtttcttacct |
| ctggtttccatgagccggtgtccacgctcggtgacgaaaaggctgtccgtgtccccgtatacagacttgagaggcctgtcctcgagcggt |
| gttccgcggtcctcctcgtatagaaactcggaccactctgagacaaaggctcgcgtccaggccagcacgaaggaggctaagtgggag |
| gggtagcggtcgttgtccactagggggtccactcgctccagggtgtgaagacacatgtcgccctcttcggcatcaaggaaggtgattgg |

TABLE 15-continued

| Ad5ACE2 with Plasmid Backbone |
|---|
| tttgtaggtgtaggccacgtgaccgggtgttcctgaagggggctataaaagggggtgggggcgcgttcgtcctcactctcttccgcatc |
| gctgtctgcgagggccagctgttggggtgagtactccctctgaaaagcgggcatgacttctgcgctaagattgtcagtttccaaaaacga |
| ggaggatttgatattcacctggcccgcggtgatgcctttgagggtggccgcatccatctggtcagaaaagacaatctttttgttgtcaagct |
| tggtggcaaacgacccgtagagggcgttggacagcaacttggcgatggagcgcagggtttggtttttgtcgcgatcggcgcgctccttg |
| gccgcgatgtttagctgcacgtattcgcgcgcaacgcaccgccattcgggaaagacggtggtgcgctcgtcgggcaccaggtgcacg |
| cgccaaccgcggttgtgcagggtgacaaggtcaacgctggtggctacctctccgcgtaggcgctcgttggtccagcagaggcggccg |
| cccttgcgcgagcagaatggcggtagggggtctagctgcgtctcgtccgggggggtctgcgtccacggtaaagaccccgggcagcag |
| gcgcgcgtcgaagtagtctatcttgcatccttgcaagtctagcgcctgctgccatgcgcgggcggcaagcgcgcgctcgtatgggttga |
| gtgggggaccccatggcatggggtgggtgagcgcggaggcgtacatgccgcaaatgtcgtaaacgtagaggggctctctgagtattc |
| caagatatgtagggtagcatcttccaccgcggatgctggcgcgcacgtaatcgtatagttcgtgcgagggagcgaggaggtcgggacc |
| gaggttgctacgggcgggctgctctgctcggaagactatctgcctgaagatggcatgtgagttggatgatatggttggacgctggaaga |
| cgttgaagctggcgtctgtgagacctaccgcgtcacgcacgaaggaggcgtaggagtcgcgcagcttgttgaccagctcggcggtga |
| cctgcacgtctagggcgcagtagtccagggtttccttgatgatgtcatacttatcctgtcccttttttttccacagctcgcggttgaggacaaa |
| ctcttcgcggtctttccagtactcttggatcggaaacccgtcggcctccgaacggtaagagcctagcatgtagaactggttgacggcctg |
| gtaggcgcagcatcccttttctacgggtagcgcgtatgcctgcgcggccttccggagcgaggtgtgggtgagcgcaaaggtgtccctg |
| accatgactttgaggtactggtatttgaagtcagtgtcgtcgcatccgccctgctcccagagcaaaaagtccgtgcgctttttggaacgcg |
| gatttggcagggcgaaggtgacatcgttgaagagtatctttcccgcgcgaggcataaagttgcgtgtgatgcggaagggtcccggcac |
| ctcggaacggttgttaattacctgggcggcgagcacgatctcgtcaaagccgttgatgttgtggcccacaatgtaaagttccaagaagcg |
| cgggatgcccttgatggaaggcaattttttaagttcctcgtaggtgagctcttcaggggagctgagcccgtgctctgaaagggcccagtct |
| gcaagatgagggttggaagcgacgaatgagctccacaggtcacgggccattagcatttgcaggtggtcgcgaaaggtcctaaactgg |
| cgacctatggccattttttctggggtgatgcagtagaaggtaagcgggtcttgttcccagcggtcccatccaaggttcgcggctaggtctc |
| gcgcggcagtcactagaggctcatctccgccgaacttcatgaccagcatgaagggcacgagctgcttcccaaaggcccccatccaagt |
| ataggtctctacatcgtaggtgacaaagagacgctcggtgcgaggatgcgagccgatcgggaagaactggatctcccgccaccaattg |
| gaggagtggctattgatgtggtgaaagtagaagtccctgcgacgggccgaacactcgtgctggcttttgtaaaaacgtgcgcagtactg |
| gcagcggtgcacgggctgtacatcctgcacgaggttgacctgacgaccgcgcacaaggaagcagagtgggaatttgagcccctcgc |
| ctggcgggtttggctggtggtcttctacttcggctgcttgtccttgaccgtctggctgctcgaggggagttacggtggatcggaccaccac |
| gccgcgcgagcccaaagtccagatgtccgcgcgcggcggtcggagcttgatgacaacatcgcgcagatgggagctgtccatggtctg |
| gagctcccgcggcgtcaggtcaggcgggagctcctgcaggtttacctcgcatagacgggtcagggcgcgggctagatccaggtgata |
| cctaatttccaggggctggttggtggcggcgtcgatggcttgcaagaggccgcatccccgcggcgcgactacggtaccgcgcggcgg |
| gcggtgggccgcgggggtgtccttggatgatgcatctaaaagcggtgacgcgggcgagcccccggaggtagggggggctccggac |
| ccgccgggagagggggcaggggcacgtcggcgccgcgcgcgggcaggagctggtgctgcgcgcgtaggttgctggcgaacgcg |
| acgacgcggcggttgatctcctgaatctggcgcctctgcgtgaagacgacgggcccggtgagcttgaacctgaaagagagttcgaca |
| gaatcaatttcggtgtcgttgacggcggcctggcgcaaaatctcctgcacgtctcctgagttgtcttgataggcgatctcggccatgaact |
| gctcgatctcttcctcctggagatctccgcgtccggctcgctccacggtggcggcgaggtcgttggaaatgcgggccatgagctgcga |
| gaaggcgttgaggcctccctcgttccagacgcggctgtagaccacgcccccttcggcatcgcgggcgcgcatgaccacctgcgcgag |
| attgagctccacgtgccgggcgaagacggcgtagtttcgcaggcgctgaaagaggtagttgagggtggtggcggtgtgttctgccacg |
| aagaagtacataacccagcgtcgcaacgtggattcgttgatatcccccaaggcctcaaggcgctccatggcctcgtagaagtccacgg |
| cgaagttgaaaaactgggagttgcgcgccgacacggttaactcctcctccagaagacggatgagctcggcgacagtgtcgcgcacctc |
| gcgctcaaaggctacaggggcctcttcttcttcttcaatctcctcttccataagggcctccccttcttcttcttctggcggcggtgggggagg |

TABLE 15-continued

| Ad5ACE2 with Plasmid Backbone |
| --- |
| ggggacacggggcgacgacggcgcaccgggaggcggtcgacaaagcgctcgatcatctccccgcggcgacggcgcatggtctc |
| ggtgacggcgcggccgttctcgcgggggcgcagttggaagacgccgcccgtcatgtcccggttatgggttggcgggggctgccat |
| gcggcagggatacggcgctaacgatgcatctcaacaattgttgtgtaggtactccgccgccgagggacctgagcgagtccgcatcgac |
| cggatcggaaaacctctcgagaaaggcgtctaaccagtcacagtcgcaaggtaggctgagcaccgtggcgggcggcagcgggcgg |
| cggtcggggttgtttctggcggaggtgctgctgatgatgtaattaaagtaggcggtcttgagacggcggatggtcgacagaagcaccat |
| gtccttgggtccggcctgctgaatgcgcaggcggtcggccatgccccaggcttcgttttgacatcggcgcaggtctttgtagtagtcttgc |
| atgagcctttctaccggcacttcttcttctccttcctcttgtcctgcatctcttgcatctatcgctgcggcggcggcggagtttggccgtaggt |
| ggcgccctcttcctcccatgcgtgtgaccccgaagcccctcatcggctgaagcagggctaggtcggcgacaacgcgctcggctaatat |
| ggcctgctgcacctgcgtgagggtagactggaagtcatccatgtccacaaagcggtggtatgcgcccgtgttgatggtgtaagtgcagtt |
| ggccataacggaccagttaacggtctggtgacccggctgcgagagctcggtgtacctgagacgcgagtaagccctcgagtcaaatac |
| gtagtcgttgcaagtccgcaccaggtactggtatcccaccaaaaagtgcggcggcggctggcggtagaggggccagcgtagggtgg |
| ccggggctccgggggcgagatcttccaacataaggcgatgatatccgtagatgtacctggacatccaggtgatgccggcggcggtggt |
| ggaggcgcgcggaaagtcgcggacgcggttccagatgttgcgcagcggcaaaaagtgctccatggtcgggacgctctggccggtca |
| ggcgcgcgcaatcgttgacgctctagaccgtgcaaaaggagagcctgtaagcgggcactcttccgtggtctggtggataaattcgcaa |
| gggtatcatggcggacgaccggggttcgagccccgtatccggccgtccgccgtgatccatgcggttaccgcccgcgtgtcgaaccca |
| ggtgtgcgacgtcagacaacgggggagtgctccttttggcttccttccaggcgcggcggctgctgcgctagcttttttggccactggccg |
| cgcgcagcgtaagcggttaggctggaaagcgaaagcattaagtggctcgctccctgtagccggagggttattttccaagggttgagtcg |
| cgggacccccggttcgagtctcggaccggccggactgcggcgaacgggggtttgcctccccgtcatgcaagaccccgcttgcaaatt |
| cctccggaaacagggacgagcccctttttgcttttcccagatgcatccggtgctgcggcagatgcgcccccctcctcagcagcggcaa |
| gagcaagagcagcggcagacatgcagggcaccctcccctcctcctaccgcgtcaggaggggcgacatccgcggttgacgcggcag |
| cagatggtgattacgaaccccccgcggcgccgggcccggcactacctggacttggaggagggcgagggcctggcgcggctaggagc |
| gccctctcctgagcggcacccaagggtgcagctgaagcgtgatacgcgtgaggcgtacgtgccgcggcagaacctgtttcgcgaccg |
| cgagggagaggagcccgaggagatgcgggatcgaaagttccacgcagggcgcgagctgcggcatggcctgaatcgcgagcggtt |
| gctgcgcgaggaggactttgagcccgacgcgcgaaccgggattagtcccgcgcgcgcacacgtggcggccgccgacctggtaacc |
| gcatacgagcagacggtgaaccaggagattaactttcaaaaaagctttaacaaccacgtgcgtacgcttgtggcgcgcgaggaggtgg |
| ctataggactgatgcatctgtgggactttgtaagcgcgctggagcaaaacccaaatagcaagccgctcatggcgcagctgttccttatag |
| tgcagcacagcagggacaacgaggcattcagggatgcgctgctaaacatagtagagcccgagggccgctggctgctcgatttgataa |
| acatcctgcagagcatagtggtgcaggagcgcagcttgagcctggctgacaaggtggccgccatcaactattccatgcttagcctgggc |
| aagttttacgcccgcaagatataccataccccttacgttcccatagacaaggaggtaaagatcgaggggttctacatgcgcatggcgctg |
| aaggtgcttaccttgagcgacgacctgggcgtttatcgcaacgagcgcatccacaaggccgtgagcgtgagccggcggcgcgagctc |
| agcgaccgcgagctgatgcacagcctgcaaagggccctggctggcacgggcagcggcgatagagaggccgagtcctactttgacg |
| cgggcgctgacctgcgctgggccccaagccgacgcgccctggaggcagctggggccggacctgggctggcggtggcacccgcgc |
| gcgctggcaacgtcggggcgtggaggaatatgacgaggacgatgagtacgagccagaggacggcgagtactaagcggtgatgttt |
| ctgatcagatgatgcaagacgcaacggacccggcggtgcgggcggcgctgcagagccagccgtccggccttaactccacggacga |
| ctggcgccaggtcatggaccgcatcatgtcgctgactgcgcgcaatcctgacgcgttccggcagcagccgcaggccaaccggctctc |
| cgcaattctggaagcggtggtcccggcgcgcgcaaaccccacgcacgagaaggtgctggcgatcgtaaacgcgctggccgaaaac |
| agggccatccggcccgacgaggccggcctggtctacgacgcgctgcttcagcgcgtggctcgttacaacagcggcaacgtgcagac |
| caacctggaccggctggtgggggatgtgcgcgaggccgtggcgcagcgtgagcgcgcgcagcagcagggcaacctgggctccat |
| ggttgcactaaacgccttcctgagtacacagcccgccaacgtgccgcggggacaggaggactacaccaactttgtgagcgcactgcg |

TABLE 15-continued

| Ad5ACE2 with Plasmid Backbone |
|---|
| gctaatggtgactgagacaccgcaaagtgaggtgtaccagtctgggccagactatttttccagaccagtagacaaggcctgcagaccg |
| taaacctgagccaggctttcaaaaacttgcaggggctgtggggggtgcgggctcccacaggcgaccgcgcgaccgtgtctagcttgct |
| gacgcccaactcgcgcctgttgctgctgctaatagcgcccttcacggacagtggcagcgtgtcccgggacacatacctaggtcacttgc |
| tgacactgtaccgcgaggccataggtcaggcgcatgtggacgagcatactttccaggagattacaagtgtcagccgcgcgctggggca |
| ggaggacacgggcagcctggaggcaaccctaaactacctgctgaccaaccggcggcagaagatcccctcgttgcacagtttaaacag |
| cgaggaggagcgcattttgcgctacgtgcagcagagcgtgagccttaacctgatgcgcgacggggtaacgcccagcgtggcgctgg |
| acatgaccgcgcgcaacatggaaccgggcatgtatgcctcaaaccggccgtttatcaaccgcctaatggactacttgcatcgcgcggc |
| cgccgtgaaccccgagtatttcaccaatgccatcttgaacccgcactggctaccgccccctggtttctacaccgggggattcgaggtgcc |
| cgagggtaacgatggattcctctgggacgacatagacgacagcgtgttttccccgcaaccgcagaccctgctagagttgcaacagcgc |
| gagcaggcagaggcggcgctgcgaaaggaaagcttccgcaggccaagcagcttgtccgatctaggcgctgcggccccgcggtcag |
| atgctagtagcccatttccaagcttgatagggtctcttaccagcactcgcaccacccgcccgcgcctgctgggcgaggaggagtaccta |
| aacaactcgctgctgcagccgcagcgcgaaaaaaacctgcctccggcatttcccaacaacgggatagagagcctagtggacaagatg |
| agtagatggaagacgtacgcgcaggagcacagggacgtgccaggcccgcgcccgcccacccgtcgtcaaaggcacgaccgtcag |
| cggggtctggtgtgggaggacgatgactcggcagacgacagcagcgtcctggatttgggagggagtggcaacccgtttgcgcacctt |
| cgccccaggctggggagaatgttttaaaaaaaaaaaaaagcatgatgcaaaataaaaaactcaccaaggccatggcaccgagcgttg |
| gttttcttgtattccccttagtatgcggcgcgcggcgatgtatgaggaaggtcctcctccctcctacgagagtgtggtgagcgcggcgcca |
| gtggcggcggcgctgggttctcccttcgatgctcccctggacccgccgtttgtgcctccgcggtacctgcggcctaccggggggagaa |
| acagcatccgttactctgagttggcacccctattcgacaccacccgtgtgtacctggtggacaacaagtcaacggatgtggcatccctga |
| actaccagaacgaccacagcaactttctgaccacggtcattcaaaacaatgactacagcccgggggaggcaagcacacagaccatca |
| atcttgacgaccggtcgcactggggcggcgacctgaaaaccatcctgcataccaacatgccaaatgtgaacgagttcatgtttaccaata |
| agtttaaggcgcgggtgatggtgtcgcgcttgcctactaaggacaatcaggtggagctgaaatacgagtgggtggagttcacgctgccc |
| gagggcaactactccgagaccatgaccatagaccttatgaacaacgcgatcgtggagcactacttgaaagtgggcagacagaacggg |
| gttctggaaagcgacatcggggtaaagtttgacacccgcaacttcagactggggtttgaccccgtcactggtcttgtcatgcctggggtat |
| atacaaacgaagccttccatccagacatcattttgctgccaggatgcggggtggacttcacccacagccgcctgagcaacttgttgggca |
| tccgcaagcggcaacccttccaggagggctttaggatcacctacgatgatctggagggtggtaacattcccgcactgttggatgtggac |
| gcctaccaggcgagcttgaaagatgacaccgaacaggggggggtggcgcaggcggcagcaacagcagtggcagcggcgcgga |
| agagaactccaacgcggcagccgcggcaatgcagccggtggaggacatgaacgatcatgccattcgcggcgacacctttgccacac |
| gggctgaggagaagcgcgctgaggccgaagcagcggccgaagctgccgcccccgctgcgcaacccgaggtcgagaagcctcag |
| aagaaaccggtgatcaaacccctgacagaggacagcaagaaacgcagttacaacctaataagcaatgacagcaccttcacccagtac |
| cgcagctggtaccttgcatacaactacggcgaccctcagaccggaatccgctcatggaccctgctttgcactcctgacgtaacctgcgg |
| ctcggagcaggtctactggtcgttgccagacatgatgcaagaccccgtgaccttccgctccacgcgccagatcagcaactttccggtgg |
| tgggcgccgagctgttgcccgtgcactccaagagcttctacaacgaccaggccgtctactcccaactcatccgccagtttacctctctga |
| cccacgtgttcaatcgctttcccgagaaccagattttggcgcgcccgccagccccaccatcaccaccgtcagtgaaaacgttcctgctc |
| tcacagatcacgggacgctaccgctgcgcaacagcatcggaggagtccagcgagtgaccattactgacgccagacgccgcacctgc |
| ccctacgtttacaaggccctgggcatagtctcgccgcgcgtcctatcgagccgcactttttgagcaagcatgtccatccttatatcgccca |
| gcaataacacaggctggggcctgcgcttcccaagcaagatgtttggcggggccaagaagcgctccgaccaacacccagtgcgcgtg |
| cgcgggcactaccgcgcgccctggggcgcgcacaaacgcggccgcactgggcgcaccaccgtcgatgacgccatcgacgcggtg |
| gtggaggaggcgcgcaactacacgcccacgccgccaccagtgtccacagtggacgcggccattcagaccgtggtgcgcggagccc |
| ggcgctatgctaaaatgaagagacggcggaggcgcgtagcacgtcgccaccgccgccgacccggcactgccgcccaacgcgcgg |

TABLE 15-continued

| Ad5ACE2 with Plasmid Backbone |
| --- |
| cggcggccctgcttaaccgcgcacgtcgcaccggccgacgggggccatgcgagcagctcgaaggctggccgcgggtattgtcact |
| gtgcccccccaggtccaggcgacgagcggccgccgcagcagccgcggccattagtgctatgactcagggtcgcaggggcaacgtgt |
| attgggtgcgcgactcggttagcggcctgcgcgtgcccgtgcgcacccgcccccccgcgcaactagattgcaagaaaaaactactta ga |
| ctcgtactgttgtatgtatccagcggcggcggcgcgcaacgaagctatgtccaagcgcaaaatcaaagaagagatgctccaggtcatc |
| gcgccggagatctatggccccccgaagaaggaagagcaggattacaagccccgaaagctaaagcgggtcaaaaagaaaaagaaag |
| atgatgatgatgaacttgacgacgaggtggaactgctgcacgctaccgcgcccaggcgacgggtacagtggaaaggtcgacgcgtaa |
| aacgtgttttgcgacccggcaccaccgtagtctttacgcccggtgagcgctccacccgcacctacaagcgcgtgtatgatgaggtgtac |
| ggcgacgaggacctgcttgagcaggccaacgagcgcctcggggagtttgcctacggaaagcggcataaggacatgctggcgttgcc |
| gctggacgagggcaacccaacacctagcctaaagcccgtaacactgcagcaggtgctgcccgcgcttgcaccgtccgaagaaaagc |
| gcggcctaaagcgcgagtctggtgacttggcacccaccgtgcagctgatggtacccaagcgccagcgactggaagatgtcttggaaa |
| aaatgaccgtggaacctgggctggagcccgaggtccgcgtgcggccaatcaagcaggtggcgccgggactgggcgtgcagaccgt |
| ggacgttcagatacccactaccagtagcaccagtattgccaccgccacagagggcatggagacacaaacgtccccggttgcctcagc |
| ggtggcggatgccgcggtgcaggcggtcgctgcggccgcgtccaagacctctacggaggtgcaaacggacccgtggatgtttcgcg |
| tttcagcccccccggcgcccgcgccgttcgaggaagtacggcgccgccagcgcgctactgcccgaatatgccctacatccttccattgc |
| gcctacccccggctatcgtggctacacctaccgccccagaagacgagcaactacccgacgccgaaccaccactggaacccgccgcc |
| gccgtcgccgtcgccagcccgtgctggccccgatttccgtgcgcagggtggctcgcgaaggaggcaggaccctggtgctgccaaca |
| gcgcgctaccaccccagcatcgtttaaaagccggtctttgtggttcttgcagatatggccctcacctgccgcctccgtttcccggtgccgg |
| gattccgaggaagaatgcaccgtaggaggggcatggccggccacggcctgacgggcggcatgcgtcgtgcgcaccaccggcggc |
| ggcgcgcgtcgcaccgtcgcatgcgcggcggtatcctgcccctccttattccactgatcgccgcggcgattggcgccgtgcccggaat |
| tgcatccgtggccttgcaggcgcagagacactgattaaaaacaagttgcatgtggaaaaatcaaaataaaaagtctggactctcacgctc |
| gcttggtcctgtaactattttgtagaatggaagacatcaactttgcgtctctggccccgcgacacggctcgcgcccgttcatgggaaactg |
| gcaagatatcggcaccagcaatatgagcggtggcgccttcagctggggctcgctgtggagcggcattaaaaatttcggttccaccgtta |
| agaactatggcagcaaggcctggaacagcagcacaggccagatgctgagggataagttgaaagagcaaaatttccaacaaaaggtg |
| gtagatggcctggcctctggcattagcggggtggtggacctggccaaccaggcagtgcaaaataagattaacagtaagcttgatcccc |
| gccctcccgtagaggagcctccaccggccgtggagacagtgtctccagaggggcgtggcgaaaagcgtccgcgccccgacaggga |
| agaaactctggtgacgcaaatagacgagcctccctcgtacgaggaggcactaaagcaaggcctgcccaccacccgtcccatcgcgcc |
| catggctaccggagtgctgggccagcacacacccgtaacgctggacctgcctcccccgccgacacccagcagaaacctgtgctgcc |
| aggcccgaccgccgttgttgtaacccgtcctagccgcgcgtccctgcgccgcgccgccagcggtccgcgatcgttgcggcccgtagc |
| cagtggcaactggcaaagcacactgaacagcatcgtgggtctgggggtgcaatccctgaagcgccgacgatgcttctgaatagctaac |
| gtgtcgtatgtgtgtcatgtatgcgtccatgtcgccgccagaggagctgctgagccgccgcgcgcccgctttccaagatggctacccctt |
| cgatgatgccgcagtggtcttacatgcacatctcgggccaggacgcctcggagtacctgagccccgggctggtgcagtttgcccgcgc |
| caccgagacgtacttcagcctgaataacaagtttagaaccccacggtggcgcctacgcacgacgtgaccacagaccggtcccagcg |
| tttgacgctgcggttcatccctgtggaccgtgaggatactgcgtactcgtacaaggcgcggttcaccctagctgtgggtgataaccgtgtg |
| ctggacatggcttccacgtactttgacatccgcggcgtgctggacaggggccctacttttaagccctactctggcactgcctacaacgcc |
| ctggctcccaagggtgccccaaatccttgcgaatgggatgaagctgctactgctcttgaaataaacctagaagaagaggacgatgacaa |
| cgaagacgaagtagacgagcaagctgagcagcaaaaactcacgtatttgggcaggcgccttattctggtataaatattacaaaggagg |
| gtattcaaataggtgtcgaaggtcaaacacctaaatatgccgataaaacatttcaacctgaacctcaaataggagaatctcagtggtacga |
| aacagaaattaatcatgcagctgggagagtcctaaaaaagactaccccaatgaaaccatgttacggttcatatgcaaaacccacaaatga |
| aaatggagggcaaggcattcttgtaaagcaacaaaatggaaagctagaaagtcaagtggaaatgcaatttttctcaactactgaggcagc |

TABLE 15-continued

| Ad5ACE2 with Plasmid Backbone |
|---|
| cgcaggcaatggtgataacttgactcctaaagtggtattgtacagtgaagatgtagatatagaaaccccagacactcatatttcttacatgc |
| ccactattaaggaaggtaactcacgagaactaatgggccaacaatctatgcccaacaggcctaattacattgcttttaggacaattttatt |
| ggtctaatgtattacaacagcacgggtaatatgggtgttctggcgggccaagcatcgcagttgaatgctgttgtagatttgcaagacagaa |
| acacagagctttcataccagcttttgcttgattccattggtgatagaaccaggtacttttctatgtggaatcaggctgttgacagctatgatcc |
| agatgttagaattattgaaaatcatggaactgaagatgaacttccaaattactgctttccactgggaggtgtgattaatacagagactcttac |
| caaggtaaaacctaaaacaggtcaggaaaatggatgggaaaaagatgctacagaattttcagataaaaatgaaataagagttggaaata |
| attttgccatggaaatcaatctaaatgccaacctgtggagaaatttcctgtactccaacatagcgctgtatttgcccgacaagctaaagtaca |
| gtccttccaacgtaaaaatttctgataacccaaacacctacgactacatgaacaagcgagtggtggctcccgggctagtggactgctaca |
| ttaaccttggagcacgctggtcccttgactatatggacaacgtcaacccatttaaccaccaccgcaatgctggcctgcgctaccgctcaat |
| gttgctgggcaatggtcgctatgtgcccttccacatccaggtgcctcagaagttctttgccattaaaaacctccttctcctgccgggctcata |
| cacctacgagtggaacttcaggaaggatgttaacatggttctgcagagctccctaggaaatgacctaagggttgacggagccagcatta |
| agtttgatagcatttgcctttacgccaccttcttccccatggcccacaacaccgcctccacgcttgaggccatgcttagaaacgacaccaa |
| cgaccagtcctttaacgactatctctccgccgccaacatgctctaccctatacccgccaacgctaccaacgtgcccatatccatcccctcc |
| cgcaactgggcggctttccgcggctgggccttcacgcgccttaagactaaggaaaccccatcactgggctcgggctacgacccttatta |
| cacctactctggctctataccctacctagatggaaccttttacctcaaccacacctttaagaaggtggccattacctttgactcttctgtcagc |
| tggcctggcaatgaccgcctgcttacccccaacgagtttgaaattaagcgctcagttgacggggagggttacaacgttgcccagtgtaac |
| atgaccaaagactggttcctggtacaaatgctagctaactataacattggctaccagggcttctatatcccagagagctacaaggaccgc |
| atgtactccttctttagaaacttccagcccatgagccgtcaggtggtggatgatactaaatacaaggactaccaacaggtgggcatcctac |
| accaacacaacaactctggatttgttggctaccttgcccccaccatgcgcgaaggacaggcctaccctgctaacttcccctatccgcttat |
| aggcaagaccgcagttgacagcattacccagaaaaagtttctttgcgatcgcaccctttggcgcatcccattctccagtaactttatgtcca |
| tgggcgcactcacagacctgggccaaaaccttctctacgccaactccgcccacgcgctagacatgacttttgaggtggatcccatggac |
| gagcccacccttctttatgttttgtttgaagtctttgacgtggtccgtgtgcaccagccgcaccgcggcgtcatcgaaaccgtgtacctgcg |
| cacgccccttctcggccggcaacgccacaacataaagaagcaagcaacatcaacaacagctgccgccatgggctccagtgagcagga |
| actgaaagccattgtcaaagatcttggttgtgggccatatttttgggcacctatgacaagcgctttccaggctttgtttctccacacaagctc |
| gcctgcgccatagtcaatacggccggtcgcgagactgggggcgtacactggatggcctttgcctggaacccgcactcaaaaacatgct |
| acctctttgagccctttggcttttctgaccagcgactcaagcaggtttaccagtttgagtacgagtcactcctgcgccgtagcgccattgctt |
| cttcccccgaccgctgtataacgctggaaaagtccacccaaagcgtacaggggcccaactcggccgcctgtggactattctgctgcatg |
| tttctccacgcctttgccaactggccccaaactcccatggatcacaaccccaccatgaaccttattaccggggtacccaactccatgctca |
| acagtccccaggtacagcccaccctgcgtcgcaaccaggaacagctctacagcttcctggagcgccactcgccctacttccgcagcca |
| cagtgcgcagattaggagcgccacttctttttgtcacttgaaaaacatgtaaaaataatgtactagagacactttcaataaaggcaaatgctt |
| ttatttgtacactctcgggtgattatttacccccacccttgccgtctgcgccgtttaaaaatcaaaggggttctgccgcgcatcgctatgcgc |
| cactggcagggacacgttgcgatactggtgtttagtgctccacttaaactcaggcacaaccatccgcggcagctcggtgaagttttcactc |
| cacaggctgcgcaccatcaccaacgcgtttagcaggtcgggcgccgatatcttgaagtcgcagttggggcctccgccctgcgcgcgc |
| gagttgcgatacacagggttgcagcactggaacactatcagcgccgggtggtgcacgctggccagcacgctcttgtcggagatcagat |
| ccgcgtccaggtcctccgcgttgctcagggcgaacggagtcaactttggtagctgccttcccaaaaagggcgcgtgcccaggctttga |
| gttgcactcgcaccgtagtggcatcaaaaggtgaccgtgcccggtctgggcgttaggatacagcgcctgcataaaagccttgatctgctt |
| aaaagccacctgagcctttgcgccttcagagaagaacatgccgcaagacttgccggaaaactgattggccggacacgcggcgtcgtg |
| cacgcagcaccttgcgtcggtgttggagatctgcaccacatttcggccccaccggttcttcacgatcttggccttgctagactgctccttca |
| gcgcgcgctgcccgttttcgctcgtcacatccatttcaatcacgtgctccttatttatcataatgcttccgtgtagacacttaagctcgccttcg |

TABLE 15-continued

| Ad5ACE2 with Plasmid Backbone |
| --- |
| atctcagcgcagcggtgcagccacaacgcgcagcccgtgggctcgtgatgcttgtaggtcacctctgcaaacgactgcaggtacgcct |
| gcaggaatcgccccatcatcgtcacaaaggtcttgttgctggtgaaggtcagctgcaacccgcggtgctcctcgttcagccaggtcttgc |
| atacggccgccagagcttccacttggtcaggcagtagtttgaagttcgcctttagatcgttatccacgtggtacttgtccatcagcgcgcgc |
| gcagcctccatgcccttctcccacgcagacacgatcggcacactcagcgggttcatcaccgtaatttcactttccgcttcgctgggctcttc |
| ctcttcctcttgcgtccgcataccacgcgccactgggtcgtcttcattcagccgccgcactgtgcgcttacctcctttgccatgcttgattag |
| caccggtgggttgctgaaacccaccatttgtagcgccacatcttctctttcttcctcgctgtccacgattacctctggtgatggcgggcgctc |
| gggcttgggagaagggcgcttctttttcttcttgggcgcaatggccaaatccgccgccgaggtcgatggccgcgggctgggtgtgcgc |
| ggcaccagcgcgtcttgtgatgagtcttcctcgtcctcggactcgatacgccgcctcatccgcttttttgggggcgcccggggaggcgg |
| cggcgacggggacggggacgacacgtcctccatggttgggggacgtcgcgccgcaccgcgtccgcgctcgggggtggtttcgcgc |
| tgctcctcttcccgactggccatttccttctcctataggcagaaaaagatcatggagtcagtcgagaagaaggacagcctaaccgccccc |
| tctgagttcgccaccaccgcctccaccgatgccgccaacgcgcctaccaccttccccgtcgaggcacccccgcttgaggaggaggaa |
| gtgattatcgagcaggacccaggttttgtaagcgaagacgacgaggaccgctcagtaccaacagaggataaaaagcaagaccaggac |
| aacgcagaggcaaacgaggaacaagtcgggggggggacgaaaggcatggcgactacctagatgtgggagacgacgtgctgttga |
| agcatctgcagcgccagtgcgccattatctgcgacgcgttgcaagagcgcagcgatgtgcccctcgccatagcggatgtcagccttgc |
| ctacgaacgccacctattctcaccgcgcgtacccccccaaacgccaagaaaacggcacatgcgagcccaacccgcgcctcaacttctac |
| cccgtatttgccgtgccagaggtgcttgccacctatcacatctttttccaaaactgcaagatacccctatcctgccgtgccaaccgcagcc |
| gagcggacaagcagctggccttgcggcagggcgctgtcatacctgatatcgcctcgctcaacgaagtgccaaaaatctttgagggtctt |
| ggacgcgacgagaagcgcgcggcaaacgctctgcaacaggaaaacagcgaaaatgaaagtcactctggagtgttggtggaactcga |
| gggtgacaacgcgcgcctagccgtactaaaacgcagcatcgaggtcacccactttgcctacccggcacttaacctacccccccaaggtc |
| atgagcacagtcatgagtgagctgatcgtgcgccgtgcgcagcccctggagagggatgcaaatttgcaagaacaaacagaggaggg |
| cctacccgcagttggcgacgagcagctagcgcgctggcttcaaacgcgcgagcctgccgacttggaggagcgacgcaaactaatgat |
| ggccgcagtgctcgttaccgtggagcttgagtgcatgcagcggttctttgctgacccggagatgcagcgcaagctagaggaaacattgc |
| actacacctttcgacagggctacgtacgccaggcctgcaagatctccaacgtggagctctgcaacctggtctcctaccttggaattttgca |
| cgaaaaccgccttgggcaaaacgtgcttcattccacgctcaagggcgaggcgcgccgcgactacgtccgcgactgcgtttacttatttct |
| atgctacacctggcagacggccatgggcgtttggcagcagtgcttggaggagtgcaacctcaaggagctgcagaaactgctaaagca |
| aaacttgaaggacctatggacggccttcaacgagcgctccgtggccgcgcacctggcggacatcattttccccgaacgcctgcttaaaa |
| ccctgcaacagggtctgccagacttcaccagtcaaagcatgttgcagaactttaggaactttatcctagagcgctcaggaatcttgcccgc |
| cacctgctgtgcacttcctagcgactttgtgcccattaagtaccgcgaatgccctccgccgctttggggccactgctaccttctgcagctag |
| ccaactaccttgcctaccactctgacataatggaagacgtgagcggtgacggtctactggagtgtcactgtcgctgcaacctatgcaccc |
| cgcaccgctccctggtttgcaattcgcagctgcttaacgaaagtcaaattatcggtacctttgagctgcagggtccctcgcctgacgaaaa |
| gtccgcggctccggggttgaaactcactccggggctgtggacgtcggcttaccttcgcaaatttgtacctgaggactaccacgcccacg |
| agattaggttctacgaagaccaatcccgcccgcctaatgcggagcttaccgcctgcgtcattacccagggccacattcttggccaattgc |
| aagccatcaacaaagcccgccaagagtttctgctacgaaagggacgggggggtttacttggacccccagtccggcgaggagctcaacc |
| caatcccccgccgccgcagccctatcagcagcagccgcgggcccttgcttcccaggatggcacccaaaaagaagctgcagctgcc |
| gccgccacccacggacgaggaggaatactgggacagtcaggcagaggaggttttggacgaggaggaggaggacatgatggaaga |
| ctgggagagcctagacgaggaagcttccgaggtcgaagaggtgtcagacgaaacaccgtcaccctcggtcgcattcccctcgccggc |
| gccccagaaatcggcaaccggttccagcatggctacaacctccgctcctcaggcgccgccggcactgcccgttcgccgacccaaccg |
| tagatgggacaccactggaaccagggccggtaagtccaagcagccgccgccgttagcccaagagcaacaacagcgccaaggctac |
| cgctcatggcgcgggcacaagaacgccatagttgcttgcttgcaagactgtgggggcaacatctccttcgcccgccgctttcttctctacc |

TABLE 15-continued

| Ad5ACE2 with Plasmid Backbone |
| --- |
| atcacggcgtggccttccccgtaacatcctgcattactaccgtcatctctacagcccatactgcaccggcggcagcggcagcggcagc |
| aacagcagcggccacacagaagcaaaggcgaccggatagcaagactctgacaaagcccaagaaatccacagcggcggcagcagc |
| aggaggaggagcgctgcgtctggcgcccaacgaacccgtatcgacccgcgagcttagaaacaggatttttcccactctgtatgctatatt |
| tcaacagagcaggggccaagaacaagagctgaaaataaaaacaggtctctgcgatccctcacccgcagctgcctgtatcacaaaag |
| cgaagatcagcttcggcgcacgctggaagacgcggaggctctcttcagtaaatactgcgcgctgactcttaaggactagtttcgcgccct |
| ttctcaaatttaagcgcgaaaactacgtcatctccagcggccacacccggcgccagcacctgttgtcagcgccattatgagcaaggaaat |
| tcccacgccctacatgtggagttaccagccacaaatgggacttgcggctggagctgcccaagactactcaacccgaataaactacatga |
| gcgcgggaccccacatgatatcccgggtcaacggaatacgcgcccaccgaaaccgaattctcctggaacaggcggctattaccacca |
| cacctcgtaataaccttaatccccgtagttggcccgctgccctggtgtaccaggaaagtcccgctcccaccactgtggtacttcccagag |
| acgcccaggccgaagttcagatgactaactcaggggcgcagcttgcgggcggctttcgtcacagggtgcggtcgcccgggcagggt |
| ataactcacctgacaatcagagggcgaggtattcagctcaacgacgagtcggtgagctcctcgcttggtctccgtccggacgggacattt |
| cagatcggcggcgccggccgctcttcattcacgcctcgtcaggcaatcctaactctgcagacctcgtcctctgagccgcgctctggagg |
| cattggaactctgcaatttattgaggagtttgtgccatcggtctactttaaccccttctcgggacctcccggccactatccggatcaatttattc |
| ctaactttgacgcggtaaaggactcggcggacggctacgactgaatgttaagtggccaatgaggcctgacgctaataatagctggtcca |
| ctgtcgccgccacaagtgctttgcccgcgactccggtgagttttgctactttgaattgcccgaggatcatatcgagggcccggcgcacgg |
| cgtccggcttaccgcccagggagagcttgcccgtagcctgattcgggagtttacccagcgcccccctgctagttgagcgggacagggg |
| accctgtgttctcactgtgatttgcaactgtcctaaccttggattacatcaagatccagatcttctagacccgggagcggccgctgtcgacc |
| tgcaggatccgaattcgatatcactagtggtaccgatcttattccctttaactaataaaaaaaaataataaagcatcacttacttaaaatcagtt |
| agcaaatttctgtccagtttattcagcagcacctccttgccctcctcccagctctggtattgcagcttcctcctggctgcaaactttctccaca |
| atctaaagggaatgtcagtttcctcctgttcctgtccatccgcacccactatcttcatgttgttgcagatgaagcgcgcaagaccgtctgaa |
| gataccttcaaccccgtgtatccatatgacacggaaaccggtcctccaactgtgccttttcttactcctccctttgtatcccccaatgggtttc |
| aagagagtccccctggggtactctctttgcgcctatccgaacctctagttacctccaatggcatgcttgcgctcaaaatgggcaacggcct |
| ctctctggacgaggccggcaaccttacctcccaaaatgtaaccactgtgagcccacctctcaaaaaaaccaagtcaaacataaacctgg |
| aaatatctgcacccctcacagttacctcagaagccctaactgtggctgccgccgcacctctaatggtcgcgggcaacacactcaccatg |
| caatcacaggccccgctaaccgtgcacgactccaaacttagcattgccacccaaggacccctcacagtgtcagaaggaaagctagccc |
| tgcaaacatcaggcccctcaccaccaccgatagcagtacccttactatcactgcctcacccccctctaactactgccactggtagcttggg |
| cattgacttgaaagagcccatttatacacaaaatggaaaactaggactaaagtacggggctcctttgcatgtaacagacgacctaaacact |
| ttgaccgtagcaactggtccaggtgtgactattaataatacttccttgcaaactaaagttactggagccttgggttttgattcacaaggcaata |
| tgcaacttaatgtagcaggaggactaaggattgattctcaaaacagacgccttatacttgatgttagttatccgtttgatgctcaaaaccaac |
| taaatctaagactaggacagggccctctttttataaactcagcccacaacttggatattaactacaacaaaggcctttacttgtttacagcttc |
| aaacaattccaaaaagcttgaggttaacctaagcactgccaaggggttgatgtttgacgctacagccatagccattaatgcaggagatgg |
| gcttgaatttggttcacctaatgcaccaaacacaaatcccctcaaaacaaaaattggccatggcctagaatttgattcaaacaaggctatgg |
| ttcctaaactaggaactggccttagttttgacagcacaggtgccattacagtaggaaacaaaaataatgataagctaactttgtggaccaca |
| ccagctccatctcctaactgtagactaaatgcagagaaagatgctaaactcactttggtcttaacaaaatgtggcagtcaaatacttgctac |
| agtttcagttttggctgttaaaggcagtttggctccaatatctggaacagttcaaagtgctcatcttattataagatttgacgaaaatggagtg |
| ctactaaacaattccttcctggacccagaatattggaactttagaaatggagatcttactgaaggcacagcctatacaaacgctgttggattt |
| atgcctaacctatcagcttatccaaaatctcacggtaaaactgccaaaagtaacattgtcagtcaagtttacttaaacggagacaaaactaa |
| acctgtaacactaaccattacactaaacggtacacaggaaacaggagacacaactccaagtgcatactctatgtcattttcatgggactgg |
| tctggccacaactacattaatgaaatatttgccacatcctcttacactttttcatacattgcccaagaataaagaatcgtttgtgttatgtttcaac |

TABLE 15-continued

| Ad5ACE2 with Plasmid Backbone |
| --- |
| gtgtttatttttcaattgcagaaaatttcaagtcatttttcattcagtagtatagccccaccaccacatagcttatacagatcaccgtaccttaatc |
| aaactcacagaaccctagtattcaacctgccacctccctcccaacacacagagtacacagtcctttctccccggctggccttaaaaagcat |
| catatcatgggtaacagacatattcttaggtgttatattccacacggtttcctgtcgagccaaacgctcatcagtgatattaataaactccccg |
| ggcagctcacttaagttcatgtcgctgtccagctgctgagccacaggctgctgtccaacttgcggttgcttaacgggcggcgaaggaga |
| agtccacgcctacatgggggtagagtcataatcgtgcatcaggatagggcggtggtgctgcagcagcgcgcgaataaactgctgccg |
| ccgccgctccgtcctgcaggaatacaacatggcagtggtctcctcagcgatgattcgcaccgcccgcagcataaggcgccttgtcctcc |
| gggcacagcagcgcaccctgatctcacttaaatcagcacagtaactgcagcacagcaccacaatattgttcaaaatcccacagtgcaag |
| gcgctgtatccaaagctcatggggggaccacagaacccacgtggccatcataccacaagcgcaggtagattaagtggcgacccctc |
| ataaacacgctggacataaacattacctcttttggcatgttgtaattcaccacctcccggtaccatataaacctctgattaaacatggcgcca |
| tccaccaccatcctaaaccagctggccaaaacctgcccgccggctatacactgcagggaaccgggactggaacaatgacagtggaga |
| gcccaggactcgtaaccatggatcatcatgctcgtcatgatatcaatgttggcacaacacaggcacacgtgcatacacttcctcaggatta |
| caagctcctcccgcgttagaaccatatcccagggaacaacccattcctgaatcagcgtaaatcccacactgcagggaagacctcgcac |
| gtaactcacgttgtgcattgtcaaagtgttacattcgggcagcagcggatgatcctccagtatggtagcgcgggtttctgtctcaaaagga |
| ggtagacgatccctactgtacggagtgcgccgagacaaccgagatcgtgttggtcgtagtgtcatgccaaatggaacgccggacgtag |
| tcatatttcctgaagcaaaaccaggtgcgggcgtgacaaacagatctgcgtctccggtctcgccgcttagatcgctctgtgtagtagttgta |
| gtatatccactctctcaaagcatccaggcgccccctggcttcgggttctatgtaaactccttcatgcgccgctgccctgataacatccacca |
| ccgcagaataagccacacccagccaacctacacattcgttctgcgagtcacacacgggaggagcgggaagagctggaagaaccatg |
| tttttttttttattccaaaagattatccaaaacctcaaaatgaagatctattaagtgaacgcgctcccctccggtggcgtggtcaaactctaca |
| gccaaagaacagataatggcatttgtaagatgttgcacaatggcttccaaaaggcaaacggccctcacgtccaagtggacgtaaaggct |
| aaacccttcagggtgaatctcctctataaacattccagcaccttcaaccatgcccaaataattctcatctcgccaccttctcaatatatctcta |
| agcaaatcccgaatattaagtccggccattgtaaaaatctgctccagagcgccctccaccttcagcctcaagcagcgaatcatgattgca |
| aaaattcaggttcctcacagacctgtataagattcaaaagcggaacattaacaaaaataccgcgatcccgtaggtcccttcgcagggcca |
| gctgaacataatcgtgcaggtctgcacggaccagcgcggccacttccccgccaggaaccatgacaaaagaacccacactgattatgac |
| acgcatactcggagctatgctaaccagcgtagccccgatgtaagcttgttgcatgggcggcgatataaaatgcaaggtgctgctcaaaa |
| aatcaggcaaagcctcgcgcaaaaaagaaagcacatcgtagtcatgctcatgcagataaaggcaggtaagctccggaaccaccacag |
| aaaaagacaccatttttctctcaaacatgtctgcgggtttctgcataaacacaaaataaaataacaaaaaaacatttaaacattagaagcctg |
| tcttacaacaggaaaaacaacccttataagcataagacggactacggccatgccggcgtgaccgtaaaaaaactggtcaccgtgattaa |
| aaagcaccaccgacagctcctcggtcatgtccggagtcataatgtaagactcggtaaacacatcaggttgattcacatcggtcagtgcta |
| aaaagcgaccgaaatagcccgggggaatacatacccgcaggcgtagagacaacattacagcccccataggaggtataacaaaattaa |
| taggagagaaaaacacataaacacctgaaaaaccctcctgcctaggcaaaatagcaccctcccgctccagaacaacatacagcgcttc |
| cacagcggcagccataacagtcagccttaccagtaaaaaagaaaacctattaaaaaaacaccactcgacacggcaccagctcaatcag |
| tcacagtgtaaaaaagggccaagtgcagagcgagtatatataggactaaaaaatgacgtaacggttaaagtccacaaaaaacacccag |
| aaaaccgcacgcgaacctacgcccagaaacgaaagccaaaaaacccacaacttcctcaaatcgtcacttccgttttcccacgttacgta |
| acttcccattttaagaaaactacaattcccaacacatacaagttactccgccctaaaacctacgtcacccgccccgttcccacgccccgcg |
| ccacgtcacaaactccaccccctcattatcatattggcttcaatccaaaataaggtatattattgatgatgttaatttgggccattagacttgaa |
| gtcaagcggccgcttacaactggaccttgctggtacatagaactgattaactgaccatttaaatcataccaacatggtcaaataaaacgaa |
| aggctcagtcgaaagactgggcctttcgttttaatctgatcggcacgtaagaggttccaactttcaccataatgaaataagatcactaccgg |
| gcgtatttttttgagttatcgagattttcaggagctaaggaagctaaaatgagccatattcaacgggaaacgtcttgctcgaggccgcgatta |
| aattccaacatggatgctgatttatatgggtataaatgggctcgcgataatgtcgggcaatcaggtgcgacaatctatcgattgtatgggaa |

TABLE 15-continued

| Ad5ACE2 with Plasmid Backbone |
|---|
| gcccgatgcgccagagttgtttctgaaacatggcaaaggtagcgttgccaatgatgttacagatgagatggtcaggctaaactggctgac |
| ggaatttatgcctcttccgaccatcaagcattttatccgtactcctgatgatgcatggttactcaccactgcgatcccagggaaaacagcatt |
| ccaggtattagaagaatatcctgattcaggtgaaaatattgttgatgcgctggcagtgttcctgcgccggttgcattcgattcctgtttgtaatt |
| gtccttttaacggcgatcgcgtatttcgtctcgctcaggcgcaatcacgaatgaataacggtttggttggtgcgagtgattttgatgacgag |
| cgtaatggctggcctgttgaacaagtctggaaagaaatgcataaacttttgccattctcaccggattcagtcgtcactcatggtgatttctca |
| cttgataaccttatttttgacgaggggaaattaataggttgtattgatgttggacgagtcggaatcgcagaccgataccaggatcttgccatc |
| ctatggaactgcctcggtgagttttctccttcattacagaaacggctttttcaaaaatatggtattgataatcctgatatgaataaattgcagttt |
| cacttgatgctcgatgagtttttctaacctaggtgacagaagtcaaaagcctccggtcggaggcttttgactttctgctagatctgtttcaatg |
| cggtgaagggccaggcagctggggattatgtcgagacccggccagcatgttggttttatcgcatattcagcgttgtcgcgtttacccagg |
| taaaatggaagcagtgtatcgtctgcgtgaatgtgcaaatcaggaacgtaaccgtggtacatagatgcagtcccttgcgggtcgttccctt |
| caacgagtaggacgcggtgcccttgcaaggctaaccattgcgcctggtgtactgcagatgaggttttataaacccctcccttgtgtgacat |
| aacggaaagtacaaccgggtttttatcgtcaggtctttggtttgggttaccaaacacactccgcatatggctaatttggtcaattgtgtagcc |
| agcgcgacgttctactcggcccctcatctcaaaatcaggagccggtagacgaccagctttttccgcgtctctgatagcctgcggtgttacg |
| ccgatcaggtctgcaacttctgttataccccagcggcgagtaatacgacgcgcttccgggctgtcatcgccgaactgtgcgatggcaata |
| gcgcgcgtcatttcctgaccgcgattgatacagtctttcagcaaattaattaacgacatcctgtttcctctcaaacatgcccttatctttgtgttt |
| ttcatcatactttacgtttttaaagcaaagcaacataaaaaaagcaaagtgacttagaaaacgcaaagttaaggttcaaatcaatttttgatg |
| cgctacagaagctatttagcttcatctaagcgcaacggtattacttacgttggtatatttaaaacctaacttaatgattttaaatgataataaatc |
| ataccaattgctatcaaaagttaagcgaacatgctgattttcacgctgtttatacactttgaggcatctctatctcttccgtctctatattgaaac |
| acaatcaaagaacatcaatccatgtgacatcccccactatctaagaacaccataacagaacacaacataggaatgcaacattaatgtatc |
| aataattcggaacatatgcactatatcatatctcaattacggaacatatcagcacacaattgcccattatacgc |

TABLE 16

| Ad5UnituxinscFv with Plasmid Backbone |
|---|
| (SEQ ID NO: 16) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |

TABLE 16-continued

| Ad5UnituxinscFv with Plasmid Backbone |
|---|
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |

TABLE 16-continued

| Ad5UnituxinscFv with Plasmid Backbone |
| --- |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttcgggtcgtttctgg |
| tcgccagccagatggatgccccggtggcgaaaccctctgcagtcgcaatttttgcgccccctgcaggtcgccaataacaaagcatgca |
| ccgacgaaatcaccgttagtgatggcgctggtctggaacttgccaccattcagatcgatacgttgccagccaacaatccgcccgtctttc |
| ttccgtccaggtgggacagaggtatcgccatgtaagttgttggtccacggctccatttcgcactgtcgtgactggtcacgcgacgtatatc |

TABLE 16-continued

| Ad5UnituxinscFv with Plasmid Backbone |
|---|
| acaagcgccaaatacgtcacgaattccctttttttaccgcataaggccaggagccatcttcagctggcgaatgttcccaggcgcgatggaa |
| agccaaccatccaagcaggcgttcctgctccatctgattgtttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccacg |
| cgtggagctagttattaatagtaatcaattacggggtcattagttcatagcccatatatggagttccgcgttacataacttacggtaaatggc |
| ccgcctggctgaccgcccaacgacccccgcccattgacgtcaataatgacgtatgttcccatagtaacgtcaatagggactttccattga |
| cgtcaatgggtggagtatttacggtaaactgcccacttggcagtacatcaagtgtatcatatgccaagtacgccccctattgacgtcaatga |
| cggtaaatggcccgcctggcattatgcccagtacatgaccttatgggactttcctacttggcagtacatctacgtattagtcatcgctattac |
| catggtgatgcggttttggcagtacatcaatgggcgtggatagcggtttgactcacggggatttccaagtctccaccccattgacgtcaat |
| gggagtttgttttgcaccaaaatcaacgggactttccaaaatgtcgtaacaactccgccccattgacgcaaatgggcggtaggcgtgtac |
| ggtgggaggtctatataagcagagctcgtttagtgaaccgtcagatcgcctggagacgccatccacgctgttttgacctccatagaagac |
| accgggaccgatccagcctccgcggattcgaatcccggccgggaacggtgcattggaacgcggattccccgtgccaagagtgacgta |
| agtaccgcctatagagtctataggcccacaaaaaatgctttcttcttttaatatactttttttgtttatcttatttctaatactttccctaatctctttcttt |
| cagggcaataatgatacaatgtatcatgcctctttgcaccattctaaagaataacagtgataatttctgggttaaggcaatagcaatatttctg |
| catataaatatttctgcatataaattgtaactgatgtaagaggtttcatattgctaatagcagctacaatccagctaccattctgcttttattttatg |
| gttgggataaggctggattattctgagtccaagctaggcccttttgctaatcatgttcatacctcttatcttcctcccacagctcctgggcaac |
| gtgctggtctgtgtgctggcccatcactttggcaaagctcctgggcaacgtgctggttattgtgctgtctcatcattttggcaaagaattccg |

TABLE 16-continued

| Ad5UnituxinscFv with Plasmid Backbone |
|---|
| ctgcgactcggcggagtcccggcggcgcgtccttgttctaacccggcgcgccagcttggcaatccggtactgttggtaaagccaccat |
| ggaactgggactgtcatggatcttcttgctggctatcctgaagggagtgcagtgtgaagttcagctgctgcagagcggacccgaactgg |
| aaaaacctggcgcctccgtgatgatcagctgcaaggcctctggcagctccttcaccggctacaacatgaactgggtccgacagaacatc |
| ggcaagagcctggaatggatcggcgccatcgatccttactacggcggcaccagctacaaccagaagttcaagggcagagccacactg |
| accgtggacaagagcagcagcacagcctacatgcatctgaagtccctgaccagcgaggacagcgccgtgtactactgtgtgtccggc |
| atggaatactggggccagggcacaagcgtgacagtctcttctggcggcggtggatctggcggaggcggaagtggtggcggcggatc |
| tgatgtggtcatgacacagacccctctgagcctgcctgtgtctctgggagatcaggccagcatcagctgtagaagcagccagagcctgg |
| tgcacagaaacggcaacacctacctgcactggtatctgcagaagcccggccagtctcctaagctgctgatccacaaggtgtccaacag |
| attcagcggcgtgcccgacagattctctggctctggaagcggcaccgacttcaccctgaagattagcagagtggaagccgaggacctg |
| ggcgtgtacttctgtagccagagcacacacgtgccacctctgacatttggcgctggcaccaagctggaactggagcctaagagctgtga |
| caagacacacacatgtcctccttgtcctgctcctgaattacttggaggaccttctgtgttcctgttccctcctaaacctaaggacaccctgat |
| gatcagcagaacacctgaagtgacctgtgtggtggttgatgtgtctcatgaggatcctgaggtgaagttcaactggtacgtggatggagt |
| ggaggtgcataatgccaagacaaagcctagagaggagcagtacaacagcacctatagagtggtgtctgtgctgacagtgctgcatcaa |
| gattggctgaatggcaaggagtacaagtgcaaggtgagcaataaggctctgcctgctcctatcgagaagacaatctctaaggccaagg |
| gacagcctagagaacctcaggtttacacacttcctcctagcagagatgagctgaccaagaatcaggtgagcctgacatgtctggtgaag |
| ggattttaccctagcgatatcgctgtggaatgggagtctaatggacagcctgagaacaactacaagaccacacctcctgtgctggattctg |
| atggctctttcttcctgtacagcaagctgacagtggacaagtctagatggcaacagggcaatgtgttcagctgttctgtgatgcatgaggct |
| ctgcacaaccactatacccagaaaagcctgagcctgtctcctggaaagtagtaataattctagagtcggggcggccggccgcttcgagc |
| agacatgataagatacattgatgagtttggacaaaccacaactagaatgcagtgaaaaaaatgctttatttgtgaaatttgtgatgctattgct |
| ttatttgtaaccattataagctgcaataaacaagttaacaacaacaattgcattcattttatgtttcaggttcagggggaggtgtgggaggtttt |
| ttaaagcaagtaaaacctctacaaatgtggtaaaatcgataaggatccgaattcgatatcactagtggtaccagtactgaaatgtgtgggc |
| gtggcttaagggtgggaaagaatatataaggtgggggtcttatgtagttttgtatctgttttgcagcagccgccgccgccatgagcaccaa |
| ctcgtttgatggaagcattgtgagctcatatttgacaacgcgcatgcccccatgggccggggtgcgtcagaatgtgatgggctccagcat |
| tgatggtcgccccgtcctgcccgcaaactctactaccttgacctacgagaccgtgtctggaacgccgttggagactgcagcctccgccg |
| ccgcttcagccgctgcagccaccgcccgcgggattgtgactgactttgctttcctgagcccgcttgcaagcagtgcagcttcccgttcatc |
| cgcccgcgatgacaagttgacggctcttttggcacaattggattctttgacccgggaacttaatgtcgtttctcagcagctgttggatctgcg |
| ccagcaggtttctgccctgaaggcttcctcccctcccaatgcggtttaacggtccgggccagagtggccaacataaataaaaaaccaga |
| ctctgtttggatttggatcaagcaagtgtcttgctgtctttatttaggggttttgcgcgcgcggtaggcccgggaccagcggtctcggtcgtt |
| gagggtcctgtgtatttttttccaggacgtggtaaaggtgactctggatgttcagatacatgggcataagcccgtctctggggtggaggtag |
| caccactgcagagcttcatgctgcggggtggtgttgtagatgatccagtcgtagcaggagcgctgggcgtggtgcctaaaaatgtctttc |
| agtagcaagctgattgccaggggcaggcccttggtgtaagtgtttacaaagcggttaagctgggatgggtgcatacgtggggatatgag |
| atgcatcttggactgtatttttaggttggctatgttcccagccatatccctccggggattcatgttgtgcagaaccaccagcacagtgtatcc |
| ggtgcacttgggaaatttgtcatgtagcttagaaggaaatgcgtggaagaacttggagacgcccttgtgacctccaagattttccatgcatt |
| cgtccataatgatggcaatgggcccacgggcggcggcctgggcgaagatatttctgggatcactaacgtcatagttgtgttccaggatg |
| agatcgtcataggccatttttacaaagcgcgggcggagggtgccagactgcggtataatggttccatccggcccaggggtagttacc |
| ctcacagatttgcatttcccacgctttgagttcagatgggggatcatgtctacctgcggggcgatgaagaaaacggtttccggggtagg |
| ggagatcagctgggaagaaagcaggttcctgagcagctgcgacttaccgcagccggtgggcccgtaaatcacacctattaccggctg |
| caactggtagttaagagagctgcagctgccgtcatccctgagcagggggccacttcgttaagcatgtccctgactcgcatgttttccctg |
| accaaatccgccagaaggcgctcgccgcccagcgatagcagttcttgcaaggaagcaaagtttttcaacggtttgagaccgtccgccgt |

TABLE 16-continued

| Ad5UnituxinscFv with Plasmid Backbone |
|---|
| aggcatgcttttgagcgtttgaccaagcagttccaggcggtcccacagctcggtcacctgctctacggcatctcgatccagcatatctcct |
| cgtttcgcgggttggggcggctttcgctgtacggcagtagtcggtgctcgtccagacgggccagggtcatgtctttccacgggcgcagg |
| gtcctcgtcagcgtagtctgggtcacggtgaaggggtgcgctccgggctgcgcgctggccagggtgcgcttgaggctggtcctgctgg |
| tgctgaagcgctgccggtcttcgccctgcgcgtcggccaggtagcatttgaccatggtgtcatagtccagcccctccgcggcgtggccc |
| ttggcgcgcagcttgcccttggaggaggcgccgcacgaggggcagtgcagacttttgagggcgtagagcttgggcgcgagaaatac |
| cgattccggggagtaggcatccgcgccgcaggccccgcagacggtctcgcattccacgagccaggtgagctctggccgttcggggtc |
| aaaaaccaggtttcccccatgcttttttgatgcgtttcttacctctggtttccatgagccggtgtccacgctcggtgacgaaaaggctgtccgt |
| gtccccgtatacagacttgagaggcctgtcctcgagcggtgttccgcggtcctcctcgtatagaaactcggaccactctgagacaaagg |
| ctcgcgtccaggccagcacgaaggaggctaagtgggaggggtagcggtcgttgtccactagggggtccactcgctccagggtgtgaa |
| gacacatgtcgccctcttcggcatcaaggaaggtgattggtttgtaggtgtaggccacgtgaccgggtgttcctgaaggggggctataaa |
| agggggtgggggcgcgttcgtcctcactctcttccgcatcgctgtctgcgagggccagctgttggggtgagtactccctctgaaaagcg |
| ggcatgacttctgcgctaagattgtcagtttccaaaaacgaggaggatttgatattcacctggcccgcggtgatgcctttgagggtggccg |
| catccatctggtcagaaaagacaatctttttgttgtcaagcttggtggcaaacgacccgtagagggcgttggacagcaacttggcgatgg |
| agcgcagggtttggtttttgtcgcgatcggcgcgctccttggccgcgatgtttagctgcacgtattcgcgcgcaacgcaccgccattcgg |
| gaaagacggtggtgcgctcgtcgggcaccaggtgcacgcgccaaccgcggttgtgcagggtgacaaggtcaacgctggtggctacc |
| tctccgcgtaggcgctcgttggtccagcagaggcggccgcccttgcgcgagcagaatggcggtagggggtctagctgcgtctcgtcc |
| ggggggtctgcgtccacggtaaagaccccgggcagcaggcgcgcgtcgaagtagtctatcttgcatccttgcaagtctagcgcctgct |
| gccatgcgcgggcggcaagcgcgcgctcgtatgggttgagtgggggaccccatggcatggggtgggtgagcgcggaggcgtacat |
| gccgcaaatgtcgtaaacgtagaggggctctctgagtattccaagatatgtagggtagcatcttccaccgcggatgctggcgcgcacgt |
| aatcgtatagttcgtgcgagggagcgaggaggtcgggaccgaggttgctacgggcgggctgctctgctcggaagactatctgcctgaa |
| gatggcatgtgagttggatgatatggttggacgctggaagacgttgaagctggcgtctgtgagacctaccgcgtcacgcacgaaggag |
| gcgtaggagtcgcgcagcttgttgaccagctcggcggtgacctgcacgtctagggcgcagtagtccagggtttccttgatgatgtcatac |
| ttatcctgtcccttttttttccacagctcgcggttgaggacaaactcttcgcggtctttccagtactcttggatcggaaacccgtcggcctccg |
| aacggtaagagcctagcatgtagaactggttgacggcctggtaggcgcagcatcccttttctacgggtagcgcgtatgcctgcgcggcc |
| ttccggagcgaggtgtgggtgagcgcaaaggtgtccctgaccatgactttgaggtactggtatttgaagtcagtgtcgtcgcatccgccc |
| tgctcccagagcaaaaagtccgtgcgctttttggaacgcggatttggcagggcgaaggtgacatcgttgaagagtatctttcccgcgcga |
| ggcataaagttgcgtgtgatgcggaagggtcccggcacctcggaacggttgttaattacctgggcggcgagcacgatctcgtcaaagc |
| cgttgatgttgtggcccacaatgtaaagttccaagaagcgcgggatgcccttgatggaaggcaattttttaagttcctcgtaggtgagctct |
| tcaggggagctgagcccgtgctctgaaagggcccagtctgcaagatgagggttggaagcgacgaatgagctccacaggtcacgggc |
| cattagcatttgcaggtggtcgcgaaaggtcctaaactggcgacctatggccattttttctggggtgatgcagtagaaggtaagcgggtct |
| tgttcccagcggtcccatccaaggttcgcggctaggtctcgcgcggcagtcactagaggctcatctccgccgaacttcatgaccagcat |
| gaagggcacgagctgcttcccaaaggcccccatccaagtataggtctctacatcgtaggtgacaaagagacgctcggtgcgaggatgc |
| gagccgatcgggaagaactggatctcccgccaccaattggaggagtggctattgatgtggtgaaagtagaagtccctgcgacgggcc |
| gaacactcgtgctggcttttgtaaaaacgtgcgcagtactggcagcggtgcacgggctgtacatcctgcacgaggttgacctgacgacc |
| gcgcacaaggaagcagagtgggaatttgagcccctcgcctggcgggtttggctggtggtcttctacttcggctgcttgtccttgaccgtct |
| ggctgctcgaggggagttacggtggatcggaccaccacgccgcgcgagcccaaagtccagatgtccgcgcgcggcggtcggagctt |
| gatgacaacatcgcgcagatgggagctgtccatggtctggagctcccgcggcgtcaggtcaggggggagctcctgcaggtttacctcg |
| catagacgggtcagggcgcgggctagatccaggtgatacctaatttccaggggctggttggtggcggcgtcgatggcttgcaagaggc |
| cgcatccccgcggcgcgactacggtaccgcgcggcgggggggccgcgggggtgtccttggatgatgcatctaaaagcggtgac |

TABLE 16-continued

| Ad5UnituxinscFv with Plasmid Backbone |
| --- |
| gcgggcgagccccggaggtaggggggggctccggacccgccgggagagggggcaggggcacgtcggcgccgcgcgcgggca |
| ggagctggtgctgcgcgcgtaggttgctggcgaacgcgacgacgcggcggttgatctcctgaatctggcgcctctgcgtgaagacga |
| cgggcccggtgagcttgaacctgaaagagagttcgacagaatcaatttcggtgtcgttgacggcggcctggcgcaaaatctcctgcac |
| gtctcctgagttgtcttgataggcgatctcggccatgaactgctcgatctcttcctcctggagatctccgcgtccggctcgctccacggtgg |
| cggcgaggtcgttggaaatgcgggccatgagctgcgagaaggcgttgaggcctccctcgttccagacgcggctgtagaccacgcccc |
| cttcggcatcgcgggcgcgcatgaccacctgcgcgagattgagctccacgtgccgggcgaagacggcgtagtttcgcaggcgctgaa |
| agaggtagttgagggtggtggcggtgtgttctgccacgaagaagtacataacccagcgtcgcaacgtggattcgttgatatcccccaag |
| gcctcaaggcgctccatggcctcgtagaagtccacggcgaagttgaaaaactgggagttgcgcgccgacacggttaactcctcctcca |
| gaagacggatgagctcggcgacagtgtcgcgcacctcgcgctcaaaggctacaggggcctcttcttcttcttcaatctcctcttccataag |
| ggcctccccttcttcttcttctggcggcggtgggggaggggggacacggcggcgacgacggcgcaccgggaggcggtcgacaaag |
| cgctcgatcatctccccgcggcgacggcgcatggtctcggtgacggcgcggccgttctcgcgggggcgcagttggaagacgccgcc |
| cgtcatgtcccggttatgggttggcgggggggctgccatgcggcagggatacggcgctaacgatgcatctcaacaattgttgtgtaggta |
| ctccgccgccgagggacctgagcgagtccgcatcgaccggatcggaaaacctctcgagaaaggcgtctaaccagtcacagtcgcaa |
| ggtaggctgagcaccgtggcgggcggcagcgggcggcggtcggggttgtttctggcggaggtgctgctgatgatgtaattaaagtag |
| gcggtcttgagacggcggatggtcgacagaagcaccatgtccttgggtccggcctgctgaatgcgcaggcggtcggccatgccccag |
| gcttcgttttgacatcggcgcaggtctttgtagtagtcttgcatgagcctttctaccggcacttcttcttctccttcctcttgtcctgcatctcttg |
| catctatcgctgcggcggcggcggagtttggccgtaggtggcgccctcttcctcccatgcgtgtgaccccgaagcccctcatcggctga |
| agcagggctaggtcggcgacaacgcgctcggctaatatggcctgctgcacctgcgtgagggtagactggaagtcatccatgtccacaa |
| agcggtggtatgcgcccgtgttgatggtgtaagtgcagttggccataacggaccagttaacggtctggtgacccggctgcgagagctcg |
| gtgtacctgagacgcgagtaagccctcgagtcaaatacgtagtcgttgcaagtccgcaccaggtactggtatcccaccaaaaagtgcgg |
| cggcggctggcggtagaggggccagcgtagggtggccggggctccgggggcgagatcttccaacataaggcgatgatatccgtag |
| atgtacctggacatccaggtgatgccggcggcggtggtggaggcgcgcggaaagtcgcggacgcggttccagatgttgcgcagcgg |
| caaaaagtgctccatggtcgggacgctctggccggtcaggcgcgcgcaatcgttgacgctctagaccgtgcaaaaggagagcctgta |
| agcgggcactcttccgtggtctggtggataaattcgcaagggtatcatggcggacgaccggggttcgagccccgtatccggccgtccg |
| ccgtgatccatgcggttaccgcccgcgtgtcgaacccaggtgtgcgacgtcagacaacgggggagtgctccttttggcttccttccagg |
| cgcggcggctgctgcgctagcttttttggccactggccgcgcgcagcgtaagcggttaggctggaaagcgaaagcattaagtggctcg |
| ctccctgtagccggagggttattttccaagggttgagtcgcgggacccccggttcgagtctcggaccggccggactgcggcgaacgg |
| gggtttgcctccccgtcatgcaagaccccgcttgcaaattcctccggaaacagggacgagcccctttttttgcttttcccagatgcatccggt |
| gctgcggcagatgcgcccccctcctcagcagcggcaagagcaagagcagcggcagacatgcagggcaccctcccctcctcctaccg |
| cgtcaggaggggcgacatccgcggttgacgcggcagcagatggtgattacgaaccccgcggcgccgggcccggcactacctgga |
| cttggaggagggcgagggcctggcgcggctaggagcgccctctcctgagcggcacccaagggtgcagctgaagcgtgatacgcgt |
| gaggcgtacgtgccgcggcagaacctgtttcgcgaccgcgagggagaggagcccgaggagatgcgggatcgaaagttccacgcag |
| ggcgcgagctgcggcatggcctgaatcgcgagcggttgctgcgcgaggaggactttgagcccgacgcgcgaaccgggattagtccc |
| gcgcgcgcacacgtggcggccgccgacctggtaaccgcatacgagcagacggtgaaccaggagattaactttcaaaaaagctttaac |
| aaccacgtgcgtacgcttgtggcgcgcgaggaggtggctataggactgatgcatctgtgggactttgtaagcgcgctggagcaaaacc |
| caaatagcaagccgctcatggcgcagctgttccttatagtgcagcacagcagggacaacgaggcattcagggatgcgctgctaaacat |
| agtagagcccgagggccgctggctgctcgatttgataaacatcctgcagagcatagtggtgcaggagcgcagcttgagcctggctgac |
| aaggtggccgccatcaactattccatgcttagcctgggcaagttttacgcccgcaagatataccatacccttacgttcccatagacaagg |
| aggtaaagatcgaggggttctacatgcgcatggcgctgaaggtgcttaccttgagcgacgacctgggcgtttatcgcaacgagcgcatc |

TABLE 16-continued

| Ad5UnituxinscFv with Plasmid Backbone |
|---|
| cacaaggccgtgagcgtgagccggcggcgcgagctcagcgaccgcgagctgatgcacagcctgcaaagggccctggctggcacg |
| ggcagcggcgatagagaggccgagtcctactttgacgcgggcgctgacctgcgctgggccccaagccgacgcgccctggaggcag |
| ctggggccggacctgggctggcggtggcacccgcgcgcgctggcaacgtcggcggcgtggaggaatatgacgaggacgatgagta |
| cgagccagaggacggcgagtactaagcggtgatgtttctgatcagatgatgcaagacgcaacggacccggcggtgcgggcggcgct |
| gcagagccagccgtccggccttaactccacggacgactggcgccaggtcatggaccgcatcatgtcgctgactgcgcgcaatcctga |
| cgcgttccggcagcagccgcaggccaaccggctctccgcaattctggaagcggtggtcccggcgcgcgcaaaccccacgcacgag |
| aaggtgctggcgatcgtaaacgcgctggccgaaaacagggccatccggcccgacgaggccggcctggtctacgacgcgctgcttca |
| gcgcgtggctcgttacaacagcggcaacgtgcagaccaacctggaccggctggtgggggatgtgcgcgaggccgtggcgcagcgt |
| gagcgcgcgcagcagcagggcaacctgggctccatggttgcactaaacgccttcctgagtacacagcccgccaacgtgccgcgggg |
| acaggaggactacaccaactttgtgagcgcactgcggctaatggtgactgagacaccgcaaagtgaggtgtaccagtctgggccaga |
| ctatttttttccagaccagtagacaaggcctgcagaccgtaaacctgagccaggctttcaaaaacttgcaggggctgtgggggtgcggg |
| ctcccacaggcgaccgcgcgaccgtgtctagcttgctgacgcccaactcgcgcctgttgctgctgctaatagcgcccttcacggacagt |
| ggcagcgtgtcccgggacacatacctaggtcacttgctgacactgtaccgcgaggccataggtcaggcgcatgtggacgagcatacttt |
| ccaggagattacaagtgtcagccgcgcgctggggcaggaggacacgggcagcctggaggcaaccctaaactacctgctgaccaacc |
| ggcggcagaagatcccctcgttgcacagtttaaacagcgaggaggagcgcattttgcgctacgtgcagcagagcgtgagccttaacct |
| gatgcgcgacggggtaacgcccagcgtggcgctggacatgaccgcgcgcaacatggaaccgggcatgtatgcctcaaaccggccgt |
| ttatcaaccgcctaatggactacttgcatcgcgcggccgccgtgaaccccgagtatttcaccaatgccatcttgaacccgcactggctac |
| cgcccccctggtttctacaccgggggattcgaggtgcccgagggtaacgatggattcctctgggacgacatagacgacagcgtgttttcc |
| ccgcaaccgcagaccctgctagagttgcaacagcgcgagcaggcagaggcggcgctgcgaaaggaaagcttccgcaggccaagc |
| agcttgtccgatctaggcgctgcggccccgcggtcagatgctagtagcccatttccaagcttgatagggtctcttaccagcactcgcacc |
| acccgcccgcgcctgctgggcgaggaggagtacctaaacaactcgctgctgcagccgcagcgcgaaaaaaacctgcctccggcattt |
| cccaacaacgggatagagagcctagtggacaagatgagtagatggaagacgtacgcgcaggagcacagggacgtgccaggcccg |
| cgcccgcccacccgtcgtcaaaggcacgaccgtcagcggggtctggtgtgggaggacgatgactcggcagacgacagcagcgtcct |
| ggatttgggagggagtggcaacccgtttgcgcaccttcgccccaggctggggagaatgttttaaaaaaaaaaaaaagcatgatgcaaa |
| ataaaaaactcaccaaggccatggcaccgagcgttggttttcttgtattccccttagtatgcggcgcgcggcgatgtatgaggaaggtcct |
| cctccctcctacgagagtgtggtgagcgcggcgccagtggcggcggcgctgggttctcccttcgatgctcccctggacccgccgtttgt |
| gcctccgcggtacctgcggcctaccggggggagaaacagcatccgttactctgagttggcacccctattcgacaccacccgtgtgtacc |
| tggtggacaacaagtcaacggatgtggcatccctgaactaccagaacgaccacagcaactttctgaccacggtcattcaaaacaatgac |
| tacagcccgggggaggcaagcacacagaccatcaatcttgacgaccggtcgcactgggggcgacctgaaaaccatcctgcatac |
| caacatgccaaatgtgaacgagttcatgtttaccaataagtttaaggcgcgggtgatggtgtcgcgcttgcctactaaggacaatcaggtg |
| gagctgaaatacgagtgggtggagttcacgctgcccgagggcaactactccgagaccatgaccatagaccttatgaacaacgcgatcg |
| tggagcactacttgaaagtgggcagacagaacggggttctggaaagcgacatcggggtaaagtttgacacccgcaacttcagactggg |
| gtttgaccccgtcactggtcttgtcatgcctggggtatatacaaacgaagccttccatccagacatcattttgctgccaggatgcggggtg |
| gacttcacccacagccgcctgagcaacttgttgggcatccgcaagcggcaacccttccaggagggctttaggatcacctacgatgatct |
| ggagggtggtaacattcccgcactgttggatgtggacgcctaccaggcgagcttgaaagatgacaccgaacagggcgggggtggcg |
| caggcggcagcaacagcagtggcagcggcgcggaagagaactccaacgcggcagccgcggcaatgcagccggtggaggacatg |
| aacgatcatgccattcgcggcgacacctttgccacacgggctgaggagaagcgcgctgaggccgaagcagcggccgaagctgccg |
| cccccgctgcgcaacccgaggtcgagaagcctcagaagaaaccggtgatcaaacccctgacagaggacagcaagaaacgcagtta |
| caacctaataagcaatgacagcaccttcacccagtaccgcagctggtaccttgcatacaactacggcgaccctcagaccggaatccgct |

TABLE 16-continued

| Ad5UnituxinscFv with Plasmid Backbone |
|---|
| catggaccctgctttgcactcctgacgtaacctgcggctcggagcaggtctactggtcgttgccagacatgatgcaagaccccgtgacct |
| tccgctccacgcgccagatcagcaactttccggtggtgggcgccgagctgttgcccgtgcactccaagagcttctacaacgaccaggc |
| cgtctactcccaactcatccgccagtttacctctctgacccacgtgttcaatcgctttcccgagaaccagattttggcgcgcccgccagcc |
| cccaccatcaccaccgtcagtgaaaacgttcctgctctcacagatcacgggacgctaccgctgcgcaacagcatcggaggagtccagc |
| gagtgaccattactgacgccagacgccgcacctgcccctacgtttacaaggccctgggcatagtctcgccgcgcgtcctatcgagccg |
| cactttttgagcaagcatgtccatccttatatcgcccagcaataacacaggctggggcctgcgcttcccaagcaagatgtttggcggggc |
| caagaagcgctccgaccaacacccagtgcgcgtgcgcgggcactaccgcgcgccctggggcgcgcacaaacgcggccgcactgg |
| gcgcaccaccgtcgatgacgccatcgacgcggtggtggaggaggcgcgcaactacacgcccacgccgccaccagtgtccacagtg |
| gacgcggccattcagaccgtggtgcgcggagcccggcgctatgctaaaatgaagagacggcggaggcgcgtagcacgtcgccacc |
| gccgccgacccggcactgccgcccaacgcgcgggggcccctgcttaaccgcgcacgtcgcaccggccgacgggggccatgc |
| gagcagctcgaaggctggccgcgggtattgtcactgtgcccccaggtccaggcgacgagcggccgccgcagcagccgcggccat |
| tagtgctatgactcagggtcgcaggggcaacgtgtattgggtgcgcgactcggttagcggcctgcgcgtgcccgtgcgcacccgcccc |
| ccgcgcaactagattgcaagaaaaaactacttagactcgtactgttgtatgtatccagcggcggcggcgcgcaacgaagctatgtccaa |
| gcgcaaaatcaaagaagagatgctccaggtcatcgcgccggagatctatggcccccgaagaaggaagagcaggattacaagcccc |
| gaaagctaaagcgggtcaaaaagaaaaagaaagatgatgatgatgaacttgacgacgaggtggaactgctgcacgctaccgcgccca |
| ggcgacgggtacagtggaaaggtcgacgcgtaaaacgtgttttgcgacccggcaccaccgtagtctttacgcccggtgagcgctccac |
| ccgcacctacaagcgcgtgtatgatgaggtgtacggcgacgaggacctgcttgagcaggccaacgagcgcctcggggagtttgccta |
| cggaaagcggcataaggacatgctggcgttgccgctggacgagggcaacccaacacctagcctaaagcccgtaacactgcagcagg |
| tgctgcccgcgcttgcaccgtccgaagaaaagcgcggcctaaagcgcgagtctggtgacttggcacccaccgtgcagctgatggtac |
| ccaagcgccagcgactggaagatgtcttggaaaaaatgaccgtggaacctgggctggagcccgaggtccgcgtgcggccaatcaag |
| caggtggcgccgggactgggcgtgcagaccgtggacgttcagatacccactaccagtagcaccagtattgccaccgccacagaggg |
| catggagacacaaacgtccccggttgcctcagcggtggcggatgccgcggtgcaggcggtcgctgcggccgcgtccaagacctcta |
| cggaggtgcaaacggacccgtggatgtttcgcgtttcagccccccggcgcccgcgccgttcgaggaagtacggcgccgccagcgcg |
| ctactgcccgaatatgccctacatccttccattgcgcctacccccggctatcgtggctacacctaccgccccagaagacgagcaactacc |
| cgacgccgaaccaccactggaacccgccgccgccgtcgccgtcgccagcccgtgctggccccgatttccgtgcgcagggtggctcg |
| cgaaggaggcaggaccctggtgctgccaacagcgcgctaccaccccagcatcgtttaaaagccggtctttgtggttcttgcagatatgg |
| ccctcacctgccgcctccgtttcccggtgccgggattccgaggaagaatgcaccgtaggaggggcatggccggccacggcctgacg |
| ggcggcatgcgtcgtgcgcaccaccggcggcggcgcgcgtcgcaccgtcgcatgcgcggcggtatcctgcccctccttattccactg |
| atcgccgcggcgattggcgccgtgcccggaattgcatccgtggccttgcaggcgcagagacactgattaaaaacaagttgcatgtgga |
| aaaatcaaaataaaaagtctggactctcacgctcgcttggtcctgtaactattttgtagaatggaagacatcaactttgcgtctctggccccg |
| cgacacggctcgcgcccgttcatgggaaactggcaagatatcggcaccagcaatatgagcggtggcgccttcagctggggctcgctgt |
| ggagcggcattaaaaatttcggttccaccgttaagaactatggcagcaaggcctggaacagcagcacaggccagatgctgagggataa |
| gttgaaagagcaaaatttccaacaaaaggtggtagatggcctggcctctggcattagcggggtggtggacctggccaaccaggcagtg |
| caaaataagattaacagtaagcttgatccccgccctcccgtagaggagcctccaccggccgtggagacagtgtctccagaggggcgtg |
| gcgaaaagcgtccgcgccccgacagggaagaaactctggtgacgcaaatagacgagcctccctcgtacgaggaggcactaaagca |
| aggcctgcccaccacccgtcccatcgcgcccatggctaccggagtgctgggccagcacacacccgtaacgctggacctgcctccccc |
| cgccgacacccagcagaaacctgtgctgccaggcccgaccgccgttgttgtaacccgtcctagccgcgcgtccctgcgccgcgccgc |
| cagcggtccgcgatcgttgcggcccgtagccagtggcaactggcaaagcacactgaacagcatcgtgggtctgggggtgcaatccct |
| gaagcgccgacgatgcttctgaatagctaacgtgtcgtatgtgtgtcatgtatgcgtccatgtcgccgccagaggagctgctgagccgcc |

TABLE 16-continued

| Ad5UnituxinscFv with Plasmid Backbone |
|---|
| gcgcgcccgctttccaagatggctaccccttcgatgatgccgcagtggtcttacatgcacatctcgggccaggacgcctcggagtacct |
| gagccccgggctggtgcagtttgcccgcgccaccgagacgtacttcagcctgaataacaagtttagaaccccacggtggcgcctacg |
| cacgacgtgaccacagaccggtcccagcgtttgacgctgcggttcatccctgtggaccgtgaggatactgcgtactcgtacaaggcgc |
| ggttcaccctagctgtgggtgataaccgtgtgctggacatggcttccacgtactttgacatccgcggcgtgctggacaggggccctacttt |
| taagccctactctggcactgcctacaacgccctggctcccaagggtgccccaaatccttgcgaatgggatgaagctgctactgctcttga |
| aataaacctagaagaagaggacgatgacaacgaagacgaagtagacgagcaagctgagcagcaaaaaactcacgtatttgggcagg |
| cgccttattctggtataaatattacaaaggagggtattcaaataggtgtcgaaggtcaaacacctaaatatgccgataaaacatttcaacct |
| gaacctcaaataggagaatctcagtggtacgaaacagaaattaatcatgcagctgggagagtcctaaaaaagactaccccaatgaaacc |
| atgttacggttcatatgcaaaacccacaaatgaaaatggagggcaaggcattcttgtaaagcaacaaaatggaaagctagaaagtcaag |
| tggaaatgcaatttttctcaactactgaggcagccgcaggcaatggtgataacttgactcctaaagtggtattgtacagtgaagatgtagat |
| atagaaaccccagacactcatatttcttacatgcccactattaaggaaggtaactcacgagaactaatgggccaacaatctatgcccaaca |
| ggcctaattacattgcttttagggacaattttattggtctaatgtattacaacagcacgggtaatatgggtgttctggcgggccaagcatcgc |
| agttgaatgctgttgtagatttgcaagacagaaacacagagctttcataccagcttttgcttgattccattggtgatagaaccaggtacttttct |
| atgtggaatcaggctgttgacagctatgatccagatgttagaattattgaaaatcatggaactgaagatgaacttccaaattactgctttcca |
| ctgggaggtgtgattaatacagagactcttaccaaggtaaaacctaaaacaggtcaggaaaatggatgggaaaaagatgctacagaatt |
| ttcagataaaaatgaaataagagttggaaataatttttgccatggaaatcaatctaaatgccaacctgtggagaaatttcctgtactccaacat |
| agcgctgtatttgcccgacaagctaaagtacagtccttccaacgtaaaaatttctgataacccaaacacctacgactacatgaacaagcga |
| gtggtggctcccgggctagtggactgctacattaaccttggagcacgctggtcccttgactatatggacaacgtcaacccatttaaccacc |
| accgcaatgctggcctgcgctaccgctcaatgttgctgggcaatggtcgctatgtgcccttccacatccaggtgcctcagaagttctttgc |
| cattaaaaacctccttctcctgccgggctcatacacctacgagtggaacttcaggaaggatgttaacatggttctgcagagctccctagga |
| aatgacctaagggttgacggagccagcattaagtttgatagcatttgcctttacgccaccttcttccccatggcccacaacaccgcctcca |
| cgcttgaggccatgcttagaaacgacaccaacgaccagtcctttaacgactatctctccgccgccaacatgctctaccctatacccgcca |
| acgctaccaacgtgcccatatccatcccctcccgcaactgggggctttccgcggctgggccttcacgcgccttaagactaaggaaacc |
| ccatcactgggctcgggctacgacccttattacacctactctggctctataccctacctagatggaaccttttacctcaaccacacctttaag |
| aaggtggccattacctttgactcttctgtcagctggcctggcaatgaccgcctgcttaccccccaacgagtttgaaattaagcgctcagttga |
| cggggagggttacaacgttgcccagtgtaacatgaccaaagactggttcctggtacaaatgctagctaactataacattggctaccaggg |
| cttctatatcccagagagctacaaggaccgcatgtactccttctttagaaacttccagcccatgagccgtcaggtggtggatgatactaaat |
| acaaggactaccaacaggtgggcatcctacaccaacacaacaactctggatttgttggctaccttgcccccaccatgcgcgaaggaca |
| ggcctaccctgctaacttcccctatccgcttataggcaagaccgcagttgacagcattacccagaaaaagtttctttgcgatcgcaccctttt |
| ggcgcatcccattctccagtaactttatgtccatgggcgcactcacagacctgggccaaaaccttctctacgccaactccgcccacgcgc |
| tagacatgacttttgaggtggatcccatggacgagcccacccttctttatgttttgtttgaagtctttgacgtggtccgtgtgcaccagccgc |
| accgcggcgtcatcgaaaccgtgtacctgcgcacgcccttctcggccggcaacgccacaacataaagaagcaagcaacatcaacaac |
| agctgccgccatgggctccagtgagcaggaactgaaagccattgtcaaagatcttggttgtgggccatatttttttgggcacctatgacaag |
| cgctttccaggctttgtttctccacacaagctcgcctgcgccatagtcaatacggccggtcgcgagactgggggcgtacactggatggc |
| ctttgcctggaacccgcactcaaaaacatgctacctctttgagccctttggcttttctgaccagcgactcaagcaggtttaccagtttgagta |
| cgagtcactcctgcgccgtagcgccattgcttcttcccccgaccgctgtataacgctggaaaagtccacccaaagcgtacaggggccca |
| actcggccgcctgtggactattctgctgcatgtttctccacgcctttgccaactggccccaaactcccatggatcacaaccccaccatgaa |
| ccttattaccggggtacccaactccatgctcaacagtccccaggtacagcccaccctgcgtcgcaaccaggaacagctctacagcttcct |
| ggagcgccactcgccctacttccgcagccacagtgcgcagattaggagcgccacttctttttgtcacttgaaaaacatgtaaaaataatgt |

TABLE 16-continued

| Ad5UnituxinscFv with Plasmid Backbone |
|---|
| actagagacactttcaataaaggcaaatgcttttatttgtacactctcgggtgattatttacccccacccttgccgtctgcgccgtttaaaaatc |
| aaaggggttctgccgcgcatcgctatgcgccactggcagggacacgttgcgatactggtgtttagtgctccacttaaactcaggcacaac |
| catccgcggcagctcggtgaagttttcactccacaggctgcgcaccatcaccaacgcgtttagcaggtcgggcgccgatatcttgaagt |
| cgcagttggggcctccgccctgcgcgcgcgagttgcgatacacagggttgcagcactggaacactatcagcgccgggggtgcacgc |
| tggccagcacgctcttgtcggagatcagatccgcgtccaggtcctccgcgttgctcagggcgaacggagtcaactttggtagctgccttc |
| ccaaaaagggcgcgtgcccaggctttgagttgcactcgcaccgtagtggcatcaaaaggtgaccgtgcccggtctgggcgttaggata |
| cagcgcctgcataaaagccttgatctgcttaaaagccacctgagcctttgcgccttcagagaagaacatgccgcaagacttgccggaaa |
| actgattggccggacacgcggcgtcgtgcacgcagcaccttgcgtcggtgttggagatctgcaccacatttcggccccaccggttcttc |
| acgatcttggccttgctagactgctccttcagcgcgcgctgcccgttttcgctcgtcacatccatttcaatcacgtgctccttatttatcataat |
| gcttccgtgtagacacttaagctcgccttcgatctcagcgcagcggtgcagccacaacgcgcagcccgtgggctcgtgatgcttgtagg |
| tcacctctgcaaacgactgcaggtacgcctgcaggaatcgccccatcatcgtcacaaaggtcttgttgctggtgaaggtcagctgcaacc |
| cgcggtgctcctcgttcagccaggtcttgcatacggccgccagagcttccacttggtcaggcagtagtttgaagttcgcctttagatcgtta |
| tccacgtggtacttgtccatcagcgcgcgcgcagcctccatgcccttctcccacgcagacacgatcggcacactcagcgggttcatcac |
| cgtaatttcactttccgcttcgctgggctcttcctcttcctcttgcgtccgcataccacgcgccactgggtcgtcttcattcagccgccgcact |
| gtgcgcttacctcctttgccatgcttgattagcaccggtgggttgctgaaacccaccatttgtagcgccacatcttctctttcttcctcgctgtc |
| cacgattacctctggtgatggcgggcgctcgggcttgggagaagggcgcttctttttcttcttgggcgcaatggccaaatccgccgccga |
| ggtcgatggccgcgggctgggtgtgcgcggcaccagcgcgtcttgtgatgagtcttcctcgtcctcggactcgatacgccgcctcatcc |
| gcttttttgggggcgcccggggaggcggcggcgacggggacggggacgacacgtcctccatggttgggggacgtcgcgccgcacc |
| gcgtccgcgctcgggggtggtttcgcgctgctcctcttcccgactggccatttccttctcctataggcagaaaaagatcatggagtcagtc |
| gagaagaaggacagcctaaccgccccctctgagttcgccaccaccgcctccaccgatgccgccaacgcgcctaccaccttccccgtc |
| gaggcacccccgcttgaggaggaggaagtgattatcgagcaggacccaggttttgtaagcgaagacgacgaggaccgctcagtacc |
| aacagaggataaaaagcaagaccaggacaacgcagaggcaaacgaggaacaagtcgggggggggacgaaaggcatggcgact |
| acctagatgtgggagacgacgtgctgttgaagcatctgcagcgccagtgcgccattatctgcgacgcgttgcaagagcgcagcgatgt |
| gcccctcgccatagcggatgtcagccttgcctacgaacgccacctattctcaccgcgcgtaccccccaaacgccaagaaaacggcaca |
| tgcgagcccaacccgcgcctcaacttctaccccgtatttgccgtgccagaggtgcttgccacctatcacatctttttccaaaactgcaagat |
| acccctatcctgccgtgccaaccgcagccgagcggacaagcagctggccttgcggcagggcgctgtcatacctgatatcgcctcgctc |
| aacgaagtgccaaaaatctttgagggtcttggacgcgacgagaagcgcgcggcaaacgctctgcaacaggaaaacagcgaaaatga |
| aagtcactctggagtgttggtggaactcgagggtgacaacgcgcgcctagccgtactaaaacgcagcatcgaggtcacccactttgcct |
| acccggcacttaacctaccccccaaggtcatgagcacagtcatgagtgagctgatcgtgcgccgtgcgcagcccctggagagggatg |
| caaatttgcaagaacaaacagaggagggcctacccgcagttggcgacgagcagctagcgcgctggcttcaaacgcgcgagcctgcc |
| gacttggaggagcgacgcaaactaatgatggccgcagtgctcgttaccgtggagcttgagtgcatgcagcggttctttgctgacccgga |
| gatgcagcgcaagctagaggaaacattgcactacacctttcgacagggctacgtacgccaggcctgcaagatctccaacgtggagctc |
| tgcaacctggtctcctaccttggaattttgcacgaaaaccgccttgggcaaaacgtgcttcattccacgctcaagggcgaggcgcgccg |
| cgactacgtccgcgactgcgtttacttatttctatgctacacctggcagacggccatgggcgtttggcagcagtgcttggaggagtgcaa |
| cctcaaggagctgcagaaactgctaaagcaaaacttgaaggacctatggacggccttcaacgagcgctccgtggccgcgcacctggc |
| ggacatcattttccccgaacgcctgcttaaaaccctgcaacagggtctgccagacttcaccagtcaaagcatgttgcagaactttaggaa |
| ctttatcctagagcgctcaggaatcttgcccgccacctgctgtgcacttcctagcgactttgtgcccattaagtaccgcgaatgccctccgc |
| cgctttggggccactgctaccttctgcagctagccaactaccttgcctaccactctgacataatggaagacgtgagcggtgacggtctact |
| ggagtgtcactgtcgctgcaacctatgcaccccgcaccgctccctggtttgcaattcgcagctgcttaacgaaagtcaaattatcggtacc |

TABLE 16-continued

| Ad5UnituxinscFv with Plasmid Backbone |
|---|
| tttgagctgcagggtccctcgcctgacgaaaagtccgcggctccggggttgaaactcactccggggctgtggacgtcggcttaccttcg |
| caaatttgtacctgaggactaccacgcccacgagattaggttctacgaagaccaatcccgcccgcctaatgcggagcttaccgcctgcg |
| tcattacccagggccacattcttggccaattgcaagccatcaacaaagcccgccaagagtttctgctacgaaagggacgggggtttact |
| tggacccccagtccggcgaggagctcaacccaatcccccgccgccgcagccctatcagcagcagccgcgggcccttgcttcccag |
| gatggcacccaaaaagaagctgcagctgccgccgccacccacggacgaggaggaatactgggacagtcaggcagaggaggttttg |
| gacgaggaggaggaggacatgatggaagactgggagagcctagacgaggaagcttccgaggtcgaagaggtgtcagacgaaaca |
| ccgtcaccctcggtcgcattcccctcgccggcgccccagaaatcggcaaccggttccagcatggctacaacctccgctcctcaggcgc |
| cgccggcactgcccgttcgccgacccaaccgtagatgggacaccactggaaccagggccggtaagtccaagcagccgccgccgtta |
| gcccaagagcaacaacagcgccaaggctaccgctcatggcgcgggcacaagaacgccatagttgcttgcttgcaagactgtggggg |
| caacatctccttcgcccgccgctttcttctctaccatcacggcgtggccttcccccgtaacatcctgcattactaccgtcatctctacagccc |
| atactgcaccggcggcagcggcagcggcagcaacagcagcggccacacagaagcaaaggcgaccggatagcaagactctgacaa |
| agcccaagaaatccacagcggcggcagcagcaggaggaggagcgctgcgtctggcgcccaacgaacccgtatcgacccgcgagc |
| ttagaaacaggatttttcccactctgtatgctatatttcaacagagcaggggccaagaacaagagctgaaaataaaaaacaggtctctgcg |
| atccctcacccgcagctgcctgtatcacaaaagcgaagatcagcttcggcgcacgctggaagacgcggaggctctcttcagtaaatact |
| gcgcgctgactcttaaggactagtttcgcgccctttctcaaatttaagcgcgaaaactacgtcatctccagcggccacacccggcgccag |
| cacctgttgtcagcgccattatgagcaaggaaattcccacgccctacatgtggagttaccagccacaaatgggacttgcggctggagct |
| gcccaagactactcaacccgaataaactacatgagcgcgggaccccacatgatatcccgggtcaacggaatacgcgcccaccgaaac |
| cgaattctcctggaacaggcggctattaccaccacacctcgtaataaccttaatccccgtagttggcccgctgccctggtgtaccaggaa |
| agtcccgctcccaccactgtggtacttcccagagacgcccaggccgaagttcagatgactaactcaggggcgcagcttgcgggcggct |
| ttcgtcacagggtgcggtcgcccgggcagggtataactcacctgacaatcagagggcgaggtattcagctcaacgacgagtcggtga |
| gctcctcgcttggtctccgtccggacgggacatttcagatcggcggcgccggccgctcttcattcacgcctcgtcaggcaatcctaactct |
| gcagacctcgtcctctgagccgcgctctggaggcattggaactctgcaatttattgaggagtttgtgccatcggtctactttaaccccttctc |
| gggacctcccggccactatccggatcaatttattcctaactttgacgcggtaaaggactcggcggacggctacgactgaatgttaagtgg |
| ccaatgaggcctgacgctaataatagctggtccactgtcgccgccacaagtgctttgcccgcgactccggtgagttttgctactttgaattg |
| cccgaggatcatatcgagggcccggcgcacggcgtccggcttaccgcccagggagagcttgcccgtagcctgattcgggagtttacc |
| cagcgcccccctgctagttgagcgggacaggggaccctgtgttctcactgtgatttgcaactgtcctaaccttggattacatcaagatccag |
| atcttctagacccgggagcggccgctgtcgacctgcaggatccgaattcgatatcactagtggtaccgatcttattccctttaactaataaa |
| aaaaaataataaagcatcacttacttaaaatcagttagcaaatttctgtccagtttattcagcagcacctccttgccctcctcccagctctggt |
| attgcagcttcctcctggctgcaaactttctccacaatctaaagggaatgtcagtttcctcctgttcctgtccatccgcacccactatcttcatg |
| ttgttgcagatgaagcgcgcaagaccgtctgaagataccttcaaccccgtgtatccatatgacacggaaaccggtcctccaactgtgcctt |
| ttcttactcctccctttgtatcccccaatgggtttcaagagagtccccctggggtactctctttgcgcctatccgaacctctagttacctccaat |
| ggcatgcttgcgctcaaaatgggcaacggcctctctctggacgaggccggcaaccttacctcccaaaatgtaaccactgtgagcccacc |
| tctcaaaaaaaccaagtcaaacataaacctggaaatatctgcacccctcacagttacctcagaagccctaactgtggctgccgccgcacc |
| tctaatggtcgcgggcaacacactcaccatgcaatcacaggccccgctaaccgtgcacgactccaaacttagcattgccacccaagga |
| cccctcacagtgtcagaaggaaagctagccctgcaaacatcaggcccccctcaccaccaccgatagcagtacccttactatcactgcctc |
| accccctctaactactgccactggtagcttgggcattgacttgaaagagcccatttatacacaaaatggaaaactaggactaaagtacgg |
| ggctcctttgcatgtaacagacgacctaaacactttgaccgtagcaactggtccaggtgtgactattaataatacttccttgcaaactaaagt |
| tactggagccttgggttttgattcacaaggcaatatgcaacttaatgtagcaggaggactaaggattgattctcaaaacagacgccttatac |
| ttgatgttagttatccgtttgatgctcaaaaccaactaaatctaagactaggacagggccctctttttataaactcagcccacaacttggatatt |

TABLE 16-continued

| Ad5UnituxinscFv with Plasmid Backbone |
|---|
| aactacaacaaaggcctttacttgtttacagcttcaaacaattccaaaaagcttgaggttaacctaagcactgccaaggggttgatgtttga |
| cgctacagccatagccattaatgcaggagatgggcttgaatttggttcacctaatgcaccaaacacaaatcccctcaaaacaaaaattgg |
| ccatggcctagaatttgattcaaacaaggctatggttcctaaactaggaactggccttagttttgacagcacaggtgccattacagtaggaa |
| acaaaaataatgataagctaactttgtggaccacaccagctccatctcctaactgtagactaaatgcagagaaagatgctaaactcactttg |
| gtcttaacaaaatgtggcagtcaaatacttgctacagtttcagttttggctgttaaaggcagtttggctccaatatctggaacagttcaaagtg |
| ctcatcttattataagatttgacgaaaatggagtgctactaaacaattccttcctggacccagaatattggaactttagaaatggagatcttac |
| tgaaggcacagcctatacaaacgctgttggatttatgcctaacctatcagcttatccaaaatctcacggtaaaactgccaaaagtaacattg |
| tcagtcaagtttacttaaacggagacaaaactaaacctgtaacactaaccattacactaaacggtacacaggaaacaggagacacaactc |
| caagtgcatactctatgtcattttcatgggactggtctggccacaactacattaatgaaatatttgccacatcctcttacactttttcatacattg |
| cccaagaataaagaatcgtttgtgttatgtttcaacgtgtttatttttcaattgcagaaaatttcaagtcatttttcattcagtagtatagccccac |
| caccacatagcttatacagatcaccgtaccttaatcaaactcacagaaccctagtattcaacctgccacctccctcccaacacacagagta |
| cacagtcctttctccccggctggccttaaaaagcatcatatcatgggtaacagacatattcttaggtgttatattccacacggtttcctgtcga |
| gccaaacgctcatcagtgatattaataaactccccgggcagctcacttaagttcatgtcgctgtccagctgctgagccacaggctgctgtc |
| caacttgcggttgcttaacgggcggcgaaggagaagtccacgcctacatgggggtagagtcataatcgtgcatcaggatagggcggtg |
| gtgctgcagcagcgcgcgaataaactgctgccgccgccgctccgtcctgcaggaatacaacatggcagtggtctcctcagcgatgatt |
| cgcaccgcccgcagcataaggcgccttgtcctccgggcacagcagcgcaccctgatctcacttaaatcagcacagtaactgcagcaca |
| gcaccacaatattgttcaaaatcccacagtgcaaggcgctgtatccaaagctcatgggggaccacagaacccacgtggccatcata |
| ccacaagcgcaggtagattaagtggcgacccctcataaacacgctggacataaacattacctcttttggcatgttgtaattcaccacctcc |
| cggtaccatataaacctctgattaaacatggcgccatccaccaccatcctaaaccagctggccaaaacctgcccgccggctatacactg |
| cagggaaccgggactggaacaatgacagtggagagcccaggactcgtaaccatggatcatcatgctcgtcatgatatcaatgttggca |
| caacacaggcacacgtgcatacacttcctcaggattacaagctcctcccgcgttagaaccatatcccagggaacaacccattcctgaatc |
| agcgtaaatcccacactgcagggaagacctcgcacgtaactcacgttgtgcattgtcaaagtgttacattcgggcagcagcggatgatc |
| ctccagtatggtagcgcgggtttctgtctcaaaaggaggtagacgatccctactgtacggagtgcgccgagacaaccgagatcgtgttg |
| gtcgtagtgtcatgccaaatggaacgccggacgtagtcatatttcctgaagcaaaaccaggtgcgggcgtgacaaacagatctgcgtct |
| ccggtctcgccgcttagatcgctctgtgtagtagttgtagtatatccactctctcaaagcatccaggcgccccctggcttcgggttctatgta |
| aactccttcatgcgccgctgccctgataacatccaccaccgcagaataagccacacccagccaacctacacattcgttctgcgagtcaca |
| cacgggaggagcgggaagagctggaagaaccatgtttttttttttattccaaaagattatccaaaacctcaaaatgaagatctattaagtg |
| aacgcgctcccctccggtggcgtggtcaaactctacagccaaagaacagataatggcatttgtaagatgttgcacaatggcttccaaaag |
| gcaaacggccctcacgtccaagtggacgtaaaggctaaacccttcagggtgaatctcctctataaacattccagcaccttcaaccatgcc |
| caaataattctcatctcgccaccttctcaatatatctctaagcaaatcccgaatattaagtccggccattgtaaaaatctgctccagagcgcc |
| ctccaccttcagcctcaagcagcgaatcatgattgcaaaaattcaggttcctcacagacctgtataagattcaaaagcggaacattaacaa |
| aaataccgcgatcccgtaggtcccttcgcagggccagctgaacataatcgtgcaggtctgcacggaccagcgcggccacttccccgcc |
| aggaaccatgacaaaagaacccacactgattatgacacgcatactcggagctatgctaaccagcgtagccccgatgtaagcttgttgcat |
| gggcggcgatataaaatgcaaggtgctgctcaaaaaatcaggcaaagcctcgcgcaaaaaagaaagcacatcgtagtcatgctcatgc |
| agataaaggcaggtaagctccggaaccaccacagaaaaagacaccatttttctctcaaacatgtctgcgggtttctgcataaacacaaaa |
| taaaataacaaaaaaacatttaaacattagaagcctgtcttacaacaggaaaaacaacccttataagcataagacggactacggccatgc |
| cggcgtgaccgtaaaaaaactggtcaccgtgattaaaaagcaccaccgacagctcctcggtcatgtccggagtcataatgtaagactcg |
| gtaaacacatcaggttgattcacatcggtcagtgctaaaaagcgaccgaaatagcccgggggaatacatacccgcaggcgtagagaca |
| acattacagcccccataggaggtataacaaaattaataggagagaaaaacacataaacacctgaaaaaccctcctgcctaggcaaaata |

TABLE 16-continued

| Ad5UnituxinscFv with Plasmid Backbone |
|---|
| gcaccctcccgctccagaacaacatacagcgcttccacagcggcagccataacagtcagccttaccagtaaaaaagaaaacctattaa |
| aaaaacaccactcgacacggcaccagctcaatcagtcacagtgtaaaaaagggccaagtgcagagcgagtatatataggactaaaaa |
| atgacgtaacggttaaagtccacaaaaaacacccagaaaaccgcacgcgaacctacgcccagaaacgaaagccaaaaaacccacaa |
| cttcctcaaatcgtcacttccgttttcccacgttacgtaacttcccattttaagaaaactacaattcccaacacatacaagttactccgccctaa |
| aacctacgtcacccgccccgttcccacgccccgcgccacgtcacaaactccaccccctcattatcatattggcttcaatccaaaataaggt |
| atattattgatgatgttaatttgggccattagacttgaagtcaagcggccgcttacaactggaccttgctggtacatagaactgattaactga |
| ccatttaaatcataccaacatggtcaaataaaacgaaaggctcagtcgaaagactgggcctttcgttttaatctgatcggcacgtaagagg |
| ttccaactttcaccataatgaaataagatcactaccgggcgtatttttttgagttatcgagattttcaggagctaaggaagctaaaatgagcca |
| tattcaacgggaaacgtcttgctcgaggccgcgattaaattccaacatggatgctgatttatatgggtataaatgggctcgcgataatgtcg |
| ggcaatcaggtgcgacaatctatcgattgtatgggaagcccgatgcgccagagttgtttctgaaacatggcaaaggtagcgttgccaatg |
| atgttacagatgagatggtcaggctaaactggctgacggaatttatgcctcttccgaccatcaagcattttatccgtactcctgatgatgcat |
| ggttactcaccactgcgatccccagggaaaacagcattccaggtattagaagaatatcctgattcaggtgaaaatattgttgatgcgctggc |
| agtgttcctgcgccggttgcattcgattcctgtttgtaattgtccttttaacggcgatcgcgtatttcgtctcgctcaggcgcaatcacgaatg |
| aataacggtttggttggtgcgagtgattttgatgacgagcgtaatggctggcctgttgaacaagtctggaaagaaatgcataaacttttgcc |
| attctcaccggattcagtcgtcactcatggtgatttctcacttgataaccttatttttgacgaggggaaattaataggttgtattgatgttggacg |
| agtcggaatcgcagaccgataccaggatcttgccatcctatggaactgcctcggtgagttttctccttcattacagaaacggctttttcaaaa |
| atatggtattgataatcctgatatgaataaattgcagtttcacttgatgctcgatgagtttttctaacctaggtgacagaagtcaaaagcctcc |
| ggtcggaggcttttgactttctgctagatctgtttcaatgcggtgaagggccaggcagctggggattatgtcgagacccggccagcatgtt |
| ggttttatcgcatattcagcgttgtcgcgtttacccaggtaaaatggaagcagtgtatcgtctgcgtgaatgtgcaaatcaggaacgtaacc |
| gtggtacatagatgcagtcccttgcgggtcgttcccttcaacgagtaggacgcggtgcccttgcaaggctaaccattgcgcctggtgtac |
| tgcagatgaggttttataaacccctcccttgtgtgacataacggaaagtacaaccgggtttttatcgtcaggtctttggtttgggttaccaaac |
| acactccgcatatggctaatttggtcaattgtgtagccagcgcgacgttctactcggcccctcatctcaaaatcaggagccggtagacga |
| ccagcttttttccgcgtctctgatagcctgcggtgttacgccgatcaggtctgcaacttctgttataccccagcggcgagtaatacgacgcg |
| cttccgggctgtcatcgccgaactgtgcgatggcaatagcgcgcgtcatttcctgaccgcgattgatacagtctttcagcaaattaattaac |
| gacatcctgtttcctctcaaacatgcccttatctttgtgtttttcatcatactttacgtttttaaagcaaagcaacataaaaaaagcaaagtgactt |
| agaaaacgcaaagttaaggttcaaatcaatttttgatgcgctacagaagctatttagcttcatctaagcgcaacggtattacttacgttggta |
| tatttaaaacctaacttaatgattttaaatgataataaatcataccaattgctatcaaaagttaagcgaacatgctgattttcacgctgtttataca |
| ctttgaggcatctctatctcttccgtctctatattgaaacacaatcaaagaacatcaatccatgtgacatcccccactatctaagaacaccata |
| acagaacacaacataggaatgcaacattaatgtatcaataattcggaacatatgcactatatcatatctcaattacggaacatatcagcaca |
| caattgcccattatacgc |

TABLE 17

| Ad5UnituxinscFv No Plasmid |
|---|
| (SEQ ID NO: 17) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |

TABLE 17-continued

| Ad5UnituxinscFv No Plasmid |
| --- |
| ggagcggccgctgtcgacctgcaggatccacgcgtggagctagttattaatagtaatcaattacggggtcattagttcatagcccatatat |
| ggagttccgcgttacataacttacggtaaatggcccgcctggctgaccgcccaacgacccccgcccattgacgtcaataatgacgtatgt |
| tcccatagtaacgtcaatagggactttccattgacgtcaatgggtggagtatttacggtaaactgcccacttggcagtacatcaagtgtatc |
| atatgccaagtacgccccctattgacgtcaatgacggtaaatggcccgcctggcattatgcccagtacatgaccttatgggactttcctact |
| tggcagtacatctacgtattagtcatcgctattaccatggtgatgcggttttggcagtacatcaatgggcgtggatagcggtttgactcacg |
| gggatttccaagtctccaccccattgacgtcaatgggagtttgttttgcaccaaaatcaacgggactttccaaaatgtcgtaacaactccgc |
| cccattgacgcaaatgggcggtaggcgtgtacggtgggaggtctatataagcagagctcgtttagtgaaccgtcagatcgcctggagac |
| gccatccacgctgttttgacctccatagaagacaccgggaccgatccagcctccgcggattcgaatcccggccgggaacggtgcattg |
| gaacgcggattccccgtgccaagagtgacgtaagtaccgcctatagagtctataggcccacaaaaaatgctttcttcttttaatatactttttt |
| gtttatcttatttctaatactttccctaatctctttctttcagggcaataatgatacaatgtatcatgcctctttgcaccattctaaagaataacagt |
| gataatttctgggttaaggcaatagcaatatttctgcatataaatatttctgcatataaattgtaactgatgtaagaggtttcatattgctaatagc |
| agctacaatccagctaccattctgcttttattttatggttgggataaggctggattattctgagtccaagctaggcccttttgctaatcatgttca |
| tacctcttatcttcctcccacagctcctgggcaacgtgctggtctgtgtgctggcccatcactttggcaaagctcctgggcaacgtgctggt |
| tattgtgctgtctcatcattttggcaaagaattccgctgcgactcggcggagtcccggcggcgcgtccttgttctaacccggcgcgccagc |
| ttggcaatccggtactgttggtaaagccaccatggaactgggactgtcatggatcttcttgctggctatcctgaagggagtgcagtgtgaa |
| gttcagctgctgcagagcggacccgaactggaaaaacctggcgcctccgtgatgatcagctgcaaggcctctggcagctccttcaccg |
| gctacaacatgaactgggtccgacagaacatcggcaagagcctggaatggatcggcgccatcgatccttactacggcggcaccagct |
| acaaccagaagttcaagggcagagccacactgaccgtggacaagagcagcagcacagcctacatgcatctgaagtccctgaccagc |
| gaggacagcgccgtgtactactgtgtgtccggcatggaatactggggccagggcacaagcgtgacagtctcttctggcggcggtggat |
| ctggcggaggcggaagtggtggcggcggatctgatgtggtcatgacacagacccctctgagcctgcctgtgtctctgggagatcaggc |
| cagcatcagctgtagaagcagccagagcctggtgcacagaaacggcaacacctacctgcactggtatctgcagaagcccggccagtc |
| tcctaagctgctgatccacaaggtgtccaacagattcagcggcgtgcccgacagattctctggctctggaagcggcaccgacttcaccct |
| gaagattagcagagtggaagccgaggacctgggcgtgtacttctgtagccagagcacacacgtgccacctctgacatttggcgctggc |
| accaagctggaactggagcctaagagctgtgacaagacacacacatgtcctccttgtcctgctcctgaattacttggaggaccttctgtgtt |
| cctgttccctcctaaacctaaggacaccctgatgatcagcagaacacctgaagtgacctgtgtggtggttgatgtgtctcatgaggatcct |
| gaggtgaagttcaactggtacgtggatggagtggaggtgcataatgccaagacaaagcctagagaggagcagtacaacagcacctat |
| agagtggtgtctgtgctgacagtgctgcatcaagattggctgaatggcaaggagtacaagtgcaaggtgagcaataaggctctgcctgc |
| tcctatcgagaagacaatctctaaggccaagggacagcctagagaacctcaggtttacacacttcctcctagcagagatgagctgacca |
| agaatcaggtgagcctgacatgtctggtgaagggattttaccctagcgatatcgctgtggaatgggagtctaatggacagcctgagaaca |
| actacaagaccacacctcctgtgctggattctgatggctctttcttcctgtacagcaagctgacagtggacaagtctagatggcaacaggg |
| caatgtgttcagctgttctgtgatgcatgaggctctgcacaaccactatacccagaaaagcctgagcctgtctcctggaaagtagtaataat |
| tctagagtcggggcggccggccgcttcgagcagacatgataagatacattgatgagtttggacaaaccacaactagaatgcagtgaaa |
| aaaatgctttatttgtgaaatttgtgatgctattgctttatttgtaaccattataagctgcaataaacaagttaacaacaacaattgcattcattttta |
| tgtttcaggttcagggggaggtgtgggaggttttttaaagcaagtaaaacctctacaaatgtggtaaaatcgataaggatccgaattcgata |
| tcactagtggtaccagtactgaaatgtgtgggcgtggcttaagggtgggaaagaatatataaggtgggggtcttatgtagttttgtatctgtt |
| ttgcagcagccgccgccgccatgagcaccaactcgtttgatggaagcattgtgagctcatatttgacaacgcgcatgcccccatgggcc |
| ggggtgcgtcagaatgtgatgggctccagcattgatggtcgccccgtcctgcccgcaaactctactaccttgacctacgagaccgtgtct |
| ggaacgccgttggagactgcagcctccgccgccgcttcagccgctgcagccaccgcccgcgggattgtgactgactttgctttcctgag |
| cccgcttgcaagcagtgcagcttcccgttcatccgcccgcgatgacaagttgacggctcttttggcacaattggattctttgacccgggaa |

TABLE 17-continued

| Ad5UnituxinscFv No Plasmid |
|---|
| cttaatgtcgtttctcagcagctgttggatctgcgccagcaggtttctgccctgaaggcttcctcccctcccaatgcggtttaacggtccgg |
| gccagagtggccaacataaataaaaaaccagactctgtttggatttggatcaagcaagtgtcttgctgtctttatttaggggttttgcgcgcg |
| cggtaggcccgggaccagcggtctcggtcgttgagggtcctgtgtatttttttccaggacgtggtaaaggtgactctggatgttcagataca |
| tgggcataagcccgtctctgggggggaggtagcaccactgcagagcttcatgctgcggggtggtgttgtagatgatccagtcgtagcag |
| gagcgctgggcgtggtgcctaaaaatgtctttcagtagcaagctgattgccaggggcaggcccttggtgtaagtgtttacaaagcggtta |
| agctgggatgggtgcatacgtggggatatgagatgcatcttggactgtatttttaggttggctatgttcccagccatatccctccggggatt |
| catgttgtgcagaaccaccagcacagtgtatccggtgcacttgggaaatttgtcatgtagcttagaaggaaatgcgtggaagaacttgga |
| gacgcccttgtgacctccaagattttccatgcattcgtccataatgatggcaatgggcccacgggcggcggcctgggcgaagatatttct |
| gggatcactaacgtcatagttgtgttccaggatgagatcgtcataggccatttttacaaagcgcgggcggagggtgccagactgcggtat |
| aatggttccatccggcccaggggcgtagttaccctcacagatttgcatttcccacgctttgagttcagatgggggggatcatgtctacctgc |
| ggggcgatgaagaaaacggtttccggggtaggggagatcagctgggaagaaagcaggttcctgagcagctgcgacttaccgcagcc |
| ggtgggcccgtaaatcacacctattaccggctgcaactggtagttaagagagctgcagctgccgtcatccctgagcaggggggccactt |
| cgttaagcatgtccctgactcgcatgttttccctgaccaaatccgccagaaggcgctcgccgcccagcgatagcagttcttgcaaggaag |
| caaagtttttcaacggtttgagaccgtccgccgtaggcatgcttttgagcgtttgaccaagcagttccaggcggtcccacagctcggtcac |
| ctgctctacggcatctcgatccagcatatctcctcgtttcgcgggttggggcggctttcgctgtacggcagtagtcggtgctcgtccagac |
| gggccagggtcatgtctttccacgggcgcagggtcctcgtcagcgtagtctgggtcacggtgaaggggtgcgctccgggctgcgcgc |
| tggccagggtgcgcttgaggctggtcctgctggtgctgaagcgctgccggtcttcgccctgcgcgtcggccaggtagcatttgaccatg |
| gtgtcatagtccagcccctccgcggcgtggcccttggcgcgcagcttgcccttggaggaggcgccgcacgaggggcagtgcagactt |
| ttgagggcgtagagcttgggcgcgagaaataccgattccggggagtaggcatccgcgccgcaggccccgcagacggtctcgcattcc |
| acgagccaggtgagctctggccgttcggggtcaaaaaccaggtttcccccatgctttttgatgcgtttcttacctctggtttccatgagccg |
| gtgtccacgctcggtgacgaaaaggctgtccgtgtccccgtatacagacttgagaggcctgtcctcgagcggtgttccgcggtcctcctc |
| gtatagaaactcggaccactctgagacaaaggctcgcgtccaggccagcacgaaggaggctaagtgggaggggtagcggtcgttgtc |
| cactagggggtccactcgctccagggtgtgaagacacatgtcgccctcttcggcatcaaggaaggtgattggtttgtaggtgtaggcca |
| cgtgaccgggtgttcctgaagggggggctataaaagggggtgggggcgcgttcgtcctcactctcttccgcatcgctgtctgcgagggc |
| cagctgttggggtgagtactccctctgaaaagcgggcatgacttctgcgctaagattgtcagtttccaaaaacgaggaggatttgatattc |
| acctggcccgcggtgatgcctttgagggtggccgcatccatctggtcagaaaagacaatctttttgttgtcaagcttggtggcaaacgacc |
| cgtagagggcgttggacagcaacttggcgatggagcgcagggtttggtttttgtcgcgatcggcgcgctccttggccgcgatgtttagct |
| gcacgtattcgcgcgcaacgcaccgccattcgggaaagacggtggtgcgctcgtcgggcaccaggtgcacgcgccaaccgcggttg |
| tgcagggtgacaaggtcaacgctggtggctacctctccgcgtaggcgctcgttggtccagcagaggcggccgcccttgcgcgagcag |
| aatggcggtagggggtctagctgcgtctcgtccggggggtctgcgtccacggtaaagaccccgggcagcaggcgcgcgtcgaagta |
| gtctatcttgcatccttgcaagtctagcgcctgctgccatgcgcgggcggcaagcgcgcgctcgtatgggttgagtgggggaccccatg |
| gcatggggtgggtgagcgcggaggcgtacatgccgcaaatgtcgtaaacgtagaggggctctctgagtattccaagatatgtagggta |
| gcatcttccaccgcggatgctggcgcgcacgtaatcgtatagttcgtgcgagggagcgaggaggtcgggaccgaggttgctacgggc |
| gggctgctctgctcggaagactatctgcctgaagatggcatgtgagttggatgatatggttggacgctggaagacgttgaagctggcgtc |
| tgtgagacctaccgcgtcacgcacgaaggaggcgtaggagtcgcgcagcttgttgaccagctcggcggtgacctgcacgtctagggc |
| gcagtagtccagggtttccttgatgatgtcatacttatcctgtcccttttttttccacagctcgcggttgaggacaaactcttcgcggtctttcc |
| agtactcttggatcggaaacccgtcggcctccgaacggtaagagcctagcatgtagaactggttgacggcctggtaggcgcagcatcc |
| cttttctacgggtagcgcgtatgcctgcgcggccttccggagcgaggtgtgggtgagcgcaaaggtgtccctgaccatgactttgaggt |
| actggtatttgaagtcagtgtcgtcgcatccgccctgctcccagagcaaaaagtccgtgcgctttttggaacgcggatttggcagggcga |

TABLE 17-continued

| Ad5UnituxinscFv No Plasmid |
|---|
| aggtgacatcgttgaagagtatctttcccgcgcgaggcataaagttgcgtgtgatgcggaagggtcccggcacctcggaacggttgtta |
| attacctgggcggcgagcacgatctcgtcaaagccgttgatgttgtggcccacaatgtaaagttccaagaagcgcgggatgcccttgat |
| ggaaggcaatttttaagttcctcgtaggtgagctcttcaggggagctgagcccgtgctctgaaagggcccagtctgcaagatgagggtt |
| ggaagcgacgaatgagctccacaggtcacgggccattagcatttgcaggtggtcgcgaaaggtcctaaactggcgacctatggccattt |
| tttctggggtgatgcagtagaaggtaagcgggtcttgttcccagcggtcccatccaaggttcgcggctaggtctcgcgcggcagtcacta |
| gaggctcatctccgccgaacttcatgaccagcatgaagggcacgagctgcttcccaaaggcccccatccaagtataggtctctacatcg |
| taggtgacaaagagacgctcggtgcgaggatgcgagccgatcgggaagaactggatctcccgccaccaattggaggagtggctattg |
| atgtggtgaaagtagaagtccctgcgacgggccgaacactcgtgctggcttttgtaaaaacgtgcgcagtactggcagcggtgcacgg |
| gctgtacatcctgcacgaggttgacctgacgaccgcgcacaaggaagcagagtgggaatttgagcccctcgcctggcgggtttggctg |
| gtggtcttctacttcggctgcttgtccttgaccgtctggctgctcgaggggagttacggtggatcggaccaccacgccgcgcgagccca |
| aagtccagatgtccgcgcgcggcggtcggagcttgatgacaacatcgcgcagatgggagctgtccatggtctggagctcccgcggcg |
| tcaggtcaggcgggagctcctgcaggtttacctcgcatagacgggtcagggcgcgggctagatccaggtgatacctaatttccagggg |
| ctggttggtggcggcgtcgatggcttgcaagaggccgcatccccgcggcgcgactacggtaccgcgcggcgggggggccgcg |
| ggggtgtccttggatgatgcatctaaaagcggtgacgcgggcgagcccccggaggtagggggggctccggacccgccgggagag |
| ggggcaggggcacgtcggcgccgcgcgcgggcaggagctggtgctgcgcgcgtaggttgctggcgaacgcgacgacgcggcgg |
| ttgatctcctgaatctggcgcctctgcgtgaagacgacgggcccggtgagcttgaacctgaaagagagttcgacagaatcaatttcggtg |
| tcgttgacggcggcctggcgcaaaatctcctgcacgtctcctgagttgtcttgataggcgatctcggccatgaactgctcgatctcttcctc |
| ctggagatctccgcgtccggctcgctccacggtggcggcgaggtcgttggaaatgcgggccatgagctgcgagaaggcgttgaggc |
| ctccctcgttccagacgcggctgtagaccacgcccccttcggcatcgcgggcgcgcatgaccacctgcgcgagattgagctccacgtg |
| ccgggcgaagacggcgtagtttcgcaggcgctgaaagaggtagttgagggtggtggcggtgtgttctgccacgaagaagtacataac |
| ccagcgtcgcaacgtggattcgttgatatcccccaaggcctcaaggcgctccatggcctcgtagaagtccacggcgaagttgaaaaact |
| gggagttgcgcgccgacacggttaactcctcctccagaagacggatgagctcggcgacagtgtcgcgcacctcgcgctcaaaggcta |
| caggggcctcttcttcttcttcaatctcctcttccataagggcctccccttcttcttcttctggcggcggtgggggaggggggacacggcg |
| gcgacgacggcgcaccgggaggcggtcgacaaagcgctcgatcatctccccgcggcgacggcgcatggtctcggtgacggcgcg |
| gccgttctcgcgggggcgcagttggaagacgccgcccgtcatgtcccggttatgggttggcgggggctgccatgcggcagggatac |
| ggcgctaacgatgcatctcaacaattgttgtgtaggtactccgccgccgagggacctgagcgagtccgcatcgaccggatcggaaaac |
| ctctcgagaaaggcgtctaaccagtcacagtcgcaaggtaggctgagcaccgtggcgggcggcagcgggggcggtcggggttgtt |
| tctggcggaggtgctgctgatgatgtaattaaagtaggcggtcttgagacggcggatggtcgacagaagcaccatgtccttgggtccgg |
| cctgctgaatgcgcaggcggtcggccatgccccaggcttcgttttgacatcggcgcaggtctttgtagtagtcttgcatgagcctttctacc |
| ggcacttcttcttctccttcctcttgtcctgcatctcttgcatctatcgctgcggcggcggcggagtttggccgtaggtggcgccctcttcctc |
| ccatgcgtgtgaccccgaagcccctcatcggctgaagcagggctaggtcggcgacaacgcgctcggctaatatggcctgctgcacct |
| gcgtgagggtagactggaagtcatccatgtccacaaagcggtggtatgcgcccgtgttgatggtgtaagtgcagttggccataacggac |
| cagttaacggtctggtgacccggctgcgagagctcggtgtacctgagacgcgagtaagccctcgagtcaaatacgtagtcgttgcaagt |
| ccgcaccaggtactggtatcccaccaaaaagtgcggcggcggctggcggtagaggggccagcgtagggtggccggggctccggg |
| ggcgagatcttccaacataaggcgatgatatccgtagatgtacctggacatccaggtgatgccggcggcggtggtggaggcgcgcgg |
| aaagtcgcggacgcggttccagatgttgcgcagcggcaaaaagtgctccatggtcgggacgctctggccggtcaggcgcgcgcaatc |
| gttgacgctctagaccgtgcaaaaggagagcctgtaagcgggcactcttccgtggtctggtggataaattcgcaagggtatcatggcgg |
| acgaccggggttcgagccccgtatccggccgtccgccgtgatccatgcggttaccgcccgcgtgtcgaacccaggtgtgcgacgtca |
| gacaacgggggagtgctccttttggcttccttccaggcgcggcggctgctgcgctagctttttggccactggccgcgcgcagcgtaag |

TABLE 17-continued

| Ad5UnituxinscFv No Plasmid |
|---|
| cggttaggctggaaagcgaaagcattaagtggctcgctccctgtagccggagggttattttccaagggttgagtcgcgggacccccggt |
| tcgagtctcggaccggccggactgcggcgaacgggggtttgcctccccgtcatgcaagaccccgcttgcaaattcctccggaaacag |
| ggacgagcccctttttttgcttttcccagatgcatccggtgctgcggcagatgcgcccccctcctcagcagcggcaagagcaagagcag |
| cggcagacatgcagggcaccctcccctcctcctaccgcgtcaggaggggcgacatccgcggttgacgcggcagcagatggtgattac |
| gaacccccgcggcgccgggcccggcactacctggacttggaggagggcgagggcctggcgcggctaggagcgccctctcctgag |
| cggcacccaagggtgcagctgaagcgtgatacgcgtgaggcgtacgtgccgcggcagaacctgtttcgcgaccgcgagggagagg |
| agcccgaggagatgcgggatcgaaagttccacgcagggcgcgagctgcggcatggcctgaatcgcgagcggttgctgcgcgagga |
| ggactttgagcccgacgcgcgaaccgggattagtcccgcgcgcgcacacgtggcggccgccgacctggtaaccgcatacgagcag |
| acggtgaaccaggagattaactttcaaaaaagctttaacaaccacgtgcgtacgcttgtggcgcgcgaggaggtggctataggactgat |
| gcatctgtgggactttgtaagcgcgctggagcaaaacccaaatagcaagccgctcatggcgcagctgttccttatagtgcagcacagca |
| gggacaacgaggcattcagggatgcgctgctaaacatagtagagcccgagggccgctggctgctcgatttgataaacatcctgcagag |
| catagtggtgcaggagcgcagcttgagcctggctgacaaggtggccgccatcaactattccatgcttagcctgggcaagttttacgccc |
| gcaagatataccataccccttacgttcccatagacaaggaggtaaagatcgaggggttctacatgcgcatggcgctgaaggtgcttacct |
| tgagcgacgacctgggcgtttatcgcaacgagcgcatccacaaggccgtgagcgtgagccggcggcgcgagctcagcgaccgcga |
| gctgatgcacagcctgcaaagggccctggctggcacgggcagcggcgatagagaggccgagtcctactttgacgcgggcgctgacc |
| tgcgctgggccccaagccgacgcgccctggaggcagctggggccggacctgggctggcggtggcacccgcgcgcgctggcaacg |
| tcggcggcgtggaggaatatgacgaggacgatgagtacgagccagaggacggcgagtactaagcggtgatgtttctgatcagatgat |
| gcaagacgcaacggacccggcggtgcgggcggcgctgcagagccagccgtccggccttaactccacggacgactggcgccaggt |
| catggaccgcatcatgtcgctgactgcgcgcaatcctgacgcgttccggcagcagccgcaggccaaccggctctccgcaattctggaa |
| gcggtggtcccggcgcgcgcaaaccccacgcacgagaaggtgctggcgatcgtaaacgcgctggccgaaaacagggccatccgg |
| cccgacgaggccggcctggtctacgacgcgctgcttcagcgcgtggctcgttacaacagcggcaacgtgcagaccaacctggaccg |
| gctggtgggggatgtgcgcgaggccgtggcgcagcgtgagcgcgcgcagcagcagggcaacctgggctccatggttgcactaaac |
| gccttcctgagtacacagcccgccaacgtgccgcggggacaggaggactacaccaactttgtgagcgcactgcggctaatggtgact |
| gagacaccgcaaagtgaggtgtaccagtctgggccagactattttttccagaccagtagacaaggcctgcagaccgtaaacctgagcc |
| aggctttcaaaaacttgcaggggctgtgggggtgcgggctcccacaggcgaccgcgcgaccgtgtctagcttgctgacgcccaact |
| cgcgcctgttgctgctgctaatagcgcccttcacggacagtggcagcgtgtcccgggacacatacctaggtcacttgctgacactgtacc |
| gcgaggccataggtcaggcgcatgtggacgagcatactttccaggagattacaagtgtcagccgcgcgctggggcaggaggacacg |
| ggcagcctggaggcaaccctaaactacctgctgaccaaccggcggcagaagatcccctcgttgcacagtttaaacagcgaggaggag |
| cgcattttgcgctacgtgcagcagagcgtgagccttaacctgatgcgcgacggggtaacgcccagcgtggcgctggacatgaccgcg |
| cgcaacatggaaccgggcatgtatgcctcaaaccggccgtttatcaaccgcctaatggactacttgcatcgcgcggccgccgtgaacc |
| ccgagtatttcaccaatgccatcttgaacccgcactggctaccgccccctggtttctacaccgggggattcgaggtgcccgagggtaac |
| gatggattcctctgggacgacatagacgacagcgtgttttccccgcaaccgcagaccctgctagagttgcaacagcgcgagcaggcag |
| aggcggcgctgcgaaaggaaagcttccgcaggccaagcagcttgtccgatctaggcgctgcggccccgcggtcagatgctagtagc |
| ccatttccaagcttgatagggtctcttaccagcactcgcaccacccgcccgcgcctgctgggcgaggaggagtacctaaacaactcgct |
| gctgcagccgcagcgcgaaaaaaacctgcctccggcatttcccaacaacgggatagagagcctagtggacaagatgagtagatggaa |
| gacgtacgcgcaggagcacagggacgtgccaggcccgcgcccgcccacccgtcgtcaaaggcacgaccgtcagcggggtctggt |
| gtgggaggacgatgactcggcagacgacagcagcgtcctggatttgggagggagtggcaacccgtttgcgcaccttcgccccaggct |
| ggggagaatgttttaaaaaaaaaaaaaagcatgatgcaaaataaaaaactcaccaaggccatggcaccgagcgttggttttcttgtattcc |
| ccttagtatgcggcgcgcggcgatgtatgaggaaggtcctcctccctcctacgagagtgtggtgagcgcggcgccagtggcggcggc |

TABLE 17-continued

| Ad5UnituxinscFv No Plasmid |
|---|
| gctgggttctcccttcgatgctcccctggacccgccgtttgtgcctccgcggtacctgcggcctaccgggggagaaacagcatccgtt |
| actctgagttggcacccctattcgacaccacccgtgtgtacctggtggacaacaagtcaacggatgtggcatccctgaactaccagaac |
| gaccacagcaactttctgaccacggtcattcaaaacaatgactacagcccgggggaggcaagcacacagaccatcaatcttgacgacc |
| ggtcgcactggggggcgacctgaaaaccatcctgcataccaacatgccaaatgtgaacgagttcatgtttaccaataagtttaaggcgc |
| gggtgatggtgtcgcgcttgcctactaaggacaatcaggtggagctgaaatacgagtgggtggagttcacgctgcccgagggcaacta |
| ctccgagaccatgaccatagaccttatgaacaacgcgatcgtggagcactacttgaaagtgggcagacagaacggggttctggaaagc |
| gacatcggggtaaagtttgacacccgcaacttcagactggggtttgaccccgtcactggtcttgtcatgcctggggtatatacaaacgaa |
| gccttccatccagacatcattttgctgccaggatgcggggtggacttcacccacagccgcctgagcaacttgttgggcatccgcaagcg |
| gcaacccttccaggagggctttaggatcacctacgatgatctggagggtggtaacattcccgcactgttggatgtggacgcctaccagg |
| cgagcttgaaagatgacaccgaacagggggggtggcgcaggcggcagcaacagcagtggcagcggcgcggaagagaactcc |
| aacgcggcagccgcggcaatgcagccggtggaggacatgaacgatcatgccattcgcggcgacacctttgccacacgggctgagga |
| gaagcgcgctgaggccgaagcagcggccgaagctgccgcccccgctgcgcaacccgaggtcgagaagcctcagaagaaaccggt |
| gatcaaacccctgacagaggacagcaagaaacgcagttacaacctaataagcaatgacagcaccttcacccagtaccgcagctggtac |
| cttgcatacaactacggcgaccctcagaccggaatccgctcatggaccctgctttgcactcctgacgtaacctgcggctcggagcaggt |
| ctactggtcgttgccagacatgatgcaagaccccgtgaccttccgctccacgcgccagatcagcaactttccggtggtgggcgccgag |
| ctgttgcccgtgcactccaagagcttctacaacgaccaggccgtctactcccaactcatccgccagtttacctctctgacccacgtgttcaa |
| tcgctttcccgagaaccagattttggcgcgcccgccagccccaccatcaccaccgtcagtgaaaacgttcctgctctcacagatcacg |
| ggacgctaccgctgcgcaacagcatcggaggagtccagcgagtgaccattactgacgccagacgccgcacctgcccctacgtttaca |
| aggccctgggcatagtctcgccgcgcgtcctatcgagccgcacttttgagcaagcatgtccatccttatatcgcccagcaataacacag |
| gctggggcctgcgcttcccaagcaagatgtttggcggggccaagaagcgctccgaccaacacccagtgcgcgtgcgcgggcactac |
| cgcgcgccctggggcgcgcacaaacgcggccgcactgggcgcaccaccgtcgatgacgccatcgacgcggtggtggaggaggcg |
| cgcaactacacgcccacgccgccaccagtgtccacagtggacgcggccattcagaccgtggtgcgcggagcccggcgctatgctaa |
| aatgaagagacggcggaggcgcgtagcacgtcgccaccgccgccgacccggcactgccgcccaacgcgcggcggcggccctgct |
| taaccgcgcacgtcgcaccggccgacgggcggccatgcgagcagctcgaaggctggccgcgggtattgtcactgtgccccccaggt |
| ccaggcgacgagcggccgccgcagcagccgcggccattagtgctatgactcagggtcgcaggggcaacgtgtattgggtgcgcgac |
| tcggttagcggcctgcgcgtgcccgtgcgcacccgcccccgcgcaactagattgcaagaaaaaactacttagactcgtactgttgtat |
| gtatccagcggcggcggcgcgcaacgaagctatgtccaagcgcaaaatcaaagaagagatgctccaggtcatcgcgccggagatct |
| atggcccccgaagaaggaagagcaggattacaagccccgaaagctaaagcgggtcaaaaagaaaaagaaagatgatgatgatgaa |
| cttgacgacgaggtggaactgctgcacgctaccgcgcccaggcgacgggtacagtggaaaggtcgacgcgtaaaacgtgttttgcga |
| cccggcaccaccgtagtctttacgcccggtgagcgctccacccgcacctacaagcgcgtgtatgatgaggtgtacggcgacgaggac |
| ctgcttgagcaggccaacgagcgcctcggggagtttgcctacggaaagcggcataaggacatgctggcgttgccgctggacgaggg |
| caacccaacacctagcctaaagcccgtaacactgcagcaggtgctgcccgcgcttgcaccgtccgaagaaaagcgcggcctaaagc |
| gcgagtctggtgacttggcacccaccgtgcagctgatggtacccaagcgccagcgactggaagatgtcttggaaaaaatgaccgtgga |
| acctgggctggagcccgaggtccgcgtgcggccaatcaagcaggtggcgccgggactgggcgtgcagaccgtggacgttcagata |
| cccactaccagtagcaccagtattgccaccgccacagagggcatggagacacaaacgtccccggttgcctcagcggtggcggatgcc |
| gcggtgcaggcggtcgctgcggccgcgtccaagacctctacggaggtgcaaacggacccgtggatgtttcgcgtttcagccccccgg |
| cgcccgcgccgttcgaggaagtacggcgccgccagcgcgctactgcccgaatatgccctacatccttccattgcgcctacccccggct |
| atcgtggctacacctaccgccccagaagacgagcaactacccgacgccgaaccaccactggaacccgccgccgccgtcgccgtcgc |
| cagcccgtgctggccccgatttccgtgcgcagggtggctcgcgaaggaggcaggaccctggtgctgccaacagcgcgctaccaccc |

TABLE 17-continued

| Ad5UnituxinscFv No Plasmid |
|---|
| cagcatcgtttaaaagccggtctttgtggttcttgcagatatggccctcacctgccgcctccgtttcccggtgccgggattccgaggaaga |
| atgcaccgtaggaggggcatggccggccacggcctgacgggcggcatgcgtcgtgcgcaccaccggcggcggcgcgcgtcgcac |
| cgtcgcatgcgcggcggtatcctgcccctccttattccactgatcgccgcggcgattggcgccgtgcccggaattgcatccgtggccttg |
| caggcgcagagacactgattaaaaacaagttgcatgtggaaaaatcaaaataaaaagtctggactctcacgctcgcttggtcctgtaact |
| attttgtagaatggaagacatcaactttgcgtctctggccccgcgacacggctcgcgcccgttcatgggaaactggcaagatatcggcac |
| cagcaatatgagcggtggcgccttcagctggggctcgctgtggagcggcattaaaaatttcggttccaccgttaagaactatggcagca |
| aggcctggaacagcagcacaggccagatgctgagggataagttgaaagagcaaaatttccaacaaaaggtggtagatggcctggcct |
| ctggcattagcggggtggtggacctggccaaccaggcagtgcaaaataagattaacagtaagcttgatccccgccctcccgtagagga |
| gcctccaccggccgtggagacagtgtctccagaggggcgtggcgaaaagcgtccgcgccccgacagggaagaaactctggtgacg |
| caaatagacgagcctccctcgtacgaggaggcactaaagcaaggcctgcccaccacccgtcccatcgcgcccatggctaccggagtg |
| ctgggccagcacacacccgtaacgctggacctgcctcccccgccgacacccagcagaaacctgtgctgccaggcccgaccgccgt |
| tgttgtaacccgtcctagccgcgcgtccctgcgccgcgccgccagcggtccgcgatcgttgcggcccgtagccagtggcaactggca |
| aagcacactgaacagcatcgtgggtctgggggtgcaatccctgaagcgccgacgatgcttctgaatagctaacgtgtcgtatgtgtgtca |
| tgtatgcgtccatgtcgccgccagaggagctgctgagccgccgcgcgcccgctttccaagatggctaccccttcgatgatgccgcagtg |
| gtcttacatgcacatctcgggccaggacgcctcggagtacctgagccccgggctggtgcagtttgcccgcgccaccgagacgtacttc |
| agcctgaataacaagtttagaaccccacggtggcgcctacgcacgacgtgaccacagaccggtcccagcgtttgacgctgcggttca |
| tccctgtggaccgtgaggatactgcgtactcgtacaaggcgcggttcaccctagctgtgggtgataaccgtgtgctggacatggcttcca |
| cgtactttgacatccgcggcgtgctggacaggggccctacttttaagccctactctggcactgcctacaacgccctggctcccaagggtg |
| ccccaaatccttgcgaatgggatgaagctgctactgctcttgaaataaacctagaagaagaggacgatgacaacgaagacgaagtaga |
| cgagcaagctgagcagcaaaaaactcacgtatttgggcaggcgccttattctggtataaatattacaaaggagggtattcaaataggtgtc |
| gaaggtcaaacacctaaatatgccgataaaacatttcaacctgaacctcaaataggagaatctcagtggtacgaaacagaaattaatcat |
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataattttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |
| ttccgcggctgggccttcacgcgccttaagactaaggaaaccccatcactgggctcgggctacgacccttattacacctactctggctcta |
| taccctacctagatggaaccttttacctcaaccacacctttaagaaggtggccattacctttgactcttctgtcagctggcctggcaatgacc |
| gcctgcttacccccaacgagtttgaaattaagcgctcagttgacggggagggttacaacgttgcccagtgtaacatgaccaaagactggt |

TABLE 17-continued

| Ad5UnituxinscFv No Plasmid |
| --- |
| tcctggtacaaatgctagctaactataacattggctaccagggcttctatatcccagagagctacaaggaccgcatgtactccttctttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttcccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttctttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggtggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgcttttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |
| ccatttccttctcctataggcagaaaaagatcatggagtcagtcgagaagaaggacagcctaaccgccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggcgggggggacgaaaggcatggcgactacctagatgtgggagacgacgtgctgttgaagcatctgcagcgcca |
| gtgcgccattatctgcgacgcgttgcaagagcgcagcgatgtgcccctcgccatagcggatgtcagccttgcctacgaacgccacctat |
| tctcaccgcgcgtaccccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |

TABLE 17-continued

| Ad5UnituxinscFv No Plasmid |
| --- |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctacccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacgggggtttacttggacccccagtccggcgaggagctcaacccaatccccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |
| aagttcagatgactaactcaggggcgcagcttgcgggcggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |

TABLE 17-continued

| Ad5UnituxinscFv No Plasmid |
| --- |
| actgtgatttgcaactgtcctaaccttggattacatcaagatccagatcttctagacccgggagcggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |
| ccgctaaccgtgcacgactccaaacttagcattgccacccaaggacccctcacagtgtcagaaggaaagctagccctgcaaacatcag |
| gccccctcaccaccaccgatagcagtacccttactatcactgcctcaccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctctttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaacaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacactttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatgggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgccatccaccaccat |
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgccccctggcttcgggttctatgtaaactccttcatgcgccgctgccctgataacatccaccaccgcagaataa |

TABLE 17-continued

| Ad5UnituxinscFv No Plasmid |
| --- |
| gccacacccagccaacctacacattcgttctgcgagtcacacacgggaggagcgggaagagctggaagaaccatgtttttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagcccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccacccccctcattatcatattggcttcaatccaaaataaggtatattattgatgatg |

TABLE 18

| Ad5-TGFβ-RES-IL10 with Plasmid Backbone |
| --- |
| (SEQ ID NO: 18) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |

TABLE 18-continued

| Ad5-TGFβ-RES-IL10 with Plasmid Backbone |
| --- |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |

TABLE 18-continued

| Ad5-TGFβ-RES-IL10 with Plasmid Backbone |
| --- |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctcctttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgattttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattccctttttttaccgcataaggccaggagccatcttcagctggcgaatgttcccaggcgcgatggaa |

TABLE 18-continued

| Ad5-TGFβ-RES-IL10 with Plasmid Backbone |
|---|
| agccaaccatccaagcaggcgttcctgctccatctgattgtttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccact |
| agttattaatagtaatcaattacggggtcattagttcatagcccatatatggagttccgcgttacataacttacggtaaatggcccgcctggct |
| gaccgcccaacgacccccgcccattgacgtcaataatgacgtatgttcccatagtaacgccaatagggactttccattgacgtcaatggg |
| tggagtatttacggtaaactgcccacttggcagtacatcaagtgtatcatatgccaagtacgccccctattgacgtcaatgacggtaaatgg |
| cccgcctggcattatgcccagtacatgaccttatgggactttcctacttggcagtacatctacgtattagtcatcgctattaccatggtcgag |
| gtgagccccacgttctgcttcactctccccatctcccccccctccccacccccaattttgtatttatttattttttaattattttgtgcagcgatgg |
| gggcgggggggggggggggggggccaggcggggcgggggggcgaggggggggcggggcgaggcggagaggtgcg |
| gcggcagccaatcagagcggcgcgctccgaaagtttccttttatggcgaggcggcggcggcggcggccctataaaaagcgaagcgc |
| gcgggggggggagtcgctgcgttgccttcgccccgtgccccgctccgcgccgcctcgcgccgcccgccccggctctgactgaccg |
| cgttactcccacaggtgagcgggggggacggcccttctcctccgggctgtaattagcgcttggtttaatgacggctcgtttcttttctgtgg |
| ctgcgtgaaagccttaaagggctccgggagggccctttgtgcggggggggagcggctcgggggggtgcgtgcgtgtgtgtgtgcgtgg |
| ggagcgccgcgtgcggctccgcgctgcccggcggctgtgagcgctgcgggcgcggcgcggggctttgtgcgctccgcagtgtgcg |
| cgaggggagcgcggccgggggcggtgccccgcggtgcgggggggggctgcgaggggaacaaaggctgcgtgcggggtgtgtgc |
| gtgggggggtgagcagggggtgtgggcgcgtcggtcgggctgcaacccccccctgcacccccctccccgagttgctgagcacggcc |
| cggcttcgggtgcggggctccgtacggggcgtggcgcggggctcgccgtgccgggcggggggggcggcaggtgggggtgccg |

TABLE 18-continued

| Ad5-TGFβ-RES-IL10 with Plasmid Backbone |
|---|
| ggcgggggggccgcctcgggccggggagggctcgggggaggggcgcggcggccccggagcgccggcggctgtcgaggc |
| gcggcgagccgcagccattgccttttatggtaatcgtgcgagagggcgcagggacttcctttgtcccaaatctgtgcggagccgaaatct |
| gggaggcgccgccgcacccctctagcgggcgcggggcgaagcggtgcggcgccggcaggaaggaaatgggcggggagggcc |
| ttcgtgcgtcgccgcgccgccgtccccttctccctctccagcctcggggctgtccgcgggggggacggctgccttcggggggacggg |
| gcagggcggggttcggcttctggcgtgtgaccggcggctctagagcctctgctaaccatgttcatgccttcttctttttcctacagctcctg |
| ggcaacgtgctggttattgtgctgtctcatcattttggcaaagaattccgctgcgactcggcggagtcccggcggcgcgtccttgttctaac |
| ccggcgcgccagcttggcaatccggtactgttggtaaagccaccaugccgcccuccgggcugcggcugcugccgcugcugcuac |
| cgcugcuguggcuacuggugcugacgccuggccggccggccggggacuauccaccugcaagacuaucgacauggagcug |
| gugaagcggaagcgcaucgaggccauccgcggccagauccuguccaagcugcggcucgccagcccccgagccagggggag |
| gugccgcccggcccgcugcccgaggccgugcucgcccuguacaacagcacccgcgaccggguggccggggagagugcaga |
| accggagcccgagccugaggccgacuacuacgccaaggaggucacccgcgugcuaaugguggaaacccacaacgaaaucua |
| ugacaaguucaagcagaguacacacagcauauauauguucuucaacacaucagagcuccgagaagcgguaccugaacccgu |
| guugcucucccgggcagagcugcgucugcugaggcucaaguuaaaaguggagcagcacguggagcuguaccagaaauaca |
| gcaacaauuccuggcgauaccucagcaaccggcugcuggcacccagcgacucgccagagugguuaucuuuugaugucacc |
| ggaguugugcggcagugguugagccguggaggggaaauugagggcuuucgccuuagcgcccacugcuccugugacagca |
| gggauaacacacugcaaguggacaucaacggguucacuaccggccgccgaggugaccuggccaccauucauggcaugaacc |
| ggccuuuccugcuucucauggccaccccgcuggagagggcccagcaucugcaaagcucccggcaccgccgagcccuggaca |
| ccaacuauugcuucagcuccacggagaagaacugcugcgugcggcagcuguacauugacuuccgcaaggaccucggcugg |
| aaguggauccacgagcccaagggcuaccaugccaacuucugccucgggcccugccccuacauuuggagccuggacacgcag |
| uacagcaagguccuggcccuguacaaccagcauaacccgggcgccucggggcgccgugcugcgugccgcaggcgcugga |
| gccgcugcccaucguguacuacgugggccgcaagcccaagguggagcagcuguccaacaugaucgugcgcuccugcaagu |
| gcagcugatccggttattttccaccatattgccgtcttttggcaatgtgagggcccggaaacctggccctgtcttcttgacgagcattccta |
| ggggtctttcccctctcgccaaaggaatgcaaggtctgttgaatgtcgtgaaggaagcagttcctctggaagcttcttgaagacaaacaa |
| cgtctgtagcgaccctttgcaggcagcggaaccccccacctggcgacaggtgcctctgcggccaaaagccacgtgtataagatacacc |
| tgcaaaggcggcacaaccccagtgccacgttgtgagttggatagttgtggaaagagtcaaatggctctcctcaagcgtattcaacaagg |
| ggctgaaggatgcccagaaggtaccccattgtatgggatctgatctggggcctcggtgcacatgctttacatgtgtttagtcgaggttaaa |
| aaacgtctaggccccccgaaccacggggacgtggttttcctttgaaaaacacgatgataataggatccatgatgcatagttctgccctgtt |
| gtgttgcttggtgctgttgacgggggttagagcgagtccaggtcaaggcacgcagtctgaaaactcctgtacacacttccccggcaacct |
| ccctaatatgctcagagaccttcgagacgccttctcccgagtaaaaactttctttcagatgaaggaccagctcgacaacttgctgttgaag |
| gaatcactcctcgaagattttaaggggtacctcggttgtcaagctctgtctgaaatgatacaattctatctcgaggaagtcatgcctcaagc |
| ggaaaaccaggacccagatattaaggcccatgtgaatagcctcggcgaaaatcttaaaactcttcgccttagactccgaagatgccatag |
| gtttttgccgtgcgaaaataaatccaaagctgtggaacaggtaaaaaatgcgtttaacaagttgcaagagaagggcatctacaaagcgat |
| gtcagagttcgatatattcataaattatattgaagcatacatgactatgaagatcaggaattaataattctagagtcggggcggccggccgc |
| ttcgagcagacatgataagatacattgatgagtttggacaaaccacaactagaatgcagtgaaaaaaatgctttatttgtgaaatttgtgatg |
| ctattgctttatttgtaaccattataagctgcaataaacaagttaacaacaacaattgcattcattttatgtttcaggttcagggggaggtgtgg |
| gaggttttttaaagcaagtaaaacctctacaaatgtggtaaaatcgataaggatccgaattcgatatcactagtggtaccagtactgaaatgt |
| gtgggcgtggcttaagggtgggaaagaatatataaggtgggggtcttatgtagttttgtatctgttttgcagcagccgccgccgccatgag |
| caccaactcgtttgatggaagcattgtgagctcatatttgacaacgcgcatgcccccatgggccggggtgcgtcagaatgtgatgggctc |
| cagcattgatggtcgccccgtcctgcccgcaaactctactaccttgacctacgagaccgtgtctggaacgccgttggagactgcagcctc |

TABLE 18-continued

| Ad5-TGFβ-RES-IL10 with Plasmid Backbone |
| --- |
| cgccgccgcttcagccgctgcagccaccgcccgcgggattgtgactgactttgctttcctgagcccgcttgcaagcagtgcagcttccc |
| gttcatccgcccgcgatgacaagttgacggctcttttggcacaattggattctttgacccgggaacttaatgtcgtttctcagcagctgttgg |
| atctgcgccagcaggtttctgccctgaaggcttcctcccctcccaatgcggtttaacggtccgggccagagtggccaacataaataaaaa |
| accagactctgtttggatttggatcaagcaagtgtcttgctgtctttatttaggggttttgcgcgcgcggtaggcccgggaccagcggtctc |
| ggtcgttgagggtcctgtgtatttttttccaggacgtggtaaaggtgactctggatgttcagatacatgggcataagcccgtctctggggtgg |
| aggtagcaccactgcagagcttcatgctgcggggtggtgttgtagatgatccagtcgtagcaggagcgctgggcgtggtgcctaaaaat |
| gtctttcagtagcaagctgattgccaggggcaggcccttggtgtaagtgtttacaaagcggttaagctgggatgggtgcatacgtgggga |
| tatgagatgcatcttggactgtatttttaggttggctatgttcccagccatatccctccggggattcatgttgtgcagaaccaccagcacagt |
| gtatccggtgcacttgggaaatttgtcatgtagcttagaaggaaatgcgtggaagaacttggagacgcccttgtgacctccaagattttcc |
| atgcattcgtccataatgatggcaatgggcccacgggcggcggcctgggcgaagatatttctgggatcactaacgtcatagttgtgttcc |
| aggatgagatcgtcataggccatttttacaaagcgcgggcggagggtgccagactgcggtataatggttccatccggcccaggggcgt |
| agttaccctcacagatttgcatttcccacgctttgagttcagatgggggggatcatgtctacctgcggggcgatgaagaaaacggtttccgg |
| ggtaggggagatcagctgggaagaaagcaggttcctgagcagctgcgacttaccgcagccggtgggcccgtaaatcacacctattac |
| cggctgcaactggtagttaagagagctgcagctgccgtcatccctgagcaggggggccacttcgttaagcatgtccctgactcgcatgtt |
| ttccctgaccaaatccgccagaaggcgctcgccgcccagcgatagcagttcttgcaaggaagcaaagtttttcaacggtttgagaccgtc |
| cgccgtaggcatgcttttgagcgtttgaccaagcagttccaggcggtcccacagctcggtcacctgctctacggcatctcgatccagcat |
| atctcctcgtttcgcgggttggggcggctttcgctgtacggcagtagtcggtgctcgtccagacgggccagggtcatgtctttccacggg |
| cgcagggtcctcgtcagcgtagtctgggtcacggtgaaggggtgcgctccgggctgcgcgctggccagggtgcgcttgaggctggtc |
| ctgctggtgctgaagcgctgccggtcttcgccctgcgcgtcggccaggtagcatttgaccatggtgtcatagtccagcccctccgcggc |
| gtggcccttggcgcgcagcttgcccttggaggaggcgccgcacgaggggcagtgcagacttttgagggcgtagagcttgggcgcga |
| gaaataccgattccggggagtaggcatccgcgccgcaggccccgcagacggtctcgcattccacgagccaggtgagctctggccgtt |
| cggggtcaaaaaccaggtttcccccatgcttttttgatgcgtttcttacctctggtttccatgagccggtgtccacgctcggtgacgaaaagg |
| ctgtccgtgtccccgtatacagacttgagaggcctgtcctcgagcggtgttccgcggtcctcctcgtatagaaactcggaccactctgag |
| acaaaggctcgcgtccaggccagcacgaaggaggctaagtgggaggggtagcggtcgttgtccactagggggtccactcgctccag |
| ggtgtgaagacacatgtcgccctcttcggcatcaaggaaggtgattggtttgtaggtgtaggccacgtgaccgggtgttcctgaagggg |
| ggctataaaagggggtgggggcgcgttcgtcctcactctcttccgcatcgctgtctgcgagggccagctgttggggtgagtactccctct |
| gaaaagcgggcatgacttctgcgctaagattgtcagtttccaaaaacgaggaggatttgatattcacctggcccgcggtgatgcctttgag |
| ggtggccgcatccatctggtcagaaaagacaatctttttgttgtcaagcttggtggcaaacgacccgtagagggcgttggacagcaactt |
| ggcgatggagcgcagggtttggtttttgtcgcgatcggcgcgctccttggccgcgatgtttagctgcacgtattcgcgcgcaacgcacc |
| gccattcgggaaagacggtggtgcgctcgtcgggcaccaggtgcacgcgccaaccgcggttgtgcagggtgacaaggtcaacgctg |
| gtggctacctctccgcgtaggcgctcgttggtccagcagaggcggccgcccttgcgcgagcagaatggcggtagggggtctagctgc |
| gtctcgtccggggggtctgcgtccacggtaaagaccccgggcagcaggcgcgcgtcgaagtagtctatcttgcatccttgcaagtctag |
| cgcctgctgccatgcgcgggcggcaagcgcgcgctcgtatgggttgagtgggggaccccatggcatggggtgggtgagcgcggag |
| gcgtacatgccgcaaatgtcgtaaacgtagaggggctctctgagtattccaagatatgtagggtagcatcttccaccgcggatgctggcg |
| cgcacgtaatcgtatagttcgtgcgagggagcgaggaggtcgggaccgaggttgctacgggcgggctgctctgctcggaagactatct |
| gcctgaagatggcatgtgagttggatgatatggttggacgctggaagacgttgaagctggcgtctgtgagacctaccgcgtcacgcacg |
| aaggaggcgtaggagtcgcgcagcttgttgaccagctcggcggtgacctgcacgtctagggcgcagtagtccagggtttccttgatgat |
| gtcatacttatcctgtcccttttttttccacagctcgcggttgaggacaaactcttcgcggtctttccagtactcttggatcggaaacccgtcg |
| gcctccgaacggtaagagcctagcatgtagaactggttgacggcctggtaggcgcagcatcccttttctacgggtagcgcgtatgcctg |

TABLE 18-continued

| Ad5-TGFβ-RES-IL10 with Plasmid Backbone |
| --- |
| cgcggccttccggagcgaggtgtgggtgagcgcaaaggtgtccctgaccatgactttgaggtactggtatttgaagtcagtgtcgtcgc |
| atccgccctgctcccagagcaaaaagtccgtgcgctttttggaacgcggatttggcagggcgaaggtgacatcgttgaagagtatctttc |
| ccgcgcgaggcataaagttgcgtgtgatgcggaagggtcccggcacctcggaacggttgttaattacctgggcggcgagcacgatctc |
| gtcaaagccgttgatgttgtggcccacaatgtaaagttccaagaagcgcgggatgcccttgatggaaggcaattttttaagttcctcgtag |
| gtgagctcttcaggggagctgagcccgtgctctgaaagggcccagtctgcaagatgagggttggaagcgacgaatgagctccacagg |
| tcacgggccattagcatttgcaggtggtcgcgaaaggtcctaaactggcgacctatggccatttttctggggtgatgcagtagaaggtaa |
| gcgggtcttgttcccagcggtcccatccaaggttcgcggctaggtctcgcgcggcagtcactagaggctcatctccgccgaacttcatg |
| accagcatgaagggcacgagctgcttcccaaaggcccccatccaagtataggtctctacatcgtaggtgacaaagagacgctcggtgc |
| gaggatgcgagccgatcgggaagaactggatctcccgccaccaattggaggagtggctattgatgtggtgaaagtagaagtccctgcg |
| acgggccgaacactcgtgctggcttttgtaaaaacgtgcgcagtactggcagcggtgcacgggctgtacatcctgcacgaggttgacct |
| gacgaccgcgcacaaggaagcagagtgggaatttgagcccctcgcctggcgggtttggctggtggtcttctacttcggctgcttgtcctt |
| gaccgtctggctgctcgaggggagttacggtggatcggaccaccacgccgcgcgagcccaaagtccagatgtccgcgcgcggcggt |
| cggagcttgatgacaacatcgcgcagatgggagctgtccatggtctggagctcccgcggcgtcaggtcaggcgggagctcctgcagg |
| tttacctcgcatagacgggtcagggcgcgggctagatccaggtgatacctaatttccaggggctggttggtggcggcgtcgatggcttg |
| caagaggccgcatccccgcggcgcgactacggtaccgcgcggcgggggggccgcgggggtgtccttggatgatgcatctaaa |
| agcggtgacgcgggcgagcccccggaggtagggggggctccggacccgccgggagagggggcaggggcacgtcggcgccgc |
| gcgcgggcaggagctggtgctgcgcgcgtaggttgctggcgaacgcgacgacgcggcggttgatctcctgaatctggcgcctctgcg |
| tgaagacgacgggcccggtgagcttgaacctgaaagagagttcgacagaatcaatttcggtgtcgttgacggcggcctggcgcaaaat |
| ctcctgcacgtctcctgagttgtcttgataggcgatctcggccatgaactgctcgatctcttcctcctggagatctccgcgtccggctcgctc |
| cacggtggcggcgaggtcgttggaaatgcgggccatgagctgcgagaaggcgttgaggcctccctcgttccagacgcggctgtagac |
| cacgccccttcggcatcgcgggcgcgcatgaccacctgcgcgagattgagctccacgtgccgggcgaagacggcgtagtttcgca |
| ggcgctgaaagaggtagttgagggtggtggcggtgtgttctgccacgaagaagtacataacccagcgtcgcaacgtggattcgttgata |
| tcccccaaggcctcaaggcgctccatggcctcgtagaagtccacggcgaagttgaaaaactgggagttgcgcgccgacacggttaact |
| cctcctccagaagacggatgagctcggcgacagtgtcgcgcacctcgcgctcaaaggctacaggggcctcttcttcttcttcaatctcct |
| cttccataagggcctccccttcttcttcttctggcggcggtgggggaggggggacacggcggcgacgacggcgcaccgggaggcgg |
| tcgacaaagcgctcgatcatctccccgcggcgacggcgcatggtctcggtgacggcgcggccgttctcgcgggggcgcagttggaa |
| gacgccgcccgtcatgtcccggttatgggttggcgggggctgccatgcggcagggatacggcgctaacgatgcatctcaacaattgt |
| tgtgtaggtactccgccgccgagggacctgagcgagtccgcatcgaccggatcggaaaacctctcgagaaaggcgtctaaccagtca |
| cagtcgcaaggtaggctgagcaccgtggcgggcggcagcgggcggcggtcggggttgtttctggcggaggtgctgctgatgatgtaa |
| ttaaagtaggcggtcttgagacggcggatggtcgacagaagcaccatgtccttgggtccggcctgctgaatgcgcaggcggtcggcca |
| tgccccaggcttcgttttgacatcggcgcaggtctttgtagtagtcttgcatgagcctttctaccggcacttcttcttctccttcctcttgtcctg |
| catctcttgcatctatcgctgcggcggcggcggagtttggccgtaggtggcgccctcttcctcccatgcgtgtgaccccgaagcccctca |
| tcggctgaagcagggctaggtcggcgacaacgcgctcggctaatatggcctgctgcacctgcgtgagggtagactggaagtcatccat |
| gtccacaaagcggtggtatgcgcccgtgttgatggtgtaagtgcagttggccataacggaccagttaacggtctggtgacccggctgcg |
| agagctcggtgtacctgagacgcgagtaagccctcgagtcaaatacgtagtcgttgcaagtccgcaccaggtactggtatcccaccaaa |
| aagtgcggcggcggctggcggtagaggggccagcgtagggtggccggggctccgggggcgagatcttccaacataaggcgatgat |
| atccgtagatgtacctggacatccaggtgatgccggcggcggtggtggaggcgcgcggaaagtcgcggacgcggttccagatgttgc |
| gcagcggcaaaaagtgctccatggtcgggacgctctggccggtcaggcgcgcgcaatcgttgacgctctagaccgtgcaaaaggag |
| agcctgtaagcgggcactcttccgtggtctggtggataaattcgcaagggtatcatggcggacgaccggggttcgagccccgtatccg |

TABLE 18-continued

| Ad5-TGFβ-RES-IL10 with Plasmid Backbone |
|---|
| gccgtccgccgtgatccatgcggttaccgcccgcgtgtcgaacccaggtgtgcgacgtcagacaacgggggagtgctccttttggcttc |
| cttccaggcgcggcggctgctgcgctagcttttttggccactggccgcgcgcagcgtaagcggttaggctggaaagcgaaagcattaa |
| gtggctcgctccctgtagccggagggttattttccaagggttgagtcgcgggacccccggttcgagtctcggaccggccggactgcgg |
| cgaacgggggtttgcctccccgtcatgcaagaccccgcttgcaaattcctccggaaacagggacgagcccctttttttgcttttcccagatg |
| catccggtgctgcggcagatgcgcccccctcctcagcagcggcaagagcaagagcagcggcagacatgcagggcaccctcccctc |
| ctcctaccgcgtcaggaggggcgacatccgcggttgacgcggcagcagatggtgattacgaacccccgcggcgccgggcccggca |
| ctacctggacttggaggagggcgagggcctggcgcggctaggagcgccctctcctgagcggcacccaagggtgcagctgaagcgt |
| gatacgcgtgaggcgtacgtgccgcggcagaacctgtttcgcgaccgcgagggagaggagcccgaggagatgcgggatcgaaagt |
| tccacgcagggcgcgagctgcggcatggcctgaatcgcgagcggttgctgcgcgaggaggactttgagcccgacgcgcgaaccgg |
| gattagtcccgcgcgcgcacacgtggcggccgccgacctggtaaccgcatacgagcagacggtgaaccaggagattaactttcaaaa |
| aagctttaacaaccacgtgcgtacgcttgtggcgcgcgaggaggtggctataggactgatgcatctgtgggactttgtaagcgcgctgg |
| agcaaaacccaaatagcaagccgctcatggcgcagctgttccttatagtgcagcacagcagggacaacgaggcattcagggatgcgc |
| tgctaaacatagtagagcccgagggccgctggctgctcgatttgataaacatcctgcagagcatagtggtgcaggagcgcagcttgag |
| cctggctgacaaggtggccgccatcaactattccatgcttagcctgggcaagttttacgcccgcaagatataccataccccttacgttccc |
| atagacaaggaggtaaagatcgaggggttctacatgcgcatggcgctgaaggtgcttaccttgagcgacgacctgggcgtttatcgcaa |
| cgagcgcatccacaaggccgtgagcgtgagccggcggcgcgagctcagcgaccgcgagctgatgcacagcctgcaaagggccct |
| ggctggcacgggcagcggcgatagagaggccgagtcctactttgacgcgggcgctgacctgcgctgggccccaagccgacgcgcc |
| ctggaggcagctggggccggacctgggctggcggtggcacccgcgcgcgctggcaacgtcggcggcgtggaggaatatgacgag |
| gacgatgagtacgagccagaggacggcgagtactaagcggtgatgtttctgatcagatgatgcaagacgcaacggacccggcggtgc |
| gggcggcgctgcagagccagccgtccggccttaactccacggacgactggcgccaggtcatggaccgcatcatgtcgctgactgcg |
| cgcaatcctgacgcgttccggcagcagccgcaggccaaccggctctccgcaattctggaagcggtggtcccggcgcgcgcaaaccc |
| cacgcacgagaaggtgctggcgatcgtaaacgcgctggccgaaaacagggccatccggcccgacgaggccggcctggtctacgac |
| gcgctgcttcagcgcgtggctcgttacaacagcggcaacgtgcagaccaacctggaccggctggtgggggatgtgcgcgaggccgt |
| ggcgcagcgtgagcgcgcgcagcagcagggcaacctgggctccatggttgcactaaacgccttcctgagtacacagcccgccaacg |
| tgccgcggggacaggaggactacaccaactttgtgagcgcactgcggctaatggtgactgagacaccgcaaagtgaggtgtaccagt |
| ctgggccagactatttttttccagaccagtagacaaggcctgcagaccgtaaacctgagccaggctttcaaaaacttgcaggggctgtgg |
| ggggtgcgggctcccacaggcgaccgcgcgaccgtgtctagcttgctgacgcccaactcgcgcctgttgctgctgctaatagcgccct |
| tcacggacagtggcagcgtgtcccgggacacatacctaggtcacttgctgacactgtaccgcgaggccataggtcaggcgcatgtgga |
| cgagcatactttccaggagattacaagtgtcagccgcgcgctggggcaggaggacacgggcagcctggaggcaaccctaaactacct |
| gctgaccaaccggcggcagaagatcccctcgttgcacagtttaaacagcgaggaggagcgcattttgcgctacgtgcagcagagcgt |
| gagccttaacctgatgcgcgacggggtaacgcccagcgtggcgctggacatgaccgcgcgcaacatggaaccgggcatgtatgcct |
| caaaccggccgtttatcaaccgcctaatggactacttgcatcgcgcggccgccgtgaaccccgagtatttcaccaatgccatcttgaacc |
| cgcactggctaccgccccctggtttctacaccgggggattcgaggtgcccgagggtaacgatggattcctctgggacgacatagacga |
| cagcgtgttttccccgcaaccgcagaccctgctagagttgcaacagcgcgagcaggcagaggcggcgctgcgaaaggaaagcttcc |
| gcaggccaagcagcttgtccgatctaggcgctgcggccccgcggtcagatgctagtagcccatttccaagcttgatagggtctcttacca |
| gcactcgcaccacccgcccgcgcctgctgggcgaggaggagtacctaaacaactcgctgctgcagccgcagcgcgaaaaaaacctg |
| cctccggcatttcccaacaacgggatagagagcctagtggacaagatgagtagatggaagacgtacgcgcaggagcacagggacgt |
| gccaggcccgcgcccgcccacccgtcgtcaaaggcacgaccgtcagcggggtctggtgtgggaggacgatgactcggcagacgac |
| agcagcgtcctggatttgggagggagtggcaacccgtttgcgcaccttcgccccaggctggggagaatgttttaaaaaaaaaaaaaag |

TABLE 18-continued

| Ad5-TGFβ-RES-IL10 with Plasmid Backbone |
| --- |
| catgatgcaaaataaaaaactcaccaaggccatggcaccgagcgttggttttcttgtattccccttagtatgcggcgcgcggcgatgtatg |
| aggaaggtcctcctccctcctacgagagtgtggtgagcgcggcgccagtggcggcggcgctgggttctcccttcgatgctcccctgga |
| cccgccgtttgtgcctccgcggtacctgcggcctaccggggggagaaacagcatccgttactctgagttggcacccctattcgacacca |
| cccgtgtgtacctggtggacaacaagtcaacggatgtggcatccctgaactaccagaacgaccacagcaactttctgaccacggtcatt |
| caaaacaatgactacagcccgggggaggcaagcacacagaccatcaatcttgacgaccggtcgcactgggggggcgacctgaaaac |
| catcctgcataccaacatgccaaatgtgaacgagttcatgtttaccaataagtttaaggcgcgggtgatggtgtcgcgcttgcctactaag |
| gacaatcaggtggagctgaaatacgagtgggtggagttcacgctgcccgagggcaactactccgagaccatgaccatagaccttatga |
| acaacgcgatcgtggagcactacttgaaagtgggcagacagaacggggttctggaaagcgacatcggggtaaagtttgacacccgca |
| acttcagactggggtttgaccccgtcactggtcttgtcatgcctggggtatatacaaacgaagccttccatccagacatcattttgctgcca |
| ggatgcggggtggacttcacccacagccgcctgagcaacttgttgggcatccgcaagcggcaacccttccaggagggctttaggatca |
| cctacgatgatctggagggtggtaacattcccgcactgttggatgtggacgcctaccaggcgagcttgaaagatgacaccgaacaggg |
| cgggggtggcgcaggcggcagcaacagcagtggcagcggcgcggaagagaactccaacgcggcagccgcggcaatgcagccg |
| gtggaggacatgaacgatcatgccattcgcggcgacacctttgccacacgggctgaggagaagcgcgctgaggccgaagcagcgg |
| ccgaagctgccgcccccgctgcgcaacccgaggtcgagaagcctcagaagaaaccggtgatcaaacccctgacagaggacagcaa |
| gaaacgcagttacaacctaataagcaatgacagcaccttcacccagtaccgcagctggtaccttgcatacaactacggcgaccctcaga |
| ccggaatccgctcatggaccctgctttgcactcctgacgtaacctgcggctcggagcaggtctactggtcgttgccagacatgatgcaag |
| accccgtgaccttccgctccacgcgccagatcagcaactttccggtggtgggcgccgagctgttgcccgtgcactccaagagcttctac |
| aacgaccaggccgtctactcccaactcatccgccagtttacctctctgacccacgtgttcaatcgctttcccgagaaccagattttggcgc |
| gcccgccagccccaccatcaccaccgtcagtgaaaacgttcctgctctcacagatcacgggacgctaccgctgcgcaacagcatcg |
| gaggagtccagcgagtgaccattactgacgccagacgccgcacctgcccctacgtttacaaggccctgggcatagtctcgccgcgcgt |
| cctatcgagccgcactttttgagcaagcatgtccatccttatatcgcccagcaataacacaggctggggcctgcgcttcccaagcaagat |
| gtttggcggggccaagaagcgctccgaccaacacccagtgcgcgtgcgcgggcactaccgcgcgccctggggcgcgcacaaacg |
| cggccgcactgggcgcaccaccgtcgatgacgccatcgacgcggtggtggaggaggcgcgcaactacacgcccacgccgccacc |
| agtgtccacagtggacgcggccattcagaccgtggtgcgcggagcccggcgctatgctaaaatgaagagacggcggaggcgcgtag |
| cacgtcgccaccgccgccgacccggcactgccgcccaacgcgcggcggcggccctgcttaaccgcgcacgtcgcaccggccgac |
| gggcggccatgcgagcagctcgaaggctggccgcgggtattgtcactgtgccccccaggtccaggcgacgagcggccgccgcagc |
| agccgcggccattagtgctatgactcagggtcgcaggggcaacgtgtattgggtgcgcgactcggttagcggcctgcgcgtgcccgtg |
| cgcacccgcccccgcgcaactagattgcaagaaaaaactacttagactcgtactgttgtatgtatccagcggcggcggcgcgcaacg |
| aagctatgtccaagcgcaaaatcaaagaagagatgctccaggtcatcgcgccggagatctatggcccccgaagaaggaagagcag |
| gattacaagccccgaaagctaaagcgggtcaaaaagaaaaagaaagatgatgatgatgaacttgacgacgaggtggaactgctgcac |
| gctaccgcgcccaggcgacgggtacagtggaaaggtcgacgcgtaaaacgtgttttgcgacccggcaccaccgtagtctttacgccc |
| ggtgagcgctccacccgcacctacaagcgcgtgtatgatgaggtgtacggcgacgaggacctgcttgagcaggccaacgagcgcct |
| cggggagtttgcctacggaaagcggcataaggacatgctggcgttgccgctggacgagggcaacccaacacctagcctaaagcccgt |
| aacactgcagcaggtgctgcccgcgcttgcaccgtccgaagaaaagcgcggcctaaagcgcgagtctggtgacttggcacccaccgt |
| gcagctgatggtacccaagcgccagcgactggaagatgtcttggaaaaaatgaccgtggaacctgggctggagcccgaggtccgcgt |
| gcggccaatcaagcaggtggcgccgggactgggcgtgcagaccgtggacgttcagatacccactaccagtagcaccagtattgccac |
| cgccacagagggcatggagacacaaacgtccccggttgcctcagcggtggcggatgccgcggtgcaggcggtcgctgcggccgcg |
| tccaagacctctacggaggtgcaaacggacccgtggatgtttcgcgtttcagccccccggcgcccgcgccgttcgaggaagtacggc |
| gccgccagcgcgctactgcccgaatatgccctacatccttccattgcgcctacccccggctatgtggctacacctaccgccccagaag |

TABLE 18-continued

| Ad5-TGFβ-RES-IL10 with Plasmid Backbone |
| --- |
| acgagcaactacccgacgccgaaccaccactggaacccgccgccgccgtcgccgtcgccagcccgtgctggccccgatttccgtgc |
| gcagggtggctcgcgaaggaggcaggaccctggtgctgccaacagcgcgctaccaccccagcatcgtttaaaagccggtctttgtggt |
| tcttgcagatatggccctcacctgccgcctccgtttcccggtgccgggattccgaggaagaatgcaccgtaggaggggcatggccggc |
| cacggcctgacgggcggcatgcgtcgtgcgcaccaccggcggcggcgcgcgtcgcaccgtcgcatgcgcggcggtatcctgcccc |
| tccttattccactgatcgccgcggcgattggcgccgtgcccggaattgcatccgtggccttgcaggcgcagagacactgattaaaaaca |
| agttgcatgtggaaaaatcaaaataaaaagtctggactctcacgctcgcttggtcctgtaactattttgtagaatggaagacatcaactttgc |
| gtctctggccccgcgacacggctcgcgcccgttcatgggaaactggcaagatatcggcaccagcaatatgagcggtggcgccttcag |
| ctggggctcgctgtggagcggcattaaaaatttcggttccaccgttaagaactatggcagcaaggcctggaacagcagcacaggccag |
| atgctgagggataagttgaaagagcaaaatttccaacaaaaggtggtagatggcctggcctctggcattagcggggtggtggacctgg |
| ccaaccaggcagtgcaaaataagattaacagtaagcttgatccccgccctcccgtagaggagcctccaccggccgtggagacagtgtc |
| tccagaggggcgtggcgaaaagcgtccgcgccccgacagggaagaaactctggtgacgcaaatagacgagcctccctcgtacgag |
| gaggcactaaagcaaggcctgcccaccacccgtcccatcgcgcccatggctaccggagtgctgggccagcacacacccgtaacgct |
| ggacctgcctcccccgccgacacccagcagaaacctgtgctgccaggcccgaccgccgttgttgtaacccgtcctagccgcgcgtc |
| cctgcgccgcgccgccagcggtccgcgatcgttgcggcccgtagccagtggcaactggcaaagcacactgaacagcatcgtgggtct |
| gggggtgcaatccctgaagcgccgacgatgcttctgaatagctaacgtgtcgtatgtgtgtcatgtatgcgtccatgtcgccgccagagg |
| agctgctgagccgccgcgcgcccgctttccaagatggctaccccttcgatgatgccgcagtggtcttacatgcacatctcgggccagga |
| cgcctcggagtacctgagccccgggctggtgcagtttgcccgcgccaccgagacgtacttcagcctgaataacaagtttagaaacccc |
| acggtggcgcctacgcacgacgtgaccacagaccggtcccagcgtttgacgctgcggttcatccctgtggaccgtgaggatactgcgt |
| actcgtacaaggcgcggttcaccctagctgtgggtgataaccgtgtgctggacatggcttccacgtactttgacatccgcggcgtgctgg |
| acaggggccctacttttaagccctactctggcactgcctacaacgccctggctcccaagggtgccccaaatccttgcgaatgggatgaa |
| gctgctactgctcttgaaataaacctagaagaagaggacgatgacaacgaagacgaagtagacgagcaagctgagcagcaaaaaact |
| cacgtatttgggcaggcgccttattctggtataaatattacaaaggagggtattcaaataggtgtcgaaggtcaaacacctaaatatgccg |
| ataaaacatttcaacctgaacctcaaataggagaatctcagtggtacgaaacagaaattaatcatgcagctgggagagtcctaaaaaaga |
| ctaccccaatgaaaccatgttacggttcatatgcaaaacccacaaatgaaaatggagggcaaggcattcttgtaaagcaacaaaatgga |
| aagctagaaagtcaagtggaaatgcaatttttctcaactactgaggcagccgcaggcaatggtgataacttgactcctaaagtggtattgt |
| acagtgaagatgtagatatagaaaccccagacactcatatttcttacatgcccactattaaggaaggtaactcacgagaactaatgggcca |
| acaatctatgcccaacaggcctaattacattgcttttagggacaattttattggtctaatgtattacaacagcacgggtaatatgggtgttctg |
| gcgggccaagcatcgcagttgaatgctgttgtagatttgcaagacagaaacacagagctttcataccagcttttgcttgattccattggtga |
| tagaaccaggtacttttctatgtggaatcaggctgttgacagctatgatccagatgttagaattattgaaaatcatggaactgaagatgaact |
| tccaaattactgctttccactgggaggtgtgattaatacagagactcttaccaaggtaaaacctaaaacaggtcaggaaaatggatggga |
| aaaagatgctacagaattttcagataaaaatgaaataagagttggaaataattttgccatggaaatcaatctaaatgccaacctgtggagaa |
| atttcctgtactccaacatagcgctgtatttgcccgacaagctaaagtacagtccttccaacgtaaaaatttctgataacccaaacacctacg |
| actacatgaacaagcgagtggtggctcccgggctagtggactgctacattaaccttggagcacgctggtcccttgactatatggacaacg |
| tcaacccatttaaccaccaccgcaatgctggcctgcgctaccgctcaatgttgctgggcaatggtcgctatgtgcccttccacatccaggt |
| gcctcagaagttctttgccattaaaaacctccttctcctgccgggctcatacacctacgagtggaacttcaggaaggatgttaacatggttct |
| gcagagctccctaggaaatgacctaagggttgacggagccagcattaagtttgatagcatttgcctttacgccaccttcttccccatggcc |
| cacaacaccgcctccacgcttgaggccatgcttagaaacgacaccaacgaccagtcctttaacgactatctctccgccgccaacatgct |
| ctaccctatacccgccaacgctaccaacgtgcccatatccatcccctcccgcaactgggggctttccgcggctgggccttcacgcgcc |
| ttaagactaaggaaaccccatcactgggctcgggctacgacccttattacacctactctggctctataccctacctagatggaacctttac |

TABLE 18-continued

| Ad5-TGFβ-RES-IL10 with Plasmid Backbone |
| --- |
| ctcaaccacacctttaagaaggtggccattacctttgactcttctgtcagctggcctggcaatgaccgcctgcttacccccaacgagtttga |
| aattaagcgctcagttgacggggagggttacaacgttgcccagtgtaacatgaccaaagactggttcctggtacaaatgctagctaactat |
| aacattggctaccagggcttctatatcccagagagctacaaggaccgcatgtactccttctttagaaacttccagcccatgagccgtcagg |
| tggtggatgatactaaatacaaggactaccaacaggtgggcatcctacaccaacacaacaactctggatttgttggctaccttgcccccca |
| ccatgcgcgaaggacaggcctaccctgctaacttcccctatccgcttataggcaagaccgcagttgacagcattacccagaaaaagtttc |
| tttgcgatcgcaccctttggcgcatcccattctccagtaactttatgtccatgggcgcactcacagacctgggccaaaaccttctctacgcc |
| aactccgcccacgcgctagacatgacttttgaggtggatcccatggacgagcccacccttctttatgttttgtttgaagtctttgacgtggtc |
| cgtgtgcaccagccgcaccgcggcgtcatcgaaaccgtgtacctgcgcacgcccttctcggccggcaacgccacaacataaagaagc |
| aagcaacatcaacaacagctgccgccatgggctccagtgagcaggaactgaaagccattgtcaaagatcttggttgtgggccatatttttt |
| gggcacctatgacaagcgctttccaggctttgtttctccacacaagctcgcctgcgccatagtcaatacggccggtcgcgagactggg |
| gcgtacactggatggcctttgcctggaacccgcactcaaaaacatgctacctctttgagccctttggcttttctgaccagcgactcaagca |
| ggtttaccagtttgagtacgagtcactcctgcgccgtagcgccattgcttcttcccccgaccgctgtataacgctggaaaagtccacccaa |
| agcgtacaggggcccaactcggccgcctgtggactattctgctgcatgtttctccacgcctttgccaactggccccaaactcccatggat |
| cacaaccccaccatgaaccttattaccggggtacccaactccatgctcaacagtccccaggtacagcccaccctgcgtcgcaaccagg |
| aacagctctacagcttcctggagcgccactcgccctacttccgcagccacagtgcgcagattaggagcgccacttctttttgtcacttgaa |
| aaacatgtaaaaataatgtactagagacactttcaataaaggcaaatgcttttatttgtacactctcgggtgattatttacccccacccttgcc |
| gtctgcgccgtttaaaaatcaaaggggttctgccgcgcatcgctatgcgccactggcagggacacgttgcgatactggtgtttagtgctc |
| cacttaaactcaggcacaaccatccgcggcagctcggtgaagttttcactccacaggctgcgcaccatcaccaacgcgtttagcaggtc |
| gggcgccgatatcttgaagtcgcagttggggcctccgccctgcgcgcgcgagttgcgatacacagggttgcagcactggaacactatc |
| agcgccgggtggtgcacgctggccagcacgctcttgtcggagatcagatccgcgtccaggtcctccgcgttgctcagggcgaacgga |
| gtcaactttggtagctgccttcccaaaaagggcgcgtgcccaggctttgagttgcactcgcaccgtagtggcatcaaaaggtgaccgtg |
| cccggtctgggcgttaggatacagcgcctgcataaaagccttgatctgcttaaaagccacctgagcctttgcgccttcagagaagaacat |
| gccgcaagacttgccggaaaactgattggccggacacgcggcgtcgtgcacgcagcaccttgcgtcggtgttggagatctgcaccac |
| atttcggccccaccggttcttcacgatcttggccttgctagactgctccttcagcgcgcgctgcccgttttcgctcgtcacatccatttcaatc |
| acgtgctccttatttatcataatgcttccgtgtagacacttaagctcgccttcgatctcagcgcagcggtgcagccacaacgcgcagcccg |
| tgggctcgtgatgcttgtaggtcacctctgcaaacgactgcaggtacgcctgcaggaatcgccccatcatcgtcacaaaggtcttgttgct |
| ggtgaaggtcagctgcaacccgcggtgctcctcgttcagccaggtcttgcatacggccgccagagcttccacttggtcaggcagtagttt |
| gaagttcgcctttagatcgttatccacgtggtacttgtccatcagcgcgcgcgcagcctccatgcccttctcccacgcagacacgatcgg |
| cacactcagcgggttcatcaccgtaatttcactttccgcttcgctgggctcttcctcttcctcttgcgtccgcataccacgcgccactgggtc |
| gtcttcattcagccgccgcactgtgcgcttacctcctttgccatgcttgattagcaccggtgggttgctgaaacccaccatttgtagcgcca |
| catcttctctttcttcctcgctgtccacgattacctctggtgatggcgggcgctcgggcttgggagaagggcgcttctttttcttcttgggcgc |
| aatggccaaatccgccgccgaggtcgatggccgcgggctgggtgtgcgcggcaccagcgcgtcttgtgatgagtcttcctcgtcctcg |
| gactcgatacgccgcctcatccgcttttttgggggcgcccggggaggcggcggcgacggggacggggacgacacgtcctccatggtt |
| gggggacgtcgcgccgcaccgcgtccgcgctcgggggtggtttcgcgctgctcctcttcccgactggccatttccttctcctataggca |
| gaaaaagatcatggagtcagtcgagaagaaggacagcctaaccgccccctctgagttcgccaccaccgcctccaccgatgccgccaa |
| cgcgcctaccaccttccccgtcgaggcacccccgcttgaggaggaggaagtgattatcgagcaggacccaggttttgtaagcgaagac |
| gacgaggaccgctcagtaccaacagaggataaaaagcaagaccaggacaacgcagaggcaaacgaggaacaagtcgggcgggg |
| ggacgaaaggcatggcgactacctagatgtgggagacgacgtgctgttgaagcatctgcagcgccagtgcgccattatctgcgacgc |
| gttgcaagagcgcagcgatgtgcccctcgccatagcggatgtcagccttgcctacgaacgccacctattctcaccgcgcgtacccccca |

TABLE 18-continued

| Ad5-TGFβ-RES-IL10 with Plasmid Backbone |
| --- |
| aacgccaagaaaacggcacatgcgagcccaacccgcgcctcaacttctaccccgtatttgccgtgccagaggtgcttgccacctatcac |
| atctttttccaaaactgcaagatacccctatcctgccgtgccaaccgcagccgagcggacaagcagctggccttgcggcagggcgctgt |
| catacctgatatcgcctcgctcaacgaagtgccaaaaatctttgagggtcttggacgcgacgagaagcgcgcggcaaacgctctgcaa |
| caggaaaacagcgaaaatgaaagtcactctggagtgttggtggaactcgagggtgacaacgcgcgcctagccgtactaaaacgcagc |
| atcgaggtcacccactttgcctacccggcacttaacctacccccaaggtcatgagcacagtcatgagtgagctgatcgtgcgccgtgc |
| gcagcccctggagagggatgcaaatttgcaagaacaaacagaggagggcctacccgcagttggcgacgagcagctagcgcgctgg |
| cttcaaacgcgcgagcctgccgacttggaggagcgacgcaaactaatgatggccgcagtgctcgttaccgtggagcttgagtgcatgc |
| agcggttctttgctgacccggagatgcagcgcaagctagaggaaacattgcactacacctttcgacagggctacgtacgccaggcctg |
| caagatctccaacgtggagctctgcaacctggtctcctaccttggaattttgcacgaaaaccgccttgggcaaaacgtgcttcattccacg |
| ctcaagggcgaggcgcgccgcgactacgtccgcgactgcgtttacttatttctatgctacacctggcagacggccatgggcgtttggca |
| gcagtgcttggaggagtgcaacctcaaggagctgcagaaactgctaaagcaaaacttgaaggacctatggacggccttcaacgagcg |
| ctccgtggccgcgcacctggcggacatcattttccccgaacgcctgcttaaaaccctgcaacagggtctgccagacttcaccagtcaaa |
| gcatgttgcagaactttaggaactttatcctagagcgctcaggaatcttgcccgccacctgctgtgcacttcctagcgactttgtgcccatta |
| agtaccgcgaatgccctccgccgctttggggccactgctaccttctgcagctagccaactaccttgcctaccactctgacataatggaag |
| acgtgagcggtgacggtctactggagtgtcactgtcgctgcaacctatgcaccccgcaccgctccctggtttgcaattcgcagctgctta |
| acgaaagtcaaattatcggtacctttgagctgcagggtccctcgcctgacgaaaagtccgcggctccggggttgaaactcactccgggg |
| ctgtggacgtcggcttaccttcgcaaatttgtacctgaggactaccacgcccacgagattaggttctacgaagaccaatcccgcccgcct |
| aatgcggagcttaccgcctgcgtcattacccagggccacattcttggccaattgcaagccatcaacaaagcccgccaagagtttctgcta |
| cgaaagggacggggggtttacttggacccccagtccggcgaggagctcaacccaatcccccgccgccgcagccctatcagcagca |
| gccgcgggcccttgcttcccaggatggcacccaaaaagaagctgcagctgccgccgccacccacggacgaggaggaatactggga |
| cagtcaggcagaggaggttttggacgaggaggaggaggacatgatggaagactgggagagcctagacgaggaagcttccgaggtc |
| gaagaggtgtcagacgaaacaccgtcaccctcggtcgcattcccctcgccggcgccccagaaatcggcaaccggttccagcatggct |
| acaacctccgctcctcaggcgccgccggcactgcccgttcgccgacccaaccgtagatgggacaccactggaaccagggccggtaa |
| gtccaagcagccgccgccgttagcccaagagcaacaacagcgccaaggctaccgctcatggcgcgggcacaagaacgccatagttg |
| cttgcttgcaagactgtgggggcaacatctccttcgcccgccgctttcttctctaccatcacggcgtggccttcccccgtaacatcctgcatt |
| actaccgtcatctctacagcccatactgcaccggcggcagcggcagcggcagcaacagcagcggccacacagaagcaaaggcgac |
| cggatagcaagactctgacaaagcccaagaaatccacagcggcggcagcagcaggaggaggagcgctgcgtctggcgcccaacg |
| aacccgtatcgacccgcgagcttagaaacaggatttttcccactctgtatgctatatttcaacagagcaggggccaagaacaagagctga |
| aaataaaaaacaggtctctgcgatccctcacccgcagctgcctgtatcacaaaagcgaagatcagcttcggcgcacgctggaagacgc |
| ggaggctctcttcagtaaatactgcgcgctgactcttaaggactagtttcgcgccctttctcaaatttaagcgcgaaaactacgtcatctcca |
| gcggccacacccggcgccagcacctgttgtcagcgccattatgagcaaggaaattcccacgccctacatgtggagttaccagccacaa |
| atgggacttgcggctggagctgcccaagactactcaacccgaataaactacatgagcgcgggaccccacatgatatcccgggtcaacg |
| gaatacgcgcccaccgaaaccgaattctcctggaacaggcggctattaccaccacacctcgtaataaccttaatccccgtagttggccc |
| gctgccctggtgtaccaggaaagtcccgctcccaccactgtggtacttcccagagacgcccaggccgaagttcagatgactaactcag |
| gggcgcagcttgcgggcggctttcgtcacagggtgcggtcgcccgggcagggtataactcacctgacaatcagagggcgaggtattc |
| agctcaacgacgagtcggtgagctcctcgcttggtctccgtccggacgggacatttcagatcggcggcgccggccgctcttcattcacg |
| cctcgtcaggcaatcctaactctgcagacctcgtcctctgagccgcgctctggaggcattggaactctgcaatttattgaggagtttgtgcc |
| atcggtctactttaaccccttctcgggacctcccggccactatccggatcaatttattcctaactttgacgcggtaaaggactcggcggacg |
| gctacgactgaatgttaagtggccaatgaggcctgacgctaataatagctggtccactgtcgccgccacaagtgctttgcccgcgactcc |

TABLE 18-continued

| Ad5-TGFβ-RES-IL10 with Plasmid Backbone |
|---|
| ggtgagttttgctactttgaattgcccgaggatcatatcgagggcccggcgcacggcgtccggcttaccgcccagggagagcttgcccg |
| tagcctgattcgggagtttacccagcgcccccctgctagttgagcgggacaggggaccctgtgttctcactgtgatttgcaactgtcctaac |
| cttggattacatcaagatccagatcttctagacccgggagcggccgctgtcgacctgcaggatccgaattcgatatcactagtggtaccg |
| atcttattccctttaactaataaaaaaaaataataaagcatcacttacttaaaatcagttagcaaatttctgtccagtttattcagcagcacctcc |
| ttgccctcctcccagctctggtattgcagcttcctcctggctgcaaactttctccacaatctaaagggaatgtcagtttcctcctgttcctgtcc |
| atccgcacccactatcttcatgttgttgcagatgaagcgcgcaagaccgtctgaagataccttcaaccccgtgtatccatatgacacggaa |
| accggtcctccaactgtgccttttcttactcctccctttgtatcccccaatgggtttcaagagagtccccctggggtactctctttgcgcctatc |
| cgaacctctagttacctccaatggcatgcttgcgctcaaaatgggcaacggcctctctctggacgaggccggcaaccttacctcccaaaa |
| tgtaaccactgtgagcccacctctcaaaaaaaccaagtcaaacataaacctggaaatatctgcacccctcacagttacctcagaagccct |
| aactgtggctgccgccgcacctctaatggtcgcgggcaacacactcaccatgcaatcacaggccccgctaaccgtgcacgactccaaa |
| cttagcattgccacccaaggacccctcacagtgtcagaaggaaagctagccctgcaaacatcaggcccccctcaccaccaccgatagca |
| gtacccttactatcactgcctcacccccctctaactactgccactggtagcttgggcattgacttgaaagagcccatttatacacaaaatgga |
| aaactaggactaaagtacggggctcctttgcatgtaacagacgacctaaacactttgaccgtagcaactggtccaggtgtgactattaata |
| atacttccttgcaaactaaagttactggagccttgggttttgattcacaaggcaatatgcaacttaatgtagcaggaggactaaggattgatt |
| ctcaaaacagacgccttatacttgatgttagttatccgtttgatgctcaaaaccaactaaatctaagactaggacagggccctctttttataaa |
| ctcagcccacaacttggatattaactacaacaaaggcctttacttgtttacagcttcaaacaattccaaaaagcttgaggttaacctaagcac |
| tgccaaggggttgatgtttgacgctacagccatagccattaatgcaggagatgggcttgaatttggttcacctaatgcaccaaacacaaat |
| cccctcaaaacaaaaattggccatggcctagaatttgattcaaacaaggctatggttcctaaactaggaactggccttagttttgacagcac |
| aggtgccattacagtaggaaacaaaaataatgataagctaactttgtggaccacaccagctccatctcctaactgtagactaaatgcagag |
| aaagatgctaaactcactttggtcttaacaaaatgtggcagtcaaatacttgctacagtttcagttttggctgttaaaggcagtttggctccaa |
| tatctggaacagttcaaagtgctcatcttattataagatttgacgaaaatggagtgctactaaacaattccttcctggacccagaatattggaa |
| ctttagaaatggagatcttactgaaggcacagcctatacaaacgctgttggatttatgcctaacctatcagcttatccaaaatctcacggtaa |
| aactgccaaaagtaacattgtcagtcaagtttacttaaacggagacaaaactaaacctgtaacactaaccattacactaaacggtacacag |
| gaaacaggagacacaactccaagtgcatactctatgtcattttcatgggactggtctggccacaactacattaatgaaatatttgccacatc |
| ctcttacactttttcatacattgcccaagaataaagaatcgtttgtgttatgtttcaacgtgtttatttttcaattgcagaaaatttcaagtcatttttc |
| attcagtagtatagccccaccaccacatagcttatacagatcaccgtaccttaatcaaactcacagaaccctagtattcaacctgccacctc |
| cctcccaacacacagagtacacagtcctttctccccggctggccttaaaaagcatcatatcatgggtaacagacatattcttaggtgttatat |
| tccacacggtttcctgtcgagccaaacgctcatcagtgatattaataaactccccgggcagctcacttaagttcatgtcgctgtccagctgc |
| tgagccacaggctgctgtccaacttgcggttgcttaacgggcggcgaaggagaagtccacgcctacatgggggtagagtcataatcgt |
| gcatcaggatagggcggtggtgctgcagcagcgcgcgaataaactgctgccgccgccgctccgtcctgcaggaatacaacatggca |
| gtggtctcctcagcgatgattcgcaccgcccgcagcataaggcgccttgtcctccgggcacagcagcgcaccctgatctcacttaaatc |
| agcacagtaactgcagcacagcaccacaatattgttcaaaatcccacagtgcaaggcgctgtatccaaagctcatggcgggggaccaca |
| gaacccacgtggccatcataccacaagcgcaggtagattaagtggcgacccctcataaacacgctggacataaacattacctcttttggc |
| atgttgtaattcaccacctcccggtaccatataaacctctgattaaacatggcgccatccaccaccatcctaaaccagctggccaaaacct |
| gcccgccggctatacactgcagggaaccgggactggaacaatgacagtggagagcccaggactcgtaaccatggatcatcatgctcg |
| tcatgatatcaatgttggcacaacacaggcacacgtgcatacacttcctcaggattacaagctcctcccgcgttagaaccatatcccaggg |
| aacaacccattcctgaatcagcgtaaatcccacactgcagggaagacctcgcacgtaactcacgttgtgcattgtcaaagtgttacattcg |
| ggcagcagcggatgatcctccagtatggtagcgcgggtttctgtctcaaaaggaggtagacgatccctactgtacggagtgcgccgag |
| acaaccgagatcgtgttggtcgtagtgtcatgccaaatggaacgccggacgtagtcatatttcctgaagcaaaaccaggtgcgggcgtg |

TABLE 18-continued

| Ad5-TGFβ-RES-IL10 with Plasmid Backbone |
|---|
| acaaacagatctgcgtctccggtctcgccgcttagatcgctctgtgtagtagttgtagtatatccactctctcaaagcatccaggcgccccc |
| tggcttcgggttctatgtaaactccttcatgcgccgctgccctgataacatccaccaccgcagaataagccacacccagccaacctacac |
| attcgttctgcgagtcacacacgggaggagcgggaagagctggaagaaccatgtttttttttttttattccaaaagattatccaaaacctcaa |
| aatgaagatctattaagtgaacgcgctcccctccggtggcgtggtcaaactctacagccaaagaacagataatggcatttgtaagatgttg |
| cacaatggcttccaaaaggcaaacggccctcacgtccaagtggacgtaaaggctaaacccttcagggtgaatctcctctataaacattcc |
| agcaccttcaaccatgcccaaataattctcatctcgccaccttctcaatatatctctaagcaaatcccgaatattaagtccggccattgtaaa |
| aatctgctccagagcgccctccaccttcagcctcaagcagcgaatcatgattgcaaaaattcaggttcctcacagacctgtataagattca |
| aaagcggaacattaacaaaaataccgcgatcccgtaggtcccttcgcagggccagctgaacataatcgtgcaggtctgcacggaccag |
| cgcggccacttccccgccaggaaccatgacaaaagaacccacactgattatgacacgcatactcggagctatgctaaccagcgtagcc |
| ccgatgtaagcttgttgcatgggcggcgatataaaatgcaaggtgctgctcaaaaaatcaggcaaagcctcgcgcaaaaaagaaagca |
| catcgtagtcatgctcatgcagataaaggcaggtaagctccggaaccaccacagaaaaagacaccatttttctctcaaacatgtctgcgg |
| gtttctgcataaacacaaaataaaataacaaaaaaacatttaaacattagaagcctgtcttacaacaggaaaaacaacccttataagcataa |
| gacggactacggccatgccggcgtgaccgtaaaaaaactggtcaccgtgattaaaaagcaccaccgacagctcctcggtcatgtccgg |
| agtcataatgtaagactcggtaaacacatcaggttgattcacatcggtcagtgctaaaaagcgaccgaaatagcccgggggaatacata |
| cccgcaggcgtagagacaacattacagcccccataggaggtataacaaaattaataggagagaaaaacacataaacacctgaaaaac |
| cctcctgcctaggcaaaatagcaccctcccgctccagaacaacatacagcgcttccacagcggcagccataacagtcagccttaccagt |
| aaaaaagaaaacctattaaaaaaacaccactcgacacggcaccagctcaatcagtcacagtgtaaaaaagggccaagtgcagagcga |
| gtatatataggactaaaaaatgacgtaacggttaaagtccacaaaaaacacccagaaaaccgcacgcgaacctacgcccagaaacga |
| aagccaaaaaacccacaacttcctcaaatcgtcacttccgttttcccacgttacgtaacttcccattttaagaaaactacaattcccaacaca |
| tacaagttactccgccctaaaacctacgtcacccgccccgttcccacgccccgcgccacgtcacaaactccacccccctcattatcatattg |
| gcttcaatccaaaataaggtatattattgatgatgttaatttgggccattagacttgaagtcaagcggccgcttacaactggaccttgctggt |
| acatagaactgattaactgaccatttaaatcataccaacatggtcaaataaaacgaaaggctcagtcgaaagactgggcctttcgttttaat |
| ctgatcggcacgtaagaggttccaactttcaccataatgaaataagatcactaccgggcgtatttttttgagttatcgagattttcaggagcta |
| aggaagctaaaatgagccatattcaacgggaaacgtcttgctcgaggccgcgattaaattccaacatggatgctgatttatatgggtataa |
| atgggctcgcgataatgtcgggcaatcaggtgcgacaatctatcgattgtatgggaagcccgatgcgccagagttgtttctgaaacatgg |
| caaaggtagcgttgccaatgatgttacagatgagatggtcaggctaaactggctgacggaatttatgcctcttccgaccatcaagcatttta |
| tccgtactcctgatgatgcatggttactcaccactgcgatccccagggaaaacagcattccaggtattagaagaatatcctgattcaggtga |
| aaatattgttgatgcgctggcagtgttcctgcgccggttgcattcgattcctgtttgtaattgtccttttaacggcgatcgcgtatttcgtctcgc |
| tcaggcgcaatcacgaatgaataacggtttggttggtgcgagtgattttgatgacgagcgtaatggctggcctgttgaacaagtctggaaa |
| gaaatgcataaacttttgccattctcaccggattcagtcgtcactcatggtgatttctcacttgataaccttatttttgacgaggggaaattaat |
| aggttgtattgatgttggacgagtcggaatcgcagaccgataccaggatcttgccatcctatggaactgcctcggtgagttttctccttcatt |
| acagaaacggctttttcaaaaatatggtattgataatcctgatatgaataaattgcagtttcacttgatgctcgatgagtttttctaacctaggtg |
| acagaagtcaaaagcctccggtcggaggcttttgactttctgctagatctgtttcaatgcggtgaagggccaggcagctggggattatgtc |
| gagacccggccagcatgttggttttatcgcatattcagcgttgtcgcgtttacccaggtaaaatggaagcagtgtatcgtctgcgtgaatgt |
| gcaaatcaggaacgtaaccgtggtacatagatgcagtcccttgcgggtcgttcccttcaacgagtaggacgcggtgcccttgcaaggct |
| aaccattgcgcctggtgtactgcagatgaggttttataaacccctcccttgtgtgacataacggaaagtacaaccgggtttttatcgtcaggt |
| ctttggtttgggttaccaaacacactccgcatatggctaatttggtcaattgtgtagccagcgcgacgttctactcggcccctcatctcaaaa |
| tcaggagccggtagacgaccagctttttccgcgtctctgatagcctgcggtgttacgccgatcaggtctgcaacttctgttataccccagc |
| ggcgagtaatacgacgcgcttccgggctgtcatcgccgaactgtgcgatggcaatagcgcgcgtcatttcctgaccgcgattgatacag |

TABLE 18-continued

| Ad5-TGFβ-RES-IL10 with Plasmid Backbone |
|---|
| tctttcagcaaattaattaacgacatcctgtttcctctcaaacatgcccttatctttgtgtttttcatcatactttacgtttttaaagcaaagcaacat |
| aaaaaaagcaaagtgacttagaaaacgcaaagttaaggttcaaatcaatttttgatgcgctacagaagctatttagcttcatctaagcgca |
| acggtattacttacgttggtatatttaaaacctaacttaatgattttaaatgataataaatcataccaattgctatcaaaagttaagcgaacatgc |
| tgattttcacgctgtttatacactttgaggcatctctatctcttccgtctctatattgaaacacaatcaaagaacatcaatccatgtgacatcccc |
| cactatctaagaacaccataacagaacacaacataggaatgcaacattaatgtatcaataattcggaacatatgcactatatcatatctcaat |
| tacggaacatatcagcacacaattgcccattatacgc |

TABLE 19

| Ad5-TGFβ-RES-IL10 No Plasmid Backbone |
|---|
| (SEQ ID NO: 19) |
| catcatcaataatataccttattttggattgaagccaatatgataatgaggggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccactagttattaatagtaatcaattacggggtcattagttcatagcccatatatggagttccgc |
| gttacataacttacggtaaatggcccgcctggctgaccgcccaacgacccccgcccattgacgtcaataatgacgtatgttcccatagta |
| acgccaatagggactttccattgacgtcaatgggtggagtatttacggtaaactgcccacttggcagtacatcaagtgtatcatatgccaa |
| gtacgccccctattgacgtcaatgacggtaaatggcccgcctggcattatgcccagtacatgaccttatgggactttcctacttggcagtac |
| atctacgtattagtcatcgctattaccatggtcgaggtgagccccacgttctgcttcactctccccatctcccccccctccccacccccaatt |
| ttgtatttatttattttttaattattttgtgcagcgatgggggcgggggggggggggggggggcgcaggcggggggggcggggcgag |
| gggcggggggggcgaggcggagaggtgcggcggcagccaatcagagcggcgcgctccgaaagtttccttttatggcgaggcgg |
| cggcggcggcggccctataaaaagcgaagcgcgcggggggggagtcgctgcgttgccttcgccccgtgccccgctccgcgccg |
| cctcgcgccgcccgccccggctctgactgaccgcgttactcccacaggtgagcgggggggacggcccttctcctccgggctgtaatta |
| gcgcttggtttaatgacggctcgtttcttttctgtggctgcgtgaaagccttaaagggctccgggggggccctttgtgcggggggggagcg |
| gctcggggggtgcgtgcgtgtgtgtgtgcgtggggagcgccgcgtgcggctccgcgctgcccggcggctgtgagcgctgcgggcg |
| cggcgcggggctttgtgcgctccgcagtgtgcgcgaggggagcgcggccgggggcggtgccccgcggtgcgggggggggctgcg |
| aggggaacaaaggctgcgtgcggggtgtgtgcgtgggggggtgagcagggggtgtgggcgcgtcggtcgggctgcaacccccccct |
| gcacccccctccccgagttgctgagcacggcccggcttcgggtgcggggctccgtacggggcgtggcgcggggctcgccgtgccg |
| ggggggggtggcggcaggtgggggtgccgggcggggggggccgcctcgggccggggagggctcgggggagggggcgcgg |
| cggcccccggagcgccggcggctgtcgaggcgcggcgagccgcagccattgccttttatggtaatcgtgcgagagggcgcaggga |
| cttcctttgtcccaaatctgtgcggagccgaaatctgggaggcgccgccgcaccccctctagcgggcgcggggcgaagcggtgcggc |
| gccggcaggaaggaaatgggcggggagggccttcgtgcgtcgccgcgccgccgtccccttctccctctccagcctcggggctgtcc |
| gcgggggggacggctgccttcgggggggacggggcagggcggggttcggcttctggcgtgtgaccggcggctctagagcctctgcta |
| accatgttcatgccttcttctttttcctacagctcctgggcaacgtgctggttattgtgctgtctcatcattttggcaaagaattccgctgcgact |
| cggcggagtcccggcggcgcgtccttgttctaacccggcgcgccagcttggcaatccggtactgttggtaaagccaccaugccgccc |
| uccgggcugcggcugcugccgcugcugcuaccgcugcuguggcuacuggugcugacgccuggccggggggggac |
| uauccaccugcaagacuaucgacauggagcugguggaagcggaagcgcaucgaggccauccgcggccagauccuguccaagc |
| ugcggcucgccagcccccgagccaggggaggugccgcccggcccgcugcccgaggccgugcucgcccuguacaacagca |

TABLE 19-continued

| Ad5-TGFβ-RES-IL10 No Plasmid Backbone |
|---|
| cccgcgaccgggugggccggggagagugcagaaccggagcccgagccugaggccgacuacuacgccaaggaggucacccgcg |
| ugcuaaugguggaaacccacaacgaaaucuaugacaaguucaagcagaguacacacagcauauauauguucuucaacacau |
| cagagcuccgagaagcgguaccugaacccguguugcucucccgggcagagcugcgucugcugaggcucaaguuaaaagug |
| gagcagcacguggagcuguaccagaaauacagcaacaauuccuggcgauaccucagcaaccggcugcuggcacccagcgac |
| ucgccagagugguuaucuuuugaugucaccggaguugugggcagugguugagccguggaggggaaauugagggcuuuc |
| gccuuagcgcccacugcuccugugacagcagggauaacacacugcaaguggacaucaacggguucacuaccggccgccgag |
| gugaccuggccaccauucauggcaugaaccggccuuuccugcuucucauggccaccccgcuggagagggcccagcaucug |
| caaagcucccggcaccgccgagcccuggacaccaacuauugcuucagcuccacggagaagaacugcugcgugcggcagcug |
| uacauugacuuccgcaaggaccucggcuggaaguggauccacgagcccaagggcuaccaugccaacuucugccucgggccc |
| ugccccuacauuuggagccuggacacgcaguacagcaagguccuggcccuguacaaccagcauaacccgggcgccucggcg |
| gcgccgugcugcgugccgcaggcgcuggagccgcugcccaucguguacuacgugggccgcaagcccaagguggagcagcu |
| guccaacaugaucgugcgcuccugcaagugcagcugatccggttattttccaccatattgccgtcttttggcaatgtgagggcccgga |
| aacctggccctgtcttcttgacgagcattcctaggggtctttcccctctcgccaaaggaatgcaaggtctgttgaatgtcgtgaaggaagc |
| agttcctctggaagcttcttgaagacaaacaacgtctgtagcgaccctttgcaggcagcggaaccccccacctggcgacaggtgcctct |
| gcggccaaaagccacgtgtataagatacacctgcaaaggcggcacaaccccagtgccacgttgtgagttggatagttgtggaaagagt |
| caaatggctctcctcaagcgtattcaacaaggggctgaaggatgcccagaaggtaccccattgtatgggatctgatctggggcctcggt |
| gcacatgctttacatgtgtttagtcgaggttaaaaaacgtctaggccccccgaaccacggggacgtggttttcctttgaaaaacacgatga |
| taataggatccatgatgcatagttctgccctgttgtgttgcttggtgctgttgacggggttagagcgagtccaggtcaaggcacgcagtct |
| gaaaactcctgtacacacttccccggcaacctccctaatatgctcagagaccttcgagacgccttctcccgagtaaaaactttctttcagat |
| gaaggaccagctcgacaacttgctgttgaaggaatcactcctcgaagattttaaggggtacctcggttgtcaagctctgtctgaaatgata |
| caattctatctcgaggaagtcatgcctcaagcggaaaaccaggacccagatattaaggcccatgtgaatagcctcggcgaaaatcttaaa |
| actcttcgccttagactccgaagatgccataggtttttgccgtgcgaaaataaatccaaagctgtggaacaggtaaaaaatgcgtttaaca |
| agttgcaagagaagggcatctacaaagcgatgtcagagttcgatatattcataaattatattgaagcatacatgactatgaagatcaggaat |
| taataattctagagtcggggcggccggccgcttcgagcagacatgataagatacattgatgagtttggacaaaccacaactagaatgca |
| gtgaaaaaaatgctttatttgtgaaatttgtgatgctattgctttatttgtaaccattataagctgcaataaacaagttaacaacaacaattgcatt |
| cattttatgtttcaggttcagggggaggtgtgggaggttttttaaagcaagtaaaacctctacaaatgtggtaaaatcgataaggatccgaat |
| tcgatatcactagtggtaccagtactgaaatgtgtgggcgtggcttaagggtgggaaagaatatataaggtgggggtcttatgtagttttgt |
| atctgttttgcagcagccgccgccgccatgagcaccaactcgtttgatggaagcattgtgagctcatatttgacaacgcgcatgcccccat |
| gggccggggtgcgtcagaatgtgatgggctccagcattgatggtcgccccgtcctgcccgcaaactctactaccttgacctacgagacc |
| gtgtctggaacgccgttggagactgcagcctccgccgccgcttcagccgctgcagccaccgcccgcgggattgtgactgactttgcttt |
| cctgagcccgcttgcaagcagtgcagcttcccgttcatccgcccgcgatgacaagttgacggctcttttggcacaattggattctttgacc |
| cgggaacttaatgtcgtttctcagcagctgttggatctgcgccagcaggtttctgccctgaaggcttcctcccctcccaatgcggtttaacg |
| gtccgggccagagtggccaacataaataaaaaaccagactctgtttggatttggatcaagcaagtgtcttgctgtctttatttaggggttttg |
| cgcgcgcggtaggcccgggaccagcggtctcggtcgttgagggtcctgtgtatttttttccaggacgtggtaaaggtgactctggatgttc |
| agatacatgggcataagcccgtctctgggggggaggtagcaccactgcagagcttcatgctgcggggtggtgttgtagatgatccagtc |
| gtagcaggagcgctgggcgtggtgcctaaaaatgtctttcagtagcaagctgattgccaggggcaggcccttggtgtaagtgtttacaaa |
| gcggttaagctgggatgggtgcatacgtggggatatgagatgcatcttggactgtatttttaggttggctatgttcccagccatatccctcc |
| ggggattcatgttgtgcagaaccaccagcacagtgtatccggtgcacttgggaaatttgtcatgtagcttagaaggaaatgcgtggaaga |
| acttggagacgcccttgtgacctccaagattttccatgcattcgtccataatgatggcaatgggcccacgggcggcggcctgggcgaag |

TABLE 19-continued

| Ad5-TGFβ-RES-IL10 No Plasmid Backbone |
| --- |
| atatttctgggatcactaacgtcatagttgtgttccaggatgagatcgtcataggccatttttacaaagcgcgggcggagggtgccagact |
| gcggtataatggttccatccggcccaggggcgtagttaccctcacagatttgcatttcccacgctttgagttcagatggggggatcatgtct |
| acctgcggggcgatgaagaaaacggtttccggggtaggggagatcagctgggaagaaagcaggttcctgagcagctgcgacttacc |
| gcagccggtgggcccgtaaatcacacctattaccggctgcaactggtagttaagagagctgcagctgccgtcatccctgagcaggggg |
| gccacttcgttaagcatgtccctgactcgcatgttttccctgaccaaatccgccagaaggcgctcgccgcccagcgatagcagttcttgca |
| aggaagcaaagtttttcaacggtttgagaccgtccgccgtaggcatgcttttgagcgtttgaccaagcagttccaggcggtcccacagct |
| cggtcacctgctctacggcatctcgatccagcatatctcctcgtttcgcgggttggggcggctttcgctgtacggcagtagtcggtgctcg |
| tccagacgggccagggtcatgtctttccacgggcgcagggtcctcgtcagcgtagtctgggtcacggtgaaggggtgcgctccgggct |
| gcgcgctggccagggtgcgcttgaggctggtcctgctggtgctgaagcgctgccggtcttcgccctgcgcgtcggccaggtagcattt |
| gaccatggtgtcatagtccagcccctccgcggcgtggcccttggcgcgcagcttgcccttggaggaggcgccgcacgaggggcagt |
| gcagacttttgagggcgtagagcttgggcgcgagaaataccgattccggggagtaggcatccgcgccgcaggccccgcagacggtc |
| tcgcattccacgagccaggtgagctctggccgttcggggtcaaaaaccaggtttcccccatgctttttgatgcgtttcttacctctggtttcc |
| atgagccggtgtccacgctcggtgacgaaaaggctgtccgtgtccccgtatacagacttgagaggcctgtcctcgagcggtgttccgcg |
| gtcctcctcgtatagaaactcggaccactctgagacaaaggctcgcgtccaggccagcacgaaggaggctaagtgggaggggtagc |
| ggtcgttgtccactagggggtccactcgctccagggtgtgaagacacatgtcgccctcttcggcatcaaggaaggtgattggtttgtagg |
| tgtaggccacgtgaccgggtgttcctgaaggggggctataaaagggggtgggggcgcgttcgtcctcactctcttccgcatcgctgtct |
| gcgagggccagctgttggggtgagtactccctctgaaaagcgggcatgacttctgcgctaagattgtcagtttccaaaaacgaggagga |
| tttgatattcacctggcccgcggtgatgcctttgagggtggccgcatccatctggtcagaaaagacaatctttttgttgtcaagcttggtggc |
| aaacgacccgtagagggcgttggacagcaacttggcgatggagcgcagggtttggtttttgtcgcgatcggcgcgctccttggccgcg |
| atgtttagctgcacgtattcgcgcgcaacgcaccgccattcgggaaagacggtggtgcgctcgtcgggcaccaggtgcacgcgccaa |
| ccgcggttgtgcagggtgacaaggtcaacgctggtggctacctctccgcgtaggcgctcgttggtccagcagaggcggccgcccttgc |
| gcgagcagaatggcggtagggggtctagctgcgtctcgtccgggggggtctgcgtccacggtaaagaccccgggcagcaggcgcgc |
| gtcgaagtagtctatcttgcatccttgcaagtctagcgcctgctgccatgcgcgggcggcaagcgcgcgctcgtatgggttgagtgggg |
| gaccccatggcatggggtgggtgagcgcggaggcgtacatgccgcaaatgtcgtaaacgtagaggggctctctgagtattccaagata |
| tgtagggtagcatcttccaccgcggatgctggcgcgcacgtaatcgtatagttcgtgcgagggagcgaggaggtcgggaccgaggttg |
| ctacgggcgggctgctctgctcggaagactatctgcctgaagatggcatgtgagttggatgatatggttggacgctggaagacgttgaa |
| gctggcgtctgtgagacctaccgcgtcacgcacgaaggaggcgtaggagtcgcgcagcttgttgaccagctcggcggtgacctgcac |
| gtctagggcgcagtagtccagggtttccttgatgatgtcatacttatcctgtcccttttttttccacagctcgcggttgaggacaaactcttcg |
| cggtctttccagtactcttggatcggaaacccgtcggcctccgaacggtaagagcctagcatgtagaactggttgacggcctggtaggc |
| gcagcatcccttttctacgggtagcgcgtatgcctgcgcggccttccggagcgaggtgtgggtgagcgcaaaggtgtccctgaccatg |
| actttgaggtactggtatttgaagtcagtgtcgtcgcatccgccctgctcccagagcaaaaagtccgtgcgctttttggaacgcggatttgg |
| cagggcgaaggtgacatcgttgaagagtatctttcccgcgcgaggcataaagttgcgtgtgatgcggaagggtcccggcacctcggaa |
| cggttgttaattacctgggcggcgagcacgatctcgtcaaagccgttgatgttgtggcccacaatgtaaagttccaagaagcgcgggatg |
| cccttgatggaaggcaatttttttaagttcctcgtaggtgagctcttcaggggagctgagcccgtgctctgaaagggcccagtctgcaagat |
| gagggttggaagcgacgaatgagctccacaggtcacgggccattagcatttgcaggtggtcgcgaaaggtcctaaactggcgacctat |
| ggccatttttttctggggtgatgcagtagaaggtaagcgggtcttgttcccagcggtcccatccaaggttcgcggctaggtctcgcgcggc |
| agtcactagaggctcatctccgccgaacttcatgaccagcatgaagggcacgagctgcttcccaaaggcccccatccaagtataggtct |
| ctacatcgtaggtgacaaagagacgctcggtgcgaggatgcgagccgatcgggaagaactggatctcccgccaccaattggaggagt |
| ggctattgatgtggtgaaagtagaagtccctgcgacgggccgaacactcgtgctggcttttgtaaaaacgtgcgcagtactggcagcgg |

TABLE 19-continued

| Ad5-TGFβ-RES-IL10 No Plasmid Backbone |
|---|
| tgcacgggctgtacatcctgcacgaggttgacctgacgaccgcgcacaaggaagcagagtgggaatttgagcccctcgcctggcggg |
| tttggctggtggtcttctacttcggctgcttgtccttgaccgtctggctgctcgaggggagttacggtggatcggaccaccacgccgcgcg |
| agcccaaagtccagatgtccgcgcgcggcggtcggagcttgatgacaacatcgcgcagatgggagctgtccatggtctggagctccc |
| gcggcgtcaggtcaggcgggagctcctgcaggtttacctcgcatagacgggtcagggcgcgggctagatccaggtgatacctaatttc |
| caggggctggttggtggcggcgtcgatggcttgcaagaggccgcatccccgcggcgcgactacggtaccgcgcggcgggcggtgg |
| gccgcgggggtgtccttggatgatgcatctaaaagcggtgacgcgggcgagcccccggaggtagggggggctccggacccgccgg |
| gagaggggggcaggggcacgtcggcgccgcgcgcgggcaggagctggtgctgcgcgcgtaggttgctggcgaacgcgacgacgc |
| ggcggttgatctcctgaatctggcgcctctgcgtgaagacgacgggcccggtgagcttgaacctgaaagagagttcgacagaatcaatt |
| tcggtgtcgttgacggcggcctggcgcaaaatctcctgcacgtctcctgagttgtcttgataggcgatctcggccatgaactgctcgatct |
| cttcctcctggagatctccgcgtccggctcgctccacggtggcggcgaggtcgttggaaatgcgggccatgagctgcgagaaggcgtt |
| gaggcctccctcgttccagacgcggctgtagaccacgcccccttcggcatcgcgggcgcgcatgaccacctgcgcgagattgagctc |
| cacgtgccgggcgaagacggcgtagtttcgcaggcgctgaaagaggtagttgagggtggtggcggtgtgttctgccacgaagaagta |
| cataacccagcgtcgcaacgtggattcgttgatatcccccaaggcctcaaggcgctccatggcctcgtagaagtccacggcgaagttga |
| aaaactgggagttgcgcgccgacacggttaactcctcctccagaagacggatgagctcggcgacagtgtcgcgcacctcgcgctcaa |
| aggctacaggggcctcttcttcttcttcaatctcctcttccataagggcctccccttcttcttcttctggcggcggtgggggaggggggaca |
| cggcggcgacgacggcgcaccgggaggcggtcgacaaagcgctcgatcatctccccgcggcgacggcgcatggtctcggtgacg |
| gcgcggccgttctcgcgggggcgcagttggaagacgccgcccgtcatgtcccggttatgggttggcggggggctgccatgcggcag |
| ggatacggcgctaacgatgcatctcaacaattgttgtgtaggtactccgccgccgagggacctgagcgagtccgcatcgaccggatcg |
| gaaaacctctcgagaaaggcgtctaaccagtcacagtcgcaaggtaggctgagcaccgtggcgggcggcagcgggcggcggtcgg |
| ggttgtttctggcggaggtgctgctgatgatgtaattaaagtaggcggtcttgagacggcggatggtcgacagaagcaccatgtccttgg |
| gtccggcctgctgaatgcgcaggcggtcggccatgccccaggcttcgttttgacatcggcgcaggtctttgtagtagtcttgcatgagcct |
| ttctaccggcacttcttcttctccttcctcttgtcctgcatctcttgcatctatcgctgcggcggcggcggagtttggccgtaggtggcgccct |
| cttcctcccatgcgtgtgaccccgaagcccctcatcggctgaagcagggctaggtcggcgacaacgcgctcggctaatatggcctgct |
| gcacctgcgtgagggtagactggaagtcatccatgtccacaaagcggtggtatgcgcccgtgttgatggtgtaagtgcagttggccata |
| acggaccagttaacggtctggtgacccggctgcgagagctcggtgtacctgagacgcgagtaagccctcgagtcaaatacgtagtcgt |
| tgcaagtccgcaccaggtactggtatcccaccaaaaagtgcggcggcggctggcggtagaggggccagcgtagggtggccggggc |
| tccgggggcgagatcttccaacataaggcgatgatatccgtagatgtacctggacatccaggtgatgccggcggcggtggtggaggc |
| gcgcggaaagtcgcggacgcggttccagatgttgcgcagcggcaaaaagtgctccatggtcgggacgctctggccggtcaggcgcg |
| cgcaatcgttgacgctctagaccgtgcaaaaggagagcctgtaagcgggcactcttccgtggtctggtggataaattcgcaagggtatc |
| atggcggacgaccggggttcgagccccgtatccggccgtccgccgtgatccatgcggttaccgcccgcgtgtcgaacccaggtgtgc |
| gacgtcagacaacgggggagtgctccttttggcttccttccaggcgcggcggctgctgcgctagcttttttggccactggccgcgcgca |
| gcgtaagcggttaggctggaaagcgaaagcattaagtggctcgctccctgtagccggagggttattttccaagggttgagtcgcgggac |
| cccccggttcgagtctcggaccggccggactgcggcgaacgggggtttgcctccccgtcatgcaagaccccgcttgcaaattcctccgg |
| aaacagggacgagcccctttttttgcttttcccagatgcatccggtgctgcggcagatgcgcccccctcctcagcagcggcaagagcaag |
| agcagcggcagacatgcagggcaccctcccctcctcctaccgcgtcaggaggggcgacatccgcggttgacgcggcagcagatggt |
| gattacgaaccccgcggcgccgggcccggcactacctggacttggaggagggcgagggcctggcgcggctaggagcgccctctc |
| ctgagcggcacccaagggtgcagctgaagcgtgatacgcgtgaggcgtacgtgccgcggcagaacctgtttcgcgaccgcgaggga |
| gaggagcccgaggagatgcgggatcgaaagttccacgcagggcgcgagctgcggcatggcctgaatcgcgagcggttgctgcgcg |
| aggaggactttgagcccgacgcgcgaaccgggattagtcccgcgcgcgcacacgtggcggccgccgacctggtaaccgcatacga |

TABLE 19-continued

| Ad5-TGFβ-RES-IL10 No Plasmid Backbone |
|---|
| gcagacggtgaaccaggagattaactttcaaaaaagctttaacaaccacgtgcgtacgcttgtggcgcgcgaggaggtggctatagga |
| ctgatgcatctgtgggactttgtaagcgcgctggagcaaaacccaaatagcaagccgctcatggcgcagctgttccttatagtgcagcac |
| agcagggacaacgaggcattcagggatgcgctgctaaacatagtagagcccgagggccgctggctgctcgatttgataaacatcctgc |
| agagcatagtggtgcaggagcgcagcttgagcctggctgacaaggtggccgccatcaactattccatgcttagcctgggcaagttttac |
| gcccgcaagatataccatacccttacgttcccatagacaaggaggtaaagatcgaggggttctacatgcgcatggcgctgaaggtgct |
| taccttgagcgacgacctgggcgtttatcgcaacgagcgcatccacaaggccgtgagcgtgagccggcggcgcgagctcagcgacc |
| gcgagctgatgcacagcctgcaaagggccctggctggcacgggcagcggcgatagagaggccgagtcctactttgacgcgggcgct |
| gacctgcgctgggccccaagccgacgcgccctggaggcagctggggccggacctgggctggcggtggcacccgcgcgcgctggc |
| aacgtcggcggcgtggaggaatatgacgaggacgatgagtacgagccagaggacggcgagtactaagcggtgatgtttctgatcaga |
| tgatgcaagacgcaacggacccggcggtgcgggcggcgctgcagagccagccgtccggccttaactccacggacgactggcgcca |
| ggtcatggaccgcatcatgtcgctgactgcgcgcaatcctgacgcgttccggcagcagccgcaggccaaccggctctccgcaattctg |
| gaagcggtggtcccggcgcgcgcaaaccccacgcacgagaaggtgctggcgatcgtaaacgcgctggccgaaaacagggccatcc |
| ggcccgacgaggccggcctggtctacgacgcgctgcttcagcgcgtggctcgttacaacagcggcaacgtgcagaccaacctggac |
| cggctggtgggggatgtgcgcgaggccgtggcgcagcgtgagcgcgcgcagcagcagggcaacctgggctccatggttgcactaa |
| acgccttcctgagtacacagcccgccaacgtgccgcggggacaggaggactacaccaactttgtgagcgcactgcggctaatggtga |
| ctgagacaccgcaaagtgaggtgtaccagtctgggccagactattttttccagaccagtagacaaggcctgcagaccgtaaacctgagc |
| caggctttcaaaaacttgcaggggctgtggggggtgcgggctcccacaggcgaccgcgcgaccgtgtctagcttgctgacgcccaac |
| tcgcgcctgttgctgctgctaatagcgcccttcacggacagtggcagcgtgtcccgggacacatacctaggtcacttgctgacactgtac |
| cgcgaggccataggtcaggcgcatgtggacgagcatactttccaggagattacaagtgtcagccgcgcgctggggcaggaggacac |
| gggcagcctggaggcaaccctaaactacctgctgaccaaccggcggcagaagatcccctcgttgcacagtttaaacagcgaggagga |
| gcgcattttgcgctacgtgcagcagagcgtgagccttaacctgatgcgcgacggggtaacgcccagcgtggcgctggacatgaccgc |
| gcgcaacatggaaccgggcatgtatgcctcaaaccggccgtttatcaaccgcctaatggactacttgcatcgcgcggccgccgtgaac |
| cccgagtatttcaccaatgccatcttgaacccgcactggctaccgccccctggtttctacaccgggggattcgaggtgcccgagggtaa |
| cgatggattcctctgggacgacatagacgacagcgtgttttccccgcaaccgcagaccctgctagagttgcaacagcgcgagcaggca |
| gaggcggcgctgcgaaaggaaagcttccgcaggccaagcagcttgtccgatctaggcgctgcggccccgcggtcagatgctagtag |
| cccatttccaagcttgatagggtctcttaccagcactcgcaccacccgcccgcgcctgctgggcgaggaggagtacctaaacaactcgc |
| tgctgcagccgcagcgcgaaaaaaacctgcctccggcatttcccaacaacgggatagagagcctagtggacaagatgagtagatgga |
| agacgtacgcgcaggagcacagggacgtgccaggcccgcgcccgcccacccgtcgtcaaaggcacgaccgtcagcggggtctgg |
| tgtgggaggacgatgactcggcagacgacagcagcgtcctggatttgggagggagtggcaacccgtttgcgcaccttcgccccaggc |
| tggggagaatgttttaaaaaaaaaaaaaagcatgatgcaaaataaaaaactcaccaaggccatggcaccgagcgttggttttcttgtattc |
| cccttagtatgcggcgcgcggcgatgtatgaggaaggtcctcctccctcctacgagagtgtggtgagcgcggcgccagtggcggcgg |
| cgctgggttctcccttcgatgctcccctggacccgccgtttgtgcctccgcggtacctgcggcctaccggggggagaaacagcatccgt |
| tactctgagttggcacccctattcgacaccacccgtgtgtacctggtggacaacaagtcaacggatgtggcatccctgaactaccagaac |
| gaccacagcaactttctgaccacggtcattcaaaacaatgactacagcccgggggaggcaagcacacagaccatcaatcttgacgacc |
| ggtcgcactggggcggcgacctgaaaaccatcctgcataccaacatgccaaatgtgaacgagttcatgtttaccaataagtttaaggcgc |
| gggtgatggtgtcgcgcttgcctactaaggacaatcaggtggagctgaaatacgagtgggtggagttcacgctgcccgagggcaacta |
| ctccgagaccatgaccatagaccttatgaacaacgcgatcgtggagcactacttgaaagtgggcagacagaacggggttctggaaagc |
| gacatcggggtaaagtttgacacccgcaacttcagactggggtttgacccccgtcactggtcttgtcatgcctggggtatatacaaacgaa |
| gccttccatccagacatcattttgctgccaggatgcggggtggacttcacccacagccgcctgagcaacttgttgggcatccgcaagcg |

TABLE 19-continued

| Ad5-TGFβ-RES-IL10 No Plasmid Backbone |
| --- |
| gcaacccttccaggagggctttaggatcacctacgatgatctggagggtggtaacattcccgcactgttggatgtggacgcctaccagg |
| cgagcttgaaagatgacaccgaacaggggggggtggcgcaggcggcagcaacagcagtggcagcggcgcggaagagaactcc |
| aacgcggcagccgcggcaatgcagccggtggaggacatgaacgatcatgccattcgcggcgacacctttgccacacgggctgagga |
| gaagcgcgctgaggccgaagcagcggccgaagctgccgcccccgctgcgcaacccgaggtcgagaagcctcagaagaaaccggt |
| gatcaaacccctgacagaggacagcaagaaacgcagttacaacctaataagcaatgacagcaccttcacccagtaccgcagctggtac |
| cttgcatacaactacggcgaccctcagaccggaatccgctcatggaccctgctttgcactcctgacgtaacctgcggctcggagcaggt |
| ctactggtcgttgccagacatgatgcaagaccccgtgaccttccgctccacgcgccagatcagcaactttccggtggtgggcgccgag |
| ctgttgcccgtgcactccaagagcttctacaacgaccaggccgtctactcccaactcatccgccagtttacctctctgacccacgtgttcaa |
| tcgctttcccgagaaccagattttggcgcgcccgccagccccccaccatcaccaccgtcagtgaaaacgttcctgctctcacagatcacg |
| ggacgctaccgctgcgcaacagcatcggaggagtccagcgagtgaccattactgacgccagacgccgcacctgcccctacgtttaca |
| aggccctgggcatagtctcgccgcgcgtcctatcgagccgcactttttgagcaagcatgtccatccttatatcgcccagcaataacacag |
| gctggggcctgcgcttcccaagcaagatgtttggcggggccaagaagcgctccgaccaacacccagtgcgcgtgcgcgggcactac |
| cgcgcgccctggggcgcgcacaaacgcggccgcactgggcgcaccaccgtcgatgacgccatcgacgcggtggtggaggaggcg |
| cgcaactacacgcccacgccgccaccagtgtccacagtggacgcggccattcagaccgtggtgcgcggagcccggcgctatgctaa |
| aatgaagagacggcggaggcgcgtagcacgtcgccaccgccgccgacccggcactgccgcccaacgcgcggcggcggccctgct |
| taaccgcgcacgtcgcaccggccgacgggcggccatgcgagcagctcgaaggctggccgcgggtattgtcactgtgccccccaggt |
| ccaggcgacgagcggccgccgcagcagccgcggccattagtgctatgactcagggtcgcaggggcaacgtgtattgggtgcgcgac |
| tcggttagcggcctgcgcgtgcccgtgcgcacccgcccccgcgcaactagattgcaagaaaaaactacttagactcgtactgttgtat |
| gtatccagcggcggcggcgcgcaacgaagctatgtccaagcgcaaaatcaaagaagagatgctccaggtcatcgcgccggagatct |
| atggcccccgaagaaggaagagcaggattacaagccccgaaagctaaagcgggtcaaaaagaaaaagaaagatgatgatgatgaa |
| cttgacgacgaggtggaactgctgcacgctaccgcgcccaggcgacgggtacagtggaaaggtcgacgcgtaaaacgtgttttgcga |
| cccggcaccaccgtagtctttacgcccggtgagcgctccacccgcacctacaagcgcgtgtatgatgaggtgtacggcgacgaggac |
| ctgcttgagcaggccaacgagcgcctcggggagtttgcctacggaaagcggcataaggacatgctggcgttgccgctggacgaggg |
| caacccaacacctagcctaaagcccgtaacactgcagcaggtgctgcccgcgcttgcaccgtccgaagaaaagcgcggcctaaagc |
| gcgagtctggtgacttggcacccaccgtgcagctgatggtacccaagcgccagcgactggaagatgtcttggaaaaaatgaccgtgga |
| acctgggctggagcccgaggtccgcgtgcggccaatcaagcaggtggcgccgggactgggcgtgcagaccgtggacgttcagata |
| cccactaccagtagcaccagtattgccaccgccacagagggcatggagacacaaacgtccccggttgcctcagcggtggcggatgcc |
| gcggtgcaggcggtcgctgcggccgcgtccaagacctctacggaggtgcaaacggacccgtggatgtttcgcgtttcagccccccgg |
| cgcccgcgccgttcgaggaagtacggcgccgccagcgcgctactgcccgaatatgccctacatccttccattgcgcctacccccggct |
| atcgtggctacacctaccgccccagaagacgagcaactacccgacgccgaaccaccactggaacccgccgccgccgtcgccgtcgc |
| cagcccgtgctggccccgatttccgtgcgcagggtggctcgcgaaggaggcaggaccctggtgctgccaacagcgcgctaccaccc |
| cagcatcgtttaaaagccggtctttgtggttcttgcagatatggccctcacctgccgcctccgtttcccggtgccgggattccgaggaaga |
| atgcaccgtaggaggggcatggccggccacggcctgacgggcggcatgcgtcgtgcgcaccaccggcggcggcgcgcgtcgcac |
| cgtcgcatgcgcggcggtatcctgcccctccttattccactgatcgccgcggcgattggcgccgtgcccggaattgcatccgtggccttg |
| caggcgcagagacactgattaaaaacaagttgcatgtggaaaaatcaaaataaaaagtctggactctcacgctcgcttggtcctgtaact |
| attttgtagaatggaagacatcaactttgcgtctctggccccgcgacacggctcgcgcccgttcatgggaaactggcaagatatcggcac |
| cagcaatatgagcggtggcgccttcagctggggctcgctgtggagcggcattaaaaatttcggttccaccgttaagaactatggcagca |
| aggcctggaacagcagcacaggccagatgctgagggataagttgaaagagcaaaatttccaacaaaaggtggtagatggcctggcct |
| ctggcattagcggggtggtggacctggccaaccaggcagtgcaaaataagattaacagtaagcttgatccccgccctcccgtagagga |

TABLE 19-continued

| Ad5-TGFβ-RES-IL10 No Plasmid Backbone |
|---|
| gcctccaccggccgtggagacagtgtctccagaggggcgtggcgaaaagcgtccgcgccccgacagggaagaaactctggtgacg |
| caaatagacgagcctccctcgtacgaggaggcactaaagcaaggcctgcccaccacccgtcccatcgcgcccatggctaccggagtg |
| ctgggccagcacacacccgtaacgctggacctgcctccccccgccgacacccagcagaaacctgtgctgccaggcccgaccgccgt |
| tgttgtaacccgtcctagccgcgcgtccctgcgccgcgccgccagcggtccgcgatcgttgcggcccgtagccagtggcaactggca |
| aagcacactgaacagcatcgtgggtctgggggtgcaatccctgaagcgccgacgatgcttctgaatagctaacgtgtcgtatgtgtgtca |
| tgtatgcgtccatgtcgccgccagaggagctgctgagccgccgcgcgcccgctttccaagatggctaccccttcgatgatgccgcagtg |
| gtcttacatgcacatctcgggccaggacgcctcggagtacctgagccccgggctggtgcagtttgcccgcgccaccgagacgtacttc |
| agcctgaataacaagtttagaaccccacggtggcgcctacgcacgacgtgaccacagaccggtcccagcgtttgacgctgcggttca |
| tccctgtggaccgtgaggatactgcgtactcgtacaaggcgcggttcaccctagctgtgggtgataaccgtgtgctggacatggcttcca |
| cgtactttgacatccgcggcgtgctggacaggggccctacttttaagccctactctggcactgcctacaacgccctggctcccaagggtg |
| ccccaaatccttgcgaatgggatgaagctgctactgctcttgaaataaacctagaagaagaggacgatgacaacgaagacgaagtaga |
| cgagcaagctgagcagcaaaaaactcacgtatttgggcaggcgccttattctggtataaatattacaaaggagggtattcaaataggtgtc |
| gaaggtcaaacacctaaatatgccgataaaacatttcaacctgaacctcaaataggagaatctcagtggtacgaaacagaaattaatcat |
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataatttttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |
| ttccgcggctgggccttcacgcgccttaagactaaggaaaccccatcactgggctcgggctacgacccttattacacctactctggctcta |
| taccctacctagatggaaccttttacctcaaccacacctttaagaaggtggccattacctttgactcttctgtcagctggcctggcaatgacc |
| gcctgcttacccccaacgagtttgaaattaagcgctcagttgacggggagggttacaacgttgcccagtgtaacatgaccaaagactggt |
| tcctggtacaaatgctagctaactataacattggctaccagggcttctatatcccagagagctacaaggaccgcatgtactccttcttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttccccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttctttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |

TABLE 19-continued

| Ad5-TGFβ-RES-IL10 No Plasmid Backbone |
|---|
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgcttttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |
| ccatttccttctcctataggcagaaaaagatcatggagtcagtcgagaagaaggacagcctaaccgccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggcggggggacgaaaggcatggcgactacctagatgtgggagacgacgtgctgttgaagcatctgcagcgcca |
| gtgcgccattatctgcgacgcgttgcaagagcgcagcgatgtgcccctcgccatagcggatgtcagccttgcctacgaacgccacctat |
| tctcaccgcgcgtaccccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctaccccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |

TABLE 19-continued

| Ad5-TGFβ-RES-IL10 No Plasmid Backbone |
| --- |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| ggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacgggggtttacttggacccccagtccggcgaggagctcaacccaatcccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttcccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |
| aagttcagatgactaactcaggggcgcagcttgcgggcggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |
| actgtgatttgcaactgtcctaaccttggattacatcaagatccagatcttctagacccgggagcggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |

TABLE 19-continued

| Ad5-TGFβ-RES-IL10 No Plasmid Backbone |
| --- |
| ccgctaaccgtgcacgactccaaacttagcattgccacccaaggacccctcacagtgtcagaaggaaagctagccctgcaaacatcag |
| gccccctcaccaccaccgatagcagtacccttactatcactgcctcacccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctcttttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaacaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacacttttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatggcggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgccatccaccaccat |
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgccccctggcttcgggttctatgtaaactccttcatgcgccgctgccctgataacatccaccaccgcagaataa |
| gccacacccagccaacctacacattcgttctgcgagtcacacacgggaggagcgggaagagctggaagaaccatgtttttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |

TABLE 19-continued

| Ad5-TGFβ-RES-IL10 No Plasmid Backbone |
|---|
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagcccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccacccccctcattatcatattggcttcaatccaaaataaggtatattattgatgatg |

TABLE 20

| Ad5-IL13 with Plasmid Backbone |
|---|
| (SEQ ID NO: 20) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttttattgaggcctgtccctacccatcccctgcaagggacggaaggattaggcggaaactgcagct |

TABLE 20-continued

| Ad5-IL13 with Plasmid Backbone |
| --- |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctataggggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcaccccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccaggtttttggatcgata |

TABLE 20-continued

| Ad5-IL13 with Plasmid Backbone |
| --- |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattccctttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |

TABLE 20-continued

| Ad5-IL13 with Plasmid Backbone |
| --- |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccacg |
| cgtggagctagttattaatagtaatcaattacggggtcattagttcatagcccatatatggagttccgcgttacataacttacggtaaatggc |
| ccgcctggctgaccgcccaacgacccccgcccattgacgtcaataatgacgtatgttcccatagtaacgtcaatagggactttccattga |
| cgtcaatgggtggagtatttacggtaaactgcccacttggcagtacatcaagtgtatcatatgccaagtacgccccctattgacgtcaatga |
| cggtaaatggcccgcctggcattatgcccagtacatgaccttatgggactttcctacttggcagtacatctacgtattagtcatcgctattac |
| catggtgatgcggttttggcagtacatcaatgggcgtggatagcggtttgactcacggggatttccaagtctccaccccattgacgtcaat |
| gggagtttgttttgcaccaaaatcaacgggactttccaaaatgtcgtaacaactccgccccattgacgcaaatgggcggtaggcgtgtac |
| ggtgggaggtctatataagcagagctcgtttagtgaaccgtcagatcgcctggagacgccatccacgctgttttgacctccatagaagac |
| accgggaccgatccagcctccgcggattcgaatcccggccgggaacggtgcattggaacgcggattccccgtgccaagagtgacgta |
| agtaccgcctatagagtctataggcccacaaaaaatgctttcttcttttaatatacttttttgtttatcttatttctaatactttccctaatctctttcttt |
| cagggcaataatgatacaatgtatcatgcctctttgcaccattctaaagaataacagtgataatttctgggttaaggcaatagcaatatttctg |
| catataaatatttctgcatataaattgtaactgatgtaagaggtttcatattgctaatagcagctacaatccagctaccattctgcttttattttatg |
| gttgggataaggctggattattctgagtccaagctaggcccttttgctaatcatgttcatacctcttatcttcctcccacagctcctgggcaac |
| gtgctggtctgtgtgctggcccatcactttggcaaagctcctgggcaacgtgctggttattgtgctgtctcatcattttggcaaagaattccg |
| ctgcgactcggcggagtcccggcggcgcgtccttgttctaacccggcgcgccagcttggcaatccggtactgttggtaaagccaccau |
| gguauggagcaucaaccugacagcuggcauguacugugcagcccuggaaucccugaucaacgugucaggcugcagugcca |
| ucgagaagacccagaggaugcugagcggauucugcccgcacaaggucucagcugggcaguuuuccagcuugcauguccga |
| gacaccaaaaucgagguggcccaguuuguaaaggaccugcucuuacauuuaaagaaacuuuuucgcgagggacaguucaa |
| cugataataattctagagtcggggcggccggccgcttcgagcagacatgataagatacattgatgagtttggacaaaccacaactagaa |
| tgcagtgaaaaaaatgctttatttgtgaaatttgtgatgctattgctttatttgtaaccattataagctgcaataaacaagttaacaacaacaatt |
| gcattcattttatgtttcaggttcagggggaggtgtgggaggttttttaaagcaagtaaaacctctacaaatgtggtaaaatcgataaggatc |
| cgaattcgatatcactagtggtaccagtactgaaatgtgtgggcgtggcttaagggtgggaaagaatatataaggtgggggtcttatgtag |
| ttttgtatctgttttgcagcagccgccgccgccatgagcaccaactcgtttgatggaagcattgtgagctcatatttgacaacgcgcatgcc |

TABLE 20-continued

| Ad5-IL13 with Plasmid Backbone |
|---|
| cccatgggccggggtgcgtcagaatgtgatgggctccagcattgatggtcgccccgtcctgcccgcaaactctactaccttgacctacg |
| agaccgtgtctggaacgccgttggagactgcagcctccgccgccgcttcagccgctgcagccaccgcccgcgggattgtgactgactt |
| tgctttcctgagcccgcttgcaagcagtgcagcttcccgttcatccgcccgcgatgacaagttgacggctcttttggcacaattggattcttt |
| gacccgggaacttaatgtcgtttctcagcagctgttggatctgcgccagcaggtttctgccctgaaggcttcctcccctcccaatgcggttt |
| aacggtccgggccagagtggccaacataaataaaaaaccagactctgtttggatttggatcaagcaagtgtcttgctgtctttatttagggg |
| ttttgcgcgcgcggtaggcccgggaccagcggtctcggtcgttgagggtcctgtgtatttttttccaggacgtggtaaaggtgactctggat |
| gttcagatacatgggcataagcccgtctctgggggggaggtagcaccactgcagagcttcatgctgcggggtggtgttgtagatgatcca |
| gtcgtagcaggagcgctgggcgtggtgcctaaaaatgtctttcagtagcaagctgattgccaggggcaggcccttggtgtaagtgtttac |
| aaagcggttaagctgggatgggtgcatacgtggggatatgagatgcatcttggactgtatttttaggttggctatgttcccagccatatccct |
| ccggggattcatgttgtgcagaaccaccagcacagtgtatccggtgcacttgggaaatttgtcatgtagcttagaaggaaatgcgtggaa |
| gaacttggagacgcccttgtgacctccaagattttccatgcattcgtccataatgatggcaatgggcccacgggggcggcctgggcga |
| agatatttctgggatcactaacgtcatagttgtgttccaggatgagatcgtcataggccatttttacaaagcgcgggcggagggtgccaga |
| ctgcggtataatggttccatccggcccaggggcgtagttaccctcacagatttgcatttcccacgctttgagttcagatgggggggatcatgt |
| ctacctgcggggcgatgaagaaaacggtttccggggtaggggagatcagctgggaagaaagcaggttcctgagcagctgcgacttac |
| cgcagccggtgggcccgtaaatcacacctattaccggctgcaactggtagttaagagagctgcagctgccgtcatccctgagcagggg |
| ggccacttcgttaagcatgtccctgactcgcatgttttccctgaccaaatccgccagaaggcgctcgccgcccagcgatagcagttcttg |
| caaggaagcaaagtttttcaacggtttgagaccgtccgccgtaggcatgcttttgagcgtttgaccaagcagttccaggcggtcccacag |
| ctcggtcacctgctctacggcatctcgatccagcatatctcctcgtttcgcgggttggggcggctttcgctgtacggcagtagtcggtgctc |
| gtccagacgggccagggtcatgtctttccacgggcgcagggtcctcgtcagcgtagtctgggtcacggtgaaggggtgcgctccggg |
| ctgcgcgctggccagggtgcgcttgaggctggtcctgctggtgctgaagcgctgccggtcttcgccctgcgcgtcggccaggtagcat |
| ttgaccatggtgtcatagtccagcccctccgcggcgtggcccttggcgcgcagcttgcccttggaggaggcgccgcacgaggggcag |
| tgcagacttttgagggcgtagagcttgggcgcgagaaataccgattccggggagtaggcatccgcgccgcaggccccgcagacggt |
| ctcgcattccacgagccaggtgagctctggccgttcggggtcaaaaaccaggtttcccccatgctttttgatgcgtttcttacctctggtttc |
| catgagccggtgtccacgctcggtgacgaaaaggctgtccgtgtccccgtatacagacttgagaggcctgtcctcgagcggtgttccgc |
| ggtcctcctcgtatagaaactcggaccactctgagacaaaggctcgcgtccaggccagcacgaaggaggctaagtgggaggggtag |
| cggtcgttgtccactagggggtccactcgctccagggtgtgaagacacatgtcgccctcttcggcatcaaggaaggtgattggtttgtag |
| gtgtaggccacgtgaccgggtgttcctgaaggggggctataaaagggggtgggggcgcgttcgtcctcactctcttccgcatcgctgtc |
| tgcgagggccagctgttggggtgagtactccctctgaaaagcgggcatgacttctgcgctaagattgtcagtttccaaaaacgaggagg |
| atttgatattcacctggcccgcggtgatgcctttgagggtggccgcatccatctggtcagaaaagacaatctttttgttgtcaagcttggtgg |
| caaacgacccgtagagggcgttggacagcaacttggcgatggagcgcagggtttggtttttgtcgcgatcggcgcgctccttggccgc |
| gatgtttagctgcacgtattcgcgcgcaacgcaccgccattcgggaaagacggtggtgcgctcgtcgggcaccaggtgcacgcgcca |
| accgcggttgtgcagggtgacaaggtcaacgctggtggctacctctccgcgtaggcgctcgttggtccagcagaggcggccgcccttg |
| cgcgagcagaatggcggtagggggtctagctgcgtctcgtccggggggtctgcgtccacggtaaagaccccgggcagcaggcgcg |
| cgtcgaagtagtctatcttgcatccttgcaagtctagcgcctgctgccatgcgcgggcggcaagcgcgcgctcgtatgggttgagtggg |
| ggaccccatggcatggggtgggtgagcgcggaggcgtacatgccgcaaatgtcgtaaacgtagaggggctctctgagtattccaagat |
| atgtagggtagcatcttccaccgcggatgctggcgcgcacgtaatcgtatagttcgtgcgagggagcgaggaggtcgggaccgaggtt |
| gctacgggcgggctgctctgctcggaagactatctgcctgaagatggcatgtgagttggatgatatggttggacgctggaagacgttga |
| agctggcgtctgtgagacctaccgcgtcacgcacgaaggaggcgtaggagtcgcgcagcttgttgaccagctcggcggtgacctgca |
| cgtctagggcgcagtagtccagggtttccttgatgatgtcatacttatcctgtcccttttttttccacagctcgcggttgaggacaaactcttc |

TABLE 20-continued

| Ad5-IL13 with Plasmid Backbone |
|---|
| gcggtctttccagtactcttggatcggaaacccgtcggcctccgaacggtaagagcctagcatgtagaactggttgacggcctggtagg |
| cgcagcatcccttttctacgggtagcgcgtatgcctgcgcggccttccggagcgaggtgtgggtgagcgcaaaggtgtccctgaccat |
| gactttgaggtactggtatttgaagtcagtgtcgtcgcatccgccctgctcccagagcaaaaagtccgtgcgctttttggaacgcggatttg |
| gcagggcgaaggtgacatcgttgaagagtatctttcccgcgcgaggcataaagttgcgtgtgatgcggaagggtcccggcacctcgga |
| acggttgttaattacctgggcggcgagcacgatctcgtcaaagccgttgatgttgtggcccacaatgtaaagttccaagaagcgcgggat |
| gcccttgatggaaggcaatttttaagttcctcgtaggtgagctcttcaggggagctgagcccgtgctctgaaagggcccagtctgcaag |
| atgagggttggaagcgacgaatgagctccacaggtcacgggccattagcatttgcaggtggtcgcgaaaggtcctaaactggcgacct |
| atggccatttttctggggtgatgcagtagaaggtaagcgggtcttgttcccagcggtcccatccaaggttcgcggctaggtctcgcgcg |
| gcagtcactagaggctcatctccgccgaacttcatgaccagcatgaagggcacgagctgcttcccaaaggcccccatccaagtataggt |
| ctctacatcgtaggtgacaaagagacgctcggtgcgaggatgcgagccgatcgggaagaactggatctcccgccaccaattggagga |
| gtggctattgatgtggtgaaagtagaagtccctgcgacgggccgaacactcgtgctggcttttgtaaaaacgtgcgcagtactggcagc |
| ggtgcacgggctgtacatcctgcacgaggttgacctgacgaccgcgcacaaggaagcagagtgggaatttgagcccctcgcctggcg |
| ggtttggctggtggtcttctacttcggctgcttgtccttgaccgtctggctgctcgaggggagttacggtggatcggaccaccacgccgcg |
| cgagcccaaagtccagatgtccgcgcgcggcggtcggagcttgatgacaacatcgcgcagatgggagctgtccatggtctggagctc |
| ccgcggcgtcaggtcaggcgggagctcctgcaggtttacctcgcatagacgggtcagggcgcgggctagatccaggtgatacctaatt |
| tccaggggctggttggtggcggcgtcgatggcttgcaagaggccgcatccccgcggcgcgactacggtaccgcgcggcgggcggt |
| gggccgcgggggtgtccttggatgatgcatctaaaagcggtgacgcgggcgagcccccggaggtagggggggctccggacccgcc |
| gggagaggggggcaggggcacgtcggcgccgcgcgcgggcaggagctggtgctgcgcgcgtaggttgctggcgaacgcgacgac |
| gcggcggttgatctcctgaatctggcgcctctgcgtgaagacgacgggcccggtgagcttgaacctgaaagagagttcgacagaatca |
| atttcggtgtcgttgacggcggcctggcgcaaaatctcctgcacgtctcctgagttgtcttgataggcgatctcggccatgaactgctcgat |
| ctcttcctcctggagatctccgcgtccggctcgctccacggtggcggcgaggtcgttggaaatgcgggccatgagctgcgagaaggcg |
| ttgaggcctccctcgttccagacgcggctgtagaccacgcccccttcggcatcgcgggcgcgcatgaccacctgcgcgagattgagct |
| ccacgtgccgggcgaagacggcgtagtttcgcaggcgctgaaagaggtagttgagggtggtggcggtgtgttctgccacgaagaagt |
| acataacccagcgtcgcaacgtggattcgttgatatcccccaaggcctcaaggcgctccatggcctcgtagaagtccacggcgaagttg |
| aaaaactgggagttgcgcgccgacacggttaactcctcctccagaagacggatgagctcggcgacagtgtcgcgcacctcgcgctca |
| aaggctacaggggcctcttcttcttcttcaatctcctcttccataagggcctccccttcttcttcttctggcggcggtgggggaggggggac |
| acggcggcgacgacggcgcaccgggaggcggtcgacaaagcgctcgatcatctccccgcggcgacggcgcatggtctcggtgac |
| ggcgcggccgttctcgcgggggcgcagttggaagacgccgcccgtcatgtcccggttatgggttggcgggggggctgccatgcggca |
| gggatacggcgctaacgatgcatctcaacaattgttgtgtaggtactccgccgccgagggacctgagcgagtccgcatcgaccggatc |
| ggaaaacctctcgagaaaggcgtctaaccagtcacagtcgcaaggtaggctgagcaccgtggcgggcggcagcgggcggcggtcg |
| gggttgtttctggcggaggtgctgctgatgatgtaattaaagtaggcggtcttgagacggcggatggtcgacagaagcaccatgtccttg |
| ggtccggcctgctgaatgcgcaggcggtcggccatgccccaggcttcgttttgacatcggcgcaggtctttgtagtagtcttgcatgagc |
| ctttctaccggcacttcttcttctccttcctcttgtcctgcatctcttgcatctatcgctgcggcggcggcggagtttggccgtaggtggcgcc |
| ctcttcctcccatgcgtgtgaccccgaagcccctcatcggctgaagcagggctaggtcggcgacaacgcgctcggctaatatggcctg |
| ctgcacctgcgtgagggtagactggaagtcatccatgtccacaaagcggtggtatgcgcccgtgttgatggtgtaagtgcagttggccat |
| aacggaccagttaacggtctggtgacccggctgcgagagctcggtgtacctgagacgcgagtaagccctcgagtcaaatacgtagtcg |
| ttgcaagtccgcaccaggtactggtatcccaccaaaaagtgcggcggcggctggcggtagaggggccagcgtagggggccgggg |
| ctccgggggcgagatcttccaacataaggcgatgatatccgtagatgtacctggacatccaggtgatgccggcggcggtggtggaggc |
| gcgcggaaagtcgcggacgcggttccagatgttgcgcagcggcaaaaagtgctccatggtcgggacgctctggccggtcaggcgcg |

TABLE 20-continued

| Ad5-IL13 with Plasmid Backbone |
|---|
| cgcaatcgttgacgctctagaccgtgcaaaaggagagcctgtaagcgggcactcttccgtggtctggtggataaattcgcaagggtatc |
| atggcggacgaccggggttcgagccccgtatccggccgtccgccgtgatccatgcggttaccgcccgcgtgtcgaacccaggtgtgc |
| gacgtcagacaacgggggagtgctccttttggcttccttccaggcgcggcggctgctgcgctagcttttttggccactggccgcgcgca |
| gcgtaagcggttaggctggaaagcgaaagcattaagtggctcgctccctgtagccggagggttattttccaagggttgagtcgcgggac |
| ccccggttcgagtctcggaccggccggactgcggcgaacgggggtttgcctccccgtcatgcaagaccccgcttgcaaattcctccgg |
| aaacagggacgagcccctttttttgcttttcccagatgcatccggtgctgcggcagatgcgcccccctcctcagcagcggcaagagcaag |
| agcagcggcagacatgcagggcaccctcccctcctcctaccgcgtcaggaggggcgacatccgcggttgacgcggcagcagatggt |
| gattacgaaccccccgcggcgccgggcccggcactacctggacttggaggagggcgagggcctggcgcggctaggagcgccctctc |
| ctgagcggcacccaagggtgcagctgaagcgtgatacgcgtgaggcgtacgtgccgcggcagaacctgtttcgcgaccgcgaggga |
| gaggagcccgaggagatgcgggatcgaaagttccacgcagggcgcgagctgcggcatggcctgaatcgcgagcggttgctgcgcg |
| aggaggactttgagcccgacgcgcgaaccgggattagtcccgcgcgcgcacacgtggcggccgccgacctggtaaccgcatacga |
| gcagacggtgaaccaggagattaactttcaaaaaagctttaacaaccacgtgcgtacgcttgtggcgcgcgaggaggtggctatagga |
| ctgatgcatctgtgggactttgtaagcgcgctggagcaaaacccaaatagcaagccgctcatggcgcagctgttccttatagtgcagcac |
| agcagggacaacgaggcattcagggatgcgctgctaaacatagtagagcccgagggccgctggctgctcgatttgataaacatcctgc |
| agagcatagtggtgcaggagcgcagcttgagcctggctgacaaggtggccgccatcaactattccatgcttagcctgggcaagttttac |
| gcccgcaagatataccataccccttacgttcccatagacaaggaggtaaagatcgaggggttctacatgcgcatggcgctgaaggtgct |
| taccttgagcgacgacctgggcgtttatcgcaacgagcgcatccacaaggccgtgagcgtgagccggcggcgcgagctcagcgacc |
| gcgagctgatgcacagcctgcaaagggccctggctggcacgggcagcggcgatagagaggccgagtcctactttgacgcgggcgct |
| gacctgcgctgggccccaagccgacgcgccctggaggcagctggggccggacctgggctggcggtggcacccgcgcgcgctggc |
| aacgtcggcggcgtggaggaatatgacgaggacgatgagtacgagccagaggacggcgagtactaagcggtgatgtttctgatcaga |
| tgatgcaagacgcaacggacccggcggtgcgggcggcgctgcagagccagccgtccggccttaactccacggacgactggcgcca |
| ggtcatggaccgcatcatgtcgctgactgcgcgcaatcctgacgcgttccggcagcagccgcaggccaaccggctctccgcaattctg |
| gaagcggtggtcccggcgcgcgcaaaccccacgcacgagaaggtgctggcgatcgtaaacgcgctggccgaaaacagggccatcc |
| ggcccgacgaggccggcctggtctacgacgcgctgcttcagcgcgtggctcgttacaacagcggcaacgtgcagaccaacctggac |
| cggctggtgggggatgtgcgcgaggccgtggcgcagcgtgagcgcgcgcagcagcagggcaacctgggctccatggttgcactaa |
| acgccttcctgagtacacagcccgccaacgtgccgcggggacaggaggactacaccaactttgtgagcgcactgcggctaatggtga |
| ctgagacaccgcaaagtgaggtgtaccagtctgggccagactatttttttccagaccagtagacaaggcctgcagaccgtaaacctgagc |
| caggctttcaaaaacttgcaggggctgtggggggtgcgggctcccacaggcgaccgcgcgaccgtgtctagcttgctgacgcccaac |
| tcgcgcctgttgctgctgctaatagcgcccttcacggacagtggcagcgtgtcccgggacacatacctaggtcacttgctgacactgtac |
| cgcgaggccataggtcaggcgcatgtggacgagcatactttccaggagattacaagtgtcagccgcgcgctggggcaggaggacac |
| gggcagcctggaggcaaccctaaactacctgctgaccaaccggcggcagaagatcccctcgttgcacagtttaaacagcgaggagga |
| gcgcattttgcgctacgtgcagcagagcgtgagccttaacctgatgcgcgacggggtaacgcccagcgtggcgctggacatgaccgc |
| gcgcaacatggaaccgggcatgtatgcctcaaaccggccgtttatcaaccgcctaatggactacttgcatcgcgcggccgccgtgaac |
| cccgagtatttcaccaatgccatcttgaacccgcactggctaccgccccctggtttctacaccgggggattcgaggtgcccgagggtaa |
| cgatggattcctctgggacgacatagacgacagcgtgttttccccgcaaccgcagaccctgctagagttgcaacagcgcgagcaggca |
| gaggcggcgctgcgaaaggaaagcttccgcaggccaagcagcttgtccgatctaggcgctgcggccccgcggtcagatgctagtag |
| cccatttccaagcttgatagggtctcttaccagcactcgcaccacccgcccgcgcctgctgggcgaggaggagtacctaaacaactcgc |
| tgctgcagccgcagcgcgaaaaaaacctgcctccggcatttcccaacaacgggatagagagcctagtggacaagatgagtagatgga |
| agacgtacgcgcaggagcacagggacgtgccaggcccgcgcccgcccacccgtcgtcaaaggcacgaccgtcagcggggtctgg |

TABLE 20-continued

| Ad5-IL13 with Plasmid Backbone |
|---|
| tgtgggaggacgatgactcggcagacgacagcagcgtcctggatttgggagggagtggcaacccgtttgcgcaccttcgccccaggc |
| tggggagaatgttttaaaaaaaaaaaaaagcatgatgcaaaataaaaaactcaccaaggccatggcaccgagcgttggttttcttgtattc |
| cccttagtatgcggcgcgcggcgatgtatgaggaaggtcctcctccctcctacgagagtgtggtgagcgcggcgccagtggcggcgg |
| cgctgggttctcccttcgatgctcccctggacccgccgtttgtgcctccgcggtacctgcggcctaccggggggagaaacagcatccgt |
| tactctgagttggcacccctattcgacaccacccgtgtgtacctggtggacaacaagtcaacggatgtggcatccctgaactaccagaac |
| gaccacagcaactttctgaccacggtcattcaaaacaatgactacagcccgggggaggcaagcacacagaccatcaatcttgacgacc |
| ggtcgcactggggcggcgacctgaaaaccatcctgcataccaacatgccaaatgtgaacgagttcatgtttaccaataagtttaaggcgc |
| gggtgatggtgtcgcgcttgcctactaaggacaatcaggtggagctgaaatacgagtgggtggagttcacgctgcccgagggcaacta |
| ctccgagaccatgaccatagaccttatgaacaacgcgatcgtggagcactacttgaaagtgggcagacagaacggggttctggaaagc |
| gacatcggggtaaagtttgacacccgcaacttcagactggggtttgaccccgtcactggtcttgtcatgcctggggtatatacaaacgaa |
| gccttccatccagacatcattttgctgccaggatgcggggtggacttcacccacagccgcctgagcaacttgttgggcatccgcaagcg |
| gcaacccttccaggagggctttaggatcacctacgatgatctggagggtggtaacattcccgcactgttggatgtggacgcctaccagg |
| cgagcttgaaagatgacaccgaacaggggggggtggcgcaggcggcagcaacagcagtggcagcggcgcggaagagaactcc |
| aacgcggcagccgcggcaatgcagccggtggaggacatgaacgatcatgccattcgcggcgacacctttgccacacgggctgagga |
| gaagcgcgctgaggccgaagcagcggccgaagctgccgcccccgctgcgcaacccgaggtcgagaagcctcagaagaaaccggt |
| gatcaaacccctgacagaggacagcaagaaacgcagttacaacctaataagcaatgacagcaccttcacccagtaccgcagctggtac |
| cttgcatacaactacggcgaccctcagaccggaatccgctcatggaccctgctttgcactcctgacgtaacctgcggctcggagcaggt |
| ctactggtcgttgccagacatgatgcaagaccccgtgaccttccgctccacgcgccagatcagcaactttccggtggtgggcgccgag |
| ctgttgcccgtgcactccaagagcttctacaacgaccaggccgtctactcccaactcatccgccagtttacctctctgacccacgtgttcaa |
| tcgctttcccgagaaccagattttggcgcgcccgccagcccccaccatcaccaccgtcagtgaaaacgttcctgctctcacagatcacg |
| ggacgctaccgctgcgcaacagcatcggaggagtccagcgagtgaccattactgacgccagacgccgcacctgcccctacgtttaca |
| aggccctgggcatagtctcgccgcgcgtcctatcgagccgcacttttttgagcaagcatgtccatccttatatcgcccagcaataacacag |
| gctggggcctgcgcttcccaagcaagatgtttggggggccaagaagcgctccgaccaacacccagtgcgcgtgcgcgggcactac |
| cgcgcgccctggggcgcgcacaaacgcggccgcactgggcgcaccaccgtcgatgacgccatcgacgcggtggtggaggaggcg |
| cgcaactacacgcccacgccgccaccagtgtccacagtggacgcggccattcagaccgtggtgcgcggagcccggcgctatgctaa |
| aatgaagagacggcggaggcgcgtagcacgtcgccaccgccgccgacccggcactgccgcccaacgcgcggcggcggccctgct |
| taaccgcgcacgtcgcaccggccgacgggcggccatgcgagcagctcgaaggctggccgcgggtattgtcactgtgccccccaggt |
| ccaggcgacgagcggccgccgcagcagccgcggccattagtgctatgactcagggtcgcaggggcaacgtgtattgggtgcgcgac |
| tcggttagcggcctgcgcgtgcccgtgcgcacccgcccccgcgcaactagattgcaagaaaaaactacttagactcgtactgttgtat |
| gtatccagcggcggcggcgcgcaacgaagctatgtccaagcgcaaaatcaaagaagagatgctccaggtcatcgcgccggagatct |
| atggcccccgaagaaggaagagcaggattacaagccccgaaagctaaagcgggtcaaaaagaaaaagaaagatgatgatgatgaa |
| cttgacgacgaggtggaactgctgcacgctaccgcgcccaggcgacgggtacagtggaaaggtcgacgcgtaaaacgtgttttgcga |
| cccggcaccaccgtagtctttacgcccggtgagcgctccacccgcacctacaagcgcgtgtatgatgaggtgtacggcgacgaggac |
| ctgcttgagcaggccaacgagcgcctcggggagtttgcctacggaaagcggcataaggacatgctggcgttgccgctggacgaggg |
| caacccaacacctagcctaaagcccgtaacactgcagcaggtgctgcccgcgcttgcaccgtccgaagaaaagcgcggcctaaagc |
| gcgagtctggtgacttggcacccaccgtgcagctgatggtacccaagcgccagcgactggaagatgtcttggaaaaaatgaccgtgga |
| acctgggctggagcccgaggtccgcgtgcggccaatcaagcaggtggcgccgggactgggcgtgcagaccgtggacgttcagata |
| cccactaccagtagcaccagtattgccaccgccacagagggcatggagacacaaacgtccccggttgcctcagcggtggcggatgcc |
| gcggtgcaggcggtcgctgcggccgcgtccaagacctctacggaggtgcaaacggacccgtggatgtttcgcgtttcagccccccgg |

TABLE 20-continued

| Ad5-IL13 with Plasmid Backbone |
| --- |
| cgcccgcgccgttcgaggaagtacggcgccgccagcgcgctactgcccgaatatgccctacatccttccattgcgcctacccccggct |
| atcgtggctacacctaccgccccagaagacgagcaactacccgacgccgaaccaccactggaacccgccgccgccgtcgccgtcgc |
| cagcccgtgctggccccgatttccgtgcgcagggtggctcgcgaaggaggcaggaccctggtgctgccaacagcgcgctaccaccc |
| cagcatcgtttaaaagccggtctttgtggttcttgcagatatggccctcacctgccgcctccgtttcccggtgccgggattccgaggaaga |
| atgcaccgtaggaggggcatggccggccacggcctgacgggcggcatgcgtcgtgcgcaccaccggcggcggcgcgcgtcgcac |
| cgtcgcatgcgcggcggtatcctgcccctccttattccactgatcgccgcggcgattggcgccgtgcccggaattgcatccgtggccttg |
| caggcgcagagacactgattaaaaacaagttgcatgtggaaaaatcaaaataaaaagtctggactctcacgctcgcttggtcctgtaact |
| attttgtagaatggaagacatcaactttgcgtctctggccccgcgacacggctcgcgcccgttcatgggaaactggcaagatatcggcac |
| cagcaatatgagcggtggcgccttcagctggggctcgctgtggagcggcattaaaaatttcggttccaccgttaagaactatggcagca |
| aggcctggaacagcagcacaggccagatgctgagggataagttgaaagagcaaaatttccaacaaaaggtggtagatggcctggcct |
| ctggcattagcggggtggtggacctggccaaccaggcagtgcaaaataagattaacagtaagcttgatccccgccctcccgtagagga |
| gcctccaccggccgtggagacagtgtctccagaggggcgtggcgaaaagcgtccgcgccccgacagggaagaaactctggtgacg |
| caaatagacgagcctccctcgtacgaggaggcactaaagcaaggcctgcccaccacccgtcccatcgcgcccatggctaccggagtg |
| ctgggccagcacacacccgtaacgctggacctgcctcccccgccgacacccagcagaaacctgtgctgccaggcccgaccgccgt |
| tgttgtaacccgtcctagccgcgcgtccctgcgccgcgccgccagcggtccgcgatcgttgcggcccgtagccagtggcaactggca |
| aagcacactgaacagcatcgtgggtctgggggtgcaatccctgaagcgccgacgatgcttctgaatagctaacgtgtcgtatgtgtgtca |
| tgtatgcgtccatgtcgccgccagaggagctgctgagccgccgcgcgcccgctttccaagatggctaccccttcgatgatgccgcagtg |
| gtcttacatgcacatctcgggccaggacgcctcggagtacctgagccccgggctggtgcagtttgcccgcgccaccgagacgtacttc |
| agcctgaataacaagtttagaaccccacggtggcgcctacgcacgacgtgaccacagaccggtcccagcgtttgacgctgcggttca |
| tccctgtggaccgtgaggatactgcgtactcgtacaaggcgcggttcaccctagctgtgggtgataaccgtgtgctggacatggcttcca |
| cgtactttgacatccgcggcgtgctggacaggggccctacttttaagccctactctggcactgcctacaacgccctggctcccaagggtg |
| ccccaaatccttgcgaatgggatgaagctgctactgctcttgaaataaacctagaagaagaggacgatgacaacgaagacgaagtaga |
| cgagcaagctgagcagcaaaaaactcacgtatttgggcaggcgccttattctggtataaatattacaaaggagggtattcaaataggtgtc |
| gaaggtcaaacacctaaatatgccgataaaacatttcaacctgaacctcaaataggagaatctcagtggtacgaaacagaaattaatcat |
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataattttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |

TABLE 20-continued

| Ad5-IL13 with Plasmid Backbone |
|---|
| ttccgcggctgggccttcacgcgccttaagactaaggaaaccccatcactgggctcgggctacgacccttattacacctactctggctcta |
| taccctacctagatggaacctttacctcaaccacacctttaagaaggtggccattacctttgactcttctgtcagctggcctggcaatgacc |
| gcctgcttacccccaacgagtttgaaattaagcgctcagttgacggggagggttacaacgttgcccagtgtaacatgaccaaagactggt |
| tcctggtacaaatgctagctaactataacattggctaccagggcttctatatcccagagagctacaaggaccgcatgtactccttcttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttcccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttctttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggtggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgctttttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |
| ccatttccttctcctataggcagaaaaagatcatggagtcagtcgagaagaaggacagcctaaccgccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggcgggggacgaaaggcatggcgactacctagatgtgggagacgacgtgctgttgaagcatctgcagcgcca |

TABLE 20-continued

| Ad5-IL13 with Plasmid Backbone |
|---|
| gtgcgccattatctgcgacgcgttgcaagagcgcagcgatgtgcccctcgccatagcggatgtcagccttgcctacgaacgccacctat |
| tctcaccgcgcgtacccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctacccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacggggggtttacttggacccccagtccggcgaggagctcaacccaatcccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |
| aagttcagatgactaactcaggggcgcagcttgcgggcggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |

TABLE 20-continued

| Ad5-IL13 with Plasmid Backbone |
| --- |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |
| actgtgatttgcaactgtcctaaccttggattacatcaagatccagatcttctagacccgggagcggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |
| ccgctaaccgtgcacgactccaaacttagcattgccacccaaggacccctcacagtgtcagaaggaaagctagccctgcaaacatcag |
| gccccctcaccaccaccgatagcagtacccttactatcactgcctcacccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctctttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaacaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacactttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatggggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgccatccaccaccat |
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |

TABLE 20-continued

| Ad5-IL13 with Plasmid Backbone |
|---|
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgccccctggcttcgggttctatgtaaactccttcatgcgccgctgccctgataacatccaccaccgcagaataa |
| gccacacccagccaacctacacattcgttctgcgagtcacacacgggaggagcgggaagagctggaagaaccatgtttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagcccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccacccctcattatcatattggcttcaatccaaaataaggtatattattgatgatgttaatttgggccattagacttgaagtcaagcggcc |
| gcttacaactggaccttgctggtacatagaactgattaactgaccatttaaatcataccaacatggtcaaataaaacgaaaggctcagtcg |
| aaagactgggcctttcgttttaatctgatcggcacgtaagaggttccaactttcaccataatgaaataagatcactaccgggcgtatttttga |
| gttatcgagattttcaggagctaaggaagctaaaatgagccatattcaacgggaaacgtcttgctcgaggccgcgattaaattccaacatg |
| gatgctgatttatatgggtataaatgggctcgcgataatgtcgggcaatcaggtgcgacaatctatcgattgtatgggaagcccgatgcgc |
| cagagttgtttctgaaacatggcaaaggtagcgttgccaatgatgttacagatgagatggtcaggctaaactggctgacggaatttatgcc |
| tcttccgaccatcaagcattttatccgtactcctgatgatgcatggttactcaccactgcgatccccagggaaaacagcattccaggtattag |
| aagaatatcctgattcaggtgaaaatattgttgatgcgctggcagtgttcctgcgccggttgcattcgattcctgtttgtaattgtccttttaac |
| ggcgatcgcgtatttcgtctcgctcaggcgcaatcacgaatgaataacggtttggttggtgcgagtgattttgatgacgagcgtaatggct |
| ggcctgttgaacaagtctggaaagaaatgcataaacttttgccattctcaccggattcagtcgtcactcatggtgatttctcacttgataacct |
| tatttttgacgaggggaaattaataggttgtattgatgttggacgagtcggaatcgcagaccgataccaggatcttgccatcctatggaact |
| gcctcggtgagttttctccttcattacagaaacggctttttcaaaaatatggtattgataatcctgatatgaataaattgcagtttcacttgatgct |
| cgatgagtttttctaacctaggtgacagaagtcaaaagcctccggtcggaggcttttgactttctgctagatctgtttcaatgcggtgaagg |
| gccaggcagctggggattatgtcgagacccggccagcatgttggttttatcgcatattcagcgttgtcgcgtttacccaggtaaaatggaa |
| gcagtgtatcgtctgcgtgaatgtgcaaatcaggaacgtaaccgtggtacatagatgcagtcccttgcgggtcgttcccttcaacgagtag |
| gacgcggtgcccttgcaaggctaaccattgcgcctggtgtactgcagatgaggttttataaacccctcccttgtgtgacataacggaaagt |
| acaaccgggtttttatcgtcaggtctttggtttgggttaccaaacacactccgcatatggctaatttggtcaattgtgtagccagcgcgacgtt |
| ctactcggcccctcatctcaaaatcaggagccggtagacgaccagctttttccgcgtctctgatagcctgcggtgttacgccgatcaggtc |

TABLE 20-continued

| Ad5-IL13 with Plasmid Backbone |
| --- |
| tgcaacttctgttataccccagcggcgagtaatacgacgcgcttccgggctgtcatcgccgaactgtgcgatggcaatagcgcgcgtcat |
| ttcctgaccgcgattgatacagtctttcagcaaattaattaacgacatcctgtttcctctcaaacatgcccttatctttgtgtttttcatcatacttt |
| acgtttttaaagcaaagcaacataaaaaaagcaaagtgacttagaaaacgcaaagttaaggttcaaatcaatttttttgatgcgctacagaa |
| gctatttagcttcatctaagcgcaacggtattacttacgttggtatatttaaaacctaacttaatgattttaaatgataataaatcataccaattgc |
| tatcaaaagttaagcgaacatgctgattttcacgctgtttatacactttgaggcatctctatctcttccgtctctatattgaaacacaatcaaaga |
| acatcaatccatgtgacatcccccactatctaagaacaccataacagaacacaacataggaatgcaacattaatgtatcaataattcggaa |
| catatgcactatatcatatctcaattacggaacatatcagcacacaattgcccattatacgc |

TABLE 21

| AD5-IL13 No Plasmid Backbone |
| --- |
| (SEQ ID NO: 21) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccacgcgtggagctagttattaatagtaatcaattacggggtcattagttcatagcccatatat |
| ggagttccgcgttacataacttacggtaaatggcccgcctggctgaccgcccaacgacccccgcccattgacgtcaataatgacgtatgt |
| tcccatagtaacgtcaatagggactttccattgacgtcaatgggtggagtatttacggtaaactgcccacttggcagtacatcaagtgtatc |
| atatgccaagtacgccccctattgacgtcaatgacggtaaatggcccgcctggcattatgcccagtacatgaccttatgggactttcctact |
| tggcagtacatctacgtattagtcatcgctattaccatggtgatgcggttttggcagtacatcaatgggcgtggatagcggtttgactcacg |
| gggatttccaagtctccaccccattgacgtcaatgggagtttgttttgcaccaaaatcaacgggactttccaaaatgtcgtaacaactccgc |
| cccattgacgcaaatgggcggtaggcgtgtacggtgggaggtctatataagcagagctcgtttagtgaaccgtcagatcgcctggagac |
| gccatccacgctgttttgacctccatagaagacaccgggaccgatccagcctccgcggattcgaatcccggccgggaacggtgcattg |
| gaacgcggattccccgtgccaagagtgacgtaagtaccgcctatagagtctataggcccacaaaaaatgctttcttcttttaatatactttttt |
| gtttatcttatttctaatactttccctaatctctttctttcagggcaataatgatacaatgtatcatgcctctttgcaccattctaaagaataacagt |
| gataatttctgggttaaggcaatagcaatatttctgcatataaatatttctgcatataaattgtaactgatgtaagaggtttcatattgctaatagc |
| agctacaatccagctaccattctgcttttattttatggttgggataaggctggattattctgagtccaagctaggcccttttgctaatcatgttca |
| tacctcttatcttcctcccacagctcctgggcaacgtgctggtctgtgtgctggcccatcactttggcaaagctcctgggcaacgtgctggt |
| tattgtgctgtctcatcattttggcaaagaattccgctgcgactcggcggagtcccggcggcgcgtccttgttctaacccggcgcgccagc |
| ttggcaatccggtactgttggtaaagccaccaugguauggagcaucaaccugacagcuggcauguacugugcagcccuggaauc |
| ccugaucaacgugucaggcugcagugccaucgagaagacccagaggaugcugagcggauucugcccgcacaaggucucag |
| cugggcaguuuuccagcuugcauguccgagacaccaaaaucgagguggcccaguuuguaaaggaccugcucuuacauuua |
| aagaaacuuuuucgcgagggacaguucaacugataataattctagagtcgggggccggccgcttcgagcagacatgataagat |
| acattgatgagtttggacaaaccacaactagaatgcagtgaaaaaaatgctttatttgtgaaatttgtgatgctattgctttatttgtaaccatta |
| taagctgcaataaacaagttaacaacaacaattgcattcattttatgtttcaggttcagggggaggtgtgggaggttttttaaagcaagtaaa |
| acctctacaaatgtggtaaaatcgataaggatccgaattcgatatcactagtggtaccagtactgaaatgtgtgggcgtggcttaagggtg |
| ggaaagaatatataaggtgggggtcttatgtagttttgtatctgttttgcagcagccgccgccgccatgagcaccaactcgtttgatggaag |
| cattgtgagctcatatttgacaacgcgcatgcccccatgggccggggtgcgtcagaatgtgatgggctccagcattgatggtcgccccgt |

TABLE 21-continued

| AD5-IL13 No Plasmid Backbone |
|---|
| cctgcccgcaaactctactaccttgacctacgagaccgtgtctggaacgccgttggagactgcagcctccgccgccgcttcagccgctg |
| cagccaccgcccgcgggattgtgactgactttgctttcctgagcccgcttgcaagcagtgcagcttcccgttcatccgcccgcgatgaca |
| agttgacggctcttttggcacaattggattctttgacccgggaacttaatgtcgtttctcagcagctgttggatctgcgccagcaggtttctgc |
| cctgaaggcttcctcccctcccaatgcggtttaacggtccgggccagagtggccaacataaataaaaaaccagactctgtttggatttgg |
| atcaagcaagtgtcttgctgtctttatttaggggttttgcgcgcgcggtaggcccgggaccagcggtctcggtcgttgagggtcctgtgtat |
| tttttccaggacgtggtaaaggtgactctggatgttcagatacatgggcataagcccgtctctgggggggaggtagcaccactgcagagc |
| ttcatgctgcggggtggtgttgtagatgatccagtcgtagcaggagcgctgggcgtggtgcctaaaaatgtctttcagtagcaagctgatt |
| gccaggggcaggcccttggtgtaagtgtttacaaagcggttaagctgggatgggtgcatacgtggggatatgagatgcatcttggactgt |
| atttttaggttggctatgttcccagccatatccctccggggattcatgttgtgcagaaccaccagcacagtgtatccggtgcacttgggaaa |
| tttgtcatgtagcttagaaggaaatgcgtggaagaacttggagacgcccttgtgacctccaagattttccatgcattcgtccataatgatgg |
| caatgggcccacgggggcggcctgggcgaagatatttctgggatcactaacgtcatagttgtgttccaggatgagatcgtcataggcc |
| atttttacaaagcgcgggcggagggtgccagactgcggtataatggttccatccggcccaggggcgtagttaccctcacagatttgcatt |
| tcccacgctttgagttcagatgggggggatcatgtctacctgcggggcgatgaagaaaacggtttccggggtaggggagatcagctggg |
| aagaaagcaggttcctgagcagctgcgacttaccgcagccggtgggcccgtaaatcacacctattaccggctgcaactggtagttaaga |
| gagctgcagctgccgtcatccctgagcaggggggccacttcgttaagcatgtccctgactcgcatgttttccctgaccaaatccgccaga |
| aggcgctcgccgcccagcgatagcagttcttgcaaggaagcaaagtttttcaacggtttgagaccgtccgccgtaggcatgcttttgagc |
| gtttgaccaagcagttccaggcggtcccacagctcggtcacctgctctacggcatctcgatccagcatatctcctcgtttcgcgggttggg |
| gcggctttcgctgtacggcagtagtcggtgctcgtccagacgggccagggtcatgtctttccacgggcgcagggtcctcgtcagcgtag |
| tctgggtcacggtgaaggggtgcgctccgggctgcgcgctggccagggtgcgcttgaggctggtcctgctggtgctgaagcgctgcc |
| ggtcttcgccctgcgcgtcggccaggtagcatttgaccatggtgtcatagtccagcccctccgcggcgtggcccttggcgcgcagcttg |
| cccttggaggaggcgccgcacgaggggcagtgcagacttttgagggcgtagagcttgggcgcgagaaataccgattccggggagta |
| ggcatccgcgccgcaggccccgcagacggtctcgcattccacgagccaggtgagctctggccgttcggggtcaaaaaccaggtttcc |
| cccatgctttttgatgcgtttcttacctctggtttccatgagccggtgtccacgctcggtgacgaaaaggctgtccgtgtccccgtatacaga |
| cttgagaggcctgtcctcgagcggtgttccgcggtcctcctcgtatagaaactcggaccactctgagacaaaggctcgcgtccaggcca |
| gcacgaaggaggctaagtgggaggggtagcggtcgttgtccactagggggtccactcgctccagggtgtgaagacacatgtcgccct |
| cttcggcatcaaggaaggtgattggtttgtaggtgtaggccacgtgaccgggtgttcctgaaggggggctataaaagggggtgggggc |
| gcgttcgtcctcactctcttccgcatcgctgtctgcgagggccagctgttggggtgagtactccctctgaaaagcgggcatgacttctgcg |
| ctaagattgtcagtttccaaaaacgaggaggatttgatattcacctggcccgcggtgatgcctttgagggtggccgcatccatctggtcag |
| aaaagacaatctttttgttgtcaagcttggtggcaaacgacccgtagagggcgttggacagcaacttggcgatggagcgcagggtttggt |
| ttttgtcgcgatcggcgcgctccttggccgcgatgtttagctgcacgtattcgcgcgcaacgcaccgccattcgggaaagacggtggtg |
| cgctcgtcgggcaccaggtgcacgcgccaaccgcggttgtgcagggtgacaaggtcaacgctggtggctacctctccgcgtaggcgc |
| tcgttggtccagcagaggcggccgcccttgcgcgagcagaatggcggtagggggtctagctgcgtctcgtccggggggtctgcgtcc |
| acggtaaagaccccgggcagcaggcgcgcgtcgaagtagtctatcttgcatccttgcaagtctagcgcctgctgccatgcgcgggcgg |
| caagcgcgcgctcgtatgggttgagtgggggaccccatggcatggggtgggtgagcgcggaggcgtacatgccgcaaatgtcgtaa |
| acgtagaggggctctctgagtattccaagatatgtagggtagcatcttccaccgcggatgctggcgcgcacgtaatcgtatagttcgtgc |
| gagggagcgaggaggtcgggaccgaggttgctacgggcgggctgctctgctcggaagactatctgcctgaagatggcatgtgagttg |
| gatgatatggttggacgctggaagacgttgaagctggcgtctgtgagacctaccgcgtcacgcacgaaggaggcgtaggagtcgcgc |
| agcttgttgaccagctcggcggtgacctgcacgtctagggcgcagtagtccagggtttccttgatgatgtcatacttatcctgtcccttttttt |
| ccacagctcgcggttgaggacaaactcttcgcggtctttccagtactcttggatcggaaacccgtcggcctccgaacggtaagagccta |

TABLE 21-continued

| AD5-IL13 No Plasmid Backbone |
|---|
| gcatgtagaactggttgacggcctggtaggcgcagcatcccttttctacgggtagcgcgtatgcctgcgcggccttccggagcgaggtg |
| tgggtgagcgcaaaggtgtccctgaccatgactttgaggtactggtatttgaagtcagtgtcgtcgcatccgccctgctcccagagcaaa |
| aagtccgtgcgctttttggaacgcggatttggcagggcgaaggtgacatcgttgaagagtatctttcccgcgcgaggcataaagttgcgt |
| gtgatgcggaagggtcccggcacctcggaacggttgttaattacctgggcggcgagcacgatctcgtcaaagccgttgatgttgtggcc |
| cacaatgtaaagttccaagaagcgcgggatgcccttgatggaaggcaattttttaagttcctcgtaggtgagctcttcaggggagctgag |
| cccgtgctctgaaagggcccagtctgcaagatgagggttggaagcgacgaatgagctccacaggtcacgggccattagcatttgcagg |
| tggtcgcgaaaggtcctaaactggcgacctatggccatttttttctggggtgatgcagtagaaggtaagcgggtcttgttcccagcggtccc |
| atccaaggttcgcggctaggtctcgcgcggcagtcactagaggctcatctccgccgaacttcatgaccagcatgaagggcacgagctg |
| cttcccaaaggccccatccaagtataggtctctacatcgtaggtgacaaagagacgctcggtgcgaggatgcgagccgatcgggaag |
| aactggatctcccgccaccaattggaggagtggctattgatgtggtgaaagtagaagtccctgcgacgggccgaacactcgtgctggct |
| tttgtaaaaacgtgcgcagtactggcagcggtgcacgggctgtacatcctgcacgaggttgacctgacgaccgcgcacaaggaagca |
| gagtgggaatttgagcccctcgcctggcgggtttggctggtggtcttctacttcggctgcttgtccttgaccgtctggctgctcgaggggga |
| gttacggtggatcggaccaccacgccgcgcgagcccaaagtccagatgtccgcgcgcggcggtcggagcttgatgacaacatcgcg |
| cagatgggagctgtccatggtctggagctcccgcggcgtcaggtcaggcgggagctcctgcaggtttacctcgcatagacgggtcag |
| ggcgcgggctagatccaggtgatacctaatttccaggggctggttggtggcggcgtcgatggcttgcaagaggccgcatccccgcgg |
| cgcgactacggtaccgcgcgggggcggtgggccgcgggggtgtccttggatgatgcatctaaaagcggtgacgcgggcgagccc |
| ccggaggtagggggggctccggacccgccgggagagggggcaggggcacgtcggcgccgcgcgcgggcaggagctggtgctg |
| cgcgcgtaggttgctggcgaacgcgacgacgcggcggttgatctcctgaatctggcgcctctgcgtgaagacgacgggcccggtgag |
| cttgaacctgaaagagagttcgacagaatcaatttcggtgtcgttgacggcggcctggcgcaaaatctcctgcacgtctcctgagttgtctt |
| gataggcgatctcggccatgaactgctcgatctcttcctcctggagatctccgcgtccggctcgctccacggtggcggcgaggtcgttg |
| gaaatgcgggccatgagctgcgagaaggcgttgaggcctccctcgttccagacgcggctgtagaccacgcccccttcggcatcgcgg |
| gcgcgcatgaccacctgcgcgagattgagctccacgtgccgggcgaagacggcgtagtttcgcaggcgctgaaagaggtagttgag |
| ggtggtggcggtgtgttctgccacgaagaagtacataacccagcgtcgcaacgtggattcgttgatatcccccaaggcctcaaggcgct |
| ccatggcctcgtagaagtccacggcgaagttgaaaaactgggagttgcgcgccgacacggttaactcctcctccagaagacggatgag |
| ctcggcgacagtgtcgcgcacctcgcgctcaaaggctacaggggcctcttcttcttcttcaatctcctcttccataagggcctccccttcttc |
| ttcttctggcggcggtgggggaggggggacacggcggcgacgacggcgcaccgggaggcggtcgacaaagcgctcgatcatctcc |
| ccgcggcgacggcgcatggtctcggtgacggcgcggccgttctcgcgggggcgcagttggaagacgccgcccgtcatgtcccggtt |
| atgggttggcgggggctgccatgcggcagggatacggcgctaacgatgcatctcaacaattgttgtgtaggtactccgccgccgagg |
| gacctgagcgagtccgcatcgaccggatcggaaaacctctcgagaaaggcgtctaaccagtcacagtcgcaaggtaggctgagcacc |
| gtggcgggcggcagcgggcggcggtcggggttgtttctggcggaggtgctgctgatgatgtaattaaagtaggcggtcttgagacggc |
| ggatggtcgacagaagcaccatgtccttgggtccggcctgctgaatgcgcaggcggtcggccatgccccaggcttcgttttgacatcgg |
| cgcaggtctttgtagtagtcttgcatgagcctttctaccggcacttcttcttctccttcctcttgtcctgcatctcttgcatctatcgctgcggcg |
| gcggcggagtttggccgtaggtggcgccctcttcctcccatgcgtgtgaccccgaagcccctcatcggctgaagcagggctaggtcgg |
| cgacaacgcgctcggctaatatggcctgctgcacctgcgtgagggtagactggaagtcatccatgtccacaaagcggtggtatgcgcc |
| cgtgttgatggtgtaagtgcagttggccataacggaccagttaacggtctggtgacccggctgcgagagctcggtgtacctgagacgcg |
| agtaagccctcgagtcaaatacgtagtcgttgcaagtccgcaccaggtactggtatcccaccaaaaagtgcggcggcggctggcggta |
| gaggggccagcgtagggtggccggggctccgggggcgagatcttccaacataaggcgatgatatccgtagatgtacctggacatcca |
| ggtgatgccggcggcggtggtggaggcgcgcggaaagtcgcggacgcggttccagatgttgcgcagcggcaaaaagtgctccatg |
| gtcgggacgctctggccggtcaggcgcgcgcaatcgttgacgctctagaccgtgcaaaaggagagcctgtaagcgggcactcttccg |

TABLE 21-continued

| AD5-IL13 No Plasmid Backbone |
|---|
| tggtctggtggataaattcgcaagggtatcatggcggacgaccggggttcgagccccgtatccggccgtccgccgtgatccatgcggtt |
| accgcccgcgtgtcgaacccaggtgtgcgacgtcagacaacgggggagtgctccttttggcttccttccaggcgcggcggctgctgcg |
| ctagcttttttggccactggccgcgcgcagcgtaagcggttaggctggaaagcgaaagcattaagtggctcgctccctgtagccggagg |
| gttattttccaagggttgagtcgcgggacccccggttcgagtctcggaccggccggactgcggcgaacgggggtttgcctccccgtcat |
| gcaagaccccgcttgcaaattcctccggaaacagggacgagcccctttttgcttttcccagatgcatccggtgctgcggcagatgcgcc |
| cccctcctcagcagcggcaagagcaagagcagcggcagacatgcagggcaccctcccctcctcctaccgcgtcaggaggggcgac |
| atccgcggttgacgcggcagcagatggtgattacgaaccccgcggcgccgggcccggcactacctggacttggaggagggcgag |
| ggcctggcgcggctaggagcgccctctcctgagcggcacccaagggtgcagctgaagcgtgatacgcgtgaggcgtacgtgccgc |
| ggcagaacctgtttcgcgaccgcgagggagaggagcccgaggagatgcgggatcgaaagttccacgcagggcgcgagctgcggc |
| atggcctgaatcgcgagcggttgctgcgcgaggaggactttgagcccgacgcgcgaaccgggattagtcccgcgcgcgcacacgtg |
| gcggccgccgacctggtaaccgcatacgagcagacggtgaaccaggagattaactttcaaaaaagctttaacaaccacgtgcgtacgc |
| ttgtggcgcgcgaggaggtggctataggactgatgcatctgtgggactttgtaagcgcgctggagcaaaacccaaatagcaagccgct |
| catggcgcagctgttccttatagtgcagcacagcagggacaacgaggcattcagggatgcgctgctaaacatagtagagcccgaggg |
| ccgctggctgctcgatttgataaacatcctgcagagcatagtggtgcaggagcgcagcttgagcctggctgacaaggtggccgccatc |
| aactattccatgcttagcctgggcaagttttacgcccgcaagatataccataccccttacgttcccatagacaaggaggtaaagatcgagg |
| ggttctacatgcgcatggcgctgaaggtgcttaccttgagcgacgacctgggcgtttatcgcaacgagcgcatccacaaggccgtgag |
| cgtgagccggcggcgcgagctcagcgaccgcgagctgatgcacagcctgcaaagggccctggctggcacgggcagcggcgatag |
| agaggccgagtcctactttgacgcgggcgctgacctgcgctgggccccaagccgacgcgccctggaggcagctggggccggacct |
| gggctggcggtggcacccgcgcgcgctggcaacgtcggcggcgtggaggaatatgacgaggacgatgagtacgagccagaggac |
| ggcgagtactaagcggtgatgtttctgatcagatgatgcaagacgcaacggacccggcggtgcgggcggcgctgcagagccagccg |
| tccggccttaactccacggacgactggcgccaggtcatggaccgcatcatgtcgctgactgcgcgcaatcctgacgcgttccggcagc |
| agccgcaggccaaccggctctccgcaattctggaagcggtggtcccggcgcgcgcaaaccccacgcacgagaaggtgctggcgat |
| cgtaaacgcgctggccgaaaacagggccatccggcccgacgaggccggcctggtctacgacgcgctgcttcagcgcgtggctcgtt |
| acaacagcggcaacgtgcagaccaacctggaccggctggtgggggatgtgcgcgaggccgtggcgcagcgtgagcgcgcgcagc |
| agcagggcaacctgggctccatggttgcactaaacgccttcctgagtacacagcccgccaacgtgccgcggggacaggaggactac |
| accaactttgtgagcgcactgcggctaatggtgactgagacaccgcaaagtgaggtgtaccagtctgggccagactatttttttccagacc |
| agtagacaaggcctgcagaccgtaaacctgagccaggctttcaaaaacttgcaggggctgtggggggtgcgggctcccacaggcga |
| ccgcgcgaccgtgtctagcttgctgacgcccaactcgcgcctgttgctgctgctaatagcgcccttcacggacagtggcagcgtgtccc |
| gggacacatacctaggtcacttgctgacactgtaccgcgaggccataggtcaggcgcatgtggacgagcatactttccaggagattaca |
| agtgtcagccgcgcgctggggcaggaggacacgggcagcctggaggcaaccctaaactacctgctgaccaaccggcggcagaag |
| atcccctcgttgcacagtttaaacagcgaggaggagcgcattttgcgctacgtgcagcagagcgtgagccttaacctgatgcgcgacgg |
| ggtaacgcccagcgtggcgctggacatgaccgcgcgcaacatggaaccgggcatgtatgcctcaaaccggccgtttatcaaccgcct |
| aatggactacttgcatcgcgcggccgccgtgaaccccgagtatttcaccaatgccatcttgaacccgcactggctaccgccccctggttt |
| ctacaccggggggattcgaggtgcccgagggtaacgatggattcctctgggacgacatagacgacagcgtgttttccccgcaaccgcag |
| accctgctagagttgcaacagcgcgagcaggcagaggcggcgctgcgaaaggaaagcttccgcaggccaagcagcttgtccgatct |
| aggcgctgcggccccgcggtcagatgctagtagcccatttccaagcttgatagggtctcttaccagcactcgcaccacccgcccgcgc |
| ctgctgggcgaggaggagtacctaaacaactcgctgctgcagccgcagcgcgaaaaaaacctgcctccggcatttcccaacaacggg |
| atagagagcctagtggacaagatgagtagatggaagacgtacgcgcaggagcacagggacgtgccaggcccgcgcccgcccaccc |
| gtcgtcaaaggcacgaccgtcagcggggtctggtgtgggaggacgatgactcggcagacgacagcagcgtcctggatttgggggg |

TABLE 21-continued

| AD5-IL13 No Plasmid Backbone |
|---|
| agtggcaacccgtttgcgcaccttcgccccaggctggggagaatgttttaaaaaaaaaaaaaagcatgatgcaaaataaaaaactcacc |
| aaggccatggcaccgagcgttggttttcttgtattccccttagtatgcggcgcgcggcgatgtatgaggaaggtcctcctccctcctacga |
| gagtgtggtgagcgcggcgccagtggcggcggcgctgggttctcccttcgatgctcccctggacccgccgtttgtgcctccgggtac |
| ctgcggcctaccggggggagaaacagcatccgttactctgagttggcacccctattcgacaccacccgtgtgtacctggtggacaacaa |
| gtcaacggatgtggcatccctgaactaccagaacgaccacagcaactttctgaccacggtcattcaaaacaatgactacagcccgggg |
| gaggcaagcacacagaccatcaatcttgacgaccggtcgcactggggcggcgacctgaaaaccatcctgcataccaacatgccaaat |
| gtgaacgagttcatgtttaccaataagtttaaggcgcgggtgatggtgtcgcgcttgcctactaaggacaatcaggtggagctgaaatac |
| gagtgggtggagttcacgctgcccgagggcaactactccgagaccatgaccatagaccttatgaacaacgcgatcgtggagcactact |
| tgaaagtgggcagacagaacggggttctggaaagcgacatcggggtaaagtttgacacccgcaacttcagactggggtttgaccccgt |
| cactggtcttgtcatgcctggggtatatacaaacgaagccttccatccagacatcattttgctgccaggatgcggggtggacttcacccac |
| agccgcctgagcaacttgttgggcatccgcaagcggcaacccttccaggagggctttaggatcacctacgatgatctggagggtggta |
| acattcccgcactgttggatgtggacgcctaccaggcgagcttgaaagatgacaccgaacaggggggggtggcgcaggcggcagc |
| aacagcagtggcagcggcgcggaagagaactccaacgcggcagccgcggcaatgcagccggtggaggacatgaacgatcatgcc |
| attcgcggcgacacctttgccacacgggctgaggagaagcgcgctgaggccgaagcagcggccgaagctgccgcccccgctgcgc |
| aacccgaggtcgagaagcctcagaagaaaccggtgatcaaacccctgacagaggacagcaagaaacgcagttacaacctaataagc |
| aatgacagcaccttcacccagtaccgcagctggtaccttgcatacaactacggcgaccctcagaccggaatccgctcatggaccctgct |
| ttgcactcctgacgtaacctgcggctcggagcaggtctactggtcgttgccagacatgatgcaagaccccgtgaccttccgctccacgc |
| gccagatcagcaactttccggtggtgggcgccgagctgttgcccgtgcactccaagagcttctacaacgaccaggccgtctactcccaa |
| ctcatccgccagtttacctctctgacccacgtgttcaatcgctttcccgagaaccagattttggcgcgcccgccagcccccaccatcacca |
| ccgtcagtgaaaacgttcctgctctcacagatcacgggacgctaccgctgcgcaacagcatcggaggagtccagcgagtgaccattac |
| tgacgccagacgccgcacctgcccctacgtttacaaggccctgggcatagtctcgccgcgcgtcctatcgagccgcactttttgagcaa |
| gcatgtccatccttatatcgcccagcaataacacaggctggggcctgcgcttcccaagcaagatgtttggggggccaagaagcgctcc |
| gaccaacacccagtgcgcgtgcgcgggcactaccgcgcgccctggggcgcgcacaaacgcggccgcactgggcgcaccaccgtc |
| gatgacgccatcgacgcggtggtggaggaggcgcgcaactacacgcccacgccgccaccagtgtccacagtggacgcggccattc |
| agaccgtggtgcgcggagcccggcgctatgctaaaatgaagagacggcggaggcgcgtagcacgtcgccaccgccgccgacccg |
| gcactgccgcccaacgcgcggcggcggccctgcttaaccgcgcacgtcgcaccggccgacgggcggccatgcgagcagctcgaa |
| ggctggccgcgggtattgtcactgtgccccccaggtccaggcgacgagcggccgccgcagcagccgcggccattagtgctatgactc |
| agggtcgcaggggcaacgtgtattgggtgcgcgactcggttagcggcctgcgcgtgcccgtgcgcacccgcccccgcgcaactag |
| attgcaagaaaaaactacttagactcgtactgttgtatgtatccagcggcggcggcgcgcaacgaagctatgtccaagcgcaaaatcaa |
| agaagagatgctccaggtcatcgcgccggagatctatggcccccgaagaaggaagagcaggattacaagccccgaaagctaaagc |
| gggtcaaaaagaaaaagaaagatgatgatgatgaacttgacgacgaggtggaactgctgcacgctaccgcgcccaggcgacgggta |
| cagtggaaaggtcgacgcgtaaaacgtgttttgcgacccggcaccaccgtagtctttacgcccggtgagcgctccacccgcacctaca |
| agcgcgtgtatgatgaggtgtacggcgacgaggacctgcttgagcaggccaacgagcgcctcggggagtttgcctacggaaagcgg |
| cataaggacatgctggcgttgccgctggacgagggcaacccaacacctagcctaaagcccgtaacactgcagcaggtgctgcccgcg |
| cttgcaccgtccgaagaaaagcgcggcctaaagcgcgagtctggtgacttggcacccaccgtgcagctgatggtacccaagcgccag |
| cgactggaagatgtcttggaaaaaatgaccgtggaacctgggctggagcccgaggtccgcgtgcggccaatcaagcaggtggcgcc |
| gggactgggcgtgcagaccgtggacgttcagatacccactaccagtagcaccagtattgccaccgccacagagggcatggagacac |
| aaacgtccccggttgcctcagcggtggcggatgccgcggtgcaggcggtcgctgcggccgcgtccaagacctctacggaggtgcaa |
| acggacccgtggatgtttcgcgtttcagccccccggcgcccgcgccgttcgaggaagtacggcgccgccagcgcgctactgcccgaa |

TABLE 21-continued

| AD5-IL13 No Plasmid Backbone |
| --- |
| tatgccctacatccttccattgcgcctacccccggctatcgtggctacacctaccgccccagaagacgagcaactacccgacgccgaac |
| caccactggaacccgccgccgccgtcgccgtcgccagcccgtgctggccccgatttccgtgcgcagggtggctcgcgaaggaggca |
| ggaccctggtgctgccaacagcgcgctaccaccccagcatcgtttaaaagccggtctttgtggttcttgcagatatggccctcacctgcc |
| gcctccgtttcccggtgccgggattccgaggaagaatgcaccgtaggaggggcatggccggccacggcctgacgggcggcatgcgt |
| cgtgcgcaccaccggcggcggcgcgcgtcgcaccgtcgcatgcgcggcggtatcctgcccctccttattccactgatcgccgcggcg |
| attggcgccgtgcccggaattgcatccgtggccttgcaggcgcagagacactgattaaaaacaagttgcatgtggaaaaatcaaaataa |
| aaagtctggactctcacgctcgcttggtcctgtaactattttgtagaatggaagacatcaactttgcgtctctggccccgcgacacggctcg |
| cgcccgttcatgggaaactggcaagatatcggcaccagcaatatgagcggtggcgccttcagctggggctcgctgtggagcggcatta |
| aaaatttcggttccaccgttaagaactatggcagcaaggcctggaacagcagcacaggccagatgctgagggataagttgaaagagca |
| aaatttccaacaaaaggtggtagatggcctggcctctggcattagcggggggggacctggccaaccaggcagtgcaaaataagatta |
| acagtaagcttgatccccgccctcccgtagaggagcctccaccggccgtggagacagtgtctccagaggggcgtggcgaaaagcgtc |
| cgcgccccgacagggaagaaactctggtgacgcaaatagacgagcctccctcgtacgaggaggcactaaagcaaggcctgcccacc |
| acccgtcccatcgcgcccatggctaccggagtgctgggccagcacacacccgtaacgctggacctgcctcccccgccgacaccca |
| gcagaaacctgtgctgccaggcccgaccgccgttgttgtaacccgtcctagccgcgcgtccctgcgccgcgccgccagcggtccgcg |
| atcgttgcggcccgtagccagtggcaactggcaaagcacactgaacagcatcgtgggtctgggggtgcaatccctgaagcgccgacg |
| atgcttctgaatagctaacgtgtcgtatgtgtgtcatgtatgcgtccatgtcgccgccagaggagctgctgagccgccgcgcgcccgcttt |
| ccaagatggctaccccttcgatgatgccgcagtggtcttacatgcacatctcgggccaggacgcctcggagtacctgagccccgggct |
| ggtgcagtttgcccgcgccaccgagacgtacttcagcctgaataacaagtttagaaccccacggtggcgcctacgcacgacgtgacc |
| acagaccggtcccagcgtttgacgctgcggttcatccctgtggaccgtgaggatactgcgtactcgtacaaggcgcggttcaccctagc |
| tgtgggtgataaccgtgtgctggacatggcttccacgtactttgacatccgcggcgtgctggacaggggccctacttttaagccctactct |
| ggcactgcctacaacgccctggctcccaagggtgccccaaatccttgcgaatgggatgaagctgctactgctcttgaaataaacctaga |
| agaagaggacgatgacaacgaagacgaagtagacgagcaagctgagcagcaaaaaactcacgtatttgggcaggcgccttattctgg |
| tataaatattacaaaggagggtattcaaataggtgtcgaaggtcaaacacctaaatatgccgataaaacatttcaacctgaacctcaaatag |
| gagaatctcagtggtacgaaacagaaattaatcatgcagctgggagagtcctaaaaaagactaccccaatgaaaccatgttacggttcat |
| atgcaaaacccacaaatgaaaatggagggcaaggcattcttgtaaagcaacaaaatggaaagctagaaagtcaagtggaaatgcaattt |
| ttctcaactactgaggcagccgcaggcaatggtgataacttgactcctaaagtggtattgtacagtgaagatgtagatatagaaaccccag |
| acactcatatttcttacatgcccactattaaggaaggtaactcacgagaactaatgggccaacaatctatgcccaacaggcctaattacatt |
| gcttttagggacaattttattggtctaatgtattacaacagcacgggtaatatgggtgttctggcgggccaagcatcgcagttgaatgctgtt |
| gtagatttgcaagacagaaacacagagctttcataccagcttttgcttgattccattggtgatagaaccaggtacttttctatgtggaatcag |
| gctgttgacagctatgatccagatgttagaattattgaaaatcatggaactgaagatgaacttccaaattactgctttccactgggaggtgtg |
| attaatacagagactcttaccaaggtaaaacctaaaacaggtcaggaaaatggatgggaaaaagatgctacagaattttcagataaaaat |
| gaaataagagttggaaataattttgccatggaaatcaatctaaatgccaacctgtggagaaatttcctgtactccaacatagcgctgtatttg |
| cccgacaagctaaagtacagtccttccaacgtaaaaatttctgataacccaaacacctacgactacatgaacaagcgagtggtggctccc |
| gggctagtggactgctacattaaccttggagcacgctggtcccttgactatatggacaacgtcaacccatttaaccaccaccgcaatgctg |
| gcctgcgctaccgctcaatgttgctgggcaatggtcgctatgtgcccttccacatccaggtgcctcagaagttctttgccattaaaaacctc |
| cttctcctgccgggctcatacacctacgagtggaacttcaggaaggatgttaacatggttctgcagagctccctaggaaatgacctaagg |
| gttgacggagccagcattaagtttgatagcatttgcctttacgccaccttcttccccatggcccacaacaccgcctccacgcttgaggccat |
| gcttagaaacgacaccaacgaccagtcctttaacgactatctctccgccgccaacatgctctaccctatacccgccaacgctaccaacgt |
| gcccatatccatcccctcccgcaactgggcggctttccgcggctgggccttcacgcgccttaagactaaggaaaccccatcactgggct |

TABLE 21-continued

| AD5-IL13 No Plasmid Backbone |
|---|
| cgggctacgacccttattacacctactctggctctataccctacctagatggaaccttttacctcaaccacacctttaagaaggtggccatta |
| cctttgactcttctgtcagctggcctggcaatgaccgcctgcttaccccaacgagtttgaaattaagcgctcagttgacggggagggtta |
| caacgttgcccagtgtaacatgaccaaagactggttcctggtacaaatgctagctaactataacattggctaccagggcttctatatcccag |
| agagctacaaggaccgcatgtactccttctttagaaacttccagcccatgagccgtcaggtggtggatgatactaaatacaaggactacc |
| aacaggtgggcatcctacaccaacacaacaactctggatttgttggctaccttgcccccaccatgcgcgaaggacaggcctaccctgct |
| aacttcccctatccgcttataggcaagaccgcagttgacagcattacccagaaaaagtttctttgcgatcgcaccctttggcgcatcccatt |
| ctccagtaactttatgtccatgggcgcactcacagacctgggccaaaaccttctctacgccaactccgcccacgcgctagacatgactttt |
| gaggtggatcccatggacgagcccacccttctttatgttttgtttgaagtctttgacgtggtccgtgtgcaccagccgcaccgcggcgtcat |
| cgaaaccgtgtacctgcgcacgcccttctcggccggcaacgccacaacataaagaagcaagcaacatcaacaacagctgccgccatg |
| ggctccagtgagcaggaactgaaagccattgtcaaagatcttggttgtgggccatatttttgggcacctatgacaagcgctttccaggctt |
| tgtttctccacacaagctcgcctgcgccatagtcaatacggccggtcgcgagactgggggcgtacactggatggcctttgcctggaacc |
| cgcactcaaaaacatgctacctctttgagccctttggcttttctgaccagcgactcaagcaggtttaccagtttgagtacgagtcactcctgc |
| gccgtagcgccattgcttcttcccccgaccgctgtataacgctggaaaagtccacccaaagcgtacaggggcccaactcggccgcctg |
| tggactattctgctgcatgtttctccacgcctttgccaactggccccaaactcccatggatcacaaccccaccatgaaccttattaccgggg |
| tacccaactccatgctcaacagtccccaggtacagcccaccctgcgtcgcaaccaggaacagctctacagcttcctggagcgccactc |
| gccctacttccgcagccacagtgcgcagattaggagcgccacttctttttgtcacttgaaaaacatgtaaaaataatgtactagagacactt |
| tcaataaaggcaaatgcttttatttgtacactctcgggtgattatttacccccacccttgccgtctgcgccgtttaaaaatcaaaggggttctg |
| ccgcgcatcgctatgcgccactggcagggacacgttgcgatactggtgtttagtgctccacttaaactcaggcacaaccatccgcggca |
| gctcggtgaagttttcactccacaggctgcgcaccatcaccaacgcgtttagcaggtcgggcgccgatatcttgaagtcgcagttgggg |
| cctccgccctgcgcgcgcgagttgcgatacacagggttgcagcactggaacactatcagcgccgggtggtgcacgctggccagcac |
| gctcttgtcggagatcagatccgcgtccaggtcctccgcgttgctcagggcgaacggagtcaactttggtagctgccttcccaaaaagg |
| gcgcgtgcccaggctttgagttgcactcgcaccgtagtggcatcaaaaggtgaccgtgcccggtctgggcgttaggatacagcgcctg |
| cataaaagccttgatctgcttaaaagccacctgagcctttgcgccttcagagaagaacatgccgcaagacttgccggaaaactgattggc |
| cggacacgcggcgtcgtgcacgcagcaccttgcgtcggtgttggagatctgcaccacatttcggccccaccggttcttcacgatcttgg |
| ccttgctagactgctccttcagcgcgcgctgcccgttttcgctcgtcacatccatttcaatcacgtgctccttatttatcataatgcttccgtgta |
| gacacttaagctcgccttcgatctcagcgcagcggtgcagccacaacgcgcagcccgtgggctcgtgatgcttgtaggtcacctctgca |
| aacgactgcaggtacgcctgcaggaatcgccccatcatcgtcacaaaggtcttgttgctggtgaaggtcagctgcaacccgcggtgctc |
| ctcgttcagccaggtcttgcatacggccgccagagcttccacttggtcaggcagtagtttgaagttcgcctttagatcgttatccacgtggt |
| acttgtccatcagcgcgcgcgcagcctccatgcccttctcccacgcagacacgatcggcacactcagcgggttcatcaccgtaatttcac |
| tttccgcttcgctgggctcttcctcttcctcttgcgtccgcataccacgcgccactgggtcgtcttcattcagccgccgcactgtgcgcttac |
| ctcctttgccatgcttgattagcaccggtgggttgctgaaacccaccatttgtagcgccacatcttctctttcttcctcgctgtccacgattacc |
| tctggtgatggcgggcgctcgggcttgggagaagggcgcttctttttcttcttgggcgcaatggccaaatccgccgccgaggtcgatgg |
| ccgcgggctgggtgtgcgcggcaccagcgcgtcttgtgatgagtcttcctcgtcctcggactcgatacgccgcctcatccgctttttttggg |
| ggcgcccggggaggcggcggcgacggggacggggacgacacgtcctccatggttgggggacgtcgcgccgcaccgcgtccgcg |
| ctcgggggtggtttcgcgctgctcctcttcccgactggccatttccttctcctataggcagaaaaagatcatggagtcagtcgagaagaag |
| gacagcctaaccgcccccctctgagttcgccaccaccgcctccaccgatgccgccaacgcgcctaccaccttccccgtcgaggcaccc |
| ccgcttgaggaggaggaagtgattatcgagcaggacccaggttttgtaagcgaagacgacgaggaccgctcagtaccaacagaggat |
| aaaaagcaagaccaggacaacgcagaggcaaacgaggaacaagtcgggggggggacgaaaggcatggcgactacctagatgtg |
| ggagacgacgtgctgttgaagcatctgcagcgccagtgcgccattatctgcgacgcgttgcaagagcgcagcgatgtgcccctcgcca |

TABLE 21-continued

| AD5-IL13 No Plasmid Backbone |
|---|
| tagcggatgtcagccttgcctacgaacgccacctattctcaccgcgcgtacccccccaaacgccaagaaaacggcacatgcgagccca |
| acccgcgcctcaacttctaccccgtatttgccgtgccagaggtgcttgccacctatcacatctttttccaaaactgcaagatacccctatcct |
| gccgtgccaaccgcagccgagcggacaagcagctggccttgcggcagggcgctgtcatacctgatatcgcctcgctcaacgaagtgc |
| caaaaatctttgagggtcttggacgcgacgagaagcgcgcggcaaacgctctgcaacaggaaaacagcgaaaatgaaagtcactctg |
| gagtgttggtggaactcgagggtgacaacgcgcgcctagccgtactaaaacgcagcatcgaggtcacccactttgcctacccggcact |
| taacctacccccaaggtcatgagcacagtcatgagtgagctgatcgtgcgccgtgcgcagcccctggagagggatgcaaatttgcaa |
| gaacaaacagaggagggcctacccgcagttggcgacgagcagctagcgcgctggcttcaaacgcgcgagcctgccgacttggagg |
| agcgacgcaaactaatgatggccgcagtgctcgttaccgtggagcttgagtgcatgcagcggttctttgctgacccggagatgcagcgc |
| aagctagaggaaacattgcactacacctttcgacagggctacgtacgccaggcctgcaagatctccaacgtggagctctgcaacctggt |
| ctcctaccttggaattttgcacgaaaaccgccttgggcaaaacgtgcttcattccacgctcaagggcgaggcgcgccgcgactacgtcc |
| gcgactgcgtttacttatttctatgctacacctggcagacggccatgggcgtttggcagcagtgcttggaggagtgcaacctcaaggagc |
| tgcagaaactgctaaagcaaaacttgaaggacctatggacggccttcaacgagcgctccgtggccgcgcacctggcggacatcattttc |
| cccgaacgcctgcttaaaaccctgcaacagggtctgccagacttcaccagtcaaagcatgttgcagaactttaggaactttatcctagag |
| cgctcaggaatcttgcccgccacctgctgtgcacttcctagcgactttgtgcccattaagtaccgcgaatgccctccgccgctttggggcc |
| actgctaccttctgcagctagccaactaccttgcctaccactctgacataatggaagacgtgagcggtgacggtctactggagtgtcactg |
| tcgctgcaacctatgcaccccgcaccgctccctggtttgcaattcgcagctgcttaacgaaagtcaaattatcggtacctttgagctgcag |
| ggtccctcgcctgacgaaaagtccgcggctccggggttgaaactcactccggggctgtggacgtcggcttaccttcgcaaatttgtacct |
| gaggactaccacgcccacgagattaggttctacgaagaccaatcccgcccgcctaatgcggagcttaccgcctgcgtcattacccagg |
| gccacattcttggccaattgcaagccatcaacaaagcccgccaagagtttctgctacgaaagggacggggggtttacttggacccccag |
| tccggcgaggagctcaacccaatcccccgccgccgcagccctatcagcagcagccgcgggcccttgcttcccaggatggcaccca |
| aaaagaagctgcagctgccgccgccacccacggacgaggaggaatactgggacagtcaggcagaggaggttttggacgaggagga |
| ggaggacatgatggaagactgggagagcctagacgaggaagcttccgaggtcgaagaggtgtcagacgaaacaccgtcaccctcg |
| gtcgcattcccctcgccggcgccccagaaatcggcaaccggttccagcatggctacaacctccgctcctcaggcgccgccggcactg |
| cccgttcgccgacccaaccgtagatgggacaccactggaaccagggccggtaagtccaagcagccgccgccgttagcccaagagca |
| acaacagcgccaaggctaccgctcatggcgcgggcacaagaacgccatagttgcttgcttgcaagactgtgggggcaacatctccttc |
| gcccgccgctttcttctctaccatcacggcgtggccttcccccgtaacatcctgcattactaccgtcatctctacagcccatactgcaccgg |
| cggcagcggcagcggcagcaacagcagcggccacacagaagcaaaggcgaccggatagcaagactctgacaaagcccaagaaat |
| ccacagcggcggcagcagcaggaggaggagcgctgcgtctggcgcccaacgaacccgtatcgacccgcgagcttagaaacaggat |
| ttttcccactctgtatgctatatttcaacagagcaggggccaagaacaagagctgaaaaaaaaaacaggtctctgcgatccctcacccgc |
| agctgcctgtatcacaaaagcgaagatcagcttcggcgcacgctggaagacgcggaggctctcttcagtaaatactgcgcgctgactct |
| taaggactagtttcgcgccctttctcaaatttaagcgcgaaaactacgtcatctccagcggccacacccggcgccagcacctgttgtcag |
| cgccattatgagcaaggaaattcccacgccctacatgtggagttaccagccacaaatgggacttgcggctggagctgcccaagactact |
| caacccgaataaactacatgagcgcgggaccccacatgatatcccgggtcaacggaatacgcgcccaccgaaaccgaattctcctgg |
| aacaggcggctattaccaccacacctcgtaataaccttaatccccgtagttggcccgctgccctggtgtaccaggaaagtcccgctccca |
| ccactgtggtacttcccagagacgcccaggccgaagttcagatgactaactcaggggcgcagcttgcgggcggctttcgtcacagggt |
| gcggtcgcccgggcagggtataactcacctgacaatcagagggcgaggtattcagctcaacgacgagtcggtgagctcctcgcttggt |
| ctccgtccggacgggacatttcagatcggcggcgccggccgctcttcattcacgcctcgtcaggcaatcctaactctgcagacctcgtcc |
| tctgagccgcgctctggaggcattggaactctgcaatttattgaggagtttgtgccatcggtctactttaaccccttctcgggacctcccgg |
| ccactatccggatcaatttattcctaactttgacgcggtaaaggactcggcggacggctacgactgaatgttaagtggccaatgaggcct |

TABLE 21-continued

| AD5-IL13 No Plasmid Backbone |
|---|
| gacgctaataatagctggtccactgtcgccgccacaagtgctttgcccgcgactccggtgagttttgctactttgaattgcccgaggatcat |
| atcgagggcccggcgcacggcgtccggcttaccgcccagggagagcttgcccgtagcctgattcgggagtttacccagcgcccccctg |
| ctagttgagcgggacaggggaccctgtgttctcactgtgatttgcaactgtcctaaccttggattacatcaagatccagatcttctagaccc |
| gggagcggccgctgtcgacctgcaggatccgaattcgatatcactagtggtaccgatcttattccctttaactaataaaaaaaaataataaa |
| gcatcacttacttaaaatcagttagcaaatttctgtccagtttattcagcagcacctccttgccctcctcccagctctggtattgcagcttcctc |
| ctggctgcaaactttctccacaatctaaagggaatgtcagtttcctcctgttcctgtccatccgcacccactatcttcatgttgttgcagatga |
| agcgcgcaagaccgtctgaagataccttcaaccccgtgtatccatatgacacggaaaccggtcctccaactgtgccttttcttactcctcc |
| ctttgtatcccccaatgggtttcaagagagtccccctggggtactctctttgcgcctatccgaacctctagttacctccaatggcatgcttgc |
| gctcaaaatgggcaacggcctctctctggacgaggccggcaaccttacctcccaaaatgtaaccactgtgagcccacctctcaaaaaaa |
| ccaagtcaaacataaacctggaaatatctgcacccctcacagttacctcagaagccctaactgtggctgccgccgcacctctaatggtcg |
| cgggcaacacactcaccatgcaatcacaggccccgctaaccgtgcacgactccaaacttagcattgccacccaaggacccctcacagt |
| gtcagaaggaaagctagccctgcaaacatcaggcccccctcaccaccaccgatagcagtacccttactatcactgcctcacccccctctaa |
| ctactgccactggtagcttgggcattgacttgaaagagcccatttatacacaaaatggaaaactaggactaaagtacggggctcctttgca |
| tgtaacagacgacctaaacactttgaccgtagcaactggtccaggtgtgactattaataatacttccttgcaaactaaagttactggagcctt |
| gggttttgattcacaaggcaatatgcaacttaatgtagcaggaggactaaggattgattctcaaaacagacgccttatacttgatgttagtta |
| tccgtttgatgctcaaaaccaactaaatctaagactaggacagggccctctttttataaactcagcccacaacttggatattaactacaacaa |
| aggcctttacttgtttacagcttcaaacaattccaaaaagcttgaggttaacctaagcactgccaaggggttgatgtttgacgctacagccat |
| agccattaatgcaggagatgggcttgaatttggttcacctaatgcaccaaacacaaatcccctcaaaacaaaaattggccatggcctaga |
| atttgattcaaacaaggctatggttcctaaactaggaactggccttagttttgacagcacaggtgccattacagtaggaaacaaaaataatg |
| ataagctaactttgtggaccacaccagctccatctcctaactgtagactaaatgcagagaaagatgctaaactcactttggtcttaacaaaa |
| tgtggcagtcaaatacttgctacagtttcagttttggctgttaaaggcagtttggctccaatatctggaacagttcaaagtgctcatcttattat |
| aagatttgacgaaaatggagtgctactaaacaattccttcctggacccagaatattggaactttagaaatggagatcttactgaaggcaca |
| gcctatacaaacgctgttggatttatgcctaacctatcagcttatccaaaatctcacggtaaaactgccaaaagtaacattgtcagtcaagttt |
| acttaaacggagacaaaactaaacctgtaacactaaccattacactaaacggtacacaggaaacaggagacacaactccaagtgcata |
| ctctatgtcattttcatgggactggtctggccacaactacattaatgaaatatttgccacatcctcttacacttttttcatacattgcccaagaata |
| aagaatcgtttgtgttatgtttcaacgtgtttatttttcaattgcagaaaatttcaagtcatttttcattcagtagtatagccccaccaccacatag |
| cttatacagatcaccgtaccttaatcaaactcacagaaccctagtattcaacctgccacctccctcccaacacacagagtacacagtccttt |
| ctccccggctggccttaaaaagcatcatatcatgggtaacagacatattcttaggtgttatattccacacggtttcctgtcgagccaaacgct |
| catcagtgatattaataaactccccgggcagctcacttaagttcatgtcgctgtccagctgctgagccacaggctgctgtccaacttgcggt |
| tgcttaacgggcggcgaaggagaagtccacgcctacatgggggtagagtcataatcgtgcatcaggatagggcggtggtgctgcagc |
| agcgcgcgaataaactgctgccgccgccgctccgtcctgcaggaatacaacatggcagtggtctcctcagcgatgattcgcaccgccc |
| gcagcataaggcgccttgtcctccgggcacagcagcgcaccctgatctcacttaaatcagcacagtaactgcagcacagcaccacaat |
| attgttcaaaatcccacagtgcaaggcgctgtatccaaagctcatgggggaccacagaacccacgtggccatcataccacaagcgc |
| aggtagattaagtggcgacccctcataaacacgctggacataaacattacctcttttggcatgttgtaattcaccacctcccggtaccatata |
| aacctctgattaaacatggcgccatccaccaccatcctaaaccagctggccaaaacctgcccgccggctatacactgcagggaaccgg |
| gactggaacaatgacagtggagagcccaggactcgtaaccatggatcatcatgctcgtcatgatatcaatgttggcacaacacaggcac |
| acgtgcatacacttcctcaggattacaagctcctcccgcgttagaaccatatcccagggaacaacccattcctgaatcagcgtaaatccca |
| cactgcagggaagacctcgcacgtaactcacgttgtgcattgtcaaagtgttacattcgggcagcagcggatgatcctccagtatggtag |
| cgcgggtttctgtctcaaaaggaggtagacgatccctactgtacggagtgcgccgagacaaccgagatcgtgttggtcgtagtgtcatg |

TABLE 21-continued

| AD5-IL13 No Plasmid Backbone |
|---|
| ccaaatggaacgccggacgtagtcatatttcctgaagcaaaaccaggtggggcgtgacaaacagatctgcgtctccggtctcgccgct |
| tagatcgctctgtgtagtagttgtagtatatccactctctcaaagcatccaggcgccccctggcttcgggttctatgtaaactccttcatgcgc |
| cgctgccctgataacatccaccaccgcagaataagccacacccagccaacctacacattcgttctgcgagtcacacacgggaggagc |
| gggaagagctggaagaaccatgtttttttttttattccaaaagattatccaaaacctcaaaatgaagatctattaagtgaacgcgctcccctc |
| cggtggcgtggtcaaactctacagccaaagaacagataatggcatttgtaagatgttgcacaatggcttccaaaaggcaaacggccctc |
| acgtccaagtggacgtaaaggctaaacccttcagggtgaatctcctctataaacattccagcaccttcaaccatgcccaaataattctcatc |
| tcgccaccttctcaatatatctctaagcaaatcccgaatattaagtccggccattgtaaaaatctgctccagagcgccctccaccttcagcct |
| caagcagcgaatcatgattgcaaaaattcaggttcctcacagacctgtataagattcaaaagcggaacattaacaaaaataccgcgatcc |
| cgtaggtcccttcgcagggccagctgaacataatcgtgcaggtctgcacggaccagcgcggccacttccccgccaggaaccatgaca |
| aaagaacccacactgattatgacacgcatactcggagctatgctaaccagcgtagccccgatgtaagcttgttgcatgggcggcgatata |
| aaatgcaaggtgctgctcaaaaaatcaggcaaagcctcgcgcaaaaaagaaagcacatcgtagtcatgctcatgcagataaaggcag |
| gtaagctccggaaccaccacagaaaaagacaccatttttctctcaaacatgtctgcgggtttctgcataaacacaaaataaaataacaaaa |
| aaacatttaaacattagaagcctgtcttacaacaggaaaaacaacccttataagcataagacggactacggccatgccggcgtgaccgt |
| aaaaaaactggtcaccgtgattaaaaagcaccaccgacagctcctcggtcatgtccggagtcataatgtaagactcggtaaacacatca |
| ggttgattcacatcggtcagtgctaaaaagcgaccgaaatagcccgggggaatacatacccgcaggcgtagagacaacattacagccc |
| ccataggaggtataacaaaattaataggagagaaaaacacataaacacctgaaaaaccctcctgcctaggcaaaatagcaccctcccg |
| ctccagaacaacatacagcgcttccacagcggcagccataacagtcagccttaccagtaaaaaagaaaacctattaaaaaaacaccact |
| cgacacggcaccagctcaatcagtcacagtgtaaaaaagggccaagtgcagagcgagtatatataggactaaaaaatgacgtaacggt |
| taaagtccacaaaaaacacccagaaaaccgcacgcgaacctacgcccagaaacgaaagccaaaaaacccacaacttcctcaaatcgt |
| cacttccgttttcccacgttacgtaacttcccattttaagaaaactacaattcccaacacatacaagttactccgccctaaaacctacgtcacc |
| cgccccgttcccacgccccgcgccacgtcacaaactccaccccctcattatcatattggcttcaatccaaaataaggtatattattgatgat |
| g |

TABLE 22

| AD5-IL8-shRNA With Plasmid Backbone |
|---|
| (SEQ ID NO: 22) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |

TABLE 22-continued

| AD5-IL8-shRNA With Plasmid Backbone |
|---|
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcaggggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |

TABLE 22-continued

| AD5-IL8-shRNA With Plasmid Backbone |
| --- |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttttttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgcccccctgcaggtcgccaataacaaagcatgca |

TABLE 22-continued

| AD5-IL8-shRNA With Plasmid Backbone |
|---|
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattcccttttttaccgcataaggccaggagccatcttcagctggcgaatgttcccaggcgcgatggaa |
| agccaaccatccaagcaggcgttcctgctccatctgattgtttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttaaaacaacttttgctcacatgtgagggcctatttcccatgattcct |
| tcatatttgcatatacgatacaaggctgttagagagataattggaattaatttgactgtaaacacaaagatattagtacaaaatacgtgacgta |
| gaaagtaataatttcttgggtagtttgcagttttaaaattatgttttaaaatggactatcatatgcttaccgtaacttgaaagtatttcgatttcttg |
| gctttatatatcttgtggaaaggacgaaacaccgagcactccataaggcacaaactcaagaagtttgtgccttatggagtgccgttttcagt |
| actgaaatgtgtgggcgtggcttaagggtgggaaagaatatataaggtgggggtcttatgtagttttgtatctgttttgcagcagccgccgc |
| cgccatgagcaccaactcgtttgatggaagcattgtgagctcatatttgacaacgcgcatgcccccatgggccggggtgcgtcagaatg |
| tgatgggctccagcattgatggtcgccccgtcctgcccgcaaactctactaccttgacctacgagaccgtgtctggaacgccgttggaga |
| ctgcagcctccgccgccgcttcagccgctgcagccaccgcccgcgggattgtgactgactttgctttcctgagcccgcttgcaagcagt |
| gcagcttcccgttcatccgcccgcgatgacaagttgacggctcttttggcacaattggattctttgacccgggaacttaatgtcgtttctcag |
| cagctgttggatctgcgccagcaggtttctgccctgaaggcttcctcccctcccaatgcggtttaacggtccgggccagagtggccaaca |
| taaataaaaaaccagactctgtttggatttggatcaagcaagtgtcttgctgtctttatttaggggttttgcgcgcgcggtaggcccgggac |
| cagcggtctcggtcgttgagggtcctgtgtatttttttccaggacgtggtaaaggtgactctggatgttcagatacatgggcataagcccgtc |

TABLE 22-continued

| AD5-IL8-shRNA With Plasmid Backbone |
|---|
| tctggggtggaggtagcaccactgcagagcttcatgctgcggggtggtgttgtagatgatccagtcgtagcaggagcgctgggcgtgg |
| tgcctaaaaatgtctttcagtagcaagctgattgccaggggcaggcccttggtgtaagtgtttacaaagcggttaagctgggatgggtgca |
| tacgtggggatatgagatgcatcttggactgtatttttaggttggctatgttcccagccatatccctccggggattcatgttgtgcagaacca |
| ccagcacagtgtatccggtgcacttgggaaatttgtcatgtagcttagaaggaaatgcgtggaagaacttggagacgcccttgtgacctc |
| caagattttccatgcattcgtccataatgatggcaatgggcccacgggcggcggcctgggcgaagatatttctgggatcactaacgtcat |
| agttgtgttccaggatgagatcgtcataggccatttttacaaagcgcgggcggagggtgccagactgcggtataatggttccatccggcc |
| caggggcgtagttaccctcacagatttgcatttcccacgctttgagttcagatggggggatcatgtctacctgcggggcgatgaagaaaa |
| cggtttccggggtaggggagatcagctgggaagaaagcaggttcctgagcagctgcgacttaccgcagccggtgggcccgtaaatca |
| cacctattaccggctgcaactggtagttaagagagctgcagctgccgtcatccctgagcaggggggccacttcgttaagcatgtccctga |
| ctcgcatgttttccctgaccaaatccgccagaaggcgctcgccgcccagcgatagcagttcttgcaaggaagcaaagtttttcaacggttt |
| gagaccgtccgccgtaggcatgcttttgagcgtttgaccaagcagttccaggcggtcccacagctcggtcacctgctctacggcatctcg |
| atccagcatatctcctcgtttcgcgggttggggcggctttcgctgtacggcagtagtcggtgctcgtccagacgggccagggtcatgtctt |
| tccacgggcgcagggtcctcgtcagcgtagtctgggtcacggtgaaggggtgcgctccgggctgcgcgctggccagggtgcgcttga |
| ggctggtcctgctggtgctgaagcgctgccggtcttcgccctgcgcgtcggccaggtagcatttgaccatggtgtcatagtccagcccct |
| ccgcggcgtggcccttggcgcgcagcttgcccttggaggaggcgccgcacgaggggcagtgcagacttttgagggcgtagagcttg |
| ggcgcgagaaataccgattccggggagtaggcatccgcgccgcaggccccgcagacggtctcgcattccacgagccaggtgagctc |
| tggccgttcggggtcaaaaaccaggtttcccccatgctttttgatgcgtttcttacctctggtttccatgagccggtgtccacgctcggtgac |
| gaaaaggctgtccgtgtccccgtatacagacttgagaggcctgtcctcgagcggtgttccgcggtcctcctcgtatagaaactcggacca |
| ctctgagacaaaggctcgcgtccaggccagcacgaaggaggctaagtgggaggggtagcggtcgttgtccactagggggtccactc |
| gctccagggtgtgaagacacatgtcgccctcttcggcatcaaggaaggtgattggtttgtaggtgtaggccacgtgaccgggtgttcctg |
| aaggggggctataaaagggggtgggggcgcgttcgtcctcactctcttccgcatcgctgtctgcgagggccagctgttggggtgagta |
| ctccctctgaaaagcgggcatgacttctgcgctaagattgtcagtttccaaaaacgaggaggatttgatattcacctggcccgcggtgatg |
| cctttgagggtggccgcatccatctggtcagaaaagacaatctttttgttgtcaagcttggtggcaaacgacccgtagagggcgttggac |
| agcaacttggcgatggagcgcagggtttggtttttgtcgcgatcggcgcgctccttggccgcgatgtttagctgcacgtattcgcgcgca |
| acgcaccgccattcgggaaagacggtggtgcgctcgtcgggcaccaggtgcacgcgccaaccgcggttgtgcagggtgacaaggtc |
| aacgctggtggctacctctccgcgtaggcgctcgttggtccagcagaggcggccgcccttgcgcgagcagaatggcggtagggggtc |
| tagctgcgtctcgtccggggggtctgcgtccacggtaaagaccccgggcagcaggcgcgcgtcgaagtagtctatcttgcatccttgca |
| agtctagcgcctgctgccatgcgcgggcggcaagcgcgcgctcgtatgggttgagtgggggaccccatggcatggggtgggtgagc |
| gcggaggcgtacatgccgcaaatgtcgtaaacgtagaggggctctctgagtattccaagatatgtagggtagcatcttccaccgcggat |
| gctggcgcgcacgtaatcgtatagttcgtgcgagggagcgaggaggtcgggaccgaggttgctacgggcgggctgctctgctcggaa |
| gactatctgcctgaagatggcatgtgagttggatgatatggttggacgctggaagacgttgaagctggcgtctgtgagacctaccgcgtc |
| acgcacgaaggaggcgtaggagtcgcgcagcttgttgaccagctcggcggtgacctgcacgtctagggcgcagtagtccagggtttc |
| cttgatgatgtcatacttatcctgtccctttttttttccacagctcgcggttgaggacaaactcttcgcggtctttccagtactcttggatcggaaa |
| cccgtcggcctccgaacggtaagagcctagcatgtagaactggttgacggcctggtaggcgcagcatcccttttctacgggtagcgcgt |
| atgcctgcgcggccttccggagcgaggtgtgggtgagcgcaaaggtgtccctgaccatgactttgaggtactggtatttgaagtcagtgt |
| cgtcgcatccgccctgctcccagagcaaaaagtccgtgcgctttttggaacgcggatttggcagggcgaaggtgacatcgttgaagagt |
| atctttcccgcgcgaggcataaagttgcgtgtgatgcggaagggtcccggcacctcggaacggttgttaattacctgggcggcgagcac |
| gatctcgtcaaagccgttgatgttgtggcccacaatgtaaagttccaagaagcgcgggatgcccttgatggaaggcaatttttttaagttcct |
| cgtaggtgagctcttcaggggagctgagcccgtgctctgaaagggcccagtctgcaagatgagggttggaagcgacgaatgagctcc |

TABLE 22-continued

| AD5-IL8-shRNA With Plasmid Backbone |
|---|
| acaggtcacgggccattagcatttgcaggtggtcgcgaaaggtcctaaactggcgacctatggccatttttttctggggtgatgcagtaga |
| aggtaagcgggtcttgttcccagcggtcccatccaaggttcgcggctaggtctcgcgcggcagtcactagaggctcatctccgccgaac |
| ttcatgaccagcatgaagggcacgagctgcttcccaaaggcccccatccaagtataggtctctacatcgtaggtgacaaagagacgctc |
| ggtgcgaggatgcgagccgatcgggaagaactggatctcccgccaccaattggaggagtggctattgatgtggtgaaagtagaagtcc |
| ctgcgacgggccgaacactcgtgctggcttttgtaaaaacgtgcgcagtactggcagcggtgcacgggctgtacatcctgcacgaggtt |
| gacctgacgaccgcgcacaaggaagcagagtgggaatttgagcccctcgcctggcgggtttggctggtggtcttctacttcggctgctt |
| gtccttgaccgtctggctgctcgaggggagttacggtggatcggaccaccacgccgcgcgagcccaaagtccagatgtccgcgcgcg |
| gcggtcggagcttgatgacaacatcgcgcagatgggagctgtccatggtctggagctcccgcggcgtcaggtcaggggggagctcct |
| gcaggtttacctcgcatagacgggtcagggcgcgggctagatccaggtgatacctaatttccaggggctggttggtggcggcgtcgat |
| ggcttgcaagaggccgcatccccgcggcgcgactacggtaccgcgcggcgggcggtgggccgcgggggtgtccttggatgatgca |
| tctaaaagcggtgacgcgggcgagcccccggaggtagggggggctccggacccgccgggagagggggcaggggcacgtcggc |
| gccgcgcgcgggcaggagctggtgctgcgcgcgtaggttgctggcgaacgcgacgacgcggcggttgatctcctgaatctggcgcc |
| tctgcgtgaagacgacgggcccggtgagcttgaacctgaaagagagttcgacagaatcaatttcggtgtcgttgacggcggcctggcg |
| caaaatctcctgcacgtctcctgagttgtcttgataggcgatctcggccatgaactgctcgatctcttcctcctggagatctccgcgtccgg |
| ctcgctccacggtggcggcgaggtcgttggaaatgcgggccatgagctgcgagaaggcgttgaggcctccctcgttccagacgcggc |
| tgtagaccacgcccccttcggcatcgcgggcgcgcatgaccacctgcgcgagattgagctccacgtgccgggcgaagacggcgtag |
| tttcgcaggcgctgaaagaggtagttgagggtggtggcggtgtgttctgccacgaagaagtacataacccagcgtcgcaacgtggattc |
| gttgatatcccccaaggcctcaaggcgctccatggcctcgtagaagtccacggcgaagttgaaaaactgggagttgcgcgccgacacg |
| gttaactcctcctccagaagacggatgagctcggcgacagtgtcgcgcacctcgcgctcaaaggctacaggggcctcttcttcttcttca |
| atctcctcttccataagggcctccccttcttcttcttctggcggcggtgggggagggggggacacggcggcgacgacggcgcaccggga |
| ggcggtcgacaaagcgctcgatcatctccccgcggcgacggcgcatggtctcggtgacggcgcggccgttctcgcgggggcgcagt |
| tggaagacgccgcccgtcatgtcccggttatgggttggcgggggggctgccatgcggcagggatacggcgctaacgatgcatctcaac |
| aattgttgtgtaggtactccgccgccgagggacctgagcgagtccgcatcgaccggatcggaaaacctctcgagaaaggcgtctaacc |
| agtcacagtcgcaaggtaggctgagcaccgtggcgggcggcagcgggcggcggtcggggttgtttctggcggaggtgctgctgatg |
| atgtaattaaagtaggcggtcttgagacggcggatggtcgacagaagcaccatgtccttgggtccggcctgctgaatgcgcaggcggt |
| cggccatgccccaggcttcgttttgacatcggcgcaggtctttgtagtagtcttgcatgagcctttctaccggcacttcttcttctccttcctct |
| tgtcctgcatctcttgcatctatcgctgcggcggcggcggagtttggccgtaggtggcgccctcttcctcccatgcgtgtgaccccgaag |
| cccctcatcggctgaagcagggctaggtcggcgacaacgcgctcggctaatatggcctgctgcacctgcgtgagggtagactggaag |
| tcatccatgtccacaaagcggtggtatgcgcccgtgttgatggtgtaagtgcagttggccataacggaccagttaacggtctggtgaccc |
| ggctgcgagagctcggtgtacctgagacgcgagtaagccctcgagtcaaatacgtagtcgttgcaagtccgcaccaggtactggtatcc |
| caccaaaaagtgcggcggcggctggcggtagaggggccagcgtagggtggccggggctccgggggcgagatcttccaacataag |
| gcgatgatatccgtagatgtacctggacatccaggtgatgccggcggcggtggtggaggcgcgcggaaagtcgcggacgcggttcc |
| agatgttgcgcagcggcaaaaagtgctccatggtcgggacgctctggccggtcaggcgcgcgcaatcgttgacgctctagaccgtgc |
| aaaaggagagcctgtaagcgggcactcttccgtggtctggtggataaattcgcaagggtatcatggcggacgaccggggttcgagccc |
| cgtatccggccgtccgccgtgatccatgcggttaccgcccgcgtgtcgaacccaggtgtgcgacgtcagacaacgggggagtgctcct |
| tttggcttccttccaggcgcggcggctgctgcgctagcttttttggccactggccgcgcgcagcgtaagcggttaggctggaaagcgaa |
| agcattaagtggctcgctccctgtagccggagggttattttccaagggttgagtcgcgggacccccggttcgagtctcggaccggccgg |
| actgcggcgaacgggggtttgcctccccgtcatgcaagaccccgcttgcaaattcctccggaaacagggacgagcccctttttttgcttttc |
| ccagatgcatccggtgctgcggcagatgcgcccccctcctcagcagcggcaagagcaagagcagcggcagacatgcagggcaccc |

TABLE 22-continued

| AD5-IL8-shRNA With Plasmid Backbone |
|---|
| tcccctcctcctaccgcgtcaggaggggcgacatccgcggttgacgcggcagcagatggtgattacgaaccccgcggcgccgggc |
| ccggcactacctggacttggaggagggcgagggcctggcgcggctaggagcgccctctcctgagcggcacccaagggtgcagctg |
| aagcgtgatacgcgtgaggcgtacgtgccgcggcagaacctgtttcgcgaccgcgagggagaggagcccgaggagatgcgggatc |
| gaaagttccacgcagggcgcgagctgcggcatggcctgaatcgcgagcggttgctgcgcgaggaggactttgagcccgacgcgcg |
| aaccgggattagtcccgcgcgcgcacacgtggcggccgccgacctggtaaccgcatacgagcagacggtgaaccaggagattaact |
| ttcaaaaaagctttaacaaccacgtgcgtacgcttgtggcgcgcgaggaggtggctataggactgatgcatctgtgggactttgtaagcg |
| cgctggagcaaaacccaaatagcaagccgctcatggcgcagctgttccttatagtgcagcacagcagggacaacgaggcattcaggg |
| atgcgctgctaaacatagtagagcccgagggccgctggctgctcgatttgataaacatcctgcagagcatagtggtgcaggagcgcag |
| cttgagcctggctgacaaggtggccgccatcaactattccatgcttagcctgggcaagttttacgcccgcaagatataccatacccctac |
| gttcccatagacaaggaggtaaagatcgaggggttctacatgcgcatggcgctgaaggtgcttaccttgagcgacgacctgggcgttta |
| tcgcaacgagcgcatccacaaggccgtgagcgtgagccggcggcgcgagctcagcgaccgcgagctgatgcacagcctgcaaag |
| ggccctggctggcacgggcagcggcgatagagaggccgagtcctactttgacgcgggcgctgacctgcgctgggccccaagccga |
| cgcgccctggaggcagctggggccggacctgggctggcggtggcacccgcgcgcgctggcaacgtcggcggcgtggaggaatat |
| gacgaggacgatgagtacgagccagaggacggcgagtactaagcggtgatgtttctgatcagatgatgcaagacgcaacggacccg |
| gcggtgcgggcggcgctgcagagccagccgtccggccttaactccacggacgactggcgccaggtcatggaccgcatcatgtcgct |
| gactgcgcgcaatcctgacgcgttccggcagcagccgcaggccaaccggctctccgcaattctggaagcggtggtcccggcgcgcg |
| caaaccccacgcacgagaaggtgctggcgatcgtaaacgcgctggccgaaaacagggccatccggcccgacgaggccggcctggt |
| ctacgacgcgctgcttcagcgcgtggctcgttacaacagcggcaacgtgcagaccaacctggaccggctggtgggggatgtgcgcga |
| ggccgtggcgcagcgtgagcgcgcgcagcagcagggcaacctgggctccatggttgcactaaacgccttcctgagtacacagcccg |
| ccaacgtgccgcggggacaggaggactacaccaactttgtgagcgcactgcggctaatggtgactgagacaccgcaaagtgaggtgt |
| accagtctgggccagactatttttttccagaccagtagacaaggcctgcagaccgtaaacctgagccaggctttcaaaaacttgcagggg |
| ctgtgggggtgcgggctcccacaggcgaccgcgcgaccgtgtctagcttgctgacgcccaactcgcgcctgttgctgctgctaatag |
| cgcccttcacggacagtggcagcgtgtcccgggacacatacctaggtcacttgctgacactgtaccgcgaggccataggtcaggcgca |
| tgtggacgagcatactttccaggagattacaagtgtcagccgcgcgctggggcaggaggacacgggcagcctggaggcaaccctaa |
| actacctgctgaccaaccggcggcagaagatcccctcgttgcacagtttaaacagcgaggaggagcgcattttgcgctacgtgcagca |
| gagcgtgagccttaacctgatgcgcgacggggtaacgcccagcgtggcgctggacatgaccgcgcgcaacatggaaccgggcatgt |
| atgcctcaaaccggccgtttatcaaccgcctaatggactacttgcatcgcgcggccgccgtgaaccccgagtatttcaccaatgccatctt |
| gaacccgcactggctaccgccccctggtttctacaccggggggattcgaggtgcccgagggtaacgatggattcctctgggacgacata |
| gacgacagcgtgttttccccgcaaccgcagaccctgctagagttgcaacagcgcgagcaggcagaggcggcgctgcgaaaggaaa |
| gcttccgcaggccaagcagcttgtccgatctaggcgctgcggccccgcggtcagatgctagtagcccatttccaagcttgatagggtct |
| cttaccagcactcgcaccacccgcccgcgcctgctgggcgaggaggagtacctaaacaactcgctgctgcagccgcagcgcgaaaa |
| aaacctgcctccggcatttcccaacaacgggatagagagcctagtggacaagatgagtagatggaagacgtacgcgcaggagcaca |
| gggacgtgccaggcccgcgcccgcccacccgtcgtcaaaggcacgaccgtcagcggggtctggtgtgggaggacgatgactcggc |
| agacgacagcagcgtcctggatttgggagggagtggcaacccgtttgcgcaccttcgccccaggctggggagaatgttttaaaaaaaa |
| aaaaaagcatgatgcaaaataaaaaactcaccaaggccatggcaccgagcgttggttttcttgtattccccttagtatgcggcgcgcggc |
| gatgtatgaggaaggtcctcctccctcctacgagagtgtggtgagcgcggcgccagtggcggcggcgctgggttctcccttcgatgctc |
| ccctggacccgccgtttgtgcctccgcggtacctgcggcctaccggggggagaaacagcatccgttactctgagttggcacccctattc |
| gacaccacccgtgtgtacctggtggacaacaagtcaacggatgtggcatccctgaactaccagaacgaccacagcaactttctgacca |
| cggtcattcaaaacaatgactacagcccgggggaggcaagcacacagaccatcaatcttgacgaccggtcgcactggggcggcgac |

TABLE 22-continued

| AD5-IL8-shRNA With Plasmid Backbone |
|---|
| ctgaaaaccatcctgcataccaacatgccaaatgtgaacgagttcatgtttaccaataagtttaaggcgcgggtgatggtgtcgcgcttgc |
| ctactaaggacaatcaggtggagctgaaatacgagtgggtggagttcacgctgcccgagggcaactactccgagaccatgaccataga |
| ccttatgaacaacgcgatcgtggagcactacttgaaagtgggcagacagaacggggttctggaaagcgacatcggggtaaagtttgac |
| acccgcaacttcagactggggtttgaccccgtcactggtcttgtcatgcctggggtatatacaaacgaagccttccatccagacatcatttt |
| gctgccaggatgcggggtggacttcacccacagccgcctgagcaacttgttgggcatccgcaagcggcaacccttccaggagggcttt |
| aggatcacctacgatgatctggagggtggtaacattcccgcactgttggatgtggacgcctaccaggcgagcttgaaagatgacaccga |
| acagggcgggggtggcgcaggcggcagcaacagcagtggcagcggcgcggaagagaactccaacgcggcagccgcggcaatg |
| cagccggtggaggacatgaacgatcatgccattcgcggcgacacctttgccacacgggctgaggagaagcgcgctgaggccgaagc |
| agcggccgaagctgccgcccccgctgcgcaacccgaggtcgagaagcctcagaagaaaccggtgatcaaacccctgacagaggac |
| agcaagaaacgcagttacaacctaataagcaatgacagcaccttcacccagtaccgcagctggtaccttgcatacaactacggcgacc |
| ctcagaccggaatccgctcatggaccctgctttgcactcctgacgtaacctgcggctcggagcaggtctactggtcgttgccagacatga |
| tgcaagaccccgtgaccttccgctccacgcgccagatcagcaactttccggtggtgggcgccgagctgttgcccgtgcactccaagag |
| cttctacaacgaccaggccgtctactcccaactcatccgccagtttacctctctgacccacgtgttcaatcgctttcccgagaaccagatttt |
| ggcgcgcccgccagcccccaccatcaccaccgtcagtgaaaacgttcctgctctcacagatcacgggacgctaccgctgcgcaacag |
| catcggaggagtccagcgagtgaccattactgacgccagacgccgcacctgcccctacgtttacaaggccctgggcatagtctcgccg |
| cgcgtcctatcgagccgcactttttgagcaagcatgtccatccttatatcgcccagcaataacacaggctggggcctgcgcttcccaagc |
| aagatgtttggcggggccaagaagcgctccgaccaacacccagtgcgcgtgcgcgggcactaccgcgcgccctggggcgcgcaca |
| aacgcggccgcactgggcgcaccaccgtcgatgacgccatcgacgcggtggtggaggaggcgcgcaactacacgcccacgccgc |
| caccagtgtccacagtggacgcggccattcagaccgtggtgcgcggagcccggcgctatgctaaaatgaagagacggcggaggcg |
| cgtagcacgtcgccaccgccgccgacccggcactgccgcccaacgcgcggcggcggccctgcttaaccgcgcacgtcgcaccggc |
| cgacgggcggccatgcgagcagctcgaaggctggccgcgggtattgtcactgtgccccccaggtccaggcgacgagcggccgccg |
| cagcagccgcggccattagtgctatgactcagggtcgcaggggcaacgtgtattgggtgcgcgactcggttagcggcctgcgcgtgc |
| ccgtgcgcacccgcccccccgcgcaactagattgcaagaaaaaactacttagactcgtactgttgtatgtatccagcggcggcggcgcg |
| caacgaagctatgtccaagcgcaaaatcaaagaagagatgctccaggtcatcgcgccggagatctatggccccccgaagaaggaag |
| agcaggattacaagccccgaaagctaaagcgggtcaaaaagaaaaagaaagatgatgatgatgaacttgacgacgaggtggaactgc |
| tgcacgctaccgcgcccaggcgacgggtacagtggaaaggtcgacgcgtaaaacgtgttttgcgacccggcaccaccgtagtctttac |
| gcccggtgagcgctccacccgcacctacaagcgcgtgtatgatgaggtgtacggcgacgaggacctgcttgagcaggccaacgagc |
| gcctcggggagtttgcctacggaaagcggcataaggacatgctggcgttgccgctggacgagggcaacccaacacctagcctaaagc |
| ccgtaacactgcagcaggtgctgcccgcgcttgcaccgtccgaagaaaagcgcggcctaaagcgcgagtctggtgacttggcaccca |
| ccgtgcagctgatggtacccaagcgccagcgactggaagatgtcttggaaaaaatgaccgtggaacctgggctggagcccgaggtcc |
| gcgtgcggccaatcaagcaggtggcgccgggactgggcgtgcagaccgtggacgttcagatacccactaccagtagcaccagtattg |
| ccaccgccacagagggcatggagacacaaacgtccccggttgcctcagcggtggcggatgccgcggtgcaggcggtcgctgcggc |
| cgcgtccaagacctctacggaggtgcaaacggacccgtggatgtttcgcgtttcagccccccggcgcccgcgccgttcgaggaagta |
| cggcgccgccagcgcgctactgcccgaatatgccctacatccttccattgcgcctacccccggctatcgtggctacacctaccgcccca |
| gaagacgagcaactacccgacgccgaaccaccactggaacccgccgccgccgtcgccgtcgccagcccgtgctggccccgatttcc |
| gtgcgcagggtggctcgcgaaggaggcaggaccctggtgctgccaacagcgcgctaccaccccagcatcgtttaaaagccggtcttt |
| gtggttcttgcagatatggccctcacctgccgcctccgtttcccggtgccgggattccgaggaagaatgcaccgtaggaggggcatggc |
| cggccacggcctgacgggcggcatgcgtcgtgcgcaccaccggcggcggcgcgcgtcgcaccgtcgcatgcgcggcggtatcctg |
| cccctccttattccactgatcgccgcggcgattggcgccgtgcccggaattgcatccgtggccttgcaggcgcagagacactgattaa |

TABLE 22-continued

| AD5-IL8-shRNA With Plasmid Backbone |
|---|
| aacaagttgcatgtggaaaaatcaaaataaaaagtctggactctcacgctcgcttggtcctgtaactattttgtagaatggaagacatcaac |
| tttgcgtctctggccccgcgacacggctcgcgcccgttcatgggaaactggcaagatatcggcaccagcaatatgagcggtggcgcctt |
| cagctggggctcgctgtggagcggcattaaaaatttcggttccaccgttaagaactatggcagcaaggcctggaacagcagcacaggc |
| cagatgctgagggataagttgaaagagcaaaatttccaacaaaaggtggtagatggcctggcctctggcattagcggggtggtggacct |
| ggccaaccaggcagtgcaaaataagattaacagtaagcttgatccccgccctcccgtagaggagcctccaccggccgtggagacagt |
| gtctccagaggggcgtggcgaaaagcgtccgcgccccgacagggaagaaactctggtgacgcaaatagacgagcctccctcgtacg |
| aggaggcactaaagcaaggcctgcccaccacccgtcccatcgcgcccatggctaccggagtgctgggccagcacacacccgtaacg |
| ctggacctgcctcccccgccgacacccagcagaaacctgtgctgccaggcccgaccgccgttgttgtaacccgtcctagccgcgcgt |
| ccctgcgccgcgccgccagcggtccgcgatcgttgcggcccgtagccagtggcaactggcaaagcacactgaacagcatcgtgggt |
| ctgggggtgcaatccctgaagcgccgacgatgcttctgaatagctaacgtgtcgtatgtgtgtcatgtatgcgtccatgtcgccgccaga |
| ggagctgctgagccgccgcgcgcccgctttccaagatggctaccccttcgatgatgccgcagtggtcttacatgcacatctcgggccag |
| gacgcctcggagtacctgagccccgggctggtgcagtttgcccgcgccaccgagacgtacttcagcctgaataacaagtttagaaacc |
| ccacggtggcgcctacgcacgacgtgaccacagaccggtcccagcgtttgacgctgcggttcatccctgtggaccgtgaggatactgc |
| gtactcgtacaaggcgcggttcaccctagctgtgggtgataaccgtgtgctggacatggcttccacgtactttgacatccgcggcgtgct |
| ggacaggggccctacttttaagccctactctggcactgcctacaacgccctggctcccaagggtgccccaaatccttgcgaatgggatg |
| aagctgctactgctcttgaaataaacctagaagaagaggacgatgacaacgaagacgaagtagacgagcaagctgagcagcaaaaaa |
| ctcacgtatttgggcaggcgccttattctggtataaatattacaaaggagggtattcaaataggtgtcgaaggtcaaacacctaaatatgcc |
| gataaaacatttcaacctgaacctcaaataggagaatctcagtggtacgaaacagaaattaatcatgcagctgggagagtcctaaaaaag |
| actaccccaatgaaaccatgttacggttcatatgcaaaacccacaaatgaaaatggagggcaaggcattcttgtaaagcaacaaaatgg |
| aaagctagaaagtcaagtggaaatgcaatttttctcaactactgaggcagccgcaggcaatggtgataacttgactcctaaagtggtattg |
| tacagtgaagatgtagatatagaaaccccagacactcatatttcttacatgcccactattaaggaaggtaactcacgagaactaatgggcc |
| aacaatctatgcccaacaggcctaattacattgcttttagggacaattttattggtctaatgtattacaacagcacgggtaatatgggtgttct |
| ggcgggccaagcatcgcagttgaatgctgttgtagatttgcaagacagaaacacagagctttcataccagcttttgcttgattccattggtg |
| atagaaccaggtacttttctatgtggaatcaggctgttgacagctatgatccagatgttagaattattgaaaatcatggaactgaagatgaac |
| ttccaaattactgctttccactgggaggtgtgattaatacagagactcttaccaaggtaaaacctaaaacaggtcaggaaaatggatggga |
| aaaagatgctacagaattttcagataaaaatgaaataagagttggaaataattttgccatggaaatcaatctaaatgccaacctgtggagaa |
| atttcctgtactccaacatagcgctgtatttgcccgacaagctaaagtacagtccttccaacgtaaaaatttctgataacccaaacacctacg |
| actacatgaacaagcgagtggtggctcccgggctagtggactgctacattaaccttggagcacgctggtcccttgactatatggacaacg |
| tcaacccatttaaccaccaccgcaatgctggcctgcgctaccgctcaatgttgctgggcaatggtcgctatgtgcccttccacatccaggt |
| gcctcagaagttctttgccattaaaaacctccttctcctgccgggctcatacacctacgagtggaacttcaggaaggatgttaacatggttct |
| gcagagctccctaggaaatgacctaagggttgacggagccagcattaagtttgatagcatttgcctttacgccaccttcttccccatggcc |
| cacaacaccgcctccacgcttgaggccatgcttagaaacgacaccaacgaccagtcctttaacgactatctctccgccgccaacatgct |
| ctaccctatacccgccaacgctaccaacgtgcccatatccatcccctcccgcaactgggggctttccgcggctgggccttcacgcgcc |
| ttaagactaaggaaaccccatcactgggctcgggctacgacccttattacacctactctggctctataccctacctagatggaacctttac |
| ctcaaccacacctttaagaaggtggccattacctttgactcttctgtcagctggcctggcaatgaccgcctgcttacccccaacgagtttga |
| aattaagcgctcagttgacggggagggttacaacgttgcccagtgtaacatgaccaaagactggttcctggtacaaatgctagctaactat |
| aacattggctaccagggcttctatatcccagagagctacaaggaccgcatgtactccttctttagaaacttccagcccatgagccgtcagg |
| tggtggatgatactaaatacaaggactaccaacaggtgggcatcctacaccaacacaacaactctggatttgttggctaccttgcccccca |
| ccatgcgcgaaggacaggcctaccctgctaacttcccctatccgcttataggcaagaccgcagttgacagcattacccagaaaaagtttc |

TABLE 22-continued

| AD5-IL8-shRNA With Plasmid Backbone |
|---|
| tttgcgatcgcaccctttggcgcatcccattctccagtaactttatgtccatgggcgcactcacagacctgggccaaaaccttctctacgcc |
| aactccgcccacgcgctagacatgacttttgaggtggatcccatggacgagcccacccttctttatgttttgtttgaagtctttgacgtggtc |
| cgtgtgcaccagccgcaccgcggcgtcatcgaaaccgtgtacctgcgcacgcccttctcggccggcaacgccacaacataaagaagc |
| aagcaacatcaacaacagctgccgccatgggctccagtgagcaggaactgaaagccattgtcaaagatcttggttgtgggccatattttt |
| gggcacctatgacaagcgctttccaggctttgtttctccacacaagctcgcctgcgccatagtcaatacggccggtcgcgagactgggg |
| gcgtacactggatggcctttgcctggaacccgcactcaaaaacatgctacctctttgagccctttggcttttctgaccagcgactcaagca |
| ggtttaccagtttgagtacgagtcactcctgcgccgtagcgccattgcttcttcccccgaccgctgtataacgctggaaaagtccacccaa |
| agcgtacaggggcccaactcggccgcctgtggactattctgctgcatgtttctccacgcctttgccaactggccccaaactcccatggat |
| cacaaccccaccatgaaccttattaccggggtacccaactccatgctcaacagtccccaggtacagcccaccctgcgtcgcaaccagg |
| aacagctctacagcttcctggagcgccactcgccctacttccgcagccacagtgcgcagattaggagcgccacttctttttgtcacttgaa |
| aaacatgtaaaaataatgtactagagacactttcaataaaggcaaatgcttttatttgtacactctcgggtgattatttacccccacccttgcc |
| gtctgcgccgtttaaaaatcaaaggggttctgccgcgcatcgctatgcgccactggcagggacacgttgcgatactggtgtttagtgctc |
| cacttaaactcaggcacaaccatccgcggcagctcggtgaagttttcactccacaggctgcgcaccatcaccaacgcgtttagcaggtc |
| gggcgccgatatcttgaagtcgcagttggggcctccgccctgcgcgcgcgagttgcgatacacagggttgcagcactggaacactatc |
| agcgccgggtggtgcacgctggccagcacgctcttgtcggagatcagatccgcgtccaggtcctccgcgttgctcagggcgaacgga |
| gtcaactttggtagctgccttcccaaaaagggcgcgtgcccaggctttgagttgcactcgcaccgtagtggcatcaaaaggtgaccgtg |
| cccggtctgggcgttaggatacagcgcctgcataaaagccttgatctgcttaaaagccacctgagcctttgcgccttcagagaagaacat |
| gccgcaagacttgccggaaaactgattggccggacacgcggcgtcgtgcacgcagcaccttgcgtcggtgttggagatctgcaccac |
| atttcggccccaccggttcttcacgatcttggccttgctagactgctccttcagcgcgcgctgcccgttttcgctcgtcacatccatttcaatc |
| acgtgctccttatttatcataatgcttccgtgtagacacttaagctcgccttcgatctcagcgcagcggtgcagccacaacgcgcagcccg |
| tgggctcgtgatgcttgtaggtcacctctgcaaacgactgcaggtacgcctgcaggaatcgccccatcatcgtcacaaaggtcttgttgct |
| ggtgaaggtcagctgcaacccgcggtgctcctcgttcagccaggtcttgcatacggccgccagagcttccacttggtcaggcagtagttt |
| gaagttcgcctttagatcgttatccacgtggtacttgtccatcagcgcgcgcgcagcctccatgcccttctcccacgcagacacgatcgg |
| cacactcagcgggttcatcaccgtaatttcactttccgcttcgctgggctcttcctcttcctcttgcgtccgcataccacgcgccactgggtc |
| gtcttcattcagccgccgcactgtgcgcttacctcctttgccatgcttgattagcaccggtgggttgctgaaacccaccatttgtagcgcca |
| catcttctctttcttcctcgctgtccacgattacctctggtgatggcgggcgctcgggcttgggagaagggcgcttctttttcttcttgggcgc |
| aatggccaaatccgccgccgaggtcgatggccgcgggctgggtgtgcgcggcaccagcgcgtcttgtgatgagtcttcctcgtcctcg |
| gactcgatacgccgcctcatccgcttttttgggggcgcccggggaggcggcggcgacggggacggggacgacacgtcctccatggtt |
| gggggacgtcgcgccgcaccgcgtccgcgctcgggggtggtttcgcgctgctcctcttcccgactggccatttccttctcctataggca |
| gaaaaagatcatggagtcagtcgagaagaaggacagcctaaccgcccccctctgagttcgccaccaccgcctccaccgatgccgccaa |
| cgcgcctaccaccttccccgtcgaggcacccccgcttgaggaggaggaagtgattatcgagcaggacccaggttttgtaagcgaagac |
| gacgaggaccgctcagtaccaacagaggataaaaagcaagaccaggacaacgcagaggcaaacgaggaacaagtcgggcgggg |
| ggacgaaaggcatggcgactacctagatgtgggagacgacgtgctgttgaagcatctgcagcgccagtgcgccattatctgcgacgc |
| gttgcaagagcgcagcgatgtgcccctcgccatagcggatgtcagccttgcctacgaacgccacctattctcaccgcgcgtacccccca |
| aacgccaagaaaacggcacatgcgagcccaacccgcgcctcaacttctaccccgtatttgccgtgccagaggtgcttgccacctatcac |
| atctttttccaaaactgcaagatacccctatcctgccgtgccaaccgcagccgagcggacaagcagctggccttgcggcagggcgctgt |
| catacctgatatcgcctcgctcaacgaagtgccaaaaatctttgagggtcttggacgcgacgagaagcgcgcggcaaacgctctgcaa |
| caggaaaacagcgaaaatgaaagtcactctggagtgttggtggaactcgagggtgacaacgcgcgcctagccgtactaaaacgcagc |
| atcgaggtcacccactttgcctacccggcacttaacctacccccccaaggtcatgagcacagtcatgagtgagctgatcgtgcgccgtgc |

TABLE 22-continued

| AD5-IL8-shRNA With Plasmid Backbone |
|---|
| gcagcccctggagagggatgcaaatttgcaagaacaaacagaggagggcctacccgcagttggcgacgagcagctagcgcgctgg |
| cttcaaacgcgcgagcctgccgacttggaggagcgacgcaaactaatgatggccgcagtgctcgttaccgtggagcttgagtgcatgc |
| agcggttctttgctgacccggagatgcagcgcaagctagaggaaacattgcactacacctttcgacagggctacgtacgccaggcctg |
| caagatctccaacgtggagctctgcaacctggtctcctaccttggaattttgcacgaaaaccgccttgggcaaaacgtgcttcattccacg |
| ctcaagggcgaggcgcgccgcgactacgtccgcgactgcgtttacttatttctatgctacacctggcagacggccatgggcgtttggca |
| gcagtgcttggaggagtgcaacctcaaggagctgcagaaactgctaaagcaaaacttgaaggacctatggacggccttcaacgagcg |
| ctccgtggccgcgcacctggcggacatcattttccccgaacgcctgcttaaaaccctgcaacagggtctgccagacttcaccagtcaaa |
| gcatgttgcagaactttaggaactttatcctagagcgctcaggaatcttgcccgccacctgctgtgcacttcctagcgactttgtgcccatta |
| agtaccgcgaatgccctccgccgctttggggccactgctaccttctgcagctagccaactaccttgcctaccactctgacataatggaag |
| acgtgagcggtgacggtctactggagtgtcactgtcgctgcaacctatgcaccccgcaccgctccctggtttgcaattcgcagctgctta |
| acgaaagtcaaattatcggtacctttgagctgcagggtccctcgcctgacgaaaagtccgcggctccggggttgaaactcactccgggg |
| ctgtggacgtcggcttaccttcgcaaatttgtacctgaggactaccacgcccacgagattaggttctacgaagaccaatcccgcccgcct |
| aatgcggagcttaccgcctgcgtcattacccagggccacattcttggccaattgcaagccatcaacaaagcccgccaagagtttctgcta |
| cgaaagggacgggggtttacttggacccccagtccggcgaggagctcaacccaatcccccgccgccgcagccctatcagcagca |
| gccgcgggcccttgcttcccaggatggcacccaaaaagaagctgcagctgccgccgccacccacggacgaggaggaatactggga |
| cagtcaggcagaggaggttttggacgaggaggaggaggacatgatggaagactgggagagcctagacgaggaagcttccgaggtc |
| gaagaggtgtcagacgaaacaccgtcaccctcggtcgcattcccctcgccggcgccccagaaatcggcaaccggttccagcatggct |
| acaacctccgctcctcaggcgccgccggcactgcccgttcgccgacccaaccgtagatgggacaccactggaaccagggccggtaa |
| gtccaagcagccgccgccgttagcccaagagcaacaacagcgccaaggctaccgctcatggcgcgggcacaagaacgccatagttg |
| cttgcttgcaagactgtgggggcaacatctccttcgcccgccgctttcttctctaccatcacggcgtggccttcccccgtaacatcctgcatt |
| actaccgtcatctctacagcccatactgcaccggcggcagcggcagcggcagcaacagcagcggccacacagaagcaaaggcgac |
| cggatagcaagactctgacaaagcccaagaaatccacagcggcggcagcagcaggaggaggagcgctgcgtctggogcccaacg |
| aacccgtatcgacccgcgagcttagaaacaggatttttcccactctgtatgctatatttcaacagagcaggggccaagaacaagagctga |
| aaataaaaaacaggtctctgcgatccctcacccgcagctgcctgtatcacaaaagcgaagatcagcttcggcgcacgctggaagacgc |
| ggaggctctcttcagtaaatactgcgcgctgactcttaaggactagtttcgcgccctttctcaaatttaagcgcgaaaactacgtcatctcca |
| gcggccacacccggcgccagcacctgttgtcagcgccattatgagcaaggaaattcccacgccctacatgtggagttaccagccacaa |
| atgggacttgcggctggagctgcccaagactactcaacccgaataaactacatgagcgcgggaccccacatgatatcccgggtcaacg |
| gaatacgcgcccaccgaaaccgaattctcctggaacaggcggctattaccaccacacctcgtaataaccttaatccccgtagttggccc |
| gctgccctggtgtaccaggaaagtcccgctcccaccactgtggtacttcccagagacgcccaggccgaagttcagatgactaactcag |
| gggcgcagcttgcgggcggctttcgtcacagggtgcggtcgcccgggcagggtataactcacctgacaatcagagggcgaggtattc |
| agctcaacgacgagtcggtgagctcctcgcttggtctccgtccggacgggacatttcagatcggcggcgccggccgctcttcattcacg |
| cctcgtcaggcaatcctaactctgcagacctcgtcctctgagccgcgctctggaggcattggaactctgcaatttattgaggagtttgtgcc |
| atcggtctactttaaccccttctcgggacctcccggccactatccggatcaatttattcctaactttgacgcggtaaaggactcggcggacg |
| gctacgactgaatgttaagtggccaatgaggcctgacgctaataatagctggtccactgtcgccgccacaagtgctttgcccgcgactcc |
| ggtgagttttgctactttgaattgcccgaggatcatatcgagggcccggcgcacggcgtccggcttaccgcccagggagagcttgcccg |
| tagcctgattcgggagtttacccagcgcccccctgctagttgagcgggacaggggaccctgtgttctcactgtgatttgcaactgtcctaac |
| cttggattacatcaagatccagatcttctagacccgggagcggccgctgtcgacctgcaggatccgaattcgatatcactagtggtaccg |
| atcttattccctttaactaataaaaaaaaataataaagcatcacttacttaaaatcagttagcaaatttctgtccagtttattcagcagcacctcc |
| ttgccctcctcccagctctggtattgcagcttcctcctggctgcaaactttctccacaatctaaagggaatgtcagtttcctcctgttcctgtcc |

TABLE 22-continued

| AD5-IL8-shRNA With Plasmid Backbone |
|---|
| atccgcacccactatcttcatgttgttgcagatgaagcgcgcaagaccgtctgaagataccttcaaccccgtgtatccatatgacacggaa |
| accggtcctccaactgtgccttttcttactcctccctttgtatcccccaatgggtttcaagagagtccccctggggtactctctttgcgcctatc |
| cgaacctctagttacctccaatggcatgcttgcgctcaaaatgggcaacggcctctctctggacgaggccggcaaccttacctcccaaaa |
| tgtaaccactgtgagcccacctctcaaaaaaaccaagtcaaacataaacctggaaatatctgcacccctcacagttacctcagaagccct |
| aactgtggctgccgccgcacctctaatggtcgcgggcaacacactcaccatgcaatcacaggccccgctaaccgtgcacgactccaaa |
| cttagcattgccacccaaggacccctcacagtgtcagaaggaaagctagccctgcaaacatcaggcccccctcaccaccaccgatagca |
| gtacccttactatcactgcctcacccccctctaactactgccactggtagcttgggcattgacttgaaagagcccatttatacacaaaatgga |
| aaactaggactaaagtacggggctcctttgcatgtaacagacgacctaaacactttgaccgtagcaactggtccaggtgtgactattaata |
| atacttccttgcaaactaaagttactggagccttgggttttgattcacaaggcaatatgcaacttaatgtagcaggaggactaaggattgatt |
| ctcaaaacagacgccttatacttgatgttagttatccgtttgatgctcaaaaccaactaaatctaagactaggacagggccctctttttataaa |
| ctcagcccacaacttggatattaactacaacaaaggcctttacttgtttacagcttcaaacaattccaaaaagcttgaggttaacctaagcac |
| tgccaaggggttgatgtttgacgctacagccatagccattaatgcaggagatgggcttgaatttggttcacctaatgcaccaaacacaaat |
| cccctcaaaacaaaaattggccatggcctagaatttgattcaaacaaggctatggttcctaaactaggaactggccttagttttgacagcac |
| aggtgccattacagtaggaaaaaaaataatgataagctaactttgtggaccacaccagctccatctcctaactgtagactaaatgcagag |
| aaagatgctaaactcactttggtcttaacaaaatgtggcagtcaaatacttgctacagtttcagttttggctgttaaaggcagtttggctccaa |
| tatctggaacagttcaaagtgctcatcttattataagatttgacgaaaatggagtgctactaaacaattccttcctggacccagaatattggaa |
| ctttagaaatggagatcttactgaaggcacagcctatacaaacgctgttggatttatgcctaacctatcagcttatccaaaatctcacggtaa |
| aactgccaaaagtaacattgtcagtcaagtttacttaaacggagacaaaactaaacctgtaacactaaccattacactaaacggtacacag |
| gaaacaggagacacaactccaagtgcatactctatgtcattttcatgggactggtctggccacaactacattaatgaaatatttgccacatc |
| ctcttacactttttcatacattgcccaagaataaagaatcgtttgtgttatgtttcaacgtgtttatttttcaattgcagaaaatttcaagtcatttttc |
| attcagtagtatagccccaccaccacatagcttatacagatcaccgtaccttaatcaaactcacagaaccctagtattcaacctgccacctc |
| cctcccaacacacagagtacacagtcctttctccccggctggccttaaaaagcatcatatcatgggtaacagacatattcttaggtgttatat |
| tccacacggtttcctgtcgagccaaacgctcatcagtgatattaataaactccccgggcagctcacttaagttcatgtcgctgtccagctgc |
| tgagccacaggctgctgtccaacttgcggttgcttaacgggcggcgaaggagaagtccacgcctacatgggggtagagtcataatcgt |
| gcatcaggatagggcggtggtgctgcagcagcgcgcgaataaactgctgccgccgccgctccgtcctgcaggaatacaacatggca |
| gtggtctcctcagcgatgattcgcaccgcccgcagcataaggcgccttgtcctccgggcacagcagcgcaccctgatctcacttaaatc |
| agcacagtaactgcagcacagcaccacaatattgttcaaaatcccacagtgcaaggcgctgtatccaaagctcatgggggaccaca |
| gaacccacgtggccatcataccacaagcgcaggtagattaagtggcgacccctcataaacacgctggacataaacattacctcttttggc |
| atgttgtaattcaccacctcccggtaccatataaacctctgattaaacatggcgccatccaccaccatcctaaaccagctggccaaaacct |
| gcccgccggctatacactgcagggaaccgggactggaacaatgacagtggagagcccaggactcgtaaccatggatcatcatgctcg |
| tcatgatatcaatgttggcacaacacaggcacacgtgcatacacttcctcaggattacaagctcctcccgcgttagaaccatatcccaggg |
| aacaacccattcctgaatcagcgtaaatcccacactgcagggaagacctcgcacgtaactcacgttgtgcattgtcaaagtgttacattcg |
| ggcagcagcggatgatcctccagtatggtagcgcgggtttctgtctcaaaaggaggtagacgatccctactgtacggagtgcgccgag |
| acaaccgagatcgtgttggtcgtagtgtcatgccaaatggaacgccggacgtagtcatatttcctgaagcaaaaccaggtgcgggcgtg |
| acaaacagatctgcgtctccggtctcgccgcttagatcgctctgtgtagtagttgtagtatatccactctctcaaagcatccaggcgccccc |
| tggcttcgggttctatgtaaactccttcatgcgccgctgccctgataacatccaccaccgcagaataagccacacccagccaacctacac |
| attcgttctgcgagtcacacacgggaggagcgggaagagctggaagaaccatgtttttttttttattccaaaagattatccaaaacctcaa |
| aatgaagatctattaagtgaacgcgctcccctccggtggcgtggtcaaactctacagccaaagaacagataatggcatttgtaagatgttg |
| cacaatggcttccaaaaggcaaacggccctcacgtccaagtggacgtaaaggctaaacccttcagggtgaatctcctctataaacattcc |

TABLE 22-continued

| AD5-IL8-shRNA With Plasmid Backbone |
|---|
| agcaccttcaaccatgcccaaataattctcatctcgccaccttctcaatatatctctaagcaaatcccgaatattaagtccggccattgtaaa |
| aatctgctccagagcgccctccaccttcagcctcaagcagcgaatcatgattgcaaaaattcaggttcctcacagacctgtataagattca |
| aaagcggaacattaacaaaaataccgcgatcccgtaggtcccttcgcagggccagctgaacataatcgtgcaggtctgcacggaccag |
| cgcggccacttccccgccaggaaccatgacaaaagaacccacactgattatgacacgcatactcggagctatgctaaccagcgtagcc |
| ccgatgtaagcttgttgcatgggcggcgatataaaatgcaaggtgctgctcaaaaaatcaggcaaagcctcgcgcaaaaaagaaagca |
| catcgtagtcatgctcatgcagataaaggcaggtaagctccggaaccaccacagaaaaagacaccatttttctctcaaacatgtctgcgg |
| gtttctgcataaacacaaaataaaataacaaaaaaacatttaaacattagaagcctgtcttacaacaggaaaaacaacccttataagcataa |
| gacggactacggccatgccggcgtgaccgtaaaaaaactggtcaccgtgattaaaaagcaccaccgacagctcctcggtcatgtccgg |
| agtcataatgtaagactcggtaaacacatcaggttgattcacatcggtcagtgctaaaaagcgaccgaaatagcccgggggaatacata |
| cccgcaggcgtagagacaacattacagcccccataggaggtataacaaaattaataggagagaaaaacacataaacacctgaaaaac |
| cctcctgcctaggcaaaatagcaccctcccgctccagaacaacatacagcgcttccacagcggcagccataacagtcagccttaccagt |
| aaaaaagaaaacctattaaaaaaacaccactcgacacggcaccagctcaatcagtcacagtgtaaaaaagggccaagtgcagagcga |
| gtatatataggactaaaaaatgacgtaacggttaaagtccacaaaaaacacccagaaaaccgcacgcgaacctacgcccagaaacga |
| aagccaaaaaacccacaacttcctcaaatcgtcacttccgttttcccacgttacgtaacttcccattttaagaaaactacaattcccaacaca |
| tacaagttactccgccctaaaacctacgtcacccgccccgttcccacgccccgcgccacgtcacaaactccaccccctcattatcatattg |
| gcttcaatccaaaataaggtatattattgatgatgttaatttgggccattagacttgaagtcaagcggccgcttacaactggaccttgctggt |
| acatagaactgattaactgaccatttaaatcataccaacatggtcaaataaaacgaaaggctcagtcgaaagactgggcctttcgttttaat |
| ctgatcggcacgtaagaggttccaactttcaccataatgaaataagatcactaccgggcgtattttttgagttatcgagattttcaggagcta |
| aggaagctaaaatgagccatattcaacgggaaacgtcttgctcgaggccgcgattaaattccaacatggatgctgatttatatgggtataa |
| atgggctcgcgataatgtcgggcaatcaggtgcgacaatctatcgattgtatgggaagcccgatgcgccagagttgtttctgaaacatgg |
| caaaggtagcgttgccaatgatgttacagatgagatggtcaggctaaactggctgacggaatttatgcctcttccgaccatcaagcatttta |
| tccgtactcctgatgatgcatggttactcaccactgcgatccccagggaaaacagcattccaggtattagaagaatatcctgattcaggtga |
| aaatattgttgatgcgctggcagtgttcctgcgccggttgcattcgattcctgtttgtaattgtccttttaacggcgatcgcgtatttcgtctcgc |
| tcaggcgcaatcacgaatgaataacggtttggttggtgcgagtgattttgatgacgagcgtaatggctggcctgttgaacaagtctggaaa |
| gaaatgcataaacttttgccattctcaccggattcagtcgtcactcatggtgatttctcacttgataaccttatttttgacgaggggaaattaat |
| aggttgtattgatgttggacgagtcggaatcgcagaccgataccaggatcttgccatcctatggaactgcctcggtgagttttctccttcatt |
| acagaaacggctttttcaaaaatatggtattgataatcctgatatgaataaattgcagtttcacttgatgctcgatgagtttttctaacctaggtg |
| acagaagtcaaaagcctccggtcggaggcttttgactttctgctagatctgtttcaatgcggtgaagggccaggcagctggggattatgtc |
| gagacccggccagcatgttggttttatcgcatattcagcgttgtcgcgtttacccaggtaaaatggaagcagtgtatcgtctgcgtgaatgt |
| gcaaatcaggaacgtaaccgtggtacatagatgcagtcccttgcgggtcgttcccttcaacgagtaggacgcggtgcccttgcaaggct |
| aaccattgcgcctggtgtactgcagatgaggttttataaacccctcccttgtgtgacataacggaaagtacaaccgggtttttatcgtcaggt |
| ctttggtttgggttaccaaacacactccgcatatggctaatttggtcaattgtgtagccagcgcgacgttctactcggcccctcatctcaaaa |
| tcaggagccggtagacgaccagctttttccgcgtctctgatagcctgcggtgttacgccgatcaggtctgcaacttctgttataccccagc |
| ggcgagtaatacgacgcgcttccgggctgtcatcgccgaactgtgcgatggcaatagcgcgcgtcatttcctgaccgcgattgatacag |
| tctttcagcaaattaattaacgacatcctgtttcctctcaaacatgcccttatctttgtgtttttcatcatactttacgtttttaaagcaaagcaacat |
| aaaaaaagcaaagtgacttagaaaacgcaaagttaaggttcaaatcaatttttttgatgcgctacagaagctatttagcttcatctaagcgca |
| acggtattacttacgttggtatatttaaaacctaacttaatgattttaaatgataataaatcataccaattgctatcaaaagttaagcgaacatgc |

TABLE 22-continued

| AD5-IL8-shRNA With Plasmid Backbone |
|---|
| tgattttcacgctgtttatacactttgaggcatctctatctcttccgtctctatattgaaacacaatcaaagaacatcaatccatgtgacatcccc<br>cactatctaagaacaccataacagaacacaacataggaatgcaacattaatgtatcaataattggaacatatgcactatatcatatctcaat<br>tacggaacatatcagcacacaattgcccattatacgc |

TABLE 23

| Ad5-IL8-shRNA with Plasmid Backbone |
|---|
| (SEQ ID NO: 23)<br>catcatcaataatataccttattttggattgaagccaatatgataatgagggggtggagtttgtgacgtggcgcggggcgtgggaacggg<br>gcgggtgacgtagtagtgtggcggaagtgtgatgttgcaagtgtggcggaacacatgtaagcgacggatgtggcaaaagtgacgtttttt<br>ggtgtgcgccggtgtacacaggaagtgacaattttcgcgcggttttaggcggatgttgtagtaaatttgggcgtaaccgagtaagatttgg<br>ccattttcgcgggaaaactgaataagaggaagtgaaatctgaataattttgtgttactcatagcgcgtaatatttgtctagggccgcgggga<br>ctttgaccgtttacgtggagactcgcccaggtgtttttctcaggtgttttccgcgttccgggtcaaagttggcgttttagatcttaaaacaactt<br>ttgctcacatgtgagggcctatttcccatgattccttcatatttgcatatacgatacaaggctgttagagagataattggaattaatttgactgta<br>aacacaaagatattagtacaaaatacgtgacgtagaaagtaataatttcttgggtagtttgcagttttaaaattatgttttaaaatggactatcat<br>atgcttaccgtaacttgaaagtatttcgatttcttggctttatatatcttgtggaaaggacgaaacaccgagcactccataaggcacaaactc<br>aagaagtttgtgccttatggagtgccgttttcagtactgaaatgtgtgggcgtggcttaagggtgggaaagaatatataaggtgggggtctt<br>atgtagttttgtatctgttttgcagcagccgccgccgccatgagcaccaactcgtttgatggaagcattgtgagctcatatttgacaacgcg<br>catgcccccatgggccggggtgcgtcagaatgtgatgggctccagcattgatggtcgccccgtcctgcccgcaaactctactaccttga<br>cctacgagaccgtgtctggaacgccgttggagactgcagcctccgccgccgcttcagccgctgcagccaccgcccgcgggattgtga<br>ctgactttgctttcctgagcccgcttgcaagcagtgcagcttcccgttcatccgcccgcgatgacaagttgacggctcttttggcacaattg<br>gattctttgacccgggaacttaatgtcgtttctcagcagctgttggatctgcgccagcaggtttctgccctgaaggcttcctcccctcccaat<br>gcggtttaacggtccgggccagagtggccaacataaataaaaaaccagactctgtttggatttggatcaagcaagtgtcttgctgtctttat<br>ttaggggttttgcgcgcgcggtaggcccgggaccagcggtctcggtcgttgagggtcctgtgtattttttccaggacgtggtaaaggtga<br>ctctggatgttcagatacatgggcataagcccgtctctggggtggaggtagcaccactgcagagcttcatgctgcggggtggtgttgtag<br>atgatccagtcgtagcaggagcgctgggcgtggtgcctaaaaatgtctttcagtagcaagctgattgccaggggcaggcccttggtgta<br>agtgtttacaaagcggttaagctgggatgggtgcatacgtggggatatgagatgcatcttggactgtatttttaggttggctatgttcccagc<br>catatccctccggggattcatgttgtgcagaaccaccagcacagtgtatccggtgcacttgggaaatttgtcatgtagcttagaaggaaat<br>gcgtggaagaacttggagacgcccttgtgacctccaagattttccatgcattcgtccataatgatggcaatgggcccacgggcggcggc<br>ctgggcgaagatatttctgggatcactaacgtcatagttgtgttccaggatgagatcgtcataggccatttttacaaagcgcgggcggagg<br>gtgccagactgcggtataatggttccatccggcccaggggcgtagttaccctcacagatttgcatttcccacgctttgagttcagatgggg<br>ggatcatgtctacctgcggggcgatgaagaaaacggtttccggggtaggggagatcagctgggaagaaagcaggttcctgagcagct<br>gcgacttaccgcagccggtgggcccgtaaatcacacctattaccggctgcaactggtagttaagagagctgcagctgccgtcatccctg<br>agcaggggggccacttcgttaagcatgtccctgactcgcatgttttccctgaccaaatccgccagaaggcgctcgccgcccagcgatag<br>cagttcttgcaaggaagcaaagtttttcaacggtttgagaccgtccgccgtaggcatgcttttgagcgtttgaccaagcagttccaggcgg<br>tcccacagctcggtcacctgctctacggcatctcgatccagcatatctcctcgtttcgcgggttggggcggctttcgctgtacggcagtag<br>tcggtgctcgtccagacgggccagggtcatgtctttccacgggcgcagggtcctcgtcagcgtagtctgggtcacggtgaaggggtgc<br>gctccgggctgcgcgctggccagggtgcgcttgaggctggtcctgctggtgctgaagcgctgccggtcttcgccctgcgcgtcggcca<br>ggtagcatttgaccatggtgtcatagtccagcccctccgcggcgtggcccttggcgcgcagcttgcccttggaggaggcgccgcacga<br>ggggcagtgcagacttttgagggcgtagagcttgggcgcgagaaataccgattccggggagtaggcatccgcgccgcaggccccgc |

TABLE 23-continued

| Ad5-IL8-shRNA with Plasmid Backbone |
| --- |
| agacggtctcgcattccacgagccaggtgagctctggccgttcggggtcaaaaaccaggtttcccccatgcttttttgatgcgtttcttacct<br>ctggtttccatgagccggtgtccacgctcggtgacgaaaaggctgtccgtgtccccgtatacagacttgagaggcctgtcctcgagcggt<br>gttccgcggtcctcctcgtatagaaactcggaccactctgagacaaaggctcgcgtccaggccagcacgaaggaggctaagtgggag<br>gggtagcggtcgttgtccactagggggtccactcgctccagggtgtgaagacacatgtcgccctcttcggcatcaaggaaggtgattgg<br>tttgtaggtgtaggccacgtgaccgggtgttcctgaaggggggctataaaagggggtgggggcgcgttcgtcctcactctcttccgcatc<br>gctgtctgcgagggccagctgttggggtgagtactccctctgaaaagcgggcatgacttctgcgctaagattgtcagtttccaaaaacga<br>ggaggatttgatattcacctggcccgcggtgatgcctttgagggtggccgcatccatctggtcagaaaagacaatctttttgttgtcaagct<br>tggtggcaaacgacccgtagagggcgttggacagcaacttggcgatggagcgcagggtttggtttttgtcgcgatcggcgcgctccttg<br>gccgcgatgtttagctgcacgtattcgcgcgcaacgcaccgccattcgggaaagacggtggtgcgctcgtcgggcaccaggtgcacg<br>cgccaaccgcggttgtgcagggtgacaaggtcaacgctggtggctacctctccgcgtaggcgctcgttggtccagcagaggcggccg<br>cccttgcgcgagcagaatggcggtagggggtctagctgcgtctcgtccgggggggtctgcgtccacggtaaagaccccgggcagcag<br>gcgcgcgtcgaagtagtctatcttgcatccttgcaagtctagcgcctgctgccatgcgcgggcggcaagcgcgcgctcgtatgggttga<br>gtgggggaccccatggcatggggtgggtgagcgcggaggcgtacatgccgcaaatgtcgtaaacgtagaggggctctctgagtattc<br>caagatatgtagggtagcatcttccaccgcggatgctggcgcgcacgtaatcgtatagttcgtgcgagggagcgaggaggtcgggacc<br>gaggttgctacgggcgggctgctctgctcggaagactatctgcctgaagatggcatgtgagttggatgatatggttggacgctggaaga<br>cgttgaagctggcgtctgtgagacctaccgcgtcacgcacgaaggaggcgtaggagtcgcgcagcttgttgaccagctcggcggtga<br>cctgcacgtctagggcgcagtagtccagggtttccttgatgatgtcatacttatcctgtccctttttttttccacagctcgcggttgaggacaaa<br>ctcttcgcggtctttccagtactcttggatcggaaacccgtcggcctccgaacggtaagagcctagcatgtagaactggttgacggcctg<br>gtaggcgcagcatccctttttctacgggtagcgcgtatgcctgcgcggccttccggagcgaggtgtgggtgagcgcaaaggtgtccctg<br>accatgactttgaggtactggtatttgaagtcagtgtcgtcgcatccgccctgctcccagagcaaaaagtccgtgcgctttttggaacgcg<br>gatttggcagggcgaaggtgacatcgttgaagagtatctttcccgcgcgaggcataaagttgcgtgtgatgcggaagggtcccggcac<br>ctcggaacggttgttaattacctgggcggcgagcacgatctcgtcaaagccgttgatgttgtggcccacaatgtaaagttccaagaagcg<br>cgggatgcccttgatggaaggcaattttttaagttcctcgtaggtgagctcttcaggggagctgagcccgtgctctgaaagggcccagtct<br>gcaagatgagggttggaagcgacgaatgagctccacaggtcacgggccattagcatttgcaggtggtcgcgaaaggtcctaaactgg<br>cgacctatggccatttttttctggggtgatgcagtagaaggtaagcgggtcttgttcccagcggtcccatccaaggttcgcggctaggtctc<br>gcgcggcagtcactagaggctcatctccgccgaacttcatgaccagcatgaagggcacgagctgcttcccaaaggcccccatccaagt<br>ataggtctctacatcgtaggtgacaaagagacgctcggtgcgaggatgcgagccgatcgggaagaactggatctcccgccaccaattg<br>gaggagtggctattgatgtggtgaaagtagaagtccctgcgacgggccgaacactcgtgctggcttttgtaaaaacgtgcgcagtactg<br>gcagcggtgcacgggctgtacatcctgcacgaggttgacctgacgaccgcgcacaaggaagcagagtgggaatttgagcccctcgc<br>ctggcgggtttggctggtggtcttctacttcggctgcttgtccttgaccgtctggctgctcgaggggagttacggtggatcggaccaccac<br>gccgcgcgagcccaaagtccagatgtccgcgcgcggcggtcggagcttgatgacaacatcgcgcagatgggagctgtccatggtctg<br>gagctcccgcggcgtcaggtcaggcgggagctcctgcaggtttacctcgcatagacgggtcagggcgcgggctagatccaggtgata<br>cctaatttccaggggctggttggtggcggcgtcgatggcttgcaagaggccgcatccccgcggcgcgactacggtaccgcgcggcgg<br>gcggtgggccgcgggggtgtccttggatgatgcatctaaaagcggtgacgcgggcgagcccccggaggtagggggggctccggac<br>ccgccgggagagggggcaggggcacgtcggcgccgcgcgcgggcaggagctggtgctgcgcgcgtaggttgctggcgaacgcg<br>acgacgcggcggttgatctcctgaatctggcgcctctgcgtgaagacgacgggcccggtgagcttgaacctgaaagagagttcgaca<br>gaatcaatttcggtgtcgttgacggcggcctggcgcaaaatctcctgcacgtctcctgagttgtcttgataggcgatctcggccatgaact<br>gctcgatctcttcctcctggagatctccgcgtccggctcgctccacggtggcggcgaggtcgttggaaatgcgggccatgagctgcga<br>gaaggcgttgaggcctccctcgttccagacgcggctgtagaccacgccccccttcggcatcgcgggcgcgcatgaccacctgcgcgag |

TABLE 23-continued

| Ad5-IL8-shRNA with Plasmid Backbone |
|---|
| attgagctccacgtgccgggcgaagacggcgtagtttcgcaggcgctgaaagaggtagttgagggtggtggcggtgtgttctgccacg |
| aagaagtacataacccagcgtcgcaacgtggattcgttgatatcccccaaggcctcaaggcgctccatggcctcgtagaagtccacgg |
| cgaagttgaaaaactgggagttgcgcgccgacacggttaactcctcctccagaagacggatgagctcggcgacagtgtcgcgcacctc |
| gcgctcaaaggctacaggggcctcttcttcttcttcaatctcctcttccataagggcctccccttcttcttcttctggcggcggtgggggagg |
| ggggacacggcggcgacgacggcgcaccgggaggcggtcgacaaagcgctcgatcatctccccgcggcgacggcgcatggtctc |
| ggtgacggcgcggccgttctcgcgggggcgcagttggaagacgccgcccgtcatgtcccggttatgggttggcgggggggctgccat |
| gcggcagggatacggcgctaacgatgcatctcaacaattgttgtgtaggtactccgccgccgagggacctgagcgagtccgcatcgac |
| cggatcggaaaacctctcgagaaaggcgtctaaccagtcacagtcgcaaggtaggctgagcaccgtggcgggcggcagcgggcgg |
| cggtcggggttgtttctggcggaggtgctgctgatgatgtaattaaagtaggcggtcttgagacggcggatggtcgacagaagcaccat |
| gtccttgggtccggcctgctgaatgcgcaggcggtcggccatgccccaggcttcgttttgacatcggcgcaggtctttgtagtagtcttgc |
| atgagcctttctaccggcacttcttcttctccttcctcttgtcctgcatctcttgcatctatcgctgcggcggcggcggagtttggccgtaggt |
| ggcgccctcttcctcccatgcgtgtgaccccgaagcccctcatcggctgaagcagggctaggtcggcgacaacgcgctcggctaatat |
| ggcctgctgcacctgcgtgagggtagactggaagtcatccatgtccacaaagcggtggtatgcgcccgtgttgatggtgtaagtgcagtt |
| ggccataacggaccagttaacggtctggtgacccggctgcgagagctcggtgtacctgagacgcgagtaagccctcgagtcaaatac |
| gtagtcgttgcaagtccgcaccaggtactggtatcccaccaaaaagtgcggcggcggctggcggtagaggggccagcgtagggtgg |
| ccggggctccgggggcgagatcttccaacataaggcgatgatatccgtagatgtacctggacatccaggtgatgccggcggcggtggt |
| ggaggcgcgcggaaagtcgcggacgcggttccagatgttgcgcagcggcaaaaagtgctccatggtcgggacgctctggccggtca |
| ggcgcgcgcaatcgttgacgctctagaccgtgcaaaaggagagcctgtaagcgggcactcttccgtggtctggtggataaattcgcaa |
| gggtatcatggcggacgaccggggttcgagccccgtatccggccgtccgccgtgatccatgcggttaccgcccgcgtgtcgaaccca |
| ggtgtgcgacgtcagacaacgggggagtgctccttttggcttccttccaggcgcggcggctgctgcgctagcttttttggccactggccg |
| cgcgcagcgtaagcggttaggctggaaagcgaaagcattaagtggctcgctccctgtagccggagggttattttccaagggttgagtcg |
| cgggacccccggttcgagtctcggaccggccggactgcggcgaacgggggtttgcctccccgtcatgcaagaccccgcttgcaaatt |
| cctccggaaacagggacgagcccctttttttgcttttcccagatgcatccggtgctgcggcagatgcgcccccctcctcagcagcggcaa |
| gagcaagagcagcggcagacatgcagggcaccctcccctcctcctaccgcgtcaggaggggcgacatccgcggttgacgcggcag |
| cagatggtgattacgaaccccgcggcgccgggcccggcactacctggacttggaggagggcgagggcctggcgcggctaggagc |
| gccctctcctgagcggcacccaagggtgcagctgaagcgtgatacgcgtgaggcgtacgtgccgcggcagaacctgtttcgcgaccg |
| cgagggagaggagcccgaggagatgcgggatcgaaagttccacgcagggcgcgagctgcggcatggcctgaatcgcgagcggtt |
| gctgcgcgaggaggactttgagcccgacgcgcgaaccgggattagtcccgcgcgcgcacacgtggcggccgccgacctggtaacc |
| gcatacgagcagacggtgaaccaggagattaactttcaaaaaagctttaacaaccacgtgcgtacgcttgtggcgcgcgaggaggtgg |
| ctataggactgatgcatctgtgggactttgtaagcgcgctggagcaaaacccaaatagcaagccgctcatggcgcagctgttccttatag |
| tgcagcacagcagggacaacgaggcattcagggatgcgctgctaaacatagtagagcccgagggccgctggctgctcgatttgataa |
| acatcctgcagagcatagtggtgcaggagcgcagcttgagcctggctgacaaggtggccgccatcaactattccatgcttagcctgggc |
| aagttttacgcccgcaagatataccatacccttacgttcccatagacaaggaggtaaagatcgaggggttctacatgcgcatggcgctg |
| aaggtgcttaccttgagcgacgacctgggcgtttatcgcaacgagcgcatccacaaggccgtgagcgtgagccggggcgcgagctc |
| agcgaccgcgagctgatgcacagcctgcaaagggccctggctggcacgggcagcggcgatagagaggccgagtcctactttgacg |
| cgggcgctgacctgcgctgggccccaagccgacgcgccctggaggcagctggggccggacctgggctggcggtggcacccgcgc |
| gcgctggcaacgtcggcggcgtggaggaatatgacgaggacgatgagtacgagccagaggacggcgagtactaagcggtgatgttt |
| ctgatcagatgatgcaagacgcaacggacccggcggtgcgggcggcgctgcagagccagccgtccggccttaactccacggacga |
| ctggcgccaggtcatggaccgcatcatgtcgctgactgcgcgcaatcctgacgcgttccggcagcagccgcaggccaaccggctctc |

TABLE 23-continued

| Ad5-IL8-shRNA with Plasmid Backbone |
| --- |
| cgcaattctggaagcggtggtcccggcgcgcgcaaaccccacgcacgagaaggtgctggcgatcgtaaacgcgctggccgaaaac |
| agggccatccggcccgacgaggccggcctggtctacgacgcgctgcttcagcgcgtggctcgttacaacagcggcaacgtgcagac |
| caacctggaccggctggtgggggatgtgcgcgaggccgtggcgcagcgtgagcgcgcgcagcagcagggcaacctgggctccat |
| ggttgcactaaacgccttcctgagtacacagcccgccaacgtgccgcggggacaggaggactacaccaactttgtgagcgcactgcg |
| gctaatggtgactgagacaccgcaaagtgaggtgtaccagtctgggccagactattttttccagaccagtagacaaggcctgcagaccg |
| taaacctgagccaggctttcaaaaacttgcaggggctgtggggggtgcgggctcccacaggcgaccgcgcgaccgtgtctagcttgct |
| gacgcccaactcgcgcctgttgctgctgctaatagcgcccttcacggacagtggcagcgtgtcccgggacacatacctaggtcacttgc |
| tgacactgtaccgcgaggccataggtcaggcgcatgtggacgagcatactttccaggagattacaagtgtcagccgcgcgctggggca |
| ggaggacacgggcagcctggaggcaaccctaaactacctgctgaccaaccggcggcagaagatcccctcgttgcacagtttaaacag |
| cgaggaggagcgcattttgcgctacgtgcagcagagcgtgagccttaacctgatgcgcgacggggtaacgcccagcgtggcgctgg |
| acatgaccgcgcgcaacatggaaccgggcatgtatgcctcaaaccggccgtttatcaaccgcctaatggactacttgcatcgcgcggc |
| cgccgtgaaccccgagtatttcaccaatgccatcttgaacccgcactggctaccgccccctggtttctacaccgggggattcgaggtgcc |
| cgagggtaacgatggattcctctgggacgacatagacgacagcgtgttttccccgcaaccgcagaccctgctagagttgcaacagcgc |
| gagcaggcagaggcggcgctgcgaaaggaaagcttccgcaggccaagcagcttgtccgatctaggcgctgcggccccgcggtcag |
| atgctagtagcccatttccaagcttgatagggtctcttaccagcactcgcaccacccgcccgcgcctgctgggcgaggaggagtaccta |
| aacaactcgctgctgcagccgcagcgcgaaaaaaacctgcctccggcatttcccaacaacgggatagagagcctagtggacaagatg |
| agtagatggaagacgtacgcgcaggagcacagggacgtgccaggcccgcgcccgcccacccgtcgtcaaaggcacgaccgtcag |
| cggggtctggtgtgggaggacgatgactcggcagacgacagcagcgtcctggatttgggagggagtggcaacccgtttgcgcacctt |
| cgccccaggctggggagaatgttttaaaaaaaaaaaaaagcatgatgcaaaataaaaaactcaccaaggccatggcaccgagcgttg |
| gttttcttgtattccccttagtatgcggcgcgcggcgatgtatgaggaaggtcctcctccctcctacgagagtgtggtgagcgcggcgcca |
| gtggcggcggcgctgggttctcccttcgatgctcccctggacccgccgtttgtgcctccgcggtacctgcggcctaccggggggagaa |
| acagcatccgttactctgagttggcacccctattcgacaccacccgtgtgtacctggtggacaacaagtcaacggatgtggcatccctga |
| actaccagaacgaccacagcaactttctgaccacggtcattcaaaacaatgactacagcccgggggaggcaagcacacagaccatca |
| atcttgacgaccggtcgcactggggcggcgacctgaaaaccatcctgcataccaacatgccaaatgtgaacgagttcatgtttaccaata |
| agtttaaggcgcgggtgatggtgtcgcgcttgcctactaaggacaatcaggtggagctgaaatacgagtgggtggagttcacgctgccc |
| gagggcaactactccgagaccatgaccatagaccttatgaacaacgcgatcgtggagcactacttgaaagtgggcagacagaacggg |
| gttctggaaagcgacatcggggtaaagtttgacacccgcaacttcagactggggtttgaccccgtcactggtcttgtcatgcctggggtat |
| atacaaacgaagccttccatccagacatcattttgctgccaggatgcggggtggacttcacccacagccgcctgagcaacttgttgggca |
| tccgcaagcggcaacccttccaggagggctttaggatcacctacgatgatctggagggtggtaacattcccgcactgttggatgtggac |
| gcctaccaggcgagcttgaaagatgacaccgaacagggggggggtggcgcaggcggcagcaacagcagtggcagcggcgcgga |
| agagaactccaacgcggcagccgcggcaatgcagccggtggaggacatgaacgatcatgccattcgcggcgacacctttgccacac |
| gggctgaggagaagcgcgctgaggccgaagcagcggccgaagctgccgcccccgctgcgcaacccgaggtcgagaagcctcag |
| aagaaaccggtgatcaaacccctgacagaggacagcaagaaacgcagttacaacctaataagcaatgacagcaccttcacccagtac |
| cgcagctggtaccttgcatacaactacggcgaccctcagaccggaatccgctcatggaccctgctttgcactcctgacgtaacctgcgg |
| ctcggagcaggtctactggtcgttgccagacatgatgcaagaccccgtgaccttccgctccacgcgccagatcagcaactttccggtgg |
| tgggcgccgagctgttgcccgtgcactccaagagcttctacaacgaccaggccgtctactcccaactcatccgccagtttacctctctga |
| cccacgtgttcaatcgctttcccgagaaccagattttggcgcgcccgccagcccccaccatcaccaccgtcagtgaaaacgttcctgctc |
| tcacagatcacgggacgctaccgctgcgcaacagcatcggaggagtccagcgagtgaccattactgacgccagacgccgcacctgc |
| ccctacgtttacaaggccctgggcatagtctcgccgcgcgtcctatcgagccgcactttttgagcaagcatgtccatccttatatcgccca |

TABLE 23-continued

| Ad5-IL8-shRNA with Plasmid Backbone |
| --- |

gcaataacacaggctggggcctgcgcttcccaagcaagatgtttggcggggccaagaagcgctccgaccaacacccagtgcgcgtg cgcgggcactaccgcgcgccctggggcgcgcacaaacgcggccgcactggggcaccaccgtcgatgacgccatcgacgcggtg gtggaggaggcgcgcaactacacgcccacgccgccaccagtgtccacagtggacgcggccattcagaccgtggtgcgcggagccc ggcgctatgctaaaatgaagagacggcggaggcgcgtagcacgtcgccaccgccgccgacccggcactgccgcccaacgcgcgg cggcggccctgcttaaccgcgcacgtcgcaccggccgacgggcggccatgcgagcagctcgaaggctggccgcgggtattgtcact gtgccccccaggtccaggcgacgagcggccgccgcagcagccgcggccattagtgctatgactcagggtcgcaggggcaacgtgt attgggtgcgcgactcggttagcggcctgcgcgtgcccgtgcgcacccgcccccgcgcaactagattgcaagaaaaaactacttaga ctcgtactgttgtatgtatccagcggcggcggcgcgcaacgaagctatgtccaagcgcaaaatcaaagaagagatgctccaggtcatc gcgccggagatctatggccccccgaagaaggaagagcaggattacaagccccgaaagctaaagcgggtcaaaaagaaaaagaaag atgatgatgatgaacttgacgacgaggtggaactgctgcacgctaccgcgcccaggcgacgggtacagtggaaaggtcgacgcgtaa aacgtgttttgcgacccggcaccaccgtagtctttacgcccggtgagcgctccacccgcacctacaagcgcgtgtatgatgaggtgtac ggcgacgaggacctgcttgagcaggccaacgagcgcctcggggagtttgcctacggaaagcggcataaggacatgctggcgttgcc gctggacgagggcaacccaacacctagcctaaagcccgtaacactgcagcaggtgctgcccgcgcttgcaccgtccgaagaaaagc gcggcctaaagcgcgagtctggtgacttggcacccaccgtgcagctgatggtacccaagcgccagcgactggaagatgtcttggaaa aaatgaccgtggaacctgggctggagcccgaggtccgcgtgcggccaatcaagcaggtggcgccgggactgggcgtgcagaccgt ggacgttcagatacccactaccagtagcaccagtattgccaccgccacagagggcatggagacacaaacgtccccggttgcctcagc ggtggcggatgccgcggtgcaggcggtcgctgcggccgcgtccaagacctctacggaggtgcaaacggacccgtggatgtttcgcg tttcagccccccggcgcccgcgccgttcgaggaagtacggcgccgccagcgcgctactgcccgaatatgccctacatccttccattgc gcctacccccggctatcgtggctacacctaccgccccagaagacgagcaactacccgacgccgaaccaccactggaacccgccgcc gccgtcgccgtcgccagcccgtgctggccccgatttccgtgcgcagggtggctcgcgaaggaggcaggaccctggtgctgccaaca gcgcgctaccaccccagcatcgtttaaaagccggtctttgtggttcttgcagatatggccctcacctgccgcctccgtttcccggtgccgg gattccgaggaagaatgcaccgtaggaggggcatggccggccacggcctgacgggcggcatgcgtcgtgcgcaccaccggcggc ggcgcgcgtcgcaccgtcgcatgcgcggcggtatcctgcccctccttattccactgatcgccgcggcgattggcgccgtgcccggaat tgcatccgtggccttgcaggcgcagagacactgattaaaaacaagttgcatgtggaaaaatcaaaataaaaagtctggactctcacgctc gcttggtcctgtaactattttgtagaatggaagacatcaactttgcgtctctggccccgcgacacggctcgcgcccgttcatgggaaactg gcaagatatcggcaccagcaatatgagcggtggcgccttcagctggggctcgctgtggagcggcattaaaaatttcggttccaccgtta agaactatggcagcaaggcctggaacagcagcacaggccagatgctgagggataagttgaaagagcaaaatttccaacaaaaggtg gtagatggcctggcctctggcattagcggggtggtggacctggccaaccaggcagtgcaaaataagattaacagtaagcttgatcccc gccctcccgtagaggagcctccaccggccgtggagacagtgtctccagaggggcgtggcgaaaagcgtccgcgccccgacaggga agaaactctggtgacgcaaatagacgagcctccctcgtacgaggaggcactaaagcaaggcctgcccaccacccgtcccatcgcgcc catggctaccggagtgctgggccagcacacacccgtaacgctggacctgcctcccccgccgacacccagcagaaacctgtgctgcc aggcccgaccgccgttgttgtaacccgtcctagccgcgcgtccctgcgccgcgccgccagcggtccgcgatcgttgcggcccgtagc cagtggcaactggcaaagcacactgaacagcatcgtgggtctgggggtgcaatccctgaagcgccgacgatgcttctgaatagctaac gtgtcgtatgtgtgtcatgtatgcgtccatgtcgccgccagaggagctgctgagccgccgcgcgcccgctttccaagatggctacccctt cgatgatgccgcagtggtcttacatgcacatctcgggccaggacgcctcggagtacctgagccccgggctggtgcagtttgcccgcgc caccgagacgtacttcagcctgaataacaagtttagaaccccacggtggcgcctacgcacgacgtgaccacagaccggtcccagcg tttgacgctgcggttcatccctgtggaccgtgaggatactgcgtactcgtacaaggcgcggttcaccctagctgtgggtgataaccgtgtg ctggacatggcttccacgtactttgacatccgcggcgtgctggacaggggccctacttttaagccctactctggcactgcctacaacgcc ctggctcccaagggtgccccaaatccttgcgaatgggatgaagctgctactgctcttgaaataaacctagaagaagaggacgatgacaa TABLE 23-continued

| Ad5-IL8-shRNA with Plasmid Backbone |
|---|
| cgaagacgaagtagacgagcaagctgagcagcaaaaaactcacgtatttgggcaggcgccttattctggtataaatattacaaaggagg |
| gtattcaaataggtgtcgaaggtcaaacacctaaatatgccgataaaacatttcaacctgaacctcaaataggagaatctcagtggtacga |
| aacagaaattaatcatgcagctgggagagtcctaaaaaagactaccccaatgaaaccatgttacggttcatatgcaaaacccacaaatga |
| aaatggagggcaaggcattcttgtaaagcaacaaaatggaaagctagaaagtcaagtggaaatgcaatttttctcaactactgaggcagc |
| cgcaggcaatggtgataacttgactcctaaagtggtattgtacagtgaagatgtagatatagaaaccccagacactcatatttcttacatgc |
| ccactattaaggaaggtaactcacgagaactaatgggccaacaatctatgcccaacaggcctaattacattgcttttagggacaattttatt |
| ggtctaatgtattacaacagcacgggtaatatgggtgttctggcgggccaagcatcgcagttgaatgctgttgtagatttgcaagacagaa |
| acacagagctttcataccagcttttgcttgattccattggtgatagaaccaggtacttttctatgtggaatcaggctgttgacagctatgatcc |
| agatgttagaattattgaaaatcatggaactgaagatgaacttccaaattactgctttccactgggaggtgtgattaatacagagactcttac |
| caaggtaaaacctaaaacaggtcaggaaaatggatgggaaaaagatgctacagaattttcagataaaaatgaaataagagttggaaata |
| attttgccatggaaatcaatctaaatgccaacctgtggagaaatttcctgtactccaacatagcgctgtatttgcccgacaagctaaagtaca |
| gtccttccaacgtaaaaatttctgataacccaaacacctacgactacatgaacaagcgagtggtggctcccgggctagtggactgctaca |
| ttaaccttggagcacgctggtcccttgactatatggacaacgtcaacccatttaaccaccaccgcaatgctggcctgcgctaccgctcaat |
| gttgctgggcaatggtcgctatgtgcccttccacatccaggtgcctcagaagttctttgccattaaaaacctccttctcctgccgggctcata |
| cacctacgagtggaacttcaggaaggatgttaacatggttctgcagagctccctaggaaatgacctaagggttgacggagccagcatta |
| agtttgatagcatttgcctttacgccaccttcttccccatggcccacaacaccgcctccacgcttgaggccatgcttagaaacgacaccaa |
| cgaccagtcctttaacgactatctctccgccgccaacatgctctaccctatacccgccaacgctaccaacgtgcccatatccatccctcc |
| cgcaactgggcggctttccgcggctgggccttcacgcgccttaagactaaggaaaccccatcactgggctcgggctacgacccttatta |
| cacctactctggctctataccctacctagatggaaccttttacctcaaccacacctttaagaaggtggccattacctttgactcttctgtcagc |
| tggcctggcaatgaccgcctgcttacccccaacgagtttgaaattaagcgctcagttgacggggagggttacaacgttgcccagtgtaac |
| atgaccaaagactggttcctggtacaaatgctagctaactataacattggctaccagggcttctatatcccagagagctacaaggaccgc |
| atgtactccttctttagaaacttccagcccatgagccgtcaggtggtggatgatactaaatacaaggactaccaacaggtgggcatcctac |
| accaacacaacaactctggatttgttggctaccttgcccccaccatgcgcgaaggacaggcctaccctgctaacttcccctatccgcttat |
| aggcaagaccgcagttgacagcattacccagaaaaagtttctttgcgatcgcaccctttggcgcatcccattctccagtaactttatgtcca |
| tgggcgcactcacagacctgggccaaaaccttctctacgccaactccgcccacgcgctagacatgacttttgaggtggatcccatggac |
| gagcccacccttctttatgttttgtttgaagtctttgacgtggtccgtgtgcaccagccgcaccgcggcgtcatcgaaaccgtgtacctgcg |
| cacgcccttctggccggcaacgccacaacataaagaagcaagcaacatcaacaacagctgccgccatgggctccagtgagcagga |
| actgaaagccattgtcaaagatcttggttgtgggccatatttttgggcacctatgacaagcgctttccaggctttgtttctccacacaagctc |
| gcctgcgccatagtcaatacggccggtcgcgagactgggggcgtacactggatggcctttgcctggaacccgcactcaaaaacatgct |
| acctctttgagccctttggcttttctgaccagcgactcaagcaggtttaccagtttgagtacgagtcactcctgcgccgtagcgccattgctt |
| cttcccccgaccgctgtataacgctggaaaagtccacccaaagcgtacaggggcccaactcggccgcctgtggactattctgctgcatg |
| tttctccacgcctttgccaactggccccaaactcccatggatcacaaccccaccatgaaccttattaccggggtacccaactccatgctca |
| acagtccccaggtacagcccaccctgcgtcgcaaccaggaacagctctacagcttcctggagcgccactcgccctacttccgcagcca |
| cagtgcgcagattaggagcgccacttctttttgtcacttgaaaaacatgtaaaaataatgtactagagacactttcaataaaggcaaatgctt |
| ttatttgtacactctcgggtgattatttaccccccacccttgccgtctgcgccgtttaaaaatcaaaggggttctgccgcgcatcgctatgcgc |
| cactggcagggacacgttgcgatactggtgtttagtgctccacttaaactcaggcacaaccatccgcggcagctcggtgaagttttcactc |
| cacaggctgcgcaccatcaccaacgcgtttagcaggtcgggcgccgatatcttgaagtcgcagttggggcctccgccctgcgcgcgc |
| gagttgcgatacacagggttgcagcactggaacactatcagcgccgggtggtgcacgctggccagcacgctcttgtcggagatcagat |
| ccgcgtccaggtcctccgcgttgctcagggcgaacggagtcaactttggtagctgccttcccaaaaagggcgcgtgcccaggctttga |

TABLE 23-continued

| Ad5-IL8-shRNA with Plasmid Backbone |
|---|
| gttgcactcgcaccgtagtggcatcaaaaggtgaccgtgcccggtctgggcgttaggatacagcgcctgcataaaagccttgatctgctt |
| aaaagccacctgagcctttgcgccttcagagaagaacatgccgcaagacttgccggaaaactgattggccggacacgcggcgtcgtg |
| cacgcagcaccttgcgtcggtgttggagatctgcaccacatttcggccccaccggttcttcacgatcttggccttgctagactgctccttca |
| gogcgcgctgcccgttttcgctcgtcacatccatttcaatcacgtgctccttatttatcataatgcttccgtgtagacacttaagctcgccttcg |
| atctcagcgcagcggtgcagccacaacgcgcagcccgtgggctcgtgatgcttgtaggtcacctctgcaaacgactgcaggtacgcct |
| gcaggaatcgccccatcatcgtcacaaaggtcttgttgctggtgaaggtcagctgcaacccgcggtgctcctcgttcagccaggtcttgc |
| atacggccgccagagcttccacttggtcaggcagtagtttgaagttcgcctttagatcgttatccacgtggtacttgtccatcagcgcgcgc |
| gcagcctccatgcccttctcccacgcagacacgatcggcacactcagcgggttcatcaccgtaatttcactttccgcttcgctgggctcttc |
| ctcttcctcttgcgtccgcataccacgcgccactgggtcgtcttcattcagccgccgcactgtgcgcttacctcctttgccatgcttgattag |
| caccggtgggttgctgaaacccaccatttgtagcgccacatcttctctttcttcctcgctgtccacgattacctctggtgatggcgggcgctc |
| gggcttgggagaagggcgcttctttttcttcttgggcgcaatggccaaatccgccgccgaggtcgatggccgcgggctgggtgtgcgc |
| ggcaccagcgcgtcttgtgatgagtcttcctcgtcctcggactcgatacgccgcctcatccgcttttttgggggcgcccggggaggcgg |
| cggcgacggggacggggacgacacgtcctccatggttgggggacgtcgcgccgcaccgcgtccgcgctcgggggtggtttcgcgc |
| tgctcctcttcccgactggccatttccttctcctataggcagaaaaagatcatggagtcagtcgagaagaaggacagcctaaccgccccc |
| tctgagttcgccaccaccgcctccaccgatgccgccaacgcgcctaccaccttccccgtcgaggcacccccgcttgaggaggaggaa |
| gtgattatcgagcaggacccaggttttgtaagcgaagacgacgaggaccgctcagtaccaacagaggataaaaagcaagaccaggac |
| aacgcagaggcaaacgaggaacaagtcgggggggggacgaaaggcatggcgactacctagatgtgggagacgacgtgctgttga |
| agcatctgcagcgccagtgcgccattatctgcgacgcgttgcaagagcgcagcgatgtgcccctcgccatagcggatgtcagccttgc |
| ctacgaacgccacctattctcaccgcgcgtacccccccaaacgccaagaaaacggcacatgcgagcccaacccgcgcctcaacttctac |
| cccgtatttgccgtgccagaggtgcttgccacctatcacatctttttccaaaactgcaagatacccctatcctgccgtgccaaccgcagcc |
| gagcggacaagcagctggccttgcggcagggcgctgtcatacctgatatcgcctcgctcaacgaagtgccaaaaatctttgagggtctt |
| ggacgcgacgagaagcgcgcggcaaacgctctgcaacaggaaaacagcgaaaatgaaagtcactctggagtgttggtggaactcga |
| gggtgacaacgcgcgcctagccgtactaaaacgcagcatcgaggtcacccactttgcctacccggcacttaacctacccccaaggtc |
| atgagcacagtcatgagtgagctgatcgtgcgccgtgcgcagcccctggagagggatgcaaatttgcaagaacaaacagaggaggg |
| cctacccgcagttggcgacgagcagctagcgcgctggcttcaaacgcgcgagcctgccgacttggaggagcgacgcaaactaatgat |
| ggccgcagtgctcgttaccgtggagcttgagtgcatgcagcggttctttgctgacccggagatgcagcgcaagctagaggaaacattgc |
| actacacctttcgacagggctacgtacgccaggcctgcaagatctccaacgtggagctctgcaacctggtctcctaccttggaattttgca |
| cgaaaaccgccttgggcaaaacgtgcttcattccacgctcaagggcgaggcgcgccgcgactacgtccgcgactgcgtttacttatttct |
| atgctacacctggcagacggccatgggcgtttggcagcagtgcttggaggagtgcaacctcaaggagctgcagaaactgctaaagca |
| aaacttgaaggacctatggacggccttcaacgagcgctccgtggccgcgcacctggcggacatcattttccccgaacgcctgcttaaaa |
| ccctgcaacagggtctgccagacttcaccagtcaaagcatgttgcagaactttaggaactttatcctagagcgctcaggaatcttgcccgc |
| cacctgctgtgcacttcctagcgactttgtgcccattaagtaccgcgaatgccctccgccgctttggggccactgctaccttctgcagctag |
| ccaactaccttgcctaccactctgacataatggaagacgtgagcggtgacggtctactggagtgtcactgtcgctgcaacctatgcaccc |
| cgcaccgctccctggtttgcaattcgcagctgcttaacgaaagtcaaattatcggtacctttgagctgcagggtccctcgcctgacgaaaa |
| gtccgcggctccggggttgaaactcactccggggctgtggacgtcggcttaccttcgcaaatttgtacctgaggactaccacgcccacg |
| agattaggttctacgaagaccaatcccgcccgcctaatgcggagcttaccgcctgcgtcattacccagggccacattcttggccaattgc |
| aagccatcaacaaagcccgccaagagtttctgctacgaaagggacgggggtttacttggacccccagtccggcgaggagctcaacc |
| caatcccccgccgccgcagccctatcagcagcagccgcgggcccttgcttcccaggatggcacccaaaaagaagctgcagctgcc |
| gccgccacccacggacgaggaggaatactgggacagtcaggcagaggaggttttggacgaggaggaggaggacatgatggaaga |

TABLE 23-continued

| Ad5-IL8-shRNA with Plasmid Backbone |
| --- |
| ctgggagagcctagacgaggaagcttccgaggtcgaagaggtgtcagacgaaacaccgtcaccctcggtcgcattcccctcgccggc |
| gccccagaaatcggcaaccggttccagcatggctacaacctccgctcctcaggcgccgccggcactgcccgttcgccgacccaaccg |
| tagatgggacaccactggaaccagggccggtaagtccaagcagccgccgccgttagcccaagagcaacaacagcgccaaggctac |
| cgctcatggcgcgggcacaagaacgccatagttgcttgcttgcaagactgtgggggcaacatctccttcgcccgccgctttcttctctacc |
| atcacggcgtggccttcccccgtaacatcctgcattactaccgtcatctctacagcccatactgcaccggcggcagcggcagcggcagc |
| aacagcagcggccacacagaagcaaaggcgaccggatagcaagactctgacaaagcccaagaaatccacagcggcggcagcagc |
| aggaggaggagcgctgcgtctggcgcccaacgaacccgtatcgacccgcgagcttagaaacaggatttttcccactctgtatgctatatt |
| tcaacagagcaggggccaagaacaagagctgaaaataaaaaacaggtctctgcgatccctcacccgcagctgcctgtatcacaaaag |
| cgaagatcagcttcggcgcacgctggaagacgcggaggctctcttcagtaaatactgcgcgctgactcttaaggactagtttcgcgccct |
| ttctcaaatttaagcgcgaaaactacgtcatctccagcggccacacccggcgccagcacctgttgtcagcgccattatgagcaaggaaat |
| tcccacgccctacatgtggagttaccagccacaaatgggacttgcggctggagctgcccaagactactcaacccgaataaactacatga |
| gcgcgggaccccacatgatatcccgggtcaacggaatacgcgcccaccgaaaccgaattctcctggaacaggggctattaccacca |
| cacctcgtaataaccttaatccccgtagttggcccgctgccctggtgtaccaggaaagtcccgctcccaccactgtggtacttcccagag |
| acgcccaggccgaagttcagatgactaactcaggggcgcagcttgcgggcggctttcgtcacagggtgcggtcgcccgggcagggt |
| ataactcacctgacaatcagagggcgaggtattcagctcaacgacgagtcggtgagctcctcgcttggtctccgtccggacgggacattt |
| cagatcggggcgccggccgctcttcattcacgcctcgtcaggcaatcctaactctgcagacctcgtcctctgagccgcgctctggagg |
| cattggaactctgcaatttattgaggagtttgtgccatcggtctactttaaccccttctcgggacctcccggccactatcoggatcaatttattc |
| ctaactttgacgcggtaaaggactcggcggacggctacgactgaatgttaagtggccaatgaggcctgacgctaataatagctggtcca |
| ctgtcgccgccacaagtgctttgcccgcgactccggtgagttttgctactttgaattgcccgaggatcatatcgagggcccggcgcacgg |
| cgtccggcttaccgcccagggagagcttgcccgtagcctgattcgggagtttacccagcgcccccctgctagttgagcgggacagggg |
| accctgtgttctcactgtgatttgcaactgtcctaaccttggattacatcaagatccagatcttctagacccgggagcggccgctgtcgacc |
| tgcaggatccgaattcgatatcactagtggtaccgatcttattccctttaactaataaaaaaaaataataaagcatcacttacttaaaatcagtt |
| agcaaatttctgtccagtttattcagcagcacctccttgccctcctcccagctctggtattgcagcttcctcctggctgcaaactttctccaca |
| atctaaagggaatgtcagtttcctcctgttcctgtccatccgcacccactatcttcatgttgttgcagatgaagcgcgcaagaccgtctgaa |
| gataccttcaaccccgtgtatccatatgacacggaaaccggtcctccaactgtgccttttcttactcctccctttgtatcccccaatgggtttc |
| aagagagtccccctggggtactctctttgcgcctatccgaacctctagttacctccaatggcatgcttgcgctcaaaatgggcaacggcct |
| ctctctggacgaggccggcaaccttacctcccaaaatgtaaccactgtgagcccacctctcaaaaaaaccaagtcaaacataaacctgg |
| aaatatctgcacccctcacagttacctcagaagccctaactgtggctgccgccgcacctctaatggtcgcgggcaacacactcaccatg |
| caatcacaggccccgctaaccgtgcacgactccaaacttagcattgccacccaaggacccctcacagtgtcagaaggaaagctagccc |
| tgcaaacatcaggcccctcaccaccaccgatagcagtacccttactatcactgcctcacccccctctaactactgccactggtagcttggg |
| cattgacttgaaagagcccatttatacacaaaatggaaaactaggactaaagtacggggctcctttgcatgtaacagacgacctaaacact |
| ttgaccgtagcaactggtccaggtgtgactattaataatacttccttgcaaactaaagttactggagccttgggttttgattcacaaggcaata |
| tgcaacttaatgtagcaggaggactaaggattgattctcaaaacagacgccttatacttgatgttagttatccgtttgatgctcaaaaccaac |
| taaatctaagactaggacagggccctctttttataaactcagcccacaacttggatattaactacaacaaaggcctttacttgtttacagcttc |
| aaacaattccaaaaagcttgaggttaacctaagcactgccaaggggttgatgtttgacgctacagccatagccattaatgcaggagatgg |
| gcttgaatttggttcacctaatgcaccaaacacaaatcccctcaaaacaaaaattggccatggcctagaatttgattcaaacaaggctatgg |
| ttcctaaactaggaactggccttagttttgacagcacaggtgccattacagtaggaaaaaaaataatgataagctaactttgtggaccaca |
| ccagctccatctcctaactgtagactaaatgcagagaaagatgctaaactcactttggtcttaacaaaatgtggcagtcaaatacttgctac |
| agtttcagttttggctgttaaaggcagtttggctccaatatctggaacagttcaaagtgctcatcttattataagatttgacgaaaatggagtg |

TABLE 23-continued

| Ad5-IL8-shRNA with Plasmid Backbone |
|---|
| ctactaaacaattccttcctggacccagaatattggaactttagaaatggagatcttactgaaggcacagcctatacaaacgctgttggattt |
| atgcctaacctatcagcttatccaaaatctcacggtaaaactgccaaaagtaacattgtcagtcaagtttacttaaacggagacaaaactaa |
| acctgtaacactaaccattacactaaacggtacacaggaaacaggagacacaactccaagtgcatactctatgtcattttcatgggactgg |
| tctggccacaactacattaatgaaatatttgccacatcctcttacactttttcatacattgcccaagaataaagaatcgtttgtgttatgtttcaac |
| gtgtttatttttcaattgcagaaaatttcaagtcatttttcattcagtagtatagccccaccaccacatagcttatacagatcaccgtaccttaatc |
| aaactcacagaaccctagtattcaacctgccacctccctcccaacacacagagtacacagtcctttctccccggctggccttaaaaagcat |
| catatcatgggtaacagacatattcttaggtgttatattccacacggtttcctgtcgagccaaacgctcatcagtgatattaataaactccccg |
| ggcagctcacttaagttcatgtcgctgtccagctgctgagccacaggctgctgtccaacttgcggttgcttaacgggcggcgaaggaga |
| agtccacgcctacatgggggtagagtcataatcgtgcatcaggatagggcggtggtgctgcagcagcgcgcgaataaactgctgccg |
| ccgccgctccgtcctgcaggaatacaacatggcagtggtctcctcagcgatgattcgcaccgcccgcagcataaggcgccttgtcctcc |
| gggcacagcagcgcaccctgatctcacttaaatcagcacagtaactgcagcacagcaccacaatattgttcaaaatcccacagtgcaag |
| gcgctgtatccaaagctcatggcggggaccacagaacccacgtggccatcataccacaagcgcaggtagattaagtggcgacccctc |
| ataaacacgctggacataaacattacctcttttggcatgttgtaattcaccacctcccggtaccatataaacctctgattaaacatggcgcca |
| tccaccaccatcctaaaccagctggccaaaacctgcccgccggctatacactgcagggaaccgggactggaacaatgacagtggaga |
| gcccaggactcgtaaccatggatcatcatgctcgtcatgatatcaatgttggcacaacacaggcacacgtgcatacacttcctcaggatta |
| caagctcctcccgcgttagaaccatatcccagggaacaacccattcctgaatcagcgtaaatcccacactgcagggaagacctcgcac |
| gtaactcacgttgtgcattgtcaaagtgttacattcgggcagcagcggatgatcctccagtatggtagcgcgggtttctgtctcaaaagga |
| ggtagacgatccctactgtacggagtgcgccgagacaaccgagatcgtgttggtcgtagtgtcatgccaaatggaacgccggacgtag |
| tcatatttcctgaagcaaaaccaggtgcgggcgtgacaaacagatctgcgtctccggtctcgccgcttagatcgctctgtgtagtagttgta |
| gtatatccactctctcaaagcatccaggcgccccctggcttcgggttctatgtaaactccttcatgcgccgctgccctgataacatccacca |
| ccgcagaataagccacacccagccaacctacacattcgttctgcgagtcacacacgggaggagcgggaagagctggaagaaccatg |
| tttttttttttttattccaaaagattatccaaaacctcaaaatgaagatctattaagtgaacgcgctcccctccggtggcgtggtcaaactctaca |
| gccaaagaacagataatggcatttgtaagatgttgcacaatggcttccaaaaggcaaacggccctcacgtccaagtggacgtaaaggct |
| aaacccttcagggtgaatctcctctataaacattccagcaccttcaaccatgcccaaataattctcatctcgccaccttctcaatatatctcta |
| agcaaatcccgaatattaagtccggccattgtaaaaatctgctccagagcgccctccaccttcagcctcaagcagcgaatcatgattgca |
| aaaattcaggttcctcacagacctgtataagattcaaaagcggaacattaacaaaaataccgcgatcccgtaggtcccttcgcagggcca |
| gctgaacataatcgtgcaggtctgcacggaccagcgcggccacttccccgccaggaaccatgacaaaagaacccacactgattatgac |
| acgcatactcggagctatgctaaccagcgtagccccgatgtaagcttgttgcatgggcggcgatataaaatgcaaggtgctgctcaaaa |
| aatcaggcaaagcctcgcgcaaaaaagaaagcacatcgtagtcatgctcatgcagataaaggcaggtaagctccggaaccaccacag |
| aaaaagacaccatttttctctcaaacatgtctgcgggtttctgcataaacacaaaataaaataacaaaaaaacatttaaacattagaagcctg |
| tcttacaacaggaaaaacaacccttataagcataagacggactacggccatgccggcgtgaccgtaaaaaaactggtcaccgtgattaa |
| aaagcaccaccgacagctcctcggtcatgtccggagtcataatgtaagactcggtaaacacatcaggttgattcacatcggtcagtgcta |
| aaaagcgaccgaaatagcccgggggaatacatacccgcaggcgtagagacaacattacagcccccataggaggtataacaaaattaa |
| taggagagaaaaacacataaacacctgaaaaaccctcctgcctaggcaaaatagcaccctcccgctccagaacaacatacagcgcttc |
| cacagcggcagccataacagtcagccttaccagtaaaaaagaaaacctattaaaaaaacaccactcgacacggcaccagctcaatcag |
| tcacagtgtaaaaaagggccaagtgcagagcgagtatatataggactaaaaaatgacgtaacggttaaagtccacaaaaaacacccag |

TABLE 23-continued

| Ad5-IL8-shRNA with Plasmid Backbone |
|---|
| aaaaccgcacgcgaacctacgcccagaaacgaaagccaaaaaacccacaacttcctcaaatcgtcacttccgttttcccacgttacgta |
| acttcccattttaagaaaactacaattcccaacacatacaagttactccgccctaaaacctacgtcacccgccccgttcccacgccccgcg |
| ccacgtcacaaactccaccccctcattatcatattggcttcaatccaaaataaggtatattattgatgatg |

TABLE 24

| Ad5-IL1-RA2A-IL10 with plasmid backbone |
|---|
| (SEQ ID NO: 24) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctcccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |

TABLE 24-continued

| Ad5-IL1-RA2A-IL10 with plasmid backbone |
| --- |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactoggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatcttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |

TABLE 24-continued

Ad5-IL1-RA2A-IL10 with plasmid backbone cgtttcgagcaaggcctgcgcgtaggcgcgtttgattttttccggatcggtttcacgtttaccgcgaagcttgtcgaaaccgataatgtattc ctgagctgtacggtcgcggcgcagcatctggatggcgtcgctggggaccacttcgccgcagaacatgccgaaatggcggtggaagtg tttctcctcaatcgatacacctgaagatatcgacgggctgtagatgaggccgtcatattttttcaccatcactttaggctggttggtgaaatcg tcgacttccttctcctgtttgtttttctggttaacgcagagaaacttttttgtcagggaactgtagtctcagctgcatggtaacgtcttcggcgaa cgtcgaactgtcggtggccagcatgattcgttcgccgcgttgcactgcagcgataacctcggtcatgatccgattttttctcggtataaaata cgcggataggcttgttggtttcgcggttgcgaacgtcgaccgggagttcaatcacgtgaatttgcagccaggcaggtaggcccagctcc tcgcgtcgcttcatcgccagttcagccaggtcaacaagcagategttggcatcggcatccaccataatggcatgctcttcagtacgcgcc agcgcgtcgataagcgtgttgaatacgcctaccgggttttccatcgcacgcccggccagaatggcacgcaggccctgtgttgcttcatc gaagccgaagaagtcatgctggcgcatcagcggttgccagcagccttta agtatggagttgatgcaaatagtcagcttgttggcatatgg cgccatttcctgatagccgggatcctgataatgcagaatgtcggctttcgcgccttt cccttcggtcatcatttcatgcaggccgcctatcag ggatacgcggtgcgcgacgaaacgccacgcgtggactgcagcatcagtggacgcaggaggcctgtcgatttaccegaccccatcc cggcgcggacaataacgatgccctgcagctgtgcggcgtatgtcatcacctcatcggtcatcctggaggttttcaaaccgtttgtaagtgat gtgtgacgggcgaaggttcgggttggtgatgcgttcactgaacgaacgtgatgtttgcgcggcacggcatttgcgattcaaccggcgcg taatgtgatctttaacggtaccgttataaatttctgcgatacccatatcccgcagcgtgctgctgaaaaggcgcataagttctttcgggctgtt tggtaccgggcatgtcagcatgccaatatcaacggcgcgaagcagttctttggcaaaagtgcgtctgttcagacgcgggagagtacgc agcttattcagcgtgatcgacaacagatcggttgcacggctcagatgatttctcgttaactggcgagcgacttccttcagccctctcaggct gtgcaggtcgttaaaatcgctgcattccagctcagggtcatcctcaaaagttgggtaaacacatttgacgccggaaaacttctccatgatgt cgaatccggtgcggaggcctgtgttgccttttccttcagctgaggatttgcggtcgttatcgagagcgcaagtgatttgcgcagccgggta catgttcaccagctgctcgacaacgtgaatcatgttgttagcggaaaccgcaatgactaccgcgtcaaagcgttttttcgggtcgtttctgg tcgccagccagatggatgccccggtggcgaaaccctctgcagtcgcaattttttgcgcccctgcaggtcgccaataacaaagcatgca ccgacgaaatcaccgttagtgatggcgctggtctggaacttgccaccattcagategatacgttgccagccaacaatccgcccgtcttttc ttccgtccaggtgggacagaggtatcgccatgtaagttgttggtccacggctccatttcgcactgtcgtgactggtcacgcgacgtatatc acaagcgccaaatacgtcacgaattccctttttaccgcataaggccaggagccatcttcagctggcgaatgttcccaggcgcgatggaa agccaaccatccaagcaggcgttcctgctccatctgattgttttttaaatcattaacgcgttgttgttcagctcggaggcggcgtgcttcagc ctggcgctccatgcgtgcacgttcttcttccggctgagcgaccacggtcgcaccattccgttgctgttcacggcgatactccgaaaacag gaatgaaaagccactccaggagccagcgtcatgcgcttttt caacgaagttaacgaaaggataactgatgccatccttgctctgctcaag gcgtgaatagatttccacacggcctttaaggctcttctgcagagcttccggggaggaattattgtaggtggtatagcgctctacaccaccg cgcggattgagctgaatcttatcagcacacgcaggccagttgataccggccatcttcgccagctcagtcagctcatcacgtgccgcgtca agcagtgaaaacggatcgctgccaaagcgctccgcgtagaattcttgtaaggtcatttttttagccttttccatgcgaattagcattttttcgggt tgaaaaaatccgcaggagcagccacaataaacgcactatctttctgaaggacgtatctgcgttatcgtggctacttcctgaaaaaggccc gagtttgccgactcggttttttttttcgtcttttttcggctgctacggtctggttcaaccccgacaaagtatagatcggattaaaccagaattata gtcagcaataaaccctgttattgtatcatctaccctcaaccatgaacgatttgatcgtaccgactacttggtgcacaaattgaagatcacttttt atcatggataacccgttgagagttagcactatcaaggtagtaatgctgctcgtcataacgggctaatcgttgaattgtgatctcgccgttatt atcacaaaccagtacatcctcacccggtacaagcgtaagtgaagaatcgaccaggataacgtctcccggctggtagtttcgctgaatctg gttcccgaccgtcagtgcgtaaacggtgttccgttgactcacgaacggcaggaatcgctctgtgttggcaggttctccaggctgccagtc tctatccggtccggtctctgtcgtaccaataacaggaacgcggtctggatcagattcagtgccatacagtatccattgcacgggcttacgc aggcatttgccagcgatagccccgatctccagcgacggcatcacgtcgccacgttctaagttttggacgcccggaagagagattcctac agcttctgccacttgcttcagcgtcagtttcagctctaaacggcgtgctttcagtcgttcgcctcgtgttttcatacccttaatcataaatgatct ctttatagctggctataattttttataaattatacctagctttaattttcacttattgattataataatcccc atgaaacccgaagaacttgtgcgcca TABLE 24-continued

| Ad5-IL1-RA2A-IL10 with plasmid backbone |
|---|
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgaggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccact |
| agttattaatagtaatcaattacggggtcattagttcatagcccatatatggagttccgcgttacataacttacggtaaatggcccgcctggct |
| gaccgcccaacgacccccgcccattgacgtcaataatgacgtatgttcccatagtaacgccaatagggactttccattgacgtcaatggg |
| tggagtatttacggtaaactgcccacttggcagtacatcaagtgtatcatatgccaagtacgccccctattgacgtcaatgacggtaaatgg |
| cccgcctggcattatgcccagtacatgaccttatgggactttcctacttggcagtacatctacgtattagtcatcgctattaccatggtcgag |
| gtgagccccacgttctgcttcactctccccatctcccccccctccccacccccaattttgtatttatttattttttaattattttgtgcagcgatgg |
| gggcgggggggggggggggggggcgcgccaggcggggcggggcggggcgaggggcggggcggggcgaggcggagaggtgcg |
| gcggcagccaatcagagcggcgcgctccgaaagtttccttttatggcgaggcggcggcggcggcggccctataaaaagcgaagcgc |
| gcggggggggagtcgctgcgttgccttcgccccgtgccccgctccgcgccgcctcgcgccgcccgccccggctctgactgaccg |
| cgttactcccacaggtgagcgggcgggacggcccttctcctccgggctgtaattagcgcttggtttaatgacggctcgtttcttttctgtgg |
| ctgcgtgaaagccttaaagggctccgggagggccctttgtgcgggggggagcggctcggggggtgcgtgcgtgtgtgtgtgcgtgg |
| ggagcgccgcgtgcggctccgcgctgcccggcggctgtgagcgctgcgggcgcggcgcggggctttgtgcgctccgcagtgtgcg |
| cgaggggagcgcggccgggggcggtgccccgcggtgcggggggggctgcgaggggaacaaaggctgcgtgcggggtgtgtgc |
| gtgggggggtgagcagggggtgtgggcgcgtcggtcgggctgcaaccccccctgcacccccctccccgagttgctgagcacggcc |
| cggcttcgggtgcggggctccgtacggggcgtggcgcggggctcgccgtgccgggcggggggtggcggcaggtgggggtgccg |
| ggcgggggggggccgcctcgggccggggagggctcgggggaggggcgcggcggcccccggagcgccggcggctgtcgaggc |
| gcggcgagccgcagccattgccttttatggtaatcgtgcgagagggcgcagggacttcctttgtcccaaatctgtgcggagccgaaatct |
| gggaggcgccgccgcaccccctctagcgggcgcggggcgaagcggtgcggcgccggcaggaaggaaatgggcggggagggcc |
| ttcgtgcgtcgccgcgccgccgtccccttctccctctccagcctcggggctgtccgcgggggggacggctgccttcggggggggacggg |
| gcagggcggggttcggcttctggcgtgtgaccggcggctctagagcctctgctaaccatgttcatgccttcttctttttcctacagctcctg |
| ggcaacgtgctggttattgtgctgtctcatcattttggcaaagaattccgctgcgactcggcggagtcccggcggcgcgtccttgttctaac |
| ccggcgcgccagcttggcaatccggtactgttggtaaagccaccatggaaatctgcagaggcctccgcagtcacctaatcactctcctc |
| ctcttcctgttccattcagagacgatctgccgaccctctgggagaaaatccagcaagatgcaagccttcagaatctgggatgttaaccaga |
| agaccttctatctgaggaacaaccaactagttgccggatacttgcaaggaccaaatgtcaatttagaagaaaagatagatgtggtacccat |
| tgagcctcatgctctgttcttgggaatccatggagggaagatgtgcctgtcctgtgtcaagtctggtgatgagaccagactccagctggag |
| gcagttaacatcactgacctgagcgagaacagaaagcaggacaagcgcttcgccttcatccgctcagacagtggccccaccaccagtt |
| ttgagtctgccgcctgccccggttggttcctctgcacagcgatggaagctgaccagcccgtcagcctcaccaatatgcctgacgaaggc |
| gtcatggtcaccaaattctacttccaggaggacgagggaagcggagctactaacttcagcctgctgaagcaggctggagacgtggagg |
| agaaccctggacctatgcatagttctgccctgttgtgttgcttggtgctgttgacgggggttagagcgagtccaggtcaaggcacgcagt |
| ctgaaaactcctgtacacacttccccggcaacctccctaatatgctcagagaccttcgagacgccttctcccgagtaaaaactttctttcag |
| atgaaggaccagctcgacaacttgctgttgaaggaatcactcctcgaagattttaaggggtacctcggttgtcaagctctgtctgaaatgat |

TABLE 24-continued

| Ad5-IL1-RA2A-IL10 with plasmid backbone |
|---|
| acaattctatctcgaggaagtcatgcctcaagcggaaaaccaggacccagatattaaggcccatgtgaatagcctcggcgaaaatcttaa |
| aactcttcgccttagactccgaagatgccataggtttttgccgtgcgaaaataaatccaaagctgtggaacaggtaaaaaatgcgtttaac |
| aagttgcaagagaagggcatctacaaagcgatgtcagagttcgatatattcataaattatattgaagcatacatgactatgaagatcagga |
| attaataattctagagtcggggcggccggccgcttcgagcagacatgataagatacattgatgagtttggacaaaccacaactagaatgc |
| agtgaaaaaaatgctttatttgtgaaatttgtgatgctattgctttatttgtaaccattataagctgcaataaacaagttaacaacaacaattgca |
| ttcattttatgtttcaggttcagggggaggtgtgggaggttttttaaagcaagtaaaacctctacaaatgtggtaaaatcgataaggatccga |
| attcgatatcactagtggtaccagtactgaaatgtgtgggcgtggcttaagggtgggaaagaatatataaggtgggggtcttatgtagtttt |
| gtatctgttttgcagcagccgccgccgccatgagcaccaactcgtttgatggaagcattgtgagctcatatttgacaacgcgcatgcccc |
| atgggccggggtgcgtcagaatgtgatgggctccagcattgatggtcgccccgtcctgcccgcaaactctactaccttgacctacgaga |
| ccgtgtctggaacgccgttggagactgcagcctccgccgccgcttcagccgctgcagccaccgcccgcgggattgtgactgactttgct |
| ttcctgagcccgcttgcaagcagtgcagcttcccgttcatccgcccgcgatgacaagttgacggctcttttggcacaattggattctttgac |
| ccgggaacttaatgtcgtttctcagcagctgttggatctgcgccagcaggtttctgccctgaaggcttcctcccctcccaatgcggtttaac |
| ggtccgggccagagtggccaacataaataaaaaaccagactctgtttggatttggatcaagcaagtgtcttgctgtctttatttaggggtttt |
| gcgcgcgcggtaggcccgggaccagcggtctcggtcgttgagggtcctgtgtattttttccaggacgtggtaaaggtgactctggatgtt |
| cagatacatgggcataagcccgtctctgggggggaggtagcaccactgcagagcttcatgctgcggggtggtgttgtagatgatccagt |
| cgtagcaggagcgctgggcgtggtgcctaaaaatgtctttcagtagcaagctgattgccaggggcaggcccttggtgtaagtgtttacaa |
| agcggttaagctgggatgggtgcatacgtggggatatgagatgcatcttggactgtatttttaggttggctatgttcccagccatatccctcc |
| ggggattcatgttgtgcagaaccaccagcacagtgtatccggtgcacttgggaaatttgtcatgtagcttagaaggaaatgcgtggaaga |
| acttggagacgcccttgtgacctccaagattttccatgcattcgtccataatgatggcaatgggcccacgggcggcggcctgggcgaag |
| atatttctgggatcactaacgtcatagttgtgttccaggatgagatcgtcataggccatttttacaaagcgcgggggagggtgccagact |
| gcggtataatggttccatccggcccaggggcgtagttaccctcacagatttgcatttcccacgctttgagttcagatgggggggatcatgtct |
| acctgcggggcgatgaagaaaacggtttccggggtaggggagatcagctgggaagaaagcaggttcctgagcagctgcgacttacc |
| gcagccggtgggcccgtaaatcacacctattaccggctgcaactggtagttaagagagctgcagctgccgtcatccctgagcaggggg |
| gccacttcgttaagcatgtccctgactcgcatgttttccctgaccaaatccgccagaaggcgctcgccgcccagcgatagcagttcttgca |
| aggaagcaaagtttttcaacggtttgagaccgtccgccgtaggcatgcttttgagcgtttgaccaagcagttccaggcggtcccacagct |
| cggtcacctgctctacggcatctcgatccagcatatctcctcgtttcgcgggttggggcggctttcgctgtacggcagtagtcggtgctcg |
| tccagacgggccagggtcatgtctttccacgggcgcagggtcctcgtcagcgtagtctgggtcacggtgaaggggtgcgctccgggct |
| gcgcgctggccagggtgcgcttgaggctggtcctgctggtgctgaagcgctgccggtcttcgccctgcgcgtcggccaggtagcattt |
| gaccatggtgtcatagtccagcccctccgcggcgtggcccttggcgcgcagcttgcccttggaggaggcgccgcacgaggggcagt |
| gcagacttttgagggcgtagagcttgggcgcgagaaataccgattccggggagtaggcatccgcgccgcaggccccgcagacggtc |
| tcgcattccacgagccaggtgagctctggccgttcggggtcaaaaaccaggtttcccccatgctttttgatgcgtttcttacctctggtttcc |
| atgagccggtgtccacgctcggtgacgaaaaggctgtccgtgtccccgtatacagacttgagaggcctgtcctcgagcggtgttccgcg |
| gtcctcctcgtatagaaactcggaccactctgagacaaaggctcgcgtccaggccagcacgaaggaggctaagtgggaggggtagc |
| ggtcgttgtccactagggggtccactcgctccagggtgtgaagacacatgtcgccctcttcggcatcaaggaaggtgattggtttgtagg |
| tgtaggccacgtgaccgggtgttcctgaagggggggctataaaagggggtgggggcgcgttcgtcctcactctcttccgcatcgctgtct |
| gcgagggccagctgttggggtgagtactccctctgaaaagcgggcatgacttctgcgctaagattgtcagtttccaaaaacgaggagga |
| tttgatattcacctggcccgcggtgatgcctttgagggtggccgcatccatctggtcagaaaagacaatctttttgttgtcaagcttggtggc |
| aaacgacccgtagagggcgttggacagcaacttggcgatggagcgcagggtttggtttttgtcgcgatcggcgcgctccttggccgcg |
| atgtttagctgcacgtattcgcgcgcaacgcaccgccattcgggaaagacggtggtgcgctcgtcgggcaccaggtgcacgcgccaa |

TABLE 24-continued

| Ad5-IL1-RA2A-IL10 with plasmid backbone |
|---|
| ccgcggttgtgcagggtgacaaggtcaacgctggtggctacctctccgcgtaggcgctcgttggtccagcagaggggccgcccttgc |
| gcgagcagaatggcggtagggggtctagctgcgtctcgtccggggggtctgcgtccacggtaaagaccccgggcagcaggcgcgc |
| gtcgaagtagtctatcttgcatccttgcaagtctagcgcctgctgccatgcgcgggcggcaagcgcgcgctcgtatgggttgagtgggg |
| gaccccatggcatggggtgggtgagcgcggaggcgtacatgccgcaaatgtcgtaaacgtagaggggctctctgagtattccaagata |
| tgtagggtagcatcttccaccgcggatgctggcgcgcacgtaatcgtatagttcgtgcgagggagcgaggaggtcgggaccgaggttg |
| ctacgggcgggctgctctgctcggaagactatctgcctgaagatggcatgtgagttggatgatatggttggacgctggaagacgttgaa |
| gctggcgtctgtgagacctaccgcgtcacgcacgaaggaggcgtaggagtcgcgcagcttgttgaccagctcggcggtgacctgcac |
| gtctagggcgcagtagtccagggtttccttgatgatgtcatacttatcctgtcccttttttttccacagctcgcggttgaggacaaactcttcg |
| cggtctttccagtactcttggatcggaaacccgtcggcctccgaacggtaagagcctagcatgtagaactggttgacggcctggtaggc |
| gcagcatcccttttctacgggtagcgcgtatgcctgcgcggccttccggagcgaggtgtgggtgagcgcaaaggtgtccctgaccatg |
| actttgaggtactggtatttgaagtcagtgtcgtcgcatccgccctgctcccagagcaaaaagtccgtgcgctttttggaacgcggatttgg |
| cagggcgaaggtgacatcgttgaagagtatctttcccgcgcgaggcataaagttgcgtgtgatgcggaagggtcccggcacctcggaa |
| cggttgttaattacctgggcggcgagcacgatctcgtcaaagccgttgatgttgtggcccacaatgtaaagttccaagaagcgcgggatg |
| cccttgatggaaggcaattttttaagttcctcgtaggtgagctcttcaggggagctgagcccgtgctctgaaagggcccagtctgcaagat |
| gagggttggaagcgacgaatgagctccacaggtcacgggccattagcatttgcaggtggtcgcgaaaggtcctaaactggcgacctat |
| ggccatttttctggggtgatgcagtagaaggtaagcgggtcttgttcccagcggtcccatccaaggttcgcggctaggtctcgcgcggc |
| agtcactagaggctcatctccgccgaacttcatgaccagcatgaagggcacgagctgcttcccaaaggcccccatccaagtataggtct |
| ctacatcgtaggtgacaaagagacgctcggtgcgaggatgcgagccgatcgggaagaactggatctcccgccaccaattggaggagt |
| ggctattgatgtggtgaaagtagaagtccctgcgacgggccgaacactcgtgctggcttttgtaaaaacgtgcgcagtactggcagcgg |
| tgcacgggctgtacatcctgcacgaggttgacctgacgaccgcgcacaaggaagcagagtgggaatttgagcccctcgcctggcggg |
| tttggctggtggtcttctacttcggctgcttgtccttgaccgtctggctgctcgaggggagttacggtggatcggaccaccacgccgcgcg |
| agcccaaagtccagatgtccgcgcgcggcggtcggagcttgatgacaacatcgcgcagatgggagctgtccatggtctggagctccc |
| gcggcgtcaggtcaggcgggagctcctgcaggtttacctcgcatagacgggtcagggcgcgggctagatccaggtgatacctaatttc |
| caggggctggttggtggcggcgtcgatggcttgcaagaggccgcatccccgcggcgcgactacggtaccgcgcggcgggcggtgg |
| gccgcgggggtgtccttggatgatgcatctaaaagcggtgacgcgggcgagcccccggaggtagggggggctccggacccgccgg |
| gagagggggcaggggcacgtcggcgccgcgcgcgggcaggagctggtgctgcgcgcgtaggttgctggcgaacgcgacgacgc |
| ggcggttgatctcctgaatctggcgcctctgcgtgaagacgacgggcccggtgagcttgaacctgaaagagagttcgacagaatcaatt |
| tcggtgtcgttgacggcggcctggcgcaaaatctcctgcacgtctcctgagttgtcttgataggcgatctcggccatgaactgctcgatct |
| cttcctcctggagatctccgcgtccggctcgctccacggtggcggcgaggtcgttggaaatgcgggccatgagctgcgagaaggcgtt |
| gaggcctccctcgttccagacgcggctgtagaccacgcccccttcggcatcgcgggcgcgcatgaccacctgcgcgagattgagctc |
| cacgtgccgggcgaagacggcgtagtttcgcaggcgctgaaagaggtagttgagggtggtggcggtgtgttctgccacgaagaagta |
| cataacccagcgtcgcaacgtggattcgttgatatcccccaaggcctcaaggcgctccatggcctcgtagaagtccacggcgaagttga |
| aaaactgggagttgcgcgccgacacggttaactcctcctccagaagacggatgagctcggcgacagtgtcgcgcacctcgcgctcaa |
| aggctacaggggcctcttcttcttcttcaatctcctcttccataagggcctccccttcttcttcttctggcggcggtgggggaggggggaca |
| cggcggcgacgacggcgcaccgggaggcggtcgacaaagcgctcgatcatctccccgcggcgacggcgcatggtctcggtgacg |
| gcgcggccgttctcgcgggggcgcagttggaagacgccgcccgtcatgtcccggttatgggttggcgggggggctgccatgcggcag |
| ggatacggcgctaacgatgcatctcaacaattgttgtgtaggtactccgccgccgagggacctgagcgagtccgcatcgaccggatcg |
| gaaaacctctcgagaaaggcgtctaaccagtcacagtcgcaaggtaggctgagcaccgtggcgggcggcagcgggcggcggtcgg |
| ggttgtttctggcggaggtgctgctgatgatgtaattaaagtaggcggtcttgagacggcggatggtcgacagaagcaccatgtccttgg |

TABLE 24-continued

| Ad5-IL1-RA2A-IL10 with plasmid backbone |
| --- |
| gtccggcctgctgaatgcgcaggcggtcggccatgccccaggcttcgttttgacatcggcgcaggtctttgtagtagtcttgcatgagcct |
| ttctaccggcacttcttcttctccttcctcttgtcctgcatctcttgcatctatcgctgcggcggcggcggagtttggccgtaggtggcgccct |
| cttcctcccatgcgtgtgaccccgaagcccctcatcggctgaagcagggctaggtcggcgacaacgcgctcggctaatatggcctgct |
| gcacctgcgtgagggtagactggaagtcatccatgtccacaaagcggtggtatgcgcccgtgttgatggtgtaagtgcagttggccata |
| acggaccagttaacggtctggtgacccggctgcgagagctcggtgtacctgagacgcgagtaagccctcgagtcaaatacgtagtcgt |
| tgcaagtccgcaccaggtactggtatcccaccaaaaagtgcggcggcggctggcggtagaggggccagcgtagggtggccggggc |
| tccgggggcgagatcttccaacataaggcgatgatatccgtagatgtacctggacatccaggtgatgccggcggcggtggtggaggc |
| gcgcggaaagtcgcggacgcggttccagatgttgcgcagcggcaaaaagtgctccatggtcgggacgctctggccggtcaggcgcg |
| cgcaatcgttgacgctctagaccgtgcaaaaggagagcctgtaagcgggcactcttccgtggtctggtggataaattcgcaagggtatc |
| atggcggacgaccggggttcgagccccgtatccggccgtccgccgtgatccatgcggttaccgcccgcgtgtcgaacccaggtgtgc |
| gacgtcagacaacgggggagtgctccttttggcttccttccaggcgcggcggctgctgcgctagcttttttggccactggccgcgcgca |
| gcgtaagcggttaggctggaaagcgaaagcattaagtggctcgctccctgtagccggagggttattttccaagggttgagtcgcgggac |
| ccccggttcgagtctcggaccggccggactgcggcgaacgggggtttgcctccccgtcatgcaagaccccgcttgcaaattcctccgg |
| aaacagggacgagcccctttttgcttttcccagatgcatccggtgctgcggcagatgcgcccccctcctcagcagcggcaagagcaag |
| agcagcggcagacatgcagggcaccctcccctcctcctaccgcgtcaggaggggcgacatccgcggttgacgcggcagcagatggt |
| gattacgaaccccgcggcgccgggcccggcactacctggacttggaggagggcgagggcctggcgcggctaggagcgccctctc |
| ctgagcggcacccaagggtgcagctgaagcgtgatacgcgtgaggcgtacgtgccgcggcagaacctgtttcgcgaccgcgaggga |
| gaggagcccgaggagatgcgggatcgaaagttccacgcagggcgcgagctgcggcatggcctgaatcgcgagcggttgctgcgcg |
| aggaggactttgagcccgacgcgcgaaccgggattagtcccgcgcgcgcacacgtggcggccgccgacctggtaaccgcatacga |
| gcagacggtgaaccaggagattaactttcaaaaaagctttaacaaccacgtgcgtacgcttgtggcgcgcgaggaggtggctatagga |
| ctgatgcatctgtgggactttgtaagcgcgctggagcaaaacccaaatagcaagccgctcatggcgcagctgttccttatagtgcagcac |
| agcagggacaacgaggcattcagggatgcgctgctaaacatagtagagcccgagggccgctggctgctcgatttgataaacatcctgc |
| agagcatagtggtgcaggagcgcagcttgagcctggctgacaaggtggccgccatcaactattccatgcttagcctgggcaagttttac |
| gcccgcaagatataccataccccttacgttcccatagacaaggaggtaaagatcgaggggttctacatgcgcatggcgctgaaggtgct |
| taccttgagcgacgacctgggcgtttatcgcaacgagcgcatccacaaggccgtgagcgtgagccggcggcgcgagctcagcgacc |
| gcgagctgatgcacagcctgcaaagggccctggctggcacgggcagcggcgatagagaggccgagtcctactttgacgcgggcgct |
| gacctgcgctgggccccaagccgacgcgccctggaggcagctggggccggacctgggctggcggtggcacccgcgcgcgctggc |
| aacgtcggcggcgtggaggaatatgacgaggacgatgagtacgagccagaggacggcgagtactaagcggtgatgtttctgatcaga |
| tgatgcaagacgcaacggacccggcggtgcgggcggcgctgcagagccagccgtccggccttaactccacggacgactggcgcca |
| ggtcatggaccgcatcatgtcgctgactgcgcgcaatcctgacgcgttccggcagcagccgcaggccaaccggctctccgcaattctg |
| gaagcggtggtcccggcgcgcgcaaaccccacgcacgagaaggtgctggcgatcgtaaacgcgctggccgaaaacagggccatcc |
| ggcccgacgaggccggcctggtctacgacgcgctgcttcagcgcgtggctcgttacaacagcggcaacgtgcagaccaacctggac |
| cggctggtgggggatgtgcgcgaggccgtggcgcagcgtgagcgcgcgcagcagcagggcaacctgggctccatggttgcactaa |
| acgccttcctgagtacacagcccgccaacgtgccgcggggacaggaggactacaccaactttgtgagcgcactgcggctaatggtga |
| ctgagacaccgcaaagtgaggtgtaccagtctgggccagactatttttttccagaccagtagacaaggcctgcagaccgtaaacctgagc |
| caggctttcaaaaacttgcaggggctgtgggggtgcgggctcccacaggcgaccgcgcgaccgtgtctagcttgctgacgcccaac |
| tcgcgcctgttgctgctgctaatagcgcccttcacggacagtggcagcgtgtcccgggacacatacctaggtcacttgctgacactgtac |
| cgcgaggccataggtcaggcgcatgtggacgagcatactttccaggagattacaagtgtcagccgcgcgctggggcaggaggacac |
| gggcagcctggaggcaaccctaaactacctgctgaccaaccggcggcagaagatcccctcgttgcacagtttaaacagcgaggagga |

TABLE 24-continued

| Ad5-IL1-RA2A-IL10 with plasmid backbone |
| --- |

gcgcattttgcgctacgtgcagcagagcgtgagccttaacctgatgcgcgacggggtaacgcccagcgtggcgctggacatgaccgc gcgcaacatggaaccgggcatgtatgcctcaaaccggccgtttatcaaccgcctaatggactacttgcatcgcgcggccgccgtgaac cccgagtatttcaccaatgccatcttgaacccgcactggctaccgccccctggtttctacaccgggggattcgaggtgcccgagggtaa cgatggattcctctgggacgacatagacgacagcgtgttttccccgcaaccgcagaccctgctagagttgcaacagcgcgagcaggca gaggcggcgctgcgaaaggaaagcttccgcaggccaagcagcttgtccgatctaggcgctgcggccccgcggtcagatgctagtag cccatttccaagcttgatagggtctcttaccagcactcgcaccacccgcccgcgcctgctgggcgaggaggagtacctaaacaactcgc tgctgcagccgcagcgcgaaaaaaacctgcctccggcatttcccaacaacgggatagagagcctagtggacaagatgagtagatgga agacgtacgcgcaggagcacagggacgtgccaggcccgcgcccgcccacccgtcgtcaaaggcacgaccgtcagcggggtctgg tgtgggaggacgatgactcggcagacgacagcagcgtcctggatttgggagggagtggcaacccgtttgcgcaccttcgccccaggc tggggagaatgttttaaaaaaaaaaaaaagcatgatgcaaaataaaaaactcaccaaggccatggcaccgagcgttggttttcttgtattc cccttagtatgcggcgcgcggcgatgtatgaggaaggtcctcctccctcctacgagagtgtggtgagcgcggcgccagtggcggcgg cgctgggttctcccttcgatgctcccctggacccgccgtttgtgcctccgcggtacctgcggcctaccggggggagaaacagcatccgt tactctgagttggcacccctattcgacaccacccgtgtgtacctggtggacaacaagtcaacggatgtggcatccctgaactaccagaac gaccacagcaactttctgaccacggtcattcaaaacaatgactacagcccgggggaggcaagcacacagaccatcaatcttgacgacc ggtcgcactggggcggcgacctgaaaaccatcctgcataccaacatgccaaatgtgaacgagttcatgtttaccaataagtttaaggcgc gggtgatggtgtcgcgcttgcctactaaggacaatcaggtggagctgaaatacgagtgggtggagttcacgctgcccgagggcaacta ctccgagaccatgaccatagaccttatgaacaacgcgatcgtggagcactacttgaaagtgggcagacagaacggggttctggaaagc gacatcggggtaaagtttgacacccgcaacttcagactggggtttgaccccgtcactggtcttgtcatgcctggggtatatacaaacgaa gccttccatccagacatcattttgctgccaggatgcggggtggacttcacccacagccgcctgagcaacttgttgggcatccgcaagcg gcaacccttccaggagggctttaggatcacctacgatgatctggagggtggtaacattcccgcactgttggatgtggacgcctaccagg cgagcttgaaagatgacaccgaacagggggggggtggcgcaggcggcagcaacagcagtggcagcggcgcggaagagaactcc aacgcggcagccgcggcaatgcagccggtggaggacatgaacgatcatgccattcgcggcgacacctttgccacacgggctgagga gaagcgcgctgaggccgaagcagcggccgaagctgccgcccccgctgcgcaacccgaggtcgagaagcctcagaagaaaccggt gatcaaacccctgacagaggacagcaagaaacgcagttacaacctaataagcaatgacagcaccttcacccagtaccgcagctggtac cttgcatacaactacggcgaccctcagaccggaatccgctcatggaccctgctttgcactcctgacgtaacctgcggctcggagcaggt ctactggtcgttgccagacatgatgcaagaccccgtgaccttccgctccacgcgccagatcagcaactttccggtggtgggcgccgag ctgttgcccgtgcactccaagagcttctacaacgaccaggccgtctactcccaactcatccgccagtttacctctctgacccacgtgttcaa tcgctttcccgagaaccagattttggcgcgcccgccagccccaccatcaccaccgtcagtgaaaacgttcctgctctcacagatcacg ggacgctaccgctgcgcaacagcatcggaggagtccagcgagtgaccattactgacgccagacgccgcacctgcccctacgtttaca aggccctgggcatagtctcgccgcgcgtcctatcgagccgcactttttgagcaagcatgtccatccttatatcgcccagcaataacacag gctggggcctgcgcttcccaagcaagatgtttggcggggccaagaagcgctccgaccaacacccagtgcgcgtgcgcgggcactac cgcgcgccctggggcgcgcacaaacgcggccgcactgggcgcaccaccgtcgatgacgccatcgacgcggtggtggaggaggcg cgcaactacacgcccacgccgccaccagtgtccacagtggacgcggccattcagaccgtggtgcgcggagcccggcgctatgctaa aatgaagagacggcggaggcgcgtagcacgtcgccaccgccgccgacccggcactgccgcccaacgcgcggcggcggccctgct taaccgcgcacgtcgcaccggccgacgggcggccatgcgagcagctcgaaggctggccgcgggtattgtcactgtgccccccaggt ccaggcgacgagcggccgccgcagcagccgcggccattagtgctatgactcagggtcgcaggggcaacgtgtattgggtgcgcgac tcggttagcggcctgcgcgtgcccgtgcgcacccgcccccgcgcaactagattgcaagaaaaaactacttagactcgtactgttgtat gtatccagcggcggcggcgcgcaacgaagctatgtccaagcgcaaaatcaaagaagagatgctccaggtcatcgcgccggagatct atggccccccgaagaaggaagagcaggattacaagccccgaaagctaaagcgggtcaaaaagaaaaagaaagatgatgatgatgaa TABLE 24-continued

| Ad5-IL1-RA2A-IL10 with plasmid backbone |
| --- |

cttgacgacgaggtggaactgctgcacgctaccgcgcccaggcgacgggtacagtggaaaggtcgacgcgtaaaacgtgttttgcga
cccggcaccaccgtagtctttacgcccggtgagcgctccacccgcacctacaagcgcgtgtatgatgaggtgtacggcgacgaggac
ctgcttgagcaggccaacgagcgcctcggggagtttgcctacggaaagcggcataaggacatgctggcgttgccgctggacgaggg
caacccaacacctagcctaaagcccgtaacactgcagcaggtgctgcccgcgcttgcaccgtccgaagaaaagcgcggcctaaagc
gcgagtctggtgacttggcacccaccgtgcagctgatggtacccaagcgccagcgactggaagatgtcttggaaaaaatgaccgtgga
acctgggctggagcccgaggtccgcgtgcggccaatcaagcaggtggcgccgggactgggcgtgcagaccgtggacgttcagata
cccactaccagtagcaccagtattgccaccgccacagagggcatggagacacaaacgtccccggttgcctcagcggtggcggatgcc
gcggtgcaggcggtcgctgcggccgcgtccaagacctctacggaggtgcaaacggacccgtggatgtttcgcgtttcagccccccgg
cgcccgcgccgttcgaggaagtacggcgccgccagcgcgctactgcccgaatatgccctacatccttccattgcgcctacccccggct
atcgtggctacacctaccgccccagaagacgagcaactacccgacgccgaaccaccactggaacccgccgccgccgtcgccgtcgc
cagcccgtgctggccccgatttccgtgcgcagggtggctcgcgaaggaggcaggaccctggtgctgccaacagcgcgctaccaccc
cagcatcgtttaaaagccggtctttgtggttcttgcagatatggccctcacctgccgcctccgtttcccggtgccgggattccgaggaaga
atgcaccgtaggaggggcatggccggccacggcctgacgggcggcatgcgtcgtgcgcaccaccggcggcggcgcgcgtcgcac
cgtcgcatgcgcggcggtatcctgcccctccttattccactgatcgccgcggcgattggcgccgtgcccggaattgcatccgtggccttg
caggcgcagagacactgattaaaaacaagttgcatgtggaaaaatcaaaataaaaagtctggactctcacgctcgcttggtcctgtaact
attttgtagaatggaagacatcaactttgcgtctctggccccgcgacacggctcgcgcccgttcatgggaaactggcaagatatcggcac
cagcaatatgagcggtggcgccttcagctggggctcgctgtggagcggcattaaaaatttcggttccaccgttaagaactatggcagca
aggcctggaacagcagcacaggccagatgctgagggataagttgaaagagcaaaatttccaacaaaaggtggtagatggcctggcct
ctggcattagcggggtggtggacctggccaaccaggcagtgcaaaataagattaacagtaagcttgatccccgccctcccgtagagga
gcctccaccggccgtggagacagtgtctccagaggggcgtggcgaaaagcgtccgcgccccgacagggaagaaactctggtgacg
caaatagacgagcctccctcgtacgaggaggcactaaagcaaggcctgcccaccacccgtcccatcgcgcccatggctaccggagtg
ctgggccagcacacacccgtaacgctggacctgcctccccccgccgacacccagcagaaacctgtgctgccaggcccgaccgccgt
tgttgtaacccgtcctagccgcgcgtccctgcgccgcgccgccagcggtccgcgatcgttgcggcccgtagccagtggcaactggca
aagcacactgaacagcatcgtgggtctgggggtgcaatccctgaagcgccgacgatgcttctgaatagctaacgtgtcgtatgtgtgtca
tgtatgcgtccatgtcgccgccagaggagctgctgagccgccgcgcgcccgctttccaagatggctaccccttcgatgatgccgcagtg
gtcttacatgcacatctcgggccaggacgcctcggagtacctgagccccgggctggtgcagtttgcccgcgccaccgagacgtacttc
agcctgaataacaagtttagaaccccacggtggcgcctacgcacgacgtgaccacagaccggtcccagcgtttgacgctgcggttca
tccctgtggaccgtgaggatactgcgtactcgtacaaggcgcggttcaccctagctgtgggtgataaccgtgtgctggacatggcttcca
cgtactttgacatccgcggcgtgctggacaggggccctacttttaagccctactctggcactgcctacaacgccctggctcccaagggtg
ccccaaatccttgcgaatgggatgaagctgctactgctcttgaaataaacctagaagaagaggacgatgacaacgaagacgaagtaga
cgagcaagctgagcagcaaaaaactcacgtatttgggcaggcgccttattctggtataaatattacaaaggagggtattcaaataggtgtc
gaaggtcaaacacctaaatatgccgataaaacatttcaacctgaacctcaaataggagaatctcagtggtacgaaacagaaattaatcat
gcagctgggagagtcctaaaaaagactaccccaatgaaaccatgttacggttcatatgcaaaacccacaaatgaaaatggagggcaag
gcattcttgtaaagcaacaaaatggaaagctagaaagtcaagtggaaatgcaattttttctcaactactgaggcagccgcaggcaatggtg
ataacttgactcctaaagtggtattgtacagtgaagatgtagatatagaaaccccagacactcatatttcttacatgcccactattaaggaag
gtaactcacgagaactaatgggccaacaatctatgcccaacaggcctaattacattgcttttagggacaattttattggtctaatgtattacaa
cagcacgggtaatatgggtgttctggcgggccaagcatcgcagttgaatgctgttgtagatttgcaagacagaaacacagagctttcata
ccagcttttgcttgattccattggtgatagaaccaggtacttttctatgtggaatcaggctgttgacagctatgatccagatgttagaattattg
aaaatcatggaactgaagatgaacttccaaattactgctttccactgggaggtgtgattaatacagagactcttaccaaggtaaaacctaaa TABLE 24-continued

| Ad5-IL1-RA2A-IL10 with plasmid backbone |
| --- |
| acaggtcaggaaaatggatgggaaaaagatgctacagaattttcagataaaaatgaaataagagttggaaataattttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |
| ttccgcggctgggccttcacgcgccttaagactaaggaaaccccatcactgggctcgggctacgacccttattacacctactctggctcta |
| taccctacctagatggaacctttacctcaaccacacctttaagaaggtggccattacctttgactcttctgtcagctggcctggcaatgacc |
| gcctgcttacccccaacgagtttgaaattaagcgctcagttgacggggagggttacaacgttgcccagtgtaacatgaccaaagactggt |
| tcctggtacaaatgctagctaactataacattggctaccagggcttctatatcccagagagctacaaggaccgcatgtactccttctttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttcccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttctttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggtggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |

TABLE 24-continued

| Ad5-IL1-RA2A-IL10 with plasmid backbone |
|---|
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgcttttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |
| ccatttccttctcctataggcagaaaaagatcatggagtcagtcgagaagaaggacagcctaaccgccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggggggggacgaaaggcatggcgactacctagatgtgggagacgacgtgctgttgaagcatctgcagcgcca |
| gtgcgccattatctgcgacgcgttgcaagagcgcagcgatgtgcccctcgccatagcggatgtcagccttgcctacgaacgccacctat |
| tctcaccgcgcgtacccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctaccccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacggggggtttacttggacccccagtccggcgaggagctcaacccaatccccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttcccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |

TABLE 24-continued

| Ad5-IL1-RA2A-IL10 with plasmid backbone |
|---|
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |
| aagttcagatgactaactcaggggcgcagcttgcgggcggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |
| actgtgatttgcaactgtcctaaccttggattacatcaagatccagatcttctagacccgggagaggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |
| ccgctaaccgtgcacgactccaaacttagcattgccacccaaggacccctcacagtgtcagaaggaaagctagccctgcaaacatcag |
| gcccccctcaccaccaccgatagcagtacccttactatcactgcctcaccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctcttttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaacaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacacttttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |

TABLE 24-continued

| Ad5-IL1-RA2A-IL10 with plasmid backbone |
| --- |

tcctgcaggaatacaacatggcagtggtctcctcagcgatgattcgcaccgcccgcagcataaggcgccttgtcctccgggcacagca gcgcaccctgatctcacttaaatcagcacagtaactgcagcacagcaccacaatattgttcaaaatcccacagtgcaaggcgctgtatcc aaagctcatggcggggaccacagaacccacgtggccatcataccacaagcgcaggtagattaagtggcgacccctcataaacacgct ggacataaacattacctcttttggcatgttgtaattcaccacctcccggtaccatataaacctctgattaaacatggcgccatccaccaccat cctaaaccagctggccaaaacctgcccgccggctatacactgcagggaaccgggactggaacaatgacagtggagagcccaggact cgtaaccatggatcatcatgctcgtcatgatatcaatgttggcacaacacaggcacacgtgcatacacttcctcaggattacaagctcctc ccgcgttagaaccatatcccagggaacaacccattcctgaatcagcgtaaatcccacactgcagggaagacctcgcacgtaactcacgt tgtgcattgtcaaagtgttacattcgggcagcagcggatgatcctccagtatggtagcgcgggtttctgtctcaaaaggaggtagacgatc cctactgtacggagtgcgccgagacaaccgagatcgtgttggtcgtagtgtcatgccaaatggaacgccggacgtagtcatatttcctga agcaaaaccaggtgcgggcgtgacaaacagatctgcgtctccggtctcgccgcttagatcgctctgtgtagtagttgtagtatatccactc tctcaaagcatccaggcgccccctggcttcgggttctatgtaaactccttcatgcgccgctgccctgataacatccaccaccgcagaataa gccacacccagccaacctacacattcgttctgcgagtcacacacgggaggagcgggaagagctggaagaaccatgtttttttttttattc caaaagattatccaaaacctcaaaatgaagatctattaagtgaacgcgctcccctccggtggcgtggtcaaactctacagccaaagaaca gataatggcatttgtaagatgttgcacaatggcttccaaaaggcaaacggccctcacgtccaagtggacgtaaaggctaaacccttcagg gtgaatctcctctataaacattccagcaccttcaaccatgcccaaataattctcatctcgccaccttctcaatatatctctaagcaaatcccga atattaagtccggccattgtaaaaatctgctccagagcgccctccaccttcagcctcaagcagcgaatcatgattgcaaaaattcaggttc ctcacagacctgtataagattcaaaagcggaacattaacaaaaataccgcgatcccgtaggtcccttcgcagggccagctgaacataat cgtgcaggtctgcacggaccagcgcggccacttccccgccaggaaccatgacaaaagaacccacactgattatgacacgcatactcg gagctatgctaaccagcgtagccccgatgtaagcttgttgcatgggcggcgatataaaatgcaaggtgctgctcaaaaaatcaggcaaa gcctcgcgcaaaaaagaaagcacatcgtagtcatgctcatgcagataaaggcaggtaagctccggaaccaccacagaaaaagacacc atttttctctcaaacatgtctgcgggtttctgcataaacacaaaataaaataacaaaaaaacatttaaacattagaagcctgtcttacaacagg aaaaacaacccttataagcataagacggactacggccatgccggcgtgaccgtaaaaaaactggtcaccgtgattaaaaagcaccacc gacagctcctcggtcatgtccggagtcataatgtaagactcggtaaacacatcaggttgattcacatcggtcagtgctaaaaagcgaccg aaatagcccgggggaatacatacccgcaggcgtagagacaacattacagcccccataggaggtataacaaaattaataggagagaaa aacacataaacacctgaaaaaccctcctgcctaggcaaaatagcaccctcccgctccagaacaacatacagcgcttccacagcggcag ccataacagtcagccttaccagtaaaaaagaaaacctattaaaaaaacaccactcgacacggcaccagctcaatcagtcacagtgtaaa aaagggccaagtgcagagcgagtatatataggactaaaaaatgacgtaacggttaaagtccacaaaaaacacccagaaaaccgcacg cgaacctacgcccagaaacgaaagccaaaaaacccacaacttcctcaaatcgtcacttccgttttcccacgttacgtaacttcccattttaa gaaaactacaattcccaacacatacaagttactccgccctaaaacctacgtcacccgccccgttcccacgccccgcgccacgtcacaaa ctccacccctcattatcatattggcttcaatccaaaataaggtatattattgatgatgttaatttgggccattagacttgaagtcaagcggcc gcttacaactggaccttgctggtacatagaactgattaactgaccatttaaatcataccaacatggtcaaataaaacgaaaggctcagtcg aaagactgggcctttcgttttaatctgatcggcacgtaagaggttccaactttcaccataatgaaataagatcactaccgggcgtatttttga gttatcgagattttcaggagctaaggaagctaaaatgagccatattcaacgggaaacgtcttgctcgaggccgcgattaaattccaacatg gatgctgatttatatgggtataaatgggctcgcgataatgtcgggcaatcaggtgcgacaatctatcgattgtatgggaagcccgatgcgc cagagttgtttctgaaacatggcaaaggtagcgttgccaatgatgttacagatgagatggtcaggctaaactggctgacggaatttatgcc tcttccgaccatcaagcattttatccgtactcctgatgatgcatggttactcaccactgcgatcccagggaaaacagcattccaggtattag aagaatatcctgattcaggtgaaaatattgttgatgcgctggcagtgttcctgcgccggttgcattcgattcctgtttgtaattgtccttttaac ggcgatcgcgtatttcgtctcgctcaggcgcaatcacgaatgaataacggtttggttggtgcgagtgattttgatgacgagcgtaatggct ggcctgttgaacaagtctggaaagaaatgcataaacttttgccattctcaccggattcagtcgtcactcatggtgatttctcacttgataacct TABLE 24-continued

| Ad5-IL1-RA2A-IL10 with plasmid backbone |
|---|
| tatttttgacgaggggaaattaataggttgtattgatgttggacgagtcggaatcgcagaccgataccaggatcttgccatcctatggaact |
| gcctcggtgagttttctccttcattacagaaacggctttttcaaaaatatggtattgataatcctgatatgaataaattgcagtttcacttgatgct |
| cgatgagtttttctaacctaggtgacagaagtcaaaagcctccggtcggaggcttttgactttctgctagatctgtttcaatgcggtgaagg |
| gccaggcagctggggattatgtcgagacccggccagcatgttggttttatcgcatattcagcgttgtcgcgtttacccaggtaaaatggaa |
| gcagtgtatcgtctgcgtgaatgtgcaaatcaggaacgtaaccgtggtacatagatgcagtcccttgcgggtcgttcccttcaacgagtag |
| gacgcggtgcccttgcaaggctaaccattgcgcctggtgtactgcagatgaggttttataaacccctcccttgtgtgacataacggaaagt |
| acaaccgggtttttatcgtcaggtctttggtttgggttaccaaacacactccgcatatggctaatttggtcaattgtgtagccagcgcgacgtt |
| ctactcggcccctcatctcaaaatcaggagccggtagacgaccagctttttccgcgtctctgatagcctgcggtgttacgccgatcaggtc |
| tgcaacttctgttataccccagcggcgagtaatacgacgcgcttccgggctgtcatcgccgaactgtgcgatggcaatagcgcgcgtcat |
| ttcctgaccgcgattgatacagtctttcagcaaattaattaacgacatcctgtttcctctcaaacatgcccttatctttgtgtttttcatcatacttt |
| acgtttttaaagcaaagcaacataaaaaaagcaaagtgacttagaaaacgcaaagttaaggttcaaatcaatttttgatgcgctacagaa |
| gctatttagcttcatctaagcgcaacggtattacttacgttggtatatttaaaacctaacttaatgattttaaatgataataaatcataccaattgc |
| tatcaaaagttaagcgaacatgctgattttcacgctgtttatacactttgaggcatctctatctcttccgtctctatattgaaacacaatcaaaga |
| acatcaatccatgtgacatcccccactatctaagaacaccataacagaacacaacataggaatgcaacattaatgtatcaataattcggaa |
| catatgcactatatcatatctcaattacggaacatatcagcacacaattgcccattatacgc |

TABLE 25

| Ad5-IL1-RA2A-IL10 No Plasmid Backbone |
|---|
| (SEQ ID NO: 25) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccactagttattaatagtaatcaattacggggtcattagttcatagcccatatatggagttccgc |
| gttacataacttacggtaaatggcccgcctggctgaccgcccaacgacccccgcccattgacgtcaataatgacgtatgttcccatagta |
| acgccaatagggactttccattgacgtcaatgggtggagtatttacggtaaactgcccacttggcagtacatcaagtgtatcatatgccaa |
| gtacgccccctattgacgtcaatgacggtaaatggcccgcctggcattatgcccagtacatgaccttatgggactttcctacttggcagtac |
| atctacgtattagtcatcgctattaccatggtcgaggtgagccccacgttctgcttcactctccccatctcccccccctccccacccccaatt |
| ttgtatttatttattttttaattattttgtgcagcgatgggggcgggggggggggggggggcgccaggcggggggggggggcgag |
| gggcggggggggcgaggcggagaggtgcggcggcagccaatcagagcggcgcgctccgaaagtttccttttatggcgaggcgg |
| cggcggcggcggccctataaaaagcgaagcgcgcggcgggggagtcgctgcgttgccttcgccccgtgccccgctccgcgccg |
| cctcgcgccgcccgccccggctctgactgaccgcgttactcccacaggtgagcgggcgggacggcccttctcctccgggctgtaatta |
| gcgcttggtttaatgacggctcgtttcttttctgtggctgcgtgaaagccttaaagggctccgggagggccctttgtgcgggggggagcg |
| gctcggggggtgcgtgcgtgtgtgtgtgcgtggggagcgccgcgtgcggctccgcgctgcccggcggctgtgagcgctgcgggcg |
| cggcgcggggctttgtgcgctccgcagtgtgcgcgaggggagcgcggccgggggcggtgccccgcggtgcgggggggggctgcg |
| aggggaacaaaggctgcgtgcggggtgtgtgcgtgggggggtgagcagggggtgtgggcgcgtcggtcgggctgcaaccccccct |
| gcaccccccctccccgagttgctgagcacggcccggcttcgggtgcggggctccgtacggggcgtggcgcggggctcgccgtgccg |
| ggcggggggggcggcaggtgggggtgccgggcggggggggccgcctcgggccggggagggctcgggggagggggcgcgg |

TABLE 25-continued

| Ad5-IL1-RA2A-IL10 No Plasmid Backbone |
|---|
| cggcccccggagcgccggcggctgtcgaggcgcggcgagccgcagccattgccttttatggtaatcgtgcgagagggcgcaggga |
| cttcctttgtcccaaatctgtgcggagccgaaatctgggaggcgccgccgcacccccctctagcgggcgcggggcgaagcggtgcggc |
| gccggcaggaaggaaatgggcggggagggccttcgtgcgtcgccgcgccgccgtccccttctccctctccagcctcggggctgtcc |
| gcgggggggacggctgccttcgggggggacggggcagggcggggttcggcttctggcgtgtgaccggggctctagagcctctgcta |
| accatgttcatgccttcttctttttcctacagctcctgggcaacgtgctggttattgtgctgtctcatcattttggcaaagaattccgctgcgact |
| cggcggagtcccggcggcgcgtccttgttctaacccggcgcgccagcttggcaatccggtactgttggtaaagccaccatggaaatct |
| gcagaggcctccgcagtcacctaatcactctcctcctcttcctgttccattcagagacgatctgccgaccctctgggagaaaatccagcaa |
| gatgcaagccttcagaatctgggatgttaaccagaagaccttctatctgaggaacaaccaactagttgccggatacttgcaaggaccaaa |
| tgtcaatttagaagaaaagatagatgtggtacccattgagcctcatgctctgttcttgggaatccatggagggaagatgtgcctgtcctgtg |
| tcaagtctggtgatgagaccagactccagctggaggcagttaacatcactgacctgagcgagaacagaaagcaggacaagcgcttcg |
| ccttcatccgctcagacagtggccccaccaccagttttgagtctgccgcctgccccggttggttcctctgcacagcgatggaagctgacc |
| agcccgtcagcctcaccaatatgcctgacgaaggcgtcatggtcaccaaattctacttccaggaggacgagggaagcggagctactaa |
| cttcagcctgctgaagcaggctggagacgtggaggagaaccctggacctatgcatagttctgccctgttgtgttgcttggtgctgttgacg |
| gggttagagcgagtccaggtcaaggcacgcagtctgaaaactcctgtacacacttccccggcaacctccctaatatgctcagagacct |
| tcgagacgccttctcccgagtaaaaactttctttcagatgaaggaccagctcgacaacttgctgttgaaggaatcactcctcgaagatttta |
| aggggtacctcggttgtcaagctctgtctgaaatgatacaattctatctcgaggaagtcatgcctcaagcggaaaaccaggacccagata |
| ttaaggcccatgtgaatagcctcggcgaaaatcttaaaactcttcgccttagactccgaagatgccataggtttttgccgtgcgaaaataaa |
| tccaaagctgtggaacaggtaaaaaatgcgtttaacaagttgcaagagaagggcatctacaaagcgatgtcagagttcgatatattcata |
| aattatattgaagcatacatgactatgaagatcaggaattaataattctagagtcggggcggccggccgcttcgagcagacatgataagat |
| acattgatgagtttggacaaaccacaactagaatgcagtgaaaaaaatgctttatttgtgaaatttgtgatgctattgctttatttgtaaccatta |
| taagctgcaataaacaagttaacaacaacaattgcattcattttatgtttcaggttcagggggaggtgtgggaggttttttaaagcaagtaaa |
| acctctacaaatgtggtaaaatcgataaggatccgaattcgatatcactagtggtaccagtactgaaatgtgtgggcgtggcttaagggtg |
| ggaaagaatatataaggtgggggtcttatgtagttttgtatctgttttgcagcagccgccgccgccatgagcaccaactcgtttgatggaag |
| cattgtgagctcatatttgacaacgcgcatgcccccatgggccggggtgcgtcagaatgtgatgggctccagcattgatggtcgccccgt |
| cctgcccgcaaactctactaccttgacctacgagaccgtgtctggaacgccgttggagactgcagcctccgccgccgcttcagccgctg |
| cagccaccgcccgcgggattgtgactgactttgctttcctgagcccgcttgcaagcagtgcagcttcccgttcatccgcccgcgatgaca |
| agttgacggctcttttggcacaattggattctttgacccgggaacttaatgtcgtttctcagcagctgttggatctgcgccagcaggtttctgc |
| cctgaaggcttcctcccctcccaatgcggtttaacggtccgggccagagtggccaacataaataaaaaaccagactctgtttggatttgg |
| atcaagcaagtgtcttgctgtctttatttaggggttttgcgcgcgcggtaggcccgggaccagcggtctcggtcgttgagggtcctgtgtat |
| tttttccaggacgtggtaaaggtgactctggatgttcagatacatgggcataagcccgtctctgggggggaggtagcaccactgcagagc |
| ttcatgctgcggggtggtgttgtagatgatccagtcgtagcaggagcgctgggcgtggtgcctaaaaatgtctttcagtagcaagctgatt |
| gccaggggcaggcccttggtgtaagtgtttacaaagcggttaagctgggatgggtgcatacgtggggatatgagatgcatcttggactgt |
| atttttaggttggctatgttcccagccatatccctccggggattcatgttgtgcagaaccaccagcacagtgtatccggtgcacttgggaaa |
| tttgtcatgtagcttagaaggaaatgcgtggaagaacttggagacgcccttgtgacctccaagattttccatgcattcgtccataatgatgg |
| caatgggcccacgggcggcggcctgggcgaagatatttctgggatcactaacgtcatagttgtgttccaggatgagatcgtcataggcc |
| atttttacaaagcgcgggcggagggtgccagactgcggtataatggttccatccggcccaggggcgtagttaccctcacagatttgcatt |
| tcccacgctttgagttcagatgggggggatcatgtctacctgcggggcgatgaagaaaacggtttccggggtaggggagatcagctggg |
| aagaaagcaggttcctgagcagctgcgacttaccgcagccggtgggcccgtaaatcacacctattaccggctgcaactggtagttaaga |
| gagctgcagctgccgtcatccctgagcagggggggccacttcgttaagcatgtccctgactcgcatgttttccctgaccaaatccgccaga |

TABLE 25-continued

| Ad5-IL1-RA2A-IL10 No Plasmid Backbone |
| --- |
| aggcgctcgccgcccagcgatagcagttcttgcaaggaagcaaagtttttcaacggtttgagaccgtccgccgtaggcatgcttttgagc |
| gtttgaccaagcagttccaggcggtcccacagctcggtcacctgctctacggcatctcgatccagcatatctcctcgtttcgcgggttggg |
| gcggctttcgctgtacggcagtagtcggtgctcgtccagacgggccagggtcatgtctttccacgggcgcagggtcctcgtcagcgtag |
| tctgggtcacggtgaaggggtgcgctccgggctgcgcgctggccagggtgcgcttgaggctggtcctgctggtgctgaagcgctgcc |
| ggtcttcgccctgcgcgtcggccaggtagcatttgaccatggtgtcatagtccagcccctccgcggcgtggcccttggcgcgcagcttg |
| cccttggaggaggcgccgcacgaggggcagtgcagacttttgagggcgtagagcttgggcgcgagaaataccgattccggggagta |
| ggcatccgcgccgcaggccccgcagacggtctcgcattccacgagccaggtgagctctggccgttcggggtcaaaaaccaggtttcc |
| cccatgctttttgatgcgtttcttacctctggtttccatgagccggtgtccacgctcggtgacgaaaaggctgtccgtgtccccgtatacaga |
| cttgagaggcctgtcctcgagcggtgttccgcggtcctcctcgtatagaaactcggaccactctgagacaaaggctcgcgtccaggcca |
| gcacgaaggaggctaagtgggaggggtagcggtcgttgtccactagggggtccactcgctccagggtgtgaagacacatgtgccct |
| cttcggcatcaaggaaggtgattggtttgtaggtgtaggccacgtgaccgggtgttcctgaaggggggctataaaagggggtgggggc |
| gcgttcgtcctcactctcttccgcatcgctgtctgcgagggccagctgttggggtgagtactccctctgaaaagcgggcatgacttctgcg |
| ctaagattgtcagtttccaaaaacgaggaggatttgatattcacctggcccgcggtgatgcctttgagggtggccgcatccatctggtcag |
| aaaagacaatctttttgttgtcaagcttggtggcaaacgacccgtagagggcgttggacagcaacttggcgatggagcgcagggtttggt |
| ttttgtcgcgatcggcgcgctccttggccgcgatgtttagctgcacgtattcgcgcgcaacgcaccgccattcgggaaagacggtggtg |
| cgctcgtcgggcaccaggtgcacgcgccaaccgcggttgtgcagggtgacaaggtcaacgctggtggctacctctccgcgtaggcgc |
| tcgttggtccagcagaggcggccgcccttgcgcgagcagaatggcggtagggggtctagctgcgtctcgtccggggggtctgcgtcc |
| acggtaaagaccccgggcagcaggcgcgcgtcgaagtagtctatcttgcatccttgcaagtctagcgcctgctgccatgcgcgggcgg |
| caagcgcgcgctcgtatgggttgagtgggggaccccatggcatggggtgggtgagcgcggaggcgtacatgccgcaaatgtcgtaa |
| acgtagaggggctctctgagtattccaagatatgtagggtagcatcttccaccgcggatgctggcgcgcacgtaatcgtatagttcgtgc |
| gagggagcgaggaggtcgggaccgaggttgctacgggggcgctgctctgctcggaagactatctgcctgaagatggcatgtgagttg |
| gatgatatggttggacgctggaagacgttgaagctggcgtctgtgagacctaccgcgtcacgcacgaaggaggcgtaggagtcgcgc |
| agcttgttgaccagctcggcggtgacctgcacgtctagggcgcagtagtccagggtttccttgatgatgtcatacttatcctgtcccttttttt |
| ccacagctcgcggttgaggacaaactcttcgcggtctttccagtactcttggatcggaaacccgtcggcctccgaacggtaagagccta |
| gcatgtagaactggttgacggcctggtaggcgcagcatcccttttctacgggtagcgcgtatgcctgcgcggccttccggagcgaggtg |
| tgggtgagcgcaaaggtgtccctgaccatgactttgaggtactggtatttgaagtcagtgtcgtcgcatccgccctgctcccagagcaaa |
| aagtccgtgcgctttttggaacgcggatttggcagggcgaaggtgacatcgttgaagagtatctttcccgcgcgaggcataaagttgcgt |
| gtgatgcggaagggtcccggcacctcggaacggttgttaattacctgggcggcgagcacgatctcgtcaaagccgttgatgttgtggcc |
| cacaatgtaaagttccaagaagcgcgggatgcccttgatggaaggcaattttttaagttcctcgtaggtgagctcttcaggggagctgag |
| cccgtgctctgaaagggcccagtctgcaagatgagggttggaagcgacgaatgagctccacaggtcacgggccattagcatttgcagg |
| tggtcgcgaaaggtcctaaactggcgacctatggccatttttctggggtgatgcagtagaaggtaagcgggtcttgttcccagcggtccc |
| atccaaggttcgcggctaggtctcgcgcggcagtcactagaggctcatctccgccgaacttcatgaccagcatgaagggcacgagctg |
| cttcccaaaggccccatccaagtataggtctctacatcgtaggtgacaaagagacgctcggtgcgaggatgcgagccgatcgggaag |
| aactggatctcccgccaccaattggaggagtggctattgatgtggtgaaagtagaagtccctgcgacgggccgaacactcgtgctggct |
| tttgtaaaaacgtgcgcagtactggcagcggtgcacgggctgtacatcctgcacgaggttgacctgacgaccgcgcacaaggaagca |
| gagtgggaatttgagcccctcgcctggcgggtttggctggtggtcttctacttcggctgcttgtccttgaccgtctggctgctcgaggga |
| gttacggtggatcggaccaccacgccgcgcgagcccaaagtccagatgtccgcgcgcggcggtcggagcttgatgacaacatcgcg |
| cagatgggagctgtccatggtctggagctcccgcggcgtcaggtcaggcgggagctcctgcaggtttacctcgcatagacgggtcag |
| ggcgcgggctagatccaggtgatacctaatttccaggggctggttggtggcggcgtcgatggcttgcaagaggccgcatccccgcgg |

TABLE 25-continued

| Ad5-IL1-RA2A-IL10 No Plasmid Backbone |
| --- |
| cgcgactacggtaccgcgcggcgggcggtgggccgcgggggtgtccttggatgatgcatctaaaagcggtgacgcgggcgagccc |
| ccggaggtagggggggctccggacccgccgggagagggggcaggggcacgtcggcgccgcgcgcgggcaggagctggtgctg |
| cgcgcgtaggttgctggcgaacgcgacgacgcggcggttgatctcctgaatctggcgcctctgcgtgaagacgacgggcccggtgag |
| cttgaacctgaaagagagttcgacagaatcaatttcggtgtcgttgacggcggcctggcgcaaaatctcctgcacgtctcctgagttgtctt |
| gataggcgatctcggccatgaactgctcgatctcttcctcctggagatctccgcgtccggctcgctccacggtggcggcgaggtcgttg |
| gaaatgcgggccatgagctgcgagaaggcgttgaggcctccctcgttccagacgcggctgtagaccacgccccccttcggcatcgcgg |
| gcgcgcatgaccacctgcgcgagattgagctccacgtgccgggcgaagacggcgtagtttcgcaggcgctgaaagaggtagttgag |
| ggtggtggcggtgtgttctgccacgaagaagtacataacccagcgtcgcaacgtggattcgttgatatcccccaaggcctcaaggcgct |
| ccatggcctcgtagaagtccacggcgaagttgaaaaactgggagttgcgcgccgacacggttaactcctcctccagaagacggatgag |
| ctcggcgacagtgtcgcgcacctcgcgctcaaaggctacaggggcctcttcttcttcttcaatctcctcttccataagggcctccccttcttc |
| ttcttctggcggcggtgggggaggggggacacggcggcgacgacggcgcaccgggaggggtcgacaaagcgctcgatcatctcc |
| ccgcggcgacggcgcatggtctcggtgacggcgcggccgttctcgcgggggcgcagttggaagacgccgcccgtcatgtcccggtt |
| atgggttggggggggctgccatgcggcagggatacggcgctaacgatgcatctcaacaattgttgtgtaggtactccgccgccgagg |
| gacctgagcgagtccgcatcgaccggatcggaaaacctctcgagaaaggcgtctaaccagtcacagtcgcaaggtaggctgagcacc |
| gtggcgggcggcagcgggcggcggtcggggttgtttctggcggaggtgctgctgatgatgtaattaaagtaggcggtcttgagacggc |
| ggatggtcgacagaagcaccatgtccttgggtccggcctgctgaatgcgcaggcggtcggccatgccccaggcttcgttttgacatcgg |
| cgcaggtctttgtagtagtcttgcatgagcctttctaccggcacttcttcttctccttcctcttgtcctgcatctcttgcatctatcgctgcggcg |
| gcggcggagtttggccgtaggtggcgccctcttcctcccatgcgtgtgaccccgaagcccctcatcggctgaagcagggctaggtcgg |
| cgacaacgcgctcggctaatatggcctgctgcacctgcgtgagggtagactggaagtcatccatgtccacaaagcggtggtatgcgcc |
| cgtgttgatggtgtaagtgcagttggccataacggaccagttaacggtctggtgacccggctgcgagagctcggtgtacctgagacgcg |
| agtaagccctcgagtcaaatacgtagtcgttgcaagtccgcaccaggtactggtatcccaccaaaaagtgcggcggcggctggcggta |
| gaggggccagcgtagggtggccggggctccgggggcgagatcttccaacataaggcgatgatatccgtagatgtacctggacatcca |
| ggtgatgccggcggcggtggtggaggcgcgcggaaagtcgcggacgcggttccagatgttgcgcagcggcaaaaagtgctccatg |
| gtcgggacgctctggccggtcaggcgcgcgcaatcgttgacgctctagaccgtgcaaaaggagagcctgtaagcgggcactcttccg |
| tggtctggtggataaattcgcaagggtatcatggcggacgaccggggttcgagccccgtatccggccgtccgccgtgatccatgcggtt |
| accgcccgcgtgtcgaacccaggtgtgcgacgtcagacaacgggggagtgctccttttggcttccttccaggcgcggcggctgctgcg |
| ctagcttttttggccactggccgcgcgcagcgtaagcggttaggctggaaagcgaaagcattaagtggctcgctccctgtagccggagg |
| gttattttccaagggttgagtcgcgggacccccggttcgagtctcggaccggccggactgcggcgaacgggggtttgcctccccgtcat |
| gcaagaccccgcttgcaaattcctccggaaacagggacgagcccctttttttgcttttcccagatgcatccggtgctgcggcagatgcgcc |
| cccctcctcagcagcggcaagagcaagagcagcggcagacatgcagggcaccctcccctcctcctaccgcgtcaggaggggcgac |
| atccgcggttgacgcggcagcagatggtgattacgaaccccgcggcgccgggcccggcactacctggacttggaggagggcgag |
| ggcctggcgcggctaggagcgccctctcctgagcggcacccaagggtgcagctgaagcgtgatacgcgtgaggcgtacgtgccgc |
| ggcagaacctgtttcgcgaccgcgagggagaggagcccgaggagatgcgggatcgaaagttccacgcagggcgcgagctgcggc |
| atggcctgaatcgcgagcggttgctgcgcgaggaggactttgagcccgacgcgcgaaccgggattagtcccgcgcgcgcacacgtg |
| gcggccgccgacctggtaaccgcatacgagcagacggtgaaccaggagattaactttcaaaaaagctttaacaaccacgtgcgtacgc |
| ttgtggcgcgcgaggaggtggctataggactgatgcatctgtgggactttgtaagcgcgctggagcaaaacccaaatagcaagccgct |
| catggcgcagctgttccttatagtgcagcacagcagggacaacgaggcattcagggatgcgctgctaaacatagtagagcccgaggg |
| ccgctggctgctcgatttgataaacatcctgcagagcatagtggtgcaggagcgcagcttgagcctggctgacaaggtggccgccatc |
| aactattccatgcttagcctgggcaagttttacgcccgcaagatataccatacccccttacgttcccatagacaaggaggtaaagatcgagg |

TABLE 25-continued

Ad5-IL1-RA2A-IL10 No Plasmid Backbone ggttctacatgcgcatggcgctgaaggtgcttaccttgagcgacgacctgggcgtttatcgcaacgagcgcatccacaaggccgtgag
cgtgagccggcggcgcgagctcagcgaccgcgagctgatgcacagcctgcaaagggccctggctggcacgggcagcggcgatag
agaggccgagtcctactttgacgcgggcgctgacctgcgctgggccccaagccgacgcgccctggaggcagctggggccggacct
gggctggcggtggcacccgcgcgcgctggcaacgtcggcggcgtggaggaatatgacgaggacgatgagtacgagccagaggac
ggcgagtactaagcggtgatgtttctgatcagatgatgcaagacgcaacggacccggcggtgcgggcggcgctgcagagccagccg
tccggccttaactccacggacgactggcgccaggtcatggaccgcatcatgtcgctgactgcgcgcaatcctgacgcgttccggcagc
agccgcaggccaaccggctctccgcaattctggaagcggtggtcccggcgcgcgcaaaccccacgcacgagaaggtgctggcgat
cgtaaacgcgctggccgaaaacagggccatccggcccgacgaggccggcctggtctacgacgcgctgcttcagcgcgtggctcgtt
acaacagcggcaacgtgcagaccaacctggaccggctggtgggggatgtgcgcgaggccgtggcgcagcgtgagcgcgcgcagc
agcagggcaacctgggctccatggttgcactaaacgccttcctgagtacacagcccgccaacgtgccgcggggacaggaggactac
accaactttgtgagcgcactgcggctaatggtgactgagacaccgcaaagtgaggtgtaccagtctgggccagactattttttccagacc
agtagacaaggcctgcagaccgtaaacctgagccaggctttcaaaaacttgcaggggctgtggggggtgcgggctcccacaggcga
ccgcgcgaccgtgtctagcttgctgacgcccaactcgcgcctgttgctgctgctaatagcgcccttcacggacagtggcagcgtgtccc
gggacacatacctaggtcacttgctgacactgtaccgcgaggccataggtcaggcgcatgtggacgagcatactttccaggagattaca
agtgtcagccgcgcgctggggcaggaggacacgggcagcctggaggcaaccctaaactacctgctgaccaaccggcggcagaag
atcccctcgttgcacagtttaaacagcgaggaggagcgcattttgcgctacgtgcagcagagcgtgagccttaacctgatgcgcgacgg
ggtaacgcccagcgtggcgctggacatgaccgcgcgcaacatggaaccgggcatgtatgcctcaaaccggccgtttatcaaccgcct
aatggactacttgcatcgcgcggccgccgtgaaccccgagtatttcaccaatgccatcttgaacccgcactggctaccgccccctggttt
ctacaccgggggattcgaggtgcccgagggtaacgatggattcctctgggacgacatagacgacagcgtgttttccccgcaaccgcag
accctgctagagttgcaacagcgcgagcaggcagaggcggcgctgcgaaaggaaagcttccgcaggccaagcagcttgtccgatct
aggcgctgcggccccgcggtcagatgctagtagcccatttccaagcttgatagggtctcttaccagcactcgcaccacccgcccgcgc
ctgctgggcgaggaggagtacctaaacaactcgctgctgcagccgcagcgcgaaaaaaacctgcctccggcatttcccaacaacggg
atagagagcctagtggacaagatgagtagatggaagacgtacgcgcaggagcacagggacgtgccaggcccgcgcccgcccaccc
gtcgtcaaaggcacgaccgtcagcggggtctggtgtgggaggacgatgactcggcagacgacagcagcgtcctggatttgggaggg
agtggcaacccgtttgcgcaccttcgccccaggctggggagaatgttttaaaaaaaaaaaaaagcatgatgcaaaataaaaaactcacc
aaggccatggcaccgagcgttggttttcttgtattccccttagtatgcggcgcgcggcgatgtatgaggaaggtcctcctccctcctacga
gagtgtggtgagcgcggcgccagtggcggcggcgctgggttctcccttcgatgctcccctggacccgccgtttgtgcctccgcggtac
ctgcggcctaccggggggagaaacagcatccgttactctgagttggcacccctattcgacaccacccgtgtgtacctggtggacaacaa
gtcaacggatgtggcatccctgaactaccagaacgaccacagcaactttctgaccacggtcattcaaaacaatgactacagcccgggg
gaggcaagcacacagaccatcaatcttgacgaccggtcgcactggggcggcgacctgaaaaccatcctgcataccaacatgccaaat
gtgaacgagttcatgtttaccaataagtttaaggcgcgggtgatggtgtcgcgcttgcctactaaggacaatcaggtggagctgaaatac
gagtgggtggagttcacgctgcccgagggcaactactccgagaccatgaccatagaccttatgaacaacgcgatcgtggagcactact
tgaaagtgggcagacagaacggggttctggaaagcgacatcggggtaaagtttgacacccgcaacttcagactggggtttgaccccgt
cactggtcttgtcatgcctggggtatatacaaacgaagccttccatccagacatcattttgctgccaggatgcgggggggacttcacccac
agccgcctgagcaacttgttgggcatccgcaagcggcaacccttccaggagggctttaggatcacctacgatgatctggagggtggta
acattcccgcactgttggatgtggacgcctaccaggcgagcttgaaagatgacaccgaacagggcgggggtggcgcaggcggcagc
aacagcagtggcagcggcgcggaagagaactccaacgcggcagccgcggcaatgcagccggtggaggacatgaacgatcatgcc
attcgcggcgacacctttgccacacgggctgaggagaagcgcgctgaggccgaagcagcggccgaagctgccgcccccgctgcgc
aacccgaggtcgagaagcctcagaagaaaccggtgatcaaacccctgacagaggacagcaagaaacgcagttacaacctaataagc TABLE 25-continued

| Ad5-IL1-RA2A-IL10 No Plasmid Backbone |
| --- |
| aatgacagcaccttcacccagtaccgcagctggtaccttgcatacaactacggcgaccctcagaccggaatccgctcatggaccctgct |
| ttgcactcctgacgtaacctgcggctcggagcaggtctactggtcgttgccagacatgatgcaagaccccgtgaccttccgctccacgc |
| gccagatcagcaactttccggtggtgggcgccgagctgttgcccgtgcactccaagagcttctacaacgaccaggccgtctactcccaa |
| ctcatccgccagtttacctctctgacccacgtgttcaatcgctttcccgagaaccagattttggcgcgcccgccagccccaccatcacca |
| ccgtcagtgaaaacgttcctgctctcacagatcacgggacgctaccgctgcgcaacagcatcggaggagtccagcgagtgaccattac |
| tgacgccagacgccgcacctgcccctacgtttacaaggccctgggcatagtctcgccgcgcgtcctatcgagccgcactttttgagcaa |
| gcatgtccatccttatatcgcccagcaataacacaggctggggcctgcgcttcccaagcaagatgtttggggggccaagaagcgctcc |
| gaccaacacccagtgcgcgtgcgcgggcactaccgcgcgccctgggggcgcacaaacgcggccgcactgggcgcaccaccgtc |
| gatgacgccatcgacgcggtggtggaggaggcgcgcaactacacgcccacgccgccaccagtgtccacagtggacgcggccattc |
| agaccgtggtgcgcggagcccggcgctatgctaaaatgaagagacggcggaggcgcgtagcacgtcgccaccgccgccgacccg |
| gcactgccgcccaacgcgcggcggcggccctgcttaaccgcgcacgtcgcaccggccgacgggcggccatgcgagcagctcgaa |
| ggctggccgcgggtattgtcactgtgccccccaggtccaggcgacgagcggccgccgcagcagccgcggccattagtgctatgactc |
| agggtcgcaggggcaacgtgtattgggtgcgcgactcggttagcggcctgcgcgtgcccgtgcgcacccgccccccgcgcaactag |
| attgcaagaaaaaactacttagactcgtactgttgtatgtatccagcggcggcggcgcgcaacgaagctatgtccaagcgcaaaatcaa |
| agaagagatgctccaggtcatcgcgccggagatctatggccccccgaagaaggaagagcaggattacaagccccgaaagctaaagc |
| gggtcaaaaagaaaaagaaagatgatgatgatgaacttgacgacgaggtggaactgctgcacgctaccgcgcccaggcgacgggta |
| cagtggaaaggtcgacgcgtaaaacgtgttttgcgacccggcaccaccgtagtctttacgcccggtgagcgctccacccgcacctaca |
| agcgcgtgtatgatgaggtgtacggcgacgaggacctgcttgagcaggccaacgagcgcctcggggagtttgcctacggaaagcgg |
| cataaggacatgctggcgttgccgctggacgagggcaacccaacacctagcctaaagcccgtaacactgcagcaggtgctgcccgcg |
| cttgcaccgtccgaagaaaagcgcggcctaaagcgcgagtctggtgacttggcacccaccgtgcagctgatggtacccaagcgccag |
| cgactggaagatgtcttggaaaaaatgaccgtggaacctgggctggagcccgaggtccgcgtgcggccaatcaagcaggtggcgcc |
| gggactgggcgtgcagaccgtggacgttcagatacccactaccagtagcaccagtattgccaccgccacagagggcatggagacac |
| aaacgtccccggttgcctcagcggtggcggatgccgcggtgcaggcggtcgctgcggccgcgtccaagacctctacggaggtgcaa |
| acggacccgtggatgtttcgcgtttcagccccccggcgcccgcgccgttcgaggaagtacggcgccgccagcgcgctactgcccgaa |
| tatgccctacatccttccattgcgcctacccccggctatcgtggctacacctaccgccccagaagacgagcaactacccgacgccgaac |
| caccactggaacccgccgccgccgtcgccgtcgccagcccgtgctggccccgatttccgtgcgcagggtggctcgcgaaggaggca |
| ggaccctggtgctgccaacagcgcgctaccaccccagcatcgtttaaaagccggtctttgtggttcttgcagatatggccctcacctgcc |
| gcctccgtttcccggtgccgggattccgaggaagaatgcaccgtaggaggggcatggccggccacggcctgacgggcggcatgcgt |
| cgtgcgcaccaccggcggcggcgcgcgtcgcaccgtcgcatgcgcggcggtatcctgcccctccttattccactgatcgccgcggcg |
| attggcgccgtgcccggaattgcatccgtggccttgcaggcgcagagacactgattaaaaacaagttgcatgtggaaaaatcaaaataa |
| aaagtctggactctcacgctcgcttggtcctgtaactattttgtagaatggaagacatcaactttgcgtctctggccccgcgacacggctcg |
| cgcccgttcatgggaaactggcaagatatcggcaccagcaatatgagcggtggcgccttcagctggggctcgctgtggagcggcatta |
| aaaatttcggttccaccgttaagaactatggcagcaaggcctggaacagcagcacaggccagatgctgagggataagttgaaagagca |
| aaatttccaacaaaaggtggtagatggcctggcctctggcattagcggggtggtggacctggccaaccaggcagtgcaaaataagatta |
| acagtaagcttgatccccgccctcccgtagaggagcctccaccggccgtggagacagtgtctccagaggggcgtggcgaaaagcgtc |
| cgcgccccgacagggaagaaactctggtgacgcaaatagacgagcctccctcgtacgaggaggcactaaagcaaggcctgcccacc |
| acccgtcccatcgcgcccatggctaccggagtgctgggccagcacacacccgtaacgctggacctgcctcccccgccgacaccca |
| gcagaaacctgtgctgccaggcccgaccgccgttgttgtaacccgtcctagccgcgcgtccctgcgccgcgccgccagcggtccgcg |
| atcgttgcggcccgtagccagtggcaactggcaaagcacactgaacagcatcgtgggtctgggggtgcaatccctgaagcgccgacg |

TABLE 25-continued

| Ad5-IL1-RA2A-IL10 No Plasmid Backbone |
|---|
| atgcttctgaatagctaacgtgtcgtatgtgtgtcatgtatgcgtccatgtcgccgccagaggagctgctgagccgccgcgcgcccgcttt |
| ccaagatggctaccccttcgatgatgccgcagtggtcttacatgcacatctcgggccaggacgcctcggagtacctgagccccgggct |
| ggtgcagtttgcccgcgccaccgagacgtacttcagcctgaataacaagtttagaaccccacggtggcgcctacgcacgacgtgacc |
| acagaccggtcccagcgtttgacgctgcggttcatccctgtggaccgtgaggatactgcgtactcgtacaaggcgcggttcaccctagc |
| tgtgggtgataaccgtgtgctggacatggcttccacgtactttgacatccgcggcgtgctggacaggggccctacttttaagccctactct |
| ggcactgcctacaacgccctggctcccaagggtgccccaaatccttgcgaatgggatgaagctgctactgctcttgaaataaacctaga |
| agaagaggacgatgacaacgaagacgaagtagacgagcaagctgagcagcaaaaaactcacgtatttgggcaggcgccttattctgg |
| tataaatattacaaaggagggtattcaaataggtgtcgaaggtcaaacacctaaatatgccgataaaacatttcaacctgaacctcaaatag |
| gagaatctcagtggtacgaaacagaaattaatcatgcagctgggagagtcctaaaaaagactaccccaatgaaaccatgttacggttcat |
| atgcaaaacccacaaatgaaaatggagggcaaggcattcttgtaaagcaacaaaatggaaagctagaaagtcaagtggaaatgcaattt |
| ttctcaactactgaggcagccgcaggcaatggtgataacttgactcctaaagtggtattgtacagtgaagatgtagatatagaaaccccag |
| acactcatatttcttacatgcccactattaaggaaggtaactcacgagaactaatgggccaacaatctatgcccaacaggcctaattacatt |
| gcttttagggacaattttattggtctaatgtattacaacagcacgggtaatatgggtgttctggcgggccaagcatcgcagttgaatgctgtt |
| gtagatttgcaagacagaaacacagagctttcataccagcttttgcttgattccattggtgatagaaccaggtacttttctatgtggaatcag |
| gctgttgacagctatgatccagatgttagaattattgaaaatcatggaactgaagatgaacttccaaattactgctttccactgggaggtgtg |
| attaatacagagactcttaccaaggtaaaacctaaaacaggtcaggaaaatggatgggaaaaagatgctacagaattttcagataaaaat |
| gaaataagagttggaaataattttgccatggaaatcaatctaaatgccaacctgtggagaaatttcctgtactccaacatagcgctgtatttg |
| cccgacaagctaaagtacagtccttccaacgtaaaaatttctgataacccaaacacctacgactacatgaacaagcgagtggtggctccc |
| gggctagtggactgctacattaaccttggagcacgctggtcccttgactatatggacaacgtcaacccatttaaccaccaccgcaatgctg |
| gcctgcgctaccgctcaatgttgctgggcaatggtcgctatgtgcccttccacatccaggtgcctcagaagttctttgccattaaaaacctc |
| cttctcctgccgggctcatacacctacgagtggaacttcaggaaggatgttaacatggttctgcagagctccctaggaaatgacctaagg |
| gttgacggagccagcattaagtttgatagcatttgcctttacgccaccttcttccccatggcccacaacaccgcctccacgcttgaggccat |
| gcttagaaacgacaccaacgaccagtcctttaacgactatctctccgccgccaacatgctctaccctatacccgccaacgctaccaacgt |
| gcccatatccatcccctcccgcaactgggcggctttccgcggctgggccttcacgcgccttaagactaaggaaaccccatcactgggct |
| cgggctacgacccttattacacctactctggctctataccctacctagatggaaccttttacctcaaccacacctttaagaaggtggccatta |
| cctttgactcttctgtcagctggcctggcaatgaccgcctgcttacccccaacgagtttgaaattaagcgctcagttgacggggagggtta |
| caacgttgcccagtgtaacatgaccaaagactggttcctggtacaaatgctagctaactataacattggctaccagggcttctatatcccag |
| agagctacaaggaccgcatgtactccttctttagaaacttccagcccatgagccgtcaggtggtggatgatactaaatacaaggactacc |
| aacaggtgggcatcctacaccaacacaacaactctggatttgttggctaccttgcccccaccatgcgcgaaggacaggcctaccctgct |
| aacttcccctatccgcttataggcaagaccgcagttgacagcattacccagaaaaagtttctttgcgatcgcaccctttggcgcatcccatt |
| ctccagtaactttatgtccatgggcgcactcacagacctgggccaaaaccttctctacgccaactccgcccacgcgctagacatgactttt |
| gaggtggatcccatggacgagcccacccttctttatgttttgtttgaagtctttgacgtggtccgtgtgcaccagccgcaccgcggcgtcat |
| cgaaaccgtgtacctgcgcacgcccttctggccggcaacgccacaacataaagaagcaagcaacatcaacaacagctgccgccatg |
| ggctccagtgagcaggaactgaaagccattgtcaaagatcttggttgtgggccatatttttgggcacctatgacaagcgctttccaggctt |
| tgtttctccacacaagctcgcctgcgccatagtcaatacggccggtcgcgagactgggggcgtacactggatggcctttgcctggaacc |
| cgcactcaaaaacatgctacctctttgagccctttggcttttctgaccagcgactcaagcaggtttaccagtttgagtacgagtcactcctgc |
| gccgtagcgccattgcttcttcccccgaccgctgtataacgctggaaaagtccacccaaagcgtacaggggcccaactcggccgcctg |
| tggactattctgctgcatgtttctccacgcctttgccaactggccccaaactcccatggatcacaaccccaccatgaaccttattaccgggg |
| tacccaactccatgctcaacagtccccaggtacagcccaccctgcgtcgcaaccaggaacagctctacagcttcctggagcgccactc |

TABLE 25-continued

| Ad5-IL1-RA2A-IL10 No Plasmid Backbone |
|---|
| gccctacttccgcagccacagtgcgcagattaggagcgccacttctttttgtcacttgaaaaacatgtaaaaataatgtactagagacactt |
| tcaataaaggcaaatgcttttatttgtacactctcgggtgattatttacccccacccttgccgtctgcgccgtttaaaaatcaaaggggttctg |
| ccgcgcatcgctatgcgccactggcagggacacgttgcgatactggtgtttagtgctccacttaaactcaggcacaaccatccgcggca |
| gctcggtgaagttttcactccacaggctgcgcaccatcaccaacgcgtttagcaggtcgggcgccgatatcttgaagtcgcagttgggg |
| cctccgccctgcgcgcgcgagttgcgatacacagggttgcagcactggaacactatcagcgccgggtggtgcacgctggccagcac |
| gctcttgtcggagatcagatccgcgtccaggtcctccgcgttgctcagggcgaacggagtcaactttggtagctgccttcccaaaaagg |
| gcgcgtgcccaggctttgagttgcactcgcaccgtagtggcatcaaaaggtgaccgtgcccggtctgggcgttaggatacagcgcctg |
| cataaaagccttgatctgcttaaaagccacctgagcctttgcgccttcagagaagaacatgccgcaagacttgccggaaaactgattggc |
| cggacacgcggcgtcgtgcacgcagcaccttgcgtcggtgttggagatctgcaccacatttcggccccaccggttcttcacgatcttgg |
| ccttgctagactgctccttcagcgcgcgctgcccgttttcgctcgtcacatccatttcaatcacgtgctccttatttatcataatgcttccgtgta |
| gacacttaagctcgccttcgatctcagcgcagcggtgcagccacaacgcgcagcccgtgggctcgtgatgcttgtaggtcacctctgca |
| aacgactgcaggtacgcctgcaggaatcgccccatcatcgtcacaaaggtcttgttgctggtgaaggtcagctgcaacccgcggtgctc |
| ctcgttcagccaggtcttgcatacggccgccagagcttccacttggtcaggcagtagtttgaagttcgcctttagatcgttatccacgtggt |
| acttgtccatcagcgcgcgcgcagcctccatgcccttctcccacgcagacacgatcggcacactcagcgggttcatcaccgtaatttcac |
| tttccgcttcgctgggctcttcctcttcctcttgcgtccgcataccacgcgccactgggtcgtcttcattcagccgccgcactgtgcgcttac |
| ctcctttgccatgcttgattagcaccggtgggttgctgaaacccaccatttgtagcgccacatcttctctttcttcctcgctgtccacgattacc |
| tctggtgatggcgggcgctcgggcttgggagaagggcgcttctttttcttcttgggcgcaatggccaaatccgccgccgaggtcgatgg |
| ccgcgggctgggtgtgcgcggcaccagcgcgtcttgtgatgagtcttcctcgtcctcggactcgatacgccgcctcatccgcttttttggg |
| ggcgcccggggaggcggcggcgacggggacggggacgacacgtcctccatggttgggggacgtcgcgccgcaccgcgtccgcg |
| ctcgggggtggtttcgcgctgctcctcttcccgactggccatttccttctcctataggcagaaaaagatcatggagtcagtcgagaagaag |
| gacagcctaaccgccccctctgagttcgccaccaccgcctccaccgatgccgccaacgcgcctaccaccttccccgtcgaggcaccc |
| ccgcttgaggaggaggaagtgattatcgagcaggacccaggttttgtaagcgaagacgacgaggaccgctcagtaccaacagaggat |
| aaaaagcaagaccaggacaacgcagaggcaaacgaggaacaagtcgggggggggacgaaaggcatggcgactacctagatgtg |
| ggagacgacgtgctgttgaagcatctgcagcgccagtgcgccattatctgcgacgcgttgcaagagcgcagcgatgtgcccctcgcca |
| tagcggatgtcagccttgcctacgaacgccacctattctcaccgcgcgtaccccccaaacgccaagaaaacggcacatgcgagccca |
| acccgcgcctcaacttctaccccgtatttgccgtgccagaggtgcttgccacctatcacatctttttccaaaactgcaagatacccctatcct |
| gccgtgccaaccgcagccgagcggacaagcagctggccttgcggcagggcgctgtcatacctgatatcgcctcgctcaacgaagtgc |
| caaaaatctttgagggtcttggacgcgacgagaagcgcgcggcaaacgctctgcaacaggaaaacagcgaaaatgaaagtcactctg |
| gagtgttggtggaactcgagggtgacaacgcgcgcctagccgtactaaaacgcagcatcgaggtcacccactttgcctacccggcact |
| taacctacccccaaggtcatgagcacagtcatgagtgagctgatgtgcgccgtgcgcagcccctggagagggatgcaaatttgcaa |
| gaacaaacagaggagggcctacccgcagttggcgacgagcagctagcgcgctggcttcaaacgcgcgagcctgccgacttggagg |
| agcgacgcaaactaatgatggccgcagtgctcgttaccgtggagcttgagtgcatgcagcggttctttgctgacccggagatgcagcgc |
| aagctagaggaaacattgcactacacctttcgacagggctacgtacgccaggcctgcaagatctccaacgtggagctctgcaacctggt |
| ctcctaccttggaattttgcacgaaaaccgccttgggcaaaacgtgcttcattccacgctcaagggcgaggcgcgccgcgactacgtcc |
| gcgactgcgtttacttatttctatgctacacctggcagacggccatgggcgtttggcagcagtgcttggaggagtgcaacctcaaggagc |
| tgcagaaactgctaaagcaaaacttgaaggacctatggacggccttcaacgagcgctccgtggccgcgcacctggcggacatcattttc |
| cccgaacgcctgcttaaaaccctgcaacagggtctgccagacttcaccagtcaaagcatgttgcagaactttaggaactttatcctagag |
| cgctcaggaatcttgcccgccacctgctgtgcacttcctagcgactttgtgcccattaagtaccgcgaatgccctccgccgctttggggcc |
| actgctaccttctgcagctagccaactaccttgcctaccactctgacataatggaagacgtgagcggtgacggtctactggagtgtcactg |

TABLE 25-continued

| Ad5-IL1-RA2A-IL10 No Plasmid Backbone |
|---|
| tcgctgcaacctatgcaccccgcaccgctccctggtttgcaattcgcagctgcttaacgaaagtcaaattatcggtacctttgagctgcag |
| ggtccctcgcctgacgaaaagtccgcggctccggggttgaaactcactccggggctgtggacgtcggcttaccttcgcaaatttgtacct |
| gaggactaccacgcccacgagattaggttctacgaagaccaatcccgcccgcctaatgcggagcttaccgcctgcgtcattacccagg |
| gccacattcttggccaattgcaagccatcaacaaagcccgccaagagtttctgctacgaaagggacgggggtttacttggacccccag |
| tccggcgaggagctcaacccaatcccccgccgccgcagccctatcagcagcagccggggcccttgcttcccaggatggcaccca |
| aaaagaagctgcagctgccgccgccacccacggacgaggaggaatactgggacagtcaggcagaggaggttttggacgaggagga |
| ggaggacatgatggaagactgggagagcctagacgaggaagcttccgaggtcgaagaggtgtcagacgaaacaccgtcaccctcg |
| gtcgcattcccctcgccggcgccccagaaatcggcaaccggttccagcatggctacaacctccgctcctcaggcgccgccggcactg |
| cccgttcgccgacccaaccgtagatgggacaccactggaaccagggccggtaagtccaagcagccgccgccgttagcccaagagca |
| acaacagcgccaaggctaccgctcatggcgcgggcacaagaacgccatagttgcttgcttgcaagactgtgggggcaacatctccttc |
| gcccgccgctttcttctctaccatcacggcgtggccttcccccgtaacatcctgcattactaccgtcatctctacagcccatactgcaccgg |
| cggcagcggcagcggcagcaacagcagcggccacacagaagcaaaggcgaccggatagcaagactctgacaaagcccaagaaat |
| ccacagcggcggcagcagcaggaggaggagcgctgcgtctggcgcccaacgaacccgtatcgacccgcgagcttagaaacaggat |
| ttttcccactctgtatgctatatttcaacagagcaggggccaagaacaagagctgaaaataaaaaacaggtctctgcgatccctcacccgc |
| agctgcctgtatcacaaaagcgaagatcagcttcggcgcacgctggaagacgcggaggctctcttcagtaaatactgcgcgctgactct |
| taaggactagtttcgcgccctttctcaaatttaagcgcgaaaactacgtcatctccagcggccacacccggcgccagcacctgttgtcag |
| cgccattatgagcaaggaaattcccacgccctacatgtggagttaccagccacaaatgggacttgcggctggagctgcccaagactact |
| caacccgaataaactacatgagcgcgggaccccacatgatatcccgggtcaacggaatacgcgcccaccgaaaccgaattctcctgg |
| aacaggcggctattaccaccacacctcgtaataaccttaatccccgtagttggcccgctgccctggtgtaccaggaaagtcccgctccca |
| ccactgtggtacttcccagagacgcccaggccgaagttcagatgactaactcaggggcgcagcttgcgggcggctttcgtcacagggt |
| gcggtcgcccgggcagggtataactcacctgacaatcagagggcgaggtattcagctcaacgacgagtcggtgagctcctcgcttggt |
| ctccgtccggacgggacatttcagatcggcggcgccggccgctcttcattcacgcctcgtcaggcaatcctaactctgcagacctcgtcc |
| tctgagccgcgctctggaggcattggaactctgcaatttattgaggagtttgtgccatcggtctactttaaccccttctcgggacctcccgg |
| ccactatccggatcaatttattcctaactttgacgcggtaaaggactcggcggacggctacgactgaatgttaagtggccaatgaggcct |
| gacgctaataatagctggtccactgtcgccgccacaagtgctttgcccgcgactccggtgagttttgctactttgaattgcccgaggatcat |
| atcgagggcccggcgcacggcgtccggcttaccgcccagggagagcttgcccgtagcctgattcgggagtttacccagcgccccctg |
| ctagttgagcgggacaggggaccctgtgttctcactgtgatttgcaactgtcctaaccttggattacatcaagatccagatcttctagaccc |
| gggagcggccgctgtcgacctgcaggatccgaattcgatatcactagtggtaccgatcttattccctttaactaataaaaaaaaataataaa |
| gcatcacttacttaaaatcagttagcaaatttctgtccagtttattcagcagcacctccttgccctcctcccagctctggtattgcagcttcctc |
| ctggctgcaaactttctccacaatctaaagggaatgtcagtttcctcctgttcctgtccatccgcacccactatcttcatgttgttgcagatga |
| agcgcgcaagaccgtctgaagataccttcaaccccgtgtatccatatgacacggaaaccggtcctccaactgtgccttttcttactcctcc |
| ctttgtatcccccaatgggtttcaagagagtccccctggggtactctctttgcgcctatccgaacctctagttacctccaatggcatgcttgc |
| gctcaaaatgggcaacggcctctctctggacgaggccggcaaccttacctcccaaaatgtaaccactgtgagcccacctctcaaaaaaa |
| ccaagtcaaacataaacctggaaatatctgcacccctcacagttacctcagaagccctaactgtggctgccgccgcacctctaatggtcg |
| cgggcaacacactcaccatgcaatcacaggccccgctaaccgtgcacgactccaaacttagcattgccacccaaggacccctcacagt |
| gtcagaaggaaagctagccctgcaaacatcaggcccccctcaccaccaccgatagcagtacccttactatcactgcctcaccccctctaa |
| ctactgccactggtagcttgggcattgacttgaaagagcccatttatacacaaaatggaaaactaggactaaagtacggggctcctttgca |
| tgtaacagacgacctaaacactttgaccgtagcaactggtccaggtgtgactattaataatacttccttgcaaactaaagttactggagcctt |
| gggttttgattcacaaggcaatatgcaacttaatgtagcaggaggactaaggattgattctcaaaacagacgccttatacttgatgttagtta |

TABLE 25-continued

| Ad5-IL1-RA2A-IL10 No Plasmid Backbone |
|---|
| tccgtttgatgctcaaaaccaactaaatctaagactaggacagggccctcttttataaactcagcccacaacttggatattaactacaacaa |
| aggcctttacttgtttacagcttcaaacaattccaaaaagcttgaggttaacctaagcactgccaaggggttgatgtttgacgctacagccat |
| agccattaatgcaggagatgggcttgaatttggttcacctaatgcaccaaacacaaatcccctcaaaacaaaaattggccatggcctaga |
| atttgattcaaacaaggctatggttcctaaactaggaactggccttagttttgacagcacaggtgccattacagtaggaaacaaaaataatg |
| ataagctaactttgtggaccacaccagctccatctcctaactgtagactaaatgcagagaaagatgctaaactcactttggtcttaacaaaa |
| tgtggcagtcaaatacttgctacagtttcagttttggctgttaaaggcagtttggctccaatatctggaacagttcaaagtgctcatcttattat |
| aagatttgacgaaaatggagtgctactaaacaattccttcctggacccagaatattggaactttagaaatggagatcttactgaaggcaca |
| gcctatacaaacgctgttggatttatgcctaacctatcagcttatccaaaatctcacggtaaaactgccaaaagtaacattgtcagtcaagttt |
| acttaaacggagacaaaactaaacctgtaacactaaccattacactaaacggtacacaggaaacaggagacacaactccaagtgcata |
| ctctatgtcattttcatgggactggtctggccacaactacattaatgaaatatttgccacatcctcttacacttttcatacattgcccaagaata |
| aagaatcgtttgtgttatgtttcaacgtgtttatttttcaattgcagaaaatttcaagtcatttttcattcagtagtatagccccaccaccacatag |
| cttatacagatcaccgtaccttaatcaaactcacagaaccctagtattcaacctgccacctccctcccaacacacagagtacacagtccttt |
| ctccccggctggccttaaaaagcatcatatcatgggtaacagacatattcttaggtgttatattccacacggtttcctgtcgagccaaacgct |
| catcagtgatattaataaactccccgggcagctcacttaagttcatgtcgctgtccagctgctgagccacaggctgctgtccaacttgcggt |
| tgcttaacgggcggcgaaggagaagtccacgcctacatgggggtagagtcataatcgtgcatcaggatagggcggtggtgctgcagc |
| agcgcgcgaataaactgctgccgccgccgctccgtcctgcaggaatacaacatggcagtggtctcctcagcgatgattcgcaccgccc |
| gcagcataaggcgccttgtcctccgggcacagcagcgcaccctgatctcacttaaatcagcacagtaactgcagcacagcaccacaat |
| attgttcaaaatcccacagtgcaaggcgctgtatccaaagctcatggggggaccacagaacccacgtggccatcataccacaagcgc |
| aggtagattaagtggcgacccctcataaacacgctggacataaacattacctcttttggcatgttgtaattcaccacctcccggtaccatata |
| aacctctgattaaacatggcgccatccaccaccatcctaaaccagctggccaaaacctgcccgccggctatacactgcagggaaccgg |
| gactggaacaatgacagtggagagcccaggactcgtaaccatggatcatcatgctcgtcatgatatcaatgttggcacaacacaggcac |
| acgtgcatacacttcctcaggattacaagctcctcccgcgttagaaccatatcccagggaacaacccattcctgaatcagcgtaaatccca |
| cactgcagggaagacctcgcacgtaactcacgttgtgcattgtcaaagtgttacattcgggcagcagcggatgatcctccagtatggtag |
| cgcgggtttctgtctcaaaaggaggtagacgatccctactgtacggagtgcgccgagacaaccgagatcgtgttggtcgtagtgtcatg |
| ccaaatggaacgccggacgtagtcatatttcctgaagcaaaaccaggtgcgggcgtgacaaacagatctgcgtctccggtctcgccgct |
| tagatcgctctgtgtagtagttgtagtatatccactctctcaaagcatccaggcgccccctggcttcgggttctatgtaaactccttcatgcgc |
| cgctgccctgataacatccaccaccgcagaataagccacacccagccaacctacacattogttctgcgagtcacacacgggaggagc |
| gggaagagctggaagaaccatgtttttttttttattccaaaagattatccaaaacctcaaaatgaagatctattaagtgaacgcgctcccctc |
| cggtggcgtggtcaaactctacagccaaagaacagataatggcatttgtaagatgttgcacaatggcttccaaaaggcaaacggccctc |
| acgtccaagtggacgtaaaggctaaacccttcagggtgaatctcctctataaacattccagcaccttcaaccatgcccaaataattctcatc |
| tcgccaccttctcaatatatctctaagcaaatcccgaatattaagtccggccattgtaaaatctgctccagagcgccctccaccttcagcct |
| caagcagcgaatcatgattgcaaaaattcaggttcctcacagacctgtataagattcaaaagcggaacattaacaaaaataccgcgatcc |
| cgtaggtcccttcgcagggccagctgaacataatcgtgcaggtctgcacggaccagcgcggccacttccccgccaggaaccatgaca |
| aaagaacccacactgattatgacacgcatactoggagctatgctaaccagcgtagccccgatgtaagcttgttgcatgggcggcgatata |
| aaatgcaaggtgctgctcaaaaaatcaggcaaagcctcgcgcaaaaaagaaagcacatcgtagtcatgctcatgcagataaaggcag |
| gtaagctccggaaccaccacagaaaaagacaccatttttctctcaaacatgtctgcgggtttctgcataaacacaaaataaaataacaaaa |
| aaacatttaaacattagaagcctgtcttacaacaggaaaaacaacccttataagcataagacggactacggccatgccggcgtgaccgt |
| aaaaaaactggtcaccgtgattaaaaagcaccaccgacagctcctcggtcatgtccggagtcataatgtaagactcggtaaacacatca |
| ggttgattcacatcggtcagtgctaaaaagcgaccgaaatagcccgggggaatacatacccgcaggcgtagagacaacattacagccc |

TABLE 25-continued

| Ad5-IL1-RA2A-IL10 No Plasmid Backbone |
|---|
| ccataggaggtataacaaaattaataggagagaaaaacacataaacacctgaaaaaccctcctgcctaggcaaaatagcaccctcccg |
| ctccagaacaacatacagcgcttccacagcggcagccataacagtcagccttaccagtaaaaaagaaaacctattaaaaaaacaccact |
| cgacacggcaccagctcaatcagtcacagtgtaaaaaagggccaagtgcagagcgagtatatataggactaaaaaatgacgtaacggt |
| taaagtccacaaaaaacacccagaaaaccgcacgcgaacctacgcccagaaacgaaagccaaaaaacccacaacttcctcaaatcgt |
| cacttccgttttcccacgttacgtaacttcccattttaagaaaactacaattcccaacacatacaagttactccgccctaaaacctacgtcacc |
| cgccccgttcccacgccccgcgccacgtcacaaactccaccccctcattatcatattggcttcaatccaaaataaggtatattattgatgat |
| g |

TABLE 26

| Ad5-IL1-RA with Plasmid Backbone |
|---|
| (SEQ ID NO: 26) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |

TABLE 26-continued

| Ad5-IL1-RA with Plasmid Backbone |
| --- |
| tgggttcctgcaggcgcggcggagagccatccagacgccgctaacccatgcgttacggtactgaaaactttgtgctatgtcgtttatcag |
| gccccgaagttcttctttctgccgccagtccagtggttcaccggcgttcttaggctcaggctcgacaaaagcatactcgccgtttttccgga |
| tagctggcagaacctogttcgtcacccacttgcggaaccgccaggctgtgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |

TABLE 26-continued

| Ad5-IL1-RA with Plasmid Backbone |
| --- |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatattttttcaccatcactttaggctggttggtgaaatcg |
| tcgacttccttctcctgtttgtttttctggttaacgcagagaaacttttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattccctttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggttttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |

TABLE 26-continued

| Ad5-IL1-RA with Plasmid Backbone |
| --- |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcataccctaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccact |
| agttattaatagtaatcaattacggggtcattagttcatagcccatatatggagttccgcgttacataacttacggtaaatggcccgcctggct |
| gaccgcccaacgacccccgcccattgacgtcaataatgacgtatgttcccatagtaacgccaatagggactttccattgacgtcaatggg |
| tggagtatttacggtaaactgcccacttggcagtacatcaagtgtatcatatgccaagtacgccccctattgacgtcaatgacggtaaatgg |
| cccgcctggcattatgcccagtacatgaccttatgggactttcctacttggcagtacatctacgtattagtcatcgctattaccatggtcgag |
| gtgagccccacgttctgcttcactctccccatctcccccccctccccacccccaattttgtatttatttattttttaattattttgtgcagcgatgg |
| gggcgggggggggggggggggggccaggcggggggggcggggcgaggggggggggggcgaggcggagaggtgcg |
| gcggcagccaatcagagcggcgcgctccgaaagtttccttttatggcgaggcggcggcggcggcggccctataaaaagcgaagcgc |
| gcggcgggggggagtcgctgcgttgccttcgccccgtgccccgctccgcgccgcctcgcgccgcccgccccggctctgactgaccg |
| cgttactcccacaggtgagcgggggggacggcccttctcctccgggctgtaattagcgcttggtttaatgacggctcgtttcttttctgtgg |
| ctgcgtgaaagccttaaagggctccgggagggccctttgtgcggggggggagcggctcggggggtgcgtgcgtgtgtgtgtgcgtgg |
| ggagcgccgcgtgcggctccgcgctgcccggcggctgtgagcgctgcgggcgcggcgcggggctttgtgcgctccgcagtgtgcg |
| cgaggggagcgcggccgggggcggtgccccgcggtgcggggggggctgcgaggggaacaaaggctgcgtgcggggtgtgtgc |
| gtgggggggtgagcagggggtgtgggcgcgtcggtcgggctgcaaccccccctgcacccccctccccgagttgctgagcacggcc |
| cggcttcgggtgcggggctccgtacggggcgtggcgcggggctcgccgtgccgggcggggggggcggcaggtgggggtgccg |
| ggcggggcggggccgcctcgggccggggagggctcgggggaggggcgcggcggcccccggagcgccggcggctgtcgaggc |
| gcggcgagccgcagccattgccttttatggtaatcgtgcgagagggcgcagggacttcctttgtcccaaatctgtgcggagccgaaatct |
| gggaggcgccgccgcaccccctctagcgggcgcggggcgaagcggtgcggcgccggcaggaaggaaatgggcggggagggcc |
| ttcgtgcgtcgccgcgccgccgtccccttctccctctccagcctcggggctgtccgcgggggggacggctgccttcgggggggacggg |
| gcagggcggggttcggcttctggcgtgtgaccggcggctctagagcctctgctaaccatgttcatgccttcttctttttcctacagctcctg |
| ggcaacgtgctggttattgtgctgtctcatcattttggcaaagaattccgctgcgactcggcggagtcccggcggcgcgtccttgttctaac |
| ccggcgcgccagcttggcaatccggtactgttggtaaagccaccatggaaatctgcagaggcctccgcagtcacctaatcactctcctc |
| ctcttcctgttccattcagagacgatctgccgaccctctgggagaaaatccagcaagatgcaagccttcagaatctgggatgttaaccaga |
| agaccttctatctgaggaacaaccaactagttgccggatacttgcaaggaccaaatgtcaatttagaagaaaagatagatgtggtaccca t |
| tgagcctcatgctctgttcttgggaatccatggagggaagatgtgcctgtcctgtgtcaagtctggtgatgagaccagactccagctggag |
| gcagttaacatcactgacctgagcgagaacagaaagcaggacaagcgcttcgccttcatccgctcagacagtggccccaccaccagtt |
| ttgagtctgccgcctgccccggttggttcctctgcacagcgatggaagctgaccagcccgtcagcctcaccaatatgcctgacgaaggc |

TABLE 26-continued

| Ad5-IL1-RA with Plasmid Backbone |
|---|
| gtcatggtcaccaaattctacttccaggaggacgagtaataataataattctagagtcggggcggccggccgcttcgagcagacatgata |
| agatacattgatgagtttggacaaaccacaactagaatgcagtgaaaaaaatgctttatttgtgaaatttgtgatgctattgctttatttgtaac |
| cattataagctgcaataaacaagttaacaacaacaattgcattcattttatgtttcaggttcagggggaggtgtgggaggttttttaaagcaa |
| gtaaaacctctacaaatgtggtaaaatcgataaggatccgaattcgatatcactagtggtaccagtactgaaatgtgtgggcgtggcttaa |
| gggtgggaaagaatatataaggtgggggtcttatgtagttttgtatctgttttgcagcagccgccgccgccatgagcaccaactcgtttgat |
| ggaagcattgtgagctcatatttgacaacgcgcatgcccccatgggccggggtgcgtcagaatgtgatgggctccagcattgatggtcg |
| ccccgtcctgcccgcaaactctactaccttgacctacgagaccgtgtctggaacgccgttggagactgcagcctccgccgccgcttcag |
| ccgctgcagccaccgcccgcgggattgtgactgactttgctttcctgagcccgcttgcaagcagtgcagcttcccgttcatccgcccgcg |
| atgacaagttgacggctcttttggcacaattggattctttgacccgggaacttaatgtcgtttctcagcagctgttggatctgcgccagcagg |
| tttctgccctgaaggcttcctcccctcccaatgcggtttaacggtccgggccagagtggccaacataaataaaaaaccagactctgtttgg |
| atttggatcaagcaagtgtcttgctgtctttatttaggggttttgcgcgcgcggtaggcccgggaccagcggtctcggtcgttgagggtcct |
| gtgtatttttttccaggacgtggtaaaggtgactctggatgttcagatacatgggcataagcccgtctctgggggggaggtagcaccactgc |
| agagcttcatgctgcggggtggtgttgtagatgatccagtcgtagcaggagcgctgggcgtggtgcctaaaaatgtctttcagtagcaag |
| ctgattgccaggggcaggcccttggtgtaagtgtttacaaagcggttaagctgggatgggtgcatacgtggggatatgagatgcatcttg |
| gactgtatttttaggttggctatgttcccagccatatccctccggggattcatgttgtgcagaaccaccagcacagtgtatccggtgcacttg |
| ggaaatttgtcatgtagcttagaaggaaatgcgtggaagaacttggagacgcccttgtgacctccaagattttccatgcattcgtccataat |
| gatggcaatgggcccacgggcggcggcctgggcgaagatatttctgggatcactaacgtcatagttgtgttccaggatgagatcgtcat |
| aggccatttttacaaagcgcgggcggagggtgccagactgcggtataatggttccatccggcccaggggcgtagttaccctcacagatt |
| tgcatttcccacgctttgagttcagatgggggggatcatgtctacctgcggggcgatgaagaaaacggtttccggggtaggggagatcag |
| ctgggaagaaagcaggttcctgagcagctgcgacttaccgcagccggtgggcccgtaaatcacacctattaccggctgcaactggtag |
| ttaagagagctgcagctgccgtcatccctgagcaggggggccacttcgttaagcatgtccctgactcgcatgttttccctgaccaaatccg |
| ccagaaggcgctcgccgcccagcgatagcagttcttgcaaggaagcaaagtttttcaacggtttgagaccgtccgccgtaggcatgcttt |
| tgagcgtttgaccaagcagttccaggcggtcccacagctcggtcacctgctctacggcatctcgatccagcatatctcctcgtttcgcggg |
| ttggggcggctttcgctgtacggcagtagtcggtgctcgtccagacgggccagggtcatgtctttccacgggcgcagggtcctcgtcag |
| cgtagtctgggtcacggtgaaggggtgcgctccgggctgcgcgctggccagggtgcgcttgaggctggtcctgctggtgctgaagcg |
| ctgccggtcttcgccctgcgcgtcggccaggtagcatttgaccatggtgtcatagtccagcccctccgcggcgtggcccttggcgcgca |
| gcttgcccttggaggaggcgccgcacgaggggcagtgcagacttttgagggcgtagagcttgggcgcgagaaataccgattccggg |
| gagtaggcatccgcgccgcaggccccgcagacggtctcgcattccacgagccaggtgagctctggccgttcggggtcaaaaaccag |
| gtttcccccatgctttttgatgcgtttcttacctctggtttccatgagccggtgtccacgctcggtgacgaaaaggctgtccgtgtccccgtat |
| acagacttgagaggcctgtcctcgagcggtgttccgcggtcctcctcgtatagaaactcggaccactctgagacaaaggctcgcgtcca |
| ggccagcacgaaggaggctaagtgggaggggtagcggtcgttgtccactagggggtccactcgctccagggtgtgaagacacatgtc |
| gccctcttcggcatcaaggaaggtgattggtttgtaggtgtaggccacgtgaccgggtgttcctgaaggggggctataaaagggggtgg |
| gggcgcgttcgtcctcactctcttccgcatcgctgtctgcgagggccagctgttggggtgagtactccctctgaaaagcgggcatgactt |
| ctgcgctaagattgtcagtttccaaaaacgaggaggatttgatattcacctggcccgcggtgatgcctttgagggtggccgcatccatctg |
| gtcagaaaagacaatctttttgttgtcaagcttggtggcaaacgacccgtagagggcgttggacagcaacttggcgatggagcgcaggg |
| tttggtttttgtcgcgatcggcgcgctccttggccgcgatgtttagctgcacgtattcgcgcgcaacgcaccgccattcgggaaagacggt |
| ggtgcgctcgtcgggcaccaggtgcacgcgccaaccgcggttgtgcagggtgacaaggtcaacgctggtggctacctctccgcgtag |
| gcgctcgttggtccagcagaggcggccgcccttgcgcgagcagaatggcggtagggggtctagctgcgtctcgtccgggggtctgc |
| gtccacggtaaagaccccgggcagcaggcgcgcgtcgaagtagtctatcttgcatccttgcaagtctagcgcctgctgccatgcgcgg |

TABLE 26-continued

| Ad5-IL1-RA with Plasmid Backbone |
|---|
| gcggcaagcgcgcgctcgtatgggttgagtgggggaccccatggcatggggtgggtgagcgcggaggcgtacatgccgcaaatgtc<br>gtaaacgtagaggggctctctgagtattccaagatatgtagggtagcatcttccaccgcggatgctggcgcgcacgtaatcgtatagttc<br>gtgcgagggagcgaggaggtcgggaccgaggttgctacgggcgggctgctctgctcggaagactatctgcctgaagatggcatgtga<br>gttggatgatatggttggacgctggaagacgttgaagctggcgtctgtgagacctaccgcgtcacgcacgaaggaggcgtaggagtcg<br>cgcagcttgttgaccagctcggcggtgacctgcacgtctagggcgcagtagtccagggtttccttgatgatgtcatacttatcctgtcccttt<br>tttttccacagctcgcggttgaggacaaactcttcgcggtctttccagtactcttggatcggaaacccgtcggcctccgaacggtaagagc<br>ctagcatgtagaactggttgacggcctggtaggcgcagcatcccttttctacgggtagcgcgtatgcctgcgcggccttccggagcgag<br>gtgtgggtgagcgcaaaggtgtccctgaccatgactttgaggtactggtatttgaagtcagtgtcgtcgcatccgccctgctcccagagc<br>aaaaagtccgtgcgctttttggaacgcggatttggcagggcgaaggtgacatcgttgaagagtatctttcccgcgcgaggcataaagttg<br>cgtgtgatgcggaagggtcccggcacctcggaacggttgttaattacctgggcggcgagcacgatctcgtcaaagccgttgatgttgtg<br>gcccacaatgtaaagttccaagaagcgcgggatgcccttgatggaaggcaatttttaagttcctcgtaggtgagctcttcaggggagct<br>gagcccgtgctctgaaagggcccagtctgcaagatgagggttggaagcgacgaatgagctccacaggtcacgggccattagcatttgc<br>aggtggtcgcgaaaggtcctaaactggcgacctatggccatttttttctggggtgatgcagtagaaggtaagcgggtcttgttcccagcgg<br>tcccatccaaggttcgcggctaggtctcgcgcggcagtcactagaggctcatctccgccgaacttcatgaccagcatgaagggcacga<br>gctgcttcccaaaggcccccatccaagtataggtctctacatcgtaggtgacaaagagacgctcggtgcgaggatgcgagccgatcgg<br>gaagaactggatctcccgccaccaattggaggagtggctattgatgtggtgaaagtagaagtccctgcgacgggccgaacactcgtgc<br>tggcttttgtaaaaacgtgcgcagtactggcagcggtgcacgggctgtacatcctgcacgaggttgacctgacgaccgcgcacaagga<br>agcagagtgggaatttgagcccctcgcctggcgggtttggctggtggtcttctacttcggctgcttgtccttgaccgtctggctgctcgag<br>gggagttacggtggatcggaccaccacgccgcgcgagcccaaagtccagatgtccgcgcgcggcggtcggagcttgatgacaacat<br>cgcgcagatgggagctgtccatggtctggagctcccgcggcgtcaggtcaggcgggagctcctgcaggtttacctcgcatagacggg<br>tcagggcgcgggctagatccaggtgatacctaatttccaggggctggttggtggcggcgtcgatggcttgcaagaggccgcatccccg<br>cggcgcgactacggtaccgcgcggcgggcggtgggccgcgggggtgtccttggatgatgcatctaaaagcggtgacgcgggcgag<br>cccccggaggtagggggggctccggacccgccgggagagggggcaggggcacgtcggcgccgcgcgcgggcaggagctggtg<br>ctgcgcgcgtaggttgctggcgaacgcgacgacgcggcggttgatctcctgaatctggcgcctctgcgtgaagacgacgggcccggt<br>gagcttgaacctgaaagagagttcgacagaatcaatttcggtgtcgttgacggcggcctggcgcaaaatctcctgcacgtctcctgagtt<br>gtcttgataggcgatctcggccatgaactgctcgatctcttcctcctggagatctccgcgtccggctcgctccacggtggcggcgaggtc<br>gttggaaatgcgggccatgagctgcgagaaggcgttgaggcctccctcgttccagacgcggctgtagaccacgcccccttcggcatcg<br>cgggcgcgcatgaccacctgcgcgagattgagctccacgtgccgggcgaagacggcgtagtttcgcaggcgctgaaagaggtagtt<br>gagggtggtggcggtgtgttctgccacgaagaagtacataacccagcgtcgcaacgtggattcgttgatatcccccaaggcctcaagg<br>cgctccatggcctcgtagaagtccacggcgaagttgaaaaactgggagttgcgcgccgacacggttaactcctcctccagaagacgga<br>tgagctcggcgacagtgtcgcgcacctcgcgctcaaaggctacaggggcctcttcttcttcttcaatctcctcttccataagggcctcccct<br>tcttcttcttctggcggcggtgggggagggggggacacggcggcgacgacggcgcaccgggaggcggtcgacaaagcgctcgatca<br>tctccccgcggcgacggcgcatggtctcggtgacggcgcggccgttctcgcgggggcgcagttggaagacgccgcccgtcatgtcc<br>cggttatgggttggcgggggggctgccatgcggcagggatacggcgctaacgatgcatctcaacaattgttgtgtaggtactccgccgcc<br>gagggacctgagcgagtccgcatcgaccggatcggaaaacctctcgagaaaggcgtctaaccagtcacagtcgcaaggtaggctga<br>gcaccgtggcgggcggcagcgggcggcggtcggggttgtttctggcggaggtgctgctgatgatgtaattaaagtaggcggtcttgag<br>acggcggatggtcgacagaagcaccatgtccttgggtccggcctgctgaatgcgcaggcggtcggccatgccccaggcttcgttttga<br>catcggcgcaggtctttgtagtagtcttgcatgagcctttctaccggcacttcttcttctccttcctcttgtcctgcatctcttgcatctatcgctg<br>cggcggcggcggagtttggccgtaggtggcgccctcttcctcccatgcgtgtgaccccgaagcccctcatcggctgaagcagggcta |

TABLE 26-continued

| Ad5-IL1-RA with Plasmid Backbone |
| --- |
| ggtcggcgacaacgcgctcggctaatatggcctgctgcacctgcgtgagggtagactggaagtcatccatgtccacaaagcggtggta |
| tgcgcccgtgttgatggtgtaagtgcagttggccataacggaccagttaacggtctggtgacccggctgcgagagctcggtgtacctga |
| gacgcgagtaagccctcgagtcaaatacgtagtcgttgcaagtccgcaccaggtactggtatcccaccaaaaagtgcggcggcggctg |
| gcggtagaggggccagcgtagggtggccggggctccgggggcgagatcttccaacataaggcgatgatatccgtagatgtacctgg |
| acatccaggtgatgccggcggcggtggtggaggcgcgcggaaagtcgcggacgcggttccagatgttgcgcagcggcaaaaagtg |
| ctccatggtcgggacgctctggccggtcaggcgcgcgcaatcgttgacgctctagaccgtgcaaaaggagagcctgtaagcgggcac |
| tcttccgtggtctggtggataaattcgcaagggtatcatggcggacgaccggggttcgagccccgtatccggccgtccgccgtgatcca |
| tgcggttaccgcccgcgtgtcgaacccaggtgtgcgacgtcagacaacgggggagtgctccttttggcttccttccaggcgcggcggc |
| tgctgcgctagcttttttggccactggccgcgcgcagcgtaagcggttaggctggaaagcgaaagcattaagtggctcgctccctgtag |
| ccggagggttattttccaagggttgagtcgcgggacccccggttcgagtctcggaccggccggactgcggcgaacgggggtttgcctc |
| cccgtcatgcaagaccccgcttgcaaattcctccggaaacagggacgagccccttttttgcttttcccagatgcatccggtgctgcggca |
| gatgcgcccccctcctcagcagcggcaagagcaagagcagcggcagacatgcagggcaccctcccctcctcctaccgcgtcaggag |
| gggcgacatccgcggttgacgcggcagcagatggtgattacgaaccccgcggcgccgggcccggcactacctggacttggagga |
| gggcgagggcctggcgcggctaggagcgccctctcctgagcggcacccaagggtgcagctgaagcgtgatacgcgtgaggcgtac |
| gtgccgcggcagaacctgtttcgcgaccgcgagggagaggagcccgaggagatgcgggatcgaaagttccacgcagggcgcgag |
| ctgcggcatggcctgaatcgcgagcggttgctgcgcgaggaggactttgagcccgacgcgcgaaccgggattagtcccgcgcgcgc |
| acacgtggcggccgccgacctggtaaccgcatacgagcagacggtgaaccaggagattaactttcaaaaaagctttaacaaccacgtg |
| cgtacgcttgtggcgcgcgaggaggtggctataggactgatgcatctgtgggactttgtaagcgcgctggagcaaaacccaaatagca |
| agccgctcatggcgcagctgttccttatagtgcagcacagcagggacaacgaggcattcagggatgcgctgctaaacatagtagagcc |
| cgagggccgctggctgctcgatttgataaacatcctgcagagcatagtggtgcaggagcgcagcttgagcctggctgacaaggtggcc |
| gccatcaactattccatgcttagcctgggcaagttttacgcccgcaagatataccataccccttacgttcccatagacaaggaggtaaaga |
| tcgaggggttctacatgcgcatggcgctgaaggtgcttaccttgagcgacgacctgggcgtttatcgcaacgagcgcatccacaaggc |
| cgtgagcgtgagccggcggcgcgagctcagcgaccgcgagctgatgcacagcctgcaaagggccctggctggcacgggcagcgg |
| cgatagagaggccgagtcctactttgacgcgggcgctgacctgcgctgggccccaagccgacgcgccctggaggcagctggggcc |
| ggacctgggctggcggtggcacccgcgcgcgctggcaacgtcggcggcgtggaggaatatgacgaggacgatgagtacgagcca |
| gaggacggcgagtactaagcggtgatgtttctgatcagatgatgcaagacgcaacggacccggcggtgcgggcggcgctgcagagc |
| cagccgtccggccttaactccacggacgactggcgccaggtcatggaccgcatcatgtcgctgactgcgcgcaatcctgacgcgttcc |
| ggcagcagccgcaggccaaccggctctccgcaattctggaagcggtggtcccggcgcgcgcaaaccccacgcacgagaaggtgct |
| ggcgatcgtaaacgcgctggccgaaaacagggccatccggcccgacgaggccggcctggtctacgacgcgctgcttcagcgcgtg |
| gctcgttacaacagcggcaacgtgcagaccaacctggaccggctggtgggggatgtgcgcgaggccgtggcgcagcgtgagcgcg |
| cgcagcagcagggcaacctgggctccatggttgcactaaacgccttcctgagtacacagcccgccaacgtgccgcggggacaggag |
| gactacaccaactttgtgagcgcactgcggctaatggtgactgagacaccgcaaagtgaggtgtaccagtctgggccagactattttttc |
| cagaccagtagacaaggcctgcagaccgtaaacctgagccaggctttcaaaaacttgcaggggctgtggggggtgcgggctcccaca |
| ggcgaccgcgcgaccgtgtctagcttgctgacgcccaactcgcgcctgttgctgctgctaatagcgcccttcacggacagtggcagcgt |
| gtcccgggacacatacctaggtcacttgctgacactgtaccgcgaggccataggtcaggcgcatgtggacgagcatactttccaggag |
| attacaagtgtcagccgcgcgctggggcaggaggacacgggcagcctggaggcaaccctaaactacctgctgaccaaccggcggc |
| agaagatcccctcgttgcacagtttaaacagcgaggaggagcgcattttgcgctacgtgcagcagagcgtgagccttaacctgatgcgc |
| gacggggtaacgcccagcgtggcgctggacatgaccgcgcgcaacatggaaccgggcatgtatgcctcaaaccggccgtttatcaac |
| cgcctaatggactacttgcatcgcgcggccgccgtgaaccccgagtatttcaccaatgccatcttgaacccgcactggctaccgcccccct |

TABLE 26-continued

| Ad5-IL1-RA with Plasmid Backbone |
|---|
| ggtttctacaccggggattcgaggtgcccgagggtaacgatggattcctctgggacgacatagacgacagcgtgttttccccgcaacc |
| gcagaccctgctagagttgcaacagcgcgagcaggcagaggcggcgctgcgaaaggaaagcttccgcaggccaagcagcttgtcc |
| gatctaggcgctgcggccccgcggtcagatgctagtagcccatttccaagcttgatagggtctcttaccagcactcgcaccacccgccc |
| gcgcctgctgggcgaggaggagtacctaaacaactcgctgctgcagccgcagcgcgaaaaaaacctgcctccggcatttcccaacaa |
| cgggatagagagcctagtggacaagatgagtagatggaagacgtacgcgcaggagcacagggacgtgccaggcccgcgcccgcc |
| cacccgtcgtcaaaggcacgaccgtcagcggggtctggtgtgggaggacgatgactcggcagacgacagcagcgtcctggatttgg |
| gagggagtggcaacccgtttgcgcaccttcgccccaggctggggagaatgttttaaaaaaaaaaaaaagcatgatgcaaaataaaaaa |
| ctcaccaaggccatggcaccgagcgttggttttcttgtattccccttagtatgcggcgcgcggcgatgtatgaggaaggtcctcctccctc |
| ctacgagagtgtggtgagcgcggcgccagtggcggcggcgctgggttctcccttcgatgctcccctggacccgccgtttgtgcctccg |
| cggtacctgcggcctaccggggggagaaacagcatccgttactctgagttggcacccctattcgacaccacccgtgtgtacctggtgga |
| caacaagtcaacggatgtggcatccctgaactaccagaacgaccacagcaactttctgaccacggtcattcaaaacaatgactacagcc |
| cgggggaggcaagcacacagaccatcaatcttgacgaccggtcgcactggggcggcgacctgaaaaccatcctgcataccaacatg |
| ccaaatgtgaacgagttcatgtttaccaataagtttaaggcgcgggtgatggtgtcgcgcttgcctactaaggacaatcaggtggagctg |
| aaatacgagtgggtggagttcacgctgcccgagggcaactactccgagaccatgaccatagaccttatgaacaacgcgatcgtggagc |
| actacttgaaagtgggcagacagaacggggttctggaaagcgacatcggggtaaagtttgacacccgcaacttcagactggggtttga |
| ccccgtcactggtcttgtcatgcctggggtatatacaaacgaagccttccatccagacatcattttgctgccaggatgcggggggacttc |
| acccacagccgcctgagcaacttgttgggcatccgcaagcggcaacccttccaggagggctttaggatcacctacgatgatctggagg |
| gtggtaacattcccgcactgttggatgtggacgcctaccaggcgagcttgaaagatgacaccgaacaggggggggtggcgcaggc |
| ggcagcaacagcagtggcagcggcgcggaagagaactccaacgcggcagccgcggcaatgcagccggtggaggacatgaacga |
| tcatgccattcgcggcgacacctttgccacacgggctgaggagaagcgcgctgaggccgaagcagcggccgaagctgccgccccc |
| gctgcgcaacccgaggtcgagaagcctcagaagaaaccggtgatcaaacccctgacagaggacagcaagaaacgcagttacaacct |
| aataagcaatgacagcaccttcacccagtaccgcagctggtaccttgcatacaactacggcgaccctcagaccggaatccgctcatgga |
| ccctgctttgcactcctgacgtaacctgcggctcggagcaggtctactggtcgttgccagacatgatgcaagaccccgtgaccttccgct |
| ccacgcgccagatcagcaactttccggtggtgggcgccgagctgttgcccgtgcactccaagagcttctacaacgaccaggccgtcta |
| ctcccaactcatccgccagtttacctctctgacccacgtgttcaatcgctttcccgagaaccagattttggcgcgcccgccagcccccacc |
| atcaccaccgtcagtgaaaacgttcctgctctcacagatcacgggacgctaccgctgcgcaacagcatcggaggagtccagcgagtga |
| ccattactgacgccagacgccgcacctgcccctacgtttacaaggccctgggcatagtctcgccgcgcgtcctatcgagccgcactttt |
| gagcaagcatgtccatccttatatcgcccagcaataacacaggctggggcctgcgcttcccaagcaagatgtttggcggggccaagaa |
| gcgctccgaccaacacccagtgcgcgtgcgcgggcactaccgcgcgccctggggcgcgcacaaacgcggccgcactgggcgcac |
| caccgtcgatgacgccatcgacgcggtggtggaggaggcgcgcaactacacgcccacgccgccaccagtgtccacagtggacgcg |
| gccattcagaccgtggtgcgcggagcccggcgctatgctaaaatgaagagacggcggaggcgcgtagcacgtcgccaccgccgcc |
| gacccggcactgccgcccaacgcgcggcggcggccctgcttaaccgcgcacgtcgcaccggccgacgggcggccatgcgagcag |
| ctcgaaggctggccgcgggtattgtcactgtgccccccaggtccaggcgacgagcggccgccgcagcagccgcggccattagtgct |
| atgactcagggtcgcaggggcaacgtgtattgggtgcgcgactcggttagcggcctgcgcgtgcccgtgcgcacccgcccccccgcg |
| caactagattgcaagaaaaaactacttagactcgtactgttgtatgtatccagcggcggcggcgcgcaacgaagctatgtccaagcgca |
| aaatcaaagaagagatgctccaggtcatcgcgccggagatctatggccccccgaagaaggaagagcaggattacaagccccgaaag |
| ctaaagcgggtcaaaaagaaaaagaaagatgatgatgatgaacttgacgacgaggtggaactgctgcacgctaccgcgcccaggcg |
| acgggtacagtggaaaggtcgacgcgtaaaacgtgttttgcgacccggcaccaccgtagtctttacgcccggtgagcgctccacccgc |
| acctacaagcgcgtgtatgatgaggtgtacggcgacgaggacctgcttgagcaggccaacgagcgcctcggggagtttgcctacgga |

TABLE 26-continued

| Ad5-IL1-RA with Plasmid Backbone |
| --- |
| aagcggcataaggacatgctggcgttgccgctggacgagggcaacccaacacctagcctaaagcccgtaacactgcagcaggtgct |
| gcccgcgcttgcaccgtccgaagaaaagcgcggcctaaagcgcgagtctggtgacttggcacccaccgtgcagctgatggtacccaa |
| gcgccagcgactggaagatgtcttggaaaaaatgaccgtggaacctgggctggagcccgaggtccgcgtgcggccaatcaagcagg |
| tggcgccgggactgggcgtgcagaccgtggacgttcagatacccactaccagtagcaccagtattgccaccgccacagagggcatgg |
| agacacaaacgtccccggttgcctcagcggtggcggatgccgcggtgcaggcggtcgctgcggccgcgtccaagacctctacggag |
| gtgcaaacggacccgtggatgtttcgcgtttcagccccccggcgcccgcgccgttcgaggaagtacggcgccgccagcgcgctactg |
| cccgaatatgccctacatccttccattgcgcctacccccggctatcgtggctacacctaccgccccagaagacgagcaactacccgacg |
| ccgaaccaccactggaacccgccgccgccgtcgccgtcgccagcccgtgctggccccgatttccgtgcgcagggtggctcgcgaag |
| gaggcaggaccctggtgctgccaacagcgcgctaccaccccagcatcgtttaaaagccggtctttgtggttcttgcagatatggccctca |
| cctgccgcctccgtttcccggtgccgggattccgaggaagaatgcaccgtaggaggggcatggccggccacggcctgacgggcggc |
| atgcgtcgtgcgcaccaccggcggcggcgcgcgtcgcaccgtcgcatgcgcggcggtatcctgcccctccttattccactgatcgccg |
| cggcgattggcgccgtgcccggaattgcatccgtggccttgcaggcgcagagacactgattaaaaacaagttgcatgtggaaaaatca |
| aaataaaaagtctggactctcacgctcgcttggtcctgtaactattttgtagaatggaagacatcaactttgcgtctctggccccgcgacac |
| ggctcgcgcccgttcatgggaaactggcaagatatcggcaccagcaatatgagcggtggcgccttcagctggggctcgctgtggagc |
| ggcattaaaaatttcggttccaccgttaagaactatggcagcaaggcctggaacagcagcacaggccagatgctgagggataagttga |
| aagagcaaaatttccaacaaaaggtggtagatggcctggcctctggcattagcggggtggtggacctggccaaccaggcagtgcaaa |
| ataagattaacagtaagcttgatccccgccctcccgtagaggagcctccaccggccgtggagacagtgtctccagaggggcgtggcg |
| aaaagcgtccgcgccccgacagggaagaaactctggtgacgcaaatagacgagcctccctcgtacgaggaggcactaaagcaagg |
| cctgcccaccacccgtcccatcgcgcccatggctaccggagtgctgggccagcacacacccgtaacgctggacctgcctccccccgc |
| cgacacccagcagaaacctgtgctgccaggcccgaccgccgttgttgtaacccgtcctagccgcgcgtccctgcgccgcgccgccag |
| cggtccgcgatcgttgcggcccgtagccagtggcaactggcaaagcacactgaacagcatcgtgggtctgggggtgcaatccctgaa |
| gcgccgacgatgcttctgaatagctaacgtgtcgtatgtgtgtcatgtatgcgtccatgtcgccgccagaggagctgctgagccgccgc |
| gcgcccgctttccaagatggctaccccttcgatgatgccgcagtggtcttacatgcacatctcgggccaggacgcctcggagtacctga |
| gccccgggctggtgcagtttgcccgcgccaccgagacgtacttcagcctgaataacaagtttagaaccccacggtggcgcctacgca |
| cgacgtgaccacagaccggtcccagcgtttgacgctgcggttcatccctgtggaccgtgaggatactgcgtactcgtacaaggcgcgg |
| ttcaccctagctgtgggtgataaccgtgtgctggacatggcttccacgtactttgacatccgcggcgtgctggacaggggccctactttta |
| agccctactctggcactgcctacaacgccctggctcccaagggtgccccaaatccttgcgaatgggatgaagctgctactgctcttgaaa |
| taaacctagaagaagaggacgatgacaacgaagacgaagtagacgagcaagctgagcagcaaaaaactcacgtatttgggcaggcg |
| ccttattctggtataaatattacaaaggagggtattcaaataggtgtcgaaggtcaaacacctaaatatgccgataaaacatttcaacctgaa |
| cctcaaataggagaatctcagtggtacgaaacagaaattaatcatgcagctgggagagtcctaaaaaagactaccccaatgaaaccatg |
| ttacggttcatatgcaaaacccacaaatgaaaatggagggcaaggcattcttgtaaagcaacaaaatggaaagctagaaagtcaagtgg |
| aaatgcaatttttctcaactactgaggcagccgcaggcaatggtgataacttgactcctaaagtggtattgtacagtgaagatgtagatata |
| gaaaccccagacactcatatttcttacatgcccactattaaggaaggtaactcacgagaactaatgggccaacaatctatgcccaacagg |
| cctaattacattgcttttagggacaattttattggtctaatgtattacaacagcacgggtaatatgggtgttctggcgggccaagcatcgcagt |
| tgaatgctgttgtagatttgcaagacagaaacacagagctttcataccagcttttgcttgattccattggtgatagaaccaggtacttttctatg |
| tggaatcaggctgttgacagctatgatccagatgttagaattattgaaaatcatggaactgaagatgaacttccaaattactgctttccactg |
| ggaggtgtgattaatacagagactcttaccaaggtaaaacctaaaacaggtcaggaaaatggatgggaaaaagatgctacagaattttca |
| gataaaaatgaaataagagttggaaataattttgccatggaaatcaatctaaatgccaacctgtggagaaatttcctgtactccaacatagc |
| gctgtatttgcccgacaagctaaagtacagtccttccaacgtaaaaatttctgataacccaaacacctacgactacatgaacaagcgagtg |

TABLE 26-continued

| Ad5-IL1-RA with Plasmid Backbone |
|---|
| gtggctcccgggctagtggactgctacattaaccttggagcacgctggtcccttgactatatggacaacgtcaacccatttaaccaccacc |
| gcaatgctggcctgcgctaccgctcaatgttgctgggcaatggtcgctatgtgcccttccacatccaggtgcctcagaagttctttgccatt |
| aaaaacctccttctcctgccgggctcatacacctacgagtggaacttcaggaaggatgttaacatggttctgcagagctccctaggaaat |
| gacctaagggttgacggagccagcattaagtttgatagcatttgcctttacgccaccttcttccccatggcccacaacaccgcctccacgc |
| ttgaggccatgcttagaaacgacaccaacgaccagtcctttaacgactatctctccgccgccaacatgctctaccctatacccgccaacg |
| ctaccaacgtgcccatatccatccccctcccgcaactgggcggctttccgcggctgggccttcacgcgccttaagactaaggaaacccca |
| tcactgggctcgggctacgacccttattacacctactctggctctataccctacctagatggaaccttttacctcaaccacacctttaagaag |
| gtggccattacctttgactcttctgtcagctggcctggcaatgaccgcctgcttacccccaacgagtttgaaattaagcgctcagttgacgg |
| ggagggttacaacgttgcccagtgtaacatgaccaaagactggttcctggtacaaatgctagctaactataacattggctaccagggcttc |
| tatatcccagagagctacaaggaccgcatgtactccttctttagaaacttccagcccatgagccgtcaggtggtggatgatactaaataca |
| aggactaccaacaggtgggcatcctacaccaacacaacaactctggatttgttggctaccttgcccccaccatgcgcgaaggacaggc |
| ctaccctgctaacttcccctatccgcttataggcaagaccgcagttgacagcattacccagaaaaagtttctttgcgatcgcaccctttggc |
| gcatcccattctccagtaactttatgtccatgggcgcactcacagacctgggccaaaaccttctctacgccaactccgcccacgcgctag |
| acatgacttttgaggtggatcccatggacgagcccacccttctttatgttttgtttgaagtctttgacgtggtccgtgtgcaccagccgcacc |
| gcggcgtcatcgaaaccgtgtacctgcgcacgcccttctggccggcaacgccacaacataaagaagcaagcaacatcaacaacagc |
| tgccgccatgggctccagtgagcaggaactgaaagccattgtcaaagatcttggttgtgggccatatttttttgggcacctatgacaagcgc |
| tttccaggctttgtttctccacacaagctcgcctgcgccatagtcaatacggccggtcgcgagactgggggcgtacactggatggcctttg |
| cctggaacccgcactcaaaaacatgctacctctttgagccctttggcttttctgaccagcgactcaagcaggtttaccagtttgagtacgag |
| tcactcctgcgccgtagcgccattgcttcttcccccgaccgctgtataacgctggaaaagtccacccaaagcgtacaggggcccaactc |
| ggccgcctgtggactattctgctgcatgtttctccacgcctttgccaactggccccaaactcccatggatcacaaccccaccatgaacctt |
| attaccggggtacccaactccatgctcaacagtccccaggtacagcccaccctgcgtcgcaaccaggaacagctctacagcttcctgga |
| gcgccactcgccctacttccgcagccacagtgcgcagattaggagcgccacttctttttgtcacttgaaaaacatgtaaaaataatgtacta |
| gagacactttcaataaaggcaaatgcttttatttgtacactctcgggtgattatttacccccacccttgccgtctgcgccgtttaaaaatcaaa |
| ggggttctgccgcgcatcgctatgcgccactggcagggacacgttgcgatactggtgtttagtgctccacttaaactcaggcacaaccat |
| ccgcggcagctcggtgaagttttcactccacaggctgcgcaccatcaccaacgcgtttagcaggtcgggcgccgatatcttgaagtcgc |
| agttggggcctccgccctgcgcgcgcgagttgcgatacacagggttgcagcactggaacactatcagcgccgggtggtgcacgctgg |
| ccagcacgctcttgtcggagatcagatccgcgtccaggtcctccgcgttgctcagggcgaacggagtcaactttggtagctgccttccca |
| aaaagggcgcgtgcccaggctttgagttgcactcgcaccgtagtggcatcaaaaggtgaccgtgcccggtctgggcgttaggatacag |
| cgcctgcataaaagccttgatctgcttaaaagccacctgagcctttgcgccttcagagaagaacatgccgcaagacttgccggaaaact |
| gattggccggacacgcggcgtcgtgcacgcagcaccttgcgtcggtgttggagatctgcaccacatttcggccccaccggttcttcacg |
| atcttggccttgctagactgctccttcagcgcgcgctgcccgttttcgctcgtcacatccatttcaatcacgtgctccttatttatcataatgctt |
| ccgtgtagacacttaagctcgccttcgatctcagcgcagcggtgcagccacaacgcgcagcccgtgggctcgtgatgcttgtaggtcac |
| ctctgcaaacgactgcaggtacgcctgcaggaatcgccccatcatcgtcacaaaggtcttgttgctggtgaaggtcagctgcaacccgc |
| ggtgctcctcgttcagccaggtcttgcatacggccgccagagcttccacttggtcaggcagtagtttgaagttcgcctttagatcgttatcc |
| acgtggtacttgtccatcagcgcgcgcgcagcctccatgcccttctcccacgcagacacgatcggcacactcagcgggttcatcaccgt |
| aatttcactttccgcttcgctgggctcttcctcttcctcttgcgtccgcataccacgcgccactgggtcgtcttcattcagccgccgcactgtg |
| cgcttacctcctttgccatgcttgattagcaccggtgggttgctgaaacccaccatttgtagcgccacatcttctctttcttcctcgctgtccac |
| gattacctctggtgatggcgggcgctcgggcttgggagaagggcgcttctttttcttcttgggcgcaatggccaaatccgccgccgaggt |
| cgatggccgcgggctgggtgtgcgcggcaccagcgcgtcttgtgatgagtcttcctcgtcctcggactcgatacgccgcctcatccgct |

TABLE 26-continued

| Ad5-IL1-RA with Plasmid Backbone |
|---|
| tttttgggggcgcccggggaggcggcggcgacggggacggggacgacacgtcctccatggttgggggacgtcgcgccgcaccgc |
| gtccgcgctcgggggtggtttcgcgctgctcctcttcccgactggccatttccttctcctataggcagaaaaagatcatggagtcagtcga |
| gaagaaggacagcctaaccgccccctctgagttcgccaccaccgcctccaccgatgccgccaacgcgcctaccaccttccccgtcga |
| ggcacccccgcttgaggaggaggaagtgattatcgagcaggacccaggttttgtaagcgaagacgacgaggaccgctcagtaccaac |
| agaggataaaaagcaagaccaggacaacgcagaggcaaacgaggaacaagtcgggggggggacgaaaggcatggcgactacc |
| tagatgtgggagacgacgtgctgttgaagcatctgcagcgccagtgcgccattatctgcgacgcgttgcaagagcgcagcgatgtgcc |
| cctcgccatagcggatgtcagccttgcctacgaacgccacctattctcaccgcgcgtaccccccaaacgccaagaaaacggcacatgc |
| gagcccaacccgcgcctcaacttctaccccgtatttgccgtgccagaggtgcttgccacctatcacatctttttccaaaactgcaagatacc |
| cctatcctgccgtgccaaccgcagccgagcggacaagcagctggccttgcggcagggcgctgtcatacctgatatcgcctcgctcaac |
| gaagtgccaaaaatctttgagggtcttggacgcgacgagaagcgcgcggcaaacgctctgcaacaggaaaacagcgaaaatgaaag |
| tcactctggagtgttggtggaactcgagggtgacaacgcgcgcctagccgtactaaaacgcagcatcgaggtcacccactttgcctacc |
| cggcacttaacctaccccccaaggtcatgagcacagtcatgagtgagctgatcgtgcgccgtgcgcagcccctggagagggatgcaa |
| atttgcaagaacaaacagaggagggcctacccgcagttggcgacgagcagctagcgcgctggcttcaaacgcgcgagcctgccgac |
| ttggaggagcgacgcaaactaatgatggccgcagtgctcgttaccgtggagcttgagtgcatgcagcggttctttgctgacccggagat |
| gcagcgcaagctagaggaaacattgcactacacctttcgacagggctacgtacgccaggcctgcaagatctccaacgtggagctctgc |
| aacctggtctcctaccttggaattttgcacgaaaaccgccttgggcaaaacgtgcttcattccacgctcaagggcgaggcgcgccgcga |
| ctacgtccgcgactgcgtttacttatttctatgctacacctggcagacggccatgggcgtttggcagcagtgcttggaggagtgcaacctc |
| aaggagctgcagaaactgctaaagcaaaacttgaaggacctatggacggccttcaacgagcgctccgtggccgcgcacctggcgga |
| catcattttccccgaacgcctgcttaaaaccctgcaacagggtctgccagacttcaccagtcaaagcatgttgcagaactttaggaacttta |
| tcctagagcgctcaggaatcttgcccgccacctgctgtgcacttcctagcgactttgtgcccattaagtaccgcgaatgccctccgccgct |
| ttggggccactgctaccttctgcagctagccaactaccttgcctaccactctgacataatggaagacgtgagcggtgacggtctactgga |
| gtgtcactgtcgctgcaacctatgcaccccgcaccgctccctggtttgcaattcgcagctgcttaacgaaagtcaaattatcggtacctttg |
| agctgcagggtccctcgcctgacgaaaagtccgcggctccggggttgaaactcactccggggctgtggacgtcggcttaccttcgcaa |
| atttgtacctgaggactaccacgcccacgagattaggttctacgaagaccaatcccgcccgcctaatgcggagcttaccgcctgcgtcat |
| tacccagggccacattcttggccaattgcaagccatcaacaaagcccgccaagagtttctgctacgaaagggacgggggggtttacttgg |
| acccccagtccggcgaggagctcaacccaatccccccgccgccgcagccctatcagcagcagccgcgggcccttgcttcccaggat |
| ggcacccaaaaagaagctgcagctgccgccgccacccacggacgaggaggaatactgggacagtcaggcagaggaggttttggac |
| gaggaggaggaggacatgatggaagactgggagagcctagacgaggaagcttccgaggtcgaagaggtgtcagacgaaacaccgt |
| caccctcggtcgcattcccctcgccggcgccccagaaatcggcaaccggttccagcatggctacaacctccgctcctcaggcgccgcc |
| ggcactgcccgttcgccgacccaaccgtagatgggacaccactggaaccagggccggtaagtccaagcagccgccgccgttagccc |
| aagagcaacaacagcgccaaggctaccgctcatggcgcgggcacaagaacgccatagttgcttgcttgcaagactgtgggggcaac |
| atctccttcgcccgccgctttcttctctaccatcacggcgtggccttcccccgtaacatcctgcattactaccgtcatctctacagcccatact |
| gcaccggcggcagcggcagcggcagcaacagcagcggccacacagaagcaaaggcgaccggatagcaagactctgacaaagcc |
| caagaaatccacagcggcggcagcagcaggaggaggagcgctgcgtctggcgcccaacgaacccgtatcgacccgcgagcttaga |
| aacaggatttttcccactctgtatgctatatttcaacagagcaggggccaagaacaagagctgaaaataaaaaacaggtctctgcgatcc |
| ctcacccgcagctgcctgtatcacaaaagcgaagatcagcttcggcgcacgctggaagacgcggaggctctcttcagtaaatactgcg |
| cgctgactcttaaggactagtttcgcgccctttctcaaatttaagcgcgaaaactacgtcatctccagcggccacacccggcgccagcac |
| ctgttgtcagcgccattatgagcaaggaaattcccacgccctacatgtggagttaccagccacaaatgggacttgcggctggagctgcc |
| caagactactcaacccgaataaactacatgagcggggaccccacatgatatcccgggtcaacggaatacgcgcccaccgaaaccga |

TABLE 26-continued

| Ad5-IL1-RA with Plasmid Backbone |
|---|
| attctcctggaacaggcggctattaccaccacacctcgtaataaccttaatccccgtagttggcccgctgccctggtgtaccaggaaagtc |
| ccgctcccaccactgtggtacttcccagagacgcccaggccgaagttcagatgactaactcaggggcgcagcttgcgggcggctttcg |
| tcacagggtgcggtcgcccgggcagggtataactcacctgacaatcagagggcgaggtattcagctcaacgacgagtcggtgagctc |
| ctcgcttggtctccgtccggacgggacatttcagatcggcggcgccggccgctcttcattcacgcctcgtcaggcaatcctaactctgca |
| gacctcgtcctctgagccgcgctctggaggcattggaactctgcaatttattgaggagtttgtgccatcggtctactttaaccccttctoggg |
| acctcccggccactatccggatcaatttattcctaactttgacgcggtaaaggactcggcggacggctacgactgaatgttaagtggcca |
| atgaggcctgacgctaataatagctggtccactgtcgccgccacaagtgctttgcccgcgactccggtgagttttgctactttgaattgccc |
| gaggatcatatcgagggcccggcgcacggcgtccggcttaccgcccagggagagcttgcccgtagcctgattcgggagtttacccag |
| cgcccccctgctagttgagcgggacaggggaccctgtgttctcactgtgatttgcaactgtcctaaccttggattacatcaagatccagatct |
| tctagacccgggagcggccgctgtcgacctgcaggatccgaattcgatatcactagtggtaccgatcttattccctttaactaataaaaaa |
| aaataataaagcatcacttacttaaaatcagttagcaaatttctgtccagtttattcagcagcacctccttgccctcctcccagctctggtattg |
| cagcttcctcctggctgcaaactttctccacaatctaaagggaatgtcagtttcctcctgttcctgtccatccgcacccactatcttcatgttgt |
| tgcagatgaagcgcgcaagaccgtctgaagataccttcaaccccgtgtatccatatgacacggaaaccggtcctccaactgtgccttttct |
| tactcctccctttgtatcccccaatgggtttcaagagagtccccctggggtactctctttgcgcctatccgaacctctagttacctccaatggc |
| atgcttgcgctcaaaatgggcaacggcctctctctggacgaggccggcaaccttacctcccaaaatgtaaccactgtgagcccacctctc |
| aaaaaaaccaagtcaaacataaacctggaaatatctgcacccctcacagttacctcagaagccctaactgtggctgccgccgcacctcta |
| atggtcgcgggcaacacactcaccatgcaatcacaggccccgctaaccgtgcacgactccaaacttagcattgccacccaaggacccc |
| tcacagtgtcagaaggaaagctagccctgcaaacatcaggcccccctcaccaccaccgatagcagtacccttactatcactgcctcaccc |
| cctctaactactgccactggtagcttgggcattgacttgaaagagcccatttatacacaaaatggaaaactaggactaaagtacggggctc |
| ctttgcatgtaacagacgacctaaacactttgaccgtagcaactggtccaggtgtgactattaataatacttccttgcaaactaaagttactg |
| gagccttgggttttgattcacaaggcaatatgcaacttaatgtagcaggaggactaaggattgattctcaaaacagacgccttatacttgat |
| gttagttatccgtttgatgctcaaaaccaactaaatctaagactaggacagggccctcttttttataaactcagcccacaacttggatattaact |
| acaacaaaggcctttacttgtttacagcttcaaacaattccaaaaagcttgaggttaacctaagcactgccaaggggttgatgtttgacgct |
| acagccatagccattaatgcaggagatgggcttgaatttggttcacctaatgcaccaaacacaaatcccctcaaaacaaaaattggccat |
| ggcctagaatttgattcaaacaaggctatggttcctaaactaggaactggccttagttttgacagcacaggtgccattacagtaggaaaca |
| aaaataatgataagctaactttgtggaccacaccagctccatctcctaactgtagactaaatgcagagaaagatgctaaactcactttggtc |
| ttaacaaaatgtggcagtcaaatacttgctacagtttcagttttggctgttaaaggcagtttggctccaatatctggaacagttcaaagtgctc |
| atcttattataagatttgacgaaaatggagtgctactaaacaattccttcctggacccagaatattggaactttagaaatggagatcttactga |
| aggcacagcctatacaaacgctgttggatttatgcctaacctatcagcttatccaaaatctcacggtaaaactgccaaaagtaacattgtca |
| gtcaagtttacttaaacggagacaaaactaaacctgtaacactaaccattacactaaacggtacacaggaaacaggagacacaactcca |
| agtgcatactctatgtcattttcatgggactggtctggccacaactacattaatgaaatatttgccacatcctcttacacttttttcatacattgcc |
| caagaataaagaatcgtttgtgttatgtttcaacgtgtttattttttcaattgcagaaaatttcaagtcatttttcattcagtagtatagccccacca |
| ccacatagcttatacagatcaccgtaccttaatcaaactcacagaaccctagtattcaacctgccacctccctoccaacacacagagtaca |
| cagtcctttctccccggctggccttaaaaagcatcatatcatgggtaacagacatattcttaggtgttatattccacacggtttcctgtcgagc |
| caaacgctcatcagtgatattaataaactccccgggcagctcacttaagttcatgtcgctgtccagctgctgagccacaggctgctgtcca |
| acttgcggttgcttaacgggcggcgaaggagaagtccacgcctacatgggggtagagtcataatcgtgcatcaggatagggcggtggt |
| gctgcagcagcgcgcgaataaactgctgccgccgccgctccgtcctgcaggaatacaacatggcagtggtctcctcagcgatgattcg |
| caccgcccgcagcataaggcgccttgtcctccgggcacagcagcgcaccctgatctcacttaaatcagcacagtaactgcagcacagc |
| accacaatattgttcaaaatcccacagtgcaaggcgctgtatccaaagctcatgggggggaccacagaacccacgtggccatcatacca |

TABLE 26-continued

| Ad5-IL1-RA with Plasmid Backbone |
|---|
| caagcgcaggtagattaagtggcgacccctcataaacacgctggacataaacattacctcttttggcatgttgtaattcaccacctcccggt |
| accatataaacctctgattaaacatggogccatccaccaccatcctaaaccagctggccaaaacctgcccgccggctatacactgcagg |
| gaaccgggactggaacaatgacagtggagagcccaggactcgtaaccatggatcatcatgctcgtcatgatatcaatgttggcacaaca |
| caggcacacgtgcatacacttcctcaggattacaagctcctcccgcgttagaaccatatcccagggaacaacccattcctgaatcagcgt |
| aaatcccacactgcagggaagacctcgcacgtaactcacgttgtgcattgtcaaagtgttacattcgggcagcagcggatgatcctccag |
| tatggtagcgcgggtttctgtctcaaaaggaggtagacgatccctactgtacggagtgcgccgagacaaccgagatcgtgttggtcgta |
| gtgtcatgccaaatggaacgccggacgtagtcatatttcctgaagcaaaaccaggtgcgggcgtgacaaacagatctgcgtctccggtc |
| tcgccgcttagatcgctctgtgtagtagttgtagtatatccactctctcaaagcatccaggcgcccccctggcttcgggttctatgtaaactcct |
| tcatgcgccgctgccctgataacatccaccaccgcagaataagccacacccagccaacctacacattcgttctgcgagtcacacacgg |
| gaggagcgggaagagctggaagaaccatgtttttttttttattccaaaagattatccaaaacctcaaaatgaagatctattaagtgaacgc |
| gctcccctccggtggcgtggtcaaactctacagccaaagaacagataatggcatttgtaagatgttgcacaatggcttccaaaaggcaaa |
| cggccctcacgtccaagtggacgtaaaggctaaacccttcagggtgaatctcctctataaacattccagcaccttcaaccatgcccaaat |
| aattctcatctcgccaccttctcaatatatctctaagcaaatcccgaatattaagtccggccattgtaaaaatctgctccagagcgccctcca |
| ccttcagcctcaagcagcgaatcatgattgcaaaaattcaggttcctcacagacctgtataagattcaaaagcggaacattaacaaaaata |
| ccgcgatcccgtaggtcccttcgcagggccagctgaacataatcgtgcaggtctgcacggaccagcgcggccacttccccgccagga |
| accatgacaaaagaacccacactgattatgacacgcatactcggagctatgctaaccagcgtagccccgatgtaagcttgttgcatggg |
| cggcgatataaaatgcaaggtgctgctcaaaaaatcaggcaaagcctcgcgcaaaaaagaaagcacatcgtagtcatgctcatgcaga |
| taaaggcaggtaagctccggaaccaccacagaaaaagacaccatttttctctcaaacatgtctgcgggtttctgcataaacacaaaataa |
| aataacaaaaaaacatttaaacattagaagcctgtcttacaacaggaaaaacaacccttataagcataagacggactacggccatgccg |
| gcgtgaccgtaaaaaaactggtcaccgtgattaaaaagcaccaccgacagctcctcggtcatgtccggagtcataatgtaagactcggt |
| aaacacatcaggttgattcacatcggtcagtgctaaaaagcgaccgaaatagcccgggggaatacatacccgcaggcgtagagacaa |
| cattacagcccccataggaggtataacaaaattaataggagagaaaaacacataaacacctgaaaaaccctcctgcctaggcaaaatag |
| caccctcccgctccagaacaacatacagcgcttccacagcggcagccataacagtcagccttaccagtaaaaaagaaaacctattaaaa |
| aaacaccactcgacacggcaccagctcaatcagtcacagtgtaaaaaagggccaagtgcagagcgagtatatataggactaaaaaatg |
| acgtaacggttaaagtccacaaaaaacacccagaaaaccgcacgcgaacctacgcccagaaacgaaagccaaaaaacccacaactt |
| cctcaaatcgtcacttccgttttcccacgttacgtaacttcccattttaagaaaactacaattcccaacacatacaagttactccgccctaaaa |
| cctacgtcacccgccccgttcccacgccccgcgccacgtcacaaactccaccccctcattatcatattggcttcaatccaaaataaggtat |
| attattgatgatgttaatttgggccattagacttgaagtcaagcggccgcttacaactggaccttgctggtacatagaactgattaactgacc |
| atttaaatcataccaacatggtcaaataaaacgaaaggctcagtcgaaagactgggcctttcgttttaatctgatcggcacgtaagaggttc |
| caactttcaccataatgaaataagatcactaccgggcgtatttttttgagttatcgagattttcaggagctaaggaagctaaaatgagccatat |
| tcaacgggaaacgtcttgctcgaggccgcgattaaattccaacatggatgctgatttatatgggtataaatgggctcgcgataatgtcggg |
| caatcaggtgcgacaatctatcgattgtatgggaagcccgatgcgccagagttgtttctgaaacatggcaaaggtagcgttgccaatgat |
| gttacagatgagatggtcaggctaaactggctgacggaatttatgcctcttccgaccatcaagcattttatccgtactcctgatgatgcatgg |
| ttactcaccactgcgatccccagggaaaacagcattccaggtattagaagaatatcctgattcaggtgaaaatattgttgatgcgctggcagt |
| gttcctgcgccggttgcattcgattcctgtttgtaattgtccttttaacggcgatcgcgtatttcgtctcgctcaggcgcaatcacgaatgaat |
| aacggtttggttggtgcgagtgattttgatgacgagcgtaatggctggcctgttgaacaagtctggaaagaaatgcataaacttttgccatt |
| ctcaccggattcagtcgtcactcatggtgatttctcacttgataaccttatttttgacgaggggaaattaataggttgtattgatgttggacgag |
| tcggaatcgcagaccgataccaggatcttgccatcctatggaactgcctcggtgagttttctccttcattacagaaacggctttttcaaaaat |
| atggtattgataatcctgatatgaataaattgcagtttcacttgatgctcgatgagtttttctaacctaggtgacagaagtcaaaagcctccgg |

TABLE 26-continued

| Ad5-IL1-RA with Plasmid Backbone |
| --- |
| tcggaggcttttgactttctgctagatctgtttcaatgcggtgaagggccaggcagctggggattatgtcgagacccggccagcatgttgg |
| ttttatcgcatattcagcgttgtcgcgtttacccaggtaaaatggaagcagtgtatcgtctgcgtgaatgtgcaaatcaggaacgtaaccgt |
| ggtacatagatgcagtcccttgcgggtcgttcccttcaacgagtaggacgcggtgcccttgcaaggctaaccattgcgcctggtgtactg |
| cagatgaggttttataaacccctcccttgtgtgacataacggaaagtacaaccgggtttttatcgtcaggtctttggtttgggttaccaaaca |
| cactccgcatatggctaatttggtcaattgtgtagccagcgcgacgttctactcggcccctcatctcaaaatcaggagccggtagacgac |
| cagctttttccgcgtctctgatagcctgcggtgttacgccgatcaggtctgcaacttctgttataccccagcggcgagtaatacgacgcgct |
| tccgggctgtcatcgccgaactgtgcgatggcaatagcgcgcgtcatttcctgaccgcgattgatacagtctttcagcaaattaattaacg |
| acatcctgtttcctctcaaacatgcccttatctttgtgtttttcatcatactttacgtttttaaagcaaagcaacataaaaaaagcaaagtgactta |
| gaaaacgcaaagttaaggttcaaatcaatttttgatgcgctacagaagctatttagcttcatctaagcgcaacggtattacttacgttggtat |
| atttaaaacctaacttaatgattttaaatgataataaatcataccaattgctatcaaaagttaagcgaacatgctgattttcacgctgtttataca |
| ctttgaggcatctctatctcttccgtctctatattgaaacacaatcaaagaacatcaatccatgtgacatcccccactatctaagaacaccata |
| acagaacacaacataggaatgcaacattaatgtatcaataattcggaacatatgcactatatcatatctcaattacggaacatatcagcaca |
| caattgcccattatacgc |

TABLE 27

| Ad5-IL1-RA No Plasmid Backbone |
| --- |
| (SEQ ID NO: 27) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccactagttattaatagtaatcaattacggggtcattagttcatagcccatatatggagttccgc |
| gttacataacttacggtaaatggcccgcctggctgaccgcccaacgacccccgcccattgacgtcaataatgacgtatgttcccatagta |
| acgccaatagggactttccattgacgtcaatgggtggagtatttacggtaaactgcccacttggcagtacatcaagtgtatcatatgccaa |
| gtacgccccctattgacgtcaatgacggtaaatggcccgcctggcattatgcccagtacatgaccttatgggactttcctacttggcagtac |
| atctacgtattagtcatcgctattaccatggtcgaggtgagccccacgttctgcttcactctccccatctcccccccctccccacccccaatt |
| ttgtatttatttattttttaattattttgtgcagcgatgggggcgggggggggggggggggggcgcgccaggcggggcggggcggggcgag |
| gggcggggcggggcgaggcggagaggtgcggcggcagccaatcagagcggcgcgctccgaaagtttccttttatggcgaggcgg |
| cggcggcggcggccctataaaaagcgaagcgcgcggcgggcgggagtcgctgcgttgccttcgccccgtgccccgctccgcgccg |
| cctcgcgccgcccgccccggctctgactgaccgcgttactcccacaggtgagcgggcgggacggcccttctcctccgggctgtaatta |
| gcgcttggtttaatgacggctcgtttcttttctgtggctgcgtgaaagccttaaagggctccgggagggccctttgtgcggggggggagcg |
| gctcggggggtgcgtgcgtgtgtgtgtgcgtggggagcgccgcgtgcggctccgcgctgcccggcggctgtgagcgctgcgggcg |
| cggcgcggggctttgtgcgctccgcagtgtgcgcgaggggagcgcggccgggggcggtgccccgcggtgcggggggggctgcg |
| aggggaacaaaggctgcgtgcggggtgtgtgcgtgggggggtgagcagggggtgtgggcgcgtcggtcgggctgcaaccccccct |
| gcaccccccctccccgagttgctgagcacggcccggcttcgggtgcggggctccgtacggggcgtggcgcggggctcgccgtgccg |
| gggggggtggcggcaggtgggggtgccgggcggggcggggccgcctcgggccggggagggctcgggggagggggcgcgg |
| cggcccccggagcgccggcggctgtcgaggcgcggcgagccgcagccattgccttttatggtaatcgtgcgagagggcgcaggga |
| cttcctttgtcccaaatctgtgcggagccgaaatctgggaggcgccgccgcaccccctctagcgggcgcggggcgaagcggtgcggc |

TABLE 27-continued

| Ad5-IL1-RA No Plasmid Backbone |
|---|
| gccggcaggaaggaaatgggcggggagggccttcgtgcgtcgccgcgccgccgtccccttctccctctccagcctcggggctgtcc |
| gcgggggggacggctgccttcgggggggacggggcagggcggggttcggcttctggcgtgtgaccggcggctctagagcctctgcta |
| accatgttcatgccttcttctttttcctacagctcctgggcaacgtgctggttattgtgctgtctcatcattttggcaaagaattccgctgcgact |
| cggcggagtcccggcggcgcgtccttgttctaacccggcgcgccagcttggcaatccggtactgttggtaaagccaccatggaaatct |
| gcagaggcctccgcagtcacctaatcactctcctcctcttcctgttccattcagagacgatctgccgaccctctgggagaaaatccagcaa |
| gatgcaagccttcagaatctgggatgttaaccagaagaccttctatctgaggaacaaccaactagttgccggatacttgcaaggaccaaa |
| tgtcaatttagaagaaaagatagatgtggtacccattgagcctcatgctctgttcttgggaatccatggagggaagatgtgcctgtcctgtg |
| tcaagtctggtgatgagaccagactccagctggaggcagttaacatcactgacctgagcgagaacagaaagcaggacaagcgcttcg |
| ccttcatccgctcagacagtggccccaccaccagttttgagtctgccgcctgccccggttggttcctctgcacagcgatggaagctgacc |
| agcccgtcagcctcaccaatatgcctgacgaaggcgtcatggtcaccaaattctacttccaggaggacgagtaataataataattctaga |
| gtcggggcggccggccgcttcgagcagacatgataagatacattgatgagtttggacaaaccacaactagaatgcagtgaaaaaaatg |
| ctttatttgtgaaatttgtgatgctattgctttatttgtaaccattataagctgcaataaacaagttaacaacaacaattgcattcattttatgtttca |
| ggttcaggggggaggtgtgggaggttttttaaagcaagtaaaacctctacaaatgtggtaaaatcgataaggatccgaattcgatatcacta |
| gtggtaccagtactgaaatgtgtgggcgtggcttaagggtgggaaagaatatataaggtgggggtcttatgtagttttgtatctgttttgcag |
| cagccgccgccgccatgagcaccaactcgtttgatggaagcattgtgagctcatatttgacaacgcgcatgcccccatgggccggggt |
| gcgtcagaatgtgatgggctccagcattgatggtcgccccgtcctgcccgcaaactctactaccttgacctacgagaccgtgtctggaac |
| gccgttggagactgcagcctccgccgccgcttcagccgctgcagccaccgcccgcgggattgtgactgactttgctttcctgagcccgc |
| ttgcaagcagtgcagcttcccgttcatccgcccgcgatgacaagttgacggctcttttggcacaattggattctttgacccgggaacttaat |
| gtcgtttctcagcagctgttggatctgcgccagcaggtttctgccctgaaggcttcctcccctcccaatgcggtttaacggtccgggccag |
| agtggccaacataaataaaaaaccagactctgtttggatttggatcaagcaagtgtcttgctgtctttatttaggggttttgcgcgcgcggta |
| ggcccgggaccagcggtctcggtcgttgagggtcctgtgtatttttttccaggacgtggtaaaggtgactctggatgttcagatacatgggc |
| ataagcccgtctctggggtggaggtagcaccactgcagagcttcatgctgcggggtggtgttgtagatgatccagtcgtagcaggagcg |
| ctgggcgtggtgcctaaaaatgtctttcagtagcaagctgattgccaggggcaggcccttggtgtaagtgtttacaaagcggttaagctg |
| ggatgggtgcatacgtggggatatgagatgcatcttggactgtatttttaggttggctatgttcccagccatatccctccggggattcatgtt |
| gtgcagaaccaccagcacagtgtatccggtgcacttgggaaatttgtcatgtagcttagaaggaaatgcgtggaagaacttggagacgc |
| ccttgtgacctccaagattttccatgcattcgtccataatgatggcaatgggcccacgggcggcggcctgggcgaagatatttctgggatc |
| actaacgtcatagttgtgttccaggatgagatcgtcataggccatttttacaaagcgcgggcggagggtgccagactgcggtataatggtt |
| ccatccggcccaggggcgtagttaccctcacagatttgcatttcccacgctttgagttcagatgggggggatcatgtctacctgcggggcg |
| atgaagaaaacggtttccggggtaggggagatcagctgggaagaaagcaggttcctgagcagctgcgacttaccgcagccggtggg |
| cccgtaaatcacacctattaccggctgcaactggtagttaagagagctgcagctgccgtcatccctgagcaggggggccacttcgttaa |
| gcatgtccctgactcgcatgttttccctgaccaaatccgccagaaggcgctcgccgcccagcgatagcagttcttgcaaggaagcaaag |
| tttttcaacggtttgagaccgtccgccgtaggcatgcttttgagcgtttgaccaagcagttccaggcggtcccacagctcggtcacctgctc |
| tacggcatctcgatccagcatatctcctcgtttcgcgggttggggcggctttcgctgtacggcagtagtcggtgctcgtccagacgggcc |
| agggtcatgtctttccacgggcgcagggtcctcgtcagcgtagtctgggtcacggtgaaggggtgcgctccgggctgcgcgctggcca |
| gggtgcgcttgaggctggtcctgctggtgctgaagcgctgccggtcttcgccctgcgcgtcggccaggtagcatttgaccatggtgtcat |
| agtccagcccctccgcggcgtggcccttggcgcgcagcttgcccttggaggaggcgccgcacgaggggcagtgcagacttttgagg |
| gcgtagagcttgggcgcgagaaataccgattccggggagtaggcatccgcgccgcaggccccgcagacggtctcgcattccacgag |
| ccaggtgagctctggccgttcggggtcaaaaaccaggtttcccccatgctttttgatgcgtttcttacctctggtttccatgagccggtgtcc |
| acgctcggtgacgaaaaggctgtccgtgtccccgtatacagacttgagaggcctgtcctcgagcggtgttccgcggtcctcctcgtatag |

TABLE 27-continued

| Ad5-IL1-RA No Plasmid Backbone |
|---|
| aaactcggaccactctgagacaaaggctcgcgtccaggccagcacgaaggaggctaagtgggaggggtagcggtcgttgtccacta |
| gggggtccactcgctccagggtgtgaagacacatgtcgccctcttcggcatcaaggaaggtgattggtttgtaggtgtaggccacgtga |
| ccgggtgttcctgaaggggggctataaaagggggtgggggcgcgttcgtcctcactctcttccgcatcgctgtctgcgagggccagct |
| gttggggtgagtactccctctgaaaagcgggcatgacttctgcgctaagattgtcagtttccaaaaacgaggaggatttgatattcacctg |
| gcccgcggtgatgcctttgagggtggccgcatccatctggtcagaaaagacaatctttttgttgtcaagcttggtggcaaacgacccgta |
| gagggcgttggacagcaacttggcgatggagcgcagggtttggtttttgtcgcgatcggcgcgctccttggccgcgatgtttagctgcac |
| gtattcgcgcgcaacgcaccgccattcgggaaagacggtggtgcgctcgtcgggcaccaggtgcacgcgccaaccgcggttgtgca |
| gggtgacaaggtcaacgctggtggctacctctccgcgtaggcgctcgttggtccagcagaggcggccgcccttgcgcgagcagaatg |
| gcggtaggggtctagctgcgtctcgtccgggggtctgcgtccacggtaaagaccccgggcagcaggcgcgcgtcgaagtagtct |
| atcttgcatccttgcaagtctagcgcctgctgccatgcgcgggcggcaagcgcgcgctcgtatgggttgagtgggggaccccatggca |
| tggggtgggtgagcgcggaggcgtacatgccgcaaatgtcgtaaacgtagaggggctctctgagtattccaagatatgtagggtagcat |
| cttccaccgcggatgctggcgcgcacgtaatcgtatagttcgtgcgagggagcgaggaggtcgggaccgaggttgctacgggcggg |
| ctgctctgctcggaagactatctgcctgaagatggcatgtgagttggatgatatggttggacgctggaagacgttgaagctggcgtctgtg |
| agacctaccgcgtcacgcacgaaggaggcgtaggagtcgcgcagcttgttgaccagctcggcggtgacctgcacgtctagggcgca |
| gtagtccagggtttccttgatgatgtcatacttatcctgtcccttttttttccacagctcgcggttgaggacaaactcttcgcggtctttccagta |
| ctcttggatcggaaacccgtcggcctccgaacggtaagagcctagcatgtagaactggttgacggcctggtaggcgcagcatcccttttt |
| ctacgggtagcgcgtatgcctgcgcggccttccggagcgaggtgtgggtgagcgcaaaggtgtccctgaccatgactttgaggtactg |
| gtatttgaagtcagtgtcgtcgcatccgccctgctcccagagcaaaaagtccgtgcgctttttggaacgcggatttggcagggcgaaggt |
| gacatcgttgaagagtatctttcccgcgcgaggcataaagttgcgtgtgatgcggaagggtcccggcacctcggaacggttgttaattac |
| ctgggcggcgagcacgatctcgtcaaagccgttgatgttgtggcccacaatgtaaagttccaagaagcgcgggatgcccttgatggaa |
| ggcaatttttttaagttcctcgtaggtgagctcttcaggggagctgagcccgtgctctgaaagggcccagtctgcaagatgagggttggaa |
| gcgacgaatgagctccacaggtcacgggccattagcatttgcaggtggtcgcgaaaggtcctaaactggcgacctatggccattttttct |
| ggggtgatgcagtagaaggtaagcgggtcttgttcccagcggtcccatccaaggttcgcggctaggtctcgcgcggcagtcactagag |
| gctcatctccgccgaacttcatgaccagcatgaagggcacgagctgcttcccaaaggcccccatccaagtataggtctctacatcgtag |
| gtgacaaagagacgctcggtgcgaggatgcgagccgatcgggaagaactggatctcccgccaccaattggaggagtggctattgatg |
| tggtgaaagtagaagtccctgcgacgggccgaacactcgtgctggcttttgtaaaaacgtgcgcagtactggcagcggtgcacgggct |
| gtacatcctgcacgaggttgacctgacgaccgcgcacaaggaagcagagtgggaatttgagcccctcgcctggcgggtttggctggtg |
| gtcttctacttcggctgcttgtccttgaccgtctggctgctcgaggggagttacggtggatcggaccaccacgccgcgcgagcccaaagt |
| ccagatgtccgcgcgcggcggtcggagcttgatgacaacatcgcgcagatgggagctgtccatggtctggagctcccgcggcgtcag |
| gtcaggcgggagctcctgcaggtttacctcgcatagacgggtcagggcgcgggctagatccaggtgatacctaatttccaggggctgg |
| ttggtggcggcgtcgatggcttgcaagaggccgcatccccgcggcgcgactacggtaccgcgcggcgggcggtgggccgcgggg |
| gtgtccttggatgatgcatctaaaagcggtgacgcgggcgagcccccggaggtagggggggctccggacccgccgggagagggg |
| gcaggggcacgtcggcgccgcgcgcgggcaggagctggtgctgcgcgcgtaggttgctggcgaacgcgacgacgcggcggttga |
| tctcctgaatctggcgcctctgcgtgaagacgacgggcccggtgagcttgaacctgaaagagagttcgacagaatcaatttcggtgtcgt |
| tgacggcggcctggcgcaaaatctcctgcacgtctcctgagttgtcttgataggcgatctcggccatgaactgctcgatctcttcctcctgg |
| agatctccgcgtccggctcgctccacggtggcggcgaggtcgttggaaatgcgggccatgagctgcgagaaggcgttgaggcctccc |
| tcgttccagacgcggctgtagaccacgccccttcggcatcgcgggcgcgcatgaccacctgcgcgagattgagctccacgtgccgg |
| gcgaagacggcgtagtttcgcaggcgctgaaagaggtagttgagggtggtggcggtgtgttctgccacgaagaagtacataacccag |
| cgtcgcaacgtggattcgttgatatcccccaaggcctcaaggcgctccatggcctcgtagaagtccacggcgaagttgaaaaactggg |

TABLE 27-continued

| Ad5-IL1-RA No Plasmid Backbone |
| --- |
| agttgcgcgccgacacggttaactcctcctccagaagacggatgagctcggcgacagtgtcgcgcacctcgcgctcaaaggctacag |
| gggcctcttcttcttcttcaatctcctcttccataagggcctccccttcttcttcttctggcggcggtgggggagggggacacggcggcg |
| acgacggcgcaccgggaggcggtcgacaaagcgctcgatcatctccccgcggcgacggcgcatggtctcggtgacggcgcggcc |
| gttctcgcgggggcgcagttggaagacgccgcccgtcatgtcccggttatgggttggcgggggctgccatgcggcagggatacgg |
| cgctaacgatgcatctcaacaattgttgtgtaggtactccgccgccgagggacctgagcgagtccgcatcgaccggatcggaaaacctc |
| tcgagaaaggcgtctaaccagtcacagtcgcaaggtaggctgagcaccgtggcgggcggcagcgggcggcggtcggggttgtttct |
| ggcggaggtgctgctgatgatgtaattaaagtaggcggtcttgagacggcggatggtcgacagaagcaccatgtccttgggtccggcct |
| gctgaatgcgcaggcggtcggccatgccccaggcttcgttttgacatcggcgcaggtctttgtagtagtcttgcatgagcctttctaccgg |
| cacttcttcttctccttcctcttgtcctgcatctcttgcatctatcgctgcggcggcggcggagtttggccgtaggtggcgccctcttcctccc |
| atgcgtgtgaccccgaagcccctcatcggctgaagcagggctaggtcggcgacaacgcgctcggctaatatggcctgctgcacctgc |
| gtgagggtagactggaagtcatccatgtccacaaagcggtggtatgcgcccgtgttgatggtgtaagtgcagttggccataacggacca |
| gttaacggtctggtgacccggctgcgagagctcggtgtacctgagacgcgagtaagccctcgagtcaaatacgtagtcgttgcaagtcc |
| gcaccaggtactggtatcccaccaaaaagtgcggcggcggctggcggtagaggggccagcgtagggtggccggggctccgggggg |
| cgagatcttccaacataaggcgatgatatccgtagatgtacctggacatccaggtgatgccggcggcggtggtggaggcgcgcggaa |
| agtcgcggacgcggttccagatgttgcgcagcggcaaaaagtgctccatggtcgggacgctctggccggtcaggcgcgcgcaatcgt |
| tgacgctctagaccgtgcaaaaggagagcctgtaagcgggcactcttccgtggtctggtggataaattcgcaagggtatcatggcggac |
| gaccggggttcgagccccgtatccggccgtccgccgtgatccatgcggttaccgcccgcgtgtcgaacccaggtgtgcgacgtcaga |
| caacgggggagtgctccttttggcttccttccaggcgcggcggctgctgcgctagcttttttggccactggccgcgcgcagcgtaagcg |
| gttaggctggaaagcgaaagcattaagtggctcgctccctgtagccggagggttattttccaagggttgagtcgcgggacccccggttc |
| gagtctcggaccggccggactgcggcgaacgggggtttgcctccccgtcatgcaagaccccgcttgcaaattcctccggaaacaggg |
| acgagcccctttttttgcttttcccagatgcatccggtgctgcggcagatgcgcccccctcctcagcagcggcaagagcaagagcagcg |
| gcagacatgcagggcaccctcccctcctcctaccgcgtcaggaggggcgacatccgcggttgacgcggcagcagatggtgattacga |
| acccccgcggcgccgggcccggcactacctggacttggaggagggcgagggcctggcgcggctaggagcgccctctcctgagcg |
| gcacccaagggtgcagctgaagcgtgatacgcgtgaggcgtacgtgccgcggcagaacctgtttcgcgaccgcgagggagaggag |
| cccgaggagatgcgggatcgaaagttccacgcagggcgcgagctgcggcatggcctgaatcgcgagcggttgctgcgcgaggagg |
| actttgagcccgacgcgcgaaccgggattagtcccgcgcgcgcacacgtggcggccgccgacctggtaaccgcatacgagcagac |
| ggtgaaccaggagattaactttcaaaaaagctttaacaaccacgtgcgtacgcttgtggcgcgcgaggaggtggctataggactgatgc |
| atctgtgggactttgtaagcgcgctggagcaaaacccaaatagcaagccgctcatggcgcagctgttccttatagtgcagcacagcagg |
| gacaacgaggcattcagggatgcgctgctaaacatagtagagcccgagggccgctggctgctcgatttgataaacatcctgcagagca |
| tagtggtgcaggagcgcagcttgagcctggctgacaaggtggccgccatcaactattccatgcttagcctgggcaagttttacgcccgc |
| aagatataccataccccttacgttcccatagacaaggaggtaaagatcgaggggttctacatgcgcatggcgctgaaggtgcttaccttg |
| agcgacgacctgggcgtttatcgcaacgagcgcatccacaaggccgtgagcgtgagccggcggcgcgagctcagcgaccgcgagc |
| tgatgcacagcctgcaaagggccctggctggcacgggcagcggcgatagagaggccgagtcctactttgacgcgggcgctgacctg |
| cgctgggccccaagccgacgcgccctggaggcagctggggccggacctgggctggcggtggcacccgcgcgcgctggcaacgtc |
| ggcggcgtggaggaatatgacgaggacgatgagtacgagccagaggacggcgagtactaagcggtgatgtttctgatcagatgatgc |
| aagacgcaacggacccggcggtgcgggcggcgctgcagagccagccgtccggccttaactccacggacgactggcgccaggtcat |
| ggaccgcatcatgtcgctgactgcgcgcaatcctgacgcgttccggcagcagccgcaggccaaccggctctccgcaattctggaagc |
| ggtggtcccggcgcgcgcaaaccccacgcacgagaaggtgctggcgatcgtaaacgcgctggccgaaaacagggccatccggccc |
| gacgaggccggcctggtctacgacgcgctgcttcagcgcgtggctcgttacaacagcggcaacgtgcagaccaacctggaccggct |

TABLE 27-continued

| Ad5-IL1-RA No Plasmid Backbone |
| --- |
| ggtgggggatgtgcgcgaggccgtggcgcagcgtgagcgcgcgcagcagcagggcaacctgggctccatggttgcactaaacgcc |
| ttcctgagtacacagcccgccaacgtgccgcggggacaggaggactacaccaactttgtgagcgcactgcggctaatggtgactgag |
| acaccgcaaagtgaggtgtaccagtctgggccagactatttttccagaccagtagacaaggcctgcagaccgtaaacctgagccagg |
| ctttcaaaaacttgcaggggctgtggggggtgcgggctcccacaggcgaccgcgcgaccgtgtctagcttgctgacgcccaactcgc |
| gcctgttgctgctgctaatagcgcccttcacggacagtggcagcgtgtcccgggacacatacctaggtcacttgctgacactgtaccgcg |
| aggccataggtcaggcgcatgtggacgagcatactttccaggagattacaagtgtcagccgcgcgctggggcaggaggacacgggc |
| agcctggaggcaaccctaaactacctgctgaccaaccggcggcagaagatcccctcgttgcacagtttaaacagcgaggaggagcgc |
| attttgcgctacgtgcagcagagcgtgagccttaacctgatgcgcgacggggtaacgcccagcgtggcgctggacatgaccgcgcgc |
| aacatggaaccgggcatgtatgcctcaaaccggccgtttatcaaccgcctaatggactacttgcatcgcgcggccgccgtgaaccccg |
| agtatttcaccaatgccatcttgaacccgcactggctaccgccccctggtttctacaccgggggattcgaggtgcccgagggtaacgatg |
| gattcctctgggacgacatagacgacagcgtgttttccccgcaaccgcagaccctgctagagttgcaacagcgcgagcaggcagagg |
| cggcgctgcgaaaggaaagcttccgcaggccaagcagcttgtccgatctaggcgctgcggccccgcggtcagatgctagtagcccat |
| ttccaagcttgatagggtctcttaccagcactcgcaccacccgcccgcgcctgctgggcgaggaggagtacctaaacaactcgctgctg |
| cagccgcagcgcgaaaaaaacctgcctccggcatttcccaacaacgggatagagagcctagtggacaagatgagtagatggaagac |
| gtacgcgcaggagcacagggacgtgccaggcccgcgcccgcccacccgtcgtcaaaggcacgaccgtcagcggggtctggtgtgg |
| gaggacgatgactcggcagacgacagcagcgtcctggatttgggagggagtggcaacccgtttgcgcaccttcgccccaggctggg |
| gagaatgttttaaaaaaaaaaaaaagcatgatgcaaaataaaaaactcaccaaggccatggcaccgagcgttggttttcttgtattcccctt |
| agtatgcggcgcgcggcgatgtatgaggaaggtcctcctccctcctacgagagtgtggtgagcgcggcgccagtggcggcggcgct |
| gggttctcccttcgatgctcccctggacccgccgtttgtgcctccgcggtacctgcggcctaccggggggagaaacagcatccgttact |
| ctgagttggcacccctattcgacaccacccgtgtgtacctggtggacaacaagtcaacggatgtggcatccctgaactaccagaacgac |
| cacagcaactttctgaccacggtcattcaaaacaatgactacagcccgggggaggcaagcacacagaccatcaatcttgacgaccggt |
| cgcactgggggcgacctgaaaaccatcctgcataccaacatgccaaatgtgaacgagttcatgtttaccaataagtttaaggcgcgg |
| gtgatggtgtcgcgcttgcctactaaggacaatcaggtggagctgaaatacgagtgggtggagttcacgctgcccgagggcaactactc |
| cgagaccatgaccatagaccttatgaacaacgcgatcgtggagcactacttgaaagtgggcagacagaacggggttctggaaagcga |
| catcggggtaaagtttgacacccgcaacttcagactggggtttgaccccgtcactggtcttgtcatgcctggggtatatacaaacgaagc |
| cttccatccagacatcattttgctgccaggatgcggggtggacttcacccacagccgcctgagcaacttgttgggcatccgcaagcggc |
| aacccttccaggagggctttaggatcacctacgatgatctggagggtggtaacattcccgcactgttggatgtggacgcctaccaggcg |
| agcttgaaagatgacaccgaacagggggggtggcgcaggcggcagcaacagcagtggcagcggcgcggaagagaactccaa |
| cgcggcagccgcggcaatgcagccggtggaggacatgaacgatcatgccattcgcggcgacacctttgccacacgggctgaggaga |
| agcgcgctgaggccgaagcagcggccgaagctgccgcccccgctgcgcaacccgaggtcgagaagcctcagaagaaaccggtga |
| tcaaacccctgacagaggacagcaagaaacgcagttacaacctaataagcaatgacagcaccttcacccagtaccgcagctggtacct |
| tgcatacaactacggcgaccctcagaccggaatccgctcatggaccctgctttgcactcctgacgtaacctgcggctcggagcaggtct |
| actggtcgttgccagacatgatgcaagaccccgtgaccttccgctccacgcgccagatcagcaactttccggtggtgggcgccgagct |
| gttgcccgtgcactccaagagcttctacaacgaccaggccgtctactcccaactcatccgccagtttacctctctgacccacgtgttcaatc |
| gctttcccgagaaccagattttggcgcgcccgccagcccccaccatcaccaccgtcagtgaaaacgttcctgctctcacagatcacggg |
| acgctaccgctgcgcaacagcatcggaggagtccagcgagtgaccattactgacgccagacgccgcacctgcccctacgtttacaag |
| gccctgggcatagtctcgccgcgcgtcctatcgagccgcactttttgagcaagcatgtccatccttatatcgcccagcaataacacaggct |
| ggggcctgcgcttcccaagcaagatgtttggcggggccaagaagcgctccgaccaacacccagtgcgcgtgcgcgggcactaccgc |
| gcgccctggggcgcgcacaaacgcggccgcactgggcgcaccaccgtcgatgacgccatcgacgcggtggtggaggaggcgcgc |

TABLE 27-continued

| Ad5-IL1-RA No Plasmid Backbone |
| --- |

aactacacgcccacgccgccaccagtgtccacagtggacgcggccattcagaccgtggtgcgcggagcccggcgctatgctaaaatg aagagacggcggaggcgcgtagcacgtcgccaccgccgccgacccggcactgccgcccaacgcgcggcggcggccctgcttaac cgcgcacgtcgcaccggccgacgggcggccatgcgagcagctcgaaggctggccgcgggtattgtcactgtgccccccaggtcca ggcgacgagcggccgccgcagcagccgcggccattagtgctatgactcagggtcgcaggggcaacgtgtattgggtgcgcgactcg gttagcggcctgcgcgtgcccgtgcgcacccgccccccgcgcaactagattgcaagaaaaaactacttagactcgtactgttgtatgtat ccagcggcggcggcgcgcaacgaagctatgtccaagcgcaaaatcaaagaagagatgctccaggtcatcgcgccggagatctatgg ccccccgaagaaggaagagcaggattacaagccccgaaagctaaagcgggtcaaaaagaaaaagaaagatgatgatgatgaacttg acgacgaggtggaactgctgcacgctaccgcgcccaggcgacgggtacagtggaaaggtcgacgcgtaaaacgtgttttgcgaccc ggcaccaccgtagtctttacgcccggtgagcgctccacccgcacctacaagcgcgtgtatgatgaggtgtacggcgacgaggacctg cttgagcaggccaacgagcgcctcggggagtttgcctacggaaagcggcataaggacatgctggcgttgccgctggacgagggcaa cccaacacctagcctaaagcccgtaacactgcagcaggtgctgcccgcgcttgcaccgtccgaagaaaagcgcggcctaaagcgcg agtctggtgacttggcacccaccgtgcagctgatggtacccaagcgccagcgactggaagatgtcttggaaaaaatgaccgtggaacc tgggctggagcccgaggtccgcgtgcggccaatcaagcaggtggcgccgggactgggcgtgcagaccgtggacgttcagataccc actaccagtagcaccagtattgccaccgccacagagggcatggagacacaaacgtccccggttgcctcagcggtggcggatgccgc ggtgcaggcggtcgctgcggccgcgtccaagacctctacggaggtgcaaacggacccgtggatgtttcgcgtttcagccccccggcg cccgcgccgttcgaggaagtacggcgccgccagcgcgctactgcccgaatatgccctacatccttccattgcgcctacccccggctatc gtggctacacctaccgccccagaagacgagcaactacccgacgccgaaccaccactggaacccgccgccgccgtcgccgtcgcca gcccgtgctggccccgatttccgtgcgcagggtggctcgcgaaggaggcaggaccctggtgctgccaacagcgcgctaccacccca gcatcgtttaaaagccggtctttgtggttcttgcagatatggccctcacctgccgcctccgtttcccggtgccgggattccgaggaagaat gcaccgtaggaggggcatggccggccacggcctgacgggcggcatgcgtcgtgcgcaccaccggcggcggcgcgcgtcgcacc gtcgcatgcgcggcggtatcctgcccctccttattccactgatcgccgcggcgattggcgccgtgcccggaattgcatccgtggccttgc aggcgcagagacactgattaaaaacaagttgcatgtggaaaaatcaaaataaaaagtctggactctcacgctcgcttggtcctgtaactat tttgtagaatggaagacatcaactttgcgtctctggccccgcgacacggctcgcgcccgttcatgggaaactggcaagatatcggcacc agcaatatgagcggtggcgccttcagctggggctcgctgtggagcggcattaaaaatttcggttccaccgttaagaactatggcagcaa ggcctggaacagcagcacaggccagatgctgagggataagttgaaagagcaaaatttccaacaaaaggtggtagatggcctggcctc tggcattagcggggtggtggacctggccaaccaggcagtgcaaaataagattaacagtaagcttgatccccgccctcccgtagaggag cctccaccggccgtggagacagtgtctccagaggggcgtggcgaaaagcgtccgcgccccgacagggaagaaactctggtgacgc aaatagacgagcctccctcgtacgaggaggcactaaagcaaggcctgcccaccacccgtcccatcgcgcccatggctaccggagtgc tgggccagcacacacccgtaacgctggacctgcctcccccgccgacacccagcagaaacctgtgctgccaggcccgaccgccgtt gttgtaacccgtcctagccgcgcgtccctgcgccgcgccgccagcggtccgcgatcgttgcggcccgtagccagtggcaactggcaa agcacactgaacagcatcgtgggtctgggggtgcaatccctgaagcgccgacgatgcttctgaatagctaacgtgtcgtatgtgtgtcat gtatgcgtccatgtcgccgccagaggagctgctgagccgccgcgcgcccgctttccaagatggctaccccttcgatgatgccgcagtg gtcttacatgcacatctcgggccaggacgcctcggagtacctgagccccgggctggtgcagtttgcccgcgccaccgagacgtacttc agcctgaataacaagtttagaaaccccacggtggcgcctacgcacgacgtgaccacagaccggtcccagcgtttgacgctgcggttca tccctgtggaccgtgaggatactgcgtactcgtacaaggcgcggttcaccctagctgtgggtgataaccgtgtgctggacatggcttcca cgtactttgacatccgcggcgtgctggacaggggccctacttttaagccctactctggcactgcctacaacgccctggctcccaagggtg ccccaaatccttgcgaatgggatgaagctgctactgctcttgaaataaacctagaagaagaggacgatgacaacgaagacgaagtaga cgagcaagctgagcagcaaaaaactcacgtatttgggcaggcgccttattctggtataaatattacaaaggagggtattcaaataggtgtc gaaggtcaaacacctaaatatgccgataaaacatttcaacctgaacctcaaataggagaatctcagtggtacgaaacagaaattaatcat TABLE 27-continued

| Ad5-IL1-RA No Plasmid Backbone |
|---|
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctgggggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataatttttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |
| ttccgcggctgggccttcacgcgccttaagactaaggaaaccccatcactgggctcgggctacgaccccttattacacctactctggctcta |
| taccctacctagatggaaccttttacctcaaccacacctttaagaaggtggccattacctttgactcttctgtcagctggcctggcaatgacc |
| gcctgcttaccccaacgagtttgaaattaagcgctcagttgacggggagggttacaacgttgcccagtgtaacatgaccaaagactggt |
| tcctggtacaaatgctagctaactataacattggctaccagggcttctatatcccagagagctacaaggaccgcatgtactccttctttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttcccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttcttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggtggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |

TABLE 27-continued

| Ad5-IL1-RA No Plasmid Backbone |
| --- |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgcttttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |
| ccatttccttctcctataggcagaaaaagatcatggagtcagtcgagaagaaggacagcctaaccgcccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggggggggacgaaaggcatggcgactacctagatgtgggagacgacgtgctgttgaagcatctgcagcgcca |
| gtgcgccattatctgcgacgcgttgcaagagcgcagcgatgtgcccctcgccatagcggatgtcagccttgcctacgaacgccacctat |
| tctcaccgcgcgtacccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctaccccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacggggggtttacttggacccccagtccggcgaggagctcaacccaatccccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |

TABLE 27-continued

| Ad5-IL1-RA No Plasmid Backbone |
|---|

ctggaaccagggccggtaagtccaagcagccgccgccgttagcccaagagcaacaacagcgccaaggctaccgctcatggcgcgg
gcacaagaacgccatagttgcttgcttgcaagactgtgggggcaacatctccttcgcccgccgctttcttctctaccatcacggcgtggcc
ttcccccgtaacatcctgcattactaccgtcatctctacagcccatactgcaccggcggcagcggcagcggcagcaacagcagcggcc
acacagaagcaaaggcgaccggatagcaagactctgacaaagcccaagaaatccacagcggcggcagcagcaggaggaggagc
gctgcgtctggcgcccaacgaacccgtatcgacccgcgagcttagaaacaggatttttcccactctgtatgctatatttcaacagagcag
gggccaagaacaagagctgaaaataaaaaacaggtctctgcgatccctcacccgcagctgcctgtatcacaaaagcgaagatcagctt
cggcgcacgctggaagacgcggaggctctcttcagtaaatactgcgcgctgactcttaaggactagtttcgcgccctttctcaaatttaag
cgcgaaaactacgtcatctccagcggccacacccggcgccagcacctgttgtcagcgccattatgagcaaggaaattcccacgcccta
catgtggagttaccagccacaaatgggacttgcggctggagctgcccaagactactcaacccgaataaactacatgagcgcgggaccc
cacatgatatcccgggtcaacggaatacgcgcccaccgaaaccgaattctcctggaacaggcggctattaccaccacacctcgtaataa
ccttaatccccgtagttggcccgctgccctggtgtaccaggaaagtcccgctcccaccactgtggtacttcccagagacgcccaggccg
aagttcagatgactaactcaggggcgcagcttgcgggcggctttcgtcacagggtgcggtcgcccgggcagggtataactcacctgac
aatcagagggcgaggtattcagctcaacgacgagtcggtgagctcctcgcttggtctccgtccggacgggacatttcagatcggcggc
gccggccgctcttcattcacgcctcgtcaggcaatcctaactctgcagacctcgtcctctgagccgcgctctggaggcattggaactctg
caatttattgaggagtttgtgccatcggtctactttaaccccttctcgggacctcccggccactatccggatcaatttattcctaactttgacgc
ggtaaaggactcggcggacggctacgactgaatgttaagtggccaatgaggcctgacgctaataatagctggtccactgtcgccgcca
caagtgctttgcccgcgactccggtgagttttgctactttgaattgcccgaggatcatatcgagggcccggcgcacggcgtccggcttac
cgcccagggagagcttgcccgtagcctgattcgggagtttacccagcgcccccctgctagttgagcgggacaggggaccctgtgttctc
actgtgatttgcaactgtcctaaccttggattacatcaagatccagatcttctagacccgggagcggccgctgtcgacctgcaggatccga
attcgatatcactagtggtaccgatcttattccctttaactaataaaaaaaaataataaagcatcacttacttaaaatcagttagcaaatttctgt
ccagtttattcagcagcacctccttgccctcctcccagctctggtattgcagcttcctcctggctgcaaactttctccacaatctaaagggaa
tgtcagtttcctcctgttcctgtccatccgcacccactatcttcatgttgttgcagatgaagcgcgcaagaccgtctgaagataccttcaacc
ccgtgtatccatatgacacggaaaccggtcctccaactgtgccttttcttactcctccctttgtatcccccaatgggtttcaagagagtcccc
ctggggtactctctttgcgcctatccgaacctctagttacctccaatggcatgcttgcgctcaaaatgggcaacggcctctctctggacga
ggccggcaaccttacctcccaaaatgtaaccactgtgagcccacctctcaaaaaaaccaagtcaaacataaacctggaaatatctgcac
ccctcacagttacctcagaagccctaactgtggctgccgccgcacctctaatggtcgcgggcaacacactcaccatgcaatcacaggcc
ccgctaaccgtgcacgactccaaacttagcattgccacccaaggacccctcacagtgtcagaaggaaagctagccctgcaaacatcag
gcccccctcaccaccaccgatagcagtacccttactatcactgcctcacccccctctaactactgccactggtagcttgggcattgacttgaa
agagcccatttatacacaaaatggaaaactaggactaaagtacggggctcctttgcatgtaacagacgacctaaacactttgaccgtagc
aactggtccaggtgtgactattaataatacttccttgcaaactaaagttactggagccttgggttttgattcacaaggcaatatgcaacttaat
gtagcaggaggactaaggattgattctcaaaacagacgccttatacttgatgttagttatccgtttgatgctcaaaaccaactaaatctaaga
ctaggacagggccctctttttataaactcagcccacaacttggatattaactacaacaaaggcctttacttgtttacagcttcaaacaattcca
aaaagcttgaggttaacctaagcactgccaaggggttgatgtttgacgctacagccatagccattaatgcaggagatgggcttgaatttgg
ttcacctaatgcaccaaacacaaatcccctcaaaacaaaaattggccatggcctagaatttgattcaaacaaggctatggttcctaaactag
gaactggccttagttttgacagcacaggtgccattacagtaggaaacaaaaataatgataagctaactttgtggaccacaccagctccatc
tcctaactgtagactaaatgcagagaaagatgctaaactcactttggtcttaacaaaatgtggcagtcaaatacttgctacagtttcagttttg
gctgttaaaggcagtttggctccaatatctggaacagttcaaagtgctcatcttattataagatttgacgaaaatggagtgctactaaacaatt
ccttcctggacccagaatattggaactttagaaatggagatcttactgaaggcacagcctatacaaacgctgttggatttatgcctaacctat
cagcttatccaaaatctcacggtaaaactgccaaaagtaacattgtcagtcaagtttacttaaacggagacaaaactaaacctgtaacacta TABLE 27-continued

| Ad5-IL1-RA No Plasmid Backbone |
|---|
| accattacactaaacggtacacaggaaacaggagacacaactccaagtgcatactctatgtcattttcatgggactggtctggccacaact |
| acattaatgaaatatttgccacatcctcttacactttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatggcggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgcccatccaccaccat |
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgccccctggcttcgggttctatgtaaactccttcatgcgccgctgccctgataacatccaccaccgcagaataa |
| gccacacccagccaacctacacattcgttctgcgagtcacacacgggaggagcgggaagagctggaagaaccatgtttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagccccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccaccccctcattatcatattggcttcaatccaaaataaggtatattattgatgatg |

TABLE 28

| Ad5eNOS with Plasmid Backbone |
| --- |

(SEQ ID NO: 28)

gcgtataatggactattgtgtgctgataaggagaacataagcgcagaacaatatgtatctattccggtgttgtgttcctttgttattctgctatta tgttctcttatagtgtgacgaaagcagcataattaatcgccacttgttctttgattgtgttacgatatccagagacttagaaacgggggaacc gggatgagcaaggtaaaaatcggtgagttgatcaacacgcttgtgaatgaggtagaggcaattgatgcctcagaccgcccacaaggcg acaaaacgaagagaattaaagccgcagccgcacggtataagaacgcgttatttaatgataaaagaaagttccgtgggaaaggattgca gaaaagaataaccgcgaatacttttaacgcctatatgagcagggcaagaaagcggtttgatgataaattacatcatagctttgataaaaata ttaataaattatcggaaaagtatcctctttacagcgaagaattatcttcatggctttctatgcctacggctaatattcgccagcacatgtcatcg ttacaatctaaattgaaagaaataatgccgcttgccgaagagttatcaaatgtaagaataggctctaaaggcagtgatgcaaaaatagcaa gactaataaaaaaatatccagattggagttttgctcttagtgatttaaacagtgatgattggaaggagcgccgtgactatctttataagttattc caacaaggctctgcgttgttagaagaactacaccagctcaaggtcaaccatgaggttctgtaccatctgcagctaagccctgcggagcgt acatctatacagcaacgatgggccgatgttctgcgcgagaagaagcgtaatgttgtggttattgactacccaacatacatgcagtctatcta tgatattttgaataatcctgcgactttatttagtttaaacactcgttctggaatggcacctttggcctttgctctggctgcggtatcagggcgaa gaatgattgagataatgtttcagggtgaatttgccgtttcaggaaagtatacggttaatttctcagggcaagctaaaaaacgctctgaagat aaaagcgtaaccagaacgatttatactttatgcgaagcaaaattattcgttgaattattaacagaattgcgttcttgctctgctgcatctgatttc gatgaggttgttaaaggatatggaaaggatgatacaaggtctgagaacggcaggataaatgctattttagcaaaagcatttaacccttggg ttaaatcatttttcggcgatgaccgtgtgtttataaagatagccgcgctatttacgctcgcatcgcttatgagatgttcttccgcgtcgatcca cggtggaaaaacgtcgacgaggatgtgttcttcatggagattctcggacacgacgatgagaacacccagctgcactataagcagttcaa gctggccaacttctccagaacctggcgacctgaagttggggatgaaaacaccaggctggtggctctgcagaaactggacgatgaaatg ccaggctttgccagaggtgacgctggcgtccgtctccatgaaaccgttaagcagctggtggagcaggacccatcagcaaaaataacca acagcactctccgggcctttaaatttagcccgacgatgattagccggtacctggagtttgccgctgatgcattggggcagttcgttggcga gaacgggcagtggcagctgaagatagagacacctgcaatcgtcctgcctgatgaagaatccgttgagaccatcgacgaaccggatgat gagtcccaagacgacgagctggatgaagatgaaattgagctcgacgagggtggcggcgatgaaccaaccgaagaggaagggccag aagaacatcagccaactgctctaaaacccgtcttcaagcctgcaaaaaataacggggacggaacgtacaagatagagtttgaatacgat ggaaagcattatgcctggtccggccccgccgatagccctatggccgcaatgcgatccgcatgggaaacgtactacagctaaaagaaaa gccaccggtgttaatcggtggctttttattgaggcctgtccctacccatcccctgcaagggacggaaggattaggcggaaactgcagct gcaactacggacatcgccgtcccgactgcagggacttccccgcgtaaagcggggcttaaattcgggctggccaaccctatttttctgca atcgctggcgatgttagtttcgtggatagcgtttccagcttttcaatggccagctcaaaatgtgctggcagcaccttctccagttccgtatca atatcggtgatcggcagctctccacaagacatactccggcgaccgccacgaactacatcgcgcagcagctcccgttcgtagacacgca tgttgcccagagccgtttctgcagccgttaatatccggcgcagctcggcgatgattgccgggagatcatccacggttattgggttcggtga tgggttcctgcaggcgcggcggagagccatccagacgccgctaacccatgcgttacggtactgaaaactttgtgctatgtcgtttatcag gccccgaagttcttctttctgccgccagtccagtggttcaccggcgttcttaggctcaggctcgacaaaagcatactcgccgtttttccgga tagctggcagaacctcgttcgtcacccacttgcggaaccgccaggctgtcgtcccctgtttcaccgcgtcgcggcagcggaggattatg gtgtagagaccagattccgataccacatttacttccctggccatccgatcaagtttttgtgcctcggttaaaccgagggtcaatttttcatcat gatccagcttacgcaatgcatcagaagggttggctatattcaatgcagcacagatatccagcgccacaaaccacgggtcaccaccgac aagaaccacccgtatagggtggctttcctgaaatgaaaagacggagagagccttcattgcgcctccccggatttcagctgctcagaaag ggacagggagcagccgcgagcttcctgcgtgagttcgcgcgcgacctgcagaagttccgcagcttcctgcaaatacagcgtggcctc ataactggagatagtgcggtgagcagagcccacaagcgcttcaacctgcagcaggcgttcctcaatcgtctccagcaggccctgggcg tttaactgaatctggttcatgcgatcacctcgctgaccgggatacgggctgacagaacgaggacaaaacggctggcgaactggcgacg agcttctcgctcggatgatgcagtggtggaaaggcggtggatatgggatttttttgtccgtgcggacgacagctgcaaatttgaatttgaac atggtatgcattcctatcttgtatagggtgctaccaccagagttgagaatctctataggggggtagcccagacagggttctcaacaccgg TABLE 28-continued

| Ad5eNOS with Plasmid Backbone |
|---|
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactoggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |

TABLE 28-continued

| Ad5eNOS with Plasmid Backbone |
|---|
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgcctttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattccctttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgaggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgcgccggtgtacacaggaagtgacaatt |
| ttcgcgcggttttaggcggatgttgtagtaaatttgggcgtaaccgagtaagatttggccattttcgcgggaaaactgaataagaggaagt |

TABLE 28-continued

| Ad5eNOS with Plasmid Backbone |
| --- |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccgat |
| gcaatttcctcattttattaggaaaggacagtgggagtggcaccttccagggtcaaggaaggcacgggggaggggcaaacaacagat |
| ggctggcaactagaaggcacagtcgaggctgatctcgaagcggccggccgccccgactctagaattattaucaggggcuguuggu |
| gucugagccgggagggucgaacgcccagggcacugcgccccgcaacugacgcuccugcaaggaaaagcucugggugcgua |
| ugcggcuugucaccuccugggugcgcagcgugagcccgaaaaugucuucgugguagcguugcugaucccgcagcacgccg |
| augacgucgccggccucguccagcuccaugucgccccucccgucgccaggaugcgcugcacggucugcaggacguugguugc |
| caugguaacaucgccgcagacaaacauguggccccgcucgaggcacagcacgcggugcaccuccgcagccagcuccguccu |
| caggauguccugcacguaggucuugggguugucagguucccgggagaaggggugaggacucggccaaacacccccgcgcu |
| gcugggcguucugcaccucgucgcgguagagauggucaaguugggagcaucggcagccgaacaccaaagucaugggagug |
| ggcugcagcccuuugcucucaaugucaugcagccgcuccugccagaaucccccggaagggggcaaugccagugccuggacc |
| caccaggaugcagggcaagcugggaucggguggcagccggaaggagggagccccccggaugaagcagggcacagggucuc |
| cgggcuugagcuggcuuagccacguggagcagacuccauagugcaggggggcccagcccauccugaguccuguaugccagc |
| acagcuacagugagguggaucucucccugggugggugcugggugccgagcugacugaguaguaccggggcuggagcagag |
| gcagcugggugaggagcaguggggcaggcagcgccaccgacgggaacugcuccagcaccuccagcagcguggggcagcgg |
| aaccacuuccacuccucguagcgucggggauccuggcugagggccuccagcuccuguguucccugggcucucuccaa |
| ggugcugagcagccgcaagagcugagggcugggugggggaggugauguccaggaagaaggugagagccuggcgcagcgug |
| cacgggggcagccgggggucccgcacccagccgggggggagggccaccagggcugcccuucuccagcugcucuacugccac |
| gggcucagugggcgccgggggguccuccacgcggcucagcagcgccuccacaaggccgggccgguuggggggcagacac |
| cuaugugguccccccggcugguacugcagccccuccuggccuccggugucccaggcgcaccaggauggugccccucguggac |
| uugcugcuuugcagguuuuccacugagcggauuguagccuggaacaucuuccgccugugcacguggaucagaccuggca |
| gcaacugcaggcccucggccugggcgcucagccgguaccucuggcgcuuccagcuccguuuggggcugaagaugucucgg |
| gcggcggccuuggcauccucucccacacagaaggucucacaggcggccuggaaggcagccugggcccagccucggaaggcc |
| uccuccuggccgcacagcucgucgcccuggcccagcugcagcagccgcuccccgcccaguuccuccagccgugugucccacg |
| gcacgagcaaaggcgcagaaguggggguaugcccgggagccgagcccgaacacacagaaccugagggugcccagggccccu |
| gcacugucuguguuacuggacuccuucccucuuccgccgccaagaggacaccagugggucugagcaggagaugcuguugaa |
| gcggaucuuauaacucuugugcuguuccggccgaggggagcuguuguaggggccggacaucuccaucagggcagcugca |
| aagcucucuccauucuccgggggauccccauucccaaaugugcugguuaccaccagcaccagcgucucguguucgaggga |
| caccacgucauacucauccauacacaggacccggggaucaaaagccuuccggaagagucuccccagcugcugugcguagcu |
| cugggcccggccggucucggagccauacaggauugucgccuucacucgcuucgccaucaccgugcccaugagcgaggcgg |
| agaucuucacggcguuggccacuucuuuaaaggucuucuuccuggugaugcggugcccuuggggcacucccccuuccag |
| gggucuggcugguagcggaaggccggggacaggaaauaguugaccaucuccugauggaaaacaggagugaggcugcccga |
| gaugggggggcacgauccaggcccagucugcagggcagccccccccuggccuucugcucauucuccaggugcuucaugaaag |
| aggccguggcggcgugguggguccacgaugguggacuuuggcuagcugguaacugugcagcacggccacguugauuuccac |
| ugcugccuugucuuuccacagggacgagguggucccggguauccagguccaugcagacagccacauccuccaggauguugu |
| agcggugagggucacacagguuccucgugccgaucucagugcucauguaccagccacugaagggggcugggggaacuccc |
| aggcccccaauuuccagcagcauguuggacacugccgggagggcguaccagcgcaggcccagggcugcaaaccacuccagc |
| gugggggugcuccaggggcaccucaaggaccagcucggggggcagaaggaagaguucugggggaucaucuggggccugca |
| gcagcaggggcagcacgucgaagcgaccguuuccugggguccagccgugcugaaugcagagcucggugaucuccacguug |

TABLE 28-continued

| Ad5eNOS with Plasmid Backbone |
|---|
| gcugggucccccgcacagagccauccugcugccgguagcccgcguagcgcaccagcuggcuguuccagauucggaaguc |
| uccucggccagggcagcgcugcgggaacacugugauggccgagcgaagguugccccgguugguggcauacuugaugugg |
| uugcagauguaggugaacauuuccugugcagaccugcagucccgggcaucgaacaccugcagcuucccccacuggauccg |
| gcccacgcagcggggagcguugcgccaggccugcuuagccccgaacaccagcucgcucucccuaagcugguaggugccug |
| uggcugccaccucggcuuccaccucuugaagccgcuguucgugggccugggagccgcuccucuuaauggagcuguaguac |
| ugguugaugaagucccgggccugacucagcagcugcucaggggccgggggccgggggggccggcccuguaguuucc |
| guggaaauaccagggagcccaggcagcgucuuggggugcagggcccauccugcugcgccugggcgcugagggugucaua |
| ggugaugcuccccaccucccaguucuucacacgagggaacuugggccccucugggggcuggguuagggggagcucggg |
| gggcuguguucuggcgcugguggggaguagggaugcuggggcccggcugggcucaggggggggggggcccc |
| uugccgcacagcccaaggcccagccccagccccaggccgcaggguggcccaggcuccugggccacgcucuucaaguugccc |
| auggtggctttaccaacagtaccggattgccaagctggcgcgccgggttagaacaaggacgcgccgccgggactccgccgagtcgc |
| agcggaattctttgccaaaatgatgagacagcacaataaccagcacgttgcccaggagaagctttttgcaaaagcctaggcctccaaaa |
| aagcctcctcactacttctggaatagctcagaggccgaggcggcctcggcctctgcataaataaaaaaaattagtcagccatggggcgg |
| agaatgggcggaactgggcggagttaggggcgggatgggcggagttaggggcgggactatggttgctgactaattgagatgcatgct |
| ttgcatacttctgcctgctggggagcctggggactttccacacctggttgctgactaattgagatgcatgctttgcatacttctgcctgctgg |
| ggagcctggggactttccacaccctaactgacacacattccacagctggttctttccgcctcagaaggtacctaaccaagttcctctttcag |
| aggttatttcaggccatggtgctgcgcaaatcgataaggatccgaattcgatatcactagtggtaccagtactgaaatgtgtgggcgtggc |
| ttaagggtgggaaagaatatataaggtgggggtcttatgtagttttgtatctgttttgcagcagccgccgccgccatgagcaccaactcgtt |
| tgatggaagcattgtgagctcatatttgacaacgcgcatgcccccatgggccggggtgcgtcagaatgtgatgggctccagcattgatg |
| gtcgccccgtcctgcccgcaaactctactaccttgacctacgagaccgtgtctggaacgccgttggagactgcagcctccgccgccgct |
| tcagccgctgcagccaccgcccgcgggattgtgactgactttgctttcctgagcccgcttgcaagcagtgcagcttcccgttcatccgcc |
| cgcgatgacaagttgacggctcttttggcacaattggattctttgacccgggaacttaatgtcgtttctcagcagctgttggatctgcgccag |
| caggtttctgccctgaaggcttcctcccctcccaatgcggtttaacggtccgggccagagtggccaacataaataaaaaaccagactctg |
| tttggatttggatcaagcaagtgtcttgctgtctttatttaggggttttgcgcgcgcggtaggcccgggaccagcggtctcggtcgttgagg |
| gtcctgtgtatttttttccaggacgtggtaaaggtgactctggatgttcagatacatgggcataagcccgtctctgggggggaggtagcacc |
| actgcagagcttcatgctgcggggtggtgttgtagatgatccagtcgtagcaggagcgctgggcgtggtgcctaaaaatgtctttcagta |
| gcaagctgattgccaggggcaggcccttggtgtaagtgtttacaaagcggttaagctgggatgggtgcatacgtggggatatgagatgc |
| atcttggactgtatttttaggttggctatgttcccagccatatccctccggggattcatgttgtgcagaaccaccagcacagtgtatccggtg |
| cacttgggaaatttgtcatgtagcttagaaggaaatgcgtggaagaacttggagacgcccttgtgacctccaagattttccatgcattcgtc |
| cataatgatggcaatgggcccacgggcggcggcctgggcgaagatatttctgggatcactaacgtcatagttgtgttccaggatgagat |
| cgtcataggccatttttacaaagcgcgggcggagggtgccagactgcggtataatggttccatccggcccaggggcgtagttaccctca |
| cagatttgcatttcccacgctttgagttcagatgggggatcatgtctacctgcggggcgatgaagaaaacggtttccggggtaggga |
| gatcagctgggaagaaagcaggttcctgagcagctgcgacttaccgcagccggtgggcccgtaaatcacacctattaccggctgcaac |
| tggtagttaagagagctgcagctgccgtcatccctgagcagggggggccacttcgttaagcatgtccctgactcgcatgttttccctgacca |
| aatccgccagaaggcgctcgccgcccagcgatagcagttcttgcaaggaagcaaagtttttcaacggtttgagaccgtccgccgtagg |
| catgcttttgagcgtttgaccaagcagttccaggcggtcccacagctcggtcacctgctctacggcatctcgatccagcatatctcctcgtt |
| tcgcgggttggggcggctttcgctgtacggcagtagtcggtgctcgtccagacgggccagggtcatgtctttccacgggcgcagggtc |
| ctcgtcagcgtagtctgggtcacggtgaaggggtgcgctccgggctgcgcgctggccagggtgcgcttgaggctggtcctgctggtgc |
| tgaagcgctgccggtcttcgccctgcgcgtcggccaggtagcatttgaccatggtgtcatagtccagcccctccgcggcgtggcccttg |

TABLE 28-continued

| Ad5eNOS with Plasmid Backbone |
|---|
| gcgcgcagcttgcccttggaggaggcgccgcacgaggggcagtgcagacttttgagggcgtagagcttgggcgcgagaaataccga |
| ttccggggagtaggcatccgcgccgcaggccccgcagacggtctcgcattccacgagccaggtgagctctggccgttcggggtcaaa |
| aaccaggtttcccccatgctttttgatgcgtttcttacctctggtttccatgagccggtgtccacgctcggtgacgaaaaggctgtccgtgtc |
| cccgtatacagacttgagaggcctgtcctcgagcggtgttccgcggtcctcctcgtatagaaactcggaccactctgagacaaaggctc |
| gcgtccaggccagcacgaaggaggctaagtgggaggggtagcggtcgttgtccactagggggtccactcgctccagggtgtgaaga |
| cacatgtcgccctcttcggcatcaaggaaggtgattggtttgtaggtgtaggccacgtgaccgggtgttcctgaaggggggctataaaag |
| ggggtgggggcgcgttcgtcctcactctcttccgcatcgctgtctgcgagggccagctgttggggtgagtactccctctgaaaagcggg |
| catgacttctgcgctaagattgtcagtttccaaaaacgaggaggatttgatattcacctggcccgcggtgatgcctttgagggtggccgca |
| tccatctggtcagaaaagacaatctttttgttgtcaagcttggtggcaaacgacccgtagagggcgttggacagcaacttggcgatggag |
| cgcagggtttggtttttgtcgcgatcggcgcgctccttggccgcgatgtttagctgcacgtattcgcgcgcaacgcaccgccattcggga |
| aagacggtggtgcgctcgtcgggcaccaggtgcacgcgccaaccgcggttgtgcagggtgacaaggtcaacgctggtggctacctct |
| ccgcgtaggcgctcgttggtccagcagaggcggccgcccttgcgcgagcagaatggcggtagggggtctagctgcgtctcgtccgg |
| ggggtctgcgtccacggtaaagaccccgggcagcaggcgcgcgtcgaagtagtctatcttgcatccttgcaagtctagcgcctgctgc |
| catgcgcgggggcaagcgcgcgctcgtatgggttgagtgggggaccccatggcatggggtgggtgagcgcggaggcgtacatgc |
| cgcaaatgtcgtaaacgtagaggggctctctgagtattccaagatatgtagggtagcatcttccaccgcggatgctggcgcgcacgtaat |
| cgtatagttcgtgcgagggagcgaggaggtcgggaccgaggttgctacgggggggctgctctgctcggaagactatctgcctgaagat |
| ggcatgtgagttggatgatatggttggacgctggaagacgttgaagctggcgtctgtgagacctaccgcgtcacgcacgaaggaggcg |
| taggagtcgcgcagcttgttgaccagctcggcggtgacctgcacgtctagggcgcagtagtccagggtttccttgatgatgtcatacttat |
| cctgtcccttttttttccacagctcgcggttgaggacaaactcttcgcggtctttccagtactcttggatcggaaacccgtcggcctccgaac |
| ggtaagagcctagcatgtagaactggttgacggcctggtaggcgcagcatcccttttctacgggtagcgcgtatgcctgcgcggccttc |
| cggagcgaggtgtgggtgagcgcaaaggtgtccctgaccatgactttgaggtactggtatttgaagtcagtgtcgtcgcatccgccctgc |
| tcccagagcaaaaagtccgtgcgctttttggaacgcggatttggcagggcgaaggtgacatcgttgaagagtatctttcccgcgcgagg |
| cataaagttgcgtgtgatgcggaagggtcccggcacctcggaacggttgttaattacctgggcggcgagcacgatctcgtcaaagccgt |
| tgatgttgtggcccacaatgtaaagttccaagaagcgcgggatgcccttgatggaaggcaattttttaagttcctcgtaggtgagctcttca |
| ggggagctgagcccgtgctctgaaagggcccagtctgcaagatgagggttggaagcgacgaatgagctccacaggtcacgggccat |
| tagcatttgcaggtggtcgcgaaaggtcctaaactggcgacctatggccatttttttctggggtgatgcagtagaaggtaagcgggtcttgtt |
| cccagcggtcccatccaaggttcgcggctaggtctcgcgcggcagtcactagaggctcatctccgccgaacttcatgaccagcatgaa |
| gggcacgagctgcttcccaaaggccccccatccaagtataggtctctacatcgtaggtgacaaagagacgctcggtgcgaggatgcga |
| gccgatcgggaagaactggatctcccgccaccaattggaggagtggctattgatgtggtgaaagtagaagtccctgcgacgggccga |
| acactcgtgctggcttttgtaaaaacgtgcgcagtactggcagcggtgcacgggctgtacatcctgcacgaggttgacctgacgaccgc |
| gcacaaggaagcagagtgggaatttgagcccctcgcctggcgggtttggctggtggtcttctacttcggctgcttgtccttgaccgtctgg |
| ctgctcgaggggagttacggtggatcggaccaccacgccgcgcgagcccaaagtccagatgtccgcgcgcggcggtcggagcttga |
| tgacaacatcgcgcagatgggagctgtccatggtctggagctcccgcggcgtcaggtcaggcgggagctcctgcaggtttacctcgca |
| tagacgggtcagggcgcgggctagatccaggtgatacctaatttccaggggctggttggtggcggcgtcgatggcttgcaagaggcc |
| gcatccccgcggcgcgactacggtaccgcgcggcgggggggggccgcgggggtgtccttggatgatgcatctaaaagcggtgacg |
| cgggcgagcccccggaggtagggggggctccggacccgccgggagagggggcaggggcacgtcggcgccgcgcgcgggcag |
| gagctggtgctgcgcgcgtaggttgctggcgaacgcgacgacgcggcggttgatctcctgaatctggcgcctctgcgtgaagacgac |
| gggcccggtgagcttgaacctgaaagagagttcgacagaatcaatttcggtgtcgttgacggcggcctggcgcaaaatctcctgcacgt |
| ctcctgagttgtcttgataggcgatctcggccatgaactgctcgatctcttcctcctggagatctccgcgtccggctcgctccacggtggc |

TABLE 28-continued

| Ad5eNOS with Plasmid Backbone |
| --- |

ggcgaggtcgttggaaatgcgggccatgagctgcgagaaggcgttgaggcctccctcgttccagacgcggctgtagaccacgccccc ttcggcatcgcgggcgcgcatgaccacctgcgcgagattgagctccacgtgccgggcgaagacggcgtagtttcgcaggcgctgaaa gaggtagttgagggtggtggcggtgtgttctgccacgaagaagtacataacccagcgtcgcaacgtggattcgttgatatcccccaagg cctcaaggcgctccatggcctcgtagaagtccacggcgaagttgaaaaactgggagttgcgcgccgacacggttaactcctcctccag aagacggatgagctcggcgacagtgtcgcgcacctcgcgctcaaaggctacaggggcctcttcttcttcttcaatctcctcttccataagg gcctccccttcttcttcttctggcggcggtgggggaggggggacacggcggcgacgacggcgcaccgggaggcggtcgacaaagc gctcgatcatctccccgcggcgacggcgcatggtctcggtgacggcgcggccgttctcgcgggggcgcagttggaagacgccgccc gtcatgtcccggttatgggttggcgggggctgccatgcggcagggatacggcgctaacgatgcatctcaacaattgttgtgtaggtact ccgccgccgagggacctgagcgagtccgcatcgaccggatcggaaaacctctcgagaaaggcgtctaaccagtcacagtcgcaagg taggctgagcaccgtgggggcggcagcgggcggcggtcggggttgtttctggcggaggtgctgctgatgatgtaattaaagtaggc ggtcttgagacggcggatggtcgacagaagcaccatgtccttgggtccggcctgctgaatgcgcaggcggtcggccatgccccaggc ttcgttttgacatcggcgcaggtctttgtagtagtcttgcatgagcctttctaccggcacttcttcttctccttcctcttgtcctgcatctcttgcat ctatcgctgcggcggcggcggagtttggccgtaggtggcgccctcttcctcccatgcgtgtgaccccgaagcccctcatcggctgaag cagggctaggtcggcgacaacgcgctcggctaatatggcctgctgcacctgcgtgagggtagactggaagtcatccatgtccacaaag cggtggtatgcgcccgtgttgatggtgtaagtgcagttggccataacggaccagttaacggtctggtgacccggctgcgagagctcggt gtacctgagacgcgagtaagccctcgagtcaaatacgtagtcgttgcaagtccgcaccaggtactggtatcccaccaaaaagtgcggc ggcggctggcggtagaggggccagcgtagggtggccggggctccgggggcgagatcttccaacataaggcgatgatatccgtagat gtacctggacatccaggtgatgccggcggcggtggtggaggcgcgcggaaagtcgcggacgcggttccagatgttgcgcagcggc aaaaagtgctccatggtcgggacgctctggccggtcaggcgcgcgcaatcgttgacgctctagaccgtgcaaaaggagagcctgtaa gcgggcactcttccgtggtctggtggataaattcgcaagggtatcatggcggacgaccggggttcgagccccgtatccggccgtccgc cgtgatccatgcggttaccgcccgcgtgtcgaacccaggtgtgcgacgtcagacaacgggggagtgctccttttggcttccttccaggc gcggcggctgctgcgctagcttttttggccactggccgcgcgcagcgtaagcggttaggctggaaagcgaaagcattaagtggctcgc tccctgtagccggagggttattttccaagggttgagtcgcgggacccccggttcgagtctcggaccggccggactgcggcgaacggg ggtttgcctccccgtcatgcaagaccccgcttgcaaattcctccggaaacagggacgagcccctttttttgcttttcccagatgcatccggtg ctgcggcagatgcgcccccctcctcagcagcggcaagagcaagagcagcggcagacatgcagggcaccctcccctcctcctaccgc gtcaggaggggcgacatccgcggttgacgcggcagcagatggtgattacgaaccccgcggcgccgggcccggcactacctggac ttggaggagggcgagggcctggcgcggctaggagcgccctctcctgagcggcacccaagggtgcagctgaagcgtgatacgcgtg aggcgtacgtgccgcggcagaacctgtttcgcgaccgcgagggagaggagcccgaggagatgcgggatcgaaagttccacgcagg gcgcgagctgcggcatggcctgaatcgcgagcggttgctgcgcgaggaggactttgagcccgacgcgcgaaccgggattagtcccg cgcgcgcacacgtggcggccgccgacctggtaaccgcatacgagcagacggtgaaccaggagattaactttcaaaaaagctttaaca accacgtgcgtacgcttgtggcgcgcgaggaggtggctataggactgatgcatctgtgggactttgtaagcgcgctggagcaaaaccc aaatagcaagccgctcatggcgcagctgttccttatagtgcagcacagcagggacaacgaggcattcagggatgcgctgctaaacata gtagagcccgagggccgctggctgctcgatttgataaacatcctgcagagcatagtggtgcaggagcgcagcttgagcctggctgaca aggtggccgccatcaactattccatgcttagcctgggcaagttttacgcccgcaagatataccatacccctttacgttcccatagacaagga ggtaaagatcgaggggttctacatgcgcatggcgctgaaggtgcttaccttgagcgacgacctgggcgtttatcgcaacgagcgcatcc acaaggccgtgagcgtgagccggggcgcgagctcagcgaccgcgagctgatgcacagcctgcaaagggccctggctggcacgg gcagcggcgatagagaggccgagtcctactttgacgcgggcgctgacctgcgctgggccccaagccgacgcgccctggaggcagc tggggccggacctgggctggcggtggcacccgcgcgcgctggcaacgtcggcggcgtggaggaatatgacgaggacgatgagtac gagccagaggacggcgagtactaagcggtgatgtttctgatcagatgatgcaagacgcaacggacccggcggtgcgggcggcgctg TABLE 28-continued

| Ad5eNOS with Plasmid Backbone |
|---|
| cagagccagccgtccggccttaactccacggacgactggcgccaggtcatggaccgcatcatgtcgctgactgcgcgcaatcctgac |
| gcgttccggcagcagccgcaggccaaccggctctccgcaattctggaagcggtggtcccggcgcgcgcaaaccccacgcacgaga |
| aggtgctggcgatcgtaaacgcgctggccgaaaacagggccatccggcccgacgaggccggcctggtctacgacgcgctgcttcag |
| cgcgtggctcgttacaacagcggcaacgtgcagaccaacctggaccggctggtgggggatgtgcgcgaggccgtggcgcagcgtg |
| agcgcgcgcagcagcagggcaacctgggctccatggttgcactaaacgccttcctgagtacacagcccgccaacgtgccgcgggga |
| caggaggactacaccaactttgtgagcgcactgcggctaatggtgactgagacaccgcaaagtgaggtgtaccagtctgggccagact |
| atttttttccagaccagtagacaaggcctgcagaccgtaaacctgagccaggctttcaaaaacttgcaggggctgtggggggtgcgggct |
| cccacaggcgaccgcgcgaccgtgtctagcttgctgacgcccaactcgcgcctgttgctgctgctaatagcgcccttcacggacagtg |
| gcagcgtgtcccgggacacatacctaggtcacttgctgacactgtaccgcgaggccataggtcaggcgcatgtggacgagcatactttc |
| caggagattacaagtgtcagccgcgcgctggggcaggaggacacgggcagcctggaggcaaccctaaactacctgctgaccaacc |
| ggcggcagaagatcccctcgttgcacagtttaaacagcgaggaggagcgcattttgcgctacgtgcagcagagcgtgagccttaacct |
| gatgcgcgacggggtaacgcccagcgtggcgctggacatgaccgcgcgcaacatggaaccgggcatgtatgcctcaaaccggccgt |
| ttatcaaccgcctaatggactacttgcatcgcgcggccgccgtgaaccccgagtatttcaccaatgccatcttgaacccgcactggctac |
| cgcccccctggtttctacaccgggggattcgaggtgcccgagggtaacgatggattcctctgggacgacatagacgacagcgtgttttcc |
| ccgcaaccgcagaccctgctagagttgcaacagcgcgagcaggcagaggcggcgctgcgaaaggaaagcttccgcaggccaagc |
| agcttgtccgatctaggcgctgcggccccgcggtcagatgctagtagcccatttccaagcttgatagggtctcttaccagcactcgcacc |
| acccgcccgcgcctgctgggcgaggaggagtacctaaacaactcgctgctgcagccgcagcgcgaaaaaaacctgcctccggcattt |
| cccaacaacgggatagagagcctagtggacaagatgagtagatggaagacgtacgcgcaggagcacagggacgtgccaggcccg |
| cgcccgcccacccgtcgtcaaaggcacgaccgtcagcggggtctggtgtgggaggacgatgactcggcagacgacagcagcgtcct |
| ggatttgggagggagtggcaacccgtttgcgcaccttcgccccaggctggggagaatgttttaaaaaaaaaaaaaagcatgatgcaaa |
| ataaaaaactcaccaaggccatggcaccgagcgttggttttcttgtattccccttagtatgcggcgcgcggcgatgtatgaggaaggtcct |
| cctccctcctacgagagtgtggtgagcgcggcgccagtggcggcggcgctgggttctcccttcgatgctcccctggacccgccgtttgt |
| gcctccgcggtacctgcggcctaccggggggagaaacagcatccgttactctgagttggcacccctattcgacaccacccgtgtgtacc |
| tggtggacaacaagtcaacggatgtggcatccctgaactaccagaacgaccacagcaactttctgaccacggtcattcaaaacaatgac |
| tacagcccgggggaggcaagcacacagaccatcaatcttgacgaccggtcgcactggggggcgacctgaaaaccatcctgcatac |
| caacatgccaaatgtgaacgagttcatgtttaccaataagtttaaggcgcgggtgatggtgtcgcgcttgcctactaaggacaatcaggtg |
| gagctgaaatacgagtgggtggagttcacgctgcccgagggcaactactccgagaccatgaccatagaccttatgaacaacgcgatcg |
| tggagcactacttgaaagtgggcagacagaacggggttctggaaagcgacatcggggtaaagtttgacacccgcaacttcagactggg |
| gtttgaccccgtcactggtcttgtcatgcctggggtatatacaaacgaagccttccatccagacatcattttgctgccaggatgcggggtg |
| gacttcacccacagccgcctgagcaacttgttgggcatccgcaagcggcaacccttccaggagggctttaggatcacctacgatgatct |
| ggagggtggtaacattcccgcactgttggatgtggacgcctaccaggcgagcttgaaagatgacaccgaacaggggggggtggcg |
| caggcggcagcaacagcagtggcagcggcgcggaagagaactccaacgcggcagccgcggcaatgcagccggtggaggacatg |
| aacgatcatgccattcgcggcgacacctttgccacacgggctgaggagaagcgcgctgaggccgaagcagcggccgaagctgccg |
| cccccgctgcgcaacccgaggtcgagaagcctcagaagaaaccggtgatcaaacccctgacagaggacagcaagaaacgcagtta |
| caacctaataagcaatgacagcaccttcacccagtaccgcagctggtaccttgcatacaactacggcgaccctcagaccggaatccgct |
| catggaccctgctttgcactcctgacgtaacctgcggctcggagcaggtctactggtcgttgccagacatgatgcaagaccccgtgacct |
| tccgctccacgcgccagatcagcaactttccggtggtgggcgccgagctgttgcccgtgcactccaagagcttctacaacgaccaggc |
| cgtctactcccaactcatccgccagtttacctctctgacccacgtgttcaatcgctttcccgagaaccagattttggcgcgcccgccagcc |
| cccaccatcaccaccgtcagtgaaaacgttcctgctctcacagatcacgggacgctaccgctgcgcaacagcatcggaggagtccagc |

TABLE 28-continued

| Ad5eNOS with Plasmid Backbone |
|---|
| gagtgaccattactgacgccagacgccgcacctgcccctacgtttacaaggccctgggcatagtctcgccgcgcgtcctatcgagccg |
| cactttttgagcaagcatgtccatccttatatcgcccagcaataacacaggctggggcctgcgcttcccaagcaagatgtttggcggggc |
| caagaagcgctccgaccaacacccagtgcgcgtgcgcgggcactaccgcgcgccctggggcgcgcacaaacgcggccgcactgg |
| gcgcaccaccgtcgatgacgccatcgacgcggtggtggaggaggcgcgcaactacacgcccacgccgccaccagtgtccacagtg |
| gacgcggccattcagaccgtggtgcgcggagcccggcgctatgctaaaatgaagagacggcggaggcgcgtagcacgtcgccacc |
| gccgccgacccggcactgccgcccaacgcgcggcggcggccctgcttaaccgcgcacgtcgcaccggccgacgggggccatgc |
| gagcagctcgaaggctggccgcgggtattgtcactgtgccccccaggtccaggcgacgagcggccgccgcagcagccgcggccat |
| tagtgctatgactcagggtcgcaggggcaacgtgtattgggtgcgcgactcggttagcggcctgcgcgtgcccgtgcgcacccgcccc |
| ccgcgcaactagattgcaagaaaaaactacttagactcgtactgttgtatgtatccagcggcggcggcgcgcaacgaagctatgtccaa |
| gcgcaaaatcaaagaagagatgctccaggtcatcgcgccggagatctatggccccccgaagaaggaagagcaggattacaagcccc |
| gaaagctaaagcgggtcaaaaagaaaaagaaagatgatgatgatgaacttgacgacgaggtggaactgctgcacgctaccgcgccca |
| ggcgacgggtacagtggaaaggtcgacgcgtaaaacgtgttttgcgacccggcaccaccgtagtctttacgcccggtgagcgctccac |
| ccgcacctacaagcgcgtgtatgatgaggtgtacggcgacgaggacctgcttgagcaggccaacgagcgcctcggggagtttgccta |
| cggaaagcggcataaggacatgctggcgttgccgctggacgagggcaacccaacacctagcctaaagcccgtaacactgcagcagg |
| tgctgcccgcgcttgcaccgtccgaagaaaagcgcggcctaaagcgcgagtctggtgacttggcacccaccgtgcagctgatggtac |
| ccaagcgccagcgactggaagatgtcttggaaaaaatgaccgtggaacctgggctggagcccgaggtccgcgtgcggccaatcaag |
| caggtggcgccgggactgggcgtgcagaccgtggacgttcagatacccactaccagtagcaccagtattgccaccgccacagaggg |
| catggagacacaaacgtccccggttgcctcagcggtggcggatgccgcggtgcaggcggtcgctgcggccgcgtccaagacctcta |
| cggaggtgcaaacggacccgtggatgtttcgcgtttcagccccccggcgcccgcgccgttcgaggaagtacggcgccgccagcgcg |
| ctactgcccgaatatgccctacatccttccattgcgcctacccccggctatcgtggctacacctaccgccccagaagacgagcaactacc |
| cgacgccgaaccaccactggaacccgccgccgccgtcgccgtcgccagcccgtgctggccccgatttccgtgcgcagggtggctcg |
| cgaaggaggcaggaccctggtgctgccaacagcgcgctaccaccccagcatcgtttaaaagccggtctttgtggttcttgcagatatgg |
| ccctcacctgccgcctccgtttcccggtgccgggattccgaggaagaatgcaccgtaggaggggcatggccggccacggcctgacg |
| ggcggcatgcgtcgtgcgcaccaccggcggcggcgcgcgtcgcaccgtcgcatgcgcggcggtatcctgcccctccttattccactg |
| atcgccgcggcgattggcgccgtgcccggaattgcatccgtggccttgcaggcgcagagacactgattaaaaacaagttgcatgtgga |
| aaaatcaaaataaaaagtctggactctcacgctcgcttggtcctgtaactattttgtagaatggaagacatcaactttgcgtctctggccccg |
| cgacacggctcgcgcccgttcatgggaaactggcaagatatcggcaccagcaatatgagcggtggcgccttcagctggggctcgctgt |
| ggagcggcattaaaaatttcggttccaccgttaagaactatggcagcaaggcctggaacagcagcacaggccagatgctgagggataa |
| gttgaaagagcaaaatttccaacaaaaggtggtagatggcctggcctctggcattagcggggggggacctggccaaccaggcagtg |
| caaaataagattaacagtaagcttgatccccgccctcccgtagaggagcctccaccggccgtggagacagtgtctccagaggggcgtg |
| gcgaaaagcgtccgcgccccgacagggaagaaactctggtgacgcaaatagacgagcctccctcgtacgaggaggcactaaagca |
| aggcctgcccaccacccgtcccatcgcgcccatggctaccggagtgctgggccagcacacacccgtaacgctggacctgcctccccc |
| cgccgacacccagcagaaacctgtgctgccaggcccgaccgccgttgttgtaacccgtcctagccgcgcgtccctgcgccgcgccgc |
| cagcggtccgcgatcgttgcggcccgtagccagtggcaactggcaaagcacactgaacagcatcgtgggtctgggggtgcaatccct |
| gaagcgccgacgatgcttctgaatagctaacgtgtcgtatgtgtgtcatgtatgcgtccatgtcgccgccagaggagctgctgagccgcc |
| gcgcgcccgctttccaagatggctaccccttcgatgatgccgcagtggtcttacatgcacatctcgggccaggacgcctcggagtacct |
| gagccccgggctggtgcagtttgcccgcgccaccgagacgtacttcagcctgaataacaagtttagaaccccacggtggcgcctacg |
| cacgacgtgaccacagaccggtcccagcgtttgacgctgcggttcatccctgtggaccgtgaggatactgcgtactcgtacaaggcgc |
| ggttcaccctagctgtgggtgataaccgtgtgctggacatggcttccacgtactttgacatccgcggcgtgctggacaggggccctacttt |

TABLE 28-continued

| Ad5eNOS with Plasmid Backbone |
| --- |
| taagccctactctggcactgcctacaacgccctggctcccaagggtgccccaaatccttgcgaatgggatgaagctgctactgctcttga |
| aataaacctagaagaagaggacgatgacaacgaagacgaagtagacgagcaagctgagcagcaaaaaactcacgtatttgggcagg |
| cgccttattctggtataaatattacaaaggagggtattcaaataggtgtcgaaggtcaaacacctaaatatgccgataaaacatttcaacct |
| gaacctcaaataggagaatctcagtggtacgaaacagaaattaatcatgcagctgggagagtcctaaaaaagactaccccaatgaaacc |
| atgttacggttcatatgcaaaacccacaaatgaaaatggagggcaaggcattcttgtaaagcaacaaaatggaaagctagaaagtcaag |
| tggaaatgcaatttttctcaactactgaggcagccgcaggcaatggtgataacttgactcctaaagtggtattgtacagtgaagatgtagat |
| atagaaaccccagacactcatatttcttacatgcccactattaaggaaggtaactcacgagaactaatgggccaacaatctatgcccaaca |
| ggcctaattacattgcttttagggacaattttattggtctaatgtattacaacagcacgggtaatatgggtgttctggcgggccaagcatcgc |
| agttgaatgctgttgtagatttgcaagacagaaacacagagctttcataccagcttttgcttgattccattggtgatagaaccaggtacttttct |
| atgtggaatcaggctgttgacagctatgatccagatgttagaattattgaaaatcatggaactgaagatgaacttccaaattactgctttcca |
| ctgggaggtgtgattaatacagagactcttaccaaggtaaaacctaaaacaggtcaggaaaatggatgggaaaaagatgctacagaatt |
| ttcagataaaaatgaaataagagttggaaataattttgccatggaaatcaatctaaatgccaacctgtggagaaatttcctgtactccaacat |
| agcgctgtatttgcccgacaagctaaagtacagtccttccaacgtaaaaatttctgataacccaaacacctacgactacatgaacaagcga |
| gtggtggctcccgggctagtggactgctacattaaccttggagcacgctggtcccttgactatatggacaacgtcaacccatttaaccacc |
| accgcaatgctggcctgcgctaccgctcaatgttgctgggcaatggtcgctatgtgcccttccacatccaggtgcctcagaagttctttgc |
| cattaaaaacctccttctcctgccgggctcatacacctacgagtggaacttcaggaaggatgttaacatggttctgcagagctccctagga |
| aatgacctaagggttgacggagccagcattaagtttgatagcatttgcctttacgccaccttcttccccatggcccacaacaccgcctcca |
| cgcttgaggccatgcttagaaacgacaccaacgaccagtcctttaacgactatctctccgccgccaacatgctctaccctatacccgcca |
| acgctaccaacgtgcccatatccatcccctcccgcaactgggcggctttccgcggctgggccttcacgcgccttaagactaaggaaacc |
| ccatcactgggctcgggctacgacccttattacacctactctggctctatacccctacctagatggaaccttttacctcaaccacacctttaag |
| aaggtggccattacctttgactcttctgtcagctggcctggcaatgaccgcctgcttacccccaacgagtttgaaattaagcgctcagttga |
| cggggagggttacaacgttgcccagtgtaacatgaccaaagactggttcctggtacaaatgctagctaactataacattggctaccaggg |
| cttctatatcccagagagctacaaggaccgcatgtactccttctttagaaacttccagcccatgagccgtcaggtggtggatgatactaaat |
| acaaggactaccaacaggtgggcatcctacaccaacacaacaactctggatttgttggctaccttgcccccaccatgcgcgaaggaca |
| ggcctaccctgctaacttcccctatccgcttataggcaagaccgcagttgacagcattacccagaaaaagtttctttgcgatcgcaccccttt |
| ggcgcatcccattctccagtaactttatgtccatgggcgcactcacagacctgggccaaaaccttctctacgccaactccgcccacgcgc |
| tagacatgacttttgaggtggatcccatggacgagcccacccttctttatgttttgtttgaagtctttgacgtggtccgtgtgcaccagccgc |
| accgcggcgtcatcgaaaccgtgtacctgcgcacgcccttctcggccggcaacgccacaacataaagaagcaagcaacatcaacaac |
| agctgccgccatgggctccagtgagcaggaactgaaagccattgtcaaagatcttggttgtgggccatatttttttgggcacctatgacaag |
| cgctttccaggctttgtttctccacacaagctcgcctgcgccatagtcaatacggccggtcgcgagactgggggcgtacactggatggc |
| ctttgcctggaacccgcactcaaaaacatgctacctctttgagccctttggcttttctgaccagcgactcaagcaggtttaccagtttgagta |
| cgagtcactcctgcgccgtagcgccattgcttcttcccccgaccgctgtataacgctggaaaagtccacccaaagcgtacaggggccca |
| actcggccgcctgtggactattctgctgcatgtttctccacgcctttgccaactggccccaaactcccatggatcacaaccccaccatgaa |
| ccttattaccggggtacccaactccatgctcaacagtccccaggtacagcccaccctgcgtcgcaaccaggaacagctctacagcttcct |
| ggagcgccactcgccctacttccgcagccacagtgcgcagattaggagcgccacttctttttgtcacttgaaaaacatgtaaaaataatgt |
| actagagacactttcaataaaggcaaatgcttttatttgtacactctcgggtgattatttacccccacccttgccgtctgcgccgtttaaaaatc |
| aaaggggttctgccgcgcatcgctatgcgccactggcagggacacgttgcgatactggtgtttagtgctccacttaaactcaggcacaac |
| catccgcggcagctcggtgaagttttcactccacaggctgcgcaccatcaccaacgcgtttagcaggtcgggcgccgatatcttgaagt |
| cgcagttggggcctccgccctgcgcgcgcgagttgcgatacacagggttgcagcactggaacactatcagcgccgggtggtgcacgc |

TABLE 28-continued

| Ad5eNOS with Plasmid Backbone |
|---|
| tggccagcacgctcttgtcggagatcagatccgcgtccaggtcctccgcgttgctcagggcgaacggagtcaactttggtagctgccttc |
| ccaaaaagggcgcgtgcccaggctttgagttgcactcgcaccgtagtggcatcaaaaggtgaccgtgcccggtctgggcgttaggata |
| cagcgcctgcataaaagccttgatctgcttaaaagccacctgagcctttgcgccttcagagaagaacatgccgcaagacttgccggaaa |
| actgattggccggacacgcggcgtcgtgcacgcagcaccttgcgtcggtgttggagatctgcaccacatttcggccccaccggttcttc |
| acgatcttggccttgctagactgctccttcagcgcgcgctgcccgttttcgctcgtcacatccatttcaatcacgtgctccttatttatcataat |
| gcttccgtgtagacacttaagctcgccttcgatctcagcgcagcggtgcagccacaacgcgcagcccgtgggctcgtgatgcttgtagg |
| tcacctctgcaaacgactgcaggtacgcctgcaggaatcgccccatcatcgtcacaaaggtcttgttgctggtgaaggtcagctgcaacc |
| cgcggtgctcctcgttcagccaggtcttgcatacggccgccagagcttccacttggtcaggcagtagtttgaagttcgcctttagatcgtta |
| tccacgtggtacttgtccatcagcgcgcgcgcagcctccatgcccttctcccacgcagacacgatcggcacactcagcgggttcatcac |
| cgtaatttcactttccgcttcgctgggctcttcctcttcctcttgcgtccgcataccacgcgccactgggtcgtcttcattcagccgccgcact |
| gtgcgcttacctcctttgccatgcttgattagcaccggtgggttgctgaaacccaccatttgtagcgccacatcttctctttcttcctcgctgtc |
| cacgattacctctggtgatggcgggcgctcgggcttgggagaagggcgcttctttttcttcttgggcgcaatggccaaatccgccgccga |
| ggtcgatggccgcgggctgggtgtgcgcggcaccagcgcgtcttgtgatgagtcttcctcgtcctcggactcgatacgccgcctcatcc |
| gctttttggggggcgcccggggaggcggcggcgacggggacggggacgacacgtcctccatggttgggggacgtcgcgccgcacc |
| gcgtccgcgctcgggggtggtttcgcgctgctcctcttcccgactggccatttccttctcctataggcagaaaaagatcatggagtcagtc |
| gagaagaaggacagcctaaccgccccctctgagttcgccaccaccgcctccaccgatgccgccaacgcgcctaccaccttccccgtc |
| gaggcacccccgcttgaggaggaggaagtgattatcgagcaggacccaggttttgtaagcgaagacgacgaggaccgctcagtacc |
| aacagaggataaaaagcaagaccaggacaacgcagaggcaaacgaggaacaagtcgggggggggacgaaaggcatggcgact |
| acctagatgtgggagacgacgtgctgttgaagcatctgcagcgccagtgcgccattatctgcgacgcgttgcaagagcgcagcgatgt |
| gcccctcgccatagggatgtcagccttgcctacgaacgccacctattctcaccgcgcgtacccccccaaacgccaagaaaacggcaca |
| tgcgagcccaacccgcgcctcaacttctaccccgtatttgccgtgccagaggtgcttgccacctatcacatctttttccaaaactgcaagat |
| acccctatcctgccgtgccaaccgcagccgagcggacaagcagctggccttgcggcagggcgctgtcatacctgatatcgcctcgctc |
| aacgaagtgccaaaaatctttgagggtcttggacgcgacgagaagcgcgcggcaaacgctctgcaacaggaaaacagcgaaaatga |
| aagtcactctggagtgttggtggaactcgagggtgacaacgcgcgcctagccgtactaaaacgcagcatcgaggtcacccactttgcct |
| acccggcacttaacctacccccccaaggtcatgagcacagtcatgagtgagctgatcgtgcgccgtgcgcagcccctggagagggatg |
| caaatttgcaagaacaaacagaggagggcctacccgcagttggcgacgagcagctagcgcgctggcttcaaacgcgcgagcctgcc |
| gacttggaggagcgacgcaaactaatgatggccgcagtgctcgttaccgtggagcttgagtgcatgcagcggttctttgctgacccgga |
| gatgcagcgcaagctagaggaaacattgcactacacctttcgacagggctacgtacgccaggcctgcaagatctccaacgtggagctc |
| tgcaacctggtctcctaccttggaattttgcacgaaaaccgccttgggcaaaacgtgcttcattccacgctcaagggcgaggcgcgccg |
| cgactacgtccgcgactgcgtttacttatttctatgctacacctggcagacggccatgggcgtttggcagcagtgcttggaggagtgcaa |
| cctcaaggagctgcagaaactgctaaagcaaaacttgaaggacctatggacggccttcaacgagcgctccgtggccgcgcacctggc |
| ggacatcattttccccgaacgcctgcttaaaaccctgcaacagggtctgccagacttcaccagtcaaagcatgttgcagaactttaggaa |
| ctttatcctagagcgctcaggaatcttgcccgccacctgctgtgcacttcctagcgactttgtgcccattaagtaccgcgaatgccctccgc |
| cgctttggggccactgctaccttctgcagctagccaactaccttgcctaccactctgacataatggaagacgtgagcggtgacggtctact |
| ggagtgtcactgtcgctgcaacctatgcaccccgcaccgctccctggtttgcaattcgcagctgcttaacgaaagtcaaattatcggtacc |
| tttgagctgcagggtccctcgcctgacgaaaagtccgcggctccggggttgaaactcactccggggctgtggacgtcggcttaccttcg |
| caaatttgtacctgaggactaccacgcccacgagattaggttctacgaagaccaatcccgcccgcctaatgcggagcttaccgcctgcg |
| tcattacccagggccacattcttggccaattgcaagccatcaacaaagcccgccaagagtttctgctacgaaagggacggggggtttact |
| tggacccccagtccggcgaggagctcaacccaatccccccgccgccgcagccctatcagcagcagccgcgggcccttgcttcccag |

TABLE 28-continued

| Ad5eNOS with Plasmid Backbone |
|---|
| gatggcacccaaaaagaagctgcagctgccgccgccacccacggacgaggaggaatactgggacagtcaggcagaggaggttttg |
| gacgaggaggaggaggacatgatggaagactgggagagcctagacgaggaagcttccgaggtcgaagaggtgtcagacgaaaca |
| ccgtcaccctcggtcgcattcccctcgccggcgccccagaaatcggcaaccggttccagcatggctacaacctccgctcctcaggcgc |
| cgccggcactgcccgttcgccgacccaaccgtagatgggacaccactggaaccagggccggtaagtccaagcagccgccgccgtta |
| gcccaagagcaacaacagcgccaaggctaccgctcatggcgcgggcacaagaacgccatagttgcttgcttgcaagactgtggggg |
| caacatctccttcgcccgccgctttcttctctaccatcacggcgtggccttcccccgtaacatcctgcattactaccgtcatctctacagccc |
| atactgcaccggcggcagcggcagcggcagcaacagcagcggccacacagaagcaaaggcgaccggatagcaagactctgacaa |
| agcccaagaaatccacagcggcggcagcagcaggaggaggagcgctgcgtctggcgcccaacgaacccgtatcgacccgcgagc |
| ttagaaacaggatttttcccactctgtatgctatatttcaacagagcaggggccaagaacaagagctgaaaaaaaaaacaggtctctgcg |
| atccctcacccgcagctgcctgtatcacaaaagcgaagatcagcttcggcgcacgctggaagacgcggaggctctcttcagtaaatact |
| gcgcgctgactcttaaggactagtttcgcgccctttctcaaatttaagcgcgaaaactacgtcatctccagcggccacacccggcgccag |
| cacctgttgtcagcgccattatgagcaaggaaattcccacgccctacatgtggagttaccagccacaaatgggacttgcggctggagct |
| gcccaagactactcaacccgaataaactacatgagcgcgggaccccacatgatatcccgggtcaacggaatacgcgcccaccgaaac |
| cgaattctcctggaacaggcggctattaccaccacacctcgtaataaccttaatccccgtagttggcccgctgccctggtgtaccaggaa |
| agtcccgctcccaccactgtggtacttcccagagacgcccaggccgaagttcagatgactaactcaggggcgcagcttgcgggcggct |
| ttcgtcacagggtgcggtcgcccgggcagggtataactcacctgacaatcagagggcgaggtattcagctcaacgacgagtcggtga |
| gctcctcgcttggtctccgtccggacgggacatttcagatcggcggcgccggccgctcttcattcacgcctcgtcaggcaatcctaactct |
| gcagacctcgtcctctgagccgcgctctggaggcattggaactctgcaatttattgaggagtttgtgccatcggtctactttaaccccttctc |
| gggacctcccggccactatccggatcaatttattcctaactttgacgcggtaaaggactcggcggacggctacgactgaatgttaagtgg |
| ccaatgaggcctgacgctaataatagctggtccactgtcgccgccacaagtgctttgcccgcgactccggtgagttttgctactttgaattg |
| cccgaggatcatatcgagggcccggcgcacggcgtccggcttaccgcccagggagagcttgcccgtagcctgattcgggagtttacc |
| cagcgcccccctgctagttgagcgggacaggggaccctgtgttctcactgtgatttgcaactgtcctaaccttggattacatcaagatccag |
| atcttctagacccgggagcggccgctgtcgacctgcaggatccgaattcgatatcactagtggtaccgatcttattccctttaactaataaa |
| aaaaaataataaagcatcacttacttaaaatcagttagcaaatttctgtccagtttattcagcagcacctccttgccctcctcccagctctggt |
| attgcagcttcctcctggctgcaaactttctccacaatctaaagggaatgtcagtttcctcctgttcctgtccatccgcacccactatcttcatg |
| ttgttgcagatgaagcgcgcaagaccgtctgaagataccttcaaccccgtgtatccatatgacacggaaaccggtcctccaactgtgcctt |
| ttcttactcctccctttgtatcccccaatgggtttcaagagagtccccctggggtactctctttgcgcctatccgaacctctagttacctccaat |
| ggcatgcttgcgctcaaaatgggcaacggcctctctctggacgaggccggcaaccttacctcccaaaatgtaaccactgtgagcccacc |
| tctcaaaaaaaccaagtcaaacataaacctggaaatatctgcacccctcacagttacctcagaagccctaactgtggctgccgccgcacc |
| tctaatggtcgcgggcaacacactcaccatgcaatcacaggccccgctaaccgtgcacgactccaaacttagcattgccacccaagga |
| cccctcacagtgtcagaaggaaagctagccctgcaaacatcaggcccccctcaccaccaccgatagcagtacccttactatcactgcctc |
| acccccctctaactactgccactggtagcttgggcattgacttgaaagagcccatttatacacaaaatggaaaactaggactaaagtacgg |
| ggctcctttgcatgtaacagacgacctaaacactttgaccgtagcaactggtccaggtgtgactattaataatacttccttgcaaactaaagt |
| tactggagccttgggttttgattcacaaggcaatatgcaacttaatgtagcaggaggactaaggattgattctcaaaacagacgccttatac |
| ttgatgttagttatccgtttgatgctcaaaaccaactaaatctaagactaggacagggccctctttttataaactcagcccacaacttggatatt |
| aactacaacaaaggcctttacttgtttacagcttcaaacaattccaaaaagcttgaggttaacctaagcactgccaaggggttgatgtttga |
| cgctacagccatagccattaatgcaggagatgggcttgaatttggttcacctaatgcaccaaacacaaatcccctcaaaacaaaaattgg |
| ccatggcctagaatttgattcaaacaaggctatggttcctaaactaggaactggccttagttttgacagcacaggtgccattacagtaggaa |
| acaaaaataatgataagctaactttgtggaccacaccagctccatctcctaactgtagactaaatgcagagaaagatgctaaactcactttg |

TABLE 28-continued

| Ad5eNOS with Plasmid Backbone |
|---|
| gtcttaacaaaatgtggcagtcaaatacttgctacagtttcagttttggctgttaaaggcagtttggctccaatatctggaacagttcaaagtg |
| ctcatcttattataagatttgacgaaaatggagtgctactaaacaattccttcctggacccagaatattggaactttagaaatggagatcttac |
| tgaaggcacagcctatacaaacgctgttggatttatgcctaacctatcagcttatccaaaatctcacggtaaaactgccaaaagtaacattg |
| tcagtcaagtttacttaaacggagacaaaactaaacctgtaacactaaccattacactaaacggtacacaggaaacaggagacacaactc |
| caagtgcatactctatgtcattttcatgggactggtctggccacaactacattaatgaaatatttgccacatcctcttacactttttcatacattg |
| cccaagaataaagaatcgtttgtgttatgtttcaacgtgtttatttttcaattgcagaaaatttcaagtcatttttcattcagtagtatagccccac |
| caccacatagcttatacagatcaccgtaccttaatcaaactcacagaaccctagtattcaacctgccacctccctcccaacacacagagta |
| cacagtcctttctccccggctggccttaaaaagcatcatatcatgggtaacagacatattcttaggtgttatattccacacggtttcctgtcga |
| gccaaacgctcatcagtgatattaataaactccccgggcagctcacttaagttcatgtcgctgtccagctgctgagccacaggctgctgtc |
| caacttgcggttgcttaacgggcggcgaaggagaagtccacgcctacatgggggtagagtcataatcgtgcatcaggatagggcggtg |
| gtgctgcagcagcgcgcgaataaactgctgccgccgccgctccgtcctgcaggaatacaacatggcagtggtctcctcagcgatgatt |
| cgcaccgcccgcagcataaggcgccttgtcctccgggcacagcagcgcaccctgatctcacttaaatcagcacagtaactgcagcaca |
| gcaccacaatattgttcaaaatcccacagtgcaaggcgctgtatccaaagctcatggggggaccacagaacccacgtggccatcata |
| ccacaagcgcaggtagattaagtggcgacccctcataaacacgctggacataaacattacctcttttggcatgttgtaattcaccacctcc |
| cggtaccatataaacctctgattaaacatggcgccatccaccaccatcctaaaccagctggccaaaacctgcccgccggctatacactg |
| cagggaaccgggactggaacaatgacagtggagagcccaggactcgtaaccatggatcatcatgctcgtcatgatatcaatgttggca |
| caacacaggcacacgtgcatacacttcctcaggattacaagctcctcccgcgttagaaccatatcccagggaacaacccattcctgaatc |
| agcgtaaatcccacactgcagggaagacctcgcacgtaactcacgttgtgcattgtcaaagtgttacattcgggcagcagcggatgatc |
| ctccagtatggtagcgcgggtttctgtctcaaaaggaggtagacgatccctactgtacggagtgcgccgagacaaccgagatcgtgttg |
| gtcgtagtgtcatgccaaatggaacgccggacgtagtcatatttcctgaagcaaaaccaggtgcgggcgtgacaaacagatctgcgtct |
| ccggtctcgccgcttagatcgctctgtgtagtagttgtagtatatccactctctcaaagcatccaggcgcccccctggcttcgggttctatgta |
| aactccttcatgcgccgctgccctgataacatccaccaccgcagaataagccacacccagccaacctacacattogttctgcgagtcaca |
| cacgggaggagcgggaagagctggaagaaccatgtttttttttttttattccaaaagattatccaaaacctcaaaatgaagatctattaagtg |
| aacgcgctcccctccggtggcgtggtcaaactctacagccaaagaacagataatggcatttgtaagatgttgcacaatggcttccaaaag |
| gcaaacggccctcacgtccaagtggacgtaaaggctaaacccttcagggtgaatctcctctataaacattccagcaccttcaaccatgcc |
| caaataattctcatctcgccaccttctcaatatatctctaagcaaatcccgaatattaagtccggccattgtaaaatctgctccagagcgcc |
| ctccaccttcagcctcaagcagcgaatcatgattgcaaaaattcaggttcctcacagacctgtataagattcaaaagcggaacattaacaa |
| aaataccgcgatcccgtaggtcccttcgcagggccagctgaacataatcgtgcaggtctgcacggaccagcgcggccacttccccgcc |
| aggaaccatgacaaaagaacccacactgattatgacacgcatactcggagctatgctaaccagcgtagccccgatgtaagcttgttgcat |
| gggcggcgatataaaatgcaaggtgctgctcaaaaaatcaggcaaagcctcgcgcaaaaaagaaagcacatcgtagtcatgctcatgc |
| agataaaggcaggtaagctccggaaccaccacagaaaaagacaccatttttctctcaaacatgtctgcgggtttctgcataaacacaaaa |
| taaaataacaaaaaaacatttaaacattagaagcctgtcttacaacaggaaaaacaacccttataagcataagacggactacggccatgc |
| cggcgtgaccgtaaaaaaactggtcaccgtgattaaaaagcaccaccgacagctcctcggtcatgtccggagtcataatgtaagactcg |
| gtaaacacatcaggttgattcacatcggtcagtgctaaaaagcgaccgaaatagcccgggggaatacatacccgcaggcgtagagaca |
| acattacagcccccataggaggtataacaaaattaataggagagaaaaacacataaacacctgaaaaaccctcctgcctaggcaaaata |
| gcaccctcccgctccagaacaacatacagcgcttccacagcggcagccataacagtcagccttaccagtaaaaaagaaaacctattaa |
| aaaaacaccactcgacacggcaccagctcaatcagtcacagtgtaaaaaagggccaagtgcagagcgagtatatataggactaaaaa |
| atgacgtaacggttaaagtccacaaaaaacacccagaaaaccgcacgcgaacctacgcccagaaacgaaagccaaaaaacccacaa |
| cttcctcaaatcgtcacttccgttttcccacgttacgtaacttcccattttaagaaaactacaattcccaacacatacaagttactccgccctaa |

TABLE 28-continued

| Ad5eNOS with Plasmid Backbone |
|---|
| aacctacgtcacccgccccgttcccacgccccgcgccacgtcacaaactccaccccctcattatcatattggcttcaatccaaaataaggt |
| atattattgatgatgttaatttgggccattagacttgaagtcaagcggccgcttacaactggaccttgctggtacatagaactgattaactga |
| ccatttaaatcataccaacatggtcaaataaaacgaaaggctcagtcgaaagactgggcctttcgttttaatctgatcggcacgtaagagg |
| ttccaactttcaccataatgaaataagatcactaccgggcgtatttttgagttatcgagattttcaggagctaaggaagctaaaatgagcca |
| tattcaacgggaaacgtcttgctcgaggccgcgattaaattccaacatggatgctgatttatatgggtataaatgggctcgcgataatgtcg |
| ggcaatcaggtgcgacaatctatcgattgtatgggaagcccgatgcgccagagttgtttctgaaacatggcaaaggtagcgttgccaatg |
| atgttacagatgagatggtcaggctaaactggctgacggaatttatgcctcttccgaccatcaagcattttatccgtactcctgatgatgcat |
| ggttactcaccactgcgatccccagggaaaacagcattccaggtattagaagaatatcctgattcaggtgaaaatattgttgatgcgctggc |
| agtgttcctgcgccggttgcattcgattcctgtttgtaattgtccttttaacggcgatcgcgtatttcgtctcgctcaggcgcaatcacgaatg |
| aataacggtttggttggtgcgagtgattttgatgacgagcgtaatggctggcctgttgaacaagtctggaaagaaatgcataaacttttgcc |
| attctcaccggattcagtcgtcactcatggtgatttctcacttgataaccttatttttgacgaggggaaattaataggttgtattgatgttggacg |
| agtcggaatcgcagaccgataccaggatcttgccatcctatggaactgcctcggtgagttttctccttcattacagaaacggctttttcaaaa |
| atatggtattgataatcctgatatgaataaattgcagtttcacttgatgctcgatgagtttttctaacctaggtgacagaagtcaaaagcctcc |
| ggtcggaggcttttgactttctgctagatctgtttcaatgcggtgaagggccaggcagctggggattatgtcgagacccggccagcatgtt |
| ggttttatcgcatattcagcgttgtcgcgtttacccaggtaaaatggaagcagtgtatcgtctgcgtgaatgtgcaaatcaggaacgtaacc |
| gtggtacatagatgcagtcccttgcgggtcgttcccttcaacgagtaggacgcggtgcccttgcaaggctaaccattgcgcctggtgtac |
| tgcagatgaggttttataaacccctcccttgtgtgacataacggaaagtacaaccgggtttttatcgtcaggtctttggtttgggttaccaaac |
| acactccgcatatggctaatttggtcaattgtgtagccagcgcgacgttctactcggcccctcatctcaaaatcaggagccggtagacga |
| ccagctttttccgcgtctctgatagcctgcggtgttacgccgatcaggtctgcaacttctgttataccccagcggcgagtaatacgacgcg |
| cttccgggctgtcatcgccgaactgtgcgatggcaatagcgcgcgtcatttcctgaccgcgattgatacagtctttcagcaaattaattaac |
| gacatcctgtttcctctcaaacatgcccttatctttgtgtttttcatcatactttacgtttttaaagcaaagcaacataaaaaaagcaaagtgactt |
| agaaaacgcaaagttaaggttcaaatcaatttttgatgcgctacagaagctatttagcttcatctaagcgcaacggtattacttacgttggta |
| tatttaaaacctaacttaatgattttaaatgataataaatcataccaattgctatcaaaagttaagcgaacatgctgattttcacgctgtttataca |
| ctttgaggcatctctatctcttccgtctctatattgaaacacaatcaaagaacatcaatccatgtgacatcccccactatctaagaacaccata |
| acagaacacaacataggaatgcaacattaatgtatcaataattcggaacatatgcactatatcatatctcaattacggaacatatcagcaca |
| caattgcccattatacgc |

TABLE 29

| Ad5eNOS No Plasmid Backbone |
|---|
| (SEQ ID NO: 29) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccgatgcaatttcctcattttattaggaaaggacagtgggagtggcaccttccagggtcaag |
| gaaggcacgggggaggggcaaacaacagatggctggcaactagaaggcacagtcgaggctgatctcgaagcggccggccgcccc |
| gactctagaattattaucaggggcuguuggugucugagccgggagggucgaacgcccagggcacugcgccccgcaacugacgc |
| uccugcaaggaaaagcucugggugcguaugcggcuugucaccuccugggugcgcagcgugagcccgaaaaugucuucgug |

TABLE 29-continued

| Ad5eNOS No Plasmid Backbone |
| --- |
| guagcguugcugaucccgcagcacgccgaugacgucgccggccucguccagcuccaugucgcccuccgucgccaggaugc |
| gcugcacggucugcaggacguugguugccaugguaacaucgccgcagacaaacauguggccccgcucgaggcacagcacg |
| cggugcaccuccgcagccagcuccguccucaggauguccugcacguaggucuugggguugucagguucccgggagaaggc |
| ggugaggacucggccaaacaccccgcgcugcugggcguucugcaccucgucgcgguagagauggucaaguugggagcauc |
| ggcagccgaacaccaaagucaugggagugggcugcagcccuuugcucucaaugucaugcagccgcuccugccagaaucccc |
| ggaagggggcaaugccagugccuggacccaccaggaugcagggcaagcugggaucggguggcagccggaaggagggagcc |
| ccccggaugaagcagggcacagggucuccgggcuugagcuggcuuagccacguggagcagacuccauagugcagggggcc |
| cagcccauccugaguccuguaugccagcacagcuacagugagguggaucucuccugggggggggggggagcuga |
| cugaguaguaccggggcuggagcagaggcagcugggugaggagcaguggggcaggcagcgccaccgacgggaacugcucc |
| agcaccuccagcagcguggggcagcggaaccacuuccacuccucguagcgucggggauccuggcugagggccuccagcuc |
| cugcuguucccugggcucuucugccaaggugcugagcagccgcaagagcugagggcuggguggggaggugauguccagg |
| aagaaggugagagccuggcgcagcgugcacgggggcagccgggggucccgcacccagccgggggggagggccaccagggcu |
| gcccuucuccagcugcucuacugccacgggcucagugggcgccgggggguccuccacgcggcucagcagcgccuccacaag |
| gccgggccgguugggggggcagacaccuaugugguccccccggcugguacugcagccccuccuggccuccggguguccaggc |
| gcaccaggaugguggcccucguggacuugcugcuuugcagguuuuccacugagcggauuguagccuggaacaucuuccg |
| ccugugcacguggaucagaccuggcagcaacugcaggcccucggccuggggcucagccgguaccucuggcgcuuccagc |
| uccguuuggggcugaagaugucucgggggcggccuuggcauccucucccacacagaaggucucacaggcggccuggaag |
| gcagccugggcccagccucggaaggccuccuccuggccgcacagcucgucgcccuggcccagcugcagcagccgcuccccg |
| cccaguuccuccagccgugugucccacggcacgagcaaaggcgcagaaguggggguaugcccgggagccgagcccgaacaca |
| cagaaccugagggugcccagggccccugcacugucuguguuacuggacuccuuccucuuccgccgccaagaggacaccag |
| ugggucugagcaggagaugcuguugaagcggaucuuauaacucuugugcuguuccggccgaggggagcuguuguagggg |
| ccggacaucuccaucagggcagcugcaaagcucucuccauucuccgggggauccccauucccaaaugugcugguuaccacc |
| agcaccagcgucucguguucgagggacaccacgucauacucauccauacacaggacccggggaucaaaagccuuccggaag |
| agucuccccagcugcugugcguagcucugggcccggccggucucggagccauacaggauugucgccuucacucgcuucgc |
| caucaccgugcccaugagcgaggcggagaucuucacggcguuggccacuucuuuaaaggucuucuuccuggugaugccgg |
| ugcccuuggggcacuccccuuccaggggucuggcugguagcggaaggccggggacaggaaauaguugaccaucuccuga |
| uggaaaacaggagugaggcugcccgagaugggggcacgauccaggcccagucugcagggcagcccccccuggccuucug |
| cucauucuccaggugcuucaugaaagaggccguggggcgugguggucccacgauggugacuuuggcuagcugguaacug |
| ugcagcacggccacguugauuuccacugcugccuugucuuuccacagggacgagguggucggguauccagguccaugca |
| gacagccacauccuccaggauguuguagcggugagggucacacagguuccucgugccgaucucagugcucauguaccagc |
| cacugaagggggcugcggggaacuccaggcccccaauuuccagcagcauguuggacacugccgggagggcguaccagcgc |
| aggcccagggcugcaaaccacuccagcgugggggugcuccaggggcaccucaaggaccagcucgggggcagaaggaagag |
| uucuggggggaucaucuggggccugcagcagcaggggcagcacgucgaagcgaccguuuccugggguccagccgugcugaa |
| ugcagagcucggugaucuccacguuggcuggguccccccgcacagagccauccugcugccgguagcccgcguagcgcacc |
| agcuggcuguuccagauucggaagucuccucggccagggcagcgcugcgggaacacugugauggccgagcgaagguugcc |
| ccgguugguggcauacuugaugugguugcagauguaggugaacauuuccugugcagaccugcagucccgggcaucgaac |
| accugcagcuucccccacuggauccggcccacgcagcggggagcguugcgccaggccugcuuagccccgaacaccagcucg |
| cucucccuaagcugguaggugccuguggcugccaccucggcuuccaccucuugaagccgcuguucgugggccugggagcc |
| gcuccucuuaauggagcuguaguacugguugaugaagucccgggccugacucagcagcugcucaggggccgggggccg |

TABLE 29-continued

| Ad5eNOS No Plasmid Backbone |
|---|
| ggggagggccggcccuguaguuuccguggaaauaccagggagcccaggcagcgucuuggggugcagggcccauccugcu |
| gcgccugggcgcugagggugucauaggugaugcuccccaccucccaguucuucacacgagggaacuugggccccucuggg |
| ggcugggguuagcggggagcucggggggcuguguucuggcgcugguggggaguagggaugcuggggcccggcugggcuca |
| ggggccggggugggcugggcccugcuugccgcacagcccaaggcccagccccagccccaggccgcaggguggcccaggcuc |
| cugggccacgcucuucaaguugcccauggtggctttaccaacagtaccggattgccaagctggcgcgcccgggttagaacaaggac |
| gcgccgccgggactccgccgagtcgcagcggaattctttgccaaaatgatgagacagcacaataaccagcacgttgcccaggagaag |
| ctttttgcaaaagcctaggcctccaaaaaagcctcctcactacttctggaatagctcagaggccgaggcggcctcggcctctgcataaat |
| aaaaaaaattagtcagccatggggcggagaatgggcggaactgggcggagttaggggcgggatgggcggagttaggggcgggact |
| atggttgctgactaattgagatgcatgctttgcatacttctgcctgctggggagcctggggactttccacacctggttgctgactaattgaga |
| tgcatgctttgcatacttctgcctgctggggagcctggggactttccacaccctaactgacacacattccacagctggttctttccgcctca |
| gaaggtacctaaccaagttcctctttcagaggttatttcaggccatggtgctgcgcaaatcgataaggatccgaattcgatatcactagtgg |
| taccagtactgaaatgtgtgggcgtggcttaagggtgggaaagaatatataaggtgggggtcttatgtagttttgtatctgttttgcagcagc |
| cgccgccgccatgagcaccaactcgtttgatggaagcattgtgagctcatatttgacaacgcgcatgcccccatgggccggggtgcgtc |
| agaatgtgatgggctccagcattgatggtcgccccgtcctgcccgcaaactctactaccttgacctacgagaccgtgtctggaacgccgt |
| tggagactgcagcctccgccgccgcttcagccgctgcagccaccgcccgcgggattgtgactgactttgctttcctgagcccgcttgca |
| agcagtgcagcttcccgttcatccgcccgcgatgacaagttgacggctcttttggcacaattggattctttgacccgggaacttaatgtcgt |
| ttctcagcagctgttggatctgcgccagcaggtttctgccctgaaggcttcctcccctcccaatgcggtttaacggtccgggccagagtgg |
| ccaacataaataaaaaaccagactctgtttggatttggatcaagcaagtgtcttgctgtctttatttaggggttttgcgcgcgcggtaggccc |
| gggaccagcggtctcggtcgttgagggtcctgtgtatttttttccaggacgtggtaaaggtgactctggatgttcagatacatgggcataag |
| cccgtctctggggtggaggtagcaccactgcagagcttcatgctgcggggtggtgttgtagatgatccagtcgtagcaggagcgctgg |
| gcgtggtgcctaaaaatgtctttcagtagcaagctgattgccaggggcaggcccttggtgtaagtgtttacaaagcggttaagctgggat |
| gggtgcatacgtggggatatgagatgcatcttggactgtatttttaggttggctatgttcccagccatatccctccggggattcatgttgtgc |
| agaaccaccagcacagtgtatccggtgcacttgggaaatttgtcatgtagcttagaaggaaatgcgtggaagaacttggagacgcccctt |
| gtgacctccaagattttccatgcattcgtccataatgatggcaatgggcccacgggcggcggcctgggcgaagatatttctgggatcact |
| aacgtcatagttgtgttccaggatgagatcgtcataggccatttttacaaagcgcgggcggagggtgccagactgcggtataatggttcc |
| atccggcccaggggcgtagttaccctcacagatttgcatttcccacgctttgagttcagatgggggggatcatgtctacctgcggggcgat |
| gaagaaaacggtttccggggtaggggagatcagctgggaagaaagcaggttcctgagcagctgcgacttaccgcagccggtgggcc |
| cgtaaatcacacctattaccggctgcaactggtagttaagagagctgcagctgccgtcatccctgagcaggggggccacttcgttaagc |
| atgtccctgactcgcatgttttccctgaccaaatccgccagaaggcgctcgccgcccagcgatagcagttcttgcaaggaagcaaagttt |
| ttcaacggtttgagaccgtccgccgtaggcatgcttttgagcgtttgaccaagcagttccaggcggtcccacagctcggtcacctgctcta |
| cggcatctcgatccagcatatctcctcgtttcgcgggttggggcggctttcgctgtacggcagtagtcggtgctcgtccagacgggccag |
| ggtcatgtctttccacgggcgcagggtcctcgtcagcgtagtctgggtcacggtgaaggggtgcgctccgggctgcgcgctggccag |
| ggtgcgcttgaggctggtcctgctggtgctgaagcgctgccggtcttcgccctgcgcgtcggccaggtagcatttgaccatggtgtcata |
| gtccagcccctccgcggcgtggcccttggcgcgcagcttgcccttggaggaggcgccgcacgaggggcagtgcagacttttgaggg |
| cgtagagcttgggcgcgagaaataccgattccggggagtaggcatccgcgccgcaggccccgcagacggtctcgcattccacgagc |
| caggtgagctctggccgttcggggtcaaaaaccaggtttcccccatgctttttgatgcgtttcttacctctggtttccatgagccggtgtcca |
| cgctcggtgacgaaaaggctgtccgtgtccccgtatacagacttgagaggcctgtcctcgagcggtgttccgcggtcctcctcgtataga |
| aactcggaccactctgagacaaaggctcgcgtccaggccagcacgaaggaggctaagtgggaggggtagcggtcgttgtccactag |
| ggggtccactcgctccagggtgtgaagacacatgtcgccctcttcggcatcaaggaaggtgattggtttgtaggtgtaggccacgtgac |

TABLE 29-continued

| Ad5eNOS No Plasmid Backbone |
|---|
| cgggtgttcctgaagggggctataaaagggggtgggggcgcgttcgtcctcactctcttccgcatcgctgtctgcgagggccagctgt |
| tggggtgagtactccctctgaaaagcgggcatgacttctgcgctaagattgtcagtttccaaaaacgaggaggatttgatattcacctggc |
| ccgcggtgatgcctttgagggtggccgcatccatctggtcagaaaagacaatctttttgttgtcaagcttggtggcaaacgacccgtaga |
| gggcgttggacagcaacttggcgatggagcgcagggtttggtttttgtcgcgatcggcgcgctccttggccgcgatgtttagctgcacgt |
| attcgcgcgcaacgcaccgccattcgggaaagacggtggtgcgctcgtcgggcaccaggtgcacgcgccaaccgcggttgtgcagg |
| gtgacaaggtcaacgctggtggctacctctccgcgtaggcgctcgttggtccagcagaggcggccgcccttgcgcgagcagaatggc |
| ggtagggggtctagctgcgtctcgtccgggggggtctgcgtccacggtaaagaccccgggcagcaggcgcgcgtcgaagtagtctatc |
| ttgcatccttgcaagtctagcgcctgctgccatgcgcgggggcaagcgcgcgctcgtatgggttgagtgggggaccccatggcatgg |
| ggtgggtgagcgcggaggcgtacatgccgcaaatgtcgtaaacgtagaggggctctctgagtattccaagatatgtagggtagcatctt |
| ccaccgcggatgctggcgcgcacgtaatcgtatagttcgtgcgagggagcgaggaggtcgggaccgaggttgctacgggcgggctg |
| ctctgctcggaagactatctgcctgaagatggcatgtgagttggatgatatggttggacgctggaagacgttgaagctggcgtctgtgag |
| acctaccgcgtcacgcacgaaggaggcgtaggagtcgcgcagcttgttgaccagctcggcggtgacctgcacgtctagggcgcagta |
| gtccagggtttccttgatgatgtcatacttatcctgtcccttttttttccacagctcgcggttgaggacaaactcttcgcggtctttccagtactc |
| ttggatcggaaacccgtcggcctccgaacggtaagagcctagcatgtagaactggttgacggcctggtaggcgcagcatcccttttcta |
| cgggtagcgcgtatgcctgcgcggccttccggagcgaggtgtgggtgagcgcaaaggtgtccctgaccatgactttgaggtactggta |
| tttgaagtcagtgtcgtcgcatccgccctgctcccagagcaaaaagtccgtgcgctttttggaacgcggatttggcagggcgaaggtgac |
| atcgttgaagagtatctttcccgcgcgaggcataaagttgcgtgtgatgcggaagggtcccggcacctcggaacggttgttaattacctg |
| ggcggcgagcacgatctcgtcaaagccgttgatgttgtggcccacaatgtaaagttccaagaagcgcgggatgcccttgatggaaggc |
| aatttttttaagttcctcgtaggtgagctcttcaggggagctgagcccgtgctctgaaagggcccagtctgcaagatgagggttggaagcg |
| acgaatgagctccacaggtcacgggccattagcatttgcaggtggtcgcgaaaggtcctaaactggcgacctatggccatttttttctggg |
| gtgatgcagtagaaggtaagcgggtcttgttcccagcggtcccatccaaggttcgcggctaggtctcgcgcggcagtcactagaggctc |
| atctccgccgaacttcatgaccagcatgaagggcacgagctgcttcccaaaggcccccatccaagtataggtctctacatcgtaggtga |
| caaagagacgctcggtgcgaggatgcgagccgatcgggaagaactggatctcccgccaccaattggaggagtggctattgatgtggt |
| gaaagtagaagtccctgcgacgggccgaacactcgtgctggcttttgtaaaaacgtgcgcagtactggcagcggtgcacgggctgtac |
| atcctgcacgaggttgacctgacgaccgcgcacaaggaagcagagtgggaatttgagcccctcgcctggcgggtttggctggtggtct |
| tctacttcggctgcttgtccttgaccgtctggctgctcgaggggagttacggtggatcggaccaccacgccgcgcgagcccaaagtcca |
| gatgtccgcgcgcggcggtcggagcttgatgacaacatcgcgcagatgggagctgtccatggtctggagctcccgcggcgtcaggtc |
| aggcgggagctcctgcaggtttacctcgcatagacgggtcagggcgcgggctagatccaggtgatacctaatttccaggggctggttg |
| gtggcggcgtcgatggcttgcaagaggccgcatccccgcggcgcgactacggtaccgcgcggcgggcggtgggccgcgggggtg |
| tccttggatgatgcatctaaaagcggtgacgcgggcgagcccccggaggtagggggggctccggacccgccgggagagggggca |
| ggggcacgtcggcgccgcgcgcgggcaggagctggtgctgcgcgcgtaggttgctggcgaacgcgacgacgcggcggttgatctc |
| ctgaatctggcgcctctgcgtgaagacgacgggcccggtgagcttgaacctgaaagagagttcgacagaatcaatttcggtgtcgttga |
| cggcggcctggcgcaaaatctcctgcacgtctcctgagttgtcttgataggcgatctcggccatgaactgctcgatctcttcctcctggag |
| atctccgcgtccggctcgctccacggtggcggcgaggtcgttggaaatgcgggccatgagctgcgagaaggcgttgaggcctccctc |
| gttccagacgcggctgtagaccacgcccccttcggcatcgcgggcgcgcatgaccacctgcgcgagattgagctccacgtgccgggc |
| gaagacggcgtagtttcgcaggcgctgaaagaggtagttgagggtggtggcggtgtgttctgccacgaagaagtacataacccagcgt |
| cgcaacgtggattcgttgatatcccccaaggcctcaaggcgctccatggcctcgtagaagtccacggcgaagttgaaaaactgggagtt |
| gcgcgccgacacggttaactcctcctccagaagacggatgagctcggcgacagtgtcgcgcacctcgcgctcaaaggctacagggg |
| cctcttcttcttcttcaatctcctcttccataagggcctccccttcttcttcttctggcggcggtgggggagggggacacggcggcgacga |

TABLE 29-continued

| Ad5eNOS No Plasmid Backbone |
|---|
| cggcgcaccgggaggcggtcgacaaagcgctcgatcatctccccgcggcgacggcgcatggtctcggtgacggcgcggccgttctc |
| gcgggggcgcagttggaagacgccgcccgtcatgtcccggttatgggttggcggggggctgccatgcggcagggatacggcgctaa |
| cgatgcatctcaacaattgttgtgtaggtactccgccgccgagggacctgagcgagtccgcatcgaccggatcggaaaacctctcgag |
| aaaggcgtctaaccagtcacagtcgcaaggtaggctgagcaccgtggcgggggcagcgggcggcggtcggggttgtttctggcgg |
| aggtgctgctgatgatgtaattaaagtaggcggtcttgagacggcggatggtcgacagaagcaccatgtccttgggtccggcctgctga |
| atgcgcaggggtcggccatgccccaggcttcgttttgacatcggcgcaggtctttgtagtagtcttgcatgagcctttctaccggcacttc |
| ttcttctccttcctcttgtcctgcatctcttgcatctatcgctgcggcggcggcggagtttggccgtaggtggcgccctcttcctcccatgcgt |
| gtgaccccgaagcccctcatcggctgaagcagggctaggtcggcgacaacgcgctcggctaatatggcctgctgcacctgcgtgagg |
| gtagactggaagtcatccatgtccacaaagcggtggtatgcgcccgtgttgatggtgtaagtgcagttggccataacggaccagttaacg |
| gtctggtgacccggctgcgagagctcggtgtacctgagacgcgagtaagccctcgagtcaaatacgtagtcgttgcaagtccgcacca |
| ggtactggtatcccaccaaaaagtgcggcggcggctggcggtagaggggccagcgtagggtggccggggctccgggggcgagat |
| cttccaacataaggcgatgatatccgtagatgtacctggacatccaggtgatgccggcggcggtggtggaggcgcgcggaaagtcgc |
| ggacgcggttccagatgttgcgcagcggcaaaaagtgctccatggtcgggacgctctggccggtcaggcgcgcgcaatcgttgacgc |
| tctagaccgtgcaaaaggagagcctgtaagcgggcactcttccgtggtctggtggataaattcgcaagggtatcatggcggacgaccg |
| gggttcgagccccgtatccggccgtccgccgtgatccatgcggttaccgcccgcgtgtcgaacccaggtgtgcgacgtcagacaacg |
| ggggagtgctccttttggcttccttccaggcgcggcggctgctgcgctagcttttttggccactggccgcgcgcagcgtaagcggttagg |
| ctggaaagcgaaagcattaagtggctcgctccctgtagccggagggttattttccaagggttgagtcgcgggacccccggttcgagtct |
| cggaccggccggactgcggcgaacgggggtttgcctccccgtcatgcaagaccccgcttgcaaattcctccggaaacagggacgag |
| ccccttttttgcttttcccagatgcatccggtgctgcggcagatgcgcccccctcctcagcagcggcaagagcaagagcagcggcagac |
| atgcagggcaccctcccctcctcctaccgcgtcaggaggggcgacatccgcggttgacgcggcagcagatggtgattacgaaccccc |
| gcggcgccgggcccggcactacctggacttggaggagggcgagggcctggcgcggctaggagcgccctctcctgagcggcaccc |
| aagggtgcagctgaagcgtgatacgcgtgaggcgtacgtgccgcggcagaacctgtttcgcgaccgcgagggagaggagcccgag |
| gagatgcgggatcgaaagttccacgcagggcgcgagctgcggcatggcctgaatcgcgagcggttgctgcgcgaggaggactttga |
| gcccgacgcgcgaaccgggattagtcccgcgcgcgcacacgtggcggccgccgacctggtaaccgcatacgagcagacggtgaac |
| caggagattaactttcaaaaaagctttaacaaccacgtgcgtacgcttgtggcgcgcgaggaggtggctataggactgatgcatctgtgg |
| gactttgtaagcgcgctggagcaaaacccaaatagcaagccgctcatggcgcagctgttccttatagtgcagcacagcagggacaacg |
| aggcattcagggatgcgctgctaaacatagtagagcccgagggccgctggctgctcgatttgataaacatcctgcagagcatagtggtg |
| caggagcgcagcttgagcctggctgacaaggtggccgccatcaactattccatgcttagcctgggcaagttttacgcccgcaagatata |
| ccataccccttacgttcccatagacaaggaggtaaagatcgaggggttctacatgcgcatggcgctgaaggtgcttaccttgagcgacg |
| acctgggcgtttatcgcaacgagcgcatccacaaggccgtgagcgtgagccggcggcgcgagctcagcgaccgcgagctgatgcac |
| agcctgcaaagggccctggctggcacgggcagcggcgatagagaggccgagtcctactttgacgcgggcgctgacctgcgctggg |
| ccccaagccgacgcgccctggaggcagctggggccggacctgggctggcggtggcacccgcgcgcgctggcaacgtcggcggc |
| gtggaggaatatgacgaggacgatgagtacgagccagaggacggcgagtactaagcggtgatgtttctgatcagatgatgcaagacg |
| caacggacccggcggtgcgggcggcgctgcagagccagccgtccggccttaactccacggacgactggcgccaggtcatggaccg |
| catcatgtcgctgactgcgcgcaatcctgacgcgttccggcagcagccgcaggccaaccggctctccgcaattctggaagcggtggtc |
| ccggcgcgcgcaaaccccacgcacgagaaggtgctggcgatcgtaaacgcgctggccgaaaacagggccatccggcccgacgag |
| gccggcctggtctacgacgcgctgcttcagcgcgtggctcgttacaacagcggcaacgtgcagaccaacctggaccggctggtgggg |
| gatgtgcgcgaggccgtggcgcagcgtgagcgcgcgcagcagcagggcaacctgggctccatggttgcactaaacgccttcctgag |
| tacacagcccgccaacgtgccgcggggacaggaggactacaccaactttgtgagcgcactgcggctaatggtgactgagacaccgc |

TABLE 29-continued

| Ad5eNOS No Plasmid Backbone |
|---|
| aaagtgaggtgtaccagtctgggccagactatttttccagaccagtagacaaggcctgcagaccgtaaacctgagccaggctttcaaaa |
| acttgcaggggctgtgggggtgcgggctcccacaggcgaccgcgcgaccgtgtctagcttgctgacgcccaactcgcgcctgttgct |
| gctgctaatagcgcccttcacggacagtggcagcgtgtcccgggacacatacctaggtcacttgctgacactgtaccgcgaggccata |
| ggtcaggcgcatgtggacgagcatactttccaggagattacaagtgtcagccgcgcgctggggcaggaggacacgggcagcctgga |
| ggcaaccctaaactacctgctgaccaaccggcggcagaagatcccctcgttgcacagtttaaacagcgaggaggagcgcattttgcgc |
| tacgtgcagcagagcgtgagccttaacctgatgcgcgacggggtaacgcccagcgtggcgctggacatgaccgcgcgcaacatgga |
| accgggcatgtatgcctcaaaccggccgtttatcaaccgcctaatggactacttgcatcgcgcggccgccgtgaaccccgagtatttcac |
| caatgccatcttgaacccgcactggctaccgccccctggtttctacaccgggggattcgaggtgcccgagggtaacgatggattcctctg |
| ggacgacatagacgacagcgtgttttccccgcaaccgcagaccctgctagagttgcaacagcgcgagcaggcagaggcggcgctgc |
| gaaaggaaagcttccgcaggccaagcagcttgtccgatctaggcgctgcggccccgcggtcagatgctagtagcccatttccaagctt |
| gatagggtctcttaccagcactcgcaccacccgcccgcgcctgctgggcgaggaggagtacctaaacaactcgctgctgcagccgca |
| gcgcgaaaaaaacctgcctccggcatttcccaacaacgggatagagagcctagtggacaagatgagtagatggaagacgtacgcgca |
| ggagcacagggacgtgccaggcccgcgcccgcccacccgtcgtcaaaggcacgaccgtcagcggggtctggtgtgggaggacga |
| tgactcggcagacgacagcagcgtcctggatttgggagggagtggcaacccgtttgcgcaccttcgccccaggctggggagaatgttt |
| taaaaaaaaaaaaaagcatgatgcaaaataaaaaactcaccaaggccatggcaccgagcgttggttttcttgtattccccttagtatgcgg |
| cgcgcggcgatgtatgaggaaggtcctcctccctcctacgagagtgtggtgagcgcggcgccagtggcggcggcgctgggttctccc |
| ttcgatgctcccctggacccgccgtttgtgcctccgcggtacctgcggcctaccggggggagaaacagcatccgttactctgagttggc |
| acccctattcgacaccacccgtgtgtacctggtggacaacaagtcaacggatgtggcatccctgaactaccagaacgaccacagcaact |
| ttctgaccacggtcattcaaaacaatgactacagcccgggggaggcaagcacacagaccatcaatcttgacgaccggtcgcactgggg |
| cggcgacctgaaaaccatcctgcataccaacatgccaaatgtgaacgagttcatgtttaccaataagtttaaggcgcgggtgatggtgtc |
| gcgcttgcctactaaggacaatcaggtggagctgaaatacgagtgggtggagttcacgctgcccgagggcaactactccgagaccatg |
| accatagaccttatgaacaacgcgatcgtggagcactacttgaaagtgggcagacagaacggggttctggaaagcgacatcggggta |
| aagtttgacacccgcaacttcagactggggtttgaccccgtcactggtcttgtcatgcctggggtatatacaaacgaagccttccatccag |
| acatcattttgctgccaggatgcggggtggacttcacccacagccgcctgagcaacttgttgggcatccgcaagcggcaacccttccag |
| gagggctttaggatcacctacgatgatctggagggtggtaacattcccgcactgttggatgtggacgcctaccaggcgagcttgaaaga |
| tgacaccgaacagggggggtggcgcaggcggcagcaacagcagtggcagcggcgcggaagagaactccaacgcggcagcc |
| gcggcaatgcagccggtggaggacatgaacgatcatgccattcgcggcgacacctttgccacacgggctgaggagaagcgcgctga |
| ggccgaagcagcggccgaagctgccgcccccgctgcgcaacccgaggtcgagaagcctcagaagaaaccggtgatcaaacccctg |
| acagaggacagcaagaaacgcagttacaacctaataagcaatgacagcaccttcacccagtaccgcagctggtaccttgcatacaact |
| acggcgaccctcagaccggaatccgctcatggaccctgctttgcactcctgacgtaacctgcggctcggagcaggtctactggtcgttg |
| ccagacatgatgcaagaccccgtgaccttccgctccacgcgccagatcagcaactttccggtggtgggcgccgagctgttgcccgtgc |
| actccaagagcttctacaacgaccaggccgtctactcccaactcatccgccagtttacctctctgacccacgtgttcaatcgctttcccgag |
| aaccagattttggcgcgcccgccagcccccaccatcaccaccgtcagtgaaaacgttcctgctctcacagatcacgggacgctaccgct |
| gcgcaacagcatcggaggagtccagcgagtgaccattactgacgccagacgccgcacctgcccctacgtttacaaggccctgggcat |
| agtctcgccgcgcgtcctatcgagccgcactttttgagcaagcatgtccatccttatatcgcccagcaataacacaggctggggcctgcg |
| cttcccaagcaagatgtttggcggggccaagaagcgctccgaccaacacccagtgcgcgtgcgcgggcactaccgcgcgccctggg |
| gcgcgcacaaacgcggccgcactgggcgcaccaccgtcgatgacgccatcgacgcggtggtggaggaggcgcgcaactacacgc |
| ccacgccgccaccagtgtccacagtggacgcggccattcagaccgtggtgcgcggagcccggcgctatgctaaaatgaagagacgg |
| cggaggcgcgtagcacgtcgccaccgccgccgacccggcactgccgcccaacgcgcggcggcggccctgcttaaccgcgcacgt |

TABLE 29-continued

| Ad5eNOS No Plasmid Backbone |
|---|
| cgcaccggccgacgggggccatgcgagcagctcgaaggctggccgcgggtattgtcactgtgccccccaggtccaggcgacgag |
| cggccgccgcagcagccgcggccattagtgctatgactcagggtcgcaggggcaacgtgtattgggtgcgcgactcggttagcggcc |
| tgcgcgtgcccgtgcgcacccgcccccgcgcaactagattgcaagaaaaaactacttagactcgtactgttgtatgtatccagcggcg |
| gcggcgcgcaacgaagctatgtccaagcgcaaaatcaaagaagagatgctccaggtcatcgcgccggagatctatggccccccgaa |
| gaaggaagagcaggattacaagccccgaaagctaaagcgggtcaaaaagaaaaagaaagatgatgatgatgaacttgacgacgagg |
| tggaactgctgcacgctaccgcgcccaggcgacgggtacagtggaaaggtcgacgcgtaaaacgtgttttgcgacccggcaccaccg |
| tagtctttacgcccggtgagcgctccacccgcacctacaagcgcgtgtatgatgaggtgtacggcgacgaggacctgcttgagcaggc |
| caacgagcgcctcggggagtttgcctacggaaagcggcataaggacatgctggcgttgccgctggacgagggcaacccaacaccta |
| gcctaaagcccgtaacactgcagcaggtgctgcccgcgcttgcaccgtccgaagaaaagcgcggcctaaagcgcgagtctggtgact |
| tggcacccaccgtgcagctgatggtacccaagcgccagcgactggaagatgtcttggaaaaaatgaccgtggaacctgggctggagc |
| ccgaggtccgcgtgcggccaatcaagcaggtggcgccgggactgggcgtgcagaccgtggacgttcagatacccactaccagtagc |
| accagtattgccaccgccacagagggcatggagacacaaacgtccccggttgcctcagcggtggcggatgccgcggtgcaggcggt |
| cgctgcggccgcgtccaagacctctacggaggtgcaaacggacccgtggatgtttcgcgtttcagccccccggcgcccgcgccgttc |
| gaggaagtacggcgccgccagcgcgctactgcccgaatatgccctacatccttccattgcgcctacccccggctatcgtggctacacct |
| accgccccagaagacgagcaactacccgacgccgaaccaccactggaacccgccgccgccgtcgccgtcgccagcccgtgctggc |
| cccgatttccgtgcgcagggtggctcgcgaaggaggcaggaccctggtgctgccaacagcgcgctaccaccccagcatcgtttaaaa |
| gccggtctttgtggttcttgcagatatggccctcacctgccgcctccgtttcccggtgccgggattccgaggaagaatgcaccgtaggag |
| gggcatggccggccacggcctgacgggcggcatgcgtcgtgcgcaccaccggcggcggcgcgcgtcgcaccgtcgcatgcgcgg |
| cggtatcctgcccctccttattccactgatcgccgcggcgattggcgccgtgcccggaattgcatccgtggccttgcaggcgcagagac |
| actgattaaaaacaagttgcatgtggaaaaatcaaaataaaaagtctggactctcacgctcgcttggtcctgtaactattttgtagaatggaa |
| gacatcaactttgcgtctctggccccgcgacacggctcgcgcccgttcatgggaaactggcaagatatcggcaccagcaatatgagcg |
| gtggcgccttcagctggggctcgctgtggagcggcattaaaaatttcggttccaccgttaagaactatggcagcaaggcctggaacagc |
| agcacaggccagatgctgagggataagttgaaagagcaaaatttccaacaaaaggtggtagatggcctggcctctggcattagcgggg |
| tggtggacctggccaaccaggcagtgcaaaataagattaacagtaagcttgatccccgccctcccgtagaggagcctccaccggccgt |
| ggagacagtgtctccagaggggcgtggcgaaaagcgtccgcgccccgacagggaagaaactctggtgacgcaaatagacgagcct |
| ccctcgtacgaggaggcactaaagcaaggcctgcccaccacccgtcccatcgcgcccatggctaccggagtgctgggccagcacac |
| acccgtaacgctggacctgcctcccccgccgacacccagcagaaacctgtgctgccaggcccgaccgccgttgttgtaacccgtcct |
| agccgcgcgtccctgcgccgcgccgccagcggtccgcgatcgttgcggcccgtagccagtggcaactggcaaagcacactgaaca |
| gcatcgtgggtctgggggtgcaatccctgaagcgccgacgatgcttctgaatagctaacgtgtcgtatgtgtgtcatgtatgcgtccatgt |
| cgccgccagaggagctgctgagccgccgcgcgcccgctttccaagatggctaccccttcgatgatgccgcagtggtcttacatgcaca |
| tctcgggccaggacgcctcggagtacctgagccccgggctggtgcagtttgcccgcgccaccgagacgtacttcagcctgaataacaa |
| gtttagaaccccacggtggcgcctacgcacgacgtgaccacagaccggtcccagcgtttgacgctgcggttcatccctgtggaccgt |
| gaggatactgcgtactcgtacaaggcgcggttcaccctagctgtgggtgataaccgtgtgctggacatggcttccacgtactttgacatcc |
| gcggcgtgctggacaggggccctacttttaagccctactctggcactgcctacaacgccctggctcccaagggtgccccaaatccttgc |
| gaatgggatgaagctgctactgctcttgaaataaacctagaagaagaggacgatgacaacgaagacgaagtagacgagcaagctgag |
| cagcaaaaaactcacgtatttgggcaggcgccttattctggtataaatattacaaaggagggtattcaaataggtgtcgaaggtcaaacac |
| ctaaatatgccgataaaacatttcaacctgaacctcaaataggagaatctcagtggtacgaaacagaaattaatcatgcagctgggagag |
| tcctaaaaaagactaccccaatgaaaccatgttacggttcatatgcaaaacccacaaatgaaaatggagggcaaggcattcttgtaaagc |
| aacaaaatggaaagctagaaagtcaagtggaaatgcaatttttctcaactactgaggcagccgcaggcaatggtgataacttgactccta |

TABLE 29-continued

| Ad5eNOS No Plasmid Backbone |
| --- |
| aagtggtattgtacagtgaagatgtagatatagaaaccccagacactcatatttcttacatgcccactattaaggaaggtaactcacgagaa |
| ctaatgggccaacaatctatgcccaacaggcctaattacattgcttttagggacaattttattggtctaatgtattacaacagcacgggtaata |
| tgggtgttctggcgggccaagcatcgcagttgaatgctgttgtagatttgcaagacagaaacacagagctttcataccagcttttgcttgatt |
| ccattggtgatagaaccaggtacttttctatgtggaatcaggctgttgacagctatgatccagatgttagaattattgaaaatcatggaactg |
| aagatgaacttccaaattactgctttccactgggaggtgtgattaatacagagactcttaccaaggtaaaacctaaaacaggtcaggaaaa |
| tggatgggaaaaagatgctacagaattttcagataaaaatgaaataagagttggaaataattttgccatggaaatcaatctaaatgccaacc |
| tgtggagaaatttcctgtactccaacatagcgctgtatttgcccgacaagctaaagtacagtccttccaacgtaaaaatttctgataacccaa |
| acacctacgactacatgaacaagcgagtggtggctcccgggctagtggactgctacattaaccttggagcacgctggtcccttgactata |
| tggacaacgtcaacccatttaaccaccaccgcaatgctggcctgcgctaccgctcaatgttgctgggcaatggtcgctatgtgcccttcca |
| catccaggtgcctcagaagttctttgccattaaaaacctccttctcctgccgggctcatacacctacgagtggaacttcaggaaggatgtta |
| acatggttctgcagagctccctaggaaatgacctaagggttgacggagccagcattaagtttgatagcatttgcctttacgccaccttcttc |
| cccatggcccacaacaccgcctccacgcttgaggccatgcttagaaacgacaccaacgaccagtcctttaacgactatctctccgccgc |
| caacatgctctaccctatacccgccaacgctaccaacgtgcccatatccatcccctcccgcaactggggctttccgcggctgggcctt |
| cacgcgccttaagactaaggaaaccccatcactgggctcgggctacgacccttattacacctactctggctctataccctacctagatgga |
| acctttacctcaaccacacctttaagaaggtggccattacctttgactcttctgtcagctggcctggcaatgaccgcctgcttacccccaac |
| gagtttgaaattaagcgctcagttgacggggagggttacaacgttgcccagtgtaacatgaccaaagactggttcctggtacaaatgcta |
| gctaactataacattggctaccagggcttctatatcccagagagctacaaggaccgcatgtactccttctttagaaacttccagcccatgag |
| ccgtcaggtggtggatgatactaaatacaaggactaccaacaggtgggcatcctacaccaacacaacaactctggatttgttggctacctt |
| gcccccaccatgcgcgaaggacaggcctaccctgctaacttcccctatccgcttataggcaagaccgcagttgacagcattacccagaa |
| aaagtttctttgcgatcgcaccctttggcgcatcccattctccagtaactttatgtccatgggcgcactcacagacctgggccaaaaccttct |
| ctacgccaactccgcccacgcgctagacatgacttttgaggtggatcccatggacgagcccacccttctttatgttttgtttgaagtctttga |
| cgtggtccgtgtgcaccagccgcaccgcggcgtcatcgaaaccgtgtacctgcgcacgcccttctcggccggcaacgccacaacata |
| aagaagcaagcaacatcaacaacagctgccgccatgggctccagtgagcaggaactgaaagccattgtcaaagatcttggttgtgggc |
| catatttttgggcacctatgacaagcgctttccaggctttgtttctccacacaagctcgcctgcgccatagtcaatacggccggtcgcgag |
| actgggggcgtacactggatggcctttgcctggaacccgcactcaaaaacatgctacctctttgagccctttggcttttctgaccagcgac |
| tcaagcaggtttaccagtttgagtacgagtcactcctgcgccgtagcgccattgcttcttcccccgaccgctgtataacgctggaaaagtc |
| cacccaaagcgtacaggggcccaactcggccgcctgtggactattctgctgcatgtttctccacgcctttgccaactggccccaaactcc |
| catggatcacaaccccaccatgaaccttattaccggggtacccaactccatgctcaacagtccccaggtacagcccaccctgcgtcgca |
| accaggaacagctctacagcttcctggagcgccactcgccctacttccgcagccacagtgcgcagattaggagcgccacttctttttgtc |
| acttgaaaaacatgtaaaaataatgtactagagacactttcaataaaggcaaatgcttttatttgtacactctcgggtgattatttacccccac |
| ccttgccgtctgcgccgtttaaaaatcaaaggggttctgccgcgcatcgctatgcgccactggcagggacacgttgcgatactggtgttta |
| gtgctccacttaaactcaggcacaaccatccgcggcagctcggtgaagttttcactccacaggctgcgcaccatcaccaacgcgtttagc |
| aggtcgggcgccgatatcttgaagtcgcagttggggcctccgccctgcgcgcgcgagttgcgatacacagggttgcagcactggaac |
| actatcagcgccgggtggtgcacgctggccagcacgctcttgtcggagatcagatccgcgtccaggtcctccgcgttgctcagggcga |
| acggagtcaactttggtagctgccttcccaaaaagggcgcgtgcccaggctttgagttgcactcgcaccgtagtggcatcaaaaggtga |
| ccgtgcccggtctgggcgttaggatacagcgcctgcataaaagccttgatctgcttaaaagccacctgagcctttgcgccttcagagaag |
| aacatgccgcaagacttgccggaaaactgattggccggacacgcggcgtcgtgcacgcagcaccttgcgtcggtgttggagatctgca |
| ccacatttcggccccaccggttcttcacgatcttggccttgctagactgctccttcagcgcgcgctgcccgttttcgctcgtcacatccattt |
| caatcacgtgctccttatttatcataatgcttccgtgtagacacttaagctcgccttcgatctcagcgcagcggtgcagccacaacgcgca |

TABLE 29-continued

| Ad5eNOS No Plasmid Backbone |
|---|
| gcccgtgggctcgtgatgcttgtaggtcacctctgcaaacgactgcaggtacgcctgcaggaatcgccccatcatcgtcacaaaggtctt |
| gttgctggtgaaggtcagctgcaacccgcggtgctcctcgttcagccaggtcttgcatacggccgccagagcttccacttggtcaggca |
| gtagtttgaagttcgcctttagatcgttatccacgtggtacttgtccatcagcgcgcgcgcagcctccatgcccttctcccacgcagacacg |
| atcggcacactcagcgggttcatcaccgtaatttcactttccgcttcgctgggctcttcctcttcctcttgcgtccgcataccacgcgccact |
| gggtcgtcttcattcagccgccgcactgtgcgcttacctcctttgccatgcttgattagcaccggtgggttgctgaaacccaccatttgtag |
| cgccacatcttctctttcttcctcgctgtccacgattacctctggtgatggcgggcgctcgggcttgggagaagggcgcttctttttcttcttg |
| ggcgcaatggccaaatccgccgccgaggtcgatggccgcgggctgggtgtgcgcggcaccagcgcgtcttgtgatgagtcttcctcg |
| tcctcggactcgatacgccgcctcatccgcttttttgggggcgcccggggaggcggcggcgacggggacggggacgacacgtcctc |
| catggttgggggacgtcgcgccgcaccgcgtccgcgctcgggggtggtttcgcgctgctcctcttcccgactggccatttccttctcctat |
| aggcagaaaaagatcatggagtcagtcgagaagaaggacagcctaaccgcccctctgagttcgccaccaccgcctccaccgatgcc |
| gccaacgcgcctaccaccttccccgtcgaggcacccccgcttgaggaggaggaagtgattatcgagcaggacccaggttttgtaagcg |
| aagacgacgaggaccgctcagtaccaacagaggataaaaagcaagaccaggacaacgcagaggcaaacgaggaacaagtcgggc |
| ggggggacgaaaggcatggcgactacctagatgtgggagacgacgtgctgttgaagcatctgcagcgccagtgcgccattatctgcg |
| acgcgttgcaagagcgcagcgatgtgcccctcgccatagcggatgtcagccttgcctacgaacgccacctattctcaccgcgcgtacc |
| ccccaaacgccaagaaaacggcacatgcgagcccaacccgcgcctcaacttctaccccgtatttgccgtgccagaggtgcttgccacc |
| tatcacatctttttccaaaactgcaagatacccctatcctgccgtgccaaccgcagccgagcggacaagcagctggccttgcggcaggg |
| cgctgtcatacctgatatcgcctcgctcaacgaagtgccaaaaatctttgagggtcttggacgcgacgagaagcgcgcggcaaacgctc |
| tgcaacaggaaaacagcgaaaatgaaagtcactctggagtgttggtggaactcgagggtgacaacgcgcgcctagccgtactaaaac |
| gcagcatcgaggtcacccactttgcctacccggcacttaacctacccccaaggtcatgagcacagtcatgagtgagctgatcgtgcgc |
| cgtgcgcagcccctggagagggatgcaaatttgcaagaacaaacagaggagggcctacccgcagttggcgacgagcagctagcgc |
| gctggcttcaaacgcgcgagcctgccgacttggaggagcgacgcaaactaatgatggccgcagtgctcgttaccgtggagcttgagtg |
| catgcagcggttctttgctgacccggagatgcagcgcaagctagaggaaacattgcactacacctttcgacagggctacgtacgccag |
| gcctgcaagatctccaacgtggagctctgcaacctggtctcctaccttggaattttgcacgaaaaccgccttgggcaaaacgtgcttcatt |
| ccacgctcaagggcgaggcgcgccgcgactacgtccgcgactgcgtttacttatttctatgctacacctggcagacggccatgggcgtt |
| tggcagcagtgcttggaggagtgcaacctcaaggagctgcagaaactgctaaagcaaaacttgaaggacctatggacggccttcaacg |
| agcgctccgtggccgcgcacctggcggacatcattttccccgaacgcctgcttaaaaccctgcaacagggtctgccagacttcaccagt |
| caaagcatgttgcagaactttaggaactttatcctagagcgctcaggaatcttgcccgccacctgctgtgcacttcctagcgactttgtgcc |
| cattaagtaccgcgaatgccctccgccgctttggggccactgctaccttctgcagctagccaactaccttgcctaccactctgacataatg |
| gaagacgtgagcggtgacggtctactggagtgtcactgtcgctgcaacctatgcaccccgcaccgctccctggtttgcaattcgcagct |
| gcttaacgaaagtcaaattatcggtacctttgagctgcagggtccctcgcctgacgaaaagtccgcggctccggggttgaaactcactcc |
| ggggctgtggacgtcggcttaccttcgcaaatttgtacctgaggactaccacgcccacgagattaggttctacgaagaccaatcccgcc |
| cgcctaatgcggagcttaccgcctgcgtcattacccagggccacattcttggccaattgcaagccatcaacaaagcccgccaagagtttc |
| tgctacgaaagggacgggggtttacttggacccccagtccggcgaggagctcaacccaatccccccgccgccgcagccctatcagc |
| agcagccgcgggcccttgcttcccaggatggcacccaaaaagaagctgcagctgccgccgccacccacggacgaggaggaatact |
| gggacagtcaggcagaggaggttttggacgaggaggaggaggacatgatggaagactgggagagcctagacgaggaagcttccga |
| ggtcgaagaggtgtcagacgaaacaccgtcaccctcggtcgcattcccctcgccggcgccccagaaatcggcaaccggttccagcat |
| ggctacaacctccgctcctcaggcgccgccggcactgcccgttcgccgacccaaccgtagatgggacaccactggaaccagggccg |
| gtaagtccaagcagccgccgccgttagcccaagagcaacaacagcgccaaggctaccgctcatggcgcgggcacaagaacgccat |
| agttgcttgcttgcaagactgtgggggcaacatctccttcgcccgccgctttcttctctaccatcacggcgtggccttccccgtaacatcc |

TABLE 29-continued

| Ad5eNOS No Plasmid Backbone |
| --- |
| tgcattactaccgtcatctctacagcccatactgcaccggcggcagcggcagcggcagcaacagcagcggccacacagaagcaaag |
| gcgaccggatagcaagactctgacaaagcccaagaaatccacagcggcggcagcagcaggaggaggagcgctgcgtctggcgcc |
| caacgaacccgtatcgacccgcgagcttagaaacaggatttttcccactctgtatgctatatttcaacagagcaggggccaagaacaaga |
| gctgaaaataaaaaacaggtctctgcgatccctcacccgcagctgcctgtatcacaaaagcgaagatcagcttcggcgcacgctggaa |
| gacgcggaggctctcttcagtaaatactgcgcgctgactcttaaggactagtttcgcgccctttctcaaatttaagcgcgaaaactacgtca |
| tctccagcggccacacccggcgccagcacctgttgtcagcgccattatgagcaaggaaattcccacgccctacatgtggagttaccagc |
| cacaaatgggacttgcggctggagctgcccaagactactcaacccgaataaactacatgagcgcgggaccccacatgatatcccggt |
| caacggaatacgcgcccaccgaaaccgaattctcctggaacaggcggctattaccaccacacctogtaataaccttaatccccgtagttg |
| gcccgctgccctggtgtaccaggaaagtcccgctcccaccactgtggtacttcccagagacgcccaggccgaagttcagatgactaac |
| tcaggggcgcagcttgcgggcggctttcgtcacagggtgcggtcgcccgggcagggtataactcacctgacaatcagagggcgaggt |
| attcagctcaacgacgagtcggtgagctcctcgcttggtctccgtccggacgggacatttcagatcggggcgccggccgctcttcattc |
| acgcctcgtcaggcaatcctaactctgcagacctcgtcctctgagccgcgctctggaggcattggaactctgcaatttattgaggagtttgt |
| gccatcggtctactttaaccccttctcgggacctcccggccactatccggatcaatttattcctaactttgacgcggtaaaggactcggcgg |
| acggctacgactgaatgttaagtggccaatgaggcctgacgctaataatagctggtccactgtcgccgccacaagtgctttgcccgcga |
| ctccggtgagttttgctactttgaattgcccgaggatcatatcgagggcccggcgcacggcgtccggcttaccgcccagggagagcttg |
| cccgtagcctgattcgggagtttacccagcgcccccctgctagttgagcgggacaggggaccctgtgttctcactgtgatttgcaactgtcc |
| taaccttggattacatcaagatccagatcttctagacccgggagcggccgctgtcgacctgcaggatccgaattcgatatcactagtggta |
| ccgatcttattccctttaactaataaaaaaaaataataaagcatcacttacttaaaatcagttagcaaatttctgtccagtttattcagcagcac |
| ctccttgccctcctcccagctctggtattgcagcttcctcctggctgcaaactttctccacaatctaaagggaatgtcagtttcctcctgttcct |
| gtccatccgcacccactatcttcatgttgttgcagatgaagcgcgcaagaccgtctgaagataccttcaaccccgtgtatccatatgacac |
| ggaaaccggtcctccaactgtgccttttcttactcctccctttgtatcccccaatgggtttcaagagagtccccctggggtactctctttgcgc |
| ctatccgaacctctagttacctccaatggcatgcttgcgctcaaaatgggcaacggcctctctctggacgaggccggcaaccttacctcc |
| caaaatgtaaccactgtgagcccacctctcaaaaaaaccaagtcaaacataaacctggaaatatctgcacccctcacagttacctcagaa |
| gccctaactgtggctgccgccgcacctctaatggtcgcgggcaacacactcaccatgcaatcacaggccccgctaaccgtgcacgact |
| ccaaacttagcattgccacccaaggacccctcacagtgtcagaaggaaagctagccctgcaaacatcaggcccccctcaccaccaccg |
| atagcagtacccttactatcactgcctcacccccctctaactactgccactggtagcttgggcattgacttgaaagagcccatttatacacaa |
| aatggaaaactaggactaaagtacggggctcctttgcatgtaacagacgacctaaacactttgaccgtagcaactggtccaggtgtgact |
| attaataatacttccttgcaaactaaagttactggagccttgggttttgattcacaaggcaatatgcaacttaatgtagcaggaggactaagg |
| attgattctcaaaacagacgccttatacttgatgttagttatccgtttgatgctcaaaaccaactaaatctaagactaggacagggccctctttt |
| tataaactcagcccacaacttggatattaactacaacaaaggcctttacttgtttacagcttcaaacaattccaaaaagcttgaggttaaccta |
| agcactgccaaggggttgatgtttgacgctacagccatagccattaatgcaggagatgggcttgaatttggttcacctaatgcaccaaaca |
| caaatcccctcaaaacaaaaattggccatggcctagaatttgattcaaacaaggctatggttcctaaactaggaactggccttagttttgac |
| agcacaggtgccattacagtaggaaacaaaaataatgataagctaactttgtggaccacaccagctccatctcctaactgtagactaaatg |
| cagagaaagatgctaaactcactttggtcttaacaaaatgtggcagtcaaatacttgctacagtttcagttttggctgttaaaggcagtttgg |
| ctccaatatctggaacagttcaaagtgctcatcttattataagatttgacgaaaatggagtgctactaaacaattccttcctggacccagaat |
| attggaactttagaaatggagatcttactgaaggcacagcctatacaaacgctgttggatttatgcctaacctatcagcttatccaaaatctc |
| acggtaaaactgccaaaagtaacattgtcagtcaagtttacttaaacggagacaaaactaaacctgtaacactaaccattacactaaacgg |
| tacacaggaaacaggagacacaactccaagtgcatactctatgtcattttcatgggactggtctggccacaactacattaatgaaatatttg |
| ccacatcctcttacactttttcatacattgcccaagaataaagaatcgtttgtgttatgtttcaacgtgtttatttttcaattgcagaaaatttcaag |

TABLE 29-continued

| Ad5eNOS No Plasmid Backbone |
| --- |
| tcatttttcattcagtagtatagccccaccaccacatagcttatacagatcaccgtaccttaatcaaactcacagaaccctagtattcaacctg |
| ccacctccctcccaacacacagagtacacagtcctttctccccggctggccttaaaaagcatcatatcatgggtaacagacatattcttag |
| gtgttatattccacacggtttcctgtcgagccaaacgctcatcagtgatattaataaactccccgggcagctcacttaagttcatgtcgctgt |
| ccagctgctgagccacaggctgctgtccaacttgcggttgcttaacgggcggcgaaggagaagtccacgcctacatgggggtagagt |
| cataatcgtgcatcaggatagggcggtggtgctgcagcagcgcgcgaataaactgctgccgccgccgctccgtcctgcaggaataca |
| acatggcagtggtctcctcagcgatgattcgcaccgcccgcagcataaggcgccttgtcctccgggcacagcagcgcaccctgatctc |
| acttaaatcagcacagtaactgcagcacagcaccacaatattgttcaaaatcccacagtgcaaggcgctgtatccaaagctcatggcgg |
| ggaccacagaacccacgtggccatcataccacaagcgcaggtagattaagtggcgacccctcataaacacgctggacataaacattac |
| ctcttttggcatgttgtaattcaccacctcccggtaccatataaacctctgattaaacatggcgccatccaccaccatcctaaaccagctggc |
| caaaacctgcccgccggctatacactgcagggaaccgggactggaacaatgacagtggagagcccaggactcgtaaccatggatcat |
| catgctcgtcatgatatcaatgttggcacaacacaggcacacgtgcatacacttcctcaggattacaagctcctcccgcgttagaaccata |
| tcccagggaacaacccattcctgaatcagcgtaaatcccacactgcagggaagacctcgcacgtaactcacgttgtgcattgtcaaagtg |
| ttacattcgggcagcagcggatgatcctccagtatggtagcgcgggtttctgtctcaaaaggaggtagacgatccctactgtacggagtg |
| cgccgagacaaccgagatcgtgttggtcgtagtgtcatgccaaatggaacgccggacgtagtcatatttcctgaagcaaaaccaggtgc |
| gggcgtgacaaacagatctgcgtctccggtctcgccgcttagatcgctctgtgtagtagttgtagtatatccactctctcaaagcatccagg |
| cgccccctggcttcgggttctatgtaaactccttcatgcgccgctgccctgataacatccaccaccgcagaataagccacacccagccaa |
| cctacacattcgttctgcgagtcacacacgggaggagcgggaagagctggaagaaccatgtttttttttttattccaaaagattatccaaa |
| acctcaaaatgaagatctattaagtgaacgcgctcccctccggtggcgtggtcaaactctacagccaaagaacagataatggcatttgta |
| agatgttgcacaatggcttccaaaaggcaaacggccctcacgtccaagtggacgtaaaggctaaacccttcagggtgaatctcctctata |
| aacattccagcaccttcaaccatgcccaaataattctcatctcgccaccttctcaatatatctctaagcaaatcccgaatattaagtccggcc |
| attgtaaaaatctgctccagagcgccctccaccttcagcctcaagcagcgaatcatgattgcaaaaattcaggttcctcacagacctgtata |
| agattcaaaagcggaacattaacaaaaataccgcgatcccgtaggtcccttcgcagggccagctgaacataatcgtgcaggtctgcacg |
| gaccagcgcggccacttccccgccaggaaccatgacaaaagaacccacactgattatgacacgcatactcggagctatgctaaccag |
| cgtagccccgatgtaagcttgttgcatgggggcgatataaaatgcaaggtgctgctcaaaaaatcaggcaaagcctcgcgcaaaaaa |
| gaaagcacatcgtagtcatgctcatgcagataaaggcaggtaagctccggaaccaccacagaaaaagacaccatttttctctcaaacat |
| gtctgcgggtttctgcataaacacaaaataaaataacaaaaaaacatttaaacattagaagcctgtcttacaacaggaaaaacaacccttat |
| aagcataagacggactacggccatgccggcgtgaccgtaaaaaaactggtcaccgtgattaaaaagcaccaccgacagctcctcggt |
| catgtccggagtcataatgtaagactcggtaaacacatcaggttgattcacatcggtcagtgctaaaaagcgaccgaaatagcccgggg |
| gaatacatacccgcaggcgtagagacaacattacagcccccataggaggtataacaaaattaataggagagaaaaacacataaacacc |
| tgaaaaaccctcctgcctaggcaaaatagcaccctcccgctccagaacaacatacagcgcttccacagoggcagccataacagtcagc |
| cttaccagtaaaaaagaaaacctattaaaaaaacaccactcgacacggcaccagctcaatcagtcacagtgtaaaaaagggccaagtg |
| cagagcgagtatatataggactaaaaaatgacgtaacggttaaagtccacaaaaaacacccagaaaaccgcacgcgaacctacgccc |
| agaaacgaaagccaaaaaacccacaacttcctcaaatcgtcacttccgttttcccacgttacgtaacttcccattttaagaaaactacaattc |
| ccaacacatacaagttactccgccctaaaacctacgtcacccgccccgttcccacgccccgcgccacgtcacaaactccacccccctcat |
| tatcatattggcttcaatccaaaataaggtatattattgatgatg |

TABLE 30

| Ad5-CFTR with Plasmid Backbone |
| --- |

(SEQ ID NO: 30)

gcgtataatggactattgtgtgctgataaggagaacataagcgcagaacaatatgtatctattccggtgttgtgttcctttgttattctgctatta tgttctcttatagtgtgacgaaagcagcataattaatcgccacttgttctttgattgtgttacgatatccagagacttagaaacgggggaacc gggatgagcaaggtaaaaatcggtgagttgatcaacacgcttgtgaatgaggtagaggcaattgatgcctcagaccgcccacaaggcg acaaaacgaagagaattaaagccgcagccgcacggtataagaacgcgttatttaatgataaaagaaagttccgtgggaaaggattgca gaaaagaataaccgcgaatacttttaacgcctatatgagcagggcaagaaagcggtttgatgataaattacatcatagctttgataaaaata ttaataaattatcggaaaagtatcctctttacagcgaagaattatcttcatggctttctatgcctacggctaatattcgccagcacatgtcatcg ttacaatctaaattgaaagaaataatgccgcttgccgaagagttatcaaatgtaagaataggctctaaaggcagtgatgcaaaaatagcaa gactaataaaaaaatatccagattggagttttgctcttagtgatttaaacagtgatgattggaaggagcgccgtgactatctttataagttattc caacaaggctctgcgttgttagaagaactacaccagctcaaggtcaaccatgaggttctgtaccatctgcagctaagccctgcggagcgt acatctatacagcaacgatgggccgatgttctgcgcgagaagaagcgtaatgttgtggttattgactacccaacatacatgcagtctatcta tgatattttgaataatcctgcgactttatttagtttaaacactcgttctggaatggcacctttggcctttgctctggctgcggtatcagggcgaa gaatgattgagataatgtttcagggtgaatttgccgtttcaggaaagtatacggttaatttctcagggcaagctaaaaaacgctctgaagat aaaagcgtaaccagaacgatttatactttatgcgaagcaaaattattcgttgaattattaacagaattgcgttcttgctctgctgcatctgatttc gatgaggttgttaaaggatatggaaaggatgatacaaggtctgagaacggcaggataaatgctattttagcaaaagcatttaacccttggg ttaaatcatttttcggcgatgaccgtcgtgtttataaagatagccgcgctatttacgctcgcatcgcttatgagatgttcttccgcgtcgatcca cggtggaaaaacgtcgacgaggatgtgttcttcatggagattctcggacacgacgatgagaacacccagctgcactataagcagttcaa gctggccaacttctccagaacctggcgacctgaagttggggatgaaaacaccaggctggtggctctgcagaaactggacgatgaaatg ccaggctttgccagaggtgacgctggcgtccgtctccatgaaaccgttaagcagctggtggagcaggacccatcagcaaaaataacca acagcactctccgggcctttaaatttagcccgacgatgattagccggtacctggagtttgccgctgatgcattggggcagttcgttggcga gaacgggcagtggcagctgaagatagagacacctgcaatcgtcctgcctgatgaagaatccgttgagaccatcgacgaaccggatgat gagtcccaagacgacgagctggatgaagatgaaattgagctcgacgagggtggcggcgatgaaccaaccgaagaggaagggccag aagaacatcagccaactgctctaaaacccgtcttcaagcctgcaaaaaataacggggacggaacgtacaagatagagtttgaatacgat ggaaagcattatgcctggtccggccccgccgatagccctatggccgcaatgcgatccgcatgggaaacgtactacagctaaaagaaaa gccaccggtgttaatcggtggctttttattgaggcctgtccctacccatcccctgcaagggacggaaggattaggcggaaactgcagct gcaactacggacatcgccgtcccgactgcagggacttccccgcgtaaagcggggcttaaattcgggctggccaaccctatttttctgca atcgctggcgatgttagtttcgtggatagcgtttccagcttttcaatggccagctcaaaatgtgctggcagcaccttctccagttccgtatca atatcggtgatcggcagctctccacaagacatactccggcgaccgccacgaactacatcgcgcagcagctcccgttcgtagacacgca tgttgcccagagccgtttctgcagccgttaatatccggcgcagctcggcgatgattgccgggagatcatccacggttattgggttcggtga tgggttcctgcaggcgcggcggagagccatccagacgccgctaacccatgcgttacggtactgaaaactttgtgctatgtcgtttatcag gccccgaagttcttctttctgccgccagtccagtggttcaccggcgttcttaggctcaggctcgacaaaagcatactcgccgtttttccgga tagctggcagaacctcgttcgtcacccacttgcggaaccgccaggctgtcgtcccctgtttcaccgcgtcgcggcagcggaggattatg gtgtagagaccagattccgataccacatttacttccctggccatccgatcaagtttttgtgcctcggttaaaccgagggtcaatttttcatcat gatccagcttacgcaatgcatcagaagggttggctatattcaatgcagcacagatatccagcgccacaaaccacgggtcaccaccgac aagaaccacccgtatagggtggctttcctgaaatgaaaagacggagagagccttcattgcgcctccccggatttcagctgctcagaaag ggacagggagcagccgcgagcttcctgcgtgagttcgcgcgcgacctgcagaagttccgcagcttcctgcaaatacagcgtggcctc ataactggagatagtgcggtgagcagagcccacaagcgcttcaacctgcagcaggcgttcctcaatcgtctccagcaggccctgggcg tttaactgaatctggttcatgcgatcacctcgctgaccgggatacgggctgacagaacgaggacaaaacggctggcgaactggcgacg agcttctcgctcggatgatgcagtggtggaaaggcggtggatatgggatttttttgtccgtgcggacgacagctgcaaatttgaatttgaac atggtatgcattcctatcttgtatagggtgctaccaccagagttgagaatctctatagggggtagcccagacagggttctcaacaccgg TABLE 30-continued

| Ad5-CFTR with Plasmid Backbone |
|---|
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactoggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgtttttttatcaactcatcgtgttcggcctggtcaggagtatcgacactcaggtg |
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |

TABLE 30-continued

| Ad5-CFTR with Plasmid Backbone |
| --- |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattccctttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |

TABLE 30-continued

| Ad5-CFTR with Plasmid Backbone |
|---|
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttctagacccgggagcggccgctgtcgacctgcaggatccaat |
| aggcaggctgttgctggtggcaagtgactgggaagggaaatggggtgcgggtgccatgtgaaagagtgtggtcaacacaggcctcac |
| tgaaacaccgaggtttgtgcaaagacatgaaagaggttgggggagcctggcaggtgcctgcggtggggagggaaccgccagtgcca |
| ggacctcaggcagggaggaggaaggtgggggggcagggggggaggcgagtcaggaaggtcatgggaccactttgcaaatgactca |
| cattcctgctgcctctcctttgctgcctctcccatttggagtttctagagggcagagcctgggtttcacatgtttcctttgtgctcagcacaat |
| gctccccctgtgtgtggcatcaggccaagaaatgttccaggcacgaagacagagccctcggcgctcacctcccactcagtgatcacca |
| gaaggtccttgatccccacctgctgggcctggcctgtgtcctgttggctcctgccacaccggcatgccccccacttagccctcagctagca |
| gcatagaaagaaggggcaagagaggcagggaaagagaagttggcggggtttgtttgtttgttcgtttctttggctttttatggccacaccc |
| gtggcatatggaagttcccaggctaggggctgaatcggagctgtagccactggcctacaccacagccacgccagatctgagccatgtc |
| tgcaatatacacttcagctcaaggcaacaccagatccttaacccactgagtgaggccagggattgaacccacatcctcatggatactggt |
| cggccttgttactgctgagtcacaataggaacttccaggaaagagagatttgaatcttgaatttgcccggtgccagtcgtgtggcgttgag |
| caaagtgctttctctctctgagcctcagtttcttcctctgggccaataatccctttcctgtagggttgtcatgaaagtacatggcaggtgtgctc |
| agcacacggtggcattttccttcaagggccctttgacccccctcgaaggggtttcattttcactttgagtggacccagaaggtgatgccctct |
| gctgccccctaggccacactggacaacaagctgggaactcccttcacctcccgagcatcccgcctagcccaccattcagtctccacga |
| cctgccacatccacatgccatgaagctatggggcctgttgaactggatgcccaaaaggccaggacccccacccgctgcccggggtcat |
| ggggaagccaggctggaacagcctccggtacccatgatgggcagccgctgtgttcaaagcctccgcaacttccagccccgaagcca |
| ggggaacagacgacccaccctctgggctggcagacgcccagtcggaaaccacgcgtcgtagcgctaccggactcagatctcgagaa |
| cacactgcaagtcctcagccctaccccccccatcaaggccccctgtctggagtgggggtgcaccctaagctagcccaggaagcctcc |
| ccgagttacttctgtctgcgcctgctggggactatgctggggctgctggggactatgctgagtgcgtttccctcaagttgtcttttttttttttttt |
| tttttttgtcttttgtccttttatggaggtccccaagctaggggtctaatcggagctgtagctgccggcctacaccacagccacagcaacgcc |
| ggatccttatcccactgagcaaggccagggatcgaacctcaacctcatggttcctagtcagattcatttccgctgcgccatgatgggagtg |
| ccgccctcaagttgtcttgtatcagggagtcaggggctggctgagattgaaagcggagtgtccaggtttaagcagacttgtgccaggca |
| gttgactaaagcaccagcagttcctgcccgggtttctctgcccacttagtcatggtgactgcatgccctggccgggtcctgactttggata |
| gtcccttcccagaggggaccctgacagtgtgtcctctgggatttggggctccccagatctggggcttgtgggcatcactgtcctccgtgc |
| acatgcagcactgtcacatgtgtcccctgatgggagcatgccaggatgacaaggttatccctgcttatcagctctttcccagcttcctctgc |
| ctgttgcttatagacatgagccctgggcgccacgtcttcctcaaataatgagaggaagtgtggtcatcggcacacagatggctgggggtt |
| ccggattgcggctcccggccaccactccctgacctgcgccccatctctcgccaggcggtcctcggctctttcctctgcagtcgacggta |
| ccctcctgggcaacgtgctggttattgtgctgtctcatcattttggcaaagaattccgctgcgactcggcggagtcccggcggcgcgtcct |
| tgttctaacccggcgcgccagcttggcaatccggtactgttggtaaagccaccatgcagaggtcgcctctggaaaaggccagcgttgtc |
| tccaaactttttttcagctggaccagaccaattttgaggaaaggatacagacagcgcctggaattgtcagacatataccaaatcccttctgtt |
| gattctgctgacaatctatctgaaaaaattggaaagagaatgggatagagagctggcttcaaagaaaaatcctaaactcattaatgcccttc |
| ggcgatgtttttttctggagatttatgttctatggaatctttttatatttaggggaagtcaccaaagcagtacagcctctcttactgggaagaatc |
| atagcttcctatgacccggataacaaggaggaacgctctatcgcgatttatctaggcataggcttatgccttctctttattgtgaggacactg |
| ctcctacacccagccatttttggccttcatcacattggaatgcagatgagaatagctatgtttagtttgatttataagaagactttaaagctgtc |
| aagccgtgttctagataaaataagtattggacaacttgttagtctcctttccaacaacctgaacaaatttgatgaaggacttgcattggcacat |
| ttcgtgtggatcgctcctttgcaagtggcactcctcatggggctaatctgggagttgttacaggcgtctgccttctgtggacttggtttcctga |
| tagtccttgcccttttttcaggctgggctagggagaatgatgatgaagtacagagatcagagagctgggaagatcagtgaaagacttgtga |
| ttacctcagaaatgattgaaaatatccaatctgttaaggcatactgctgggaagaagcaatggaaaaaatgattgaaaacttaagacaaac |

TABLE 30-continued

| Ad5-CFTR with Plasmid Backbone |
|---|
| agaactgaaactgactcggaaggcagcctatgtgagatacttcaatagctcagccttcttcttctcagggttctttgtggtgtttttatctgtgc<br>ttccctatgcactaatcaaaggaatcatcctccggaaaatattcaccaccatctcattctgcattgttctgcgcatggcggtcactcggcaat<br>ttccctgggctgtacaaacatggtatgactctcttggagcaataaacaaaatacaggatttcttacaaaagcaagaatataagacattggaa<br>tataacttaacgactacagaagtagtgatggagaatgtaacagccttctgggaggagggatttggggaattatttgagaaagcaaaacaa<br>aacaataacaatagaaaaacttctaatggtgatgacagcctcttcttcagtaatttctcacttcttggtactcctgtcctgaaagatattaatttc<br>aagatagaaagaggacagttgttggcggttgctggatccactggagcaggcaagacttcacttctaatgatgattatgggagaactgga<br>gccttcagagggtaaaattaagcacagtggaagaatttcattctgttctcagttttcctggattatgcctggcaccattaaagaaaatatcatc<br>tttggtgtttcctatgatgaatatagatacagaagcgtcatcaaagcatgccaactagaagaggacatctccaagtttgcagagaaagaca<br>atatagttcttggagaaggtggaatcacactgagtggaggtcaacgagcaagaatttctttagcaagagcagtatacaaagatgctgattt<br>gtatttattagactctccttttggatacctagatgttttaacagaaaaagaaatatttgaaagctgtgtctgtaaactgatggctaacaaaacta<br>ggattttggtcacttctaaaatggaacatttaaagaaagctgacaaaatattaattttgcatgaaggtagcagctatttttatgggacattttca<br>gaactccaaaatctacagccagactttagctcaaaactcatgggatgtgattctttcgaccaatttagtgcagaaagaagaaattcaatcct<br>aactgagaccttacaccgtttctcattagaaggagatgctcctgtctcctggacagaaacaaaaaaacaatcttttaaacagactggagag<br>tttggggaaaaaaggaagaattctattctcaatccaatcaactctatacgaaaattttccattgtgcaaaagactcccttacaaatgaatggc<br>atcgaagaggattctgatgagcctttagagagaaggctgtccttagtaccagattctgagcagggagaggcgatactgcctcgcatcag<br>cgtgatcagcactggccccacgcttcaggcacgaaggaggcagtctgtcctgaacctgatgacacactcagttaaccaaggtcagaac<br>attcaccgaaagacaacagcatccacacgaaaagtgtcactggcccctcaggcaaacttgactgaactggatatatattcaagaaggtta<br>tctcaagaaactggcttggaaataagtgaagaaattaacgaagaagacttaaaggagtgctttttttgatgatatggagagcataccagcag<br>tgactacatggaacacataccttcgatatattactgtccacaagagcttaatttttgtgctaatttggtgcttagtaatttttctggcagaggtgg<br>ctgcttctttggttgtgctgtggctccttggaaacactcctcttcaagacaaagggaatagtactcatagtagaaataacagctatgcagtga<br>ttatcaccagcaccagttcgtattatgtgttttacatttacgtgggagtagccgacactttgcttgctatgggattcttcagaggtctaccactg<br>gtgcatactctaatcacagtgtcgaaaattttacaccacaaaatgttacattctgttcttcaagcacctatgtcaaccctcaacacgttgaaag<br>caggtgggattcttaatagattctccaaagatatagcaattttggatgaccttctgcctcttaccatatttgacttcatccagttgttattaattgt<br>gattggagctatagcagttgtcgcagttttacaaccctacatctttgttgcaacagtgccagtgatagtggcttttattatgttgagagcatattt<br>cctccaaacctcacagcaactcaaacaactggaatctgaaggcaggagtccaattttcactcatcttgttacaagcttaaaaggactatgg<br>acacttcgtgccttcggacggcagccttactttgaaactctgttccacaaagctctgaatttacatactgccaactggttcttgtacctgtcaa<br>cactgcgctggttccaaatgagaatagaaatgattttgtcatcttcttcattgctgttaccttcatttccattttaacaacaggagaaggagaa<br>ggaagagttggtattatcctgactttagccatgaatatcatgagtacattgcagtgggctgtaaactccagcatagatgtggatagcttgatg<br>cgatctgtgagccgagtctttaagttcattgacatgccaacagaaggtaaacctaccaagtcaaccaaaccatacaagaatggccaactc<br>tcgaaagttatgattattgagaattcacacgtgaagaaagatgacatctggccctcagggggccaaatgactgtcaaagatctcacagca<br>aaatacacagaaggtggaaatgccatattagagaacatttccttctcaataagtcctggccagagggggcctcttgggaagaactgga<br>tcagggaagagtactttgttatcagctttttttgagactactgaacactgaaggagaaatccagatcgatggtgtgtcttgggattcaataactt<br>tgcaacagtggaggaaagcctttggagtgataccacagaaagtatttatttttctggaacatttagaaaaaacttggatccctatgaacagt<br>ggagtgatcaagaaatatggaaagttgcagatgaggttgggctcagatctgtgatagaacagtttcctgggaagcttgactttgtccttgtg<br>gatgggggctgtgtcctaagccatggccacaagcagttgatgtgcttggctagatctgttctcagtaaggcgaagatcttgctgcttgatg<br>aacccagtgctcatttggatccagtaacataccaaataattagaagaactctaaaacaagcatttgctgattgcacagtaattctctgtgaac<br>acaggatagaagcaatgctggaatgccaacaatttttggtcatagaagagaacaaagtgcggcagtacgattccatccagaaactgctg<br>aacgagaggagcctcttccggcaagccatcagcccctccgacagggtgaagctctttccccaccggaactcaagcaagtgcaagtcta<br>agccccagattgctgctctgaaagaggagacagaagaagaggtgcaagatacaaggctttagtaataattctagagtcggggcggccg |

TABLE 30-continued

| Ad5-CFTR with Plasmid Backbone |
| --- |
| gccgcttcgagagctagagctttcttgctgtccaatttctattaaaggttcctttgttccctaagtccaactactaaactgggggatattatgaa |
| gggccttgagcatctggattctgcctaataaaaaacatttattttcattgcaatgatgtattttaaaatcgataaggatccgaattcgatatcact |
| agtggtaccagtactgaaatgtgtgggcgtggcttaagggtgggaaagaatatataaggtgggggtcttatgtagttttgtatctgttttgca |
| gcagccgccgccgccatgagcaccaactcgtttgatggaagcattgtgagctcatatttgacaacgcgcatgcccccatgggccgggg |
| tgcgtcagaatgtgatgggctccagcattgatggtcgccccgtcctgcccgcaaactctactaccttgacctacgagaccgtgtctggaa |
| cgccgttggagactgcagcctccgccgccgcttcagccgctgcagccaccgcccgcgggattgtgactgactttgctttcctgagcccg |
| cttgcaagcagtgcagcttcccgttcatccgcccgcgatgacaagttgacggctcttttggcacaattggattctttgacccgggaacttaa |
| tgtcgtttctcagcagctgttggatctgcgccagcaggtttctgccctgaaggcttcctcccctcccaatgcggtttaacggtccgggcca |
| gagtggccaacataaataaaaaaccagactctgtttggatttggatcaagcaagtgtcttgctgtctttatttaggggttttgcgcgcgcggt |
| aggcccgggaccagcggtctcggtcgttgagggtcctgtgtatttttttccaggacgtggtaaaggtgactctggatgttcagatacatggg |
| cataagcccgtctctgggggggaggtagcaccactgcagagcttcatgctgcggggtggtgttgtagatgatccagtcgtagcaggagc |
| gctgggcgtggtgcctaaaaatgtctttcagtagcaagctgattgccaggggcaggcccttggtgtaagtgtttacaaagcggttaagct |
| gggatgggtgcatacgtggggatatgagatgcatcttggactgtatttttaggttggctatgttcccagccatatccctccggggattcatgt |
| tgtgcagaaccaccagcacagtgtatccggtgcacttgggaaatttgtcatgtagcttagaaggaaatgcgtggaagaacttggagacg |
| cccttgtgacctccaagattttccatgcattcgtccataatgatggcaatgggcccacgggcggcggcctgggcgaagatatttctgggat |
| cactaacgtcatagttgtgttccaggatgagatcgtcataggccatttttacaaagcgcgggcggagggtgccagactgcggtataatgg |
| ttccatccggcccaggggcgtagttaccctcacagatttgcatttcccacgctttgagttcagatgggggggatcatgtctacctgcggggc |
| gatgaagaaaacggtttccggggtaggggagatcagctgggaagaaagcaggttcctgagcagctgcgacttaccgcagccggtgg |
| gcccgtaaatcacacctattaccggctgcaactggtagttaagagagctgcagctgccgtcatccctgagcaggggggccacttcgtta |
| agcatgtccctgactcgcatgttttccctgaccaaatccgccagaaggcgctcgccgcccagcgatagcagttcttgcaaggaagcaaa |
| gtttttcaacggtttgagaccgtccgccgtaggcatgcttttgagcgtttgaccaagcagttccaggcggtcccacagctcggtcacctgc |
| tctacggcatctcgatccagcatatctcctcgtttcgcgggttggggcggctttcgctgtacggcagtagtcggtgctcgtccagacgggc |
| cagggtcatgtctttccacgggcgcagggtcctcgtcagcgtagtctgggtcacggtgaaggggtgcgctccgggctgcgcgctggcc |
| agggtgcgcttgaggctggtcctgctggtgctgaagcgctgccggtcttcgccctgcgcgtcggccaggtagcatttgaccatggtgtc |
| atagtccagcccctccgcggcgtggcccttggcgcgcagcttgcccttggaggaggcgccgcacgaggggcagtgcagacttttgag |
| ggcgtagagcttgggcgcgagaaataccgattccggggagtaggcatccgcgccgcaggccccgcagacggtctcgcattccacga |
| gccaggtgagctctggccgttcggggtcaaaaaccaggtttcccccatgctttttgatgcgtttcttacctctggtttccatgagccggtgtc |
| cacgctcggtgacgaaaaggctgtccgtgtccccgtatacagacttgagaggcctgtcctcgagcggtgttccgcggtcctcctcgtata |
| gaaactcggaccactctgagacaaaggctcgcgtccaggccagcacgaaggaggctaagtgggaggggtagcggtcgttgtccact |
| agggggtccactcgctccagggtgtgaagacacatgtcgccctcttcggcatcaaggaaggtgattggtttgtaggtgtaggccacgtg |
| accgggtgttcctgaaggggggctataaaagggggtgggggcgcgttcgtcctcactctcttccgcatcgctgtctgcgagggccagct |
| gttggggtgagtactccctctgaaaagcgggcatgacttctgcgctaagattgtcagtttccaaaaacgaggaggatttgatattcacctg |
| gcccgcggtgatgcctttgagggtggccgcatccatctggtcagaaaagacaatctttttgttgtcaagcttggtggcaaacgacccgta |
| gagggcgttggacagcaacttggcgatggagcgcagggtttggtttttgtcgcgatcggcgcgctccttggccgcgatgtttagctgcac |
| gtattcgcgcgcaacgcaccgccattcgggaaagacggtggtgcgctcgtcgggcaccaggtgcacgcgccaaccgcggttgtgca |
| gggtgacaaggtcaacgctggtggctacctctccgcgtaggcgctcgttggtccagcagaggggccgcccttgcgcgagcagaatg |
| gcggtagggggtctagctgcgtctcgtccgggggggtctgcgtccacggtaaagaccccgggcagcaggcgcgcgtcgaagtagtct |
| atcttgcatccttgcaagtctagcgcctgctgccatgcgcgggcggcaagcgcgcgctcgtatgggttgagtgggggaccccatggca |
| tggggtgggtgagcgcggaggcgtacatgccgcaaatgtcgtaaacgtagaggggctctctgagtattccaagatatgtagggtagcat |

TABLE 30-continued

| Ad5-CFTR with Plasmid Backbone |
|---|
| cttccaccgcggatgctggcgcgcacgtaatcgtatagttcgtgcgagggagcgaggaggtcgggaccgaggttgctacgggcggg |
| ctgctctgctcggaagactatctgcctgaagatggcatgtgagttggatgatatggttggacgctggaagacgttgaagctggcgtctgtg |
| agacctaccgcgtcacgcacgaaggaggcgtaggagtcgcgcagcttgttgaccagctcggcggtgacctgcacgtctagggcgca |
| gtagtccagggtttccttgatgatgtcatacttatcctgtcccttttttttccacagctcgcggttgaggacaaactcttcgcggtctttccagta |
| ctcttggatcggaaacccgtcggcctccgaacggtaagagcctagcatgtagaactggttgacggcctggtaggcgcagcatcccttttt |
| ctacgggtagcgcgtatgcctgcgcggccttccggagcgaggtgtgggtgagcgcaaaggtgtccctgaccatgactttgaggtactg |
| gtatttgaagtcagtgtcgtcgcatccgccctgctcccagagcaaaaagtccgtgcgctttttggaacgcggatttggcagggcgaaggt |
| gacatcgttgaagagtatctttcccgcgcgaggcataaagttgcgtgtgatgcggaagggtcccggcacctcggaacggttgttaattac |
| ctgggcggcgagcacgatctcgtcaaagccgttgatgttgtggcccacaatgtaaagttccaagaagcgcgggatgcccttgatggaa |
| ggcaatttttttaagttcctcgtaggtgagctcttcaggggagctgagcccgtgctctgaaagggcccagtctgcaagatgagggttggaa |
| gcgacgaatgagctccacaggtcacgggccattagcatttgcaggtggtcgcgaaaggtcctaaactggcgacctatggccatttttct |
| ggggtgatgcagtagaaggtaagcgggtcttgttcccagcggtcccatccaaggttcgcggctaggtctcgcgcggcagtcactagag |
| gctcatctccgccgaacttcatgaccagcatgaagggcacgagctgcttcccaaaggcccccatccaagtataggtctctacatcgtag |
| gtgacaaagagacgctcggtgcgaggatgcgagccgatcgggaagaactggatctcccgccaccaattggaggagtggctattgatg |
| tggtgaaagtagaagtccctgcgacgggccgaacactcgtgctggcttttgtaaaaacgtgcgcagtactggcagcggtgcacgggct |
| gtacatcctgcacgaggttgacctgacgaccgcgcacaaggaagcagagtgggaatttgagcccctcgcctggcgggtttggctggtg |
| gtcttctacttcggctgcttgtccttgaccgtctggctgctcgaggggagttacggtggatcggaccaccacgccgcgcgagcccaaagt |
| ccagatgtccgcgcgcggcggtcggagcttgatgacaacatcgcgcagatgggagctgtccatggtctggagctcccgcggcgtcag |
| gtcaggcgggagctcctgcaggtttacctcgcatagacgggtcagggcgcgggctagatccaggtgatacctaatttccaggggctgg |
| ttggtggcggcgtcgatggcttgcaagaggccgcatccccgcggcgcgactacggtaccgcgcggcgggcggtgggccgcgggg |
| gtgtccttggatgatgcatctaaaagcggtgacgcgggcgagcccccggaggtagggggggctccggacccgccgggagagggg |
| gcaggggcacgtcggcgccgcgcgcgggcaggagctggtgctgcgcgcgtaggttgctggcgaacgcgacgacgcggcggttga |
| tctcctgaatctggcgcctctgcgtgaagacgacgggcccggtgagcttgaacctgaaagagagttcgacagaatcaatttcggtgtcgt |
| tgacggcggcctggcgcaaaatctcctgcacgtctcctgagttgtcttgataggcgatctcggccatgaactgctcgatctcttcctcctgg |
| agatctccgcgtccggctcgctccacggtggcggcgaggtcgttggaaatgcgggccatgagctgcgagaaggcgttgaggcctccc |
| tcgttccagacgcggctgtagaccacgcccccttcggcatcgcggggcgcatgaccacctgcgcgagattgagctccacgtgccgg |
| gcgaagacggcgtagtttcgcaggcgctgaaagaggtagttgagggtggtggcggtgtgttctgccacgaagaagtacataacccag |
| cgtcgcaacgtggattcgttgatatcccccaaggcctcaaggcgctccatggcctcgtagaagtccacggcgaagttgaaaaactggg |
| agttgcgcgccgacacggttaactcctcctccagaagacggatgagctcggcgacagtgtcgcgcacctcgcgctcaaaggctacag |
| gggcctcttcttcttcttcaatctcctcttccataagggcctccccttcttcttcttctggcggcggtgggggaggggggacacggcggcg |
| acgacggcgcaccgggaggcggtcgacaaagcgctcgatcatctccccgcggcgacggcgcatggtctcggtgacggcgcggcc |
| gttctcgcgggggcgcagttggaagacgccgcccgtcatgtcccggttatgggttggcgggggggctgccatgcggcagggatacgg |
| cgctaacgatgcatctcaacaattgttgtgtaggtactccgccgccgagggacctgagcgagtccgcatcgaccggatcggaaaacctc |
| tcgagaaaggcgtctaaccagtcacagtcgcaaggtaggctgagcaccgtgggggcggcagcgggcggcggtcggggttgtttct |
| ggcggaggtgctgctgatgatgtaattaaagtaggcggtcttgagacggcggatggtcgacagaagcaccatgtccttgggtccggcct |
| gctgaatgcgcaggcggtcggccatgccccaggcttcgttttgacatcggcgcaggtctttgtagtagtcttgcatgagcctttctaccgg |
| cacttcttcttctccttcctcttgtcctgcatctcttgcatctatcgctgcggcggcggcggagtttggccgtaggtggcgccctcttcctccc |
| atgcgtgtgaccccgaagcccctcatcggctgaagcagggctaggtcggcgacaacgcgctcggctaatatggcctgctgcacctgc |
| gtgagggtagactggaagtcatccatgtccacaaagcggtggtatgcgcccgtgttgatggtgtaagtgcagttggccataacggacca |

TABLE 30-continued

| Ad5-CFTR with Plasmid Backbone |
| --- |
| gttaacggtctggtgacccggctgcgagagctcggtgtacctgagacgcgagtaagccctcgagtcaaatacgtagtcgttgcaagtcc |
| gcaccaggtactggtatcccaccaaaaagtgcggcggcggctggcggtagaggggccagcgtagggtggccggggctccgggggg |
| cgagatcttccaacataaggcgatgatatccgtagatgtacctggacatccaggtgatgccggcggcggtggtggaggcgcgcggaa |
| agtcgcggacgcggttccagatgttgcgcagcggcaaaaagtgctccatggtcgggacgctctggccggtcaggcgcgcgcaatcgt |
| tgacgctctagaccgtgcaaaaggagagcctgtaagcgggcactcttccgtggtctggtggataaattcgcaagggtatcatggcggac |
| gaccggggttcgagccccgtatccggccgtccgccgtgatccatgcggttaccgcccgcgtgtcgaacccaggtgtgcgacgtcaga |
| caacgggggagtgctccttttggcttccttccaggcgcggcggctgctgcgctagcttttttggccactggccgcgcgcagcgtaagcg |
| gttaggctggaaagcgaaagcattaagtggctcgctccctgtagccggagggttattttccaagggttgagtcgcgggacccccggttc |
| gagtctcggaccggccggactgcggcgaacgggggtttgcctccccgtcatgcaagaccccgcttgcaaattcctccggaaacaggg |
| acgagcccctttttttgcttttcccagatgcatccggtgctgcggcagatgcgcccccctcctcagcagcggcaagagcaagagcagcg |
| gcagacatgcagggcaccctcccctcctcctaccgcgtcaggaggggcgacatccgcggttgacgcggcagcagatggtgattacga |
| acccccgcggcgccgggcccggcactacctggacttggaggagggcgagggcctggcgcggctaggagcgccctctcctgagcg |
| gcacccaagggtgcagctgaagcgtgatacgcgtgaggcgtacgtgccgcggcagaacctgtttcgcgaccgcgagggagaggag |
| cccgaggagatgcgggatcgaaagttccacgcagggcgcgagctgcggcatggcctgaatcgcgagcggttgctgcgcgaggagg |
| actttgagcccgacgcgcgaaccgggattagtcccgcgcgcgcacacgtggggccgccgacctggtaaccgcatacgagcagac |
| ggtgaaccaggagattaactttcaaaaaagctttaacaaccacgtgcgtacgcttgtggcgcgcgaggaggtggctataggactgatgc |
| atctgtgggactttgtaagcgcgctggagcaaaacccaaatagcaagccgctcatggcgcagctgttccttatagtgcagcacagcagg |
| gacaacgaggcattcagggatgcgctgctaaacatagtagagcccgagggccgctggctgctcgatttgataaacatcctgcagagca |
| tagtggtgcaggagcgcagcttgagcctggctgacaaggtggccgccatcaactattccatgcttagcctgggcaagttttacgcccgc |
| aagatataccatacccttacgttcccatagacaaggaggtaaagatcgaggggttctacatgcgcatggcgctgaaggtgcttaccttg |
| agcgacgacctgggcgtttatcgcaacgagcgcatccacaaggccgtgagcgtgagccggcggcgcgagctcagcgaccgcgagc |
| tgatgcacagcctgcaaagggccctggctggcacgggcagcggcgatagagaggccgagtcctactttgacgcgggcgctgacctg |
| cgctgggccccaagccgacgcgccctggaggcagctggggccggacctgggctggcggtggcacccgcgcgcgctggcaacgtc |
| ggcggcgtggaggaatatgacgaggacgatgagtacgagccagaggacggcgagtactaagcggtgatgtttctgatcagatgatgc |
| aagacgcaacggacccggcggtgcgggcggcgctgcagagccagccgtccggccttaactccacggacgactggcgccaggtcat |
| ggaccgcatcatgtcgctgactgcgcgcaatcctgacgcgttccggcagcagccgcaggccaaccggctctccgcaattctggaagc |
| ggtggtcccggcgcgcgcaaaccccacgcacgagaaggtgctggcgatcgtaaacgcgctggccgaaaacagggccatccggccc |
| gacgaggccggcctggtctacgacgcgctgcttcagcgcgtggctcgttacaacagcggcaacgtgcagaccaacctggaccggct |
| ggtgggggatgtgcgcgaggccgtggcgcagcgtgagcgcgcgcagcagcagggcaacctgggctccatggttgcactaaacgcc |
| ttcctgagtacacagcccgccaacgtgccgcggggacaggaggactacaccaactttgtgagcgcactgcggctaatggtgactgag |
| acaccgcaaagtgaggtgtaccagtctgggccagactattttttccagaccagtagacaaggcctgcagaccgtaaacctgagccagg |
| ctttcaaaaacttgcaggggctgtggggggtgcgggctcccacaggcgaccgcgcgaccgtgtctagcttgctgacgcccaactcgc |
| gcctgttgctgctgctaatagcgcccttcacggacagtggcagcgtgtcccgggacacatacctaggtcacttgctgacactgtaccgcg |
| aggccataggtcaggcgcatgtggacgagcatactttccaggagattacaagtgtcagccgcgcgctggggcaggaggacacgggc |
| agcctggaggcaaccctaaactacctgctgaccaaccggcggcagaagatcccctcgttgcacagtttaaacagcgaggaggagcgc |
| attttgcgctacgtgcagcagagcgtgagccttaacctgatgcgcgacggggtaacgcccagcgtggcgctggacatgaccgcgcgc |
| aacatggaaccgggcatgtatgcctcaaaccggccgtttatcaaccgcctaatggactacttgcatcgcgcggccgccgtgaaccccg |
| agtatttcaccaatgccatcttgaacccgcactggctaccgccccctggtttctacaccgggggattcgaggtgcccgagggtaacgatg |
| gattcctctgggacgacatagacgacagcgtgttttccccgcaaccgcagaccctgctagagttgcaacagcgcgagcaggcagagg |

TABLE 30-continued

| Ad5-CFTR with Plasmid Backbone |
| --- |
| cggcgctgcgaaaggaaagcttccgcaggccaagcagcttgtccgatctaggcgctgcggccccgcggtcagatgctagtagcccat |
| ttccaagcttgatagggtctcttaccagcactcgcaccacccgcccgcgcctgctgggcgaggaggagtacctaaacaactcgctgctg |
| cagccgcagcgcgaaaaaaacctgcctccggcatttcccaacaacgggatagagagcctagtggacaagatgagtagatggaagac |
| gtacgcgcaggagcacagggacgtgccaggcccgcgcccgcccacccgtcgtcaaaggcacgaccgtcagcggggtctggtgtgg |
| gaggacgatgactcggcagacgacagcagcgtcctggatttgggagggagtggcaacccgtttgcgcaccttcgccccaggctggg |
| gagaatgttttaaaaaaaaaaaaaagcatgatgcaaaataaaaaactcaccaaggccatggcaccgagcgttggttttcttgtattccctt |
| agtatgcggcgcgcggcgatgtatgaggaaggtcctcctccctcctacgagagtgtggtgagcgcggcgccagtggcggcggcgct |
| gggttctcccttcgatgctcccctggacccgccgtttgtgcctccgcggtacctgcggcctaccgggggagaaacagcatccgttact |
| ctgagttggcacccctattcgacaccacccgtgtgtacctggtggacaacaagtcaacggatgtggcatccctgaactaccagaacgac |
| cacagcaactttctgaccacggtcattcaaaacaatgactacagcccgggggaggcaagcacacagaccatcaatcttgacgaccggt |
| cgcactggggcggcgacctgaaaaccatcctgcataccaacatgccaaatgtgaacgagttcatgtttaccaataagtttaaggcgcgg |
| gtgatggtgtcgcgcttgcctactaaggacaatcaggtggagctgaaatacgagtgggggagttcacgctgcccgagggcaactactc |
| cgagaccatgaccatagaccttatgaacaacgcgatcgtggagcactacttgaaagtgggcagacagaacggggttctggaaagcga |
| catcggggtaaagtttgacacccgcaacttcagactggggtttgaccccgtcactggtcttgtcatgcctggggtatatacaaacgaagc |
| cttccatccagacatcattttgctgccaggatgcgggggacttcacccacagccgcctgagcaacttgttgggcatccgcaagcggc |
| aacccttccaggagggctttaggatcacctacgatgatctggagggtggtaacattcccgcactgttggatgtggacgcctaccaggcg |
| agcttgaaagatgacaccgaacagggggggtggcgcaggcggcagcaacagcagtggcagcggcgcggaagagaactccaa |
| cgcggcagccgcggcaatgcagccggtggaggacatgaacgatcatgccattcgcggcgacacctttgccacacgggctgaggaga |
| agcgcgctgaggccgaagcagcggccgaagctgccgcccccgctgcgcaacccgaggtcgagaagcctcagaagaaaccggtga |
| tcaaacccctgacagaggacagcaagaaacgcagttacaacctaataagcaatgacagcaccttcacccagtaccgcagctggtacct |
| tgcatacaactacggcgaccctcagaccggaatccgctcatggaccctgctttgcactcctgacgtaacctgcggctcggagcaggtct |
| actggtcgttgccagacatgatgcaagaccccgtgaccttccgctccacgcgccagatcagcaactttccggtggtgggcgccgagct |
| gttgcccgtgcactccaagagcttctacaacgaccaggccgtctactcccaactcatccgccagtttacctctctgacccacgtgttcaatc |
| gctttcccgagaaccagattttggcgcgcccgccagccccaccatcaccaccgtcagtgaaaacgttcctgctctcacagatcacggg |
| acgctaccgctgcgcaacagcatcggaggagtccagcgagtgaccattactgacgccagacgccgcacctgcccctacgtttacaag |
| gccctgggcatagtctcgccgcgcgtcctatcgagccgcactttttgagcaagcatgtccatccttatatcgcccagcaataacacaggct |
| ggggcctgcgcttcccaagcaagatgtttggcggggccaagaagcgctccgaccaacacccagtgcgcgtgcgcgggcactaccgc |
| gcgccctggggcgcgcacaaacgcggccgcactgggcgcaccaccgtcgatgacgccatcgacgcggtggtggaggaggcgcgc |
| aactacacgcccacgccgccaccagtgtccacagtggacgcggccattcagaccgtggtgcgcggagcccggcgctatgctaaaatg |
| aagagacggcggaggcgcgtagcacgtcgccaccgccgccgacccggcactgccgcccaacgcgcggcggcggccctgcttaac |
| cgcgcacgtcgcaccggccgacgggcggccatgcgagcagctcgaaggctggccgcgggtattgtcactgtgccccccaggtcca |
| ggcgacgagcggccgccgcagcagccgcggccattagtgctatgactcagggtcgcaggggcaacgtgtattgggtgcgcgactcg |
| gttagcggcctgcgcgtgcccgtgcgcacccgcccccccgcgcaactagattgcaagaaaaaactacttagactcgtactgttgtatgtat |
| ccagcggcggcggcgcgcaacgaagctatgtccaagcgcaaaatcaaagaagagatgctccaggtcatcgcgccggagatctatgg |
| ccccccgaagaaggaagagcaggattacaagccccgaaagctaaagcgggtcaaaaagaaaaagaaagatgatgatgatgaacttg |
| acgacgaggtggaactgctgcacgctaccgcgcccaggcgacgggtacagtggaaaggtcgacgcgtaaaacgtgttttgcgaccc |
| ggcaccaccgtagtctttacgcccggtgagcgctccacccgcacctacaagcgcgtgtatgatgaggtgtacggcgacgaggacctg |
| cttgagcaggccaacgagcgcctcggggagtttgcctacggaaagcggcataaggacatgctggcgttgccgctggacgagggcaa |
| cccaacacctagcctaaagcccgtaacactgcagcaggtgctgcccgcgcttgcaccgtccgaagaaaagcgcggcctaaagcgcg |

TABLE 30-continued

| Ad5-CFTR with Plasmid Backbone |
| --- |
| agtctggtgacttggcacccaccgtgcagctgatggtacccaagcgccagcgactggaagatgtcttggaaaaaatgaccgtggaacc |
| tgggctggagcccgaggtccgcgtgcggccaatcaagcaggtggcgccgggactgggcgtgcagaccgtggacgttcagataccc |
| actaccagtagcaccagtattgccaccgccacagagggcatggagacacaaacgtccccggttgcctcagcggtggcggatgccgc |
| ggtgcaggcggtcgctgcggccgcgtccaagacctctacggaggtgcaaacggacccgtggatgtttcgcgtttcagccccccggcg |
| cccgcgccgttcgaggaagtacggcgccgccagcgcgctactgcccgaatatgccctacatccttccattgcgcctacccccggctatc |
| gtggctacacctaccgccccagaagacgagcaactacccgacgccgaaccaccactggaacccgccgccgccgtcgccgtcgcca |
| gcccgtgctggccccgatttccgtgcgcagggtggctcgcgaaggaggcaggaccctggtgctgccaacagcgcgctaccaccccca |
| gcatcgtttaaaagccggtctttgtggttcttgcagatatggccctcacctgccgcctccgtttcccggtgccgggattccgaggaagaat |
| gcaccgtaggaggggcatggccggccacggcctgacgggcggcatgcgtcgtgcgcaccaccggcggcggcgcgcgtcgcacc |
| gtcgcatgcgcggcggtatcctgcccctccttattccactgatcgccgcggcgattggcgccgtgcccggaattgcatccgtggccttgc |
| aggcgcagagacactgattaaaaacaagttgcatgtggaaaaatcaaaataaaaagtctggactctcacgctcgcttggtcctgtaactat |
| tttgtagaatggaagacatcaactttgcgtctctggccccgcgacacggctcgcgcccgttcatgggaaactggcaagatatcggcacc |
| agcaatatgagcggtggcgccttcagctggggctcgctgtggagcggcattaaaaatttcggttccaccgttaagaactatggcagcaa |
| ggcctggaacagcagcacaggccagatgctgagggataagttgaaagagcaaaatttccaacaaaaggtggtagatggcctggcctc |
| tggcattagcggggtggtggacctggccaaccaggcagtgcaaaataagattaacagtaagcttgatccccgccctcccgtagaggag |
| cctccaccggccgtggagacagtgtctccagaggggcgtggcgaaaagcgtccgcgccccgacagggaagaaactctggtgacgc |
| aaatagacgagcctccctcgtacgaggaggcactaaagcaaggcctgcccaccacccgtcccatcgcgcccatggctaccggagtgc |
| tgggccagcacacacccgtaacgctggacctgcctcccccgccgacacccagcagaaacctgtgctgccaggcccgaccgccgtt |
| gttgtaacccgtcctagccgcgcgtccctgcgccgcgccgccagcggtccgcgatcgttgcggcccgtagccagtggcaactggcaa |
| agcacactgaacagcatcgtgggtctgggggtgcaatccctgaagcgccgacgatgcttctgaatagctaacgtgtcgtatgtgtgtcat |
| gtatgcgtccatgtcgccgccagaggagctgctgagccgccgcgcgcccgctttccaagatggctaccccttcgatgatgccgcagtg |
| gtcttacatgcacatctcgggccaggacgcctcggagtacctgagccccgggctggtgcagtttgcccgcgccaccgagacgtacttc |
| agcctgaataacaagtttagaaccccacggtggcgcctacgcacgacgtgaccacagaccggtcccagcgtttgacgctgcggttca |
| tccctgtggaccgtgaggatactgcgtactcgtacaaggcgcggttcaccctagctgtgggtgataaccgtgtgctggacatggcttcca |
| cgtactttgacatccgcggcgtgctggacaggggccctacttttaagccctactctggcactgcctacaacgccctggctcccaagggtg |
| ccccaaatccttgcgaatgggatgaagctgctactgctcttgaaataaacctagaagaagaggacgatgacaacgaagacgaagtaga |
| cgagcaagctgagcagcaaaaaactcacgtatttgggcaggcgccttattctggtataaatattacaaaggagggtattcaaataggtgtc |
| gaaggtcaaacacctaaatatgccgataaaacatttcaacctgaacctcaaataggagaatctcagtggtacgaaacagaaattaatcat |
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataattttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |

TABLE 30-continued

| Ad5-CFTR with Plasmid Backbone |
|---|
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggcggct |
| ttccgcggctgggccttcacgcgccttaagactaaggaaaccccatcactgggctcgggctacgacccttattacacctactctggctcta |
| taccctacctagatggaacctttacctcaaccacacctttaagaaggtggccattacctttgactcttctgtcagctggcctggcaatgacc |
| gcctgcttacccccaacgagtttgaaattaagcgctcagttgacggggagggttacaacgttgcccagtgtaacatgaccaaagactggt |
| tcctggtacaaatgctagctaactataacattggctaccagggcttctatatcccagagagctacaaggaccgcatgtactccttctttaga |
| aacttccagcccatgagccgtcaggtggtggatgatactaaatacaaggactaccaacaggtgggcatcctacaccaacacaacaactc |
| tggatttgttggctaccttgcccccaccatgcgcgaaggacaggcctaccctgctaacttcccctatccgcttataggcaagaccgcagtt |
| gacagcattacccagaaaaagtttctttgcgatcgcaccctttggcgcatcccattctccagtaactttatgtccatgggcgcactcacaga |
| cctgggccaaaaccttctctacgccaactccgcccacgcgctagacatgacttttgaggtggatcccatggacgagcccacccttctttat |
| gttttgtttgaagtctttgacgtggtccgtgtgcaccagccgcaccgcggcgtcatcgaaaccgtgtacctgcgcacgcccttctcggccg |
| gcaacgccacaacataaagaagcaagcaacatcaacaacagctgccgccatgggctccagtgagcaggaactgaaagccattgtcaa |
| agatcttggttgtgggccatatttttgggcacctatgacaagcgctttccaggctttgtttctccacacaagctcgcctgcgccatagtcaat |
| acggccggtcgcgagactgggggcgtacactggatggcctttgcctggaacccgcactcaaaaacatgctacctctttgagccctttgg |
| cttttctgaccagcgactcaagcaggtttaccagtttgagtacgagtcactcctgcgccgtagcgccattgcttcttcccccgaccgctgta |
| taacgctggaaaagtccacccaaagcgtacaggggcccaactcggccgcctgtggactattctgctgcatgtttctccacgcctttgcca |
| actggccccaaactcccatggatcacaaccccaccatgaaccttattaccggggtacccaactccatgctcaacagtccccaggtacag |
| cccaccctgcgtcgcaaccaggaacagctctacagcttcctggagcgccactcgccctacttccgcagccacagtgcgcagattagga |
| gcgccacttctttttgtcacttgaaaaacatgtaaaaataatgtactagagacactttcaataaaggcaaatgcttttatttgtacactctcggg |
| tgattatttacccccacccttgccgtctgcgccgtttaaaaatcaaaggggttctgccgcgcatcgctatgcgccactggcagggacacgt |
| tgcgatactggtgtttagtgctccacttaaactcaggcacaaccatccgcggcagctcggtgaagttttcactccacaggctgcgcaccat |
| caccaacgcgtttagcaggtcgggcgccgatatcttgaagtcgcagttggggcctccgccctgcgcgcgcgagttgcgatacacagg |
| gttgcagcactggaacactatcagcgccgggtggtgcacgctggccagcacgctcttgtcggagatcagatccgcgtccaggtcctcc |
| gcgttgctcagggcgaacggagtcaactttggtagctgccttcccaaaaagggcgcgtgcccaggctttgagttgcactcgcaccgtag |
| tggcatcaaaaggtgaccgtgcccggtctgggcgttaggatacagcgcctgcataaaagccttgatctgcttaaaagccacctgagcctt |
| tgcgccttcagagaagaacatgccgcaagacttgccggaaaactgattggccggacacgcggcgtcgtgcacgcagcaccttgcgtc |
| ggtgttggagatctgcaccacatttcggccccaccggttcttcacgatcttggccttgctagactgctccttcagcgcgcgctgcccgtttt |
| cgctcgtcacatccatttcaatcacgtgctccttatttatcataatgcttccgtgtagacacttaagctcgccttcgatctcagcgcagcggtg |
| cagccacaacgcgcagcccgtgggctcgtgatgcttgtaggtcacctctgcaaacgactgcaggtacgcctgcaggaatcgccccatc |
| atcgtcacaaaggtcttgttgctggtgaaggtcagctgcaacccgcggtgctcctcgttcagccaggtcttgcatacggccgccagagct |
| tccacttggtcaggcagtagtttgaagttcgcctttagatcgttatccacgtggtacttgtccatcagcgcgcgcgcagcctccatgcccttc |
| tcccacgcagacacgatcggcacactcagcgggttcatcaccgtaatttcactttccgcttcgctgggctcttcctcttcctcttgcgtccgc |
| ataccacgcgccactgggtcgtcttcattcagccgccgcactgtgcgcttacctcctttgccatgcttgattagcaccggtgggttgctgaa |
| acccaccatttgtagcgccacatcttctctttcttcctcgctgtccacgattacctctggtgatggcgggcgctcgggcttgggagaaggg |
| cgcttctttttcttcttgggcgcaatggccaaatccgccgccgaggtcgatggccgcgggctgggtgtgcgcggcaccagcgcgtcttgt |
| gatgagtcttcctcgtcctcggactcgatacgccgcctcatccgctttttgggggcgcccggggaggcggcggcgacggggacggg |
| gacgacacgtcctccatggttgggggacgtcgcgccgcaccgcgtccgcgctcgggggtggtttcgcgctgctcctcttcccgactgg |

TABLE 30-continued

| Ad5-CFTR with Plasmid Backbone |
|---|
| ccatttccttctcctataggcagaaaaagatcatggagtcagtcgagaagaaggacagcctaaccgccccctctgagttcgccaccacc |
| gcctccaccgatgccgccaacgcgcctaccaccttccccgtcgaggcacccccgcttgaggaggaggaagtgattatcgagcaggac |
| ccaggttttgtaagcgaagacgacgaggaccgctcagtaccaacagaggataaaaagcaagaccaggacaacgcagaggcaaacg |
| aggaacaagtcgggcgggggacgaaaggcatggcgactacctagatgtgggagacgacgtgctgttgaagcatctgcagcgcca |
| gtgcgccattatctgcgacgcgttgcaagagcgcagcgatgtgcccctcgccatagcggatgtcagccttgcctacgaacgccacctat |
| tctcaccgcgcgtaccccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctacccggcacttaacctaccccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacggggggtttacttggacccccagtccggcgaggagctcaacccaatccccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttcccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |

TABLE 30-continued

| Ad5-CFTR with Plasmid Backbone |
| --- |
| aagttcagatgactaactcaggggcgcagcttgcgggcggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |
| actgtgatttgcaactgtcctaaccttggattacatcaagatccagatcttctagacccgggagcggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |
| ccgctaaccgtgcacgactccaaacttagcattgccacccaaggacccctcacagtgtcagaaggaaagctagccctgcaaacatcag |
| gccccctcaccaccaccgatagcagtacccttactatcactgcctcaccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctctttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaaaaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacactttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatggggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgccatccaccaccat |

TABLE 30-continued

| Ad5-CFTR with Plasmid Backbone |
|---|
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgccccctggcttcgggttctatgtaaactccttcatgcgccgctgccctgataacatccaccaccgcagaataa |
| gccacacccagccaacctacacattcgttctgcgagtcacacacgggaggagcgggaagagctggaagaaccatgtttttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagcccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccacccctcattatcatattggcttcaatccaaaataaggtatattattgatgatgttaatttgggccattagacttgaagtcaagcggcc |
| gcttacaactggaccttgctggtacatagaactgattaactgaccatttaaatcataccaacatggtcaaataaaacgaaaggctcagtcg |
| aaagactgggcctttcgttttaatctgatcggcacgtaagaggttccaactttcaccataatgaaataagatcactaccgggcgtattttttga |
| gttatcgagattttcaggagctaaggaagctaaaatgagccatattcaacgggaaacgtcttgctcgaggccgcgattaaattccaacatg |
| gatgctgatttatatgggtataaatgggctcgcgataatgtcgggcaatcaggtgcgacaatctatcgattgtatgggaagcccgatgcgc |
| cagagttgtttctgaaacatggcaaaggtagcgttgccaatgatgttacagatgagatggtcaggctaaactggctgacggaatttatgcc |
| tcttccgaccatcaagcattttatccgtactcctgatgatgcatggttactcaccactgcgatccccgggaaaacagcattccaggtattag |
| aagaatatcctgattcaggtgaaaatattgttgatgcgctggcagtgttcctgcgccggttgcattcgattcctgtttgtaattgtccttttaac |
| ggcgatcgcgtatttcgtctcgctcaggcgcaatcacgaatgaataacggtttggttggtgcgagtgattttgatgacgagcgtaatggct |
| ggcctgttgaacaagtctggaaagaaatgcataaacttttgccattctcaccggattcagtcgtcactcatggtgatttctcacttgataacct |
| tatttttgacgaggggaaattaataggttgtattgatgttggacgagtcggaatcgcagaccgataccaggatcttgccatcctatggaact |
| gcctcggtgagttttctccttcattacagaaacggctttttcaaaaatatggtattgataatcctgatatgaataaattgcagtttcacttgatgct |
| cgatgagtttttctaacctaggtgacagaagtcaaaagcctccggtcggaggcttttgactttctgctagatctgtttcaatgcggtgaagg |
| gccaggcagctggggattatgtcgagacccggccagcatgttggttttatcgcatattcagcgttgtcgcgtttacccaggtaaaatggaa |

TABLE 30-continued

| Ad5-CFTR with Plasmid Backbone |
|---|
| gcagtgtatcgtctgcgtgaatgtgcaaatcaggaacgtaaccgtggtacatagatgcagtcccttgcgggtcgttcccttcaacgagtag |
| gacgcggtgcccttgcaaggctaaccattgcgcctggtgtactgcagatgaggttttataaacccctcccttgtgtgacataacggaaagt |
| acaaccgggtttttatcgtcaggtctttggtttgggttaccaaacacactccgcatatggctaatttggtcaattgtgtagccagcgcgacgtt |
| ctactcggcccctcatctcaaaatcaggagccggtagacgaccagctttttccgcgtctctgatagcctgcggtgttacgccgatcaggtc |
| tgcaacttctgttataccccagcggcgagtaatacgacgcgcttccgggctgtcatcgccgaactgtgcgatggcaatagcgcgcgtcat |
| ttcctgaccgcgattgatacagtctttcagcaaattaattaacgacatcctgtttcctctcaaacatgcccttatctttgtgtttttcatcatacttt |
| acgtttttaaagcaaagcaacataaaaaaagcaaagtgacttagaaaacgcaaagttaaggttcaaatcaatttttttgatgcgctacagaa |
| gctatttagcttcatctaagcgcaacggtattacttacgttggtatatttaaaacctaacttaatgattttaaatgataataaatcataccaattgc |
| tatcaaaagttaagcgaacatgctgattttcacgctgtttatacactttgaggcatctctatctcttccgtctctatattgaaacacaatcaaaga |
| acatcaatccatgtgacatcccccactatctaagaacaccataacagaacacaacataggaatgcaacattaatgtatcaataattcggaa |
| catatgcactatatcatatctcaattacggaacatatcagcacacaattgcccattatacgc |

TABLE 31

| Ad5-CFTR No Plasmid Backbone |
|---|
| (SEQ ID NO: 31) |
| catcatcaataatataccttattttggattgaagccaatatgataatgagggggtggagtttgtgacgtggcgcggggcgtgggaacggg |
| gcgggtgacgtagtagtgtggcggaagtgtgatgttgcaagtgtggcggaacacatgtaagcgacggatgtggcaaaagtgacgtttttt |
| ggtgtgcgccggtgtacacaggaagtgacaattttcgcgcggttttaggcggatgttgtagtaaatttgggcgtaaccgagtaagatttgg |
| ccattttcgcgggaaaactgaataagaggaagtgaaatctgaataattttgtgttactcatagcgcgtaatatttgtctagggccgcgggga |
| ctttgaccgtttacgtggagactcgcccaggtgtttttctcaggtgttttccgcgttccgggtcaaagttggcgttttagatcttctagacccg |
| ggagcggccgctgtcgacctgcaggatccaataggcaggctgttgctggtggcaagtgactgggaagggaaatggggtgcgggtgc |
| catgtgaaagagtgtggtcaacacaggcctcactgaaacaccgaggtttgtgcaaagacatgaaagaggttgggggagcctggcagg |
| tgcctgcggtggggagggaaccgccagtgccaggacctcaggcagggaggaggaaggtgggggggcagggggggaggcgagtc |
| aggaaggtcatgggaccactttgcaaatgactcacattcctgctgcctctcctttgctgcctctcccattttggagtttctagagggcagagc |
| ctgggtttcacatgtttcctttgtgctcagcacaatgctcccccctgtgtgtggcatcaggccaagaaatgttccaggcacgaagacagagc |
| cctcggcgctcacctcccactcagtgatcaccagaaggtccttgatccccacctgctgggcctggcctgtgtcctgttggctcctgccac |
| accggcatgcccccacttagccctcagctagcagcatagaaagaaggggcaagagaggcagggaaagagaagttggcggggtttgt |
| ttgtttgttcgtttctttggctttttatggccacacccgtggcatatggaagttcccaggctaggggctgaatcggagctgtagccactggcc |
| tacaccacagccacgccagatctgagccatgtctgcaatatacacttcagctcaaggcaacaccagatccttaacccactgagtgaggc |
| cagggattgaacccacatcctcatggatactggtcggccttgttactgctgagtcacaataggaacttccaggaaagagagatttgaatct |
| tgaatttgcccggtgccagtcgtgtggcgttgagcaaagtgctttctctctctgagcctcagtttcttcctctgggccaataatccctttcctgt |
| agggttgtcatgaaagtacatggcaggtgtgctcagcacacggtggcattttccttcaagggccctttgacccccctcgaaggggtttcattt |
| tcactttgagtggacccagaaggtgatgccctctgctgccccctaggccacactggacaacaagctgggaactcccttcacctcccgag |
| catcccgcctagcccaccattcagtctccacgacctgccacatccacatgccatgaagctatggggcctgttgaactggatgcccaaaa |
| ggccaggacccccacccgctgcccggggtcatggggaagccaggctggaacagcctccggtacccatgatgggcagccgctgtgtt |
| caaagcctccgcaacttccagccccgaagccaggggaacagacgacccaccctctgggctggcagacgcccagtcggaaaccacg |
| cgtcgtagcgctaccggactcagatctcgagaacacactgcaagtcctcagccctacccccccccatcaaggccccctgtctggagtg |
| ggggtgcaccctaagctagcccaggaagcctccccgagttacttctgtctgcgcctgctggggactatgctggggctgctggggactat |
| gctgagtgcgtttccctcaagttgtctttttttttttttttttttttgtcttttgtccttttatggaggtccccaagctaggggtctaatcggagctgta |

TABLE 31-continued

| Ad5-CFTR No Plasmid Backbone |
| --- |
| gctgccggcctacaccacagccacagcaacgccggatccttatcccactgagcaaggccagggatcgaacctcaacctcatggttcct |
| agtcagattcatttccgctgcgccatgatgggagtgccgccctcaagttgtcttgtatcagggagtcaggggctggctgagattgaaagc |
| ggagtgtccaggtttaagcagacttgtgccaggcagttgactaaagcaccagcagttcctgcccgggtttctctgcccacttagtcatggt |
| gactgcatgccctggccgggtcctgactttggatagtcccttcccagaggggaccctgacagtgtgtcctctgggatttggggctcccca |
| gatctggggcttgtgggcatcactgtcctccgtgcacatgcagcactgtcacatgtgtcccctgatgggagcatgccaggatgacaaggt |
| tatccctgcttatcagctctttcccagcttcctctgcctgttgcttatagacatgagccctgggcgccacgtcttcctcaaataatgagagga |
| agtgtggtcatcggcacacagatggctggggggttccggattgcggctcccggccaccactccctgacctgcgccccccatctctcgcca |
| ggcggtcctcggctctttcctctgcagtcgacggtaccctcctgggcaacgtgctggttattgtgctgtctcatcattttggcaaagaattcc |
| gctgcgactcggcggagtcccggcggcgcgtccttgttctaacccggcgcgccagcttggcaatccggtactgttggtaaagccacca |
| tgcagaggtcgcctctggaaaaggccagcgttgtctccaaactttttttcagctggaccagaccaattttgaggaaaggatacagacagc |
| gcctggaattgtcagacatataccaaatcccttctgttgattctgctgacaatctatctgaaaaattggaaagagaatgggatagagagctg |
| gcttcaaagaaaaatcctaaactcattaatgcccttcggcgatgtttttctggagatttatgttctatggaatctttttatatttaggggaagtca |
| ccaaagcagtacagcctctcttactgggaagaatcatagcttcctatgacccggataacaaggaggaacgctctatcgcgatttatctagg |
| cataggcttatgccttctctttattgtgaggacactgctcctacacccagccatttttggccttcatcacattggaatgcagatgagaatagct |
| atgtttagtttgatttataagaagactttaaagctgtcaagccgtgttctagataaaataagtattggacaacttgttagtctcctttccaacaac |
| ctgaacaaatttgatgaaggacttgcattggcacatttcgtgtggatcgctcctttgcaagtggcactcctcatggggctaatctgggagtt |
| gttacaggcgtctgccttctgtggacttggtttcctgatagtccttgcccttttttcaggctgggctagggagaatgatgatgaagtacagaga |
| tcagagagctgggaagatcagtgaaagacttgtgattacctcagaaatgattgaaaatatccaatctgttaaggcatactgctgggaagaa |
| gcaatggaaaaaatgattgaaaacttaagacaaacagaactgaaactgactcggaaggcagcctatgtgagatacttcaatagctcagc |
| cttcttcttctcagggttctttgtggtgtttttatctgtgcttccctatgcactaatcaaaggaatcatcctccggaaaatattcaccaccatctca |
| ttctgcattgttctgcgcatggcggtcactcggcaatttccctgggctgtacaaacatggtatgactctcttggagcaataaacaaaataca |
| ggatttcttacaaaagcaagaatataagacattggaatataacttaacgactacagaagtagtgatggagaatgtaacagccttctgggag |
| gagggatttggggaattatttgagaaagcaaaacaaaacaataacaatagaaaaacttctaatggtgatgacagcctcttcttcagtaattt |
| ctcacttcttggtactcctgtcctgaaagatattaatttcaagatagaaagaggacagttgttggcggttgctggatccactggagcaggca |
| agacttcacttctaatgatgattatgggagaactggagccttcagagggtaaaattaagcacagtggaagaatttcattctgttctcagttttc |
| ctggattatgcctggcaccattaaagaaaatatcatctttggtgtttcctatgatgaatatagatacagaagcgtcatcaaagcatgccaact |
| agaagaggacatctccaagtttgcagagaaagacaatatagttcttggagaaggtggaatcacactgagtggaggtcaacgagcaaga |
| atttctttagcaagagcagtatacaaagatgctgatttgtatttattagactctccttttggatacctagatgttttaacagaaaaagaaatatttg |
| aaagctgtgtctgtaaactgatggctaacaaaactaggattttggtcacttctaaaatggaacatttaaagaaagctgacaaaatattaatttt |
| gcatgaaggtagcagctatttttatgggacattttcagaactccaaaatctacagccagactttagctcaaaactcatgggatgtgattctttc |
| gaccaatttagtgcagaaagaagaaattcaatcctaactgagaccttacaccgtttctcattagaaggagatgctcctgtctcctggacaga |
| aacaaaaaaacaatcttttaaacagactggagagtttggggaaaaaaggaagaattctattctcaatccaatcaactctatacgaaaatttttc |
| cattgtgcaaaagactcccttacaaatgaatggcatcgaagaggattctgatgagcctttagagagaaggctgtccttagtaccagattct |
| gagcagggagaggcgatactgcctcgcatcagcgtgatcagcactggccccacgcttcaggcacgaaggaggcagtctgtcctgaac |
| ctgatgacacactcagttaaccaaggtcagaacattcaccgaaagacaacagcatccacacgaaaagtgtcactggcccctcaggcaa |
| acttgactgaactggatatatattcaagaaggttatctcaagaaactggcttggaaataagtgaagaaattaacgaagaagacttaaagga |
| gtgcttttttgatgatatggagagcataccagcagtgactacatggaacacataccttcgatatattactgtccacaagagcttaatttttgtg |
| ctaatttggtgcttagtaatttttctggcagaggtggctgcttctttggttgtgctgtggctccttggaaacactcctcttcaagacaaaggga |
| atagtactcatagtagaaataacagctatgcagtgattatcaccagcaccagttcgtattatgtgttttacatttacgtgggagtagccgaca |

TABLE 31-continued

| Ad5-CFTR No Plasmid Backbone |
|---|
| ctttgcttgctatgggattcttcagaggtctaccactggtgcatactctaatcacagtgtcgaaaattttacaccacaaaatgttacattctgttc |
| ttcaagcacctatgtcaaccctcaacacgttgaaagcaggggggattcttaatagattctccaaagatatagcaattttggatgaccttctgc |
| ctcttaccatatttgacttcatccagttgttattaattgtgattggagctatagcagttgtcgcagttttacaaccctacatctttgttgcaacagt |
| gccagtgatagtggcttttattatgttgagagcatatttcctccaaacctcacagcaactcaaacaactggaatctgaaggcaggagtcca |
| attttcactcatcttgttacaagcttaaaaggactatggacacttcgtgccttcggacggcagccttactttgaaactctgttccacaaagctc |
| tgaatttacatactgccaactggttcttgtacctgtcaacactgcgctggttccaaatgagaatagaaatgattttgtcatcttcttcattgctgt |
| taccttcatttccattttaacaacaggagaaggagaaggaagagttggtattatcctgactttagccatgaatatcatgagtacattgcagtg |
| ggctgtaaactccagcatagatgtggatagcttgatgcgatctgtgagccgagtctttaagttcattgacatgccaacagaaggtaaacct |
| accaagtcaaccaaaccatacaagaatggccaactctcgaaagttatgattattgagaattcacacgtgaagaaagatgacatctggccc |
| tcaggggggccaaatgactgtcaaagatctcacagcaaaatacacagaaggtggaaatgccatattagagaacatttccttctcaataagt |
| cctggccagagggtgggcctcttgggaagaactggatcagggaagagtactttgttatcagctttttttgagactactgaacactgaagga |
| gaaatccagatcgatggtgtgtcttgggattcaataactttgcaacagtggaggaaagcctttggagtgataccacagaaagtatttattttt |
| ctggaacatttagaaaaaacttggatccctatgaacagtggagtgatcaagaaatatggaaagttgcagatgaggttgggctcagatctgt |
| gatagaacagtttcctgggaagcttgactttgtccttgtggatgggggctgtgtcctaagccatggccacaagcagttgatgtgcttggcta |
| gatctgttctcagtaaggcgaagatcttgctgcttgatgaacccagtgctcatttggatccagtaacataccaaataattagaagaactctaa |
| aacaagcatttgctgattgcacagtaattctctgtgaacacaggatagaagcaatgctggaatgccaacaattttttggtcatagaagagaa |
| caaagtgcggcagtacgattccatccagaaactgctgaacgagaggagcctcttccggcaagccatcagcccctccgacagggtgaa |
| gctctttccccaccggaactcaagcaagtgcaagtctaagccccagattgctgctctgaaagaggagacagaagaagaggtgcaagat |
| acaaggctttagtaataattctagagtcggggcggccggccgcttcgagagctagagctttcttgctgtccaatttctattaaaggttccttt |
| gttccctaagtccaactactaaactgggggatattatgaagggccttgagcatctggattctgcctaataaaaaacatttattttcattgcaat |
| gatgtattttaaaatcgataaggatccgaattcgatatcactagtggtaccagtactgaaatgtgtgggcgtggcttaagggtgggaaaga |
| atatataaggtgggggtcttatgtagttttgtatctgttttgcagcagccgccgccgccatgagcaccaactcgtttgatggaagcattgtga |
| gctcatatttgacaacgcgcatgcccccatgggccggggtgcgtcagaatgtgatgggctccagcattgatggtcgccccgtcctgccc |
| gcaaactctactaccttgacctacgagaccgtgtctggaacgccgttggagactgcagcctccgccgccgcttcagccgctgcagcca |
| ccgcccgcgggattgtgactgactttgctttcctgagcccgcttgcaagcagtgcagcttcccgttcatccgcccgcgatgacaagttga |
| cggctcttttggcacaattggattctttgacccgggaacttaatgtcgtttctcagcagctgttggatctgcgccagcaggtttctgccctga |
| aggcttcctcccctcccaatgcggtttaacggtccgggccagagtggccaacataaataaaaaaccagactctgtttggatttggatcaa |
| gcaagtgtcttgctgtctttatttaggggttttgcgcgcgcggtaggcccgggaccagcggtctcggtcgttgagggtcctgtgtattttttc |
| caggacgtggtaaaggtgactctggatgttcagatacatgggcataagcccgtctctgggggggaggtagcaccactgcagagcttcat |
| gctgcggggtggtgttgtagatgatccagtcgtagcaggagcgctgggcgtggtgcctaaaaatgtctttcagtagcaagctgattgcca |
| ggggcaggcccttggtgtaagtgtttacaaagcggttaagctgggatgggtgcatacgtggggatatgagatgcatcttggactgtatttttt |
| aggttggctatgttcccagccatatccctccggggattcatgttgtgcagaaccaccagcacagtgtatccggtgcacttgggaaatttgtc |
| atgtagcttagaaggaaatgcgtggaagaacttggagacgcccttgtgacctccaagattttccatgcattcgtccataatgatggcaatg |
| ggcccacgggcggcggcctgggcgaagatatttctgggatcactaacgtcatagttgtgttccaggatgagatcgtcataggccattttta |
| caaagcgcgggcggagggtgccagactgcggtataatggttccatccggcccaggggcgtagttaccctcacagatttgcatttcccac |
| gctttgagttcagatgggggggatcatgtctacctgcggggcgatgaagaaaacggtttccggggtaggggagatcagctgggaagaaa |
| gcaggttcctgagcagctgcgacttaccgcagccggtgggcccgtaaatcacacctattaccggctgcaactggtagttaagagagctg |
| cagctgccgtcatccctgagcagggggggccacttcgttaagcatgtccctgactcgcatgttttccctgaccaaatccgccagaaggcg |
| ctcgccgcccagcgatagcagttcttgcaaggaagcaaagtttttcaacggtttgagaccgtccgccgtaggcatgcttttgagcgtttga |

TABLE 31-continued

| Ad5-CFTR No Plasmid Backbone |
| --- |
| ccaagcagttccaggcggtcccacagctcggtcacctgctctacggcatctcgatccagcatatctcctcgtttcgcgggttggggcggc |
| tttcgctgtacggcagtagtcggtgctcgtccagacgggccagggtcatgtctttccacgggcgcagggtcctcgtcagcgtagtctgg |
| gtcacggtgaaggggtgcgctccgggctgcgcgctggccagggtgcgcttgaggctggtcctgctggtgctgaagcgctgccggtctt |
| cgccctgcgcgtcggccaggtagcatttgaccatggtgtcatagtccagcccctccgcggcgtggcccttggcgcgcagcttgcccttg |
| gaggaggcgccgcacgaggggcagtgcagacttttgagggcgtagagcttgggcgcgagaaataccgattccggggagtaggcatc |
| cgcgccgcaggccccgcagacggtctcgcattccacgagccaggtgagctctggccgttcggggtcaaaaaccaggtttcccccatg |
| ctttttgatgcgtttcttacctctggtttccatgagccggtgtccacgctcggtgacgaaaaggctgtccgtgtccccgtatacagacttgag |
| aggcctgtcctcgagcggtgttccgcggtcctcctcgtatagaaactcggaccactctgagacaaaggctcgcgtccaggccagcacg |
| aaggaggctaagtgggaggggtagcggtcgttgtccactagggggtccactcgctccagggtgtgaagacacatgtcgccctcttcgg |
| catcaaggaaggtgattggtttgtaggtgtaggccacgtgaccgggtgttcctgaaggggggctataaaagggggtgggggcgcgttc |
| gtcctcactctcttccgcatcgctgtctgcgagggccagctgttggggtgagtactccctctgaaaagcgggcatgacttctgcgctaaga |
| ttgtcagtttccaaaaacgaggaggatttgatattcacctggcccgcggtgatgcctttgagggtggccgcatccatctggtcagaaaaga |
| caatctttttgttgtcaagcttggtggcaaacgacccgtagagggcgttggacagcaacttggcgatggagcgcagggtttggtttttgtc |
| gcgatcggcgcgctccttggccgcgatgtttagctgcacgtattcgcgcgcaacgcaccgccattcgggaaagacggtggtgcgctcg |
| tcgggcaccaggtgcacgcgccaaccgcggttgtgcagggtgacaaggtcaacgctggtggctacctctccgcgtaggcgctcgttg |
| gtccagcagaggcggccgcccttgcgcgagcagaatggcggtagggggtctagctgcgtctcgtccgggggggtctgcgtccacggt |
| aaagaccccgggcagcaggcgcgcgtcgaagtagtctatcttgcatccttgcaagtctagcgcctgctgccatgcgcgggcggcaag |
| cgcgcgctcgtatgggttgagtgggggaccccatggcatggggtgggtgagcgcggaggcgtacatgccgcaaatgtcgtaaacgta |
| gaggggctctctgagtattccaagatatgtagggtagcatcttccaccgcggatgctggcgcgcacgtaatcgtatagttcgtgcgaggg |
| agcgaggaggtcgggaccgaggttgctacgggcgggctgctctgctcggaagactatctgcctgaagatggcatgtgagttggatgat |
| atggttggacgctggaagacgttgaagctggcgtctgtgagacctaccgcgtcacgcacgaaggaggcgtaggagtcgcgcagcttg |
| ttgaccagctcggcggtgacctgcacgtctagggcgcagtagtccagggtttccttgatgatgtcatacttatcctgtcccttttttttccaca |
| gctcgcggttgaggacaaactcttcgcggtctttccagtactcttggatcggaaacccgtcggcctccgaacggtaagagcctagcatgt |
| agaactggttgacggcctggtaggcgcagcatcccttttctacgggtagcgcgtatgcctgcgcggccttccggagcgaggtgtgggt |
| gagcgcaaaggtgtccctgaccatgactttgaggtactggtatttgaagtcagtgtcgtcgcatccgccctgctcccagagcaaaaagtc |
| cgtgcgctttttggaacgcggatttggcagggcgaaggtgacatcgttgaagagtatctttcccgcgcgaggcataaagttgcgtgtgat |
| gcggaagggtcccggcacctcggaacggttgttaattacctgggcggcgagcacgatctcgtcaaagccgttgatgttgtggcccaca |
| atgtaaagttccaagaagcgcgggatgcccttgatggaaggcaattttttaagttcctcgtaggtgagctcttcaggggagctgagcccgt |
| gctctgaaagggcccagtctgcaagatgagggttggaagcgacgaatgagctccacaggtcacgggccattagcatttgcaggtggtc |
| gcgaaaggtcctaaactggcgacctatggccatttttctggggtgatgcagtagaaggtaagcgggtcttgttcccagcggtcccatcc |
| aaggttcgcggctaggtctcgcgcggcagtcactagaggctcatctccgccgaacttcatgaccagcatgaagggcacgagctgcttc |
| ccaaaggcccccatccaagtataggtctctacatcgtaggtgacaaagagacgctcggtgcgaggatgcgagccgatcgggaagaac |
| tggatctcccgccaccaattggaggagtggctattgatgtggtgaaagtagaagtccctgcgacgggccgaacactcgtgctggcttttg |
| taaaaacgtgcgcagtactggcagcggtgcacgggctgtacatcctgcacgaggttgacctgacgaccgcgcacaaggaagcagagt |
| gggaatttgagcccctcgcctggcgggtttggctggtggtcttctacttcggctgcttgtccttgaccgtctggctgctcgaggggagttac |
| ggtggatcggaccaccacgccgcgcgagcccaaagtccagatgtccgcgcgcggcggtcggagcttgatgacaacatcgcgcagat |
| gggagctgtccatggtctggagctcccgcggcgtcaggtcaggcgggagctcctgcaggtttacctcgcatagacgggtcagggcgc |
| gggctagatccaggtgatacctaatttccaggggctggttggtggcggcgtcgatggcttgcaagaggccgcatccccgcggcgcga |
| ctacggtaccgcgcggcgggcggtgggccgcgggggtgtccttggatgatgcatctaaaagcggtgacgcgggcgagcccccgga |

TABLE 31-continued

| Ad5-CFTR No Plasmid Backbone |
| --- |
| ggtagggggggctccggacccgccgggagagggggcaggggcacgtcggcgccgcgcgcgggcaggagctggtgctgcgcgc |
| gtaggttgctggcgaacgcgacgacgcggcggttgatctcctgaatctggcgcctctgcgtgaagacgacgggcccggtgagcttga |
| acctgaaagagagttcgacagaatcaatttcggtgtcgttgacggcggcctggcgcaaaatctcctgcacgtctcctgagttgtcttgata |
| ggcgatctcggccatgaactgctcgatctcttcctcctggagatctccgcgtccggctcgctccacggtggcggcgaggtcgttggaaat |
| gcgggccatgagctgcgagaaggcgttgaggcctccctcgttccagacgcggctgtagaccacgcccccttcggcatcgcgggcgc |
| gcatgaccacctgcgcgagattgagctccacgtgccgggcgaagacggcgtagtttcgcaggcgctgaaagaggtagttgagggtgg |
| tggcggtgtgttctgccacgaagaagtacataacccagcgtcgcaacgtggattogttgatatcccccaaggcctcaaggcgctccatg |
| gcctcgtagaagtccacggcgaagttgaaaaactgggagttgcgcgccgacacggttaactcctcctccagaagacggatgagctcg |
| gcgacagtgtcgcgcacctcgcgctcaaaggctacaggggcctcttcttcttcttcaatctcctcttccataagggcctccccttcttcttctt |
| ctggcggcggtgggggagggggacacggcggcgacgacggcgcaccgggaggcggtcgacaaagcgctcgatcatctccccg |
| cggcgacggcgcatggtctcggtgacggcgcggccgttctcgcgggggcgcagttggaagacgccgcccgtcatgtcccggttatg |
| ggttggcgggggctgccatgcggcagggatacggcgctaacgatgcatctcaacaattgttgtgtaggtactccgccgccgaggga |
| cctgagcgagtccgcatcgaccggatcggaaaacctctcgagaaaggcgtctaaccagtcacagtcgcaaggtaggctgagcaccgt |
| ggcgggcggcagcgggcggcggtcggggttgtttctggcggaggtgctgctgatgatgtaattaaagtaggcggtcttgagacggcg |
| gatggtcgacagaagcaccatgtccttgggtccggcctgctgaatgcgcaggcggtcggccatgccccaggcttcgttttgacatcggc |
| gcaggtctttgtagtagtcttgcatgagcctttctaccggcacttcttcttctccttcctcttgtcctgcatctcttgcatctatcgctgcggcgg |
| cggcggagtttggccgtaggtggcgccctcttcctcccatgcgtgtgaccccgaagcccctcatcggctgaagcagggctaggtcggc |
| gacaacgcgctcggctaatatggcctgctgcacctgcgtgagggtagactggaagtcatccatgtccacaaagcggtggtatgcgccc |
| gtgttgatggtgtaagtgcagttggccataacggaccagttaacggtctggtgacccggctgcgagagctcggtgtacctgagacgcga |
| gtaagccctcgagtcaaatacgtagtcgttgcaagtccgcaccaggtactggtatcccaccaaaaagtgcggcggcggctggcggtag |
| aggggccagcgtagggtggccggggctccgggggcgagatcttccaacataaggcgatgatatccgtagatgtacctggacatccag |
| gtgatgccggcggcggtggtggaggcgcgcggaaagtcgcggacgcggttccagatgttgcgcagcggcaaaaagtgctccatggt |
| cgggacgctctggccggtcaggcgcgcgcaatcgttgacgctctagaccgtgcaaaaggagagcctgtaagcgggcactcttccgtg |
| gtctggtggataaattcgcaagggtatcatggcggacgaccggggttcgagccccgtatccggccgtccgccgtgatccatgcggttac |
| cgcccgcgtgtcgaacccaggtgtgcgacgtcagacaacgggggagtgctccttttggcttccttccaggcgcggcggctgctgcgct |
| agctttttggccactggccgcgcgcagcgtaagcggttaggctggaaagcgaaagcattaagtggctcgctccctgtagccggaggg |
| ttattttccaagggttgagtcgcgggacccccggttcgagtctcggaccggccggactgcggcgaacgggggtttgcctccccgtcatg |
| caagaccccgcttgcaaattcctccggaaacagggacgagccccttttttgcttttcccagatgcatccggtgctgcggcagatgcgccc |
| ccctcctcagcagcggcaagagcaagagcagcggcagacatgcagggcaccctcccctcctcctaccgcgtcaggaggggcgaca |
| tccgcggttgacgcggcagcagatggtgattacgaacccccgcggcgccgggcccggcactacctggacttggaggagggcgagg |
| gcctggcgcggctaggagcgccctctcctgagcggcacccaagggtgcagctgaagcgtgatacgcgtgaggcgtacgtgccgcg |
| gcagaacctgtttcgcgaccgcgagggagaggagcccgaggagatgcgggatcgaaagttccacgcagggcgcgagctgcggcat |
| ggcctgaatcgcgagcggttgctgcgcgaggaggactttgagcccgacgcgcgaaccgggattagtcccgcgcgcgcacacgtggc |
| ggccgccgacctggtaaccgcatacgagcagacggtgaaccaggagattaactttcaaaaaagctttaacaaccacgtgcgtacgctt |
| gtggcgcgcgaggaggtggctataggactgatgcatctgtgggactttgtaagcgcgctggagcaaaacccaaatagcaagccgctc |
| atggcgcagctgttccttatagtgcagcacagcagggacaacgaggcattcagggatgcgctgctaaacatagtagagcccgagggc |
| cgctggctgctcgatttgataaacatcctgcagagcatagtggtgcaggagcgcagcttgagcctggctgacaaggtggccgccatca |
| actattccatgcttagcctgggcaagttttacgcccgcaagatataccataccccttacgttcccatagacaaggaggtaaagatcgaggg |
| gttctacatgcgcatggcgctgaaggtgcttaccttgagcgacgacctgggcgtttatcgcaacgagcgcatccacaaggccgtgagc |

TABLE 31-continued

| Ad5-CFTR No Plasmid Backbone |
| --- |
| gtgagccggcggcgcgagctcagcgaccgcgagctgatgcacagcctgcaaagggccctggctggcacgggcagcggcgataga |
| gaggccgagtcctactttgacgcgggcgctgacctgcgctgggccccaagccgacgcgccctggaggcagctggggccggacctg |
| ggctggcggtggcacccgcgcgcgctggcaacgtcggcggcgtggaggaatatgacgaggacgatgagtacgagccagaggacg |
| gcgagtactaagcggtgatgtttctgatcagatgatgcaagacgcaacggacccggcggtgcgggcggcgctgcagagccagccgt |
| ccggccttaactccacggacgactggcgccaggtcatggaccgcatcatgtcgctgactgcgcgcaatcctgacgcgttccggcagca |
| gccgcaggccaaccggctctccgcaattctggaagcggtggtcccggcgcgcgcaaaccccacgcacgagaaggtgctggcgatc |
| gtaaacgcgctggccgaaaacagggccatccggcccgacgaggccggcctggtctacgacgcgctgcttcagcgcgtggctcgtta |
| caacagcggcaacgtgcagaccaacctggaccggctggtgggggatgtgcgcgaggccgtggcgcagcgtgagcgcgcgcagca |
| gcagggcaacctgggctccatggttgcactaaacgccttcctgagtacacagcccgccaacgtgccgcggggacaggaggactaca |
| ccaactttgtgagcgcactgcggctaatggtgactgagacaccgcaaagtgaggtgtaccagtctgggccagactatttttttccagacca |
| gtagacaaggcctgcagaccgtaaacctgagccaggctttcaaaaacttgcaggggctgtgggggtgcgggctcccacaggcgac |
| cgcgcgaccgtgtctagcttgctgacgcccaactcgcgcctgttgctgctgctaatagcgcccttcacggacagtggcagcgtgtcccg |
| ggacacatacctaggtcacttgctgacactgtaccgcgaggccataggtcaggcgcatgtggacgagcatactttccaggagattacaa |
| gtgtcagccgcgcgctggggcaggaggacacgggcagcctggaggcaaccctaaactacctgctgaccaaccggcggcagaagat |
| cccctcgttgcacagtttaaacagcgaggaggagcgcattttgcgctacgtgcagcagagcgtgagccttaacctgatgcgcgacggg |
| gtaacgcccagcgtggcgctggacatgaccgcgcgcaacatggaaccgggcatgtatgcctcaaaccggccgtttatcaaccgccta |
| atggactacttgcatcgcgcggccgccgtgaaccccgagtatttcaccaatgccatcttgaacccgcactggctaccgccccctggtttct |
| acaccgggggattcgaggtgcccgagggtaacgatggattcctctgggacgacatagacgacagcgtgttttccccgcaaccgcaga |
| ccctgctagagttgcaacagcgcgagcaggcagaggcggcgctgcgaaaggaaagcttccgcaggccaagcagcttgtccgatcta |
| ggcgctgcggccccgcggtcagatgctagtagcccatttccaagcttgatagggtctcttaccagcactcgcaccacccgcccgcgcct |
| gctgggcgaggaggagtacctaaacaactcgctgctgcagccgcagcgcgaaaaaaacctgcctccggcatttcccaacaacgggat |
| agagagcctagtggacaagatgagtagatggaagacgtacgcgcaggagcacagggacgtgccaggcccgcgcccgcccacccg |
| tcgtcaaaggcacgaccgtcagcggggtctggtgtgggaggacgatgactcggcagacgacagcagcgtcctggatttgggaggga |
| gtggcaacccgtttgcgcaccttcgccccaggctggggagaatgttttaaaaaaaaaaaaaagcatgatgcaaaataaaaaactcacca |
| aggccatggcaccgagcgttggttttcttgtattccccttagtatgcggcgcgcggcgatgtatgaggaaggtcctcctccctcctacgag |
| agtgtggtgagcgcggcgccagtggcggcggcgctgggttctcccttcgatgctcccctggacccgccgtttgtgcctccgcggtacct |
| gcggcctaccggggggagaaacagcatccgttactctgagttggcacccctattcgacaccacccgtgtgtacctggtggacaacaag |
| tcaacggatgtggcatccctgaactaccagaacgaccacagcaactttctgaccacggtcattcaaaacaatgactacagcccgggggg |
| aggcaagcacacagaccatcaatcttgacgaccggtcgcactggggcggcgacctgaaaaccatcctgcataccaacatgccaaatgt |
| gaacgagttcatgtttaccaataagtttaaggcgcgggtgatggtgtcgcgcttgcctactaaggacaatcaggtggagctgaaatacga |
| gtgggtggagttcacgctgcccgagggcaactactccgagaccatgaccatagaccttatgaacaacgcgatcgtggagcactacttg |
| aaagtgggcagacagaacggggttctggaaagcgacatcggggtaaagtttgacacccgcaacttcagactggggtttgaccccgtca |
| ctggtcttgtcatgcctggggtatatacaaacgaagccttccatccagacatcattttgctgccaggatgcggggtggacttcacccacag |
| ccgcctgagcaacttgttgggcatccgcaagcggcaacccttccaggagggctttaggatcacctacgatgatctggaggggtaaca |
| ttcccgcactgttggatgtggacgcctaccaggcgagcttgaaagatgacaccgaacaggggggggtggcgcaggcggcagcaac |
| agcagtggcagcggcgcggaagagaactccaacgcggcagccgcggcaatgcagccggtggaggacatgaacgatcatgccattc |
| gcggcgacacctttgccacacgggctgaggagaagcgcgctgaggccgaagcagcggccgaagctgccgcccccgctgcgcaac |
| ccgaggtcgagaagcctcagaagaaaccggtgatcaaacccctgacagaggacagcaagaaacgcagttacaacctaataagcaat |
| gacagcaccttcacccagtaccgcagctggtaccttgcatacaactacggcgaccctcagaccggaatccgctcatggaccctgctttg |

TABLE 31-continued

| Ad5-CFTR No Plasmid Backbone |
|---|
| cactcctgacgtaacctgcggctcggagcaggtctactggtcgttgccagacatgatgcaagaccccgtgaccttccgctccacgcgcc |
| agatcagcaactttccggtggtgggcgccgagctgttgcccgtgcactccaagagcttctacaacgaccaggccgtctactcccaactc |
| atccgccagtttacctctctgacccacgtgttcaatcgctttcccgagaaccagattttggcgcgcccgccagccccaccatcaccacc |
| gtcagtgaaaacgttcctgctctcacagatcacgggacgctaccgctgcgcaacagcatcggaggagtccagcgagtgaccattactg |
| acgccagacgccgcacctgcccctacgtttacaaggccctgggcatagtctcgccgcgcgtcctatcgagccgcactttttgagcaagc |
| atgtccatccttatatcgcccagcaataacacaggctggggcctgcgcttcccaagcaagatgtttggcggggccaagaagcgctccga |
| ccaacacccagtgcgcgtgcgcgggcactaccgcgcgccctggggcgcgcacaaacgcggccgcactgggcgcaccaccgtcga |
| tgacgccatcgacgcggtggtggaggaggcgcgcaactacacgcccacgccgccaccagtgtccacagtggacgcggccattcag |
| accgtggtgcgcggagcccggcgctatgctaaaatgaagagacggcggaggcgcgtagcacgtcgccaccgccgccgacccggc |
| actgccgcccaacgcgcggcggcggccctgcttaaccgcgcacgtcgcaccggccgacgggcggccatgcgagcagctcgaagg |
| ctggccgcgggtattgtcactgtgccccccaggtccaggcgacgagcggccgccgcagcagccgcggccattagtgctatgactcag |
| ggtcgcaggggcaacgtgtattgggtgcgcgactcggttagcggcctgcgcgtgcccgtgcgcacccgccccccgcgcaactagatt |
| gcaagaaaaaactacttagactcgtactgttgtatgtatccagcggcggcggcgcgcaacgaagctatgtccaagcgcaaaatcaaag |
| aagagatgctccaggtcatcgcgccggagatctatggccccccgaagaaggaagagcaggattacaagccccgaaagctaaagcgg |
| gtcaaaaagaaaaagaaagatgatgatgatgaacttgacgacgaggtggaactgctgcacgctaccgcgcccaggcgacgggtaca |
| gtggaaaggtcgacgcgtaaaacgtgttttgcgacccggcaccaccgtagtctttacgcccggtgagcgctccacccgcacctacaag |
| cgcgtgtatgatgaggtgtacggcgacgaggacctgcttgagcaggccaacgagcgcctcggggagtttgcctacggaaagcggcat |
| aaggacatgctggcgttgccgctggacgagggcaacccaacacctagcctaaagcccgtaacactgcagcaggtgctgcccgcgctt |
| gcaccgtccgaagaaaagcgcggcctaaagcgcgagtctggtgacttggcacccaccgtgcagctgatggtacccaagcgccagcg |
| actggaagatgtcttggaaaaaatgaccgtggaacctgggctggagcccgaggtccgcgtgcggccaatcaagcaggtggcgccgg |
| gactgggcgtgcagaccgtggacgttcagatacccactaccagtagcaccagtattgccaccgccacagagggcatggagacacaaa |
| cgtccccggttgcctcagcggtggggatgccgcggtgcaggcggtcgctgcggccgcgtccaagacctctacggaggtgcaaacg |
| gacccgtggatgtttcgcgtttcagccccccggcgcccgcgccgttcgaggaagtacggcgccgccagcgcgctactgcccgaatat |
| gccctacatccttccattgcgcctacccccggctatcgtggctacacctaccgccccagaagacgagcaactacccgacgccgaacca |
| ccactggaacccgccgccgccgtcgccgtcgccagcccgtgctggccccgatttccgtgcgcagggggctcgcgaaggaggcag |
| gaccctggtgctgccaacagcgcgctaccaccccagcatcgtttaaaagccggtctttgtggttcttgcagatatggccctcacctgccg |
| cctccgtttcccggtgccgggattccgaggaagaatgcaccgtaggaggggcatggccggccacggcctgacgggcggcatgcgtc |
| gtgcgcaccaccggcggcggcgcgcgtcgcaccgtcgcatgcgcggcggtatcctgcccctccttattccactgatcgccgcggcga |
| ttggcgccgtgcccggaattgcatccgtggccttgcaggcgcagagacactgattaaaaacaagttgcatgtggaaaaatcaaaataaa |
| aagtctggactctcacgctcgcttggtcctgtaactattttgtagaatggaagacatcaactttgcgtctctggccccgcgacacggctcgc |
| gcccgttcatgggaaactggcaagatatcggcaccagcaatatgagcggtggcgccttcagctggggctcgctgtggagcggcattaa |
| aaatttcggttccaccgttaagaactatggcagcaaggcctggaacagcagcacaggccagatgctgagggataagttgaaagagcaa |
| aatttccaacaaaaggtggtagatggcctggcctctggcattagcggggtggtggacctggccaaccaggcagtgcaaaataagattaa |
| cagtaagcttgatccccgccctcccgtagaggagcctccaccggccgtggagacagtgtctccagaggggcgtggcgaaaagcgtcc |
| gcgccccgacagggaagaaactctggtgacgcaaatagacgagcctccctcgtacgaggaggcactaaagcaaggcctgcccacca |
| cccgtcccatcgcgcccatggctaccggagtgctgggccagcacacacccgtaacgctggacctgcctccccccgccgacacccag |
| cagaaacctgtgctgccaggcccgaccgccgttgttgtaacccgtcctagccgcgcgtccctgcgccgcgccgccagcggtccgcga |
| tcgttgcggcccgtagccagtggcaactggcaaagcacactgaacagcatcgtgggtctgggggtgcaatccctgaagcgccgacga |
| tgcttctgaatagctaacgtgtcgtatgtgtgtcatgtatgcgtccatgtcgccgccagaggagctgctgagccgccgcgcgcccgctttc |

TABLE 31-continued

| Ad5-CFTR No Plasmid Backbone |
|---|
| caagatggctaccccttcgatgatgccgcagtggtcttacatgcacatctcgggccaggacgcctcggagtacctgagccccgggctg |
| gtgcagtttgcccgcgccaccgagacgtacttcagcctgaataacaagtttagaaccccacggtggcgcctacgcacgacgtgacca |
| cagaccggtcccagcgtttgacgctgcggttcatccctgtggaccgtgaggatactgcgtactcgtacaaggcgcggttcaccctagct |
| gtgggtgataaccgtgtgctggacatggcttccacgtactttgacatccgcggcgtgctggacaggggccctacttttaagccctactctg |
| gcactgcctacaacgccctggctcccaagggtgccccaaatccttgcgaatgggatgaagctgctactgctcttgaaataaacctagaa |
| gaagaggacgatgacaacgaagacgaagtagacgagcaagctgagcagcaaaaaactcacgtatttgggcaggcgccttattctggt |
| ataaatattacaaaggagggtattcaaataggtgtcgaaggtcaaacacctaaatatgccgataaaacatttcaacctgaacctcaaatag |
| gagaatctcagtggtacgaaacagaaattaatcatgcagctgggagagtcctaaaaaagactaccccaatgaaaccatgttacggttcat |
| atgcaaaacccacaaatgaaaatggagggcaaggcattcttgtaaagcaacaaaatggaaagctagaaagtcaagtggaaatgcaattt |
| ttctcaactactgaggcagccgcaggcaatggtgataacttgactcctaaagtggtattgtacagtgaagatgtagatatagaaaccccag |
| acactcatatttcttacatgcccactattaaggaaggtaactcacgagaactaatgggccaacaatctatgcccaacaggcctaattacatt |
| gcttttagggacaattttattggtctaatgtattacaacagcacgggtaatatgggtgttctggcgggccaagcatcgcagttgaatgctgtt |
| gtagatttgcaagacagaaacacagagctttcataccagcttttgcttgattccattggtgatagaaccaggtacttttctatgtggaatcag |
| gctgttgacagctatgatccagatgttagaattattgaaaatcatggaactgaagatgaacttccaaattactgctttccactgggaggtgtg |
| attaatacagagactcttaccaaggtaaaacctaaaacaggtcaggaaaatggatgggaaaaagatgctacagaattttcagataaaaat |
| gaaataagagttggaaataattttgccatggaaatcaatctaaatgccaacctgtggagaaatttcctgtactccaacatagcgctgtatttg |
| cccgacaagctaaagtacagtccttccaacgtaaaaatttctgataacccaaacacctacgactacatgaacaagcgagtggtggctccc |
| gggctagtggactgctacattaaccttggagcacgctggtcccttgactatatggacaacgtcaacccatttaaccaccaccgcaatgctg |
| gcctgcgctaccgctcaatgttgctgggcaatggtcgctatgtgcccttccacatccaggtgcctcagaagttctttgccattaaaaacctc |
| cttctcctgccgggctcatacacctacgagtggaacttcaggaaggatgttaacatggttctgcagagctccctaggaaatgacctaagg |
| gttgacggagccagcattaagtttgatagcatttgcctttacgccaccttcttccccatggcccacaacaccgcctccacgcttgaggccat |
| gcttagaaacgacaccaacgaccagtcctttaacgactatctctccgccgccaacatgctctaccctatacccgccaacgctaccaacgt |
| gcccatatccatcccctcccgcaactgggcggctttccgcggctgggccttcacgcgccttaagactaaggaaaccccatcactgggct |
| cgggctacgacccttattacacctactctggctctataccctacctagatggaaccttttacctcaaccacacctttaagaaggtggccatta |
| cctttgactcttctgtcagctggcctggcaatgaccgcctgcttacccccaacgagtttgaaattaagcgctcagttgacggggagggtta |
| caacgttgcccagtgtaacatgaccaaagactggttcctggtacaaatgctagctaactataacattggctaccagggcttctatatcccag |
| agagctacaaggaccgcatgtactccttctttagaaacttccagcccatgagccgtcaggtggtggatgatactaaatacaaggactacc |
| aacaggtgggcatcctacaccaacacaacaactctggatttgttggctaccttgcccccaccatgcgcgaaggacaggcctaccctgct |
| aacttcccctatccgcttataggcaagaccgcagttgacagcattacccagaaaaagtttctttgcgatcgcaccctttggcgcatcccatt |
| ctccagtaactttatgtccatgggcgcactcacagacctgggccaaaaccttctctacgccaactccgcccacgcgctagacatgactttt |
| gaggtggatcccatggacgagcccacccttctttatgttttgtttgaagtctttgacgtggtccgtgtgcaccagccgcaccgcggcgtcat |
| cgaaaccgtgtacctgcgcacgcccttctcggccggcaacgccacaacataaagaagcaagcaacatcaacaacagctgccgccatg |
| ggctccagtgagcaggaactgaaagccattgtcaaagatcttggttgtgggccatatttttgggcacctatgacaagcgctttccaggctt |
| tgtttctccacacaagctcgcctgcgccatagtcaatacggccggtcgcgagactgggggcgtacactggatggcctttgcctggaacc |
| cgcactcaaaaacatgctacctctttgagccctttggcttttctgaccagcgactcaagcaggtttaccagtttgagtacgagtcactcctgc |
| gccgtagcgccattgcttcttcccccgaccgctgtataacgctggaaaagtccacccaaagcgtacaggggcccaactcggccgcctg |
| tggactattctgctgcatgtttctccacgcctttgccaactggccccaaactcccatggatcacaaccccaccatgaaccttattaccgggg |
| tacccaactccatgctcaacagtccccaggtacagcccaccctgcgtcgcaaccaggaacagctctacagcttcctggagcgccactc |
| gccctacttccgcagccacagtgcgcagattaggagcgccacttctttttgtcacttgaaaaacatgtaaaaataatgtactagagacactt |

TABLE 31-continued

| Ad5-CFTR No Plasmid Backbone |
| --- |
| tcaataaaggcaaatgcttttatttgtacactctcgggtgattatttaccccccacccttgccgtctgcgccgtttaaaaatcaaaggggttctg |
| ccgcgcatcgctatgcgccactggcagggacacgttgcgatactggtgtttagtgctccacttaaactcaggcacaaccatccgcggca |
| gctcggtgaagttttcactccacaggctgcgcaccatcaccaacgcgtttagcaggtcgggcgccgatatcttgaagtcgcagttgggg |
| cctccgccctgcgcgcgcgagttgcgatacacagggttgcagcactggaacactatcagcgccgggtggtgcacgctggccagcac |
| gctcttgtcggagatcagatccgcgtccaggtcctccgcgttgctcagggcgaacggagtcaactttggtagctgccttcccaaaaagg |
| gcgcgtgcccaggctttgagttgcactcgcaccgtagtggcatcaaaaggtgaccgtgcccggtctgggcgttaggatacagcgcctg |
| cataaaagccttgatctgcttaaaagccacctgagcctttgcgccttcagagaagaacatgccgcaagacttgccggaaaactgattggc |
| cggacacgcggcgtcgtgcacgcagcaccttgcgtcggtgttggagatctgcaccacatttcggccccaccggttcttcacgatcttgg |
| ccttgctagactgctccttcagcgcgcgctgcccgttttcgctcgtcacatccatttcaatcacgtgctccttatttatcataatgcttccgtgta |
| gacacttaagctcgccttcgatctcagcgcagcggtgcagccacaacgcgcagcccgtgggctcgtgatgcttgtaggtcacctctgca |
| aacgactgcaggtacgcctgcaggaatcgccccatcatcgtcacaaaggtcttgttgctggtgaaggtcagctgcaacccgcggtgctc |
| ctcgttcagccaggtcttgcatacggccgccagagcttccacttggtcaggcagtagtttgaagttcgcctttagatcgttatccacgtggt |
| acttgtccatcagcgcgcgcgcagcctccatgcccttctcccacgcagacacgatcggcacactcagcgggttcatcaccgtaatttcac |
| tttccgcttcgctgggctcttcctcttcctcttgcgtccgcataccacgcgccactgggtcgtcttcattcagccgccgcactgtgcgcttac |
| ctcctttgccatgcttgattagcaccggtgggttgctgaaacccaccatttgtagcgccacatcttctctttcttcctcgctgtccacgattacc |
| tctggtgatggcgggcgctcgggcttgggagaagggcgcttctttttcttcttgggcgcaatggccaaatccgccgccgaggtcgatgg |
| ccgcgggctgggtgtgcgcggcaccagcgcgtcttgtgatgagtcttcctcgtcctcggactcgatacgccgcctcatccgcttttttggg |
| ggcgcccggggaggcggcggcgacggggacggggacgacacgtcctccatggttgggggacgtcgcgccgcaccgcgtccgcg |
| ctcgggggtggtttcgcgctgctcctcttcccgactggccatttccttctcctataggcagaaaaagatcatggagtcagtcgagaagaag |
| gacagcctaaccgcccccctctgagttcgccaccaccgcctccaccgatgccgccaacgcgcctaccaccttccccgtcgaggcaccc |
| ccgcttgaggaggaggaagtgattatcgagcaggacccaggttttgtaagcgaagacgacgaggaccgctcagtaccaacagaggat |
| aaaaagcaagaccaggacaacgcagaggcaaacgaggaacaagtcgggggggggggacgaaaggcatggcgactacctagatgtg |
| ggagacgacgtgctgttgaagcatctgcagcgccagtgcgccattatctgcgacgcgttgcaagagcgcagcgatgtgcccctcgcca |
| tagcggatgtcagccttgcctacgaacgccacctattctcaccgcgcgtaccccccaaacgccaagaaaacggcacatgcgagccca |
| acccgcgcctcaacttctaccccgtatttgccgtgccagaggtgcttgccacctatcacatctttttccaaaactgcaagatacccctatcct |
| gccgtgccaaccgcagccgagcggacaagcagctggccttgcggcagggcgctgtcatacctgatatcgcctcgctcaacgaagtgc |
| caaaaatctttgagggtcttggacgcgacgagaagcgcgcggcaaacgctctgcaacaggaaaacagcgaaaatgaaagtcactctg |
| gagtgttggtggaactcgagggtgacaacgcgcgcctagccgtactaaaacgcagcatcgaggtcacccactttgcctacccggcact |
| taacctaccccccaaggtcatgagcacagtcatgagtgagctgatcgtgcgccgtgcgcagcccctggagagggatgcaaatttgcaa |
| gaacaaacagaggagggcctacccgcagttggcgacgagcagctagcgcgctggcttcaaacgcgcgagcctgccgacttggagg |
| agcgacgcaaactaatgatggccgcagtgctcgttaccgtggagcttgagtgcatgcagcggttctttgctgacccggagatgcagcgc |
| aagctagaggaaacattgcactacacctttcgacagggctacgtacgccaggcctgcaagatctccaacgtggagctctgcaacctggt |
| ctcctaccttggaattttgcacgaaaaccgccttgggcaaaacgtgcttcattccacgctcaagggcgaggcgcgccgcgactacgtcc |
| gcgactgcgtttacttatttctatgctacacctggcagacggccatgggcgtttggcagcagtgcttggaggagtgcaacctcaaggagc |
| tgcagaaactgctaaagcaaaacttgaaggacctatggacggccttcaacgagcgctccgtggccgcgcacctggcggacatcattttc |
| cccgaacgcctgcttaaaaccctgcaacagggtctgccagacttcaccagtcaaagcatgttgcagaactttaggaactttatcctagag |
| cgctcaggaatcttgcccgccacctgctgtgcacttcctagcgactttgtgcccattaagtaccgcgaatgccctccgccgctttggggcc |
| actgctaccttctgcagctagccaactaccttgcctaccactctgacataatggaagacgtgagcggtgacggtctactggagtgtcactg |
| tcgctgcaacctatgcaccccgcaccgctccctggtttgcaattcgcagctgcttaacgaaagtcaaattatcggtacctttgagctgcag |

TABLE 31-continued

| Ad5-CFTR No Plasmid Backbone |
| --- |
| ggtccctcgcctgacgaaaagtccgcggctccggggttgaaactcactccggggctgtggacgtcggcttaccttcgcaaatttgtacct |
| gaggactaccacgcccacgagattaggttctacgaagaccaatcccgcccgcctaatgcggagcttaccgcctgcgtcattacccagg |
| gccacattcttggccaattgcaagccatcaacaaagcccgccaagagtttctgctacgaaagggacgggggggtttacttggacccccag |
| tccggcgaggagctcaacccaatccccccgccgccgcagccctatcagcagcagccgcgggcccttgcttcccaggatggcaccca |
| aaaagaagctgcagctgccgccgccacccacggacgaggaggaatactgggacagtcaggcagaggaggttttggacgaggagga |
| ggaggacatgatggaagactgggagagcctagacgaggaagcttccgaggtcgaagaggtgtcagacgaaacaccgtcaccctcg |
| gtcgcattcccctcgccggcgccccagaaatcggcaaccggttccagcatggctacaacctccgctcctcaggcgccgccggcactg |
| cccgttcgccgacccaaccgtagatgggacaccactggaaccagggccggtaagtccaagcagccgccgccgttagcccaagagca |
| acaacagcgccaaggctaccgctcatggcgcgggcacaagaacgccatagttgcttgcttgcaagactgtgggggcaacatctccttc |
| gcccgccgctttcttctctaccatcacggcgtggccttcccccgtaacatcctgcattactaccgtcatctctacagcccatactgcaccgg |
| cggcagcggcagcggcagcaacagcagcggccacacagaagcaaaggcgaccggatagcaagactctgacaaagcccaagaaat |
| ccacagcggcggcagcagcaggaggaggagcgctgcgtctggcgcccaacgaacccgtatcgacccgcgagcttagaaacaggat |
| ttttcccactctgtatgctatatttcaacagagcaggggccaagaacaagagctgaaaaaaaaaacaggtctctgcgatccctcacccgc |
| agctgcctgtatcacaaaagcgaagatcagcttcggcgcacgctggaagacgcggaggctctcttcagtaaatactgcgcgctgactct |
| taaggactagtttcgcgccctttctcaaatttaagcgcgaaaactacgtcatctccagcggccacacccggcgccagcacctgttgtcag |
| cgccattatgagcaaggaaattcccacgccctacatgtggagttaccagccacaaatgggacttgcggctggagctgcccaagactact |
| caacccgaataaactacatgagcgcgggaccccacatgatatcccgggtcaacggaatacgcgcccaccgaaaccgaattctcctgg |
| aacaggcggctattaccaccacacctcgtaataaccttaatccccgtagttggcccgctgccctggtgtaccaggaaagtcccgctccca |
| ccactgtggtacttcccagagacgcccaggccgaagttcagatgactaactcaggggcgcagcttgcgggcggctttcgtcacagggt |
| gcggtcgcccgggcagggtataactcacctgacaatcagagggcgaggtattcagctcaacgacgagtcggtgagctcctcgcttggt |
| ctccgtccggacgggacatttcagatcggcggcgccggccgctcttcattcacgcctcgtcaggcaatcctaactctgcagacctcgtcc |
| tctgagccgcgctctggaggcattggaactctgcaatttattgaggagtttgtgccatcggtctactttaaccccttctcgggacctcccgg |
| ccactatccggatcaatttattcctaactttgacgcggtaaaggactcggcggacggctacgactgaatgttaagtggccaatgaggcct |
| gacgctaataatagctggtccactgtcgccgccacaagtgctttgcccgcgactccggtgagttttgctactttgaattgcccgaggatcat |
| atcgagggcccggcgcacggcgtccggcttaccgcccagggagagcttgcccgtagcctgattcgggagtttacccagcgcccctg |
| ctagttgagcgggacaggggaccctgtgttctcactgtgatttgcaactgtcctaaccttggattacatcaagatccagatcttctagaccc |
| gggagcggccgctgtcgacctgcaggatccgaattcgatatcactagtggtaccgatcttattccctttaactaataaaaaaaaataataaa |
| gcatcacttacttaaaatcagttagcaaatttctgtccagtttattcagcagcacctccttgccctcctcccagctctggtattgcagcttcctc |
| ctggctgcaaactttctccacaatctaaagggaatgtcagtttcctcctgttcctgtccatccgcacccactatcttcatgttgttgcagatga |
| agcgcgcaagaccgtctgaagataccttcaaccccgtgtatccatatgacacggaaaccggtcctccaactgtgccttttcttactcctcc |
| ctttgtatcccccaatgggtttcaagagagtccccctggggtactctctttgcgcctatccgaacctctagttacctccaatggcatgcttgc |
| gctcaaaatgggcaacggcctctctctggacgaggccggcaaccttacctcccaaaatgtaaccactgtgagcccacctctcaaaaaaa |
| ccaagtcaaacataaacctggaaatatctgcacccctcacagttacctcagaagccctaactgtggctgccgccgcacctctaatggtcg |
| cgggcaacacactcaccatgcaatcacaggccccgctaaccgtgcacgactccaaacttagcattgccacccaaggacccctcacagt |
| gtcagaaggaaagctagccctgcaaacatcaggcccccctcaccaccaccgatagcagtacccttactatcactgcctcaccccctctaa |
| ctactgccactggtagcttgggcattgacttgaaagagcccatttatacacaaaatggaaaactaggactaaagtacggggctcctttgca |
| tgtaacagacgacctaaacactttgaccgtagcaactggtccaggtgtgactattaataatacttccttgcaaactaaagttactggagcctt |
| gggttttgattcacaaggcaatatgcaacttaatgtagcaggaggactaaggattgattctcaaaacagacgccttatacttgatgttagtta |
| tccgtttgatgctcaaaaccaactaaatctaagactaggacagggccctctttttataaactcagcccacaacttggatattaactacaacaa |

TABLE 31-continued

| Ad5-CFTR No Plasmid Backbone |
| --- |
| aggcctttacttgtttacagcttcaaacaattccaaaaagcttgaggttaacctaagcactgccaaggggttgatgtttgacgctacagccat |
| agccattaatgcaggagatgggcttgaatttggttcacctaatgcaccaaacacaaatcccctcaaaacaaaaattggccatggcctaga |
| atttgattcaaacaaggctatggttcctaaactaggaactggccttagttttgacagcacaggtgccattacagtaggaaacaaaaataatg |
| ataagctaactttgtggaccacaccagctccatctcctaactgtagactaaatgcagagaaagatgctaaactcactttggtcttaacaaaa |
| tgtggcagtcaaatacttgctacagtttcagttttggctgttaaaggcagtttggctccaatatctggaacagttcaaagtgctcatcttattat |
| aagatttgacgaaaatggagtgctactaaacaattccttcctggacccagaatattggaactttagaaatggagatcttactgaaggcaca |
| gcctatacaaacgctgttggatttatgcctaacctatcagcttatccaaaatctcacggtaaaactgccaaaagtaacattgtcagtcaagttt |
| acttaaacggagacaaaactaaacctgtaacactaaccattacactaaacggtacacaggaaacaggagacacaactccaagtgcata |
| ctctatgtcattttcatgggactggtctggccacaactacattaatgaaatatttgccacatcctcttacactttttcatacattgcccaagaata |
| aagaatcgtttgtgttatgtttcaacgtgtttatttttcaattgcagaaaatttcaagtcatttttcattcagtagtatagccccaccaccacatag |
| cttatacagatcaccgtaccttaatcaaactcacagaaccctagtattcaacctgccacctccctcccaacacacagagtacacagtccttt |
| ctccccggctggccttaaaaagcatcatatcatgggtaacagacatattcttaggtgttatattccacacggtttcctgtcgagccaaacgct |
| catcagtgatattaataaactccccgggcagctcacttaagttcatgtcgctgtccagctgctgagccacaggctgctgtccaacttgcggt |
| tgcttaacgggcggcgaaggagaagtccacgcctacatgggggtagagtcataatcgtgcatcaggatagggcggtggtgctgcagc |
| agcgcgcgaataaactgctgccgccgccgctccgtcctgcaggaatacaacatggcagtggtctcctcagcgatgattcgcaccgccc |
| gcagcataaggcgccttgtcctccgggcacagcagcgcaccctgatctcacttaaatcagcacagtaactgcagcacagcaccacaat |
| attgttcaaaatcccacagtgcaaggcgctgtatccaaagctcatggggggaccacagaacccacgtggccatcataccacaagcgc |
| aggtagattaagtggcgacccctcataaacacgctggacataaacattacctcttttggcatgttgtaattcaccacctcccggtaccatata |
| aacctctgattaaacatggcgccatccaccaccatcctaaaccagctggccaaaacctgcccgccggctatacactgcagggaaccgg |
| gactggaacaatgacagtggagagcccaggactcgtaaccatggatcatcatgctcgtcatgatatcaatgttggcacaacacaggcac |
| acgtgcatacacttcctcaggattacaagctcctcccgcgttagaaccatatcccagggaacaacccattcctgaatcagcgtaaatccca |
| cactgcagggaagacctcgcacgtaactcacgttgtgcattgtcaaagtgttacattcgggcagcagcggatgatcctccagtatggtag |
| cgcgggtttctgtctcaaaaggaggtagacgatccctactgtacggagtgcgccgagacaaccgagatcgtgttggtcgtagtgtcatg |
| ccaaatggaacgccggacgtagtcatatttcctgaagcaaaaccaggtgcgggcgtgacaaacagatctgcgtctccggtctcgccgct |
| tagatcgctctgtgtagtagttgtagtatatccactctctcaaagcatccaggcgccccctggcttcgggttctatgtaaactccttcatgcgc |
| cgctgccctgataacatccaccaccgcagaataagccacacccagccaacctacacattogttctgcgagtcacacacgggaggagc |
| gggaagagctggaagaaccatgtttttttttttattccaaaagattatccaaaacctcaaaatgaagatctattaagtgaacgcgctcccctc |
| cggtggcgtggtcaaactctacagccaaagaacagataatggcatttgtaagatgttgcacaatggcttccaaaaggcaaacggccctc |
| acgtccaagtggacgtaaaggctaaacccttcagggtgaatctcctctataaacattccagcaccttcaaccatgcccaaataattctcatc |
| tcgccaccttctcaatatatctctaagcaaatcccgaatattaagtccggccattgtaaaaatctgctccagagcgccctccaccttcagcct |
| caagcagcgaatcatgattgcaaaaattcaggttcctcacagacctgtataagattcaaaagcggaacattaacaaaaataccgcgatcc |
| cgtaggtcccttcgcagggccagctgaacataatcgtgcaggtctgcacggaccagcgcggccacttccccgccaggaaccatgaca |
| aaagaacccacactgattatgacacgcatactcggagctatgctaaccagcgtagccccgatgtaagcttgttgcatgggcggcgatata |
| aaatgcaaggtgctgctcaaaaaatcaggcaaagcctcgcgcaaaaaagaaagcacatcgtagtcatgctcatgcagataaaggcag |
| gtaagctccggaaccaccacagaaaaagacaccatttttctctcaaacatgtctgcgggtttctgcataaacacaaaataaaataacaaaa |
| aaacatttaaacattagaagcctgtcttacaacaggaaaaacaacccttataagcataagacggactacggccatgccggcgtgaccgt |
| aaaaaaactggtcaccgtgattaaaaagcaccaccgacagctcctcggtcatgtccggagtcataatgtaagactcggtaaacacatca |
| ggttgattcacatcggtcagtgctaaaaagcgaccgaaatagcccgggggaatacatacccgcaggcgtagagacaacattacagccc |
| ccataggaggtataacaaaattaataggagagaaaaacacataaacacctgaaaaaccctcctgcctaggcaaaatagcaccctcccg |

TABLE 31-continued

| Ad5-CFTR No Plasmid Backbone |
|---|
| ctccagaacaacatacagcgcttccacagcggcagccataacagtcagccttaccagtaaaaaagaaaacctattaaaaaaacaccact |
| cgacacggcaccagctcaatcagtcacagtgtaaaaaagggccaagtgcagagcgagtatatataggactaaaaaatgacgtaacggt |
| taaagtccacaaaaaacacccagaaaaccgcacgcgaacctacgcccagaaacgaaagccaaaaaacccacaacttcctcaaatcgt |
| cacttccgttttcccacgttacgtaacttcccattttaagaaaactacaattcccaacacatacaagttactccgccctaaaacctacgtcacc |
| cgccccgttcccacgccccgcgccacgtcacaaactccaccccctcattatcatattggcttcaatccaaaataaggtatattattgatgat |
| g |

TABLE 32

| Ad5-B4Gal-Cas9 with Plasmid Backbone |
|---|
| (SEQ ID NO: 32) |
| gcgtataatggactattgtgtgctgataaggagaacataagcgcagaacaatatgtatctattccggtgttgtgttcctttgttattctgctatta |
| tgttctcttatagtgtgacgaaagcagcataattaatcgccacttgttctttgattgtgttacgatatccagagacttagaaacgggggaacc |
| gggatgagcaaggtaaaaatcggtgagttgatcaacacgcttgtgaatgaggtagaggcaattgatgcctcagaccgcccacaaggcg |
| acaaaacgaagagaattaaagccgcagccgcacggtataagaacgcgttatttaatgataaaagaaagttccgtgggaaaggattgca |
| gaaaagaataaccgcgaatacttttaacgcctatatgagcagggcaagaaagcggtttgatgataaattacatcatagctttgataaaaata |
| ttaataaattatcggaaaagtatcctctttacagcgaagaattatcttcatggctttctatgcctacggctaatattcgccagcacatgtcatcg |
| ttacaatctaaattgaaagaaataatgccgcttgccgaagagttatcaaatgtaagaataggctctaaaggcagtgatgcaaaaatagcaa |
| gactaataaaaaaatatccagattggagttttgctcttagtgatttaaacagtgatgattggaaggagcgccgtgactatctttataagttattc |
| caacaaggctctgcgttgttagaagaactacaccagctcaaggtcaaccatgaggttctgtaccatctgcagctaagccctgcggagcgt |
| acatctatacagcaacgatgggccgatgttctgcgcgagaagaagcgtaatgttgtggttattgactacccaacatacatgcagtctatcta |
| tgatattttgaataatcctgcgactttatttagtttaaacactcgttctggaatggcacctttggcctttgctctggctgcggtatcagggcgaa |
| gaatgattgagataatgtttcagggtgaatttgccgtttcaggaaagtatacggttaatttctcagggcaagctaaaaaacgctctgaagat |
| aaaagcgtaaccagaacgatttatactttatgcgaagcaaaattattcgttgaattattaacagaattgcgttcttgctctgctgcatctgatttc |
| gatgaggttgttaaaggatatggaaaggatgatacaaggtctgagaacggcaggataaatgctattttagcaaaagcatttaacccttggg |
| ttaaatcatttttcggcgatgaccgtcgtgtttataaagatagccgcgctatttacgctcgcatcgcttatgagatgttcttccgcgtcgatcca |
| cggtggaaaaacgtcgacgaggatgtgttcttcatggagattctcggacacgacgatgagaacacccagctgcactataagcagttcaa |
| gctggccaacttctccagaacctggcgacctgaagttggggatgaaaacaccaggctggtggctctgcagaaactggacgatgaaatg |
| ccaggctttgccagaggtgacgctggcgtccgtctccatgaaaccgttaagcagctggtggagcaggacccatcagcaaaaataacca |
| acagcactctccgggcctttaaatttagcccgacgatgattagccggtacctggagtttgccgctgatgcattggggcagttcgttggcga |
| gaacgggcagtggcagctgaagatagagacacctgcaatcgtcctgcctgatgaagaatccgttgagaccatcgacgaaccggatgat |
| gagtcccaagacgacgagctggatgaagatgaaattgagctcgacgagggtggcggcgatgaaccaaccgaagaggaagggccag |
| aagaacatcagccaactgctctaaaacccgtcttcaagcctgcaaaaaataacggggacggaacgtacaagatagagtttgaatacgat |
| ggaaagcattatgcctggtccggccccgccgatagccctatggccgcaatgcgatccgcatgggaaacgtactacagctaaaagaaaa |
| gccaccggtgttaatcggtggctttttttattgaggcctgtccctacccatcccctgcaagggacggaaggattaggcggaaactgcagct |
| gcaactacggacatcgccgtcccgactgcagggacttccccgcgtaaagcggggcttaaattcgggctggccaaccctatttttctgca |
| atcgctggcgatgttagtttcgtggatagcgtttccagcttttcaatggccagctcaaaatgtgctggcagcaccttctccagttccgtatca |
| atatcggtgatcggcagctctccacaagacatactccggcgaccgccacgaactacatcgcgcagcagctcccgttcgtagacacgca |
| tgttgcccagagccgtttctgcagccgttaatatccggcgcagctcggcgatgattgccgggagatcatccacggttattgggttcggtga |
| tgggttcctgcaggcgcggcggagagccatccagacgccgctaacccatgcgttacggtactgaaaactttgtgctatgtcgtttatcag |

TABLE 32-continued

| Ad5-B4Gal-Cas9 with Plasmid Backbone |
| --- |
| gccccgaagttcttctttctgccgccagtccagtggttcaccggcgttcttaggctcaggctcgacaaaagcatactcgccgtttttccgga |
| tagctggcagaacctcgttcgtcacccacttgcggaaccgccaggctgtcgtcccctgtttcaccgcgtcgcggcagcggaggattatg |
| gtgtagagaccagattccgataccacatttacttccctggccatccgatcaagtttttgtgcctcggttaaaccgagggtcaatttttcatcat |
| gatccagcttacgcaatgcatcagaagggttggctatattcaatgcagcacagatatccagcgccacaaaccacgggtcaccaccgac |
| aagaaccacccgtatagggtggctttcctgaaatgaaaagacggagagagccttcattgcgcctccccggatttcagctgctcagaaag |
| ggacagggagcagccgcgagcttcctgcgtgagttcgcgcgcgacctgcagaagttccgcagcttcctgcaaatacagcgtggcctc |
| ataactggagatagtgcggtgagcagagcccacaagcgcttcaacctgcagcaggcgttcctcaatcgtctccagcaggccctgggcg |
| tttaactgaatctggttcatgcgatcacctcgctgaccgggatacgggctgacagaacgaggacaaaacggctggcgaactggcgacg |
| agcttctcgctcggatgatgcagtggtggaaaggcggtggatatgggatttttttgtccgtgcggacgacagctgcaaatttgaatttgaac |
| atggtatgcattcctatcttgtatagggtgctaccaccagagttgagaatctctatagggggtagcccagacagggttctcaacaccgg |
| tacaagaagaaaccggcccaaccgaagttggccccatctgagccaccataattcaggtatgcgcagatttaacacacaaaaaaacacg |
| ctggcgcgtgttgtgcgcttcttgtcattcggggttgagaggcccggctgcagattttgctgcagcggggtaactctaccgccaaagcag |
| aacgcacgtcaataatttaggtggatattttaccccgtgaccagtcacgtgcacaggtgtttttatagtttgctttactgactgatcagaacct |
| gatcagttattggagtccggtaatcttattgatgaccgcagccaccttagatgttgtctcaaaccccatacggccacgaatgagccactgg |
| aacggaatagtcagcaggtacagcggaacgaaccacaaacggttcagacgctgccagaacgtcgcatcacgacgttccatccattcg |
| gtattgtcgacgacctggtaagcgtattgtcctggcgtttttgctgcttccgagtagcaatcctcttcaccacaaagaaagttacttatctgctt |
| ccagttttcgaacccttcttctttgagccgcttttccagctcattcctccacaaaacaggcacccatcctctgcgataaatcatgattatttgtc |
| ctttaaataaggctgtagaactgcaaaatcgctctcgttcacatgctgtacgtagatgcgtagcaaattgccgttccatccctgtaatccacc |
| ttctttggaaagatcgtccttgacctcacgaagaactttatccaatagccctgcggcacaagaaattgcctgctctggatcagcaaattcat |
| attgattaataggtgattgccacacaccaaaaaacaggaatcatcttttcggctaaacgcctctcctgttctttcttaatctcaagttgtaagcg |
| gaccagctcaccatccatcatttttttgtagatcatgcgccactattcacccccactggccatcagcaaataaagcttcatactcggacaccg |
| gcaggcggcttccacggattgaaaggtcaagccaaccacgtccagatgggtcagccttatccgattcttcccaccgttctgcagctgtag |
| caaccaggcattctaccgccttcatgtagtcttctgtacggaaccagccgtagttaatgccaccatcagtaactgcccaggccatctttttct |
| cttcggcctcaatagcccggatgcggttatcgcacagctcgcgacagtacttcagctgttcgtaatccagttgcttcaggaactctggtgtc |
| gacgtcatagtggcttcaccttataggcttttagaagcgccctggcttcgtctgtgtggtcttccatgctcttatcgctggcaatgcagcaata |
| aactccctcactatctgagaacccgttcatccgaatgatcgtgaatggaagttcccggccagttttataatcgctatagcttgtcgcgtcgtg |
| gctgaccttgaccacataagggtcgtagccctccacgatgacaaggcattcccgttgttttcccattacccctccggttatatcgccacgg |
| cttgccgctggcttagaaacgctttcagcagccttatttcgcgtactgatagcaggtccataaattcggtcatgtacagcgaggcgaacgtt |
| ctcgcgatgctggccactggccacaggcgtaccgcctccatttcggttgctggcaacgcgttctccgcccacgcctccggtaccgccac |
| cgggatagcctccagtgcctggataattactgattgtggggcgtccggaacgtgctctgttttggatcgagggttaccatgtatatctatatt |
| tagatccaaatcgcgatccacttcgatggtggtttttttccaccttacgtgcgtgaattgataaaccggcctcgcggcgcttctccacgatatt |
| catgaggaactcgaccgagtccgggtcaatggaacgcatcgtggggcgtgcatcgccgtctctggcgcgtctggtcttactggatagcc |
| ccatagactccaggatgcctatgcagaggtctgcaggcgctttcttcttgcctttctctgtgttgaagccgccgatgcgtaaaacgttgttta |
| gcagatcgcgccgttccggcgtgagcaggttatctctggcgcgtttgagggcgtccatgtctgcttcaccttccagggtttttggatcgata |
| ccgcagtcgcggaagtactgctgcagcgtcgccgatttgagggtgtagaaaccacgcatgcctatctcaacagcaggggtcgatttcac |
| tcggtaatcggttatggccgggaatttagcctggaactctgcgtcggcctgttcccgcgtcatggccgtagtgacgaactgctgccatctt |
| ccggcaacgcgataagcgtaggtaaagtgaatcaacgcttcttcacggtcaaggcgacgggcggttatctcatccagctgcatggtttca |
| aacaggcgcactttttttcaggccgccgtcgaaatagaattttaacgccacctcgtcgacatccagctgcagctccttttcgatgtcccagc |
| ggaccagctgggcctgctcatccagggacagggtgcgttttttttatcaactcatcgtgttcggcctggtcaggagtatcgacactcaggtg |

TABLE 32-continued

| Ad5-B4Gal-Cas9 with Plasmid Backbone |
|---|
| gcgctccataagctgctcaaagaccagttcacgggcttctttacgtaaatccttaccgatgctgtttgcaagcgcgtcggtggccataggc |
| gcgacctgatagccatcatcatgcatgatgcaaatcatgttgctggcataatcatttctggccgatgcctcgagcgcggcggctttaatttt |
| gagctgcatgaatgaagagttagccacgccgagtgaaattcggtcaccgtcaaagacaacgtctgtcagcagcccggagtggccagc |
| cgtttcgagcaaggcctgcgcgtaggcgcgtttgatttttttccggatcggtttcacgtttaccgcgaagcttgtcgaaaccgataatgtattc |
| ctgagctgtacggtcgcggcgcagcatctggatggcgtcgctggggaccacttcgccgcagaacatgccgaaatggcggtggaagtg |
| tttctcctcaatcgatacacctgaagatatcgacgggctgtagatgaggccgtcatatttttttcaccatcactttaggctggttggtgaaatcg |
| tcgacttccttctcctgtttgtttttctggttaacgcagagaaactttttgtcagggaactgtagtctcagctgcatggtaacgtcttcggcgaa |
| cgtcgaactgtcggtggccagcatgattcgttcgccgcgttgcactgcagcgataacctcggtcatgatccgatttttctcggtataaaata |
| cgcggataggcttgttggtttcgcggttgcgaacgtcgaccgggagttcaatcacgtgaatttgcagccaggcaggtaggcccagctcc |
| tcgcgtcgcttcatcgccagttcagccaggtcaacaagcagatcgttggcatcggcatccaccataatggcatgctcttcagtacgcgcc |
| agcgcgtcgataagcgtgttgaatacgcctaccgggttttccatcgcacgcccggccagaatggcacgcaggccctgtgttgcttcatc |
| gaagccgaagaagtcatgctggcgcatcagcggttgccagcagcctttaagtatggagttgatgcaaatagtcagcttgttggcatatgg |
| cgccatttcctgatagccgggatcctgataatgcagaatgtcggctttcgcgcctttcccttcggtcatcatttcatgcaggccgcctatcag |
| ggatacgcggtgcgcgacggaaacgccacgcgtggactgcagcatcagtggacgcaggaggcctgtcgatttacccgaccccatcc |
| cggcgcggacaataacgatgccctgcagctgtgcggcgtatgtcatcacctcatcggtcatcctggaggtttcaaaccgtttgtaagtgat |
| gtgtgacgggcgaaggttcgggttggtgatgcgttcactgaacgaacgtgatgtttgcgcggcacggcatttgcgattcaaccggcgcg |
| taatgtgatctttaacggtaccgttataaatttctgcgatacccatatcccgcagcgtgctgctgaaaaggcgcataagttctttcgggctgtt |
| tggtaccgggcatgtcagcatgccaatatcaacggcgcgaagcagttctttggcaaaagtgcgtctgttcagacgcgggagagtacgc |
| agcttattcagcgtgatcgacaacagatcggttgcacggctcagatgatttctcgttaactggcgagcgacttccttcagccctctcaggct |
| gtgcaggtcgttaaaatcgctgcattccagctcagggtcatcctcaaaagttgggtaaacacatttgacgccggaaaacttctccatgatgt |
| cgaatccggtgcggaggcctgtgttgccttttccttcagctgaggatttgcggtcgttatcgagagcgcaagtgatttgcgcagccgggta |
| catgttcaccagctgctcgacaacgtgaatcatgttgttagcggaaaccgcaatgactaccgcgtcaaagcgtttttttcgggtcgtttctgg |
| tcgccagccagatggatgccccggtggcgaaaccctctgcagtcgcaatttttttgcgccccctgcaggtcgccaataacaaagcatgca |
| ccgacgaaatcaccgttagtgatggcgctggtctggaacttgccaccattcagatcgatacgttgccagccaacaatccgcccgtcttttc |
| ttccgtccaggtgggacagaggtatcgccatgtaagttgttggtccacggctccatttcgcactgtcgtgactggtcacgcgacgtatatc |
| acaagcgccaaatacgtcacgaattcccttttttaccgcataaggccaggagccatcttcagctggcgaatgttcccaggcgcgatggaa |
| agccaaccatccaagcaggcgttcctgctccatctgattgtttttttaaatcattaacgcgttgttgttcagctcggaggcggcgtgcttcagc |
| ctggcgctccatgcgtgcacgttcttcttccggctgagcgaccacggtcgcaccattccgttgctgttcacggcgatactccgaaaacag |
| gaatgaaaagccactccaggagccagcgtcatgcgctttttcaacgaagttaacgaaaggataactgatgccatccttgctctgctcaag |
| gcgtgaatagatttccacacggcctttaaggctcttctgcagagcttccggggaggaattattgtaggtggtatagcgctctacaccaccg |
| cgcggattgagctgaatcttatcagcacacgcaggccagttgataccggccatcttcgccagctcagtcagctcatcacgtgccgcgtca |
| agcagtgaaaacggatcgctgccaaagcgctccgcgtagaattcttgtaaggtcatttttttagcctttccatgcgaattagcatttttttcgggt |
| tgaaaaaatccgcaggagcagccacaataaacgcactatctttctgaaggacgtatctgcgttatcgtggctacttcctgaaaaaggccc |
| gagtttgccgactcggtttttttttcgtctttttttcggctgctacggtctggttcaaccccgacaaagtatagatcggattaaaccagaattata |
| gtcagcaataaaccctgttattgtatcatctaccctcaaccatgaacgatttgatcgtaccgactacttggtgcacaaattgaagatcactttt |
| atcatggataacccgttgagagttagcactatcaaggtagtaatgctgctcgtcataacgggctaatcgttgaattgtgatctcgccgttatt |
| atcacaaaccagtacatcctcacccggtacaagcgtaagtgaagaatcgaccaggataacgtctcccggctggtagtttcgctgaatctg |
| gttcccgaccgtcagtgcgtaaacggtgttccgttgactcacgaacggcaggaatcgctctgtgttggcaggttctccaggctgccagtc |
| tctatccggtccggtctctgtcgtaccaataacaggaacgcggtctggatcagattcagtgccatacagtatccattgcacgggcttacgc |

TABLE 32-continued

| Ad5-B4Gal-Cas9 with Plasmid Backbone |
|---|
| aggcattttgccagcgatagcccgatctccagcgacggcatcacgtcgccacgttctaagttttggacgcccggaagagagattcctac |
| agcttctgccacttgcttcagcgtcagtttcagctctaaacggcgtgctttcagtcgttcgcctcgtgttttcatacccttaatcataaatgatct |
| ctttatagctggctataatttttataaattatacctagctttaattttcacttattgattataataatccccatgaaacccgaagaacttgtgcgcca |
| tttcggcgatgtggaaaaagcagcggttggcgtgggcgtgacacccggcgcagtctatcaatggctgcaagctggggagattccacct |
| ctacgacaaagcgatatagaggtccgtaccgcgtacaaattaaagagtgatttcacctctcagcgcatgggtaaggaagggcataacaa |
| ggggatcctctagacgcagaaaggcccacccgaaggtgagccagtgtgattacatttgcggcctaactgtggccagtccagttacgctg |
| gagtcactagtgcggccgcgacaacttgtctagggcccaatggcccaaattaattaacatcatcaataatataccttattttggattgaagc |
| caatatgataatgagggggtggagtttgtgacgtggcgcggggcgtgggaacggggcgggtgacgtagtagtgtggcggaagtgtga |
| tgttgcaagtgtggcggaacacatgtaagcgacggatgtggcaaaagtgacgtttttggtgtgcgccggtgtacacaggaagtgacaatt |
| ttcgcgcggttttaggcggatgttgtagtaaatttgggcgtaaccgagtaagatttggccattttcgcgggaaaactgaataagaggaagt |
| gaaatctgaataattttgtgttactcatagcgcgtaatatttgtctagggccgcggggactttgaccgtttacgtggagactcgcccaggtgt |
| ttttctcaggtgttttccgcgttccgggtcaaagttggcgttttagatcttaaaacaaaaaagcaccgactcggtgccactttttcaagttgata |
| acggactagccttattttaacttgctatttctagctctaaaaccaagatattgatggtgctttcggtgtttcgtcctttccacaagatatataaag |
| ccaagaaatcgaaatactttcaagttacggtaagcatatgatagtccattttaaaacataattttaaaactgcaaactacccaagaaattatta |
| ctttctacgtcacgtattttgtactaatatctttgtgtttacagtcaaattaattccaattatctctctaacagccttgtatcgtatatgcaaatatga |
| aggaatcatgggaaataggccctcacatgtgagcaaaagtcgacctgcaggatcctgattattgactagttattaatagtaatcaattacgg |
| ggtcattagttcatagcccatatatggagttccgcgttacataacttacggtaaatggcccgcctggctgaccgcccaacgacccccgcc |
| cattgacgtcaataatgacgtatgttcccatagtaacgccaatagggactttccattgacgtcaatgggtggagtatttacggtaaactgcc |
| cacttggcagtacatcaagtgtatcatatgccaagtccgccccctattgacgtcaatgacggtaaatggcccgcctggcattatgcccagt |
| acatgaccttacgggactttcctacttggcagtacatctacgtattagtcatcgctattaccatgctgatgcggttttggcagtacaccaatgg |
| gcgtggatagcggtttgactcacggggatttccaagtctccaccccattgacgtcaatgggagtttgttttggcaccaaaatcaacgggac |
| tttccaaaatgtcgtaataaccccgccccgttgacgcaaatgggcggtaggcgtgtacggtgggaggtctatataagcagagctcgttta |
| gtgaaccgtcagatcactagaagctttattgcggtagtttatcacagttaaattgctaacgcagtcaggccaacagagaccacacccaag |
| ctggccgccaccatggccccaaagaagaagcggaaggtcggtatccacggagtcccagcagccgacaagaagtacagcatcggcc |
| tggacatcggcaccaactctgtgggctgggccgtgatcaccgacgagtacaaggtgcccagcaagaaattcaaggtgctgggcaaca |
| ccgaccggcacagcatcaagaagaacctgatcggagccctgctgttcgacagcggcgaaacagccgaggccacccggctgaagag |
| aaccgccagaagaagatacaccagacggaagaaccggatctgctatctgcaagagatcttcagcaacgagatggccaaggtggacg |
| acagcttcttccacagactggaagagtccttcctggtggaagaggataagaagcacgagcggcaccccatcttcggcaacatcgtgga |
| cgaggtggcctaccacgagaagtaccccaccatctaccacctgagaaagaaactggtggacagcaccgacaaggccgacctgcggc |
| tgatctatctggccctggcccacatgatcaagttccggggccacttcctgatcgagggcgacctgaaccccgacaacagcgacgtgga |
| caagctgttcatccagctggtgcagacctacaaccagctgttcgaggaaaaccccatcaacgccagcggcgtggacgccaaggccat |
| cctgtctgccagactgagcaagagcagacggctggaaaatctgatcgcccagctgcccggcgagaagaagaatggcctgttcggaaa |
| cctgattgccctgagcctgggcctgacccccaacttcaagagcaacttcgacctggccgaggatgccaaactgcagctgagcaaggac |
| acctacgacgacgacctggacaacctgctggcccagatcggcgaccagtacgccgacctgtttctggccgccaagaacctgtccgac |
| gccatcctgctgagcgacatcctgagagtgaacaccgagatcaccaaggcccccctgagcgcctctatgatcaagagatacgacgag |
| caccaccaggacctgaccctgctgaaagctctcgtgcggcagcagctgcctgagaagtacaaagagattttcttcgaccagagcaaga |
| acggctacgccggctacattgacggcggagccagccaggaagagttctacaagttcatcaagcccatcctggaaaagatggacggca |
| ccgaggaactgctcgtgaagctgaacagagaggacctgctgcggaagcagcggaccttcgacaacggcagcatccccccaccagatc |
| cacctgggagagctgcacgccattctgcggcggcaggaagattttacccattcctgaaggacaaccgggaaaagatcgagaagatcc |

TABLE 32-continued

| Ad5-B4Gal-Cas9 with Plasmid Backbone |
|---|
| tgaccttccgcatcccctactacgtgggccctctggccaggggaaacagcagattcgcctggatgaccagaaagagcgaggaaacca |
| tcacccccctggaacttcgaggaagtggtggacaagggcgcttccgcccagagcttcatcgagcggatgaccaacttcgataagaacct |
| gcccaacgagaaggtgctgcccaagcacagcctgctgtacgagtacttcaccgtgtataacgagctgaccaaagtgaaatacgtgacc |
| gagggaatgagaaagcccgccttcctgagcggcgagcagaaaaaggccatcgtggacctgctgttcaagaccaaccggaaagtgac |
| cgtgaagcagctgaaagaggactacttcaagaaaatcgagtgcttcgactccgtggaaatctccggcgtggaagatcggttcaacgcct |
| ccctgggcacataccacgatctgctgaaaattatcaaggacaaggacttcctggacaatgaggaaaacgaggacattctggaagatatc |
| gtgctgaccctgacactgtttgaggacagagagatgatcgaggaacggctgaaaacctatgcccacctgttcgacgacaaagtgatga |
| agcagctgaagcggcggagatacaccggctggggcaggctgagccggaagctgatcaacggcatccgggacaagcagtccggca |
| agacaatcctggatttcctgaagtccgacggcttcgccaacagaaacttcatgcagctgatccacgacgacagcctgacctttaaagag |
| gacatccagaaagcccaggtgtccggccagggcgatagcctgcacgagcacattgccaatctggccggcagccccgccattaagaa |
| gggcatcctgcagacagtgaaggtggtggacgagctcgtgaaagtgatgggccggcacaagcccgagaacatcgtgatcgaaatgg |
| ccagagagaaccagaccacccagaagggacagaagaacagccgcgagagaatgaagcggatcgaagagggcatcaaagagctg |
| ggcagccagatcctgaaagaacaccccgtggaaaacacccagctgcagaacgagaagctgtacctgtactacctgcagaatgggcg |
| ggatatgtacgtggaccaggaactggacatcaaccggctgtccgactacgatgtggaccatatcgtgcctcagagctttctgaaggacg |
| actccatcgacaacaaggtgctgaccagaagcgacaagaaccggggcaagagcgacaacgtgccctccgaagaggtcgtgaagaa |
| gatgaagaactactggcggcagctgctgaacgccaagctgattacccagagaaagttcgacaatctgaccaaggccgagagaggcg |
| gcctgagcgaactggataaggccggcttcatcaagagacagctggtggaaacccggcagatcacaaagcacgtggcacagatcctg |
| gactcccggatgaacactaagtacgacgagaatgacaagctgatccgggaagtgaaagtgatcaccctgaagtccaagctggtgtccg |
| atttccggaaggatttccagttttacaaagtgcgcgagatcaacaactaccaccacgcccacgacgcctacctgaacgccgtcgtggga |
| accgccctgatcaaaaagtaccctaagctggaaagcgagttcgtgtacggcgactacaaggtgtacgacgtgcggaagatgatcgcca |
| agagcgagcaggaaatcggcaaggctaccgccaagtacttcttctacagcaacatcatgaactttttcaagaccgagattaccctggcca |
| acggcgagatccggaagcggcctctgatcgagacaaacggcgaaaccggggagatcgtgtgggataagggccgggattttgccacc |
| gtgcggaaagtgctgagcatgccccaagtgaatatcgtgaaaaagaccgaggtgcagacaggcggcttcagcaaagagtctatcctg |
| cccaagaggaacagcgataagctgatcgccagaaagaaggactgggaccctaagaagtacggcggcttcgacagccccaccgtgg |
| cctattctgtgctggtggtggccaaagtggaaaagggcaagtccaagaaactgaagagtgtgaaagagctgctggggatcaccatcat |
| ggaaagaagcagcttcgagaagaatcccatcgactttctggaagccaagggctacaaagaagtgaaaaaggacctgatcatcaagctg |
| cctaagtactccctgttcgagctggaaaacggccggaagagaatgctggcctctgccggcgaactgcagaagggaaacgaactggcc |
| ctgccctccaaatatgtgaacttcctgtacctggccagccactatgagaagctgaagggctcccccgaggataatgagcagaaacagct |
| gtttgtggaacagcacaagcactacctggacgagatcatcgagcagatcagcgagttctccaagagagtgatcctggccgacgctaatc |
| tggacaaagtgctgtccgcctacaacaagcaccgggataagcccatcagagagcaggccgagaatatcatccacctgtttaccctgac |
| caatctgggagcccctgccgccttcaagtactttgacaccaccatcgaccggaagaggtacaccagcaccaaagaggtgctggacgc |
| caccctgatccaccagagcatcaccggcctgtacgagacacggatcgacctgtctcagctgggaggcgacaaaaggccggcggcca |
| cgaaaaaggccggccaggcaaaaaagaaaaagtaataattctagagtcggggcggccggccgcttcgagagctagagctttcttgct |
| gtccaatttctattaaaggttcctttgttccctaagtccaactactaaactgggggatattatgaagggccttgagcatctggattctgcctaat |
| aaaaaacatttattttcattgcaatgatgtattttaaaatcgataaggatccgaattcgatatcactagtggtaccagtactgaaatgtgtgggc |
| gtggcttaagggtgggaaagaatatataaggtgggggtcttatgtagttttgtatctgttttgcagcagccgccgccgccatgagcaccaa |
| ctcgtttgatggaagcattgtgagctcatatttgacaacgcgcatgcccccatgggccggggtgcgtcagaatgtgatgggctccagcat |
| tgatggtcgccccgtcctgcccgcaaactctactaccttgacctacgagaccgtgtctggaacgccgttggagactgcagcctccgccg |
| ccgcttcagccgctgcagccaccgcccgcgggattgtgactgactttgctttcctgagcccgcttgcaagcagtgcagcttcccgttcatc |

TABLE 32-continued

| Ad5-B4Gal-Cas9 with Plasmid Backbone |
|---|
| cgcccgcgatgacaagttgacggctcttttggcacaattggattctttgacccgggaacttaatgtcgtttctcagcagctgttggatctgcg |
| ccagcaggtttctgccctgaaggcttcctcccctcccaatgcggtttaacggtccgggccagagtggccaacataaataaaaaaccaga |
| ctctgtttggatttggatcaagcaagtgtcttgctgtctttatttaggggttttgcgcgcgcggtaggcccgggaccagcggtctcggtcgtt |
| gagggtcctgtgtatttttttccaggacgtggtaaaggtgactctggatgttcagatacatgggcataagcccgtctctggggtggaggtag |
| caccactgcagagcttcatgctgcggggtggtgttgtagatgatccagtcgtagcaggagcgctgggcgtggtgcctaaaaatgtctttc |
| agtagcaagctgattgccaggggcaggcccttggtgtaagtgtttacaaagcggttaagctgggatgggtgcatacgtggggatatgag |
| atgcatcttggactgtatttttaggttggctatgttcccagccatatccctccggggattcatgttgtgcagaaccaccagcacagtgtatcc |
| ggtgcacttgggaaatttgtcatgtagcttagaaggaaatgcgtggaagaacttggagacgcccttgtgacctccaagattttccatgcatt |
| cgtccataatgatggcaatgggcccacgggcggcggcctgggcgaagatatttctgggatcactaacgtcatagttgtgttccaggatg |
| agatcgtcataggccatttttacaaagcgcgggcggagggtgccagactgcggtataatggttccatccggcccaggggcgtagttacc |
| ctcacagatttgcatttcccacgctttgagttcagatgggggatcatgtctacctgcggggcgatgaagaaaacggtttccggggtagg |
| ggagatcagctgggaagaaagcaggttcctgagcagctgcgacttaccgcagccggtgggcccgtaaatcacacctattaccggctg |
| caactggtagttaagagagctgcagctgccgtcatccctgagcaggggggccacttcgttaagcatgtccctgactcgcatgttttccctg |
| accaaatccgccagaaggcgctcgccgcccagcgatagcagttcttgcaaggaagcaaagtttttcaacggtttgagaccgtccgccgt |
| aggcatgcttttgagcgtttgaccaagcagttccaggcggtcccacagctcggtcacctgctctacggcatctcgatccagcatatctcct |
| cgtttcgcgggttggggcggctttcgctgtacggcagtagtcggtgctcgtccagacgggccagggtcatgtctttccacgggcgcagg |
| gtcctcgtcagcgtagtctgggtcacggtgaaggggtgcgctccgggctgcgcgctggccagggtgcgcttgaggctggtcctgctgg |
| tgctgaagcgctgccggtcttcgccctgcgcgtcggccaggtagcatttgaccatggtgtcatagtccagcccctccgcggcgtggccc |
| ttggcgcgcagcttgcccttggaggaggcgccgcacgaggggcagtgcagacttttgagggcgtagagcttgggcgcgagaaatac |
| cgattccggggagtaggcatccgcgccgcaggccccgcagacggtctcgcattccacgagccaggtgagctctggccgttcggggtc |
| aaaaaccaggtttcccccatgctttttgatgcgtttcttacctctggtttccatgagccggtgtccacgctcggtgacgaaaaggctgtccgt |
| gtccccgtatacagacttgagaggcctgtcctcgagcggtgttccgcggtcctcctcgtatagaaactcggaccactctgagacaaagg |
| ctcgcgtccaggccagcacgaaggaggctaagtgggaggggtagcggtcgttgtccactagggggtccactcgctccagggtgtgaa |
| gacacatgtcgccctcttcggcatcaaggaaggtgattggtttgtaggtgtaggccacgtgaccgggtgttcctgaaggggggctataaa |
| agggggtgggggcgcgttcgtcctcactctcttccgcatcgctgtctgcgagggccagctgttggggtgagtactccctctgaaaagcg |
| ggcatgacttctgcgctaagattgtcagtttccaaaaacgaggaggatttgatattcacctggcccgcggtgatgcctttgagggtggccg |
| catccatctggtcagaaaagacaatctttttgttgtcaagcttggtggcaaacgacccgtagagggcgttggacagcaacttggcgatgg |
| agcgcagggtttggtttttgtcgcgatcggcgcgctccttggccgcgatgtttagctgcacgtattcgcgcgcaacgcaccgccattcgg |
| gaaagacggtggtgcgctcgtcgggcaccaggtgcacgcgccaaccgcggttgtgcagggtgacaaggtcaacgctggtggctacc |
| tctccgcgtaggcgctcgttggtccagcagaggcggccgcccttgcgcgagcagaatggcggtagggggtctagctgcgtctcgtcc |
| ggggtctgcgtccacggtaaagaccccgggcagcaggcgcgcgtcgaagtagtctatcttgcatccttgcaagtctagcgcctgct |
| gccatgcgcgggcggcaagcgcgcgctcgtatgggttgagtgggggaccccatggcatggggtgggtgagcgcggaggcgtacat |
| gccgcaaatgtcgtaaacgtagaggggctctctgagtattccaagatatgtagggtagcatcttccaccgcggatgctggcgcgcacgt |
| aatcgtatagttcgtgcgagggagcgaggaggtcgggaccgaggttgctacgggggctgctctgctcggaagactatctgcctgaa |
| gatggcatgtgagttggatgatatggttggacgctggaagacgttgaagctggcgtctgtgagacctaccgcgtcacgcacgaaggag |
| gcgtaggagtcgcgcagcttgttgaccagctcggcggtgacctgcacgtctagggcgcagtagtccagggtttccttgatgatgtcatac |
| ttatcctgtcccttttttttccacagctcgcggttgaggacaaactcttcgcggtctttccagtactcttggatcggaaacccgtcggcctccg |
| aacggtaagagcctagcatgtagaactggttgacggcctggtaggcgcagcatcccttttctacgggtagcgcgtatgcctgcgcggcc |
| ttccggagcgaggtgtgggtgagcgcaaaggtgtccctgaccatgactttgaggtactggtatttgaagtcagtgtcgtcgcatccgccc |

TABLE 32-continued

| Ad5-B4Gal-Cas9 with Plasmid Backbone |
|---|
| tgctcccagagcaaaaagtccgtgcgctttttggaacgcggatttggcagggcgaaggtgacatcgttgaagagtatctttcccgcgcga |
| ggcataaagttgcgtgtgatgcggaagggtcccggcacctcggaacggttgttaattacctgggcggcgagcacgatctcgtcaaagc |
| cgttgatgttgtggcccacaatgtaaagttccaagaagcgcgggatgcccttgatggaaggcaattttttaagttcctcgtaggtgagctct |
| tcaggggagctgagcccgtgctctgaaagggcccagtctgcaagatgagggttggaagcgacgaatgagctccacaggtcacgggc |
| cattagcatttgcaggtggtcgcgaaaggtcctaaactggcgacctatggccattttttctggggtgatgcagtagaaggtaagcgggtct |
| tgttcccagcggtcccatccaaggttcgcggctaggtctcgcgcggcagtcactagaggctcatctccgccgaacttcatgaccagcat |
| gaagggcacgagctgcttcccaaaggcccccatccaagtataggtctctacatcgtaggtgacaaagagacgctcggtgcgaggatgc |
| gagccgatcgggaagaactggatctcccgccaccaattggaggagtggctattgatgtggtgaaagtagaagtccctgcgacgggcc |
| gaacactcgtgctggcttttgtaaaaacgtgcgcagtactggcagcggtgcacgggctgtacatcctgcacgaggttgacctgacgacc |
| gcgcacaaggaagcagagtgggaatttgagcccctcgcctggcgggtttggctggtggtcttctacttcggctgcttgtccttgaccgtct |
| ggctgctcgaggggagttacggtggatcggaccaccacgccgcgcgagcccaaagtccagatgtccgcgcgcggcggtcggagctt |
| gatgacaacatcgcgcagatgggagctgtccatggtctggagctcccgcggcgtcaggtcaggcgggagctcctgcaggtttacctcg |
| catagacgggtcagggcgcgggctagatccaggtgatacctaatttccaggggctggttggtggcggcgtcgatggcttgcaagaggc |
| cgcatccccgcggcgcgactacggtaccgcgcgggggcggtgggccgcgggggtgtccttggatgatgcatctaaaagcggtgac |
| gcgggcgagcccccggaggtagggggggctccggacccgccgggagagggggcaggggcacgtcggcgccgcgcgcgggca |
| ggagctggtgctgcgcgcgtaggttgctggcgaacgcgacgacgcggcggttgatctcctgaatctggcgcctctgcgtgaagacga |
| cgggcccggtgagcttgaacctgaaagagagttcgacagaatcaatttcggtgtcgttgacggcggcctggcgcaaaatctcctgcac |
| gtctcctgagttgtcttgataggcgatctcggccatgaactgctcgatctcttcctcctggagatctccgcgtccggctcgctccacggtgg |
| cggcgaggtcgttggaaatgcgggccatgagctgcgagaaggcgttgaggcctccctcgttccagacgcggctgtagaccacgcccc |
| cttcggcatcgcgggcgcgcatgaccacctgcgcgagattgagctccacgtgccgggcgaagacggcgtagtttcgcaggcgctgaa |
| agaggtagttgagggtggtggcggtgtgttctgccacgaagaagtacataacccagcgtcgcaacgtggattcgttgatatcccccaag |
| gcctcaaggcgctccatggcctcgtagaagtccacggcgaagttgaaaaactgggagttgcgcgccgacacggttaactcctcctcca |
| gaagacggatgagctcggcgacagtgtcgcgcacctcgcgctcaaaggctacaggggcctcttcttcttcttcaatctcctcttccataag |
| ggcctccccttcttcttcttctggcggcggtgggggaggggggacacggcggcgacgacggcgcaccgggaggcggtcgacaaag |
| cgctcgatcatctccccgcggcgacggcgcatggtctcggtgacggcgcggccgttctcgcgggggcgcagttggaagacgccgcc |
| cgtcatgtcccggttatgggttggcgggggctgccatgcggcagggatacggcgctaacgatgcatctcaacaattgttgtgtaggta |
| ctccgccgccgagggacctgagcgagtccgcatcgaccggatcggaaaacctctcgagaaaggcgtctaaccagtcacagtcgcaa |
| ggtaggctgagcaccgtggcgggcggcagcgggcggcggtcggggttgtttctggcggaggtgctgctgatgatgtaattaaagtag |
| gcggtcttgagacggcggatggtcgacagaagcaccatgtccttgggtccggcctgctgaatgcgcaggcggtcggccatgccccag |
| gcttcgttttgacatcggcgcaggtctttgtagtagtcttgcatgagcctttctaccggcacttcttcttctccttcctcttgtcctgcatctcttg |
| catctatcgctgcggcggcggcggagtttggccgtaggtggcgccctcttcctcccatgcgtgtgaccccgaagcccctcatcggctga |
| agcagggctaggtcggcgacaacgcgctcggctaatatggcctgctgcacctgcgtgagggtagactggaagtcatccatgtccacaa |
| agcggtggtatgcgcccgtgttgatggtgtaagtgcagttggccataacggaccagttaacggtctggtgacccggctgcgagagctcg |
| gtgtacctgagacgcgagtaagccctcgagtcaaatacgtagtcgttgcaagtccgcaccaggtactggtatcccaccaaaaagtgcgg |
| cggcggctggcggtagaggggccagcgtagggtggccggggctccgggggcgagatcttccaacataaggcgatgatatccgtag |
| atgtacctggacatccaggtgatgccggcggcggtggtggaggcgcgcggaaagtcgcggacgcggttccagatgttgcgcagcgg |
| caaaaagtgctccatggtcgggacgctctggccggtcaggcgcgcgcaatcgttgacgctctagaccgtgcaaaaggagagcctgta |
| agcgggcactcttccgtggtctggtggataaattcgcaagggtatcatggcggacgaccggggttcgagccccgtatccggccgtccg |
| ccgtgatccatgcggttaccgcccgcgtgtcgaacccaggtgtgcgacgtcagacaacgggggagtgctccttttggcttccttccagg |

TABLE 32-continued

| Ad5-B4Gal-Cas9 with Plasmid Backbone |
| --- |
| cgcggcggctgctgcgctagctttttggccactggccgcgcgcagcgtaagcggttaggctggaaagcgaaagcattaagtggctcg |
| ctccctgtagccggagggttattttccaagggttgagtcgcgggacccccggttcgagtctcggaccggccggactgcggcgaacgg |
| gggtttgcctccccgtcatgcaagaccccgcttgcaaattcctccggaaacagggacgagcccctttttttgcttttcccagatgcatccggt |
| gctgcggcagatgcgcccccctcctcagcagcggcaagagcaagagcagcggcagacatgcagggcaccctcccctcctcctaccg |
| cgtcaggaggggcgacatccgcggttgacgcggcagcagatggtgattacgaacccccgcggcgccgggcccggcactacctgga |
| cttggaggagggcgagggcctggcgcggctaggagcgccctctcctgagcggcacccaagggtgcagctgaagcgtgatacgcgt |
| gaggcgtacgtgccgcggcagaacctgtttcgcgaccgcgagggagaggagcccgaggagatgcgggatcgaaagttccacgcag |
| ggcgcgagctgcggcatggcctgaatcgcgagcggttgctgcgcgaggaggactttgagcccgacgcgcgaaccgggattagtccc |
| gcgcgcgcacacgtggcggccgccgacctggtaaccgcatacgagcagacggtgaaccaggagattaactttcaaaaaagctttaac |
| aaccacgtgcgtacgcttgtggcgcgcgaggaggtggctataggactgatgcatctgtgggactttgtaagcgcgctggagcaaaacc |
| caaatagcaagccgctcatggcgcagctgttccttatagtgcagcacagcagggacaacgaggcattcagggatgcgctgctaaacat |
| agtagagcccgagggccgctggctgctcgatttgataaacatcctgcagagcatagtggtgcaggagcgcagcttgagcctggctgac |
| aaggtggccgccatcaactattccatgcttagcctgggcaagttttacgcccgcaagatataccatacccttacgttcccatagacaagg |
| aggtaaagatcgaggggttctacatgcgcatggcgctgaaggtgcttaccttgagcgacgacctgggcgtttatcgcaacgagcgcatc |
| cacaaggccgtgagcgtgagccggggcgcgagctcagcgaccgcgagctgatgcacagcctgcaaagggccctggctggcacg |
| ggcagcggcgatagagaggccgagtcctactttgacgcgggcgctgacctgcgctgggccccaagccgacgcgccctggaggcag |
| ctggggccggacctgggctggcggtggcacccgcgcgcgctggcaacgtcggcggcgtggaggaatatgacgaggacgatgagta |
| cgagccagaggacggcgagtactaagcggtgatgtttctgatcagatgatgcaagacgcaacggacccggcggtgcgggcggcgct |
| gcagagccagccgtccggccttaactccacggacgactggcgccaggtcatggaccgcatcatgtcgctgactgcgcgcaatcctga |
| cgcgttccggcagcagccgcaggccaaccggctctccgcaattctggaagcggtggtcccggcgcgcgcaaaccccacgcacgag |
| aaggtgctggcgatcgtaaacgcgctggccgaaaacagggccatccggcccgacgaggccggcctggtctacgacgcgctgcttca |
| gcgcgtggctcgttacaacagcggcaacgtgcagaccaacctggaccggctggtgggggatgtgcgcgaggccgtggcgcagcgt |
| gagcgcgcgcagcagcagggcaacctgggctccatggttgcactaaacgccttcctgagtacacagcccgccaacgtgccgcgggg |
| acaggaggactacaccaactttgtgagcgcactgcggctaatggtgactgagacaccgcaaagtgaggtgtaccagtctgggccaga |
| ctatttttttccagaccagtagacaaggcctgcagaccgtaaacctgagccaggctttcaaaaacttgcaggggctgtggggggtgcggg |
| ctcccacaggcgaccgcgcgaccgtgtctagcttgctgacgcccaactcgcgcctgttgctgctgctaatagcgcccttcacggacagt |
| ggcagcgtgtcccgggacacatacctaggtcacttgctgacactgtaccgcgaggccataggtcaggcgcatgtggacgagcatacttt |
| ccaggagattacaagtgtcagccgcgcgctggggcaggaggacacgggcagcctggaggcaaccctaaactacctgctgaccaacc |
| ggcggcagaagatcccctcgttgcacagtttaaacagcgaggaggagcgcattttgcgctacgtgcagcagagcgtgagccttaacct |
| gatgcgcgacggggtaacgcccagcgtggcgctggacatgaccgcgcgcaacatggaaccgggcatgtatgcctcaaaccggccgt |
| ttatcaaccgcctaatggactacttgcatcgcgcggccgccgtgaaccccgagtatttcaccaatgccatcttgaacccgcactggctac |
| cgccccctggtttctacaccgggggattcgaggtgcccgagggtaacgatggattcctctgggacgacatagacgacagcgtgttttcc |
| ccgcaaccgcagaccctgctagagttgcaacagcgcgagcaggcagaggcggcgctgcgaaaggaaagcttccgcaggccaagc |
| agcttgtccgatctaggcgctgcggccccgcggtcagatgctagtagcccatttccaagcttgatagggtctcttaccagcactcgcacc |
| acccgcccgcgcctgctgggcgaggaggagtacctaaacaactcgctgctgcagccgcagcgcgaaaaaaacctgcctccggcattt |
| cccaacaacgggatagagagcctagtggacaagatgagtagatggaagacgtacgcgcaggagcacagggacgtgccaggcccg |
| cgcccgcccacccgtcgtcaaaggcacgaccgtcagcggggtctggtgtgggaggacgatgactcggcagacgacagcagcgtcct |
| ggatttgggagggagtggcaacccgtttgcgcaccttcgccccaggctggggagaatgttttaaaaaaaaaaaaaagcatgatgcaaa |
| ataaaaaactcaccaaggccatggcaccgagcgttggttttcttgtattccccttagtatgcggcgcgcggcgatgtatgaggaaggtcct |

TABLE 32-continued

| Ad5-B4Gal-Cas9 with Plasmid Backbone |
|---|
| cctccctcctacgagagtgtggtgagcgcggcgccagtggcggcggcgctgggttctcccttcgatgctcccctggacccgccgtttgt |
| gcctccgcggtacctgcggcctaccggggggagaaacagcatccgttactctgagttggcacccctattcgacaccacccgtgtgtacc |
| tggtggacaacaagtcaacggatgtggcatccctgaactaccagaacgaccacagcaactttctgaccacggtcattcaaaacaatgac |
| tacagcccgggggaggcaagcacacagaccatcaatcttgacgaccggtcgcactggggcggcgacctgaaaaccatcctgcatac |
| caacatgccaaatgtgaacgagttcatgtttaccaataagtttaaggcgcgggtgatggtgtcgcgcttgcctactaaggacaatcaggtg |
| gagctgaaatacgagtgggtggagttcacgctgcccgagggcaactactccgagaccatgaccatagaccttatgaacaacgcgatcg |
| tggagcactacttgaaagtgggcagacagaacggggttctggaaagcgacatcggggtaaagtttgacacccgcaacttcagactggg |
| gtttgaccccgtcactggtcttgtcatgcctggggtatatacaaacgaagccttccatccagacatcattttgctgccaggatgcggggtg |
| gacttcacccacagccgcctgagcaacttgttgggcatccgcaagcggcaacccttccaggagggctttaggatcacctacgatgatct |
| ggagggggtaacattcccgcactgttggatgtggacgcctaccaggcgagcttgaaagatgacaccgaacagggggggtggcg |
| caggcggcagcaacagcagtggcagcggcgcggaagagaactccaacgcggcagccgcggcaatgcagccggtggaggacatg |
| aacgatcatgccattcgcggcgacacctttgccacacgggctgaggagaagcgcgctgaggccgaagcagcggccgaagctgccg |
| cccccgctgcgcaacccgaggtcgagaagcctcagaagaaaccggtgatcaaacccctgacagaggacagcaagaaacgcagtta |
| caacctaataagcaatgacagcaccttcacccagtaccgcagctggtaccttgcatacaactacggcgaccctcagaccggaatccgct |
| catggaccctgctttgcactcctgacgtaacctgcggctcggagcaggtctactggtcgttgccagacatgatgcaagaccccgtgacct |
| tccgctccacgcgccagatcagcaactttccggtggtgggcgccgagctgttgcccgtgcactccaagagcttctacaacgaccaggc |
| cgtctactcccaactcatccgccagtttacctctctgacccacgtgttcaatcgctttcccgagaaccagattttggcgcgcccgccagcc |
| cccaccatcaccaccgtcagtgaaaacgttcctgctctcacagatcacgggacgctaccgctgcgcaacagcatcggaggagtccagc |
| gagtgaccattactgacgccagacgccgcacctgcccctacgtttacaaggccctgggcatagtctcgccgcgcgtcctatcgagccg |
| cactttttgagcaagcatgtccatccttatatcgcccagcaataacacaggctggggcctgcgcttcccaagcaagatgtttggcggggc |
| caagaagcgctccgaccaacacccagtgcgcgtgcgcgggcactaccgcgcgccctggggcgcgcacaaacgcggccgcactgg |
| gcgcaccaccgtcgatgacgccatcgacgcggtggtggaggaggcgcgcaactacacgcccacgccgccaccagtgtccacagtg |
| gacgcggccattcagaccgtggtgcgcggagcccggcgctatgctaaaatgaagagacggcggaggcgcgtagcacgtcgccacc |
| gccgccgacccggcactgccgcccaacgcgcggcggcggccctgcttaaccgcgcacgtcgcaccggccgacgggcggccatgc |
| gagcagctcgaaggctggccgcgggtattgtcactgtgccccccaggtccaggcgacgagcggccgccgcagcagccgcggccat |
| tagtgctatgactcagggtcgcaggggcaacgtgtattgggtgcgcgactcggttagcggcctgcgcgtgcccgtgcgcacccgcccc |
| ccgcgcaactagattgcaagaaaaaactacttagactcgtactgttgtatgtatccagcggcggcggcgcgcaacgaagctatgtccaa |
| gcgcaaaatcaaagaagagatgctccaggtcatcgcgccggagatctatggcccccgaagaaggaagagcaggattacaagcccc |
| gaaagctaaagcgggtcaaaaagaaaaagaaagatgatgatgatgaacttgacgacgaggtggaactgctgcacgctaccgcgccca |
| ggcgacgggtacagtggaaaggtcgacgcgtaaaacgtgttttgcgacccggcaccaccgtagtctttacgcccggtgagcgctccac |
| ccgcacctacaagcgcgtgtatgatgaggtgtacggcgacgaggacctgcttgagcaggccaacgagcgcctcggggagtttgccta |
| cggaaagcggcataaggacatgctggcgttgccgctggacgagggcaacccaacacctagcctaaagcccgtaacactgcagcagg |
| tgctgcccgcgcttgcaccgtccgaagaaaagcgcggcctaaagcgcgagtctggtgacttggcacccaccgtgcagctgatggtac |
| ccaagcgccagcgactggaagatgtcttggaaaaaatgaccgtggaacctgggctggagcccgaggtccgcgtgcggccaatcaag |
| caggtggcgccgggactgggcgtgcagaccgtggacgttcagatacccactaccagtagcaccagtattgccaccgccacagaggg |
| catggagacacaaacgtccccggttgcctcagcggtggcggatgccgcggtgcaggcggtcgctgcggccgcgtccaagacctcta |
| cggaggtgcaaacggacccgtggatgtttcgcgtttcagccccccggcgcccgcgccgttcgaggaagtacggcgccgccagcgcg |
| ctactgcccgaatatgccctacatccttccattgcgcctacccccggctatcgtggctacacctaccgccccagaagacgagcaactacc |
| cgacgccgaaccaccactggaacccgccgccgccgtcgccgtcgccagcccgtgctggccccgatttccgtgcgcagggtggctcg |

TABLE 32-continued

| Ad5-B4Gal-Cas9 with Plasmid Backbone |
|---|
| cgaaggaggcaggaccctggtgctgccaacagcgcgctaccaccccagcatcgtttaaaagccggtctttgtggttcttgcagatatgg |
| ccctcacctgccgcctccgtttcccggtgccgggattccgaggaagaatgcaccgtaggaggggcatggccggccacggcctgacg |
| ggcggcatgcgtcgtgcgcaccaccggcggcggcgcgcgtcgcaccgtcgcatgcgcggcggtatcctgcccctccttattccactg |
| atcgccgcggcgattggcgccgtgcccggaattgcatccgtggccttgcaggcgcagagacactgattaaaaacaagttgcatgtgga |
| aaaatcaaaataaaaagtctggactctcacgctcgcttggtcctgtaactattttgtagaatggaagacatcaactttgcgtctctggccccg |
| cgacacggctcgcgcccgttcatgggaaactggcaagatatcggcaccagcaatatgagcggtggcgccttcagctggggctcgctgt |
| ggagcggcattaaaaatttcggttccaccgttaagaactatggcagcaaggcctggaacagcagcacaggccagatgctgagggataa |
| gttgaaagagcaaaatttccaacaaaaggtggtagatggcctggcctctggcattagcggggtggtggacctggccaaccaggcagtg |
| caaaataagattaacagtaagcttgatccccgccctcccgtagaggagcctccaccggccgtggagacagtgtctccagaggggcgtg |
| gcgaaaagcgtccgcgccccgacagggaagaaactctggtgacgcaaatagacgagcctccctcgtacgaggaggcactaaagca |
| aggcctgcccaccacccgtcccatcgcgcccatggctaccggagtgctgggccagcacacacccgtaacgctggacctgcctccccc |
| cgccgacacccagcagaaacctgtgctgccaggcccgaccgccgttgttgtaacccgtcctagccgcgcgtccctgcgccgcgccgc |
| cagcggtccgcgatcgttgcggcccgtagccagtggcaactggcaaagcacactgaacagcatcgtgggtctgggggtgcaatccct |
| gaagcgccgacgatgcttctgaatagctaacgtgtcgtatgtgtgtcatgtatgcgtccatgtcgccgccagaggagctgctgagccgcc |
| gcgcgcccgctttccaagatggctaccccttcgatgatgccgcagtggtcttacatgcacatctcgggccaggacgcctcggagtacct |
| gagccccgggctggtgcagtttgcccgcgccaccgagacgtacttcagcctgaataacaagtttagaaccccacggtggcgcctacg |
| cacgacgtgaccacagaccggtcccagcgtttgacgctgcggttcatccctgtggaccgtgaggatactgcgtactcgtacaaggcgc |
| ggttcaccctagctgtgggtgataaccgtgtgctggacatggcttccacgtactttgacatccgcggcgtgctggacaggggccctacttt |
| taagccctactctggcactgcctacaacgccctggctcccaagggtgccccaaatccttgcgaatgggatgaagctgctactgctcttga |
| aataaacctagaagaagaggacgatgacaacgaagacgaagtagacgagcaagctgagcagcaaaaaactcacgtatttgggcagg |
| cgccttattctggtataaatattacaaaggagggtattcaaataggtgtcgaaggtcaaacacctaaatatgccgataaaacatttcaacct |
| gaacctcaaataggagaatctcagtggtacgaaacagaaattaatcatgcagctgggagagtcctaaaaaagactaccccaatgaaacc |
| atgttacggttcatatgcaaaacccacaaatgaaaatggagggcaaggcattcttgtaaagcaacaaaatggaaagctagaaagtcaag |
| tggaaatgcaatttttctcaactactgaggcagccgcaggcaatggtgataacttgactcctaaagtggtattgtacagtgaagatgtagat |
| atagaaaccccagacactcatatttcttacatgcccactattaaggaaggtaactcacgagaactaatgggccaacaatctatgcccaaca |
| ggcctaattacattgcttttagggacaattttattggtctaatgtattacaacagcacgggtaatatgggtgttctggcgggccaagcatcgc |
| agttgaatgctgttgtagatttgcaagacagaaacacagagctttcataccagcttttgcttgattccattggtgatagaaccaggtacttttct |
| atgtggaatcaggctgttgacagctatgatccagatgttagaattattgaaaatcatggaactgaagatgaacttccaaattactgctttcca |
| ctgggaggtgtgattaatacagagactcttaccaaggtaaaacctaaaacaggtcaggaaaatggatgggaaaaagatgctacagaatt |
| ttcagataaaaatgaaataagagttggaaataattttgccatggaaatcaatctaaatgccaacctgtggagaaatttcctgtactccaacat |
| agcgctgtatttgcccgacaagctaaagtacagtccttccaacgtaaaaatttctgataacccaaacacctacgactacatgaacaagcga |
| gtggtggctcccgggctagtggactgctacattaaccttggagcacgctggtcccttgactatatggacaacgtcaacccatttaaccacc |
| accgcaatgctggcctgcgctaccgctcaatgttgctgggcaatggtcgctatgtgcccttccacatccaggtgcctcagaagttctttgc |
| cattaaaaacctccttctcctgccgggctcatacacctacgagtggaacttcaggaaggatgttaacatggttctgcagagctccctagga |
| aatgacctaagggttgacggagccagcattaagtttgatagcatttgcctttacgccaccttcttccccatggcccacaacaccgcctcca |
| cgcttgaggccatgcttagaaacgacaccaacgaccagtcctttaacgactatctctccgccgccaacatgctctaccctatacccgcca |
| acgctaccaacgtgcccatatccatcccctcccgcaactgggggctttccgcggctgggccttcacgcgccttaagactaaggaaacc |
| ccatcactgggctcgggctacgacccttattacacctactctggctctataccctacctagatggaacctttacctcaaccacacctttaag |
| aaggtggccattacctttgactcttctgtcagctggcctggcaatgaccgcctgcttacccccaacgagtttgaaattaagcgctcagttga |

TABLE 32-continued

| Ad5-B4Gal-Cas9 with Plasmid Backbone |
|---|
| cggggagggttacaacgttgcccagtgtaacatgaccaaagactggttcctggtacaaatgctagctaactataacattggctaccaggg |
| cttctatatcccagagagctacaaggaccgcatgtactccttctttagaaacttccagcccatgagccgtcaggtggtggatgatactaaat |
| acaaggactaccaacaggtgggcatcctacaccaacacaacaactctggatttgttggctaccttgcccccaccatgcgcgaaggaca |
| ggcctaccctgctaacttcccctatccgcttataggcaagaccgcagttgacagcattacccagaaaaagtttctttgcgatcgcaccctttt |
| ggcgcatcccattctccagtaactttatgtccatgggcgcactcacagacctgggccaaaaccttctctacgccaactccgcccacgcgc |
| tagacatgacttttgaggtggatcccatggacgagcccacccttctttatgttttgtttgaagtctttgacgtggtccgtgtgcaccagccgc |
| accgcggcgtcatcgaaaccgtgtacctgcgcacgcccttctcggccggcaacgccacaacataaagaagcaagcaacatcaacaac |
| agctgccgccatgggctccagtgagcaggaactgaaagccattgtcaaagatcttggttgtgggccatatttttgggcacctatgacaag |
| cgctttccaggctttgtttctccacacaagctcgcctgcgccatagtcaatacggccggtcgcgagactgggggcgtacactggatggc |
| ctttgcctggaacccgcactcaaaaacatgctacctctttgagccctttggcttttctgaccagcgactcaagcaggtttaccagtttgagta |
| cgagtcactcctgcgccgtagcgccattgcttcttcccccgaccgctgtataacgctggaaaagtccacccaaagcgtacaggggccca |
| actcggccgcctgtggactattctgctgcatgtttctccacgcctttgccaactggccccaaactcccatggatcacaaccccaccatgaa |
| ccttattaccggggtacccaactccatgctcaacagtccccaggtacagcccaccctgcgtcgcaaccaggaacagctctacagcttcct |
| ggagcgccactcgccctacttccgcagccacagtgcgcagattaggagcgccacttctttttgtcacttgaaaaacatgtaaaaataatgt |
| actagagacactttcaataaaggcaaatgcttttatttgtacactctcgggtgattatttacccccacccttgccgtctgcgccgtttaaaaatc |
| aaaggggttctgccgcgcatcgctatgcgccactggcagggacacgttgcgatactggtgtttagtgctccacttaaactcaggcacaac |
| catccgcggcagctcggtgaagttttcactccacaggctgcgcaccatcaccaacgcgtttagcaggtcgggcgccgatatcttgaagt |
| cgcagttggggcctccgccctgcgcgcgcgagttgcgatacacagggttgcagcactggaacactatcagcgccgggtggtgcacgc |
| tggccagcacgctcttgtcggagatcagatccgcgtccaggtcctccgcgttgctcagggcgaacggagtcaactttggtagctgccttc |
| ccaaaaagggcgcgtgcccaggctttgagttgcactcgcaccgtagtggcatcaaaaggtgaccgtgcccggtctgggcgttaggata |
| cagcgcctgcataaaagccttgatctgcttaaaagccacctgagcctttgcgccttcagagaagaacatgccgcaagacttgccggaaa |
| actgattggccggacacgcggcgtcgtgcacgcagcaccttgcgtcggtgttggagatctgcaccacatttcggccccaccggttcttc |
| acgatcttggccttgctagactgctccttcagcgcgcgctgcccgttttcgctcgtcacatccatttcaatcacgtgctccttatttatcataat |
| gcttccgtgtagacacttaagctcgccttcgatctcagcgcagcggtgcagccacaacgcgcagcccgtgggctcgtgatgcttgtagg |
| tcacctctgcaaacgactgcaggtacgcctgcaggaatcgccccatcatcgtcacaaaggtcttgttgctggtgaaggtcagctgcaacc |
| cgcggtgctcctcgttcagccaggtcttgcatacggccgccagagcttccacttggtcaggcagtagtttgaagttcgcctttagatcgtta |
| tccacgtggtacttgtccatcagcgcgcgcgcagcctccatgcccttctcccacgcagacacgatcggcacactcagcgggttcatcac |
| cgtaatttcactttccgcttcgctgggctcttcctcttcctcttgcgtccgcataccacgcgccactgggtcgtcttcattcagccgccgcact |
| gtgcgcttacctcctttgccatgcttgattagcaccggtgggttgctgaaacccaccatttgtagcgccacatcttctctttcttcctcgctgtc |
| cacgattacctctggtgatggcgggcgctcgggcttgggagaagggcgcttctttttcttcttgggcgcaatggccaaatccgccgccga |
| ggtcgatggccgcgggctgggtgtgcgcggcaccagcgcgtcttgtgatgagtcttcctcgtcctcggactcgatacgccgcctcatcc |
| gctttttttgggggcgcccggggaggcggcggcgacggggacggggacgacacgtcctccatggttgggggacgtcgcgccgcacc |
| gcgtccgcgctcgggggtggtttcgcgctgctcctcttcccgactggccatttccttctcctataggcagaaaaagatcatggagtcagtc |
| gagaagaaggacagcctaaccgccccctctgagttcgccaccaccgcctccaccgatgccgccaacgcgcctaccaccttccccgtc |
| gaggcacccccgcttgaggaggaggaagtgattatcgagcaggacccaggttttgtaagcgaagacgacgaggaccgctcagtacc |
| aacagaggataaaaagcaagaccaggacaacgcagaggcaaacgaggaacaagtcgggggggggacgaaaggcatggcgact |
| acctagatgtgggagacgacgtgctgttgaagcatctgcagcgccagtgcgccattatctgcgacgcgttgcaagagcgcagcgatgt |
| gcccctcgccatagcggatgtcagccttgcctacgaacgccacctattctcaccgcgcgtacccccaaacgccaagaaaacggcaca |
| tgcgagcccaacccgcgcctcaacttctaccccgtatttgccgtgccagaggtgcttgccacctatcacatctttttccaaaactgcaagat |

TABLE 32-continued

| Ad5-B4Gal-Cas9 with Plasmid Backbone |
|---|
| acccctatcctgccgtgccaaccgcagccgagcggacaagcagctggccttgcggcagggcgctgtcatacctgatatcgcctcgctc |
| aacgaagtgccaaaaatctttgagggtcttggacgcgacgagaagcgcgcggcaaacgctctgcaacaggaaaacagcgaaaatga |
| aagtcactctggagtgttggtggaactcgagggtgacaacgcgcgcctagccgtactaaaacgcagcatcgaggtcacccactttgcct |
| acccggcacttaacctacccccaaggtcatgagcacagtcatgagtgagctgatcgtgcgccgtgcgcagcccctggagagggatg |
| caaatttgcaagaacaaacagaggagggcctacccgcagttggcgacgagcagctagcgcgctggcttcaaacgcgcgagcctgcc |
| gacttggaggagcgacgcaaactaatgatggccgcagtgctcgttaccgtggagcttgagtgcatgcagcggttctttgctgacccgga |
| gatgcagcgcaagctagaggaaacattgcactacacctttcgacagggctacgtacgccaggcctgcaagatctccaacgtggagctc |
| tgcaacctggtctcctaccttggaattttgcacgaaaaccgccttgggcaaaacgtgcttcattccacgctcaagggcgaggcgcgccg |
| cgactacgtccgcgactgcgtttacttatttctatgctacacctggcagacggccatgggcgtttggcagcagtgcttggaggagtgcaa |
| cctcaaggagctgcagaaactgctaaagcaaaacttgaaggacctatggacggccttcaacgagcgctccgtggccgcgcacctggc |
| ggacatcattttccccgaacgcctgcttaaaaccctgcaacagggtctgccagacttcaccagtcaaagcatgttgcagaactttaggaa |
| ctttatcctagagcgctcaggaatcttgcccgccacctgctgtgcacttcctagcgactttgtgcccattaagtaccgcgaatgccctccgc |
| cgctttggggccactgctaccttctgcagctagccaactaccttgcctaccactctgacataatggaagacgtgagcggtgacggtctact |
| ggagtgtcactgtcgctgcaacctatgcaccccgcaccgctccctggtttgcaattcgcagctgcttaacgaaagtcaaattatcggtacc |
| tttgagctgcagggtccctcgcctgacgaaaagtccgcggctccggggttgaaactcactccggggctgtggacgtcggcttaccttcg |
| caaatttgtacctgaggactaccacgcccacgagattaggttctacgaagaccaatcccgcccgcctaatgcggagcttaccgcctgcg |
| tcattacccagggccacattcttggccaattgcaagccatcaacaaagcccgccaagagtttctgctacgaaagggacggggggtttact |
| tggacccccagtccggcgaggagctcaacccaatcccccgccgccgcagccctatcagcagcagccgcgggcccttgcttcccag |
| gatggcacccaaaaagaagctgcagctgccgccgccacccacggacgaggaggaatactgggacagtcaggcagaggaggttttg |
| gacgaggaggaggaggacatgatggaagactgggagagcctagacgaggaagcttccgaggtcgaagaggtgtcagacgaaaca |
| ccgtcaccctcggtcgcattcccctcgccggcgccccagaaatcggcaaccggttccagcatggctacaacctccgctcctcaggcgc |
| cgccggcactgcccgttcgccgacccaaccgtagatgggacaccactggaaccagggccggtaagtccaagcagccgccgccgtta |
| gcccaagagcaacaacagcgccaaggctaccgctcatggcgcgggcacaagaacgccatagttgcttgcttgcaagactgtggggg |
| caacatctccttcgcccgccgctttcttctctaccatcacggcgtggccttcccccgtaacatcctgcattactaccgtcatctctacagccc |
| atactgcaccggcggcagcggcagcggcagcaacagcagcggccacacagaagcaaaggcgaccggatagcaagactctgacaa |
| agcccaagaaatccacagcggcggcagcagcaggaggaggagcgctgcgtctggcgcccaacgaacccgtatcgacccgcgagc |
| ttagaaacaggatttttcccactctgtatgctatatttcaacagagcaggggccaagaacaagagctgaaaataaaaaacaggtctctgcg |
| atccctcacccgcagctgcctgtatcacaaaagcgaagatcagcttcggcgcacgctggaagacgcggaggctctcttcagtaaatact |
| gcgcgctgactcttaaggactagtttcgcgccctttctcaaatttaagcgcgaaaactacgtcatctccagcggccacacccggcgccag |
| cacctgttgtcagcgccattatgagcaaggaaattcccacgccctacatgtggagttaccagccacaaatgggacttgcggctggagct |
| gcccaagactactcaacccgaataaactacatgagcgcgggaccccacatgatatcccgggtcaacggaatacgcgcccaccgaaac |
| cgaattctcctggaacaggcggctattaccaccacacctcgtaataaccttaatccccgtagttggcccgctgccctggtgtaccaggaa |
| agtcccgctcccaccactgtggtacttcccagagacgcccaggccgaagttcagatgactaactcaggggcgcagcttgcgggcggct |
| ttcgtcacagggtgcggtcgcccgggcagggtataactcacctgacaatcagagggcgaggtattcagctcaacgacgagtcggtga |
| gctcctcgcttggtctccgtccggacgggacatttcagatcggcggcgccggccgctcttcattcacgcctcgtcaggcaatcctaactct |
| gcagacctcgtcctctgagccgcgctctggaggcattggaactctgcaatttattgaggagtttgtgccatcggtctactttaaccccttctc |
| gggacctcccggccactatccggatcaatttattcctaactttgacgcggtaaaggactcggcggacggctacgactgaatgttaagtgg |
| ccaatgaggcctgacgctaataatagctggtccactgtcgccgccacaagtgctttgcccgcgactccggtgagttttgctactttgaattg |
| cccgaggatcatatcgagggcccggcgcacggcgtccggcttaccgcccagggagagcttgcccgtagcctgattogggagtttacc |

TABLE 32-continued

| Ad5-B4Gal-Cas9 with Plasmid Backbone |
|---|
| cagcgccccctgctagttgagcgggacaggggaccctgtgttctcactgtgatttgcaactgtcctaaccttggattacatcaagatccag |
| atcttctagacccgggagcggccgctgtcgacctgcaggatccgaattcgatatcactagtggtaccgatcttattccctttaactaataaa |
| aaaaaataataaagcatcacttacttaaaatcagttagcaaatttctgtccagtttattcagcagcacctccttgccctcctcccagctctggt |
| attgcagcttcctcctggctgcaaactttctccacaatctaaagggaatgtcagtttcctcctgttcctgtccatccgcacccactatcttcatg |
| ttgttgcagatgaagcgcgcaagaccgtctgaagataccttcaaccccgtgtatccatatgacacggaaaccggtcctccaactgtgcctt |
| ttcttactcctccctttgtatcccccaatgggtttcaagagagtccccctggggtactctctttgcgcctatccgaacctctagttacctccaat |
| ggcatgcttgcgctcaaaatgggcaacggcctctctctggacgaggccggcaaccttacctcccaaaatgtaaccactgtgagcccacc |
| tctcaaaaaaaccaagtcaaacataaacctggaaatatctgcacccctcacagttacctcagaagccctaactgtggctgccgccgcacc |
| tctaatggtcgcgggcaacacactcaccatgcaatcacaggccccgctaaccgtgcacgactccaaacttagcattgccacccaagga |
| cccctcacagtgtcagaaggaaagctagccctgcaaacatcaggcccccctcaccaccaccgatagcagtacccttactatcactgcctc |
| accccctctaactactgccactggtagcttgggcattgacttgaaagagcccatttatacacaaaatggaaaactaggactaaagtacgg |
| ggctcctttgcatgtaacagacgacctaaacactttgaccgtagcaactggtccaggtgtgactattaataatacttccttgcaaactaaagt |
| tactggagccttgggttttgattcacaaggcaatatgcaacttaatgtagcaggaggactaaggattgattctcaaaacagacgccttatac |
| ttgatgttagttatccgtttgatgctcaaaaccaactaaatctaagactaggacagggccctctttttataaactcagcccacaacttggatatt |
| aactacaacaaaggcctttacttgtttacagcttcaaacaattccaaaaagcttgaggttaacctaagcactgccaaggggttgatgtttga |
| cgctacagccatagccattaatgcaggagatgggcttgaatttggttcacctaatgcaccaaacacaaatcccctcaaaacaaaaattgg |
| ccatggcctagaatttgattcaaacaaggctatggttcctaaactaggaactggccttagttttgacagcacaggtgccattacagtaggaa |
| acaaaaataatgataagctaactttgtggaccacaccagctccatctcctaactgtagactaaatgcagagaaagatgctaaactcactttg |
| gtcttaacaaaatgtggcagtcaaatacttgctacagtttcagttttggctgttaaaggcagtttggctccaatatctggaacagttcaaagtg |
| ctcatcttattataagatttgacgaaaatggagtgctactaaacaattccttcctggacccagaatattggaactttagaaatggagatcttac |
| tgaaggcacagcctatacaaacgctgttggatttatgcctaacctatcagcttatccaaaatctcacggtaaaactgccaaaagtaacattg |
| tcagtcaagtttacttaaacggagacaaaactaaacctgtaacactaaccattacactaaacggtacacaggaaacaggagacacaactc |
| caagtgcatactctatgtcattttcatgggactggtctggccacaactacattaatgaaatatttgccacatcctcttacactttttcatacattg |
| cccaagaataaagaatcgtttgtgttatgtttcaacgtgtttatttttcaattgcagaaaatttcaagtcatttttcattcagtagtatagccccac |
| caccacatagcttatacagatcaccgtaccttaatcaaactcacagaaccctagtattcaacctgccacctccctcccaacacacagagta |
| cacagtcctttctccccggctggccttaaaaagcatcatatcatgggtaacagacatattcttaggtgttatattccacacggtttcctgtcga |
| gccaaacgctcatcagtgatattaataaactccccgggcagctcacttaagttcatgtcgctgtccagctgctgagccacaggctgctgtc |
| caacttgcggttgcttaacgggcggcgaaggagaagtccacgcctacatgggggtagagtcataatcgtgcatcaggatagggcggtg |
| gtgctgcagcagcgcgcgaataaactgctgccgccgccgctccgtcctgcaggaatacaacatggcagtggtctcctcagcgatgatt |
| cgcaccgcccgcagcataaggcgccttgtcctccgggcacagcagcgcaccctgatctcacttaaatcagcacagtaactgcagcaca |
| gcaccacaatattgttcaaaatcccacagtgcaaggcgctgtatccaaagctcatggcgggaccacagaacccacgtggccatcata |
| ccacaagcgcaggtagattaagtggcgacccctcataaacacgctggacataaacattacctcttttggcatgttgtaattcaccacctcc |
| cggtaccatataaacctctgattaaacatggcgccatccaccaccatcctaaaccagctggccaaaacctgcccgccggctatacactg |
| cagggaaccgggactggaacaatgacagtggagagcccaggactcgtaaccatggatcatcatgctcgtcatgatatcaatgttggca |
| caacacaggcacacgtgcatacacttcctcaggattacaagctcctcccgcgttagaaccatatcccagggaacaacccattcctgaatc |
| agcgtaaatcccacactgcagggaagacctcgcacgtaactcacgttgtgcattgtcaaagtgttacattcgggcagcagcggatgatc |
| ctccagtatggtagcgcgggtttctgtctcaaaaggaggtagacgatccctactgtacggagtgcgccgagacaaccgagatcgtgttg |
| gtcgtagtgtcatgccaaatggaacgccggacgtagtcatatttcctgaagcaaaaccaggtgcgggcgtgacaaacagatctgcgtct |
| ccggtctcgccgcttagatcgctctgtgtagtagttgtagtatatccactctctcaaagcatccaggcgccccctggcttcgggttctatgta |

TABLE 32-continued

| Ad5-B4Gal-Cas9 with Plasmid Backbone |
| --- |
| aactccttcatgcgccgctgccctgataacatccaccaccgcagaataagccacacccagccaacctacacattogttctgcgagtcaca |
| cacgggaggagcgggaagagctggaagaaccatgtttttttttttttattccaaaagattatccaaaacctcaaaatgaagatctattaagtg |
| aacgcgctcccctccggtggcgtggtcaaactctacagccaaagaacagataatggcatttgtaagatgttgcacaatggcttccaaaag |
| gcaaacggccctcacgtccaagtggacgtaaaggctaaacccttcagggtgaatctcctctataaacattccagcaccttcaaccatgcc |
| caaataattctcatctcgccaccttctcaatatatctctaagcaaatcccgaatattaagtccggccattgtaaaaatctgctccagagcgcc |
| ctccaccttcagcctcaagcagcgaatcatgattgcaaaaattcaggttcctcacagacctgtataagattcaaaagcggaacattaacaa |
| aaataccgcgatcccgtaggtcccttcgcagggccagctgaacataatcgtgcaggtctgcacggaccagcgcggccacttccccgcc |
| aggaaccatgacaaaagaacccacactgattatgacacgcatactcggagctatgctaaccagcgtagccccgatgtaagcttgttgcat |
| gggcggcgatataaaatgcaaggtgctgctcaaaaaatcaggcaaagcctcgcgcaaaaaagaaagcacatcgtagtcatgctcatgc |
| agataaaggcaggtaagctccggaaccaccacagaaaaagacaccatttttctctcaaacatgtctgcgggtttctgcataaacacaaaa |
| taaaataacaaaaaaacatttaaacattagaagcctgtcttacaacaggaaaaacaacccttataagcataagacggactacggccatgc |
| cggcgtgaccgtaaaaaaactggtcaccgtgattaaaaagcaccaccgacagctcctcggtcatgtccggagtcataatgtaagactcg |
| gtaaacacatcaggttgattcacatcggtcagtgctaaaaagcgaccgaaatagcccgggggaatacatacccgcaggcgtagagaca |
| acattacagcccccataggaggtataacaaaattaataggagagaaaaacacataaacacctgaaaaaccctcctgcctaggcaaaata |
| gcaccctcccgctccagaacaacatacagcgcttccacagcggcagccataacagtcagccttaccagtaaaaaagaaaacctattaa |
| aaaaacaccactcgacacggcaccagctcaatcagtcacagtgtaaaaaagggccaagtgcagagcgagtatatataggactaaaaa |
| atgacgtaacggttaaagtccacaaaaaacacccagaaaaccgcacgcgaacctacgcccagaaacgaaagccaaaaaacccacaa |
| cttcctcaaatcgtcacttcogttttcccacgttacgtaacttcccattttaagaaaactacaattcccaacacatacaagttactccgccctaa |
| aacctacgtcacccgccccgttcccacgccccgcgccacgtcacaaactccaccccctcattatcatattggcttcaatccaaaataaggt |
| atattattgatgatgttaatttgggccattagacttgaagtcaagcggccgcttacaactggaccttgctggtacatagaactgattaactga |
| ccatttaaatcataccaacatggtcaaataaaacgaaaggctcagtcgaaagactgggcctttcgttttaatctgatcggcacgtaagagg |
| ttccaactttcaccataatgaaataagatcactaccgggcgtattttttgagttatcgagattttcaggagctaaggaagctaaaatgagcca |
| tattcaacgggaaacgtcttgctcgaggccgcgattaaattccaacatggatgctgatttatatgggtataaatgggctcgcgataatgtcg |
| ggcaatcaggtgcgacaatctatcgattgtatgggaagcccgatgcgccagagttgtttctgaaacatggcaaaggtagcgttgccaatg |
| atgttacagatgagatggtcaggctaaactggctgacggaatttatgcctcttccgaccatcaagcattttatccgtactcctgatgatgcat |
| ggttactcaccactgcgatccccagggaaaacagcattccaggtattagaagaatatcctgattcaggtgaaaatattgttgatgcgctggc |
| agtgttcctgcgccggttgcattcgattcctgtttgtaattgtccttttaacggcgatcgcgtatttcgtctcgctcaggcgcaatcacgaatg |
| aataacggtttggttggtgcgagtgattttgatgacgagcgtaatggctggcctgttgaacaagtctggaaagaaatgcataaacttttgcc |
| attctcaccggattcagtcgtcactcatggtgatttctcacttgataaccttatttttgacgaggggaaattaataggttgtattgatgttggacg |
| agtcggaatcgcagaccgataccaggatcttgccatcctatggaactgcctcggtgagttttctccttcattacagaaacggctttttcaaaa |
| atatggtattgataatcctgatatgaataaattgcagtttcacttgatgctcgatgagtttttctaacctaggtgacagaagtcaaaagcctcc |
| ggtcggaggcttttgactttctgctagatctgtttcaatgcggtgaagggccaggcagctggggattatgtcgagacccggccagcatgtt |
| ggttttatcgcatattcagcgttgtcgcgtttacccaggtaaaatggaagcagtgtatcgtctgcgtgaatgtgcaaatcaggaacgtaacc |
| gtggtacatagatgcagtcccttgcgggtcgttcccttcaacgagtaggacgcggtgcccttgcaaggctaaccattgcgcctggtgtac |
| tgcagatgaggttttataaacccctcccttgtgtgacataacggaaagtacaaccgggtttttatcgtcaggtctttggtttgggttaccaaac |
| acactccgcatatggctaatttggtcaattgtgtagccagcgcgacgttctactcggcccctcatctcaaaatcaggagccggtagacga |
| ccagctttttccgcgtctctgatagcctgcggtgttacgccgatcaggtctgcaacttctgttataccccagcggcgagtaatacgacgcg |
| cttccgggctgtcatcgccgaactgtgcgatggcaatagcgcgcgtcatttcctgaccgcgattgatacagtctttcagcaaattaattaac |
| gacatcctgtttcctctcaaacatgcccttatctttgtgtttttcatcatactttacgtttttaaagcaaagcaacataaaaaaagcaaagtgactt |

TABLE 32-continued

| Ad5-B4Gal-Cas9 with Plasmid Backbone |
| --- |
| agaaaacgcaaagttaaggttcaaatcaatttttgatgcgctacagaagctatttagcttcatctaagcgcaacggtattacttacgttggta<br>tatttaaaacctaacttaatgattttaaatgataataaatcataccaattgctatcaaaagttaagcgaacatgctgattttcacgctgtttataca<br>ctttgaggcatctctatctcttccgtctctatattgaaacacaatcaaagaacatcaatccatgtgacatcccccactatctaagaacaccata<br>acagaacacaacataggaatgcaacattaatgtatcaataattcggaacatatgcactatatcatatctcaattacggaacatatcagcaca<br>caattgcccattatacgc |

TABLE 33

| Ad5-B4Gal-Cas9 No Plasmid Backbone |
| --- |
| (SEQ ID NO: 33)<br>catcatcaataatataccttattttggattgaagccaatatgataatgagggggtggagtttgtgacgtggcgcggggcgtgggaacggg<br>gcgggtgacgtagtagtgtggcggaagtgtgatgttgcaagtgtggcggaacacatgtaagcgacggatgtggcaaaagtgacgttttt<br>ggtgtgcgccggtgtacacaggaagtgacaattttcgcgcggttttaggcggatgttgtagtaaatttgggcgtaaccgagtaagatttgg<br>ccattttcgcgggaaaactgaataagaggaagtgaaatctgaataattttgtgttactcatagcgcgtaatatttgtctagggccgcgggga<br>ctttgaccgtttacgtggagactcgcccaggtgtttttctcaggtgttttccgcgttccgggtcaaagttggcgttttagatcttaaaacaaaa<br>aagcaccgactcggtgccactttttcaagttgataacggactagccttattttaacttgctatttctagctctaaaaccaagatattgatggtgc<br>tttcggtgtttcgtcctttccacaagatatataaagccaagaaatcgaaatactttcaagttacggtaagcatatgatagtccattttaaaacat<br>aattttaaaactgcaaactacccaagaaattattactttctacgtcacgtattttgtactaatatctttgtgtttacagtcaaattaattccaattatc<br>tctctaacagccttgtatcgtatatgcaaatatgaaggaatcatgggaaataggccctcacatgtgagcaaaagtcgacctgcaggatcct<br>gattattgactagttattaatagtaatcaattacggggtcattagttcatagcccatatatggagttccgcgttacataacttacggtaaatggc<br>ccgcctggctgaccgcccaacgacccccgcccattgacgtcaataatgacgtatgttcccatagtaacgccaatagggactttccattga<br>cgtcaatgggtggagtatttacggtaaactgcccacttggcagtacatcaagtgtatcatatgccaagtccgccccctattgacgtcaatga<br>cggtaaatggcccgcctggcattatgcccagtacatgaccttacgggactttcctacttggcagtacatctacgtattagtcatcgctattac<br>catgctgatgcggttttggcagtacaccaatgggcgtggatagcggtttgactcacggggatttccaagtctccaccccattgacgtcaat<br>gggagtttgttttggcaccaaaatcaacgggactttccaaaatgtcgtaataaccccgccccgttgacgcaaatgggcggtaggcgtgta<br>cggtgggaggtctatataagcagagctcgtttagtgaaccgtcagatcactagaagctttattgcggtagtttatcacagttaaattgctaac<br>gcagtcaggccaacagagaccacacccaagctggccgccaccatggccccaaagaagaagcggaaggtcggtatccacggagtcc<br>cagcagccgacaagaagtacagcatcggcctggacatcggcaccaactctgtgggctgggccgtgatcaccgacgagtacaaggtg<br>cccagcaagaaattcaaggtgctgggcaacaccgaccggcacagcatcaagaagaacctgatcggagccctgctgttcgacagcgg<br>cgaaacagccgaggccacccggctgaagagaaccgccagaagaagatacaccagacggaagaaccggatctgctatctgcaagag<br>atcttcagcaacgagatggccaaggtggacgacagcttcttccacagactggaagagtccttcctggtggaagaggataagaagcacg<br>agcggcaccccatcttcggcaacatcgtggacgaggtggcctaccacgagaagtaccccaccatctaccacctgagaaagaaactgg<br>tggacagcaccgacaaggccgacctgcggctgatctatctggccctggcccacatgatcaagttccggggccacttcctgatcgaggg<br>cgacctgaaccccgacaacagcgacgtggacaagctgttcatccagctggtgcagacctacaaccagctgttcgaggaaaaccccatc<br>aacgccagcggcgtggacgccaaggccatcctgtctgccagactgagcaagagcagacggctggaaaatctgatcgcccagctgcc<br>cggcgagaagaagaatggcctgttcggaaacctgattgccctgagcctgggcctgacccccaacttcaagagcaacttcgacctggcc<br>gaggatgccaaactgcagctgagcaaggacacctacgacgacgacctggacaacctgctggcccagatcggcgaccagtacgccg<br>acctgtttctggccgccaagaacctgtccgacgccatcctgctgagcgacatcctgagagtgaacaccgagatcaccaaggccccct<br>gagcgcctctatgatcaagagatacgacgagcaccaccaggacctgaccctgctgaaagctctcgtgcggcagcagctgcctgagaa<br>gtacaaagagattttcttcgaccagagcaagaacggctacgccggctacattgacggcggagccagccaggaagagttctacaagttc |

TABLE 33-continued

| Ad5-B4Gal-Cas9 No Plasmid Backbone |
| --- |
| atcaagcccatcctggaaaagatggacggcaccgaggaactgctcgtgaagctgaacagagaggacctgctgcggaagcagcgga |
| ccttcgacaacggcagcatcccccaccagatccacctgggagagctgcacgccattctgcggcggcaggaagatttttacccattcctg |
| aaggacaaccgggaaaagatcgagaagatcctgaccttccgcatcccctactacgtgggccctctggccaggggaaacagcagattc |
| gcctggatgaccagaaagagcgaggaaaccatcacccccctggaacttcgaggaagtggtggacaagggcgcttccgcccagagctt |
| catcgagcggatgaccaacttcgataagaacctgcccaacgagaaggtgctgcccaagcacagcctgctgtacgagtacttcaccgtg |
| tataacgagctgaccaaagtgaaatacgtgaccgagggaatgagaaagcccgccttcctgagcggcgagcagaaaaaggccatcgt |
| ggacctgctgttcaagaccaaccggaaagtgaccgtgaagcagctgaaagaggactacttcaagaaaatcgagtgcttcgactccgtg |
| gaaatctccggcgtggaagatcggttcaacgcctccctgggcacataccacgatctgctgaaaattatcaaggacaaggacttcctgga |
| caatgaggaaaacgaggacattctggaagatatcgtgctgaccctgacactgtttgaggacagagagatgatcgaggaacggctgaaa |
| acctatgcccacctgttcgacgacaaagtgatgaagcagctgaagcggcggagatacaccggctggggcaggctgagccggaagct |
| gatcaacggcatccgggacaagcagtccggcaagacaatcctggatttcctgaagtccgacggcttcgccaacagaaacttcatgcag |
| ctgatccacgacgacagcctgacctttaaagaggacatccagaaagcccaggtgtccggccagggcgatagcctgcacgagcacatt |
| gccaatctggccggcagccccgccattaagaagggcatcctgcagacagtgaaggtggtggacgagctcgtgaaagtgatgggccg |
| gcacaagcccgagaacatcgtgatcgaaatggccagagagaaccagaccacccagaagggacagaagaacagccgcgagagaat |
| gaagcggatcgaagagggcatcaaagagctgggcagccagatcctgaaagaacaccccgtggaaaacacccagctgcagaacgag |
| aagctgtacctgtactacctgcagaatgggcgggatatgtacgtggaccaggaactggacatcaaccggctgtccgactacgatgtgga |
| ccatatcgtgcctcagagctttctgaaggacgactccatcgacaacaaggtgctgaccagaagcgacaagaaccggggcaagagcga |
| caacgtgccctccgaagaggtcgtgaagaagatgaagaactactggcggcagctgctgaacgccaagctgattacccagagaaagtt |
| cgacaatctgaccaaggccgagagaggcggcctgagcgaactggataaggccggcttcatcaagagacagctggtggaaacccgg |
| cagatcacaaagcacgtggcacagatcctggactcccggatgaacactaagtacgacgagaatgacaagctgatccgggaagtgaaa |
| gtgatcaccctgaagtccaagctggtgtccgatttccggaaggatttccagttttacaaagtgcgcgagatcaacaactaccaccacgcc |
| cacgacgcctacctgaacgccgtcgtgggaaccgccctgatcaaaaagtaccctaagctggaaagcgagttcgtgtacggcgactaca |
| aggtgtacgacgtgcggaagatgatcgccaagagcgagcaggaaatcggcaaggctaccgccaagtacttcttctacagcaacatcat |
| gaactttttcaagaccgagattaccctggccaacggcgagatccggaagcggcctctgatcgagacaaacggcgaaaccggggagat |
| cgtgtgggataagggccgggattttgccaccgtgcggaaagtgctgagcatgccccaagtgaatatcgtgaaaaagaccgaggtgca |
| gacaggcggcttcagcaaagagtctatcctgcccaagaggaacagcgataagctgatcgccagaaagaaggactgggaccctaaga |
| agtacggcggcttcgacagccccaccgtggcctattctgtgctggtggtggccaaagtggaaaagggcaagtccaagaaactgaaga |
| gtgtgaaagagctgctggggatcaccatcatggaaagaagcagcttcgagaagaatcccatcgactttctggaagccaagggctacaa |
| agaagtgaaaaaggacctgatcatcaagctgcctaagtactccctgttcgagctggaaaacggccggaagagaatgctggcctctgcc |
| ggcgaactgcagaagggaaacgaactggccctgccctccaaatatgtgaacttcctgtacctggccagccactatgagaagctgaagg |
| gctcccccgaggataatgagcagaaacagctgtttgtggaacagcacaagcactacctggacgagatcatcgagcagatcagcgagtt |
| ctccaagagagtgatcctggccgacgctaatctggacaaagtgctgtccgcctacaacaagcaccgggataagcccatcagagagca |
| ggccgagaatatcatccacctgtttaccctgaccaatctgggagcccctgccgccttcaagtactttgacaccaccatcgaccggaagag |
| gtacaccagcaccaaagaggtgctggacgccaccctgatccaccagagcatcaccggcctgtacgagacacggatcgacctgtctca |
| gctgggaggcgacaaaaggccggcggccacgaaaaaggccggccaggcaaaaaagaaaaagtaataattctagagtcggggcgg |
| ccggccgcttcgagagctagagctttcttgctgtccaatttctattaaaggttcctttgttccctaagtccaactactaaactggggatattat |
| gaagggccttgagcatctggattctgcctaataaaaaacatttattttcattgcaatgatgtattttaaaatcgataaggatccgaattcgatat |
| cactagtggtaccagtactgaaatgtgtgggcgtggcttaagggtgggaaagaatatataaggtgggggtcttatgtagttttgtatctgttt |
| tgcagcagccgccgccgccatgagcaccaactcgtttgatggaagcattgtgagctcatatttgacaacgcgcatgcccccatgggccg |

TABLE 33-continued

| Ad5-B4Gal-Cas9 No Plasmid Backbone |
| --- |
| gggtgcgtcagaatgtgatgggctccagcattgatggtcgccccgtcctgcccgcaaactctactaccttgacctacgagaccgtgtctg |
| gaacgccgttggagactgcagcctccgccgccgcttcagccgctgcagccaccgcccgcgggattgtgactgactttgctttcctgagc |
| ccgcttgcaagcagtgcagcttcccgttcatccgcccgcgatgacaagttgacggctcttttggcacaattggattctttgacccgggaac |
| ttaatgtcgtttctcagcagctgttggatctgcgccagcaggtttctgccctgaaggcttcctcccctcccaatgcggtttaacggtccggg |
| ccagagtggccaacataaataaaaaaccagactctgtttggatttggatcaagcaagtgtcttgctgtctttatttaggggttttgcgcgcgc |
| ggtaggcccgggaccagcggtctcggtcgttgagggtcctgtgtatttttttccaggacgtggtaaaggtgactctggatgttcagatacat |
| gggcataagcccgtctctgggggggaggtagcaccactgcagagcttcatgctgcggggtggtgttgtagatgatccagtcgtagcag |
| gagcgctgggcgtggtgcctaaaaatgtctttcagtagcaagctgattgccaggggcaggcccttggtgtaagtgtttacaaagcggtta |
| agctgggatgggtgcatacgtggggatatgagatgcatcttggactgtatttttaggttggctatgttcccagccatatccctccggggatt |
| catgttgtgcagaaccaccagcacagtgtatccggtgcacttgggaaatttgtcatgtagcttagaaggaaatgcgtggaagaacttgga |
| gacgcccttgtgacctccaagattttccatgcattcgtccataatgatggcaatgggcccacgggcggcggcctgggcgaagatatttct |
| gggatcactaacgtcatagttgtgttccaggatgagatcgtcataggccatttttacaaagcgcgggcggagggtgccagactgcggtat |
| aatggttccatccggcccaggggcgtagttaccctcacagatttgcatttcccacgctttgagttcagatgggggggatcatgtctacctgc |
| ggggcgatgaagaaaacggtttccggggtaggggagatcagctgggaagaaagcaggttcctgagcagctgcgacttaccgcagcc |
| ggtgggcccgtaaatcacacctattaccggctgcaactggtagttaagagagctgcagctgccgtcatccctgagcaggggggccactt |
| cgttaagcatgtccctgactcgcatgttttccctgaccaaatccgccagaaggcgctcgccgcccagcgatagcagttcttgcaaggaag |
| caaagtttttcaacggtttgagaccgtccgccgtaggcatgcttttgagcgtttgaccaagcagttccaggcggtcccacagctcggtcac |
| ctgctctacggcatctcgatccagcatatctcctcgtttcgcgggttggggcggctttcgctgtacggcagtagtcggtgctcgtccagac |
| gggccagggtcatgtctttccacgggcgcagggtcctcgtcagcgtagtctgggtcacggtgaaggggtgcgctccgggctgcgcgc |
| tggccagggtgcgcttgaggctggtcctgctggtgctgaagcgctgccggtcttcgccctgcgcgtcggccaggtagcatttgaccatg |
| gtgtcatagtccagcccctccgcggcgtggcccttggcgcgcagcttgcccttggaggaggcgccgcacgaggggcagtgcagactt |
| ttgagggcgtagagcttgggcgcgagaaataccgattccggggagtaggcatccgcgccgcaggccccgcagacggtctcgcattcc |
| acgagccaggtgagctctggccgttcggggtcaaaaaccaggtttcccccatgctttttgatgcgtttcttacctctggtttccatgagccg |
| gtgtccacgctcggtgacgaaaaggctgtccgtgtccccgtatacagacttgagaggcctgtcctcgagcggtgttccgcggtcctcctc |
| gtatagaaactcggaccactctgagacaaaggctcgcgtccaggccagcacgaaggaggctaagtgggaggggtagcggtcgttgtc |
| cactagggggtccactcgctccagggtgtgaagacacatgtcgccctcttcggcatcaaggaaggtgattggtttgtaggtgtaggcca |
| cgtgaccgggtgttcctgaaggggggctataaaagggggtgggggcgcgttcgtcctcactctcttccgcatcgctgtctgcgagggc |
| cagctgttggggtgagtactccctctgaaaagcgggcatgacttctgcgctaagattgtcagtttccaaaaacgaggaggatttgatattc |
| acctggcccgcggtgatgcctttgagggtggccgcatccatctggtcagaaaagacaatctttttgttgtcaagcttggtggcaaacgacc |
| cgtagagggcgttggacagcaacttggcgatggagcgcagggtttggtttttgtcgcgatcggcgcgctccttggccgcgatgtttagct |
| gcacgtattcgcgcgcaacgcaccgccattcgggaaagacggtggtgcgctcgtcgggcaccaggtgcacgcgccaaccgcggttg |
| tgcagggtgacaaggtcaacgctggtggctacctctccgcgtaggcgctcgttggtccagcagaggcggccgcccttgcgcgagcag |
| aatggcggtagggggtctagctgcgtctcgtccgggggggtctgcgtccacggtaaagaccccgggcagcaggcgcgcgtcgaagta |
| gtctatcttgcatccttgcaagtctagcgcctgctgccatgcgcgggcggcaagcgcgcgctcgtatgggttgagtgggggaccccatg |
| gcatggggtgggtgagcgcggaggcgtacatgccgcaaatgtcgtaaacgtagaggggctctctgagtattccaagatatgtagggta |
| gcatcttccaccgcggatgctggcgcgcacgtaatcgtatagttcgtgcgagggagcgaggaggtcgggaccgaggttgctacgggc |
| gggctgctctgctcggaagactatctgcctgaagatggcatgtgagttggatgatatggttggacgctggaagacgttgaagctggcgtc |
| tgtgagacctaccgcgtcacgcacgaaggaggcgtaggagtcgcgcagcttgttgaccagctcggcggtgacctgcacgtctagggc |
| gcagtagtccagggtttccttgatgatgtcatacttatcctgtcccttttttttccacagctcgcggttgaggacaaactcttcgcggtctttcc |

TABLE 33-continued

| Ad5-B4Gal-Cas9 No Plasmid Backbone |
|---|
| agtactcttggatcggaaacccgtcggcctccgaacggtaagagcctagcatgtagaactggttgacggcctggtaggcgcagcatcc |
| cttttctacgggtagcgcgtatgcctgcgcggccttccggagcgaggtgtgggtgagcgcaaaggtgtccctgaccatgactttgaggt |
| actggtatttgaagtcagtgtcgtcgcatccgccctgctcccagagcaaaaagtccgtgcgctttttggaacgcggatttggcagggcga |
| aggtgacatcgttgaagagtatctttcccgcgcgaggcataaagttgcgtgtgatgcggaagggtcccggcacctcggaacggttgtta |
| attacctgggcggcgagcacgatctcgtcaaagccgttgatgttgtggcccacaatgtaaagttccaagaagcgcgggatgcccttgat |
| ggaaggcaatttttttaagttcctcgtaggtgagctcttcaggggagctgagcccgtgctctgaaagggcccagtctgcaagatgagggtt |
| ggaagcgacgaatgagctccacaggtcacgggccattagcatttgcaggtggtcgcgaaaggtcctaaactggcgacctatggccattt |
| tttctggggtgatgcagtagaaggtaagcgggtcttgttcccagcggtcccatccaaggttcgcggctaggtctcgcgcggcagtcacta |
| gaggctcatctccgccgaacttcatgaccagcatgaagggcacgagctgcttcccaaaggcccccatccaagtataggtctctacatcg |
| taggtgacaaagagacgctcggtgcgaggatgcgagccgatcgggaagaactggatctcccgccaccaattggaggagtggctattg |
| atgtggtgaaagtagaagtccctgcgacgggccgaacactcgtgctggcttttgtaaaaacgtgcgcagtactggcagcggtgcacgg |
| gctgtacatcctgcacgaggttgacctgacgaccgcgcacaaggaagcagagtgggaatttgagcccctcgcctggcgggtttggctg |
| gtggtcttctacttcggctgcttgtccttgaccgtctggctgctcgaggggagttacggtggatcggaccaccacgccgcgcgagccca |
| aagtccagatgtccgcgcgcggcggtcggagcttgatgacaacatcgcgcagatgggagctgtccatggtctggagctcccgcggcg |
| tcaggtcaggcgggagctcctgcaggtttacctcgcatagacgggtcagggcgcgggctagatccaggtgatacctaatttccagggg |
| ctggttggtggcggcgtcgatggcttgcaagaggccgcatccccgcggcgcgactacggtaccgcgcggcgggggggccgcg |
| ggggtgtccttggatgatgcatctaaaagcggtgacgcgggcgagcccccggaggtagggggggctccggacccgccgggagag |
| ggggcaggggcacgtcggcgccgcgcgcgggcaggagctggtgctgcgcgcgtaggttgctggcgaacgcgacgacgcggcgg |
| ttgatctcctgaatctggcgcctctgcgtgaagacgacgggcccggtgagcttgaacctgaaagagagttcgacagaatcaatttcggtg |
| tcgttgacggcggcctggcgcaaaatctcctgcacgtctcctgagttgtcttgataggcgatctcggccatgaactgctcgatctcttcctc |
| ctggagatctccgcgtccggctcgctccacggtggcggcgaggtcgttggaaatgcgggccatgagctgcgagaaggcgttgaggc |
| ctccctcgttccagacgcggctgtagaccacgcccccttcggcatcgcgggcgcgcatgaccacctgcgcgagattgagctccacgtg |
| ccgggcgaagacggcgtagtttcgcaggcgctgaaagaggtagttgagggtggtggcggtgtgttctgccacgaagaagtacataac |
| ccagcgtcgcaacgtggattcgttgatatcccccaaggcctcaaggcgctccatggcctcgtagaagtccacggcgaagttgaaaaact |
| gggagttgcgcgccgacacggttaactcctcctccagaagacggatgagctcggcgacagtgtcgcgcacctcgcgctcaaaggcta |
| caggggcctcttcttcttcttcaatctcctcttccataagggcctccccttcttcttcttctggcggcggtgggggagggggacacggcg |
| gcgacgacggcgcaccgggaggcggtcgacaaagcgctcgatcatctccccgcggcgacggcgcatggtctcggtgacggcgcg |
| gccgttctcgcgggggcgcagttggaagacgccgcccgtcatgtcccggttatgggttgggggggctgccatgcggcagggatac |
| ggcgctaacgatgcatctcaacaattgttgtgtaggtactccgccgccgagggacctgagcgagtccgcatcgacoggatcggaaaac |
| ctctcgagaaaggcgtctaaccagtcacagtcgcaaggtaggctgagcaccgtggcgggcggcagcgggcggcggtcggggttgtt |
| tctggcggaggtgctgctgatgatgtaattaaagtaggcggtcttgagacggcggatggtcgacagaagcaccatgtccttgggtccgg |
| cctgctgaatgcgcaggcggtcggccatgccccaggcttcgttttgacatcggcgcaggtctttgtagtagtcttgcatgagcctttctacc |
| ggcacttcttcttctccttcctcttgtcctgcatctcttgcatctatcgctgcggcggcggcggagtttggccgtaggtggcgccctcttcctc |
| ccatgcgtgtgaccccgaagcccctcatcggctgaagcagggctaggtcggcgacaacgcgctcggctaatatggcctgctgcacct |
| gcgtgagggtagactggaagtcatccatgtccacaaagcggtggtatgcgcccgtgttgatggtgtaagtgcagttggccataacggac |
| cagttaacggtctggtgacccggctgcgagagctcggtgtacctgagacgcgagtaagccctcgagtcaaatacgtagtcgttgcaagt |
| ccgcaccaggtactggtatcccaccaaaaagtgcggcggcggctggcggtagaggggccagcgtagggtggccggggctccggg |
| ggcgagatcttccaacataaggcgatgatatccgtagatgtacctggacatccaggtgatgccggcggcggtggtggaggcgcgcgg |
| aaagtcgcggacgcggttccagatgttgcgcagcggcaaaaagtgctccatggtcgggacgctctggccggtcaggcgcgcgcaatc |

TABLE 33-continued

| Ad5-B4Gal-Cas9 No Plasmid Backbone |
|---|
| gttgacgctctagaccgtgcaaaaggagagcctgtaagcgggcactcttccgtggtctggtggataaattcgcaagggtatcatggcgg<br>acgaccggggttcgagccccgtatccggccgtccgccgtgatccatgcggttaccgcccgcgtgtcgaacccaggtgtgcgacgtca<br>gacaacgggggagtgctccttttggcttccttccaggcgcggcggctgctgcgctagcttttttggccactggccgcgcgcagcgtaag<br>cggttaggctggaaagcgaaagcattaagtggctcgctccctgtagccggagggttattttccaagggttgagtcgcgggacccccggt<br>tcgagtctcggaccggccggactgcggcgaacgggggtttgcctccccgtcatgcaagaccccgcttgcaaattcctccggaaacag<br>ggacgagcccctttttttgcttttcccagatgcatccggtgctgcggcagatgcgcccccctcctcagcagcggcaagagcaagagcag<br>cggcagacatgcagggcaccctcccctcctcctaccgcgtcaggaggggcgacatccgcggttgacgcggcagcagatggtgattac<br>gaacccccgcggcgccgggcccggcactacctggacttggaggagggcgagggcctggcgcggctaggagcgccctctcctgag<br>cggcacccaagggtgcagctgaagcgtgatacgcgtgaggcgtacgtgccgcggcagaacctgtttcgcgaccgcgagggagagg<br>agcccgaggagatgcgggatcgaaagttccacgcagggcgcgagctgcggcatggcctgaatcgcgagcggttgctgcgcgagga<br>ggactttgagcccgacgcgcgaaccgggattagtcccgcgcgcgcacacgtggcggccgccgacctggtaaccgcatacgagcag<br>acggtgaaccaggagattaactttcaaaaaagctttaacaaccacgtgcgtacgcttgtggcgcgcgaggaggtggctataggactgat<br>gcatctgtgggactttgtaagcgcgctggagcaaaacccaaatagcaagccgctcatggcgcagctgttccttatagtgcagcacagca<br>gggacaacgaggcattcagggatgcgctgctaaacatagtagagcccgagggccgctggctgctcgatttgataaacatcctgcagag<br>catagtggtgcaggagcgcagcttgagcctggctgacaaggtggccgccatcaactattccatgcttagcctgggcaagttttacgccc<br>gcaagatataccataccccttacgttcccatagacaaggaggtaaagatcgaggggttctacatgcgcatggcgctgaaggtgcttacct<br>tgagcgacgacctgggcgtttatcgcaacgagcgcatccacaaggccgtgagcgtgagccggcggcgcgagctcagcgaccgcga<br>gctgatgcacagcctgcaaagggccctggctggcacgggcagcggcgatagagaggccgagtcctactttgacgcgggcgctgacc<br>tgcgctgggccccaagccgacgcgccctggaggcagctggggccggacctgggctggcggtggcacccgcgcgcgctggcaacg<br>tcggcggcgtggaggaatatgacgaggacgatgagtacgagccagaggacggcgagtactaagcggtgatgtttctgatcagatgat<br>gcaagacgcaacggacccggcggtgcgggcggcgctgcagagccagccgtccggccttaactccacggacgactggcgccaggt<br>catggaccgcatcatgtcgctgactgcgcgcaatcctgacgcgttccggcagcagccgcaggccaaccggctctccgcaattctggaa<br>gcggtggtcccggcgcgcgcaaaccccacgcacgagaaggtgctggcgatcgtaaacgcgctggccgaaaacagggccatccgg<br>cccgacgaggccggcctggtctacgacgcgctgcttcagcgcgtggctcgttacaacagcggcaacgtgcagaccaacctggaccg<br>gctggtggggdatgtgcgcgaggccgtggcgcagcgtgagcgcgcgcagcagcagggcaacctgggctccatggttgcactaaac<br>gccttcctgagtacacagcccgccaacgtgccgcggggacaggaggactacaccaactttgtgagcgcactgcggctaatggtgact<br>gagacaccgcaaagtgaggtgtaccagtctgggccagactattttttccagaccagtagacaaggcctgcagaccgtaaacctgagcc<br>aggctttcaaaaacttgcaggggctgtgggggtgcgggctcccacaggcgaccgcgcgaccgtgtctagcttgctgacgcccaact<br>cgcgcctgttgctgctgctaatagcgcccttcacggacagtggcagcgtgtcccgggacacatacctaggtcacttgctgacactgtacc<br>gcgaggccataggtcaggcgcatgtggacgagcatactttccaggagattacaagtgtcagccgcgcgctggggcaggaggacacg<br>ggcagcctggaggcaaccctaaactacctgctgaccaaccggggcagaagatcccctcgttgcacagtttaaacagcgaggaggag<br>cgcattttgcgctacgtgcagcagagcgtgagccttaacctgatgcgcgacggggtaacgcccagcgtggcgctggacatgaccgcg<br>cgcaacatggaaccgggcatgtatgcctcaaaccggccgtttatcaaccgcctaatggactacttgcatcgcgcggccgccgtgaacc<br>ccgagtatttcaccaatgccatcttgaacccgcactggctaccgccccctggtttctacaccgggggattcgaggtgcccgagggtaac<br>gatggattcctctgggacgacatagacgacagcgtgttttccccgcaaccgcagaccctgctagagttgcaacagcgcgagcaggcag<br>aggcggcgctgcgaaaggaaagcttccgcaggccaagcagcttgtccgatctaggcgctgcggccccgcggtcagatgctagtagc<br>ccatttccaagcttgatagggtctcttaccagcactcgcaccacccgcccgcgcctgctgggcgaggaggagtacctaaacaactcgct<br>gctgcagccgcagcgcgaaaaaaacctgcctccggcatttcccaacaacgggatagagagcctagtggacaagatgagtagatggaa<br>gacgtacgcgcaggagcacagggacgtgccaggcccgcgcccgcccacccgtcgtcaaaggcacgaccgtcagcggggtctggt |

TABLE 33-continued

| Ad5-B4Gal-Cas9 No Plasmid Backbone |
|---|
| gtgggaggacgatgactcggcagacgacagcagcgtcctggatttgggagggagtggcaacccgtttgcgcaccttcgccccaggct |
| ggggagaatgttttaaaaaaaaaaaaaaagcatgatgcaaaataaaaaactcaccaaggccatggcaccgagcgttggttttcttgtattcc |
| ccttagtatgcggcgcgcggcgatgtatgaggaaggtcctcctccctcctacgagagtgtggtgagcgcggcgccagtggcggcggc |
| gctgggttctcccttcgatgctcccctggacccgccgtttgtgcctccgcggtacctgcggcctaccggggggagaaacagcatccgtt |
| actctgagttggcacccctattcgacaccacccgtgtgtacctggtggacaacaagtcaacggatgtggcatccctgaactaccagaac |
| gaccacagcaactttctgaccacggtcattcaaaacaatgactacagcccgggggaggcaagcacacagaccatcaatcttgacgacc |
| ggtcgcactgggggggcgacctgaaaaccatcctgcataccaacatgccaaatgtgaacgagttcatgtttaccaataagtttaaggcgc |
| gggtgatggtgtcgcgcttgcctactaaggacaatcaggtggagctgaaatacgagtgggtggagttcacgctgcccgagggcaacta |
| ctccgagaccatgaccatagaccttatgaacaacgcgatcgtggagcactacttgaaagtgggcagacagaacggggttctggaaagc |
| gacatcggggtaaagtttgacacccgcaacttcagactggggtttgaccccgtcactggtcttgtcatgcctggggtatatacaaacgaa |
| gccttccatccagacatcattttgctgccaggatgcggggtggacttcacccacagccgcctgagcaacttgttgggcatccgcaagcg |
| gcaacccttccaggagggctttaggatcacctacgatgatctggagggtggtaacattcccgcactgttggatgtggacgcctaccagg |
| cgagcttgaaagatgacaccgaacagggggggggtggcgcaggcggcagcaacagcagtggcagcggcgcggaagagaactcc |
| aacgcggcagccgcggcaatgcagccggtggaggacatgaacgatcatgccattcgcggcgacacctttgccacacgggctgagga |
| gaagcgcgctgaggccgaagcagcggccgaagctgccgcccccgctgcgcaacccgaggtcgagaagcctcagaagaaaccggt |
| gatcaaacccctgacagaggacagcaagaaacgcagttacaacctaataagcaatgacagcaccttcacccagtaccgcagctggtac |
| cttgcatacaactacggcgaccctcagaccggaatccgctcatggaccctgctttgcactcctgacgtaacctgcggctcggagcaggt |
| ctactggtcgttgccagacatgatgcaagaccccgtgaccttccgctccacgcgccagatcagcaactttccggtggtgggcgccgag |
| ctgttgcccgtgcactccaagagcttctacaacgaccaggccgtctactcccaactcatccgccagtttacctctctgacccacgtgttcaa |
| tcgctttcccgagaaccagattttggcgcgcccgccagccccccaccatcaccaccgtcagtgaaaacgttcctgctctcacagatcacg |
| ggacgctaccgctgcgcaacagcatcggaggagtccagcgagtgaccattactgacgccagacgccgcacctgcccctacgtttaca |
| aggccctgggcatagtctcgccgcgcgtcctatcgagccgcactttttgagcaagcatgtccatccttatatcgcccagcaataacacag |
| gctggggcctgcgcttcccaagcaagatgtttggcggggccaagaagcgctccgaccaacacccagtgcgcgtgcgcgggcactac |
| cgcgcgccctggggcgcgcacaaacgcggccgcactgggcgcaccaccgtcgatgacgccatcgacgcggtggtggaggaggcg |
| cgcaactacacgcccacgccgccaccagtgtccacagtggacgcggccattcagaccgtggtgcgcggagcccggcgctatgctaa |
| aatgaagagacggcggaggcgcgtagcacgtcgccaccgccgccgacccggcactgccgcccaacgcgcggcggcggccctgct |
| taaccgcgcacgtcgcaccggccgacgggcggccatgcgagcagctcgaaggctggccgcgggtattgtcactgtgccccccaggt |
| ccaggcgacgagcggccgccgcagcagccgcggccattagtgctatgactcagggtcgcaggggcaacgtgtattgggtgcgcgac |
| tcggttagcggcctgcgcgtgcccgtgcgcacccgcccccgcgcaactagattgcaagaaaaaactacttagactcgtactgttgtat |
| gtatccagcggcggcggcgcgcaacgaagctatgtccaagcgcaaaatcaaagaagagatgctccaggtcatcgcgccggagatct |
| atggccccccgaagaaggaagagcaggattacaagccccgaaagctaaagcgggtcaaaaagaaaaagaaagatgatgatgatgaa |
| cttgacgacgaggtggaactgctgcacgctaccgcgcccaggcgacgggtacagtggaaaggtcgacgcgtaaaacgtgttttgcga |
| cccggcaccaccgtagtctttacgcccggtgagcgctccacccgcacctacaagcgcgtgtatgatgaggtgtacggcgacgaggac |
| ctgcttgagcaggccaacgagcgcctcggggagtttgcctacggaaagcggcataaggacatgctggcgttgccgctggacgaggg |
| caacccaacacctagcctaaagcccgtaacactgcagcaggtgctgcccgcgcttgcaccgtccgaagaaaagcgcggcctaaagc |
| gcgagtctggtgacttggcacccaccgtgcagctgatggtacccaagcgccagcgactggaagatgtcttggaaaaaatgaccgtgga |
| acctgggctggagcccgaggtccgcgtgcggccaatcaagcaggtggcgccgggactgggcgtgcagaccgtggacgttcagata |
| cccactaccagtagcaccagtattgccaccgccacagagggcatggagacacaaacgtccccggttgcctcagcggtggcggatgcc |
| gcggtgcaggcggtcgctgcggccgcgtccaagacctctacggaggtgcaaacggacccgtggatgtttcgcgtttcagccccccgg |

TABLE 33-continued

| Ad5-B4Gal-Cas9 No Plasmid Backbone |
| --- |
| cgcccgcgccgttcgaggaagtacggcgccgccagcgcgctactgcccgaatatgccctacatccttccattgcgcctacccccggct |
| atcgtggctacacctaccgccccagaagacgagcaactacccgacgccgaaccaccactggaacccgccgccgccgtcgccgtcgc |
| cagcccgtgctggccccgatttccgtgcgcagggtggctcgcgaaggaggcaggaccctggtgctgccaacagcgcgctaccaccc |
| cagcatcgtttaaaagccggtctttgtggttcttgcagatatggccctcacctgccgcctccgtttcccggtgccgggattccgaggaaga |
| atgcaccgtaggaggggcatggccggccacggcctgacgggcggcatgcgtcgtgcgcaccaccggcggcggcgcgcgtcgcac |
| cgtcgcatgcgcggcggtatcctgcccctccttattccactgatcgccgcggcgattggcgccgtgcccggaattgcatccgtggccttg |
| caggcgcagagacactgattaaaaacaagttgcatgtggaaaaatcaaaataaaaagtctggactctcacgctcgcttggtcctgtaact |
| attttgtagaatggaagacatcaactttgcgtctctggccccgcgacacggctcgcgcccgttcatgggaaactggcaagatatcggcac |
| cagcaatatgagcggtggcgccttcagctggggctcgctgtggagcggcattaaaaatttcggttccaccgttaagaactatggcagca |
| aggcctggaacagcagcacaggccagatgctgagggataagttgaaagagcaaaatttccaacaaaaggtggtagatggcctggcct |
| ctggcattagcggggtggtggacctggccaaccaggcagtgcaaaataagattaacagtaagcttgatccccgccctcccgtagagga |
| gcctccaccggccgtggagacagtgtctccagaggggcgtggcgaaaagcgtccgcgccccgacagggaagaaactctggtgacg |
| caaatagacgagcctccctcgtacgaggaggcactaaagcaaggcctgcccaccacccgtcccatcgcgcccatggctaccggagtg |
| ctgggccagcacacacccgtaacgctggacctgcctcccccgccgacacccagcagaaacctgtgctgccaggcccgaccgccgt |
| tgttgtaacccgtcctagccgcgcgtccctgcgccgcgccgccagcggtccgcgatcgttgcggcccgtagccagtggcaactggca |
| aagcacactgaacagcatcgtgggtctgggggtgcaatccctgaagcgccgacgatgcttctgaatagctaacgtgtcgtatgtgtgtca |
| tgtatgcgtccatgtcgccgccagaggagctgctgagccgccgcgcgcccgctttccaagatggctaccccttcgatgatgccgcagtg |
| gtcttacatgcacatctcgggccaggacgcctcggagtacctgagccccgggctggtgcagtttgcccgcgccaccgagacgtacttc |
| agcctgaataacaagtttagaaccccacggtggcgcctacgcacgacgtgaccacagaccggtcccagcgtttgacgctgcggttca |
| tccctgtggaccgtgaggatactgcgtactcgtacaaggcgcggttcaccctagctgtgggtgataaccgtgtgctggacatggcttcca |
| cgtactttgacatccgcggcgtgctggacaggggccctacttttaagccctactctggcactgcctacaacgccctggctcccaagggtg |
| ccccaaatccttgcgaatgggatgaagctgctactgctcttgaaataaacctagaagaagaggacgatgacaacgaagacgaagtaga |
| cgagcaagctgagcagcaaaaaactcacgtatttgggcaggcgccttattctggtataaatattacaaaggagggtattcaaataggtgtc |
| gaaggtcaaacacctaaatatgccgataaaacatttcaacctgaacctcaaataggagaatctcagtggtacgaaacagaaattaatcat |
| gcagctgggagagtcctaaaaaagactaccccaatgaaaccatgttacggttcatatgcaaaacccacaaatgaaaatggagggcaag |
| gcattcttgtaaagcaacaaaatggaaagctagaaagtcaagtggaaatgcaatttttctcaactactgaggcagccgcaggcaatggtg |
| ataacttgactcctaaagtggtattgtacagtgaagatgtagatatagaaaccccagacactcatatttcttacatgcccactattaaggaag |
| gtaactcacgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttcata |
| ccagcttttgcttgattccattggtgatagaaccaggtacttttctatgtggaatcaggctgttgacagctatgatccagatgttagaattattg |
| aaaatcatggaactgaagatgaacttccaaattactgctttccactgggaggtgtgattaatacagagactcttaccaaggtaaaacctaaa |
| acaggtcaggaaaatggatgggaaaaagatgctacagaattttcagataaaaatgaaataagagttggaaataattttgccatggaaatc |
| aatctaaatgccaacctgtggagaaatttcctgtactccaacatagcgctgtatttgcccgacaagctaaagtacagtccttccaacgtaaa |
| aatttctgataacccaaacacctacgactacatgaacaagcgagtggtggctcccgggctagtggactgctacattaaccttggagcacg |
| ctggtcccttgactatatggacaacgtcaacccatttaaccaccaccgcaatgctggcctgcgctaccgctcaatgttgctgggcaatggt |
| cgctatgtgcccttccacatccaggtgcctcagaagttctttgccattaaaaacctccttctcctgccgggctcatacacctacgagtggaa |
| cttcaggaaggatgttaacatggttctgcagagctccctaggaaatgacctaagggttgacggagccagcattaagtttgatagcatttgc |
| ctttacgccaccttcttccccatggcccacaacaccgcctccacgcttgaggccatgcttagaaacgacaccaacgaccagtcctttaac |
| gactatctctccgccgccaacatgctctaccctatacccgccaacgctaccaacgtgcccatatccatcccctcccgcaactgggggct |

TABLE 33-continued

| Ad5-B4Gal-Cas9 No Plasmid Backbone |
|---|

ttccgcggctgggccttcacgcgccttaagactaaggaaaccccatcactgggctcgggctacgacccttattacacctactctggctcta taccctacctagatggaaccttttacctcaaccacacctttaagaaggtggccattacctttgactcttctgtcagctggcctggcaatgacc gcctgcttacccccaacgagtttgaaattaagcgctcagttgacggggagggttacaacgttgcccagtgtaacatgaccaaagactggt tcctggtacaaatgctagctaactataacattggctaccagggcttctatatcccagagagctacaaggaccgcatgtactccttctttaga aacttccagcccatgagccgtcaggtggtggatgatactaaatacaaggactaccaacaggtgggcatcctacaccaacacaacaactc tggatttgttggctaccttgcccccaccatgcgcgaaggacaggcctaccctgctaacttccccctatccgcttataggcaagaccgcagtt gacagcattacccagaaaaagtttctttgcgatcgcaccctttggcgcatcccattctccagtaactttatgtccatgggcgcactcacaga cctgggccaaaaccttctctacgccaactccgcccacgcgctagacatgacttttgaggtggatcccatggacgagcccacccttcttttat gttttgtttgaagtctttgacgtggtccgtgtgcaccagccgcaccgcggcgtcatcgaaaccgtgtacctgcgcacgcccttctcggccg gcaacgccacaacataaagaagcaagcaacatcaacaacagctgccgccatgggctccagtgagcaggaactgaaagccattgtcaa agatcttggttgtgggccatatttttgggcacctatgacaagcgctttccaggctttgtttctccacacaagctcgcctgcgccatagtcaat acggccggtcgcgagactgggggcgtacactggatggcctttgcctggaacccgcactcaaaaacatgctacctctttgagccctttgg cttttctgaccagcgactcaagcaggtttaccagtttgagtacgagtcactcctgcgccgtagcgccattgcttcttcccccgaccgctgta taacgctggaaaagtccacccaaagcgtacaggggcccaactcggccgcctgtggactattctgctgcatgtttctccacgcctttgcca actggccccaaactcccatggatcacaaccccaccatgaaccttattaccggggtacccaactccatgctcaacagtccccaggtacag cccaccctgcgtcgcaaccaggaacagctctacagcttcctggagcgccactcgccctacttccgcagccacagtgcgcagattagga gcgccacttctttttgtcacttgaaaaacatgtaaaaataatgtactagagacactttcaataaaggcaaatgcttttatttgtacactctcggg tgattatttaccccccaccttgccgtctgcgccgtttaaaaatcaaaggggttctgccgcgcatcgctatgcgccactggcagggacacgt tgcgatactggtgtttagtgctccacttaaactcaggcacaaccatccgcggcagctcggtgaagttttcactccacaggctgcgcaccat caccaacgcgtttagcaggtcgggcgccgatatcttgaagtcgcagttggggcctccgccctgcgcgcgcgagttgcgatacacagg gttgcagcactggaacactatcagcgccgggggtgcacgctggccagcacgctcttgtcggagatcagatccgcgtccaggtcctcc gcgttgctcagggcgaacggagtcaactttggtagctgccttcccaaaaagggcgcgtgcccaggctttgagttgcactcgcaccgtag tggcatcaaaaggtgaccgtgcccggtctgggcgttaggatacagcgcctgcataaaagccttgatctgcttaaaagccacctgagcctt tgcgccttcagagaagaacatgccgcaagacttgccggaaaactgattggccggacacgcggcgtcgtgcacgcagcaccttgcgtc ggtgttggagatctgcaccacatttcggccccaccggttcttcacgatcttggccttgctagactgctccttcagcgcgcgctgcccgtttt cgctcgtcacatccatttcaatcacgtgctccttatttatcataatgcttccgtgtagacacttaagctcgccttcgatctcagcgcagcggtg cagccacaacgcgcagcccgtgggctcgtgatgcttgtaggtcacctctgcaaacgactgcaggtacgcctgcaggaatcgccccatc atcgtcacaaaggtcttgttgctggtgaaggtcagctgcaacccgcggtgctcctcgttcagccaggtcttgcatacggccgccagagct tccacttggtcaggcagtagtttgaagttcgcctttagatcgttatccacgtggtacttgtccatcagcgcgcgcgcagcctccatgcccttc tcccacgcagacacgatcggcacactcagcgggttcatcaccgtaatttcactttccgcttcgctgggctcttcctcttcctcttgcgtccgc ataccacgcgccactgggtcgtcttcattcagccgccgcactgtgcgcttacctcctttgccatgcttgattagcaccggtgggttgctgaa acccaccatttgtagcgccacatcttctctttcttcctcgctgtccacgattacctctggtgatggcgggcgctcgggcttgggagaaggg cgcttctttttcttcttgggcgcaatggccaaatccgccgccgaggtcgatggccgcgggctgggtgtgcgcggcaccagcgcgtcttgt gatgagtcttcctcgtcctcggactcgatacgccgcctcatccgcttttttgggggcgcccggggaggcggcggcgacggggacggg gacgacacgtcctccatggttgggggacgtcgcgccgcaccgcgtccgcgctcgggggtggtttcgcgctgctcctcttcccgactgg ccatttccttctcctataggcagaaaaagatcatggagtcagtcgagaagaaggacagcctaaccgccccctctgagttcgccaccacc gcctccaccgatgccgccaacgcgcctaccaccttccccgtcgaggcacccccgcttgaggaggaggaagtgattatcgagcaggac ccaggttttgtaagcgaagacgacgaggaccgctcagtaccaacagaggataaaaagcaagaccaggacaacgcagaggcaaacg aggaacaagtcgggcgggggacgaaaggcatggcgactacctagatgtgggagacgacgtgctgttgaagcatctgcagcgcca TABLE 33-continued

| Ad5-B4Gal-Cas9 No Plasmid Backbone |
|---|
| gtgcgccattatctgcgacgcgttgcaagagcgcagcgatgtgcccctcgccatagcggatgtcagccttgcctacgaacgccacctat |
| tctcaccgcgcgtacccccaaacgccaagaaaacggcacatgcgagcccaacccgcgcctcaacttctaccccgtatttgccgtgcc |
| agaggtgcttgccacctatcacatctttttccaaaactgcaagatacccctatcctgccgtgccaaccgcagccgagcggacaagcagct |
| ggccttgcggcagggcgctgtcatacctgatatcgcctcgctcaacgaagtgccaaaaatctttgagggtcttggacgcgacgagaagc |
| gcgcggcaaacgctctgcaacaggaaaacagcgaaaatgaaagtcactctggagtgttggtggaactcgagggtgacaacgcgcgc |
| ctagccgtactaaaacgcagcatcgaggtcacccactttgcctaccoggcacttaacctaccccccaaggtcatgagcacagtcatgag |
| tgagctgatcgtgcgccgtgcgcagcccctggagagggatgcaaatttgcaagaacaaacagaggagggcctacccgcagttggcg |
| acgagcagctagcgcgctggcttcaaacgcgcgagcctgccgacttggaggagcgacgcaaactaatgatggccgcagtgctcgtta |
| ccgtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgccttggg |
| caaaacgtgcttcattccacgctcaagggcgaggcgcgccgcgactacgtccgcgactgcgtttacttatttctatgctacacctggcag |
| acggccatgggcgtttggcagcagtgcttggaggagtgcaacctcaaggagctgcagaaactgctaaagcaaaacttgaaggacctat |
| ggacggccttcaacgagcgctccgtggccgcgcacctggcggacatcattttccccgaacgcctgcttaaaaccctgcaacagggtct |
| gccagacttcaccagtcaaagcatgttgcagaactttaggaactttatcctagagcgctcaggaatcttgcccgccacctgctgtgcactt |
| cctagcgactttgtgcccattaagtaccgcgaatgccctccgccgctttggggccactgctaccttctgcagctagccaactaccttgcct |
| accactctgacataatggaagacgtgagcggtgacggtctactggagtgtcactgtcgctgcaacctatgcaccccgcaccgctccctg |
| gtttgcaattcgcagctgcttaacgaaagtcaaattatcggtacctttgagctgcagggtccctcgcctgacgaaaagtccgcggctccg |
| gggttgaaactcactccggggctgtggacgtcggcttaccttcgcaaatttgtacctgaggactaccacgcccacgagattaggttctac |
| gaagaccaatcccgcccgcctaatgcggagcttaccgcctgcgtcattacccagggccacattcttggccaattgcaagccatcaacaa |
| agcccgccaagagtttctgctacgaaagggacgggggtttacttggacccccagtccggcgaggagctcaacccaatccccccgcc |
| gccgcagccctatcagcagcagccgcgggcccttgcttcccaggatggcacccaaaaagaagctgcagctgccgccgccacccacg |
| gacgaggaggaatactgggacagtcaggcagaggaggttttggacgaggaggaggaggacatgatggaagactgggagagcctag |
| acgaggaagcttccgaggtcgaagaggtgtcagacgaaacaccgtcaccctcggtcgcattcccctcgccggcgccccagaaatcgg |
| caaccggttccagcatggctacaacctccgctcctcaggcgccgccggcactgcccgttcgccgacccaaccgtagatgggacacca |
| ctggaaccagggccggtaagtccaagcagccgccgccgttagcccaagagcaacaacagcgccaaggctaccgctcatggcgcgg |
| gcacaagaacgccatagttgcttgcttgcaagactgtgggggcaacatctccttcgcccgccgctttcttctctaccatcacggcgtggcc |
| ttccccgtaacatcctgcattactaccgtcatctctacagcccatactgcaccggcggcagcggcagcggcagcaacagcagcggcc |
| acacagaagcaaaggcgaccggatagcaagactctgacaaagcccaagaaatccacagcggcggcagcagcaggaggaggagc |
| gctgcgtctggcgcccaacgaacccgtatcgacccgcgagcttagaaacaggatttttcccactctgtatgctatatttcaacagagcag |
| gggccaagaacaagagctgaaaataaaaaacaggtctctgcgatccctcacccgcagctgcctgtatcacaaaagcgaagatcagctt |
| cggcgcacgctggaagacgcggaggctctcttcagtaaatactgcgcgctgactcttaaggactagtttcgcgccctttctcaaatttaag |
| cgcgaaaactacgtcatctccagcggccacacccggcgccagcacctgttgtcagcgccattatgagcaaggaaattcccacgcccta |
| catgtggagttaccagccacaaatgggacttgcggctggagctgcccaagactactcaacccgaataaactacatgagcgcgggaccc |
| cacatgatatcccgggtcaacggaatacgcgcccaccgaaaccgaattctcctggaacaggcggctattaccaccacacctcgtaataa |
| ccttaatccccgtagttggcccgctgccctggtgtaccaggaaagtcccgctcccaccactgtggtacttcccagagacgcccaggccg |
| aagttcagatgactaactcaggggcgcagcttgcgggggctttcgtcacagggtgcggtcgcccgggcagggtataactcacctgac |
| aatcagagggcgaggtattcagctcaacgacgagtcggtgagctcctcgcttggtctccgtccggacgggacatttcagatcggcggc |
| gccggccgctcttcattcacgcctcgtcaggcaatcctaactctgcagacctcgtcctctgagccgcgctctggaggcattggaactctg |
| caatttattgaggagtttgtgccatcggtctactttaaccccttctcgggacctcccggccactatccggatcaatttattcctaactttgacgc |

TABLE 33-continued

| Ad5-B4Gal-Cas9 No Plasmid Backbone |
| --- |
| ggtaaaggactcggcggacggctacgactgaatgttaagtggccaatgaggcctgacgctaataatagctggtccactgtcgccgcca |
| caagtgctttgcccgcgactccggtgagttttgctactttgaattgcccgaggatcatatcgagggcccggcgcacggcgtccggcttac |
| cgcccagggagagcttgcccgtagcctgattcgggagtttacccagcgcccccctgctagttgagcgggacaggggaccctgtgttctc |
| actgtgatttgcaactgtcctaaccttggattacatcaagatccagatcttctagacccgggagcggccgctgtcgacctgcaggatccga |
| attcgatatcactagtggtaccgatcttattccctttaactaataaaaaaaaataataaagcatcacttacttaaaatcagttagcaaatttctgt |
| ccagtttattcagcagcacctccttgccctcctcccagctctggtattgcagcttcctcctggctgcaaactttctccacaatctaaagggaa |
| tgtcagtttcctcctgttcctgtccatccgcacccactatcttcatgttgttgcagatgaagcgcgcaagaccgtctgaagataccttcaacc |
| ccgtgtatccatatgacacggaaaccggtcctccaactgtgccttttcttactcctccctttgtatcccccaatgggtttcaagagagtcccc |
| ctggggtactctctttgcgcctatccgaacctctagttacctccaatggcatgcttgcgctcaaaatgggcaacggcctctctctggacga |
| ggccggcaaccttacctcccaaaatgtaaccactgtgagcccacctctcaaaaaaaccaagtcaaacataaacctggaaatatctgcac |
| ccctcacagttacctcagaagccctaactgtggctgccgccgcacctctaatggtcgcgggcaacacactcaccatgcaatcacaggcc |
| ccgctaaccgtgcacgactccaaacttagcattgccacccaaggacccctcacagtgtcagaaggaaagctagccctgcaaacatcag |
| gcccccctcaccaccaccgatagcagtacccttactatcactgcctcacccccctctaactactgccactggtagcttgggcattgacttgaa |
| agagcccatttatacacaaaatggaaaactaggactaaagtacggggctcctttgcatgtaacagacgacctaaacactttgaccgtagc |
| aactggtccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaatctaaga |
| ctaggacagggccctctttttataaactcagcccacaacttggatattaactacaacaaaggcctttacttgtttacagcttcaaacaattcca |
| aaaagcttgaggttaacctaagcactgccaaggggttgatgtttgacgctacagccatagccattaatgcaggagatgggcttgaatttgg |
| ttcacctaatgcaccaaacacaaatcccctcaaaacaaaaattggccatggcctagaatttgattcaaacaaggctatggttcctaaactag |
| gaactggccttagttttgacagcacaggtgccattacagtaggaaacaaaaataatgataagctaactttgtggaccacaccagctccatc |
| tcctaactgtagactaaatgcagagaaagatgctaaactcactttggtcttaacaaaatgtggcagtcaaatacttgctacagtttcagttttg |
| gctgttaaaggcagtttggctccaatatctggaacagttcaaagtgctcatcttattataagatttgacgaaaatggagtgctactaaacaatt |
| ccttcctggacccagaatattggaactttagaaatggagatcttactgaaggcacagcctatacaaacgctgttggatttatgcctaacctat |
| cagcttatccaaaatctcacggtaaaactgccaaaagtaacattgtcagtcaagtttacttaaacggagacaaaactaaacctgtaacacta |
| accattacactaaacggtacacaggaaacaggagacacaactccaagtgcatactctatgtcattttcatgggactggtctggccacaact |
| acattaatgaaatatttgccacatcctcttacactttttcatacattgcccaagaataaagaatcgtttgtgttatgtttcaacgtgtttatttttcaa |
| ttgcagaaaatttcaagtcatttttcattcagtagtatagccccaccaccacatagcttatacagatcaccgtaccttaatcaaactcacagaa |
| ccctagtattcaacctgccacctccctcccaacacacagagtacacagtcctttctccccggctggccttaaaaagcatcatatcatgggt |
| aacagacatattcttaggtgttatattccacacggtttcctgtcgagccaaacgctcatcagtgatattaataaactccccgggcagctcact |
| taagttcatgtcgctgtccagctgctgagccacaggctgctgtccaacttgcggttgcttaacgggcggcgaaggagaagtccacgcct |
| acatgggggtagagtcataatcgtgcatcaggatagggcggtggtgctgcagcagcgcgcgaataaactgctgccgccgccgctccg |
| tcctgcaggaatacaacatggcagtggtctcctcagcgatgattcgcaccgcccgcagcataaggcgccttgtcctccgggcacagca |
| gcgcaccctgatctcacttaaatcagcacagtaactgcagcacagcaccacaatattgttcaaaatcccacagtgcaaggcgctgtatcc |
| aaagctcatggcggggaccacagaacccacgtggccatcataccacaagcgcaggtagattaagtggcgacccctcataaacacgct |
| ggacataaacattacctcttttggcatgttgtaattcaccacctcccggtaccatataaacctctgattaaacatggcgccatccaccaccat |
| cctaaaccagctggccaaaacctgcccgccggctatacactgcagggaaccgggactggaacaatgacagtggagagcccaggact |
| cgtaaccatggatcatcatgctcgtcatgatatcaatgttggcacaacacaggcacacgtgcatacacttcctcaggattacaagctcctc |
| ccgcgttagaaccatatcccagggaacaacccattcctgaatcagcgtaaatcccacactgcagggaagacctcgcacgtaactcacgt |
| tgtgcattgtcaaagtgttacattcgggcagcagcggatgatcctccagtatggtagcgcgggtttctgtctcaaaaggaggtagacgatc |

TABLE 33-continued

| Ad5-B4Gal-Cas9 No Plasmid Backbone |
| --- |
| cctactgtacggagtgcgccgagacaaccgagatcgtgttggtcgtagtgtcatgccaaatggaacgccggacgtagtcatatttcctga |
| agcaaaaccaggtgcgggcgtgacaaacagatctgcgtctccggtctcgccgcttagatcgctctgtgtagtagttgtagtatatccactc |
| tctcaaagcatccaggcgcccctggcttcgggttctatgtaaactccttcatgcgccgctgccctgataacatccaccaccgcagaataa |
| gccacacccagccaacctacacattogttctgcgagtcacacacgggaggagcgggaagagctggaagaaccatgtttttttttttattc |
| caaaagattatccaaaacctcaaaatgaagatctattaagtgaacgcgctcccctccggtggcgtggtcaaactctacagccaaagaaca |
| gataatggcatttgtaagatgttgcacaatggcttccaaaaggcaaacggccctcacgtccaagtggacgtaaaggctaaacccttcagg |
| gtgaatctcctctataaacattccagcaccttcaaccatgcccaaataattctcatctcgccaccttctcaatatatctctaagcaaatcccga |
| atattaagtccggccattgtaaaaatctgctccagagcgccctccaccttcagcctcaagcagcgaatcatgattgcaaaaattcaggttc |
| ctcacagacctgtataagattcaaaagcggaacattaacaaaaataccgcgatcccgtaggtcccttcgcagggccagctgaacataat |
| cgtgcaggtctgcacggaccagcgcggccacttccccgccaggaaccatgacaaaagaacccacactgattatgacacgcatactcg |
| gagctatgctaaccagcgtagccccgatgtaagcttgttgcatgggcggcgatataaaatgcaaggtgctgctcaaaaaatcaggcaaa |
| gcctcgcgcaaaaaagaaagcacatcgtagtcatgctcatgcagataaaggcaggtaagctccggaaccaccacagaaaaagacacc |
| atttttctctcaaacatgtctgcgggtttctgcataaacacaaaataaaataacaaaaaaacatttaaacattagaagcctgtcttacaacagg |
| aaaaacaacccttataagcataagacggactacggccatgccggcgtgaccgtaaaaaaactggtcaccgtgattaaaaagcaccacc |
| gacagctcctcggtcatgtccggagtcataatgtaagactcggtaaacacatcaggttgattcacatcggtcagtgctaaaaagcgaccg |
| aaatagcccgggggaatacatacccgcaggcgtagagacaacattacagcccccataggaggtataacaaaattaataggagagaaa |
| aacacataaacacctgaaaaaccctcctgcctaggcaaaatagcaccctcccgctccagaacaacatacagcgcttccacagcggcag |
| ccataacagtcagccttaccagtaaaaaagaaaacctattaaaaaaacaccactcgacacggcaccagctcaatcagtcacagtgtaaa |
| aaagggccaagtgcagagcgagtatatataggactaaaaaatgacgtaacggttaaagtccacaaaaaacacccagaaaaccgcacg |
| cgaacctacgcccagaaacgaaagccaaaaaacccacaacttcctcaaatcgtcacttccgttttcccacgttacgtaacttcccattttaa |
| gaaaactacaattcccaacacatacaagttactccgccctaaaacctacgtcacccgccccgttcccacgccccgcgccacgtcacaaa |
| ctccacccccctcattatcatattggcttcaatccaaaataaggtatattattgatgatg |

SEQUENCE LISTING

The patent contains a lengthy sequence listing. A copy of the sequence listing is available in electronic form from the USPTO web site (https://seqdata.uspto.gov/?pageRequest=docDetail&DocID=US12227754B2). An electronic copy of the sequence listing will also be available from the USPTO upon request and payment of the fee set forth in 37 CFR 1.19(b)(3).

What is claimed is:

1. A non-replicating adenovirus expression vector comprising:

a) one or more mutations that render the adenovirus replication incompetent; and b) at least one nucleotide sequence encoding a gene product, wherein the vector comprises a nucleotide sequence having at least 95% sequence identity over the entire sequence of SEQ ID NO: 1 or SEQ ID NO: 2, or the entire complementary sequence thereto.

2. The vector of claim 1, wherein the vector comprises a nucleic acid sequence having at least 96%, 97%, 98%, or 99% sequence identity to SEQ ID NO: 1 or SEQ ID NO: 2.

3. The vector of claim 1, wherein the vector comprises an adenovirus serotype 5 vector.

4. The vector of claim 1, wherein the one or more mutations comprise deletion of either an E1 gene or an E3 gene or both.

5. The vector of claim 1, wherein the at least one nucleotide sequence encoding a gene product further comprises a polyadenylation signal.

6. The vector of claim 5, wherein the polyadenylation signal comprises an SV40 region, a full poly A signal, or both an SV40 region and a full poly A signal.

7. The vector of claim 4, wherein insertion of the at least one nucleotide sequence encoding a gene product replaces the E1 gene but leaves a pIX gene intact.

* * * * *